US006916642B1

(12) United States Patent
Kilian et al.

(10) Patent No.: US 6,916,642 B1
(45) Date of Patent: Jul. 12, 2005

(54) VERTEBRATE TELOMERASE GENES AND PROTEINS AND USES THEREOF

(75) Inventors: Andrzej Kilian, Canberra (AU); David Bowtell, Coburg (AU)

(73) Assignee: The Monticello Group, LTD, Seattle, WA (US)

( * ) Notice: Subject to any disclaimer, the term of this patent is extended or adjusted under 35 U.S.C. 154(b) by 0 days.

(21) Appl. No.: 09/502,424

(22) Filed: Feb. 11, 2000

Related U.S. Application Data

(63) Continuation of application No. 09/108,401, filed on Jun. 30, 1998, now abandoned.
(60) Provisional application No. 60/058,287, filed on Sep. 9, 1997, provisional application No. 60/054,642, filed on Aug. 4, 1997, provisional application No. 60/053,329, filed on Jul. 21, 1997, provisional application No. 60/053,018, filed on Jul. 19, 1997, and provisional application No. 60/051,410, filed on Jul. 1, 1997.

(51) Int. Cl.[7] .......................... C12N 9/12; C12N 15/00; C12N 5/00; C07H 21/04; C12Q 1/68
(52) U.S. Cl. .................... 435/194; 536/23.1; 536/23.2; 536/24.3; 536/24.31; 435/6; 435/320.1; 435/325; 435/252.3; 435/254.2; 435/353; 435/354; 435/363; 435/366
(58) Field of Search .................... 435/194, 6, 320.1, 435/325, 353, 354, 363, 366, 254.2; 536/23.1, 23.2, 23.5, 24.31

(56) References Cited

U.S. PATENT DOCUMENTS

| 5,489,508 A | | 2/1996 | West et al. ..................... 435/6 |
| 5,639,613 A | | 6/1997 | Shay et al. ..................... 435/6 |
| 5,645,986 A | | 7/1997 | West et al. ..................... 435/6 |
| 5,770,422 A | | 6/1998 | Collins ......................... 435/194 |
| 5,919,656 A | | 7/1999 | Harrington et al. ......... 435/69.1 |
| 6,093,809 A | * | 7/2000 | Cech et al. ................. 536/23.5 |
| 6,166,178 A | * | 12/2000 | Cech et al. ................. 530/342 |
| 6,309,867 B1 | * | 10/2001 | Cech et al. ................. 435/194 |

FOREIGN PATENT DOCUMENTS

| WO | WO 95/13382 | 5/1995 |
| WO | WO 96/01835 | 1/1996 |
| WO | WO 96/19580 | 6/1996 |
| WO | WO 98/11207 | 3/1998 |
| WO | WO 98/14592 | 4/1998 |
| WO | WO 98/14593 | 4/1998 |
| WO | WO 98/21343 | 5/1998 |
| WO | WO 98/37181 | 8/1998 |

OTHER PUBLICATIONS

Wick M. et al. Genomic organization and promoter characterization of the gene encoding the human telomerase reverse transcriptase (hTERT), Gene, 1999, 232, 97–106.*

Leem S–H. et al. The human telomerase gene: complete genomic sequence and analysis of tandem repeat polymorphism in intronic regions, Oncogene, 2002, 21, 769–777.*
Adams et al., "EST12462 Uterus Tumor I *Homo sapiens* cDNA 5' End," *EMBL Database Entry HSZZ05016*:Accession No. AA299878, 1997.
Belair et al., "Telomerase Activity: A Biomarker of Cell Proliferation, Not Malignant Transformation," *Proc. Natl. Acad. Sci. USA* 94:13677–13682, 1997.
Holt et al., "Lack of Cell Cycle Regulation of Telomerase Activity in Human Cells," *Proc. Natl. Acad. Sci. USA* 94:10687–10692, 1997.
Kilian et al., "Isolation of a Candidate Human Telomerase Catalytic Subunit Gene, Which Reveals Complex Splicing Patterns in Different Cell Types," *Human Molecular Genetics* 6(12):2011–2019, 1997.
Kim et al., "Specific Association of Human Telomerase Activity with Immortal Cells and Cancer," *Science* 266:2011–2015, 1994.
Lingner et al., "Reverse Transcriptase Motifs in the Catalytic Subunit of Telomerase," *Science* 276:561–567, 1997.
Meyerson et al., "*hEST2*, the Putative Human Telomerase Catalytic Subunit Gene, Is Up–Regulated in Tumor Cells and During Immoralization," *Cell* 90:785–795, 1997.
Nakamura et al., "Telomerase Catalytic Subunit Homologs from Fission Yeast and Human," *Science* 277:955–958, 1997.
Nakayama et al., "*TLP1*, A Gene Encoding a Protein Component of Mammalian Telomerase Is a Novel Member of WD Repeats Family," *Cell* 88:875–884, 1997.
Ngo et al., "Computational Complexity, Protein Structure Prediction, and the ILevinthal Paradox," *The Protein Folding Problem and Tertiary Structure Prediction*, Merz et al. (eds.), Birkhauser et al., Boston, MA, 1994, pp. 491–495.
Raymond et al., "Agents that Target Telomerase and Telomeres," *Current Opinion in Biotechnology* 7:583–591, 1996.
Rudinger, "Characteristics of the Amino Acids as Components of a Peptide Hormone Sequence," in *Peptide Hormones*, J. A. Parsons (ed.), University Park Press, Baltimore, MD, 1976, pp. 1–7.
Thornton et al., "Protein Engineering: Editorial Overview," *Current Opinion in Biotechnology* 6(4):367–369, 1995.
Wallace, "Understanding Cytochrome c Function: Engineering Protein Structure by Semisynthesis," *The FASEB Journal* 7:505–515, 1993.

* cited by examiner

*Primary Examiner*—Rebecca E. Prouty
*Assistant Examiner*—Malgorzata A. Walicka
(74) *Attorney, Agent, or Firm*—Carol Nottenburg

(57) ABSTRACT

Nucleic acid molecules encoding vertebrate telomerase are provided. Gene products, expression vectors and host cells suitable for expressing telomerase are also provided. Methods for identifying inhibitors of telomerase activity and inhibitor compositions are disclosed.

30 Claims, 72 Drawing Sheets

```
ATGCCGCGCGCTCCCCGCTGCCGAGCCGTGCGCTCCCTGCTGCGCAGCCACTACCGCGAG    60
MetProArgAlaProArgCysArgAlaValArgSerLeuLeuArgSerHisTyrArgGlu    20

GTGCTGCCGCTGGCCACGTTCGTGCGGCGCCTGGGGCCCCAGGGCTGGCGGCTGGTGCAG   120
ValLeuProLeuAlaThrPheValArgArgLeuGlyProGlnGlyTrpArgLeuValGln    40

CGCGGGGACCCGGCGGCTTTCCGCGCGCTGGTGGCCCAGTGCCTGGTGTGCGTGCCCTGG   180
ArgGlyAspProAlaAlaPheArgAlaLeuValAlaGlnCysLeuValCysValProTrp    60

GACGCACGGCCGCCCCCCGCCGCCCCCTCCTTCCGCCAGGTGTCCTGCCTGAAGGAGCTG   240
AspAlaArgProProProAlaAlaProSerPheArgGlnValSerCysLeuLysGluLeu    80

GTGGCCCGAGTGCTGCAGAGGCTGTGCGAGCGCGGCGCGAAGAACGTGCTGGCCTTCGGC   300
ValAlaArgValLeuGlnArgLeuCysGluArgGlyAlaLysAsnValLeuAlaPheGly   100

TTCGCGCTGCTGGACGGGGCCCGCGGGGGCCCCCCCGAGGCCTTCACCACCAGCGTGCGC   360
PheAlaLeuLeuAspGlyAlaArgGlyGlyProProGluAlaPheThrThrSerValArg   120

AGCTACCTGCCCAACACGGTGACCGACGCACTGCGGGGGAGCGGGGCGTGGGGGCTGCTG   420
SerTyrLeuProAsnThrValThrAspAlaLeuArgGlySerGlyAlaTrpGlyLeuLeu   140

TTGCGCCGCGTGGGCGACGACGTGCTGGTTCACCTGCTGGCACGCTGCGCGCTCTTTGTG   480
LeuArgArgValGlyAspAspValLeuValHisLeuLeuAlaArgCysAlaLeuPheVal   160

CTGGTGGCTCCCAGCTGCGCCTACCAGGTGTGCGGGCCGCCGCTGTACCAGCTCGGCGCT   540
LeuValAlaProSerCysAlaTyrGlnValCysGlyProProLeuTyrGlnLeuGlyAla   180

GCCACTCAGGCCCGGCCCCCGCCACACGCTAGTGGACCCCGAAGGCGTCTGGGATGCGAA   600
AlaThrGlnAlaArgProProProHisAlaSerGlyProArgArgArgLeuGlyCysGlu   200

CGGGCCTGGAACCATAGCGTCAGGGAGGCCGGGGTCCCCCTGGGCCTGCCAGCCCCGGGT   660
ArgAlaTrpAsnHisSerValArgGluAlaGlyValProLeuGlyLeuProAlaProGly   220

GCGAGGAGGCGCGGGGGCAGTGCCAGCCGAAGTCTGCCGTTGCCCAAGAGGCCCAGGCGT   720
AlaArgArgArgGlyGlySerAlaSerArgSerLeuProLeuProLysArgProArgArg   240
```

*Fig. 1A*

```
GGCGCTGCCCCTGAGCCGGAGCGGACGCCCGTTGGGCAGGGGTCCTGGGCCCACCCGGGC       780
GlyAlaAlaProGluProGluArgThrProValGlyGlnGlySerTrpAlaHisProGly       260

AGGACGCGTGGACCGAGTGACCGTGGTTTCTGTGTGGTGTCACCTGCCAGACCCGCCGAA       840
ArgThrArgGlyProSerAspArgGlyPheCysValValSerProAlaArgProAlaGlu       280

GAAGCCACCTCTTTGGAGGGTGCGCTCTCTGGCACGCGCCACTCCCACCCATCCGTGGGC       900
GluAlaThrSerLeuGluGlyAlaLeuSerGlyThrArgHisSerHisProSerValGly       300

CGCCAGCACCACGCGGGCCCCCCATCCACATCGCGGCCACCACGTCCCTGGGACACGCCT       960
ArgGlnHisHisAlaGlyProProSerThrSerArgProProArgProTrpAspThrPro       320

TGTCCCCCGGTGTACGCCGAGACCAAGCACTTCCTCTACTCCTCAGGCGACAAGGAGCAG      1020
CysProProValTyrAlaGluThrLysHisPheLeuTyrSerSerGlyAspLysGluGln       340

CTGCGGCCCTCCTTCCTACTCAGCTCTCTGAGGCCCAGCCTGACTGGCGCTCGGAGGCTC      1080
LeuArgProSerPheLeuLeuSerSerLeuArgProSerLeuThrGlyAlaArgArgLeu       360

GTGGAGACCATCTTTCTGGGTTCCAGGCCCTGGATGCCAGGGACTCCCCGCAGGTTGCCC      1140
ValGluThrIlePheLeuGlySerArgProTrpMetProGlyThrProArgArgLeuPro       380

CGCCTGCCCCAGCGCTACTGGCAAATGCGGCCCCTGTTTCTGGAGCTGCTTGGGAACCAC      1200
ArgLeuProGlnArgTyrTrpGlnMetArgProLeuPheLeuGluLeuLeuGlyAsnHis       400

GCGCAGTGCCCCTACGGGGTGCTCCTCAAGACGCACTGCCCGCTGCGAGCTGCGGTCACC      1260
AlaGlnCysProTyrGlyValLeuLeuLysThrHisCysProLeuArgAlaAlaValThr       420

CCAGCAGCCGGTGTCTGTGCCCGGGAGAAGCCCCAGGGCTCTGTGGCGGCCCCCGAGGAG      1320
ProAlaAlaGlyValCysAlaArgGluLysProGlnGlySerValAlaAlaProGluGlu       440

GAGGACACAGACCCCCGTCGCCTGGTGCAGCTGCTCCGCCAGCACAGCAGCCCCTGGCAG      1380
GluAspThrAspProArgArgLeuValGlnLeuLeuArgGlnHisSerSerProTrpGln       460

GTGTACGGCTTCGTGCGGGCCTGCCTGCGCCGGCTGGTGCCCCCAGGCCTCTGGGGCTCC      1440
ValTyrGlyPheValArgAlaCysLeuArgArgLeuValProProGlyLeuTrpGlySer       480

AGGCACAACGAACGCCGCTTCCTCAGGAACACCAAGAAGTTCATCTCCCTGGGGAAGCAT      1500
ArgHisAsnGluArgArgPheLeuArgAsnThrLysLysPheIleSerLeuGlyLysHis       500
```

*Fig. 1B*

```
GCCAAGCTCTCGCTGCAGGAGCTGACGTGGAAGATGAGCGTGCGGGGCTGCGCTTGGCTG    1560
AlaLysLeuSerLeuGlnGluLeuThrTrpLysMetSerValArgAspCysAlaTrpLeu     520

CGCAGGAGCCCAGGGGTTGGCTGTGTTCCGGCCGCAGAGCACCGTCTGCGTGAGGAGATC    1620
ArgArgSerProGlyValGlyCysValProAlaAlaGluHisArgLeuArgGluGluIle     540

CTGGCCAAGTTCCTGCACTGGCTGATGAGTGTGTACGTCGTCGAGCTGCTCAGGTCTTTC    1680
LeuAlaLysPheLeuHisTrpLeuMetSerValTyrValValGluLeuLeuArgSerPhe     560

TTTTATGTCACGGAGACCACGTTTCAAAAGAACAGGCTCTTTTTCTACCGGAAGAGTGTC    1740
PheTyrValThrGluThrThrPheGlnLysAsnArgLeuPhePheTyrArgLysSerVal     580

TGGAGCAAGTTGCAAAGCATTGGAATCAGACAGCACTTGAAGAGGGTGCAGCTGCGGGAG    1800
TrpSerLysLeuGlnSerIleGlyIleArgGlnHisLeuLysArgValGlnLeuArgGlu     600

CTGTCGGAAGCAGAGGTCAGGCAGCATCGGGAAGCCAGGCCCGCCCTGCTGACGTCCAGA    1860
LeuSerGluAlaGluValArgGlnHisArgGluAlaArgProAlaLeuLeuThrSerArg     620

CTCCGCTTCATCCCCAAGCCTGACGGGCTGCGGCCCGATTGTGAACATGGACTACGTCGTG    1920
LeuArgPheIleProLysProAspGlyLeuArgProIleValAsnMetAspTyrValVal     640

GGAGCCAGAACGTTCCGCAGAGAAAAGAGGGCCGAGCGTCTCACCTCGAGGGTGAAGGCA    1980
GlyAlaArgThrPheArgArgGluLysArgAlaGluArgLeuThrSerArgValLysAla     660

CTGTTCAGCGTGCTCAACTACGAGCGGGCGCGGCGCCCCGGCCTCCTGGGCGCCTCTGTG    2040
LeuPheSerValLeuAsnTyrGluArgAlaArgArgProGlyLeuLeuGlyAlaSerVal     680

CTGGGCCTGGACGATATCCACAGGGCCTGGCGCACCTTCGTGCTGCGTGTGCGGGCCCAG    2100
LeuGlyLeuAspAspIleHisArgAlaTrpArgThrPheValLeuArgValArgAlaGln    700

GACCCGCCGCCTGAGCTGTACTTTGTCAAGGTGGATGTGACGGGCGCGTACGACACCATC    2160
AspProProProGluLeuTyrPheValLysValAspValThrGlyAlaTyrAspThrIle     720

CCCCAGGACAGGCTCACGGAGGTCATCGCCAGCATCATCAAACCCCAGAACACGTACTGC    2220
ProGlnAspArgLeuThrGluValIleAlaSerIleIleLysProGlnAsnThrTyrCys     740

GTGCGTCGGTATGCCGTGGTCCAGAAGGCCGCCCATGGGCACGTCCGCAAGGCCTTCAAG    2280
ValArgArgTyrAlaValValGlnLysAlaAlaHisGlyHisValArgLysAlaPheLys    760
```

*Fig. 1C*

```
AGCCACGTCTCTACCTTGACAGACCTCCAGCCGTACATGCGACAGTTCGTGGCTCACCTG      2340
SerHisValSerThrLeuThrAspLeuGlnProTyrMetArgGlnPheValAlaHisLeu        780

CAGGAGACCAGCCCGCTGAGGGATGCCGTCGTCATCGAGCAGAGCTCCTCCCTGAATGAG      2400
GlnGluThrSerProLeuArgAspAlaValValIleGlnSerSerSerLeuAsnGlu           800

GCCAGCAGTGGCCTCTTCGACGTCTTCCTACGCTTCATGTGCCACCACGCCGTGCGCATC      2460
AlaSerSerGlyLeuPheAspValPheLeuArgPheMetCysHisHisAlaValArgIle        820

AGGGGCAAGTCCTACGTCCAGTGCCAGGGGATCCCGCAGGGCTCCATCCTCTCCACGCTG      2520
ArgGlyLysSerTyrValGlnCysGlnGlyIleProGlnGlySerIleLeuSerThrLeu        840

CTCTGCAGCCTGTGCTACGGCGACATGGAGAACAAGCTGTTTGCGGGGATTCGGCGGGAC      2580
LeuCysSerLeuCysTyrGlyAspMetGluAsnLysLeuPheAlaGlyIleArgArgAsp        860

GGGCTGCTCCTGCGTTTGGTGGATGATTTCTTGTTGGTGACACCTCACCTCACCCACGCG      2640
GlyLeuLeuLeuArgLeuValAspAspPheLeuLeuValThrProHisLeuThrHisAla        880

AAAACCTTCCTCAGGACCCTGGTCCGAGGTGTCCCTGAGTATGGCTGCGTGGTGAACTTG      2700
LysThrPheLeuArgThrLeuValArgGlyValProGluTyrGlyCysValValAsnLeu        900

CGGAAGACAGTGGTGAACTTCCCTGTAGAAGACGAGGCCCTGGGTGGCACGGCTTTTGTT      2760
ArgLysThrValValAsnPheProValGluAspGluAlaLeuGlyGlyThrAlaPheVal        920

CAGATGCCGGCCCACGGCCTATTCCCCTGGTGCGGCCTGCTGCTGGATACCCGGACCCTG      2820
GlnMetProAlaHisGlyLeuPheProTrpCysGlyLeuLeuLeuAspThrArgThrLeu        940

GAGGTGCAGAGCGACTACTCCAGCTATGCCCGGACCTCCATCAGAGCCAGTCTCACCTTC      2880
GluValGlnSerAspTyrSerSerTyrAlaArgThrSerIleArgAlaSerLeuThrPhe        960

AACCGCGGCTTCAAGGCTGGGAGGAACATGCGTCGCAAACTCTTTGGGGTCTTGCGGCTG      2940
AsnArgGlyPheLysAlaGlyArgAsnMetArgArgLysLeuPheGlyValLeuArgLeu        980

AAGTGTCACAGCCTGTTTCTGGATTTGCAGGTGAACAGCCTCCAGACGGTGTGCACCAAC      3000
LysCysHisSerLeuPheLeuAspLeuGlnValAsnSerLeuGlnThrValCysThrAsn      1000

ATCTACAAGATCCTCCTGCTGCAGGCGTACAGGTTTCACGCATGTGTGCTGCAGCTCCCA      3060
IleTyrLysIleLeuLeuLeuGlnAlaTyrArgPheHisAlaCysValLeuGlnLeuPro      1020
```

*Fig. 1D*

```
TTTCATCAGCAAGTTTGGAAGAACCCCACATTTTTCCTGCGCGTCATCTCTGACACGGCC      3120
PheHisGlnGlnValTrpLysAsnProThrPhePheLeuArgValIleSerAspThrAla      1040

TCCCTCTGCTACTCCATCCTGAAAGCCAAGAACGCAGGGATGTCGCTGGGGGCCAAGGGC      3180
SerLeuCysTyrSerIleLeuLysAlaLysAsnAlaGlyMetSerLeuGlyAlaLysGly      1060

GCCGCCGGCCCTCTGCCCTCCGAGGCCGTGCAGTGGCTGTGCCACCAAGCATTCCTGCTC      3240
AlaAlaGlyProLeuProSerGluAlaValGlnTrpLeuCysHisGlnAlaPheLeuLeu      1080

AAGCTGACTCGACACCGTGTCACCTACGTGCCACTCCTGGGGTCACTCAGGACAGCCCAG      3300
LysLeuThrArgHisArgValThrTyrValProLeuLeuGlySerLeuArgThrAlaGln      1100

ACGCAGCTGAGTCGGAAGCTCCCGGGGACGACGCTGACTGCCCTGGAGGCCGCAGCCAAC      3360
ThrGlnLeuSerArgLysLeuProGlyThrThrLeuThrAlaLeuGluAlaAlaAlaAsn      1120

CCGGCACTGCCCTCAGACTTCAAGACCATCCTGGACtgatggccacccgcccacagccag      3420
ProAlaLeuProSerAspPheLysThrIleLeuAsp                             1132

Gccgagagcagacaccagcagccctgtcacgccgggctctacgtcccagggagggagggg     3480
Cggcccacacccaggcccgcaccgctgggagtctgaggcctgagtgagtgtttggccgag    3540
gcctgcatgtccggctgaaggctgagtgtccggctgaggcctgagcgagtgtccagccaa    3600
gggctgagtgtccagcacacctgccgtcttcacttccccacaggctggcgctcggctcca    3660
ccccagggccagcttttcctcaccaggagcccggcttccactccccacataggaatagtc    3720
catccccagattcgccattgttcacccctcgccctgccctcctttgccttccaccccac     3780
catccaggtggagaccctgagaaggaccctgggagctctgggaatttggagtgaccaaag    3840
gtgtgccctgtacacaggcgaggaccctgcacctggatgggggtccctgtgggtcaaatt    3900
gggggaggtgctgtgggagtaaaatactgaatatatgagttttcagttttgaaaaaa      3960
aaaa                                                           3964
```

*Fig. 1E*

```
Euplotes    1   ---------------------MEVDVDNQADNHGIHSALKTCEEIKEAKTLYSWIQKVIRCR--NQSQSHYKDLEDIN
HT1         1   RRLGPQGWRLVQRGDPAAFRALVAQCLVCVPWDAR-PPPAAPSFRQVSCLKELVARVLQRLCERGAKNVLAFGFALLDGA
EST2        1   ------------------------------MKILFEFIQDKLDID--LQTNSTYKENLKCG Euplotes    56  IFAQTNIVATPRDYNEEDFKVIARK---------EVFSTGLMIELIDKCLVELLSSSDVSDRQKLQCFGFQLKGNC-LAN
HT1         80  RGGPPEAFTTSVRSYLPNTVTDALRGSGAWGLLLRRVGDDVLVHLLARCALFVLVAPSCAY---QVCGPPLYCLGAATQA
EST2        30  HFNGLDEILTT-CFALPNSRKIALP---------CLPGDLSHKAVIDHCIIYLLTGELYNN---VLTFGYKIARWEDVNN Euplotes    126 THLLTALSTQKQYFFQDEWNQVRAMIGNELFRHLYTKYLIFQRTSEGTLVQFCGNNVFDHLKVNDKFDKKQKGGAADMNE
HT1         157 RPPPHASGPRRRLGCERAWNHSVREAGVPLGLPAPGARRRGGSASRSLPLPKRPRRGAAPEPERTPVGQGSWAHPGRTRG
EST2        97  SLFCHSANVNVTLLKGAAWKMFHSLVGTYAFVDLLINYTVIQFNGQ-FFTQIVGNRCNEPHLPPKWVQRSSSS-------

Euplotes    206 PRCCSTCKYNVKNEKDHFLNNI---------------------------NVPNWNNMKSRTRIFYCTHFNRNNQFF
HT1         237 PSDRGFCVVSPARPAEEATSLEGALSGTRHSHPSVGRQHHAGPPSTSRPPRPWDTPCPPVYAETKHFLYSSGDK--EQLR
EST2        169 ----SATAAQIKQLTEPVTN-------------------------------------KQFLHKLNIN-SSSFF Euplotes    255 KKHEFVSNKNNISAM-DRAQTIFTNI--------FRFNRIRKKLKDKVIEKIAYMLEKVKDFNFNYYLTKSCPLPENWRE
HT1         315 PSFLLSSLRPSLTGARRLVETIFLGSRPWMPGTPRRLPRLPQRY-WQMRPLFLELLGNHAQCPYGVLLKTHCPLRAAVTP
EST2        200 PYSKILPSSSSIKKLTDLREAIFP---------TNLVKIPQRLKVRINLTLQKLLKRHKRLNYVSILNSICPPLEGT--
                                                                              Telomerase domain
Euplotes    326 RK-----QKIENLINKTREEKS--KYYEELFSYTTDNKCVTQFINEFFYNILPKDFLTGR-NRKNFQKKVKKYVELNKHE
HT1         394 AAGVCAREKPQGSVAAPEEEDTDPRRLVQLLRQHSSPWQVYGFVRACLRRLVPPGLWGSRHNERRFLRNTKKFISLGKHA
EST2        268 ---------VLDLSHLSRQ--------------SPKERVLKFIIVILQKLLPQEMFGSKKNKGKIIKNLNLLLSLPLNG Euplotes    398 LIHKNLLLEKINTREISWMQVET-SAKHFYYFDHENIYVLWKLLRWIFEDLVVSLIRCFFYVTEQQKSYSKTYYYRKNIW
HT1         474 KLSLQELTWKMSVRDCAWLRRSPGVGCVPAAEHRLREEILAKFLHWLMSVYVVELLRSFFYVTETTFQKNRLFFYRKSVW
EST2        324 YLPFDSLLKKLRLKDFRWLFISD-IWFTKHNFENLN-QLAICFISWLFRQLIPKIIQTFFYCTEIS-STVTIVYFRHDTW
                                                                              Motif 1    Motif2
Euplotes    477 DVIMKMSIADLKK-ETLAEVQEKEVEEWKKSL-GFAPGKLRLIPKKTT--FRPIMTFNKKIVNSDRK--TTKLTTNTKLL
HT1         554 SKLQSIGIRQHLKRVQLRELSEAEVRQHREARPALLTSRLRFIPKPDG--LRPIVNMDYVVGARTFRREKRAERLTSRVK
EST2        401 NKLITPFIVEYFK-TYLVENNVCRNHNSYTLS-NFNHSKMRIIPKKSNNEFRIIAIPCRGADEEEFT--IYKENHKNAIQ
```

*Fig. 2A*

```
                                                                    Motif A
Euplotes  551 NSHLMLKTLKN-RMFKDPFGFAVFNYDDVMKKYEEFVCKWKQVGQP-KLFFATMDIEKCYDSVNREKLSTFLKTTKLLSS
HT1       632 ALFSVLNYERARR--PGLLGASVLGLDDIHRAWRTFVLRVRAQDPPPELYFVKVDVTGAYDTIPQDRLTEVIASIIKPQN
EST2      477 PTQKILEYLRNKRPTSFTKIYSPTQIADRIKEFKQRLLKKFNNVLP-ELYFMKFDVKSCYDSIPRMECMRILKDALKNEN Euplotes  629 DFWIMTAQILKRKWNIVIDSKNFRKKEMKDYFRQKFQKIALEGGQYPTLFSVLENEQNDLNAKKTLIVEAK-CRNYFKKD
HT1       710 TYCVRRYAVVQKAAHGHVRKAFKSHVS------------TLTDLQPYMRQFVAHLQETSPLRDAVVIEQSSSLNEASSG
EST2      556 GFFVRSQYFFN-TNTGVLKLFNVVN--------------A--SRVPKPYELYIDNVRTVHLSNQDVINVV-EMEIFKT-
                      Motif B                                            Motif C
Euplotes  708 NLLQPVINICQYNYINFNGKFYKQTKGIPQGLCVSSILSSFYYATLEESSLGFLRDESMNPENPNVNLLMRLTDDYLLIT
HT1       777 LFDVFLRFMCHHAVRIR-GKSYVQCQGIPQGSILSTLLCSLCYGDMEN---KLFAGIRRD------GLLLRLVDDFLLVT
EST2      616 --ALWVEDKCYIR----------EDGLFQGSSLSAPIVDLVYDDLEFYSEFKASPSQD------TLILKLADDFLIIS
                      Motif D                           Motif E
Euplotes  788 TQENNAVLFIEKLINVSRENGFKFNMKKLQTSFPLSPSKFAKYGMDSVEEQNIVQDYCDWIGISIDMKTLALMPNINLRI
HT1       847 PHLTHAKTFLRTLVRGVPEYGCVVNLRKTVVNFPVEDEALGG-TAFVQMPAHGLFPWCGLLLDTRTLEVQSDYSSYAR--
EST2      677 TDQQ-QVINIKKLAMG----GFQKYNAKANRDKILAVS--------SQSDDDTVIQFCAMHIFVKELEVWKHSSTMW---

Euplotes  868 EGILCTLNLNMQTKKASMWLKKKLKSFLMNNITHYFRKTITTTEDFANKTLNKLFISGGYKYMQCAKEY--KDHFKKNLAM
HT1       924 TSIRASLTFNRGFKAGRNMRRKLFGVLRLKCHSLFLDLQVNSLQTVCTNIYKILLLQAYRFHACVLQLPFHQQVWKNPTF
EST2      741 -------NFHIRSKSS----KGIFRSLIALFNTRISYKTIDTNLNSTNTVLMQIDHVVKNISECYKSA--FKDLSINVTQ Euplotes  946 SSMIDLEVSKIIYSVTRAFFKYLVCNIKDTIFGEEHYPDFFLSTLKHFIEIFSTKKYIFNRVCMILKAKEAKLKSDQCQS
HT1       1004 FLRVISDTASLCYSILKAKNAGMSLGAKGAAGPLPSEAVQWLC-HQAFLLKLTRHRVTYVPLLGSLRTAQTQLSRKLPGT
EST2      808 NMQFHSFLQRIIEMTVSG----CPITKCDPLIEYEVR--FTI--LNGFLESLSSNTSKF-KDNIILLRKEIQHLQAYIYI Euplotes  1026 LIQYDA---------------
HT1       1083 TLTALEAAANPALPSDFKTILD
EST2      879 YIHIVN---------------
```

*Fig. 2B*

| Variants: | 1 | α | β | 2 | 3 |
|---|---|---|---|---|---|
| RT-PCR product | NO | + | + | NO | + & - |
| PCR from LIM1215 lib. | - | + | - | + | NO |
| RT-PCR product | NO | - | + | NO | + |
| 53.2 cDNA | - | - | - | - | NO |

```
          222                                              223
Y    5'-CCAGGTG|ggcctc                                gcaggtg|TCCTGCC-3'

1950                                             1952
1    5'-AAAGAGG|GTGGCTG.........................AACAGAA|GCCGAGC-3'

2130                                             2167
a    5'-TGTCAAG|gtggatg.........................cccccag|GACAGGC-3'

2286                                             2468
b    5'-GAGCCAC|gtctcta.........................ggggcaa|GTCCTAC-3'

2843                                             2844
2    5'-ACTCCAG|GTGAGCG.........................XXXXXXX|CTATGCC-3'

3157
3    5'-AACGCAG|CCGAAGAAAACATTTCTGTCGTGACTCCTGCGGTGCTTGGGTCGGGACAGCCAGAGATGG
            T  A  A   E  E  N  I  L  V  V  T  P  A  V  L  G  S  G  Q  P  E  M  E

AGCCACCCCGCAGACCGTCGGGTGTGGGCAGCTTTCCGGTGTCTCCTGGGAGGGGAGTTG
          P  P  R  R  P  S  G  V  G  S  F  P  V  S  P  G  R  G  V  G

3158
         GGCTGGGCCTGTGACTCCTCAGCCTCTGTTTTCCCCCAG|GGATGTC-3'
          L  G  L  *
```

Fig. 7C sequence "Y" 104-105 bases
GGCCTCCCCGGGGTCGGCGTCCGGCTGGGGTTGAGGGCGGCCGGGGGGAACCAG
GlyLeuProGlyValGlyValArgLeuGlyLeuArgAlaAlaGlyGlyAsnGln
 AlaSerProGlySerAlaSerGlyTrpGly * GlyArgProGlyGlyThrSer
  ProProArgGlyArgArgProAlaGlyValGluGlyGlyArgGlyGluProAla CGACATGCGGAGAGCAGCGCAGGCGACTCAGGGCGCTTCCCCCGCAGGTG
ArgHisAlaGluSerSerAlaGlyAspSerGlyArgPheProArgArg
 AspMetArgArgAlaAlaGlnAlaThrGlnGlyAlaSerProAlaGly
  ThrCysGlyGluGlnArgArgArgLeuArgAlaLeuProProGlnVal sequence "1" 38 bases
GTGGCTGTGCTTTGGTTTAACTTCCTTTTTAACCAGAA
ValAlaValLeuTrpPheAsnPheLeuPheAsnGlnLys sequence "α" 36 bases
GTGGATGTGACGGGCGCGTACGACACCATCCCCCAG
ValAspValThrGlyAlaTyrAspThrIleProGln sequence "β" 182 bases
GTCTCTACCTTGACAGACCTCCAGCCGTACATGCGACAGTTCGTGGCTCACCTG
ValSerThrLeuThrAspLeuGlnProTyrMetArgGlnPheValAlaHisLeu CAGGAGACCAGCCCGCTGAGGGATGCCGTCGTCATCGAGCAGAGCTCCTCCCTG
GlnGluThrSerProLeuArgAspAlaValValIleGluGlnSerSerSerLeu AATGAGGCCAGCAGTGGCCTCTTCGACGTCTTCCTACGCTTCATGTGCCACCAC
AsnGluAlaSerSerGlyLeuPheAspValPheLeuArgPheMetCysHisHis GCCGTGCGCATCAGGGGCAA
AlaValArgIleArgGlyLys partial sequence "2" unknown length
GTGAGCGCACCTGGCCGGAAGTGGAGCCTGTGCCCGGCTGGGGCAGGTGCTGCTGCAG
 Ter GGCCGTTGCGTCCACCTCTGCTTCCGTGTGGGGCAGGCGACTGCCAATCCCAAAGGGT
CAGATGCCACAGGGTGCCCCTCGTCCCATCTGGGGCTGAGCACAAATGCATCTTTCTG
TGGGAGTGAGGGTGCCTCACAACGGGAGCAGTTTTCTGTGCTATTTTGGTAA...

*Fig. 10A* sequence "3" 159 bases
CCGAAGAAAACATTTCTGTCGTGACTCCTGCGGTGCTTGGGTCGGGACAGCCAGAG
AlaGluGluAsnIleSerValValThrProAlaValLeuGlySerGlyGlnProGlu ATGGAGCCACCCCGCAGACCGTCGGGTGTGGGCAGCTTTCCGGTGTCTCCTGGGAGG
MetGluProProArgArgProSerGlyValGlySerPheProValSerProGlyArg GGAGTTGGGCTGGGCCTGTGACTCCTCAGCCTCTGTTTTCCCCCAG
GlyValGlyLeuGlyLeu * sequence "X" unknown length
...GACAGTCACCAGGGGGGTTGACCGCCGGACTGGGCGTCCCCAGGGTTGACTATAGGA
CCAGGTGTCCAGGTGCCCTGCAAGTAGAGGGGCTCTCAGAGGCGTCTGGCTGGCATGG
GTGGACGTGGCCCCGGGCATGGCCTTCTGCGTGTGCTGCCGTGGGTGCCCTGAGCCCT
CACTGAGTCGGTGGGGGCTTGTGGCTTCCCGTGAGCTTCCCCCTAGTCTGTTGTCTGG
CTGAGCAAGCCTCCTGAGGGGCTCTCTATTG partial sequence of genomic intron (approximately 2.7 kb)
GTGGCTGTGCTTTGGTTTAACTTCCTTTTTAACCAGAAGTGCGTTTGAGCCCCACATT
TGGTATCAGCTTAGATGAAGGGCCCGGAGGAGGGGCCACGGGACACAGCCAGGGCCAT
GGCACGGCGCCCACCCATTTGTGCGCACAGTGAGGTGGCCGAGGTGCCGGTGCCTCCA
GAAAAGCAGCGTGGGGGTGTAGGGGGAGCTCCTGGGGCAGGGAC....

*Fig. 10B*

Truncated telomerase

```
                                     ATGCCGCGCGCTCCCCGCTGCCGAGCCGTGCGCTCCCTGCTGCGCAGCCACTACCGCGAGGTGCTGCCGCTGGCCACGTTCGTG
                                     M  P  R  A  P  R  C  R  A  V  R  S  L  L  R  S  H  Y  R  E  V  L  P  L  A  T  F  V

CGGCGCCTGGGGCCCCAGGGCTGGCGGCTGGTGCAGCGCGGGGACCCGGCGGCTTTCCGCGCGCTGGTGGCCCAGTGCCTGGTGTGCGTGCCCTGGGACGCACGGCCGCCCCCGCCGC
R  R  L  G  P  Q  G  W  R  L  V  Q  R  G  D  P  A  A  F  R  A  L  V  A  Q  C  L  V  C  V  P  W  D  A  R  P  P  P  A  A

CCCCTCCTTCCGCCAGGTGTCCTGCCTGAAGGAGCTGGTGGCCCGAGTGCTGCAGAGGCTGTGCGAGCGCGGCGCGAAGAACGTGCTGGCCTTCGGCTTCGCGCTGCTGGACGGGGCCCG
P  S  F  R  Q  V  S  C  L  K  E  L  V  A  R  V  L  Q  R  L  C  E  R  G  A  K  N  V  L  A  F  G  F  A  L  L  D  G  A  R

CGGGGGCCCCCCCGAGGCCTTCACCACCAGCGTGCGCAGCTACCTGCCCAACACGGTGACCGACGCACTGCGGGGGAGCGGGGCGTGGGGGCTGCTGCTGCGCCGCGTGGGCGACGACGT
G  G  P  P  E  A  F  T  T  S  V  R  S  Y  L  P  N  T  V  T  D  A  L  R  G  S  G  A  W  G  L  L  L  R  R  V  G  D  D  V

GCTGGTTCACCTGCTGGCACGCTGCGCGCTCTTTGTGCTGGTGGCTCCCAGCTGCGCCTACCAGGTGTGCGGGCCGCCGCTGTACCAGCTCGGCGCTGCCACTCAGGCCCGGCCCCCGCC
L  V  H  L  L  A  R  C  A  L  F  V  L  V  A  P  S  C  A  Y  Q  V  C  G  P  P  L  Y  Q  L  G  A  A  T  Q  A  R  P  P  P

ACACGCTAGTGGACCCCGAAGGCGTCTGGGATGCGAACGGGCCTGGAACCATAGCGTCAGGGAGGCCGGGGTCCCCCTGGGCCTGCCAGCCCCGGGTGCGAGGAGGCGCGGGGGCAGTGC
H  A  S  G  P  R  R  R  L  G  C  E  R  A  W  N  H  S  V  R  E  A  G  V  P  L  G  L  P  A  P  G  A  R  R  R  G  G  S  A

CAGCCGAAGTCTGCCGTTGCCCAAGAGGCCCAGGCGTGGCGCTGCCCCTGAGCCGGAGCGGACGCCCGTTGGGCAGGGGTCCTGGGCCCACCCGGGCAGGACGCGTGGACCGAGTGACCG
S  R  S  L  P  L  P  K  R  P  R  R  G  A  A  P  E  P  E  R  T  P  V  G  Q  G  S  W  A  H  P  G  R  T  R  G  P  S  D  R

TGGTTTCTGTGTGGTGTCACCTGCCAGACCCGCCGAAGAAGCCACCTCTTTGGAGGGTGCGCTCTCTGGCACGCGCCACTCCCACCCATCCGTGGGCCGCCAGCACCACGCGGCCCCCC
G  F  C  V  V  S  P  A  R  P  A  E  E  A  T  S  L  E  G  A  L  S  G  T  R  H  S  H  P  S  V  G  R  Q  H  H  A  G  P  P

ATCCACATCGCGGCCACCACGTCCCTGGGACACGCCTTGTCCCCCGGTGTACGCCGAGACCAAGCACTTCCTCTACTCCTCAGGCGACAAGGAGCAGCTGCGGCCCTCCTTCCTACTCAG
S  T  S  R  P  P  R  P  W  D  T  P  C  P  P  V  Y  A  E  T  K  H  F  L  Y  S  S  G  D  K  E  Q  L  R  P  S  F  L  L  S

CTCTCTGAGGCCCAGCCTGACTGGCGCTCGGAGGCTCGTGGAGACCATCTTTCTGGGTTCCAGGCCCTGGATGCCAGGGACTCCCCGCAGGTTGCCCCGCCTGCCCCAGCGCTACTGGCA
S  L  R  P  S  L  T  G  A  R  R  L  V  E  T  I  F  L  G  S  R  P  W  M  P  G  T  P  R  R  L  P  R  L  P  Q  R  Y  W  Q

AATGCGGCCCCTGTTTCTGGAGCTGCTTGGGAACCACGCGCAGTGCCCCTACGGGGTGCTCCTCAAGACGCACTGCCCGCTGCGAGCTGCGGTCACCCCAGCAGCCGGTGTCTGTGCCCG
M  R  P  L  F  L  E  L  L  G  N  H  A  Q  C  P  Y  G  V  L  L  K  T  H  C  P  L  R  A  A  V  T  P  A  A  G  V  C  A  R

GGAGAAGCCCCAGGGCTCTGTGGCGGCCCCCGAGGAGGAGGACACAGACCCCCGTCGCCTGGTGCAGCTGCTCCGCCAGCACAGCAGCCCCTGGCAGGTGTACGGCTTCGTGCGGGCCTG
E  K  P  Q  G  S  V  A  A  P  E  E  E  D  T  D  P  R  R  L  V  Q  L  L  R  Q  H  S  S  P  W  Q  V  Y  G  F  V  R  A  C

CCTGCGCCGGCTGGTGCCCCCAGGCCTCTGGGGCTCCAGGCACAACGAACGCCGCTTCCTCAGGAACACCAAGAAGTTCATCTCCCTGGGGAAGCATGCCAAGCTCTCGCTGCAGGAGCT
L  R  R  L  V  P  P  G  L  W  G  S  R  H  N  E  R  R  F  L  R  N  T  K  K  F  I  S  L  G  K  H  A  K  L  S  L  Q  E  L

GACGTGGAAGATGAGCGTGCGGGACTGCGCTTGGCTGCGCAGGAGCCCAGGGGTTGGCTGTGTTCCGGCCGCAGAGCACCGTCTGCGTGAGGAGATCCTGGCCAAGTTCCTGCACTGGCT
T  W  K  M  S  V  R  D  C  A  W  L  R  R  S  P  G  V  G  C  V  P  A  A  E  H  R  L  R  E  E  I  L  A  K  F  L  H  W  L

GATGAGTGTGTACGTCGTCGAGCTGCTCAGGTCTTTCTTTTATGTCACGGAGACCACGTTTCAAAAGAACAGGCTCTTTTTCTACCGGAAGAGTGTCTGGAGCAAGTTGCAAAGCATTGG
M  S  V  Y  V  V  E  L  L  R  S  F  F  Y  V  T  E  T  T  F  Q  K  N  R  L  F  F  Y  R  K  S  V  W  S  K  L  Q  S  I  G

AAT--NNN--GACAGTCACCAGGGGGGTTGACCGCCGGACTGGGCGTCCCCAGGGTTGACTATAGGACCAGGTGTCCAGGTGCCCTGCAAGTAGAGGGGCTCTCAGAGGCGTCTGGCTGG
```

*Fig. 11A*

CATGGGTGGACGTGGCCCCGGGCATGGCCTTCTGCGTGTGCTGCCGTGGGTGCCCTGAGCCCTCACTGAGTCGGTGGGGGCTTGTGGCTTCCCGTGAGCTTCCCCCTAGTCTGTTGTCTG

GCTGAGCAAGCCTCCTGAGGGGCTCTCTATTG_

*Fig. 11B*

Truncated protein 1

```
                                        ATGCCGCGCGCTCCCCGCTGCCGAGCCGTGCGCTCCCTGCTGCGCAGCCACTACCGCGAGGTGCTGCCGCTGGCCACGTTCGTG
                                        M  P  R  A  P  R  C  R  A  V  R  S  L  L  R  S  H  Y  R  E  V  L  P  L  A  T  F  V

CGGCGCCTGGGGCCCCAGGGCTGGCGGCTGGTGCAGCGCGGGGACCCGGCGGCTTTCCGCGCGCTGGTGGCCCAGTGCCTGGTGTGCGTGCCCTGGGACGCACGGCCGCCCCCCGCCGC
R  R  L  G  P  Q  G  W  R  L  V  Q  R  G  D  P  A  A  F  R  A  L  V  A  Q  C  L  V  C  V  P  W  D  A  R  P  P  P  A  A

CCCCTCCTTCCGCCAGGTGTCCTGCCTGAAGGAGCTGGTGGCCCGAGTGCTGCAGAGGCTGTGCGAGCGCGGCGCGAAGAACGTGCTGGCCTTCGGCTTCGCGCTGCTGGACGGGGCCCG
P  S  F  R  Q  V  S  C  L  K  E  L  V  A  R  V  L  Q  R  L  C  E  R  G  A  K  N  V  L  A  F  G  F  A  L  L  D  G  A  R

CGGGGGCCCCCCCGAGGCCTTCACCACCAGCGTGCGCAGCTACCTGCCCAACACGGTGACCGACGCACTGCGGGGGAGCGGGGCGTGGGGGCTGCTGCTGCGCCGCGTGGGCGACGACGT
G  G  P  P  E  A  F  T  T  S  V  R  S  Y  L  P  N  T  V  T  D  A  L  R  G  S  G  A  W  G  L  L  L  R  R  V  G  D  D  V

GCTGGTTCACCTGCTGGCACGCTGCGCGCTCTTTGTGCTGGTGGCTCCCAGCTGCGCCTACCAGGTGCGGGCCGCCGCTGTACCAGCTCGGCGCTGCCACTCAGGCCCGGCCCCCGCC
L  V  H  L  L  A  R  C  A  L  F  V  L  V  A  P  S  C  A  Y  Q  V  C  G  P  P  L  Y  Q  L  G  A  A  T  Q  A  R  P  P  P

ACACGCTAGTGGACCCCGAAGGCGTCTGGGATGCGAACGGGCCTGGAACCATAGCGTCAGGGAGGCCGGGGTCCCCTGGGCCTGCCAGCCCCGGGTGCGAGGAGGCGCGGGGGCAGTGC
H  A  S  G  P  R  R  R  L  G  C  E  R  A  W  N  H  S  V  R  E  A  G  V  P  L  G  L  P  A  P  G  A  R  R  R  G  G  S  A

CAGCCGAAGTCTGCCGTTGCCCAAGAGGCCCAGGCGTGGCGCTGCCCCTGAGCCGGAGCGGACGCCCGTTGGGCAGGGGTCCTGGGCCCACCCGGGCAGGACGCGTGGACCGAGTGACCG
S  R  S  L  P  L  P  K  R  P  R  R  G  A  A  P  E  P  E  R  T  P  V  G  Q  G  S  W  A  H  P  G  R  T  R  G  P  S  D  R

TGGTTTCTGTGTGGTGTCACCTGCCAGACCCGCCGAAGAAGCCACCTCTTTGGAGGGTGCGCTCTCTGGCACGCGCCACTCCCACCCATCCGTGGGCCGCCAGCACCACGCGGGCCCCC
G  F  C  V  V  S  P  A  R  P  A  E  E  A  T  S  L  E  G  A  L  S  G  T  R  H  S  H  P  S  V  G  R  Q  H  H  A  G  P  P

ATCCACATCGCGGCCACCACGTCCCTGGGACACGCCTTGTCCCCCGGTGTACGCCGAGACCAAGCACTTCCTCTACTCCTCAGGCGACAAGGAGCAGCTGCGGCCCTCCTTCCTACTCAG
S  T  S  R  P  P  R  P  W  D  T  P  C  P  P  V  Y  A  E  T  K  H  F  L  Y  S  S  G  D  K  E  Q  L  R  P  S  F  L  L  S

CTCTCTGAGGCCCAGCCTGACTGGCGCTCGGAGGCTCGTGGAGACCATCTTTCTGGGTTCCAGGCCCTGGATGCCAGGGACTCCCCGCAGGTTGCCCCGCCTGCCCCAGCGCTACTGGCA
S  L  R  P  S  L  T  G  A  R  R  L  V  E  T  I  F  L  G  S  R  P  W  M  P  G  T  P  R  R  L  P  R  L  P  Q  R  Y  W  Q

AATGCGGCCCCTGTTTCTGGAGCTGCTTGGGAACCACGCGCAGTGCCCCTACGGGGTGCTCCTCAAGACGCACTGCCCGCTGCGAGCTGCGGTCACCCCAGCAGCCGGTGTCTGTGCCCG
M  R  P  L  F  L  E  L  L  G  N  H  A  Q  C  P  Y  G  V  L  L  K  T  H  C  P  L  R  A  A  V  T  P  A  A  G  V  C  A  R

GGAGAAGCCCCAGGGCTCTGTGGCGGCCCCCGAGGAGGAGGACACAGACCCCCGTCGCCTGGTGCAGCTGCTCCGCCAGCACAGCAGCCCCTGGCAGGTGTACGGCTTCGTGCGGGCCTG
E  K  P  Q  G  S  V  A  A  P  E  E  D  T  D  P  R  R  L  V  Q  L  L  R  Q  H  S  S  P  W  Q  V  Y  G  F  V  R  A  C

CCTGCGCCGGCTGGTGCCCCCAGGCCTCTGGGGCTCCAGGCACAACGAACGCCGCTTCCTCAGGAACACCAAGAAGTTCATCTCCCTGGGGAAGCATGCCAAGCTCTCGCTGCAGGAGCT
L  R  R  L  V  P  P  G  L  W  G  S  R  H  N  E  R  R  F  L  R  N  T  K  K  F  I  S  L  G  K  H  A  K  L  S  L  Q  E  L

GACGTGGAAGATGAGCGTGCGGGACTGCGCTTGGCTGCGCAGGAGCCCAGGGGTTGGCTGTGTTCCGGCCGCAGAGCACCGTCTGCGTGAGGAGATCCTGGCCAAGTTCCTGCACTGGCT
T  W  K  M  S  V  R  D  C  A  W  L  R  R  S  P  G  V  G  C  V  P  A  A  E  H  R  L  R  E  E  I  L  A  K  F  L  H  W  L

GATGAGTGTGTACGTCGTCGAGCTGCTCAGGTCTTTCTTTTATGTCACGGAGACCACGTTTCAAAAGAACAGGCTCTTTTTCTACCGGAAGAGTGTCTGGAGCAAGTTGCAAAGCATTGG
M  S  V  Y  V  V  E  L  L  R  S  F  F  Y  V  T  E  T  T  F  Q  K  N  R  L  F  F  Y  R  K  S  V  W  S  K  L  Q  S  I  G
```

*Fig. 11C*

```
AATCAGACAGCACTTGAAGAGGGTGCAGCTGCGGGAGCTGTCGGAAGCAGAGGTCAGGCAGCATCGGGAAGCCAGGCCCGCCCTGCTGACGTCCAGACTCCGCTTCATCCCCAAGCCTGA
 I  R  Q  H  L  K  R  V  Q  L  R  E  L  S  E  A  E  V  R  Q  H  R  E  A  R  P  A  L  L  T  S  R  L  R  F  I  P  K  P  D

GTGGCTGTGCTTTGGTTTAACTTCCTTTTTAACCAGAA
                                                     V  A  V  L  W  F  T  F  L  F  N  Q  K
                                                        |
CGGGCTGCGGCCGATTGTGAACATGGACTACGTCGTGGGAGCCAGAACGTTCCGCAGAGAAAAGAGGGCCCGAGCGTCTCACCTCGAGGGTGAAGGCACTGTTCAGCGTGCTCAACTACGA
 G  L  R  P  I  V  N  M  D  Y  V  V  G  A  R  T  F  R  R  E  K  R  P  S  Y  S  F  R  G  *
```

*Fig. 11D*

Truncated protein 2

```
                                                          ATGCCGCGCGCTCCCCGCTGCCGAGCCGTGCGCTCCCTGCTGCGCAGCCACTACCGCGAGGTGCTGCCGCTGGCCACGTTCGTG
                                                          M  P  R  A  P  R  C  R  A  V  R  S  L  L  R  S  H  Y  R  E  V  L  P  L  A  T  F  V

CGGCGCCTGGGGCCCCAGGGCTGGCGGCTGGTGCAGCGCGGGGACCCGGCGGCTTTCCGCGCGCTGGTGGCCCAGTGCCTGGTGTGCGTGCCCTGGGACGCACGGCCGCCCCCCGCCGC
R  R  L  G  P  Q  G  W  R  L  V  Q  R  G  D  P  A  A  F  R  A  L  V  A  Q  C  L  V  C  V  P  W  D  A  R  P  P  P  A  A

CCCCTCCTTCCGCCAGGTGTCCTGCCTGAAGGAGCTGGTGGCCCGAGTGCTGCAGAGGCTGTGCGAGCGCGGCGCGAAGAACGTGCTGGCCTTCGGCTTCGCGCTGCTGGACGGGGCCCG
P  S  F  R  Q  V  S  C  L  K  E  L  V  A  R  V  L  Q  R  L  C  E  R  G  A  K  N  V  L  A  F  G  F  A  L  L  D  G  A  R

CGGGGGCCCCCCGAGGCCTTCACCACCAGCGTGCGCAGCTACCTGCCCAACACGGTGACCGACGCACTGCGGGGGAGCGGGGCGTGGGGGCTGCTGCTGCGCCGCGTGGGCGACGACGT
G  G  P  P  E  A  F  T  T  S  V  R  S  Y  L  P  N  T  V  T  D  A  L  R  G  S  G  A  W  G  L  L  L  R  R  V  G  D  D  V

GCTGGTTCACCTGCTGGCACGCTGCGCGCTCTTTGTGCTGGTGGCTCCCAGCTGCGCCTACCAGGTGTGCGGGCCGCCGCTGTACCAGCTCGGCGCTGCCACTCAGGCCCGGCCCCCGCC
L  V  H  L  L  A  R  C  A  L  F  V  L  V  A  P  S  C  A  Y  Q  V  C  G  P  P  L  Y  Q  L  G  A  A  T  Q  A  R  P  P  P

ACACGCTAGTGGACCCCGAAGGCGTCTGGGATGCGAACGGGCCTGGAACCATAGCGTCAGGGAGGCCGGGGTCCCCCTGGGCCTGCCAGCCCCGGGTGCGAGGAGGCGCGGGGGCAGTGC
H  A  S  G  P  R  R  R  L  G  C  E  R  A  W  N  H  S  V  R  E  A  G  V  P  L  G  L  P  A  P  G  A  R  R  R  G  G  S  A

CAGCCGAAGTCTGCCGTTGCCCAAGAGGCCCAGGCGTGGCGCTGCCCCTGAGCCGGAGCGGACGCCCGTTGGGCAGGGGTCCTGGGCCCACCCGGGCAGGACGCGTGGACCGAGTGACCG
S  R  S  L  P  L  P  K  R  P  R  R  G  A  A  P  E  P  E  R  T  P  V  G  Q  G  S  W  A  H  P  G  R  T  R  G  P  S  D  R

TGGTTTCTGTGTGGTGTCACCTGCCAGACCCGCCGAAGAAGCCACCTCTTTGGAGGGTGCGCTCTCTGGCACGCGCCACTCCCACCCATCCGTGGGCCGCCAGCACCACGCGGGCCCCC
G  F  C  V  V  S  P  A  R  P  A  E  E  A  T  S  L  E  G  A  L  S  G  T  R  H  S  H  P  S  V  G  R  Q  H  H  A  G  P  P

ATCCACATCGCGGCCACCACGTCCCTGGGACACGCCTTGTCCCCGGTGTACGCCGAGACCAAGCACTTCCTCTACTCCTCAGGCGACAAGGAGCAGCTGCGGCCCTCCTTCCTACTCAG
S  T  S  R  P  P  R  P  W  D  T  P  C  P  P  V  Y  A  E  T  K  H  F  L  Y  S  S  G  D  K  E  Q  L  R  P  S  F  L  L  S

CTCTCTGAGGCCCAGCCTGACTGGCGCTCGGAGGCTCGTGGAGACCATCTTTCTGGGTTCCAGGCCCTGGATGCCAGGGACTCCCCGCAGGTTGCCCCGCCTGCCCCAGCGCTACTGGCA
S  L  R  P  S  L  T  G  A  R  R  L  V  E  T  I  F  L  G  S  R  P  W  M  P  G  T  P  R  R  L  P  R  L  P  Q  R  Y  W  Q

AATGCGGCCCCTGTTTCTGGAGCTGCTTGGGAACCACGCGCAGTGCCCCTACGGGGTGCTCCTCAAGACGCACTGCCCGCTGCGAGCTGCGGTCACCCCAGCAGCCGGTGTCTGTGCCCG
M  R  P  L  F  L  E  L  L  G  N  H  A  Q  C  P  Y  G  V  L  L  K  T  H  C  P  L  R  A  A  V  T  P  A  A  G  V  C  A  R

GGAGAAGCCCCAGGGCTCTGTGGCGGCCCCCGAGGAGGAGGACACAGACCCCGTCGCCTGGTGCAGCTGCTCCGCCAGCACAGCAGCCCCTGGCAGGTGTACGGCTTCGTGCGGGCCTG
E  K  P  Q  G  S  V  A  A  P  E  E  E  D  T  D  P  R  R  L  V  Q  L  L  R  Q  H  S  S  P  W  Q  V  Y  G  F  V  R  A  C

CCTGCGCCGGCTGGTGCCCCCAGGCCTCTGGGGCTCCAGGCACAACGAACGCCGCTTCCTCAGGAACACCAAGAAGTTCATCTCCCTGGGGAAGCATGCCAAGCTCTCGCTGCAGGAGCT
L  R  R  L  V  P  P  G  L  W  G  S  R  H  N  E  R  R  F  L  R  N  T  K  K  F  I  S  L  G  K  H  A  K  L  S  L  Q  E  L

GACGTGGAAGATGAGCGTGCGGGACTGCGCCTTGGCTGCGCAGGAGCCCAGGGGTTGGCTGTGTTCCGGCCCCAGAGCACCGTCTGCGTGAGGAGATCCTGGCCAAGTTCCTGCACTGGCT
T  W  K  M  S  V  R  D  C  A  W  L  R  R  S  P  G  V  G  C  V  P  A  A  E  H  R  L  R  E  E  I  L  A  K  F  L  H  W  L

GATGAGTGTGTACGTCGTCGAGCTGCTCAGGTCTTTCTTTTATGTCACGGAGACCACGTTTCAAAAGAACAGGCTCTTTTTCTACCGGAAGAGTGTCTGGAGCAAGTTGCAAAGCATTGG
M  S  V  Y  V  V  E  L  L  R  S  F  F  Y  V  T  E  T  T  F  Q  K  N  R  L  F  F  Y  R  K  S  V  W  S  K  L  Q  S  I  G
```

*Fig. 11E*

```
AATCAGACAGCACTTGAAGAGGGTGCAGCTGCGGGAGCTGTCGGAAGCAGAGGTCAGGCAGCATCGGGAAGCCAGGCCCGCCCTGCTGACGTCCAGACTCCGCTTCATCCCCAAGCCTGA
 I  R  Q  H  L  K  R  V  Q  L  R  E  L  S  E  A  E  V  R  Q  H  R  E  A  R  P  A  L  L  T  S  R  L  R  F  I  P  K  P  D

CGGGCTGCGGCCGATTGTGAACATGGACTACGTCGTGGGAGCCAGAACGTTCCGCAGAGAAAAGAGGGCCGAGCGTCTCACCTCGAGGGTGAAGGCACTGTTCAGCGTGCTCAACTACGA
 G  L  R  P  I  V  N  M  D  Y  V  V  G  A  R  T  F  R  R  E  K  R  A  E  R  L  T  S  R  V  K  A  L  F  S  V  L  N  Y  E

GCGGGCGCGGCGCCCCGGCCTCCTGGGCGCCTCTGTGCTGGGCCTGGACGATATCCACAGGGCCTGGCGCACCTTCGTGCTGCGTGTGCGGGCCCAGGACCCGCCGCCTGAGCTGTACTT
 R  A  R  R  P  G  L  L  G  A  S  V  L  G  L  D  D  I  H  R  A  W  R  T  F  V  L  R  V  R  A  Q  D  P  P  P  E  L  Y  F

TGTCAAGGTGGATGTGACGGGCGCGTACGACACCATCCCCCAGGACAGGCTCACGGAGGTCATCGCCAGCATCATCAAACCCCAGAACACGTACTGCGTGCGTCGGTATGCCGTGGTCCA
 V  K  V  D  V  T  G  A  Y  D  T  I  P  Q  D  R  L  T  E  V  I  A  S  I  I  K  P  Q  N  T  Y  C  V  R  R  Y  A  V  V  Q

GAAGGCCGCCCATGGGCACGTCCGCAAGGCCTTCAAGAGCCAC
 K  A  A  H  G  H  V  R  K  A  F  K  S  H

GTCCTACGTCCAGTG
                                                                                                        V  L  R  P  V

CCAGGGGATCCCGCAGGGCTCCATCCTCTCCACGCTGCTCTGCAGCCTGTGCTACGGCGACATGGAGAACAAGCTGTTTGCGGGGATTCGGCGGGACGGGCTGCTCCTGCGTTTGGTGGA
 P  G  D  P  A  G  L  H  P  L  H  A  A  L  Q  P  V  L  R  R  H  G  E  Q  A  V  C  G  D  S  A  G  R  A  A  P  A  F  G  G

TGATTTCTTGTTGGTGACACCTCACCTCACCCACGCGAAAACCTTCCTCAGGACCCTGGTCCGAGGTGTCCCTGAGTATGGCTGCGTGGTGAACTTGCGGAAGACAGTGGTGAACTTCCC
 *
```

*Fig. 11F*

Reference protein

| | |
|---|---|
| ATGCCGCGCGCTCCCCGCTGCCGAGCCGTGCGCTCCCTGCTGCGCAGCCACTACCGCGAG | 60 |
| MetProArgAlaProArgCysArgAlaValArgSerLeuLeuArgSerHisTyrArgGlu | 20 |
| | |
| GTGCTGCCGCTGGCCACGTTCGTGCGGCGCCTGGGGCCCCAGGGCTGGCGGCTGGTGCAG | 120 |
| ValLeuProLeuAlaThrPheValArgArgLeuGlyProGlnGlyTrpArgLeuValGln | 40 |
| | |
| CGCGGGGACCCGGCGGCTTTCCGCGCGCTGGTGGCCCAGTGCCTGGTGTGCGTGCCCTGG | 180 |
| ArgGlyAspProAlaAlaPheArgAlaLeuValAlaGlnCysLeuValCysValProTrp | 60 |
| | |
| GACGCACGGCCGCCCCCGCCGCCCCCTCCTTCCGCCAGGTGTCCTGCCTGAAGGAGCTG | 240 |
| AspAlaArgProProProAlaAlaProSerPheArgGlnValSerCysLeuLysGluLeu | 80 |
| | |
| GTGGCCCGAGTGCTGCAGAGGCTGTGCGAGCGCGGCGCGAAGAACGTGCTGGCCTTCGGC | 300 |
| ValAlaArgValLeuGlnArgLeuCysGluArgGlyAlaLysAsnValLeuAlaPheGly | 100 |
| | |
| TTCGCGCTGCTGGACGGGGCCCGCGGGGGCCCCCCCGAGGCCTTCACCACCAGCGTGCGC | 360 |
| PheAlaLeuLeuAspGlyAlaArgGlyGlyProProGluAlaPheThrThrSerValArg | 120 |
| | |
| AGCTACCTGCCCAACACGGTGACCGACGCACTGCGGGGGAGCGGGGCGTGGGGGCTGCTG | 420 |
| SerTyrLeuProAsnThrValThrAspAlaLeuArgGlySerGlyAlaTrpGlyLeuLeu | 140 |
| | |
| TTGCGCCGCGTGGGCGACGACGTGCTGGTTCACCTGCTGGCACGCTGCGCGCTCTTTGTG | 480 |
| LeuArgArgValGlyAspAspValLeuValHisLeuLeuAlaArgCysAlaLeuPheVal | 160 |
| | |
| CTGGTGGCTCCCAGCTGCGCCCTACCAGGTGTGCGGGCCGCCGCTGTACCAGCTCGGCGCT | 540 |
| LeuValAlaProSerCysAlaTyrGlnValCysGlyProProLeuTyrGlnLeuGlyAla | 180 |
| | |
| GCCACTCAGGCCCGGCCCCCGCCACACGCTAGTGGACCCCGAAGGCGTCTGGGATGCGAA | 600 |
| AlaThrGlnAlaArgProProProHisAlaSerGlyProArgArgArgLeuGlyCysGlu | 200 |
| | |
| CGGGCCTGGAACCATAGCGTCAGGGAGGCCGGGGTCCCCCTGGGCCTGCCAGCCCCGGGT | 660 |
| ArgAlaTrpAsnHisSerValArgGluAlaGlyValProLeuGlyLeuProAlaProGly | 220 |
| | |
| GCGAGGAGGCGCGGGGGCAGTGCCAGCCGAAGTCTGCCGTTGCCCAAGAGGCCCAGGCGT | 720 |
| AlaArgArgArgGlyGlySerAlaSerArgSerLeuProLeuProLysArgProArgArg | 240 |
| | |
| GGCGCTGCCCCTGAGCCGGAGCGGACGCCCGTTGGGCAGGGGTCCTGGGCCCACCCGGGC | 780 |
| GlyAlaAlaProGluProGluArgThrProValGlyGlnGlySerTrpAlaHisProGly | 260 |
| | |
| AGGACGCGTGGACCGAGTGACCGTGGTTTCTGTGTGGTGTCACCTGCCAGACCCGCCGAA | 840 |
| ArgThrArgGlyProSerAspArgGlyPheCysValValSerProAlaArgProAlaGlu | 280 |
| | |
| GAAGCCACCTCTTTGGAGGGTGCGCTCTCTGGCACGCGCCACTCCCACCCATCCGTGGGC | 900 |
| GluAlaThrSerLeuGluGlyAlaLeuSerGlyThrArgHisSerHisProSerValGly | 300 |

*Fig. 11G*

```
CGCCAGCACCACGCGGGCCCCCCATCCACATCGCGGCCACCACGTCCCTGGGACACGCCT      960
ArgGlnHisHisAlaGlyProProSerThrSerArgProProArgProTrpAspThrPro      320

TGTCCCCCGGTGTACGCCGAGACCAAGCACTTCCTCTACTCCTCAGGCGACAAGGAGCAG     1020
CysProProValTyrAlaGluThrLysHisPheLeuTyrSerSerGlyAspLysGluGln      340

CTGCGGCCCTCCTTCCTACTCAGCTCTCTGAGGCCCAGCCTGACTGGCGCTCGGAGGCTC     1080
LeuArgProSerPheLeuLeuSerSerLeuArgProSerLeuThrGlyAlaArgArgLeu      360

GTGGAGACCATCTTTCTGGGTTCCAGGCCCTGGATGCCAGGGACTCCCCGCAGGTTGCCC     1140
ValGluThrIlePheLeuGlySerArgProTrpMetProGlyThrProArgArgLeuPro      380

CGCCTGCCCCAGCGCTACTGGCAAATGCGGCCCCTGTTTCTGGAGCTGCTTGGGAACCAC     1200
ArgLeuProGlnArgTyrTrpGlnMetArgProLeuPheLeuGluLeuLeuGlyAsnHis      400

GCGCAGTGCCCCTACGGGGTGCTCCTCAAGACGCACTGCCCGCTGCGAGCTGCGGTCACC     1260
AlaGlnCysProTyrGlyValLeuLeuLysThrHisCysProLeuArgAlaAlaValThr      420

CCAGCAGCCGGTGTCTGTGCCCGGGAGAAGCCCCAGGGCTCTGTGGCGGCCCCCGAGGAG     1320
ProAlaAlaGlyValCysAlaArgGluLysProGlnGlySerValAlaAlaProGluGlu      440

GAGGACACAGACCCCCGTCGCCTGGTGCAGCTGCTCCGCCAGCACAGCAGCCCCTGGCAG     1380
GluAspThrAspProArgArgLeuValGlnLeuLeuArgGlnHisSerSerProTrpGln      460

GTGTACGGCTTCGTGCGGGCCTGCCTGCGCCGGCTGGTGCCCCCAGGCCTCTGGGGCTCC     1440
ValTyrGlyPheValArgAlaCysLeuArgArgLeuValProProGlyLeuTrpGlySer      480

AGGCACAACGAACGCCGCTTCCTCAGGAACACCAAGAAGTTCATCTCCCTGGGGAAGCAT     1500
ArgHisAsnGluArgArgPheLeuArgAsnThrLysLysPheIleSerLeuGlyLysHis      500

GCCAAGCTCTCGCTGCAGGAGCTGACGTGGAAGATGAGCGTGCGGGGCTGCGCTTGGCTG     1560
AlaLysLeuSerLeuGlnGluLeuThrTrpLysMetSerValArgAspCysAlaTrpLeu      520

CGCAGGAGCCCAGGGGTTGGCTGTGTTCCGGCCGCAGAGCACCGTCTGCGTGAGGAGATC     1620
ArgArgSerProGlyValGlyCysValProAlaAlaGluHisArgLeuArgGluGluIle      540

CTGGCCAAGTTCCTGCACTGGCTGATGAGTGTGTACGTCGTCGAGCTGCTCAGGTCTTTC     1680
LeuAlaLysPheLeuHisTrpLeuMetSerValTyrValValGluLeuLeuArgSerPhe      560

TTTTATGTCACGGAGACCACGTTTCAAAAGAACAGGCTCTTTTTCTACCGGAAGAGTGTC     1740
PheTyrValThrGluThrThrPheGlnLysAsnArgLeuPhePheTyrArgLysSerVal      580

TGGAGCAAGTTGCAAAGCATTGGAATCAGACAGCACTTGAAGAGGGTGCAGCTGCGGGAG     1800
TrpSerLysLeuGlnSerIleGlyIleArgGlnHisLeuLysArgValGlnLeuArgGlu      600

CTGTCGGAAGCAGAGGTCAGGCAGCATCGGGAAGCCAGGCCCGCCCTGCTGACGTCCAGA     1860
LeuSerGluAlaGluValArgGlnHisArgGluAlaArgProAlaLeuLeuThrSerArg      620
```

*Fig. 11H*

```
CTCCGCTTCATCCCCAAGCCTGACGGGCTGCGGCCGATTGTGAACATGGACTACGTCGTG        1920
LeuArgPheIleProLysProAspGlyLeuArgProIleValAsnMetAspTyrValVal         640

GGAGCCAGAACGTTCCGCAGAGAAAAGAGGGCCGAGCGTCTCACCTCGAGGGTGAAGGCA        1980
GlyAlaArgThrPheArgArgGluLysArgAlaGluArgLeuThrSerArgValLysAla         660

CTGTTCAGCGTGCTCAACTACGAGCGGGCGCGGCGCCCCGGCCTCCTGGGCGCCTCTGTG        2040
LeuPheSerValLeuAsnTyrGluArgAlaArgArgProGlyLeuLeuGlyAlaSerVal         680

CTGGGCCTGGACGATATCCACAGGGCCTGGCGCACCTTCGTGCTGCGTGTGCGGGCCCAG        2100
LeuGlyLeuAspAspIleHisArgAlaTrpArgThrPheValLeuArgValArgAlaGln         700

GACCCGCCGCCTGAGCTGTACTTTGTCAAGGTGGATGTGACGGGCGCGTACGACACCATC        2160
AspProProProGluLeuTyrPheValLysValAspValThrGlyAlaTyrAspThrIle         720

CCCCAGGACAGGCTCACGGAGGTCATCGCCAGCATCATCAAACCCCAGAACACGTACTGC        2220
ProGlnAspArgLeuThrGluValIleAlaSerIleIleLysProGlnAsnThrTyrCys         740

GTGCGTCGGTATGCCGTGGTCCAGAAGGCCGCCCATGGGCACGTCCGCAAGGCCTTCAAG        2280
ValArgArgTyrAlaValValGlnLysAlaAlaHisGlyHisValArgLysAlaPheLys         760

AGCCACGTCTCTACCTTGACAGACCTCCAGCCGTACATGCGACAGTTCGTGGCTCACCTG        2340
SerHisValSerThrLeuThrAspLeuGlnProTyrMetArgGlnPheValAlaHisLeu         780

CAGGAGACCAGCCCGCTGAGGGATGCCGTCGTCATCGAGCAGAGCTCCTCCCTGAATGAG        2400
GlnGluThrSerProLeuArgAspAlaValValIleGluGlnSerSerSerLeuAsnGlu         800

GCCAGCAGTGGCCTCTTCGACGTCTTCCTACGCTTCATGTGCCACCACGCCGTGCGCATC        2460
AlaSerSerGlyLeuPheAspValPheLeuArgPheMetCysHisHisAlaValArgIle         820

AGGGGCAAGTCCTACGTCCAGTGCCAGGGGATCCCGCAGGGCTCCATCCTCTCCACGCTG        2520
ArgGlyLysSerTyrValGlnCysGlnGlyIleProGlnGlySerIleLeuSerThrLeu         840

CTCTGCAGCCTGTGCTACGGCGACATGGAGAACAAGCTGTTTGCGGGGATTCGGCGGGAC        2580
LeuCysSerLeuCysTyrGlyAspMetGluAsnLysLeuPheAlaGlyIleArgArgAsp         860

GGGCTGCTCCTGCGTTTGGTGGATGATTTCTTGTTGGTGACACCTCACCTCACCCACGCG        2640
GlyLeuLeuLeuArgLeuValAspAspPheLeuLeuValThrProHisLeuThrHisAla         880

AAAACCTTCCTCAGGACCCTGGTCCGAGGTGTCCCTGAGTATGGCTGCGTGGTGAACTTG        2700
LysThrPheLeuArgThrLeuValArgGlyValProGluTyrGlyCysValValAsnLeu         900

CGGAAGACAGTGGTGAACTTCCCTGTAGAAGACGAGGCCCTGGGTGGCACGGCTTTTGTT        2760
ArgLysThrValValAsnPheProValGluAspGluAlaLeuGlyGlyThrAlaPheVal         920

CAGATGCCGGCCCACGGCCTATTCCCCTGGTGCGGCCTGCTGCTGGATACCCGGACCCTG        2820
GlnMetProAlaHisGlyLeuPheProTrpCysGlyLeuLeuLeuAspThrArgThrLeu         940
```

*Fig. 11I*

| | |
|---|---|
| GAGGTGCAGAGCGACTACTCCAGCTATGCCCGGACCTCCATCAGAGCCAGTCTCACCTTC | 2880 |
| GluValGlnSerAspTyrSerSerTyrAlaArgThrSerIleArgAlaSerLeuThrPhe | 960 |
| | |
| AACCGCGGCTTCAAGGCTGGGAGGAACATGCGTCGCAAACTCTTTGGGGTCTTGCGGCTG | 2940 |
| AsnArgGlyPheLysAlaGlyArgAsnMetArgArgLysLeuPheGlyValLeuArgLeu | 980 |
| | |
| AAGTGTCACAGCCTGTTTCTGGATTTGCAGGTGAACAGCCTCCAGACGGTGTGCACCAAC | 3000 |
| LysCysHisSerLeuPheLeuAspLeuGlnValAsnSerLeuGlnThrValCysThrAsn | 1000 |
| | |
| ATCTACAAGATCCTCCTGCTGCAGGCGTACAGGTTTCACGCATGTGTGCTGCAGCTCCCA | 3060 |
| IleTyrLysIleLeuLeuLeuGlnAlaTyrArgPheHisAlaCysValLeuGlnLeuPro | 1020 |
| | |
| TTTCATCAGCAAGTTTGGAAGAACCCCACATTTTTCCTGCGCGTCATCTCTGACACGGCC | 3120 |
| PheHisGlnGlnValTrpLysAsnProThrPhePheLeuArgValIleSerAspThrAls | 1040 |
| | |
| TCCCTCTGCTACTCCATCCTGAAAGCCAAGAACGCAGGGATGTCGCTGGGGGCCAAGGGC | 3180 |
| SerLeuCysTyrSerIleLeuLysAlaLysAsnAlaGlyMetSerLeuGlyAlaLysGly | 1060 |
| | |
| GCCGCCGGCCCTCTGCCCTCCGAGGCCGTGCAGTGGCTGTGCCACCAAGCATTCCTGCTC | 3240 |
| AlaAlaGlyProLeuProSerGluAlaValGlnTrpLeuCysHisGlnAlaPheLeuLeu | 1080 |
| | |
| AAGCTGACTCGACACCGTGTCACCTACGTGCCACTCCTGGGGTCACTCAGGACAGCCCAG | 3300 |
| LysLeuThrArgHisArgValThrTyrValProLeuLeuGlySerLeuArgThrAlaGln | 1100 |
| | |
| ACGCAGCTGAGTCGGAAGCTCCCGGGGACGACGCTGACTGCCCTGGAGGCCGCAGCCAAC | 3360 |
| ThrGlnLeuSerArgLysLeuProGlyThrThrLeuThrAlaLeuGluAlaAlaAlaAsn | 1120 |
| | |
| CCGGCACTGCCCTCAGACTTCAAGACCATCCTGGAC | 3420 |
| ProAlaLeuProSerAspPheLysThrIleLeuAsp | 1132 |

*Fig. 11J*

Truncated protein 3

```
                                        ATGCCGCGCGCTCCCCGCTGCCGAGCCGTGCGCTCCCTGCTGCGCAGCCACTACCGCGAGGTGCTGCCGCTGGCCACGTTCGTG
                                        M  P  R  A  P  R  C  A  V  R  S  L  L  R  S  H  Y  R  E  V  L  P  L  A  T  F  V

CGGCGCCTGGGGCCCCAGGGCTGGCGCTGGTGCAGCGCGGGGACCCGGCCGCTTTCCGCGCGCTGGTGGCCCAGTGCCTGGTGTGCGTGCCCTGGGACGCACGGCCGCCCCCCGCCGC
R  R  L  G  P  Q  G  W  R  L  V  Q  R  G  D  P  A  A  F  R  A  L  V  A  Q  C  L  V  C  V  P  W  D  A  R  P  P  P  A  A

CCCCTCCTTCCGCCAGGTGTCCTGCCTGAAGGAGCTGGTGGCCCGAGTGCTGCAGAGGCTGTGCGAGCGCGGCGCGAAGAACGTGCTGGCCTTCGGCTTCGCGCTGCTGGACGGGGCCCG
P  S  F  R  Q  V  S  C  L  K  E  L  V  A  R  V  L  Q  R  L  C  E  R  G  A  K  N  V  L  A  F  G  F  A  L  L  D  G  A  R

CGGGGGCCCCCCGAGGCCTTCACCACCAGCGTGCGCAGCTACCTGCCCAACACGGTGACCGACGCACTGCGGGGGAGCGGGGCGTGGGGGCTGCTGCTGCGCCGCGTGGGCGACGACGT
G  G  P  P  E  A  F  T  T  S  V  R  S  Y  L  P  N  T  V  T  D  A  L  R  G  S  G  A  W  G  L  L  L  R  R  V  G  D  D  V

GCTGGTTCACCTGCTGGCACGCTGCGCGCTCTTTGTGCTGGTGGCTCCCAGCTGCGCCTACCAGGTGCGGGCCGCCGCTGTACCAGCTCGGCGCTGCCACTCAGGCCCGGCCCCCGCC
L  V  H  L  L  A  R  C  A  L  F  V  L  V  A  P  S  C  A  Y  Q  V  C  G  P  P  L  Y  Q  L  G  A  A  T  Q  A  R  P  P  P

ACACGCTAGTGGACCCCGAAGGCGTCTGGGATGCGAACGGGCCTGGAACCATAGCGTCAGGGAGGCCGGGGTCCCCCTGGGCCTGCCAGCCCCGGGTGCGAGGAGGCGCGGGGGCAGTGC
H  A  S  G  P  R  R  R  L  G  C  E  R  A  W  N  H  S  V  R  E  A  G  V  P  L  G  L  P  A  P  G  A  R  R  R  G  G  S  A

CAGCCGAAGTCTGCCGTTGCCCAAGAGGCCCAGGCGTGGCGCTGCCCCTGAGCCGGAGCGGACGCCCGTTGGGCAGGGGTCCTGGGCCCACCCGGGCAGGACGCGTGGACCGAGTGACCG
S  R  S  L  P  L  P  K  R  P  R  R  G  A  A  P  E  P  E  R  T  P  V  G  Q  G  S  W  A  H  P  G  R  T  R  G  P  S  D  R

TGGTTTCTGTGTGGTGTCACCTGCCAGACCCGCCGAAGAAGCCACCTCTTTGGAGGGTGCGCTCTCTGGCACGCGCCACTCCCACCCATCCGTGGGCCGCCAGCACCACGCGGGCCCCC
G  F  C  V  V  S  P  A  R  P  A  E  E  A  T  S  L  E  G  A  L  S  G  T  R  H  S  H  P  S  V  G  R  Q  H  H  A  G  P  P

ATCCACATCGCGGCCACCACGTCCCTGGGACACGCCTTGTCCCCCGGTGTACGCCGAGACCAAGCACTTCCTCTACTCCTCAGGCGACAAGGAGCAGCTGCGGCCCTCCTTCCTACTCAG
S  T  S  R  P  P  R  P  W  D  T  P  C  P  P  V  Y  A  E  T  K  H  F  L  Y  S  S  G  D  K  E  Q  L  R  P  S  F  L  L  S

CTCTCTGAGGCCCAGCCTGACTGGCGCTCGGAGGCTCGTGGAGACCATCTTTCTGGGTTCCAGGCCCTGGATGCCAGGGACTCCCCGCAGGTTGCCCCGCCTGCCCCAGCGCTACTGGCA
S  L  R  P  S  L  T  G  A  R  R  L  V  E  T  I  F  L  G  S  R  P  W  M  P  G  T  P  R  R  L  P  R  L  P  Q  R  Y  W  Q

AATGCGGCCCCTGTTTCTGGAGCTGCTTGGGAACCACGCGCAGTGCCCCTACGGGGTGCTCCTCAAGACGCACTGCCCGCTGCGAGCTGCGGTCACCCCAGCAGCCGGTGTCTGTGCCCG
N  R  P  L  F  L  E  L  L  G  N  H  A  Q  C  P  Y  G  V  L  L  K  T  H  C  P  L  R  A  A  V  T  P  A  A  G  V  C  A  R

GGAGAAGCCCCAGGGCTCTGTGGCGGCCCCCGAGGAGGAGGACACAGACCCCGTCGCCTGGTGCAGCTGCTCCGCCAGCACAGCAGCCCCTGGCAGGTGTACGGCTTCGTGCGGGCCTG
E  K  P  Q  G  S  V  A  A  P  E  E  E  D  T  D  P  R  R  L  V  Q  L  L  R  Q  H  S  S  P  W  Q  V  Y  G  F  V  R  A  C

CCTGCGCCGGCTGGTGCCCCCAGGCCTCTGGGGCTCCAGGCACAACGAACGCCGCTTCCTCAGGAACACCAAGAAGTTCATCTCCCTGGGGAAGCATGCCAAGCTCTCGCTGCAGGAGCT
L  R  R  L  V  P  P  G  L  W  G  S  R  H  N  E  R  R  F  L  R  N  T  K  K  F  I  S  L  G  K  H  A  K  L  S  L  Q  E  L

GACGTGGAAGATGAGCGTGCGGGACTGCGCCTTGGCTGCGCAGGAGCCCAGGGGTTGGCTGTGTTCCGGCCGCAGAGCACCGTCTGCGTGAGGAGATCCTGGCCAAGTTCCTGCACTGGCT
T  W  K  M  S  V  R  D  C  A  W  L  R  R  S  P  G  V  G  C  V  P  A  A  E  H  R  L  R  E  E  I  L  A  K  F  L  H  W  L

GATGAGTGTGTACGTCGTCGAGCTGCTCAGGTCTTTCTTTTATGTCACGGAGACCACGTTTCAAAAGAACAGGCTCTTTTTCTACCGGAAGAGTGTCTGGAGCAAGTTGCAAAGCATTGG
M  S  V  Y  V  V  E  L  L  R  S  F  F  Y  V  T  E  T  T  F  Q  K  N  R  L  F  F  Y  R  K  S  V  W  S  K  L  Q  S  I  G
```

*Fig. 11K*

```
AATCAGACAGCACTTGAAGAGGGTGCAGCTGCGGGAGCTGTCGGAAGCAGAGGTCAGGCAGCATCGGGAAGCCAGGCCCGCCCTGCTGACGTCCAGACTCCGCTTCATCCCCAAGCCTGA
 I  R  Q  H  L  K  R  V  Q  L  R  E  L  S  E  A  E  V  R  Q  H  R  E  A  R  P  A  L  L  T  S  R  L  R  F  I  P  K  P  D

CGGGCTGCCGGCCGATTGTGAACATGGACTACGTCGTGGGAGCCAGAACGTTCCGCAGAGAAAAGAGGGCCGAGCGTCTCACCTCGAGGGTGAAGGCACTGTTCAGCGTGCTCAACTACGA
 G  L  R  P  I  V  N  M  D  Y  V  V  G  A  R  T  F  R  R  E  K  R  A  E  R  L  T  S  R  V  K  A  L  F  S  V  L  N  Y  E

GCGGGCGCGGCGCCCCGGCCTCCTGGGCGCCTCTGTGCTGGGCCTGGACGATATCCACAGGGCCTGGCGCACCTTCGTGCTGCGTGTGCGGGCCCAGGACCCGCCGCCTGAGCTGTACTT
 R  A  R  R  P  G  L  L  G  A  S  V  L  G  L  D  D  I  H  R  A  W  R  T  F  V  L  R  V  R  A  Q  D  P  P  P  E  L  Y  F

TGTCAAGGTGGATGTGACGGGCGCGTACGACACCATCCCCCAGGACAGGCTCACGGAGGTCATCGCCAGCATCATCAAACCCCAGAACACGTACTGCGTGCGTCGGTATGCCGTGGTCCA
 V  K  V  D  V  T  G  A  Y  D  T  I  P  Q  D  R  L  T  E  V  I  A  S  I  I  K  P  Q  N  T  Y  C  V  R  R  Y  A  V  V  Q

GAAGGCCGCCCATGGGCACGTCCGCAAGGCCTTCAAGAGCCACGTCTCTACCTTGACAGACCTCCAGCCGTACATGCGACAGTTCGTGGCTCACCTGCAGGAGACCAGCCCGCTGAGGGA
 K  A  A  H  G  H  V  R  K  A  F  K  S  H  V  S  T  L  T  D  L  Q  P  Y  M  R  Q  F  V  A  H  L  Q  E  T  S  P  L  R  D

TGCCGTCGTCATCGAGCAGAGCTCCTCCCTGAATGAGGCCAGCAGTGGCCTCTTCGACGTCTTCCTACGCTTCATGTGCCACCACGCCGTGCGCATCAGGGGCAAGTCCTACGTCCAGTG
 A  V  V  I  E  Q  S  S  S  L  N  E  A  S  S  G  L  F  D  V  F  L  R  F  M  C  H  H  A  V  R  I  R  G  K  S  Y  V  Q  C

CCAGGGGATCCCGCAGGGCTCCATCCTCTCCACGCTGCTCTGCAGCCTGTGCTACGGCGACATGGAGAACAAGCTGTTTGCGGGGATTCGGCGGGACGGGCTGCTCCTGCGTTTGGTGGA
 Q  G  I  P  Q  G  S  I  L  S  T  L  L  C  S  L  C  Y  G  D  M  E  N  K  L  F  A  G  I  R  R  D  G  L  L  L  R  L  V  D

TGATTTCTTGTTGGTGACACCTCACCTCACCCACGCGAAAACCTTCCTCAGGACCCTGGTCCGAGGTGTCCCTGAGTATGGCTGCGTGGTGAACTTGCGGAAGACAGTGGTGAACTTCCC
 D  F  L  L  V  T  P  H  L  T  H  A  K  T  F  L  R  T  L  V  R  G  V  P  E  Y  G  C  V  V  N  L  R  K  T  V  V  N  F  P

TGTAGAAGACGAGGCCCTGGGTGGCACGGCTTTTGTTCAGATGCCGGCCCACGGCCTATTCCCCTGGTGCGGCCTGCTGCTGGATACCCGGACCCTGGAGGTGCAGAGCGACTACTCCAG
 V  E  D  E  A  L  G  G  T  A  F  V  Q  M  P  A  H  G  L  F  P  W  C  G  L  L  L  D  T  R  T  L  E  V  Q  S  D  Y  S  R

GTGAGCGCACCTGGCCGGAAGTGGAGCCTGTGCCCGGCTGGGGCAGGTGCTGCTGCAGGGCCGTTGCGTCCACCTCTGCTTCCGTGTGGGGCAGGCGACTGCCAATCCCAAAGGGTCAGA
*

TGCCACAGGGTGCCCCTCGTCCCATCTGGGGCTGAGCACAAATGCATCTTTCTGTGGGAGTGAGGGTGCCTCACAACGGGAGCAGTTTTCTGTGCTATTTTGGTAA...
```

*Fig. 11L*

Altered C-terminus protein

```
                                        ATGCCGCGCGCTCCCCGCTGCCGAGCCGTGCGCTCCCTGCTGCGCAGCCACTACCGCGAGGTGCTGCCGCTGGCCACGTTCGTG
                                         M  P  R  A  P  R  C  R  A  V  R  S  L  L  R  S  H  Y  R  E  V  L  P  L  A  T  F  V

CGGCGCCTGGGGCCCCAGGGCTGGCGGCTGGTGCAGCGCGGGGACCCGGCGGCTTTCCGCGCGCTGGTGGCCCAGTGCCTGGTGTGCGTGCCCTGGGACGCACGGCCGCCCCCGCCGC
 R  R  L  G  P  Q  G  W  R  L  V  Q  R  G  D  P  A  A  F  R  A  L  V  A  Q  C  L  V  C  V  P  W  D  A  R  P  P  P  A  A

CCCCTCCTTCCGCCAGGTGTCCTGCCTGAAGGAGCTGGTGGCCCGAGTGCTGCAGAGGCTGTGCGAGCGCGGCGCGAAGAACGTGCTGGCCTTCGGCTTCGCGCTGCTGGACGGGGCCG
 P  S  F  R  Q  V  S  C  L  K  E  L  V  A  R  V  L  Q  R  L  C  E  R  G  A  K  N  V  L  A  F  G  F  A  L  L  D  G  A  R

CGGGGGCCCCCCGAGGCCTTCACCACCAGCGTGCGCAGCTACCTGCCCAACACGGTGACCGACGCACTGCGGGGGAGCGGGGCGTGGGGGCTGCTGCTGCGCCGCGTGGGCGACGACGT
 G  G  P  P  E  A  F  T  T  S  V  R  S  Y  L  P  N  T  V  T  D  A  L  R  G  S  G  A  W  G  L  L  L  R  R  V  G  D  D  V

GCTGGTTCACCTGCTGGCACGCTGCGCGCTCTTTGTGCTGGTGGCTCCCAGCTGCGCCTACCAGGTGTGCGGGCCGCCGCTGTACCAGCTCGGCGCTGCCACTCAGGCCCGGCCCCCGCC
 L  V  H  L  L  A  R  C  A  L  F  V  L  V  A  P  S  C  A  Y  Q  V  C  G  P  P  L  Y  Q  L  G  A  A  T  Q  A  R  P  P  P

ACACGCTAGTGGACCCCGAAGGCGTCTGGGATGCGAACGGGCCTGGAACCATAGCGTCAGGGAGGCCGGGGTCCCCCTGGGCCTGCCAGCCCCGGGTGCGAGGAGCGCGCGGGGCAGTGC
 H  A  S  G  P  R  R  R  L  G  C  E  R  A  W  N  H  S  V  R  E  A  G  V  P  L  G  L  P  A  P  G  A  R  R  R  G  G  S  A

CAGCCGAAGTCTGCCGTTGCCCAAGAGCCCCAGGCGTGGCGCTGCCCCTGAGCCGGAGCGGACGCCCGTTGGGCAGGGGTCCTGGGCCCACCCGGGCAGGACGCGTGGACCGAGTGACCG
 S  R  S  L  P  L  P  K  R  P  R  R  G  A  A  P  E  P  E  R  T  P  V  G  Q  G  S  W  A  H  P  G  R  T  R  G  P  S  D  R

TGGTTTCTGTGTGGTGTCACCTGCCAGACCCGCCGAAGAAGCCACCTCTTTGGAGGGTGCGCTCTCTGGCACGCGCCACTCCCACCCATCCGTGGGCCGCCAGCACCACGCGGGCCCCC
 G  F  C  V  V  S  P  A  R  P  A  E  E  A  T  S  L  E  G  A  L  S  G  T  R  H  S  H  P  S  V  G  R  Q  H  H  A  G  P  P

ATCCACATCGCGGCCACCACGTCCCTGGGACACGCCTTGTCCCCCGGTGTACGCCGAGACCAAGCACTTCCTCTACTCCTCAGGCGACAAGGAGCAGCTGCGGCCCTCCTTCCTACTCAG
 S  T  S  R  P  P  R  P  W  D  T  P  C  P  P  V  Y  A  E  T  K  H  F  L  Y  S  S  G  D  K  E  Q  L  R  P  S  F  L  L  S

CTCTCTGAGGCCCAGCCTGACTGGCGCTCGGAGGCTCGTGGAGACCATCTTTCTGGGTTCCAGGCCCTGGATGCCAGGGACTCCCCGCAGGTTGCCCCGCCTGCCCCAGCGCTACTGGCA
 S  L  R  P  S  L  T  G  A  R  R  L  V  E  T  I  F  L  G  S  R  P  W  M  P  G  T  P  R  R  L  P  R  L  P  Q  R  Y  W  Q

AATGCGGCCCCTGTTTCTGGAGCTGCTTGGGAACCACGCGCAGTGCCCCTACGGGGTGCTCCTCAAGACGCACTGCCCGCTGCGAGCTGCGGTCACCCCAGCAGCCGGTGTCTGTGCCCG
 N  A  A  P  V  S  G  A  A  W  E  P  R  A  V  P  L  R  G  A  P  Q  R  H  C  P  L  R  A  A  V  T  P  A  A  G  V  C  A  R

GGAGAAGCCCCAGGGCTCTGTGGCGGCCCCCGAGGAGGAGGACACAGACCCCGTCGCCTGGTGCAGCTGCTCCGCCAGCACAGCAGCCCCTGGCAGGTGTACGGCTTCGTGCGGGCCTG
 E  K  P  Q  G  S  V  A  A  P  E  E  E  D  T  D  P  R  R  L  V  Q  L  L  R  Q  H  S  S  P  W  Q  V  Y  G  F  V  R  A  C

CCTGCGCCGGCTGGTGCCCCCAGGCCTCTGGGGCTCCAGGCACAACGAACGCCGCTTCCTCAGGAACACCAAGAAGTTCATCTCCCTGGGGAAGCATGCCAAGCTCTCGCTGCAGGAGCT
 L  R  R  L  V  P  P  G  L  W  G  S  R  H  N  E  R  R  F  L  R  N  T  K  K  F  I  S  L  G  K  H  A  K  L  S  L  Q  E  L

GACGTGGAAGATGAGCGTGCGGGACTGCGCTTGGCTGCGCAGGAGCCCAGGGGTTGGCTGTGTTCCGGCCGCAGAGCACCGTCTGCGTGAGGAGATCCTGGCCAAGTTCCTGCACTGGCT
 T  W  K  M  S  V  R  D  C  A  W  L  R  R  S  P  G  V  G  C  V  P  A  A  E  H  R  L  R  E  E  I  L  A  K  F  L  H  W  L

GATGAGTGTGTACGTCGTCGAGCTGCTCAGGTCTTTCTTTTATGTCACGGAGACCACGTTTCAAAAGAACAGGCTCTTTTTCTACCGGAAGAGTGTCTGGAGCAAGTTGCAAAGCATTGG
 M  S  V  Y  V  V  E  L  L  R  S  F  F  Y  V  T  E  T  T  F  Q  K  N  R  L  F  F  Y  R  K  S  V  W  S  K  L  Q  S  I  G
```

*Fig. 11M*

```
AATCAGACAGCACTTGAAGAGGGTGCAGCTGCGGGAGCTGTCGGAAGCAGAGGTCAGGCAGCATCGGGAAGCCAGGCCCGCCCTGCTGACGTCCAGACTCCGCTTCATCCCCAAGCCTGA
 I  R  Q  H  L  K  R  V  Q  L  R  E  L  S  E  A  E  V  R  Q  H  R  E  A  R  P  A  L  L  T  S  R  L  R  F  I  P  K  P  D

CGGGCTGCGGCCGATTGTGAACATGGACTACGTCGTGGGAGCCAGAACGTTCCGCAGAGAAAAGAGGGCCGAGCGTCTCACCTCGAGGGTGAAGGCACTGTTCAGCGTGCTCAACTACGA
 G  L  R  P  I  V  N  M  D  Y  V  V  G  A  R  T  F  R  R  E  K  R  A  E  R  L  T  S  R  V  K  A  L  F  S  V  L  N  Y  E

GCGGGCGCGGCGCCCGGCCTCCTGGGCGCCTCTGTGCTGGGCCTGGACGATATCCACAGGGCCTGGCGCACCTTCGTGCTGCGTGTGCGGGCCCAGGACCCGCCGCCTGAGCTGTACTT
 R  A  R  R  P  G  L  L  G  A  S  V  L  G  L  D  D  I  H  R  A  W  R  T  F  V  L  R  V  R  A  Q  D  P  P  P  E  L  Y  F

TGTCAAGGTGGATGTGACGGGCGCGTACGACACCATCCCCCAGGACAGGCTCACGGAGGTCATCGCCAGCATCATCAAACCCCAGAACACGTACTGCGTGCGTCGGTATGCCGTGGTCCA
 V  K  V  D  V  T  G  A  Y  D  T  I  P  Q  D  R  L  T  E  V  I  A  S  I  I  K  P  Q  N  T  Y  C  V  R  R  Y  A  V  V  Q

GAAGGCCGCCCATGGGCACGTCCGCAAGGCCTTCAAGAGCCACGTCTCTACCTTGACAGACCTCCAGCCGTACATGCGACAGTTCGTGGCTCACCTGCAGGAGACCAGCCCGCTGAGGGA
 K  A  A  H  G  H  V  R  K  A  F  K  S  H  V  S  T  L  T  D  L  Q  P  Y  M  R  Q  F  V  A  H  L  Q  E  T  S  P  L  R  D

TGCCGTCGTCATCGAGCAGAGCTCCTCCCTGAATGAGGCCAGCAGTGGCCTCTTCGACGTCTTCCTACGCTTCATGTGCCACCACGCCGTGCGCATCAGGGGCAAGTCCTACGTCCAGTG
 A  V  V  I  E  Q  S  S  S  L  N  E  A  S  S  G  L  F  D  V  F  L  R  F  M  C  H  H  A  V  R  I  R  G  K  S  Y  V  Q  C

CCAGGGGATCCCGCAGGGCTCCATCCTCTCCACGCTGCTCTGCAGCCTGTGCTACGGCGACATGGAGAACAAGCTGTTTGCGGGGATTCGGCGGGACGGGCTGCTCCTGCGTTTGGTGGA
 Q  G  I  P  Q  G  S  I  L  S  T  L  L  C  S  L  C  Y  G  D  M  E  N  K  L  F  A  G  I  R  R  D  G  L  L  L  R  L  V  D

TGATTTCTTGTTGGTGACACCTCACCTCACCCACGCGAAAACCTTCCTCAGGACCCTGGTCCGAGGTGTCCCTGAGTATGGCTGCGTGGTGAACTTGCGGAAGACAGTGGTGAACTTCCC
 D  F  L  L  V  T  P  H  L  T  H  A  K  T  F  L  R  T  L  V  R  G  V  P  E  Y  G  C  V  V  N  L  R  K  T  V  V  N  F  P

TGTAGAAGACGAGGCCCTGGGTGGCACGGCTTTTGTTCAGATGCCGGCCCACGGCCTATTCCCCTGGTGCGGCCTGCTGCTGGATACCCGGACCCTGGAGGTGCAGAGCGACTACTCCAG
 V  E  D  E  A  L  G  G  T  A  F  V  Q  M  P  A  H  G  L  F  P  W  C  G  L  L  L  D  T  R  T  L  E  V  Q  S  D  Y  S  S

CTATGCCCGGACCTCCATCAGAGCCAGTCTCACCTTCAACCGCGGCTTCAAGGCTGGGAGGAACATGCGTCGCAAACTCTTTGGGGTCTTGCGGCTGAAGTGTCACAGCCTGTTTCTGGA
 Y  A  R  T  S  I  R  A  S  L  T  F  N  R  G  F  K  A  G  R  N  M  R  R  K  L  F  G  V  L  R  L  K  C  H  S  L  F  L  D

TTTGCAGGTGAACAGCCTCCAGACGGTGTGCACCAACATCTACAAGATCCTCCTGCTGCAGGCGTACAGGTTTCACGCATGTGTGCTGCAGCTCCCATTTCATCAGCAAGTTTGGAAGAA
 L  Q  V  N  S  L  Q  T  V  C  T  N  I  Y  K  I  L  L  L  Q  A  Y  R  F  H  A  C  V  L  Q  L  P  F  H  Q  Q  V  W  K  N

CCCCACATTTTTCCTGCGCGTCATCTCTGACACGGCCTCCCTCTGCTACTCCATCCTGAAAGCCAAGAACGCAGGGATGTCGCTGGGGGCCAAGGGCGCCGCCGGCCCTCTGCCCTCCGA
 P  T  F  F  L  R  V  I  S  D  T  A  S  L  C  Y  S  I  L  K  A  K  N  A  E
                                                                        |
                                          CCGAAGAAAACATTTCTGTCGTGACTCCTGCGGTGCTTGGGTC
                                           E  E  N  I  L  V  V  T  P  A  V  L  G  S

GGGACAGCCAGAGATGGAGCCACCCCGCAGACCGTCGGGTGTGGGCAGCTTTCCGGTGTCTCCTGGGAGGGGAGTTGGGCTGGGCCTGTGACTCCTCAGCCTCTGTTTTCCCCCAG
 G  Q  P  E  M  E  P  P  R  R  P  S  G  V  G  S  F  P  V  S  P  G  R  G  V  G  L  *
```

*Fig. 11N*

Protein that lacks motif A

```
                        ATGCCGCGCGCTCCCCGCTGCCGAGCCGTGCGCTCCCTGCTGCGCAGCCACTACCGCGAGGTGCTGCCGCTGGCCACGTTCGTG
                        M  P  R  A  P  R  C  A  V  R  S  L  L  R  S  H  Y  R  E  V  L  P  L  A  T  F  V

CGGCGCCTGGGGCCCCAGGGCTGGCGGCTGGTGCAGCGCGGGGACCCGGCCGCTTTCCGCGCGCTGGTGGCCCAGTGCCTGGTGTGCGTGCCCTGGGACGCACAGGCCGCCCCCCGCCGC
R  R  L  G  P  Q  G  W  R  L  V  Q  R  G  D  P  A  A  F  R  A  L  V  A  Q  C  L  V  C  V  P  W  D  A  R  P  P  P  A  A

CCCCTCCTTCCGCCAGGTGTCCTGCCTGAAGGAGCTGGTGGCCCGAGTGCTGCAGAGGCTGTGCGAGCGCGGCGCGAAGAACGTGCTGGCCTTCGGCTTCGCGCTGCTGGACGGGGCCCG
P  S  F  R  Q  V  S  C  L  K  E  L  V  A  R  V  L  Q  R  L  C  E  R  G  A  K  N  V  L  A  F  G  F  A  L  L  D  G  A  R

CGGGGGCCCCCCCGAGGCCTTCACCACCAGCGTGCGCAGCTACCTGCCCAACACGGTGACCGACGCACTGCGGGGGAGCGGGGCGTGGGGCTGCTGCTGCGCCGCGTGGGCGACGACGT
G  G  P  P  E  A  F  T  T  S  V  R  S  Y  L  P  N  T  V  T  D  A  L  R  G  S  G  A  W  G  L  L  L  R  R  V  G  D  D  V

GCTGGTTCACCTGCTGGCACGCTGCGCGCTCTTTGTGCTGGTGGCTCCCAGCTGCGCCTACCAGGTGCGGGCCGCCGCTGTACCAGCTCGGCGCTGCCACTCAGGCCCGGCCCCCGCC
L  V  H  L  L  A  R  C  A  L  F  V  L  V  A  P  S  C  A  Y  Q  V  C  G  P  P  L  Y  Q  L  G  A  A  T  Q  A  R  P  P  P

ACACGCTAGTGGACCCCGAAGGCGTCTGGGATGCGAACGGGCCTGGAACCATAGCGTCAGGGAGGCCGGGGTCCCCCTGGGCCTGCCAGCCCCGGGTGCGAGGAGGCGCGGGGGCAGTGC
H  A  S  G  P  R  R  R  L  G  C  E  R  A  W  N  H  S  V  R  E  A  G  V  P  L  G  L  P  A  P  G  A  R  R  R  G  G  S  A

CAGCCGAAGTCTGCCGTTGCCCAAGAGGCCCAGGCGTGGCGCTGCCCCTGAGCCGGAGCGGACGCCCGTTGGGCAGGGGTCCTGGGCCCACCCGGGCAGGACGCGTGGACCGAGTGACCG
S  R  S  L  P  L  P  K  R  P  R  R  G  A  A  P  E  P  E  R  T  P  V  G  Q  G  S  W  A  H  P  G  R  T  R  G  P  S  D  R

TGGTTTCTGTGTGGTGTCACCTGCCAGACCCGCCGAAGAAGCCACCTCTTTGGAGGGTGCGCTCTCTGGCACGCGCCACTCCCACCCATCCGTGGGCCGCCAGCACCACGCGGGCCCCC
G  F  C  V  V  S  P  A  R  P  A  E  E  A  T  S  L  E  G  A  L  S  G  T  R  H  S  H  P  S  V  G  R  Q  H  H  A  G  P  P

ATCCACATCGCGGCCACCACGTCCCTGGGACACGCCTTGTCCCCGGTGTACGCCGAGACCAAGCACTTCCTCTACTCCTCAGGCGACAAGGAGCAGCTGCGGCCCTCCTTCCTACTCAG
S  T  S  R  P  P  R  P  W  D  T  P  C  P  P  V  Y  A  E  T  K  H  F  L  Y  S  S  G  D  K  E  Q  L  R  P  S  F  L  L  S

CTCTCTGAGGCCCAGCCTGACTGGCGCTCGGAGGCTCGTGGAGACCATCTTTCTGGGTTCCAGGCCCTGGATGCCAGGGACTCCCGCAGGTTGCCCCGCCTGCCCCAGCGCTACTGGCA
S  L  R  P  S  L  T  G  A  R  R  L  V  E  T  I  F  L  G  S  R  P  W  M  P  G  T  P  R  R  L  P  R  L  P  Q  R  Y  W  Q

AATGCGGCCCCTGTTTCTGGAGCTGCTTGGGAACCACGCGCAGTGCCCCTACGGGGTGCTCCTCAAGACGCACTGCCCGCTGCGAGCTGCGGTCACCCCAGCAGCCGGTGTCTGTGCCCG
N  R  P  L  F  L  E  L  L  G  N  H  A  Q  C  P  Y  G  V  L  L  K  T  H  C  P  L  R  A  A  V  T  P  A  A  G  V  C  A  R

GGAGAAGCCCCAGGGCTCTGTGGCGGCCCCCGAGGAGGAGGACACAGACCCCCGTCGCCTGGTGCAGCTGCTCCGCCAGCACAGCAGCCCCTGGCAGGTGTACGGCTTCGTGCGGGCCTG
E  K  P  Q  G  S  V  A  A  P  E  E  E  D  T  D  P  R  R  L  V  Q  L  L  R  Q  H  S  S  P  W  Q  V  Y  G  F  V  R  A  C

CCTGCGCCGGCTGGTGCCCCCAGGCCTCTGGGGCTCCAGGCACAACGAACGCCGCTTCCTCAGGAACACCAAGAAGTTCATCTCCCTGGGGAAGCATGCCAAGCTCTCGCTGCAGGAGCT
L  R  R  L  V  P  P  G  L  W  G  S  R  H  N  E  R  R  F  L  R  N  T  K  K  F  I  S  L  G  K  H  A  K  L  S  L  Q  E  L

GACGTGGAAGATGAGCGTGCGGGACTGCGCTTGGCTGCGCAGGAGCCCAGGGGTTGGCTGTGTTCCGGCCGCAGAGCACCGTCTGCGTGAGGAGATCCTGGCCAAGTTCCTGCACTGGCT
T  W  K  M  S  V  R  D  C  A  W  L  R  R  S  P  G  V  G  C  V  P  A  A  E  H  R  L  R  E  E  I  L  A  K  F  L  H  W  L

GATGAGTGTGTACGTCGTCGAGCTGCTCAGGTCTTTCTTTTATGTCACGGAGACCACGTTTCAAAAGAACAGGCTCTTTTTCTACCGGAAGAGTGTCTGGAGCAAGTTGCAAAGCATTGG
M  S  V  Y  V  V  E  L  L  R  S  F  F  Y  V  T  E  T  T  F  Q  K  N  R  L  F  F  Y  R  K  S  V  W  S  K  L  Q  S  I  G
```

*Fig. 11O*

AATCAGACAGCACTTGAAGAGGGTGCAGCTGCGGGAGCTGTCGGAAGCAGAGGTCAGGCAGCATCGGGAAGCCAGGCCCGCCCTGCTGACGTCCAGACTCCGCTTCATCCCCAAGCCTGA
I R Q H L K R V Q L R E L S E A E V R Q H R E A R P A L L T S R L R F I P K P D

CGGGCTGCGGCCGATTGTGAACATGGACTACGTCGTGGGAGCCAGAACGTTCCGCAGAGAAAAGAGGGCCGAGCGTCTCACCTCGAGGGTGAAGGCACTGTTCAGCGTGCTCAACTACGA
G L R P I V N M D Y V V G A R T F R R E K R A E R L T S R V K A L F S V L N Y E

GCGGGCGCGGCGCCCCGGCCTCCTGGGCGCCTCTGTGCTGGGCCTGGACGATATCCACAGGGCCTGGCGCACCTTCGTGCTGCGTGTGCGGGCCCAGGACCCGCCGCCTGAGCTGTACTT
R A R R P G L L G A S V L G L D D I H R A W R T F V L R V R A Q D P P P E L Y F

TGTCAAG                             GACAGGCTCACGGAGGTCATCGCCAGCATCATCAAACCCCAGAACACGTACTGCGTGCGTCGGTATGCCGTGGTCCA
V K                                 D R L T E V I A S I I K P Q N T Y C V R R Y A V V Q

GAAGGCCGCCCATGGGCACGTCCGCAAGGCCTTCAAGAGCCACGTCTCTACCTTGACAGACCTCCAGCCGTACATGCGACAGTTCGTGGCTCACCTGCAGGAGACCAGCCCGCTGAGGGA
K A A H G H V R K A F K S H V S T L T D L Q P Y M R Q F V A H L Q E T S P L R D

TGCCGTCGTCATCGAGCAGAGCTCCTCCCTGAATGAGGCCAGCAGTGGCCTCTTCGACGTCTTCCTACGCTTCATGTGCCACCACGCCGTGCGCATCAGGGGCAAGTCCTACGTCCAGTG
A V V I E Q S S S L N E A S S G L F D V F L R F M C H H A V R I R G K S Y V Q C

CCAGGGGATCCCGCAGGGCTCCATCCTCTCCACGCTGCTCTGCAGCCTGTGCTACGGCGACATGGAGAACAAGCTGTTTGCGGGGATTCGGCGGGACGGGCTGCTCCTGCGTTTGGTGGA
Q G I P Q G S I L S T L L C S L C Y G D M E N K L F A G I R R D G L L L R L V D

TGATTTCTTGTTGGTGACACCTCACCTCACCCACGCGAAAACCTTCCTCAGGACCCTGGTCCGAGGTGTCCCTGAGTATGGCTGCGTGGTGAACTTGCGGAAGACAGTGGTGAACTTCCC
D F L L V T P H L T H A K T F L R T L V R G V P E Y G C V V N L R K T V V N F P

TGTAGAAGACGAGGCCCTGGGTGGCACGGCTTTTGTTCAGATGCCGGCCCACGGCCTATTCCCCTGGTGCGGCCTGCTGCTGGATACCCGGACCCTGGAGGTGCAGAGCGACTACTCCAG
V E D E A L G G T A F V Q M P A H G L F P W C G L L L D T R T L E V Q S D Y S S

CTATGCCCGGACCTCCATCAGAGCCAGTCTCACCTTCAACCGCGGCTTCAAGGCTGGGAGGAACATGCGTCGCAAACTCTTTGGGGTCTTGCGGCTGAAGTGTCACAGCCTGTTTCTGGA
Y A R T S I R A S L T F N R G F K A G R N M R R K L F G V L R L K C H S L F L D

TTTGCAGGTGAACAGCCTCCAGACGGTGTGCACCAACATCTACAAGATCCTCCTGCTGCAGGCGTACAGGTTTCACGCATGTGTGCTGCAGCTCCCATTTCATCAGCAAGTTTGGAAGAA
L Q V N S L Q T V C T N I Y K I L L L Q A Y R F H A C V L Q L P F H Q Q V W K N

CCCCACATTTTTCCTGCGCGTCATCTCTGACACGGCCTCCCTCTGCTACTCCATCCTGAAAGCCAAGAACGCAGGGATGTCGCTGGGGGCCAAGGGCGCCGCCGGCCCTCTGCCCTCCGA
P T F F L R V I S D T A S L C Y S I L K A K N A G M S L G A K G A A G P L P S E

GGCCGTGCAGTGGCTGTGCCACCAAGCATTCCTGCTCAAGCTGACTCGACACCGTGTCACCTACGTGCCACTCCTGGGGTCACTCAGGACAGCCCAGACGCAGCTGAGTCGGAAGCTCCC
A V Q W L C H Q A F L L K L T R H R V T Y V P L L G S L R T A Q T Q L S R K L P

GGGGACGACGCTGACTGCCCTGGAGGCCGCAGCCAACCCGGCACTGCCCTCAGACTTCAAGACCATCCTGGACTGATGGCCACCCGCCCACAGCCAGGCCGAGAGCAGACACCAGCAGCC
G T T L T A L E A A A N P A L P S D F K T I L D

CTGTCACGCCGGGCTCTACGTCCCAGGGAGGGAGGGGCGGCCCACACCCAGGCCCGCACCGCTGGGAGTCTGAGGCCTGAGTGAGTGTTTGGCCGAGGCCTGCATGTCCGGCTGAAGGCT

GAGTGTCCGGCTGAGGCCTGAGCGAGTGTCCAGCCAAGGGCTGAGTGTCCAGCACACCTGCCGTCTTCACTTCCCCACAGGCTGGCGCTCGGCTCCACCCCAGGGCCAGCTTTTCCTCAC

CAGGAGCCCGGCTTCCACTCCCCACATAGGAATAGTCCATCCCCAGATTCGCCATTGTTCACCCCTCGCCCTGCCCTCCTTTGCCTTCCACCCCCACCATCCAGGTGGAGACCCTGAGAA

*Fig. 11P*

```
GGACCCTGGGAGCTCTGGGAATTTGGAGTGACCAAAGGTGTGCCCTGTACACAGGCGAGGACCCTGCACCTGGATGGGGGTCCCTGTGGGTCAAATTGGGGGGAGGTGCTGTGGGAGTAA
AATACTGAATATATGAGTTTTTCAGTTTTGA
```

Fig. 11Q

Truncated protein that lacks motif A

```
ATGCCGCGCGCTCCCCGCTGCCGAGCCGTGCGCTCCCTGCTGCGCAGCCACTACCGCGAGGTGCTGCCGCTGGCCACGTTCGTG
 M  P  R  A  P  R  C  A  V  R  S  L  L  R  S  H  Y  R  E  V  L  P  L  A  T  F  V

CGGCGCCTGGGGCCCCAGGGCTGGCGGCTGGTGCAGCGCGGGGACCCGGCGGCTTTCCGCGCGCTGGTGGCCCAGTGCCTGGTGTGCGTGCCCTGGGACGCACGGCCGCCCCCCGCCGC
 R  R  L  G  P  Q  G  W  R  L  V  Q  R  G  D  P  A  A  F  R  A  L  V  A  Q  C  L  V  C  V  P  W  D  A  R  P  P  P  A  A

CCCCTCCTTCCGCCAGGTGTCCTGCCTGAAGGAGCTGGTGGCCCGAGTGCTGCAGAGGCTGTGCGAGCGCGGCGCGAAGAACGTGCTGGCCTTCGGCTTCGCGCTGCTGGACGGGGCCCG
 P  S  F  R  Q  V  S  C  L  K  E  L  V  A  R  V  L  Q  R  L  C  E  R  G  A  K  N  V  L  A  F  G  F  A  L  L  D  G  A  R

CGGGGGCCCCCCCGAGGCCTTCACCACCAGCGTGCGCAGCTACCTGCCCAACACGGTGACCGACGCACTGCGGGGGAGCGGGGCGTGGGGGCTGCTGCTGCGCCGCGTGGGCGACGACGT
 G  G  P  P  E  A  F  T  T  S  V  R  S  Y  L  P  N  T  V  T  D  A  L  R  G  S  G  A  W  G  L  L  L  R  R  V  G  D  D  V

GCTGGTTCACCTGCTGGCACGCTGCGCGCTCTTTGTGCTGGTGGCTCCCAGCTGCGCCTACCAGGTGCGGGCCGCCGCTGTACCAGCTCGGCGCTGCCACTCAGGCCCGGCCCCCGCC
 L  V  H  L  L  A  R  C  A  L  F  V  L  V  A  P  S  C  A  Y  Q  V  C  G  P  P  L  Y  Q  L  G  A  A  T  Q  A  R  P  P  P

ACACGCTAGTGGACCCCGAAGGCGTCTGGGATGCGAACGGGCCTGGAACCATAGCGTCAGGGAGGCCGGGGTCCCCCTGGGCCTGCCAGCCCCGGGTGCGAGGAGGCGCGGGGGCAGTGC
 H  A  S  G  P  R  R  R  L  G  C  E  R  A  W  N  H  S  V  R  E  A  G  V  P  L  G  L  P  A  P  G  A  R  R  R  G  G  S  A

CAGCCGAAGTCTGCCGTTGCCCAAGAGCCCCAGGCGTGGCGCTGCCCCTGAGCCGGAGCCGACGCCCGTTGGGCAGGGGTCCTGGGCCCACCCGGGCAGGACGCGTGGACCGAGTGACCG
 S  R  S  L  P  L  P  K  R  P  R  R  G  A  A  P  E  P  E  R  T  P  V  G  Q  G  S  W  A  H  P  G  R  T  R  G  P  S  D  R

TGGTTTCTGTGTGGTGTCACCTGCCAGACCCGCCGAAGAAGCCACCTCTTTGGAGGGTGCGCTCTCTGGCACGCGCCACTCCCACCCATCCGTGGGCCGCCAGCACCACGCGGGCCCCC
 G  F  C  V  V  S  P  A  R  P  A  E  E  A  T  S  L  E  G  A  L  S  G  T  R  H  S  H  P  S  V  G  R  Q  H  H  A  G  P  P

ATCCACATCGCGGCCACCACGTCCCTGGGACACGCCTTGTCCCCCGGTGTACGCCGAGACCAAGCACTTCCTCTACTCCTCAGGCGACAAGGAGCAGCTGCGGCCCTCCTTCCTACTCAG
 S  T  S  R  P  P  R  P  W  D  T  P  C  P  P  V  Y  A  E  T  K  H  F  L  Y  S  S  G  D  K  E  Q  L  R  P  S  F  L  L  S

CTCTCTGAGGCCCAGCCTGACTGGCGCTCGGAGGCTCGTGGAGACCATCTTTCTGGGTTCCAGGCCCTGGATGCCAGGGACTCCCCGCAGGTTGCCCCGCCTGCCCCAGCGCTACTGGCA
 S  L  R  P  S  L  T  G  A  R  R  L  V  E  T  I  F  L  G  S  R  P  W  M  P  G  T  P  R  R  L  P  R  L  P  Q  R  Y  W  Q

AATGCGGCCCCTGTTTCTGGAGCTGCTTGGGAACCACGCGCAGTGCCCCTACGGGGTGCTCCTCAAGACGCACTGCCCGCTGCGAGCTGCGGTCACCCCAGCAGCCGGTGTCTGTGCCCG
 M  R  P  L  F  L  E  L  L  G  N  H  A  Q  C  P  Y  G  V  L  L  K  T  H  C  P  L  R  A  A  V  T  P  A  A  G  V  C  A  R

GGAGAAGCCCCAGGGCTCTGTGGCGGCCCCCGAGGAGGAGGACACAGACCCCCGTCGCCTGGTGCAGCTGCTCCGCCAGCACAGCAGCCCCTGGCAGGTGTACGGCTTCGTGCGGGCCTG
 E  K  P  Q  G  S  V  A  A  P  E  E  E  D  T  D  P  R  R  L  V  Q  L  L  R  Q  H  S  S  P  W  Q  V  Y  G  F  V  R  A  C

CCTGCGCCGGCTGGTGCCCCCAGGCCTCTGGGGCTCCAGGCACAACGAACGCCGCTTCCTCAGGAACACCAAGAAGTTCATCTCCCTGGGGAAGCATGCCAAGCTCTCGCTGCAGGAGCT
 L  R  R  L  V  P  P  G  L  W  G  S  R  H  N  E  R  R  F  L  R  N  T  K  K  F  I  S  L  G  K  H  A  K  L  S  L  Q  E  L

GACGTGGAAGATGAGCGTGCGGGACTGCGCCTTGGCTGCGCAGGAGCCCAGGGGTTGGCTGTGTTCCGGCCGCAGAGCACCGTCTGCGTGAGGAGATCCTGGCCAAGTTCCTGCACTGGCT
 T  W  K  M  S  V  R  D  C  A  W  L  R  R  S  P  G  V  G  C  V  P  A  A  E  H  R  L  R  E  E  I  L  A  K  F  L  H  W  L

GATGAGTGTGTACGTCGTCGAGCTGCTCAGGTCTTTCTTTTATGTCACGGAGACCACGTTTCAAAAGAACAGGCTCTTTTTCTACCGGAAGAGTGTCTGGAGCAAGTTGCAAAGCATTGG
 M  S  V  Y  V  V  E  L  L  R  S  F  F  Y  V  T  E  T  T  F  Q  K  N  R  L  F  F  Y  R  K  S  V  W  S  K  L  Q  S  I  G
```

*Fig. 11R*

```
AATCAGACAGCACTTGAAGAGGGTGCAGCTGCGGGAGCTGTCGGAAGCAGAGGTCAGGCAGCATCGGAAGCCAGGCCCGCCCTGCTGACGTCCAGACTCCGCTTCATCCCCAAGCCTGA
 I  R  Q  H  L  K  R  V  Q  L  R  E  L  S  E  A  E  V  R  Q  H  R  E  A  R  P  A  L  L  T  S  R  L  R  F  I  P  K  P  D

CGGGCTGCGGCCGATTGTGAACATGGACTACGTCGTGGGAGCCAGAACGTTCCGCAGAGAAAAGAGGGCCGAGCGTCTCACCTCGAGGGTGAAGGCACTGTTCAGCGTGCTCAACTACGA
 G  L  R  P  I  V  N  M  D  Y  V  V  G  A  R  T  F  R  R  E  K  R  A  E  R  L  T  S  R  V  K  A  L  F  S  V  L  N  Y  E

GCGGGCGCGGCGCCCCGGCCTCCTGGGCGCCTCTGTGCTGGGCCTGGACGATATCCACAGGGCCTGGCGCACCTTCGTGCTGCGTGTGCGGGCCCAGGACCCGCCGCCTGAGCTGTACTT
 R  A  R  R  P  G  L  L  G  A  S  V  L  G  L  D  D  I  H  R  A  W  R  T  F  V  L  R  V  R  A  Q  D  P  P  P  E  L  Y  F

TGTCAAG                    GACAGGCTCACGGAGGTCATCGCCAGCATCATCAAACCCCAGAACACGTACTGCGTGCGTCGGTATGCCGTGGTCCA
 V  K                       D  R  L  T  E  V  I  A  S  I  I  K  P  Q  N  T  Y  C  V  R  R  Y  A  V  V  Q

GAAGGCCGCCCATGGGCACGTCCGCAAGGCCTTCAAGAGCCACGTCTCTACCTTGACAGACCTCCAGCCGTACATGCGACAGTTCGTGGCTCACCTGCAGGAGACCAGCCCGCTGAGGGA
 K  A  A  H  G  H  V  R  K  A  F  K  S  H  V  S  T  L  T  D  L  Q  P  Y  M  R  Q  F  V  A  H  L  Q  E  T  S  P  L  R  D

TGCCGTCGTCATCGAGCAGAGCTCCTCCCTGAATGAGGCCAGCAGTGGCCTCTTCGACGTCTTCCTACGCTTCATGTGCCACCACGCCGTGCGCATCAGGGGCAAGTCCTACGTCCAGTG
 A  V  V  I  E  Q  S  S  S  L  N  E  A  S  S  G  L  F  D  V  F  L  R  F  M  C  H  H  A  V  R  I  R  G  K  S  Y  V  Q  C

CCAGGGGATCCCGCAGGGCTCCATCCTCTCCACGCTGCTCTGCAGCCTGTGCTACGGCGACATGGAGAACAAGCTGTTTGCGGGGATTCGGCGGGACGGGCTGCTCCTGCGTTTGGTGGA
 Q  G  I  P  Q  G  S  I  L  S  T  L  L  C  S  L  C  Y  G  D  M  E  N  K  L  F  A  G  I  R  R  D  G  L  L  L  R  L  V  D

TGATTTCTTGTTGGTGACACCTCACCTCACCCACGCGAAAACCTTCCTCAGGACCCTGGTCCGAGGTGTCCCTGAGTATGGCTGCGTGGTGAACTTGCGGAAGACAGTGGTGAACTTCCC
 D  F  L  L  V  T  P  H  L  T  H  A  K  T  F  L  R  T  L  V  R  G  V  P  E  Y  G  C  V  V  N  L  R  K  T  V  V  N  F  P

TGTAGAAGACGAGGCCCTGGGTGGCACGGCTTTTGTTCAGATGCCGGCCCACGGCCTATTCCCCTGGTGCGGCCTGCTGCTGGATACCCGGACCCTGGAGGTGCAGAGCGACTACTCCAG
 V  E  D  E  A  L  G  G  T  A  F  V  Q  M  P  A  H  G  L  F  P  W  C  G  L  L  L  D  T  R  T  L  E  V  Q  S  D  Y  S  R

GTGAGCGCACCTGGCCGGAAGTGGAGCCTGTGCCCGGCTGGGGCAGGTGCTGCTGCAGGGCCGTTGCGTCCACCTCTGCTTCCGTGTGGGGCAGGCGACTGCCAATCCCAAAGGGTCAGA
 *

TGCCACAGGGTGCCCCTCGTCCCATCTGGGGCTGAGCACAAATGCATCTTTCTGTGGGAGTGAGGGTGCCTCACAACGGGAGCAGTTTTCTGTGCTATTTTGGTAA__
```

*Fig. 11S*

Lacks motif A and altered C-terminus

```
                                            ATGCCGCGCGCTCCCCGCTGCCGAGCCGTGCGCTCCCTGCTGCGCAGCCACTACCGCGAGGTGCTGCCGCTGGCCACGTTCGTG
                                            M  P  R  A  P  R  C  A  V  R  S  L  L  R  S  H  Y  R  E  V  L  P  L  A  T  F  V

CGGCGCCTGGGGCCCCAGGGCTGGCGGCTGGTGCAGCGCGGGGACCCGGCGGCTTTCCGCGCGCTGGTGGCCCAGTGCCTGGTGTGCGTGCCCTGGGACGCACGGCCGCCCCCGCCGC
R  R  L  G  P  Q  G  W  R  L  V  Q  R  G  D  P  A  A  F  R  A  L  V  A  Q  C  L  V  C  V  P  W  D  A  R  P  P  P  A  A

CCCCTCCTTCCGCCAGGTGTCCTGCCTGAAGGAGCTGGTGGCCCGAGTGCTGCAGAGGCTGTGCGAGCGCGGCGCGAAGAACGTGCTGGCCTTCGGCTTCGCGCTGCTGGACGGGGCCCG
P  S  F  R  Q  V  S  C  L  K  E  L  V  A  R  V  L  Q  R  L  C  E  R  G  A  K  N  V  L  A  F  G  F  A  L  L  D  G  A  R

CGGGGGCCCCCCGAGGCCTTCACCACCAGCGTGCGCAGCTACCTGCCCAACACGGTGACCGACGCACTGCGGGGGAGCGGGGCGTGGGGGCTGCTGCTGCGCCGCGTGGGCGACGACGT
G  G  P  P  E  A  F  T  T  S  V  R  S  Y  L  P  N  T  V  T  D  A  L  R  G  S  G  A  W  G  L  L  L  R  R  V  G  D  D  V

GCTGGTTCACCTGCTGGCACGCTGCGCGCTCTTTGTGCTGGTGGCTCCCAGCTGCGCCTACCAGGTGTGCGGGCCGCCGCTGTACCAGCTCGGCGCTGCCACTCAGGCCCGGCCCCCGCC
L  V  H  L  L  A  R  C  A  L  F  V  L  V  A  P  S  C  A  Y  Q  V  C  G  P  P  L  Y  Q  L  G  A  A  T  Q  A  R  P  P  P

ACACGCTAGTGGACCCCGAAGGCGTCTGGGATGCGAACGGGCCTGGAACCATAGCGTCAGGGAGGCCGGGGTCCCCCTGGGCCTGCCAGCCCCGGGTGCGAGGAGGCGCGGGGCAGTGC
H  A  S  G  P  R  R  R  L  G  C  E  R  A  W  N  H  S  V  R  E  A  G  V  P  L  G  L  P  A  P  G  A  R  R  R  G  G  S  A

CAGCCGAAGTCTGCCGTTGCCCAAGAGGCCCAGGCGTGGCGCTGCCCCTGAGCCGGAGCGGACGCCCGTTGGGCAGGGGTCCTGGGCCCACCCGGGCAGGACGCGTGGACCGAGTGACCG
S  R  S  L  P  L  P  K  R  P  R  R  G  A  A  P  E  P  E  R  T  P  V  G  Q  G  S  W  A  H  P  G  R  T  R  G  P  S  D  R

TGGTTTCTGTGTGGTGTCACCTGCCAGACCCGCCGAAGAAGCCACCTCTTTGGAGGGTGCGCTCTCTGGCACGCGCCACTCCCACCCATCCGTGGGCCGCCAGCACCACGCGGGCCCCC
G  F  C  V  V  S  P  A  R  P  A  E  E  A  T  S  L  E  G  A  L  S  G  T  R  H  S  H  P  S  V  G  R  Q  H  H  A  G  P  P

ATCCACATCGCGGCCACCACGTCCCTGGGACACGCCTTGTCCCCCGGTGTACGCCGAGACCAAGCACTTCCTCTACTCCTCAGGCGACAAGGAGCAGCTGCGGCCCTCCTTCCTACTCAG
S  T  S  R  P  P  R  P  W  D  T  P  C  P  P  V  Y  A  E  T  K  H  F  L  Y  S  S  G  D  K  E  Q  L  R  P  S  F  L  L  S

CTCTCTGAGGCCCAGCCTGACTGGCGCTCGGAGGCTCGTGGAGACCATCTTTCTGGGTTCCAGGCCCTGGATGCCAGGGACTCCCCGCAGGTTGCCCCGCCTGCCCCAGCGCTACTGGCA
S  L  R  P  S  L  T  G  A  R  R  L  V  E  T  I  F  L  G  S  R  P  W  M  P  G  T  P  R  R  L  P  R  L  P  Q  R  Y  W  Q

AATGCGGCCCCTGTTTCTGGAGCTGCTTGGGAACCACGCGCAGTGCCCCTACGGGGTGCTCCTCAAGACGCACTGCCCGCTGCGAGCTGCGGTCACCCCAGCAGCCGGTGTCTGTCCCG
M  R  P  L  F  L  E  L  L  G  N  H  A  Q  C  P  Y  G  V  L  L  K  T  H  C  P  L  R  A  A  V  T  P  A  A  G  V  C  A  R

GGAGAAGCCCCAGGGCTCTGTGGCGGCCCCCGAGGAGGAGGACACAGACCCCCGTCGCCTGGTGCAGCTGCTCCGCCAGCACAGCAGCCCCTGGCAGGTGTACGGCTTCGTGCGGGCCTG
E  K  P  Q  G  S  V  A  A  P  E  E  E  D  T  D  P  R  R  L  V  Q  L  L  R  Q  H  S  S  P  W  Q  V  Y  G  F  V  R  A  C

CCTGCGCCGGCTGGTGCCCCCAGGCCTCTGGGGCTCCAGGCACAACGAACGCCGCTTCCTCAGGAACACCAAGAAGTTCATCTCCCTGGGGAAGCATGCCAAGCTCTCGCTGCAGGAGCT
L  R  R  L  V  P  P  G  L  W  G  S  R  H  N  E  R  R  F  L  R  N  T  K  K  F  I  S  L  G  K  H  A  K  L  S  L  Q  E  L

GACGTGGAAGATGAGCGTGCGGGACTGCGCTTGGCTGCGCAGGAGCCCAGGGGTTGGCTGTGTTCCGGCCGCAGAGCACCGTCTGCGTGAGGAGATCCTGGCCAAGTTCCTGCACTGGCT
T  W  K  M  S  V  R  D  C  A  W  L  R  R  S  P  G  V  G  C  V  P  A  A  E  H  R  L  R  E  E  I  L  A  K  F  L  H  W  L

GATGAGTGTGTACGTCGTCCAGCTGCTCAGGTCTTTCTTTTATGTCACGGAGACCACGTTTCAAAAGAACAGGCTCTTTTTCTACCGGAAGAGTGTCTGGAGCAAGTTGCAAAGCATTGG
M  S  V  Y  V  V  E  L  L  R  S  F  F  Y  V  T  E  T  T  F  Q  K  N  R  L  F  F  Y  R  K  S  V  W  S  K  L  Q  S  I  G
```

*Fig. 11T*

```
AATCAGACAGCACTTGAAGAGGGTGCAGCTGCGGGAGCTGTCGGAAGCAGAGGTCAGGCAGCATCGGGAAGCCAGGCCCGCCCTGCTGACGTCCAGACTCCGCTTCATCCCCAAGCCTGA
 I  R  Q  H  L  K  R  V  Q  L  R  E  L  S  E  A  E  V  R  Q  H  R  E  A  R  P  A  L  L  T  S  R  L  R  F  I  P  K  P  D

CGGGCTGCGGCCGATTGTGAACATGGACTACGTCGTGGGAGCCAGAACGTTCCGCAGAGAAAAGAGGGCCGAGCGTCTCACCTCGAGGGTGAAGGCACTGTTCAGCGTGCTCAACTACGA
 G  L  R  P  I  V  N  M  D  Y  V  V  G  A  R  T  F  R  R  E  K  R  A  E  R  L  T  S  R  V  K  A  L  F  S  V  L  N  Y  E

GCGGGCGCGGCGCCCCGGCCTCCTGGGCGCCTCTGTGCTGGGCCTGGACGATATCCACAGGGCCTGGCGCACCTTCGTGCTGCGTGTGCGGGCCCAGGACCCGCCGCCTGAGCTGTACTT
 R  A  R  R  P  G  L  L  G  A  S  V  L  G  L  D  D  I  H  R  A  W  R  T  F  V  L  R  V  R  A  Q  D  P  P  P  E  L  Y  F

TGTCAAG                         GACAGGCTCACGGAGGTCATCGCCAGCATCATCAAACCCCAGAACACGTACTGCGTGCGTCGGTATGCCGTGGTCCA
 V  K                            D  R  L  T  E  V  I  A  S  I  I  K  P  Q  N  T  Y  C  V  R  R  Y  A  V  V  Q

GAAGGCCGCCCATGGGCACGTCCGCAAGGCCTTCAAGAGCCACGTCTCTACCTTGACAGACCTCCAGCCGTACATGCGACAGTTCGTGGCTCACCTGCAGGAGACCAGCCCGCTGAGGGA
 K  A  A  H  G  H  V  R  K  A  F  K  S  H  V  S  T  L  T  D  L  Q  P  Y  M  R  Q  F  V  A  H  L  Q  E  T  S  P  L  R  D

TGCCGTCGTCATCGAGCAGAGCTCCTCCCTGAATGAGGCCAGCAGTGGCCTCTTCGACGTCTTCCTACGCTTCATGTGCCACCACGCCGTGCGCATCAGGGGCAAGTCCTACGTCCAGTG
 A  V  V  I  E  Q  S  S  S  L  N  E  A  S  S  G  L  F  D  V  F  L  R  F  M  C  H  H  A  V  R  I  R  G  K  S  Y  V  Q  C

CCAGGGGATCCCGCAGGGCTCCATCCTCTCCACGCTGCTCTGCAGCCTGTGCTACGGCGACATGGAGAACAAGCTGTTTGCGGGGATTCGGCGGGACGGGCTGCTCCTGCGTTTGGTGGA
 Q  G  I  P  Q  G  S  I  L  S  T  L  L  C  S  L  C  Y  G  D  M  E  N  K  L  F  A  G  I  R  R  D  G  L  L  L  R  L  V  D

TGATTTCTTGTTGGTGACACCTCACCTCACCCACGCGAAAACCTTCCTCAGGACCCTGGTCCGAGGTGTCCCTGAGTATGGCTGCGTGGTGAACTTGCGGAAGACAGTGGTGAACTTCCC
 D  F  L  L  V  T  P  H  L  T  H  A  K  T  F  L  R  T  L  V  R  G  V  P  E  Y  G  C  V  V  N  L  R  K  T  V  V  N  F  P

TGTAGAAGACGAGGCCCTGGGTGGCACGGCTTTTGTTCAGATGCCGGCCCACGGCCTATTCCCCTGGTGCGGCCTGCTGCTGGATACCCGGACCCTGGAGGTGCAGAGCGACTACTCCAG
 V  E  D  E  A  L  G  G  T  A  F  V  Q  M  P  A  H  G  L  F  P  W  C  G  L  L  L  D  T  R  T  L  E  V  Q  S  D  Y  S  S

CTATGCCCGGACCTCCATCAGAGCCAGTCTCACCTTCAACCGCGGCTTCAAGGCTGGGAGGAACATGCGTCGCAAACTCTTTGGGGTCTTGCGGCTGAAGTGTCACAGCCTGTTTCTGGA
 Y  A  R  T  S  I  R  A  S  L  T  F  N  R  G  F  K  A  G  R  N  M  R  R  K  L  F  G  V  L  R  L  K  C  H  S  L  F  L  D

TTTGCAGGTGAACAGCCTCCAGACGGTGTGCACCAACATCTACAAGATCCTCCTGCTGCAGGCGTACAGGTTTCACGCATGTGTGCTGCAGCTCCCATTTCATCAGCAAGTTTGGAAGAA
 L  Q  V  N  S  L  Q  T  V  C  T  N  I  Y  K  I  L  L  L  Q  A  Y  R  F  H  A  C  V  L  Q  L  P  F  H  Q  Q  V  W  K  N

CCCCACATTTTTCCTGCGCGTCATCTCTGACACGGCCTCCCTCTGCTACTCCATCCTGAAAGCCAAGAACGCAGGGATGTCGCTGGGGGCCAAGGGCGCCGCCGGCCCTCTGCCCTCCGA
 P  T  F  F  L  R  V  I  S  D  T  A  S  L  C  Y  S  I  L  K  A  K  N  A  E
                                                                         |
                                        CCGAAGAAAACATTTCTGTCGTGACTCCTGCGGTGCTTGGGTC
                                         E  E  N  I  L  V  V  T  P  A  V  L  G  S

GGGACAGCCAGAGATGGAGCCACCCCGCAGACCGTCGGGTGTGGGCAGCTTTCCGGTGTCTCCTGGGAGGGGAGTTGGGCTGGGCCTGTGACTCCTCAGCCTCTGTTTTCCCCAG
 G  Q  P  E  M  E  P  P  R  R  P  S  G  V  G  S  F  P  V  S  P  G  R  G  V  G  L  G  L  *
```

*Fig. 11U*

Truncated telomerase (ver. 2)

```
                          ATGCCGCGCGCTCCCCGCTGCCGAGCCGTGCGCTCCCTGCTGCGCAGCCACTACCGCGAGGTGCTGCCGCTGGCCACGTTCGTG
                          M  P  R  A  P  R  C  R  A  V  R  S  L  L  R  S  H  Y  R  E  V  L  P  L  A  T  F  V

CGGCGCCTGGGGCCCCAGGGCTGGCGGCTGGTGCAGCGCGGGGACCCGGCGGCTTTCCGCGCGCTGGTGGCCCAGTGCCTGGTGTGCGTGCCCTGGGACGCACGGCCGCCCCCCGCCGC
R  R  L  G  P  Q  G  W  R  L  V  Q  R  G  D  P  A  A  F  R  A  L  V  A  Q  C  L  V  C  V  P  W  D  A  R  P  P  P  A  A

GGCCTCCCCGGGGTCGGCGTCCGGCTGGGGTTGAGGGCGGCCGGGGGGAACCAGCGACATGCGGAGAGCAGCGCAGGCGACTCAGGGCGCTTCCCCCGCAGGTG
              G  L  P  G  V  G  V  R  L  G  L  R  A  A  G  G  N  Q  R  H  A  E  S  S  A  G  D  S  G  R  F  P  R  R
              A  S  P  G  S  A  S  G  W  G  *  G  R  P  G  G  T  S  D  N  R  R  A  A  Q  A  T  Q  G  A  S  P  A  G
              P  P  R  G  R  R  P  A  G  V  E  G  G  R  G  E  P  A  T  C  G  E  Q  R  R  L  R  A  L  P  P  Q  V

CCCCTCCTTCCGCCAGGTGTCCTGCCTGAAGGAGCTGGTGGCCCGAGTGCTGCAGAGGCTGTGCGAGCGCGGCGCGAAGAACGTGCTGGCCTTCGGCTTCGCGCTGCTGGACGGGGCCCG
P  S  F  R  Q  V  S  C  L  K  E  L  V  A  R  V  L  Q  R  L  C  E  R  G  A  K  N  V  L  A  F  G  F  A  L  L  D  G  A  R

CGGGGGCCCCCCGAGGCCTTCACCACCAGCGTGCGCAGCTACCTGCCCAACACGGTGACCGACGCACTGCGGGGGAGCGGGGCGTGGGGGCTGCTGCTGCGCCGCGTGGGCGACGACGT
G  G  P  P  E  A  F  T  T  S  V  R  S  Y  L  P  N  T  V  T  D  A  L  R  G  S  G  A  W  G  L  L  L  R  R  V  G  D  D  V

GCTGGTTCACCTGCTGGCACGCTGCGCGCTCTTTGTGCTGGTGGCTCCCAGCTGCGCCTACCAGGTGTGCGGGCCGCCGCTGTACCAGCTCGGCGCTGCCACTCAGGCCCGGCCCCCGCC
L  V  H  L  L  A  R  C  A  L  F  V  L  V  A  P  S  C  A  Y  Q  V  C  G  P  P  L  Y  Q  L  G  A  A  T  Q  A  R  P  P  P

ACACGCTAGTGGACCCCGAAGGCGTCTGGGATGCGAACGGGCCTGGAACCATAGCGTCAGGGAGGCCGGGGTCCCCCTGGGCCTGCCAGCCCCGGGTGCGAGGAGCGCGGGGGCAGTGC
H  A  S  G  P  R  R  R  L  G  C  E  R  A  W  N  H  S  V  R  E  A  G  V  P  L  G  L  P  A  P  G  A  R  R  R  G  G  S  A

CAGCCGAAGTCTGCCGTTGCCCAAGAGGCCCAGGCGTGGCGCTGCCCCTGAGCCGGAGCGGACGCCCGTTGGGCAGGGGTCCTGGGCCCACCCGGGCAGGACGCGTGGACCGAGTGACCG
S  R  S  L  P  L  P  K  R  P  R  R  G  A  A  P  E  P  E  R  T  P  V  G  Q  G  S  W  A  H  P  G  R  T  R  G  P  S  D  R

TGGTTTCTGTGTGGTGTCACCTGCCAGACCCGCCGAAGAAGCCACCTCTTTGGAGGGTGCGCTCTCTGGCACGCGCCACTCCCACCCATCCGTGGGCCGCCAGCACCACGCGGGCCCCC
G  F  C  V  V  S  P  A  R  P  A  E  E  A  T  S  L  E  G  A  L  S  G  T  R  H  S  H  P  S  V  G  R  Q  H  H  A  G  P  P

ATCCACATCGCGGCCACCACGTCCCTGGGACACGCCTTGTCCCCCGGTGTACGCCGAGACCAAGCACTTCCTCTACTCCTCAGGCGACAAGGAGCAGCTGCGGCCCTCCTTCCTACTCAG
S  T  S  R  P  P  R  P  W  D  T  P  C  P  P  V  Y  A  E  T  K  H  F  L  Y  S  S  G  D  K  E  Q  L  R  P  S  F  L  L  S

CTCTCTGAGGCCCAGCCTGACTGGCGCTCGGAGGCTCGTGGAGACCATCTTTCTGGGTTCCAGGCCCTGGATGCCAGGGACTCCCCGCAGGTTGCCCCGCCTGCCCCAGCGCTACTGGCA
S  L  R  P  S  L  T  G  A  R  R  L  V  E  T  I  F  L  G  S  R  P  W  M  P  G  T  P  R  R  L  P  R  L  P  Q  R  Y  W  Q

AATGCGGCCCCTGTTTCTGGAGCTGCTTGGGAACCACGCGCAGTGCCCCTACGGGGTGCTCCTCAAGACGCACTGCCCGCTGCGAGCTGCGGTCACCCCAGCAGCCGGTGTCTGTGCCCG
N  R  P  L  F  L  E  L  L  G  N  H  A  Q  C  P  Y  G  V  L  L  K  T  H  C  P  L  R  A  A  V  T  P  A  A  G  V  C  A  R

GGAGAAGCCCCAGGGCTCTGTGGCGGCCCCCGAGGAGGAGGACACAGACCCCGTCGCCTGGTGCAGCTGCTCCGCCAGCACAGCAGCCCCTGGCAGGTGTACGGCTTCGTGCGGGCCTG
E  K  P  Q  G  S  V  A  A  P  E  E  E  D  T  D  P  R  R  L  V  Q  L  L  R  Q  H  S  S  P  W  Q  V  Y  G  F  V  R  A  C

CCTGCGCCGGCTGGTGCCCCCAGGCCTCTGGGGCTCCAGGCACAACGAACGCCGCTTCCTCAGGAACACCAAGAAGTTCATCTCCCTGGGGAAGCATGCCAAGCTCTCGCTGCAGGAGCT
L  R  R  L  V  P  P  G  L  W  G  S  R  H  N  E  R  R  F  L  R  N  T  K  K  F  I  S  L  G  K  H  A  K  L  S  L  Q  E  L
```

Fig. 11V

```
GACGTGGAAGATGAGCGTGCGGGACTGCGCTTGGCTGCGCAGGAGCCCAGGGGTTGGCTGTGTTCCGGCCGCAGAGCACCGTCTGCGTGAGGACATCCTGGCCAAGTTCCTGCACTGGCT
 T  W  K  M  S  V  R  D  C  A  W  L  R  R  S  P  G  V  G  C  V  P  A  A  E  H  R  L  R  E  E  I  L  A  K  F  L  H  W  L

GATGAGTGTGTACGTCGTCGAGCTGCTCAGGTCTTTCTTTTATGTCACGGAGACCACGTTTCAAAAGAACAGGCTCTTTTTCTACCGGAAGAGTGTCTGGAGCAAGTTGCAAAGCATTGG
 M  S  V  Y  V  V  E  L  L  R  S  F  F  Y  V  T  E  T  T  F  Q  K  N  R  L  F  F  Y  R  K  S  V  W  S  K  L  Q  S  I  G

AAT--NNN--GACAGTCACCAGGGGGGTTGACCGCCGGACTGGGCGTCCCCAGGGTTGACTATAGGACCAGGTGTCCAGGTGCCCTGCAAGTAGAGGGGCTCTCAGAGGCGTCTGGCTGG

CATGGGTGGACGTGGCCCCGGGCATGGCCTTCTGCGTGTGCTGCCGTGGGTGCCCTGAGCCCTCACTGAGTCGGTGGGGGCTTGTGGCTTCCCGTGAGCTTCCCCCTAGTCTGTTGTCTG

GCTGAGCAAGCCTCCTGAGGGGCTCTCTATTG...
```

*Fig. 11W*

Truncated protein 1 (ver. 2)

```
                            ATGCCGCGCGCTCCCCGCTGCCGAGCCGTGCGCTCCCTGCTGCGCAGCCACTACCGCGAGGTGCTGCCCGCTGGCCACGTTCGTG
                             M  P  R  A  P  R  C  R  A  V  R  S  L  L  R  S  H  Y  R  E  V  L  P  L  A  T  F  V
CGGCGCCTGGGGCCCCAGGGCTGGCGGCTGGTGCAGCGCGGGGACCCGGCGGCTTTCCGCGCGCTGGTGGCCCAGTGCCTGGTGTGCGTGCCCTGGGACGCACGGCCGCCCCCCGCCGC
 R  R  L  G  P  Q  G  W  R  L  V  Q  R  G  D  P  A  A  F  R  A  L  V  A  Q  C  L  V  C  V  P  W  D  A  R  P  P  P  A  A

GGCCTCCCCGGGGTCGGCGTCCGGCTGGGGTTGAGGGCGGCCGGGGGGAACCAGCGACATGCGGAGAGCAGCGCAGGCGACTCAGGGCGCTTCCCCCGCAGGTG
                 G  L  P  G  V  G  V  R  L  G  L  R  A  A  G  G  N  Q  R  H  A  E  S  S  A  G  D  S  G  R  F  P  R  R
                  A  S  P  G  S  A  S  G  W  G  *  G  R  P  G  G  T  S  D  M  R  R  A  A  Q  A  T  Q  G  A  S  P  A  G
                   P  P  R  G  R  R  P  A  G  V  E  G  G  R  G  E  P  A  T  C  G  E  Q  R  R  R  L  R  A  L  P  P  Q  V
CCCCTCCTTCCGCCAGGTGTCCTGCCTGAAGGAGCTGGTGGCCCGAGTGCTGCAGAGGCTGTGCGAGCGCGGCGCGAAGAACGTGCTGGCCTTCGGCTTCGCGCTGCTGGACGGGCCCG
 P  S  F  R  Q  V  S  C  L  K  E  L  V  A  R  V  L  Q  R  L  C  E  R  G  A  K  N  V  L  A  F  G  F  A  L  L  D  G  A  R

CGGGGGCCCCCCGAGGCCTTCACCACCAGCGTGCGCAGCTACCTGCCCAACACGGTGACCGACGCACTGCGGGGGAGCGGGGCGTGGGGGCTGCTGCTGCGCCGCGTGGGCGACGACGT
 G  G  P  P  E  A  F  T  T  S  V  R  S  Y  L  P  N  T  V  T  D  A  L  R  G  S  G  A  W  G  L  L  L  R  R  V  G  D  D  V

GCTGGTTCACCTGCTGGCACGCTGCGCGCTCTTTGTGCTGGTGGCTCCCAGCTGCGCCTACCAGGTGTGCGGGCCGCCGCTGTACCAGCTCGGCGCTGCCACTCAGGCCCGGCCCCCGCC
 L  V  H  L  L  A  R  C  A  L  F  V  L  V  A  P  S  C  A  Y  Q  V  C  G  P  P  L  Y  Q  L  G  A  A  T  Q  A  R  P  P  P

ACACGCTAGTGGACCCCGAAGGCGTCTGGGATGCGAACGGGCCTGGAACCATAGCGTCAGGGAGGCCGGGGTCCCCTGGGCCTGCCAGCCCCGGGTGCGAGGAGGCGCGGGGCAGTGC
 H  A  S  G  P  R  R  R  L  G  C  E  R  A  W  N  H  S  V  R  E  A  G  V  P  L  G  L  P  A  P  G  A  R  R  R  G  G  S  A

CAGCCGAAGTCTGCCGTTGCCCAAGAGGCCCAGGCGTGGCGCTGCCCCTGAGCCGGAGCGGACGCCCGTTGGGCAGGGGTCCTGGGCCCACCCGGGCAGGACGCGTGGACCGAGTGACCG
 S  R  S  L  P  L  P  K  R  P  R  R  G  A  A  P  E  P  E  R  T  P  V  G  Q  G  S  W  A  H  P  G  R  T  R  G  P  S  D  R

TGGTTTCTGTGTGGTGTCACCTGCCAGACCCGCCGAAGAAGCCACCTCTTTGGAGGGTGCGCTCTCTGGCACGCGCCACTCCCACCCATCCGTGGGCCGCCAGCACCACGCGGGCCCCC
 G  F  C  V  V  S  P  A  R  P  A  E  E  A  T  S  L  E  G  A  L  S  G  T  R  H  S  H  P  S  V  G  R  Q  H  H  A  G  P  P

ATCCACATCGCGGCCACCACGTCCCTGGGACACGCCTTGTCCCCCGGTGTACGCCGAGACCAAGCACTTCCTCTACTCCTCAGGCGACAAGGAGCAGCTGCGGCCCTCCTTCCTACTCAG
 S  T  S  R  P  P  R  P  W  D  T  P  C  P  P  V  Y  A  E  T  K  H  F  L  Y  S  S  G  D  K  E  Q  L  R  P  S  F  L  L  S

CTCTCTGAGGCCCAGCCTGACTGGCGCTCGGAGGCTCGTGGAGACCATCTTTCTGGGTTCCAGGCCCTGGATGCCAGGGACTCCCCGCAGGTTGCCCCGCCTGCCCCAGCGCTACTGGCA
 S  L  R  P  S  L  T  G  A  R  R  L  V  E  T  I  F  L  G  S  R  P  W  M  P  G  T  P  R  R  L  P  R  L  P  Q  R  Y  W  Q

AATGCGGCCCCTGTTTCTGGAGCTGCTTGGGAACCACGCGCAGTGCCCCTACGGGGTGCTCCTCAAGACGCACTGCCCGCTGCGAGCTGCGGTCACCCCAGCAGCCGGTGTCTGCCCG
 M  R  P  L  F  L  E  L  L  G  N  H  A  Q  C  P  Y  G  V  L  L  K  T  H  C  P  L  R  A  A  V  T  P  A  A  G  V  C  A  R

GGAGAAGCCCCAGGGCTCTGTGGCGGCCCCCGAGGAGGAGGACACAGACCCCCGTCGCCTGGTGCAGCTGCTCCGCCAGCACAGCAGCCCCTGGCAGGTGTACGGCTTCGTGCGGGCCTG
 E  K  P  Q  G  S  V  A  A  P  E  E  E  D  T  D  P  R  R  L  V  Q  L  L  R  Q  H  S  S  P  W  Q  V  Y  G  F  V  R  A  C

CCTGCGCCGGCTGGTGCCCCCAGGCCTCTGGGGCTCCAGGCACAACGAACGCCGCTTCCTCAGGAACACCAAGAAGTTCATCTCCCTGGGGAAGCATGCCAAGCTCTCGCTGCAGGAGCT
 L  R  R  L  V  P  P  G  L  W  G  S  R  H  N  E  R  R  F  L  R  N  T  K  K  F  I  S  L  G  K  H  A  K  L  S  L  Q  E  L
```

*Fig. 11X*

```
GACGTGGAAGATGAGCGTGCGGGACTGCGCTTGGCTGCGCAGGAGCCCAGGGGTTGGCTGTGTTCCGGCCGCAGAGCACCGTCTGCGTGAGGAGATCCTGGCCAAGTTCCTGCACTGGCT
 T  W  K  M  S  V  R  D  C  A  W  L  R  R  S  P  G  V  G  C  V  P  A  A  E  H  R  L  R  E  E  I  L  A  K  F  L  H  W  L

GATGAGTGTGTACGTCGTCGAGCTGCTCAGGTCTTTCTTTTATGTCACGGAGACCACGTTTCAAAAGAACAGGCTCTTTTTCTACCGGAAGAGTGTCTGGAGCAAGTTGCAAAGCATTGG
 M  S  V  Y  V  V  E  L  L  R  S  F  F  Y  V  T  E  T  T  F  Q  K  N  R  L  F  F  Y  R  K  S  V  W  S  K  L  Q  S  I  G

AATCAGACAGCACTTGAAGAGGGTGCAGCTGCGGGAGCTGTCGGAAGCAGAGGTCAGGCAGCATCGGGAAGCCAGGCCCGCCCTGCTGACGTCCAGACTCCGCTTCATCCCCAAGCCTGA
 I  R  Q  H  L  K  R  V  Q  L  R  E  L  S  E  A  E  V  R  Q  H  R  E  A  R  P  A  L  L  T  S  R  L  R  F  I  P  K  P  D

GTGGCTGTGCTTTGGTTTAACTTCCTTTTTAACCAGAA
                                                  V  A  V  L  W  F  T  F  L  F  N  Q  K
                                                                      |
CGGGCTGCGGCCCGATTGTGAACATGGACTACGTCGTGGGAGCCAGAACGTTCCGCAGAGAAAAGAGGGCCCGAGCGTCTCACCTCGAGGGTGAAGGCACTGTTCAGCGTGCTCAACTACGA
 G  L  R  P  I  V  N  M  D  Y  V  V  G  A  R  T  F  R  R  E  K  R  P  S  V  S  F  R  G  *
```

*Fig. 11Y*

Truncated protein 2 (ver. 2)

```
                                    ATGCCGCGCGCTCCCCGCTGCCGAGCCGTGCGCTCCCTGCTGCGCAGCCACTACCGCGAGGTGCTGCCGCTGGCCACGTTCGTG
                                    M  P  R  A  P  R  C  R  A  V  R  S  L  L  R  S  H  Y  R  E  V  L  P  L  A  T  F  V

CGGCGCCTGGGGCCCCAGGGCTGGCGGCTGGTGCAGCGCGGGGACCCGGCGGCTTTCCGCGCGCTGGTGGCCCAGTGCCTGGTGTGCGTGCCCTGGGACGCACGGCCGCCCCCCGCCGC
R  R  L  G  P  Q  G  W  R  L  V  Q  R  G  D  P  A  A  F  R  A  L  V  A  Q  C  L  V  C  V  P  W  D  A  R  P  P  P  A  A

GGCCTCCCCGGGGTCGGCGTCCGGCTGGGGTTGAGGGCGGCCGGGGGGAACCAGCGACATGCGGAGAGCAGCGCAGGCGACTCAGGGCGCTTCCCCCGCAGGTG
            G  L  P  G  V  G  V  R  L  G  L  R  A  A  G  G  N  Q  R  H  A  E  S  S  A  G  D  S  G  R  F  P  R  R
            A  S  P  G  S  A  S  G  W  G  *  G  R  P  G  G  T  S  D  M  R  R  A  A  Q  A  T  Q  G  A  S  P  A  G
               P  P  R  G  R  R  P  A  G  V  E  G  G  R  G  E  P  A  T  C  G  E  Q  R  R  R  L  R  A  L  P  P  Q  V
CCCCTCCTTCCGCCAGGTGTCCTGCCTGAAGGAGCTGGTGGCCCGAGTGCTGCAGAGGCTGTGCGAGCGCGGCGCGAAGAACGTGCTGGCCTTCGGCTTCGCGCTGCTGGACGGGGCCCG
P  S  F  R  Q  V  S  C  L  K  E  L  V  A  R  V  L  Q  R  L  C  E  R  G  A  K  N  V  L  A  F  G  F  A  L  L  D  G  A  R

CGGGGGCCCCCCCGAGGCCTTCACCACCAGCGTGCGCAGCTACCTGCCCAACACGGTGACCGACGCACTGCGCGGGGAGCGGGGCGTGGGGGCTGCTGCTGCGCCGCGTGGGCGACGACGT
G  G  P  P  E  A  F  T  T  S  V  R  S  Y  L  P  N  T  V  T  D  A  L  R  G  S  G  A  W  G  L  L  L  R  R  V  G  D  D  V

GCTGGTTCACCTGCTGGCACGCTGCGCGCTCTTTGTGCTGGTGGCTCCCAGCTGCGCCTACCAGGTGTGCGGGCCGCCGCTGTACCAGCTCGGCGCTGCCACTCAGGCCCGGCCCCCGCC
L  V  H  L  L  A  R  C  A  L  F  V  L  V  A  P  S  C  A  Y  Q  V  C  G  P  P  L  Y  Q  L  G  A  A  T  Q  A  R  P  P  P

ACACGCTAGTGGACCCCGAAGGCGTCTGGGATGCGAACGGGCCTGGAACCATAGCGTCAGGGAGGCCGGGGTCCCCTGGGCCTGCCAGCCCCGGGTGCGAGGAGGCGCGGGGGCAGTGC
H  A  S  G  P  R  R  R  L  G  C  E  R  A  W  N  H  S  V  R  E  A  G  V  P  L  G  L  P  A  P  G  A  R  R  R  G  G  S  A

CAGCCGAAGTCTGCCGTTGCCCAAGAGGCCCAGGCGTGGCGCTGCCCCTGAGCCGGAGCGGACGCCCGTTGGGCAGGGGTCCTGGGCCCACCCGGGCAGGACGCGTGGACCGAGTGACCG
S  R  S  L  P  L  P  K  R  P  R  R  G  A  A  P  E  P  E  R  T  P  V  G  Q  G  S  W  A  H  P  G  R  T  R  G  P  S  D  R

TGGTTTCTGTGTGGTGTCACCTGCCAGACCCGCCGAAGAAGCCACCTCTTTGGAGGGTGCGCTCTCTGGCACGCGCCACTCCCACCCATCCGTGGGCCGCCAGCACCACGCGGGCCCCC
G  F  C  V  V  S  P  A  R  P  A  E  E  A  T  S  L  E  G  A  L  S  G  T  R  H  S  H  P  S  V  G  R  Q  H  H  A  G  P  P

ATCCACATCGCGGCCACCACGTCCCTGGGACACGCCTTGTCCCCCGGTGTACGCCGAGACCAAGCACTTCCTCTACTCCTCAGGCGACAAGGAGCAGCTGCGGCCCTCCTTCCTACTCAG
S  T  S  R  P  P  R  P  W  D  T  P  C  P  P  V  Y  A  E  T  K  H  F  L  Y  S  S  G  D  K  E  Q  L  R  P  S  F  L  L  S

CTCTCTGAGGCCCAGCCTGACTGGCGCTCGGAGGCTCGTGGAGACCATCTTTCTGGGTTCCAGGCCCTGGATGCCAGGGACTCCCCGCAGGTTGCCCCGCCTGCCCCAGCGCTACTGGCA
S  L  R  P  S  L  T  G  A  R  R  L  V  E  T  I  F  L  G  S  R  P  W  M  P  G  T  P  R  R  L  P  R  L  P  Q  R  Y  W  Q

AATGCGGCCCCTGTTTCTGGAGCTGCTTGGGAACCACGCCAGTGCCCCTACGGGGTGCTCCTCAAGACGCACTGCCCGCTGCGAGCTGCGGTCACCCCAGCAGCCGGTGTCTGTGCCCG
N  R  P  L  F  L  E  L  L  G  N  H  A  Q  C  P  Y  G  V  L  L  K  T  H  C  P  L  R  A  A  V  T  P  A  A  G  V  C  A  R

GGAGAAGCCCCAGGGCTCTGTGGCGGCCCCCGAGGAGGAGGACACAGACCCCCGTCGCCTGGTGCAGCTGCTCCGCCAGCACAGCAGCCCCTGGCAGGTGTACGGCTTCGTGCGGGCCTG
E  K  P  Q  G  S  V  A  A  P  E  E  E  D  T  D  P  R  R  L  V  Q  L  L  R  Q  H  S  S  P  W  Q  V  Y  G  F  V  R  A  C

CCTGCGCCGGCTGGTGCCCCCAGGCCTCTGGGGCTCCAGGCACAACGAACGCCGCTTCCTCAGGAACACCAAGAAGTTCATCTCCCTGGGGAAGCATGCCAAGCTCTCGCTGCAGGAGCT
L  R  R  L  V  P  P  G  L  W  G  S  R  H  N  E  R  R  F  L  R  N  T  K  K  F  I  S  L  G  K  H  A  K  L  S  L  Q  E  L
```

*Fig. 11Z*

```
GACGTGGAAGATGAGCGTGCGGGACTGCGCTTGGCTGCGCAGGAGCCCAGGGGTTGGCTGTGTTCCGGCCGCAGAGCACCGTCTGCGTGAGGAGATCCTGGCCAAGTTCCTGCACTGGCT
 T  W  K  M  S  V  R  D  C  A  W  L  R  R  S  P  G  V  G  C  V  P  A  A  E  H  R  L  R  E  E  I  L  A  K  F  L  H  W  L

GATGAGTGTGTACGTCGTCGAGCTGCTCAGGTCTTTCTTTTATGTCACGGAGACCACGTTTCAAAAGAACAGGCTCTTTTTCTACCGGAAGAGTGTCTGGAGCAAGTTGCAAAGCATTGG
 M  S  V  Y  V  V  E  L  L  R  S  F  F  Y  V  T  E  T  T  F  Q  K  N  R  L  F  F  Y  R  K  S  V  W  S  K  L  Q  S  I  G

AATCAGACAGCACTTGAAGAGGGTGCAGCTGCGGGAGCTGTCGGAAGCAGAGGTCAGGCAGCATCGGGAAGCCAGGCCCGCCCTGCTGACGTCCAGACTCCGCTTCATCCCCAAGCCTGA
 I  R  Q  H  L  K  R  V  Q  L  R  E  L  S  E  A  E  V  R  Q  H  R  E  A  R  P  A  L  L  T  S  R  L  R  F  I  P  K  P  D

CGGGCTGCGGCCGATTGTGAACATGGACTACGTCGTGGGAGCCAGAACGTTCCGCAGAGAAAAGAGGGCCGAGCGTCTCACCTCGAGGGTGAAGGCACTGTTCAGCGTGCTCAACTACGA
 G  L  R  P  I  V  N  M  D  Y  V  V  G  A  R  T  F  R  R  E  K  R  A  E  R  L  T  S  R  V  K  A  L  F  S  V  L  N  Y  E

GCGGGCGCGGCCGCCCCGGCCTCCTGGGCGCCTCTGTGCTGGGCCTGGACGATATCCACAGGGCCTGGCGCACCTTCGTGCTGCGTGTGCGGGCCCAGGACCCGCCGCCTGAGCTGTACTT
 R  A  R  R  P  G  L  L  G  A  S  V  L  G  L  D  D  I  H  R  A  W  R  T  F  V  L  R  V  R  A  Q  D  P  P  P  E  L  Y  F

TGTCAAGGTGGATGTGACGGGCGCGTACGACACCATCCCCCAGGACAGGCTCACGGAGGTCATCGCCAGCATCATCAAACCCCAGAACACGTACTGCGTGCGTCGGTATGCCGTGGTCCA
 V  K  V  D  V  T  G  A  Y  D  T  I  P  Q  D  R  L  T  E  V  I  A  S  I  I  K  P  Q  N  T  Y  C  V  R  R  Y  A  V  V  Q

GAAGGCCGCCCATGGGCACGTCCGCAAGGCCTTCAAGAGCCAC
 K  A  A  H  G  H  V  R  K  A  F  K  S  H

GTCCTACGTCCAGTG
                                                                                                       V  L  R  P  V

CCAGGGGATCCCGCAGGGCTCCATCCTCTCCACGCTGCTCTGCAGCCTGTGCTACGGCGACATGGAGAACAAGCTGTTTGCGGGGATTCGGCGGGACGGGCTGCTCCTGCGTTTGGTGGA
 P  G  D  P  A  G  L  H  P  L  H  A  A  L  Q  P  V  L  R  R  H  G  E  Q  A  V  C  G  D  S  A  G  R  A  A  P  A  F  G  G

TGATTTCTTGTTGGTGACACCTCACCTCACCCACGCGAAAACCTTCCTCAGGACCCTGGTCCGAGGTGTCCCTGAGTATGGCTGCGTGGTGAACTTGCGGAAGACAGTGGTGAACTTCCC
 *
```

Fig. 11AA

Reference protein (ver. 2)

```
ATGCCGCGCGCTCCCCGCTGCCGAGCCGTGCGCTCCCTGCTGCGCAGCCACTACCGCGAG      60
MetProArgAlaProArgCysArgAlaValArgSerLeuLeuArgSerHisTyrArgGlu      20

GTGCTGCCGCTGGCCACGTTCGTGCGGCGCCTGGGGCCCCAGGGCTGGCGGCTGGTGCAG     120
ValLeuProLeuAlaThrPheValArgArgLeuGlyProGlnGlyTrpArgLeuValGln      40

CGCGGGGACCCGGCGGCTTTCCGCGCGCTGGTGGCCCAGTGCCTGGTGTGCGTGCCCTGG     180
ArgGlyAspProAlaAlaPheArgAlaLeuValAlaGlnCysLeuValCysValProTrp      60

GACGCACGGCCGCCCCCCGCCGCCCCCTCCTTCCGCCAGGTG
AspAlaArgProProProAlaAlaProSerPheArgGlnVal

GGCCTCCCCGGGGTCGGCGTCCGGCTGGGGTTGAGGGCGGCCGGGGGGAACCAGCGACATGCGGAG
G  L  P  G  V .G  V  R  L  G  L  R  A  A  G  G  N  Q  R  H  A  E
 A  S  P  G  S  A  S  G  W  G  *  G  R  P  G  G  T  S  D  M  R  R
  P  P  R  G  R  R  P  A  G  V  E  G  G  R  G  E  P  A  T  C  G  E

AGCAGCGCAGGCGACTCAGGGCGCTTCCCCCGCAGGTG
S  S  A  G  D  S  G  R  F  P  R  R
 A  A  Q  A  T  Q  G  A  S  P  A  G
  Q  R  R  R  L  R  A  L  P  P  Q  V

TCCTGCCTGAAGGAGCTG      240
SerCysLeuLysGluLeu       80

GTGGCCCGAGTGCTGCAGAGGCTGTGCGAGCGCGGCGCGAAGAACGTGCTGGCCTTCGGC     300
ValAlaArgValLeuGlnArgLeuCysGluArgGlyAlaLysAsnValLeuAlaPheGly     100

TTCGCGCTGCTGGACGGGGCCCGCGGGGGCCCCCCCGAGGCCTTCACCACCAGCGTGCGC     360
PheAlaLeuLeuAspGlyAlaArgGlyGlyProProGluAlaPheThrThrSerValArg     120

AGCTACCTGCCCAACACGGTGACCGACGCACTGCGGGGGAGCGGGGCGTGGGGGCTGCTG     420
SerTyrLeuProAsnThrValThrAspAlaLeuArgGlySerGlyAlaTrpGlyLeuLeu     140

TTGCGCCGCGTGGGCGACGACGTGCTGGTTCACCTGCTGGCACGCTGCGCGCTCTTTGTG     480
LeuArgArgValGlyAspAspValLeuValHisLeuLeuAlaArgCysAlaLeuPheVal     160

CTGGTGGCTCCCAGCTGCGCCTACCAGGTGTGCGGGCCGCCGCTGTACCAGCTCGGCGCT     540
LeuValAlaProSerCysAlaTyrGlnValCysGlyProProLeuTyrGlnLeuGlyAla     180

GCCACTCAGGCCCGGCCCCCGCCACACGCTAGTGGACCCCGAAGGCGTCTGGGATGCGAA     600
AlaThrGlnAlaArgProProProHisAlaSerGlyProArgArgArgLeuGlyCysGlu     200
```

*Fig. 11AB*

| | |
|---|---|
| CGGGCCTGGAACCATAGCGTCAGGGAGGCCGGGGTCCCCCTGGGCCTGCCAGCCCCGGGT | 660 |
| ArgAlaTrpAsnHisSerValArgGluAlaGlyValProLeuGlyLeuProAlaProGly | 220 |
| | |
| GCGAGGAGGCGCGGGGGCAGTGCCAGCCGAAGTCTGCCGTTGCCCAAGAGGCCCAGGCGT | 720 |
| AlaArgArgArgGlyGlySerAlaSerArgSerLeuProLeuProLysArgProArgArg | 240 |
| | |
| GGCGCTGCCCCTGAGCCGGAGCGGACGCCCGTTGGGCAGGGGTCCTGGGCCCACCCGGGC | 780 |
| GlyAlaAlaProGluProGluArgThrProValGlyGlnGlySerTrpAlaHisProGly | 260 |
| | |
| AGGACGCGTGGACCGAGTGACCGTGGTTTCTGTGTGGTGTCACCTGCCAGACCCGCCGAA | 840 |
| ArgThrArgGlyProSerAspArgGlyPheCysValValSerProAlaArgProAlaGlu | 280 |
| | |
| GAAGCCACCTCTTTGGAGGGTGCGCTCTCTGGCACGCGCCACTCCCACCCATCCGTGGGC | 900 |
| GluAlaThrSerLeuGluGlyAlaLeuSerGlyThrArgHisSerHisProSerValGly | 300 |
| | |
| CGCCAGCACCACGCGGGCCCCCCATCCACATCGCGGCCACCACGTCCCTGGGACACGCCT | 960 |
| ArgGlnHisHisAlaGlyProProSerThrSerArgProProArgProTrpAspThrPro | 320 |
| | |
| TGTCCCCCGGTGTACGCCGAGACCAAGCACTTCCTCTACTCCTCAGGCGACAAGGAGCAG | 1020 |
| CysProProValTyrAlaGluThrLysHisPheLeuTyrSerSerGlyAspLysGluGln | 340 |
| | |
| CTGCGGCCCTCCTTCCTACTCAGCTCTCTGAGGCCCAGCCTGACTGGCGCTCGGAGGCTC | 1080 |
| LeuArgProSerPheLeuLeuSerSerLeuArgProSerLeuThrGlyAlaArgArgLeu | 360 |
| | |
| GTGGAGACCATCTTTCTGGGTTCCAGGCCCTGGATGCCAGGGACTCCCCGCAGGTTGCCC | 1140 |
| ValGluThrIlePheLeuGlySerArgProTrpMetProGlyThrProArgArgLeuPro | 380 |
| | |
| CGCCTGCCCCAGCGCTACTGGCAAATGCGGCCCCTGTTTCTGGAGCTGCTTGGGAACCAC | 1200 |
| ArgLeuProGlnArgTyrTrpGlnMetArgProLeuPheLeuGluLeuLeuGlyAsnHis | 400 |
| | |
| GCGCAGTGCCCCTACGGGGTGCTCCTCAAGACGCACTGCCCGCTGCGAGCTGCGGTCACC | 1260 |
| AlaGlnCysProTyrGlyValLeuLeuLysThrHisCysProLeuArgAlaAlaValThr | 420 |
| | |
| CCAGCAGCCGGTGTCTGTGCCCGGGAGAAGCCCCAGGGCTCTGTGGCGGCCCCCGAGGAG | 1320 |
| ProAlaAlaGlyValCysAlaArgGluLysProGlnGlySerValAlaAlaProGluGlu | 440 |
| | |
| GAGGACACAGACCCCCGTCGCCTGGTGCAGCTGCTCCGCCAGCACAGCAGCCCCTGGCAG | 1380 |
| GluAspThrAspProArgArgLeuValGlnLeuLeuArgGlnHisSerSerProTrpGln | 460 |
| | |
| GTGTACGGCTTCGTGCGGGCCTGCCTGCGCCGGCTGGTGCCCCCAGGCCTCTGGGGCTCC | 1440 |
| ValTyrGlyPheValArgAlaCysLeuArgArgLeuValProProGlyLeuTrpGlySer | 480 |
| | |
| AGGCACAACGAACGCCGCTTCCTCAGGAACACCAAGAAGTTCATCTCCCTGGGGAAGCAT | 1500 |
| ArgHisAsnGluArgArgPheLeuArgAsnThrLysLysPheIleSerLeuGlyLysHis | 500 |
| | |
| GCCAAGCTCTCGCTGCAGGAGCTGACGTGGAAGATGAGCGTGCGGGGCTGCGCTTGGCTG | 1560 |
| AlaLysLeuSerLeuGlnGluLeuThrTrpLysMetSerValArgAspCysAlaTrpLeu | 520 |

*Fig. 11AC*

```
CGCAGGAGCCCAGGGGTTGGCTGTGTTCCGGCCGCAGAGCACCGTCTGCGTGAGGAGATC    1620
ArgArgSerProGlyValGlyCysValProAlaAlaGluHisArgLeuArgGluGluIle     540

CTGGCCAAGTTCCTGCACTGGCTGATGAGTGTGTACGTCGTCGAGCTGCTCAGGTCTTTC    1680
LeuAlaLysPheLeuHisTrpLeuMetSerValTyrValValGluLeuLeuArgSerPhe     560

TTTTATGTCACGGAGACCACGTTTCAAAAGAACAGGCTCTTTTTCTACCGGAAGAGTGTC    1740
PheTyrValThrGluThrThrPheGlnLysAsnArgLeuPhePheTyrArgLysSerVal     580

TGGAGCAAGTTGCAAAGCATTGGAATCAGACAGCACTTGAAGAGGGTGCAGCTGCGGGAG    1800
TrpSerLysLeuGlnSerIleGlyIleArgGlnHisLeuLysArgValGlnLeuArgGlu     600

CTGTCGGAAGCAGAGGTCAGGCAGCATCGGGAAGCCAGGCCCGCCCTGCTGACGTCCAGA    1860
LeuSerGluAlaGluValArgGlnHisArgGluAlaArgProAlaLeuLeuThrSerArg    620

CTCCGCTTCATCCCCAAGCCTGACGGGCTGCGGCCGATTGTGAACATGGACTACGTCGTG    1920
LeuArgPheIleProLysProAspGlyLeuArgProIleValAsnMetAspTyrValVal     640

GGAGCCAGAACGTTCCGCAGAGAAAAGAGGGCCGAGCGTCTCACCTCGAGGGTGAAGGCA    1980
GlyAlaArgThrPheArgArgGluLysArgAlaGluArgLeuThrSerArgValLysAla    660

CTGTTCAGCGTGCTCAACTACGAGCGGGCGCGGCGCCCCGGCCTCCTGGGCGCCTCTGTG    2040
LeuPheSerValLeuAsnTyrGluArgAlaArgArgProGlyLeuLeuGlyAlaSerVal     680

CTGGGCCTGGACGATATCCACAGGGCCTGGCGCACCTTCGTGCTGCGTGTGCGGGCCCAG    2100
LeuGlyLeuAspAspIleHisArgAlaTrpArgThrPheValLeuArgValArgAlaGln    700

GACCCGCCGCCTGAGCTGTACTTTGTCAAGGTGGATGTGACGGGCGCGTACGACACCATC    2160
AspProProProGluLeuTyrPheValLysValAspValThrGlyAlaTyrAspThrIle    720

CCCCAGGACAGGCTCACGGAGGTCATCGCCAGCATCATCAAACCCCAGAACACGTACTGC    2220
ProGlnAspArgLeuThrGluValIleAlaSerIleIleLysProGlnAsnThrTyrCys    740

GTGCGTCGGTATGCCGTGGTCCAGAAGGCCGCCCATGGGCACGTCCGCAAGGCCTTCAAG    2280
ValArgArgTyrAlaValValGlnLysAlaAlaHisGlyHisValArgLysAlaPheLys    760

AGCCACGTCTCTACCTTGACAGACCTCCAGCCGTACATGCGACAGTTCGTGGCTCACCTG    2340
SerHisValSerThrLeuThrAspLeuGlnProTyrMetArgGlnPheValAlaHisLeu    780

CAGGAGACCAGCCCGCTGAGGGATGCCGTCGTCATCGAGCAGAGCTCCTCCCTGAATGAG    2400
GlnGluThrSerProLeuArgAspAlaValValIleGluGlnSerSerSerLeuAsnGlu    800

GCCAGCAGTGGCCTCTTCGACGTCTTCCTACGCTTCATGTGCCACCACGCCGTGCGCATC    2460
AlaSerSerGlyLeuPheAspValPheLeuArgPheMetCysHisHisAlaValArgIle    820

AGGGGCAAGTCCTACGTCCAGTGCCAGGGGATCCCGCAGGGCTCCATCCTCTCCACGCTG    2520
ArgGlyLysSerTyrValGlnCysGlnGlyIleProGlnGlySerIleLeuSerThrLeu    840
```

*Fig. 11AD*

```
CTCTGCAGCCTGTGCTACGGCGACATGGAGAACAAGCTGTTTGCGGGGATTCGGCGGGAC    2580
LeuCysSerLeuCysTyrGlyAspMetGluAsnLysLeuPheAlaGlyIleArgArgAsp     860

GGGCTGCTCCTGCGTTTGGTGGATGATTTCTTGTTGGTGACACCTCACCTCACCCACGCG    2640
GlyLeuLeuLeuArgLeuValAspAspPheLeuLeuValThrProHisLeuThrHisAla     880

AAAACCTTCCTCAGGACCCTGGTCCGAGGTGTCCCTGAGTATGGCTGCGTGGTGAACTTG    2700
LysThrPheLeuArgThrLeuValArgGlyValProGluTyrGlyCysValValAsnLeu     900

CGGAAGACAGTGGTGAACTTCCCTGTAGAAGACGAGGCCCTGGGTGGCACGGCTTTTGTT    2760
ArgLysThrValValAsnPheProValGluAspGluAlaLeuGlyGlyThrAlaPheVal     920

CAGATGCCGGCCCACGGCCTATTCCCCTGGTGCGGCCTGCTGCTGGATACCCGGACCCTG    2820
GlnMetProAlaHisGlyLeuPheProTrpCysGlyLeuLeuLeuAspThrArgThrLeu     940

GAGGTGCAGAGCGACTACTCCAGCTATGCCCGGACCTCCATCAGAGCCAGTCTCACCTTC    2880
GluValGlnSerAspTyrSerSerTyrAlaArgThrSerIleArgAlaSerLeuThrPhe     960

AACCGCGGCTTCAAGGCTGGGAGGAACATGCGTCGCAAACTCTTTGGGGTCTTGCGGCTG    2940
AsnArgGlyPheLysAlaGlyArgAsnMetArgArgLysLeuPheGlyValLeuArgLeu     980

AAGTGTCACAGCCTGTTTCTGGATTTGCAGGTGAACAGCCTCCAGACGGTGTGCACCAAC    3000
LysCysHisSerLeuPheLeuAspLeuGlnValAsnSerLeuGlnThrValCysThrAsn    1000

ATCTACAAGATCCTCCTGCTGCAGGCGTACAGGTTTCACGCATGTGTGCTGCAGCTCCCA    3060
IleTyrLysIleLeuLeuLeuGlnAlaTyrArgPheHisAlaCysValLeuGlnLeuPro    1020

TTTCATCAGCAAGTTTGGAAGAACCCCACATTTTTCCTGCGCGTCATCTCTGACACGGCC    3120
PheHisGlnGlnValTrpLysAsnProThrPhePheLeuArgValIleSerAspThrAla    1040

TCCCTCTGCTACTCCATCCTGAAAGCCAAGAACGCAGGGATGTCGCTGGGGGCCAAGGGC    3180
SerLeuCysTyrSerIleLeuLysAlaLysAsnAlaGlyMetSerLeuGlyAlaLysGly    1060

GCCGCCGGCCCTCTGCCCTCCGAGGCCGTGCAGTGGCTGTGCCACCAAGCATTCCTGCTC    3240
AlaAlaGlyProLeuProSerGluAlaValGlnTrpLeuCysHisGlnAlaPheLeuLeu    1080

AAGCTGACTCGACACCGTGTCACCTACGTGCCACTCCTGGGGTCACTCAGGACAGCCCAG    3300
LysLeuThrArgHisArgValThrTyrValProLeuLeuGlySerLeuArgThrAlaGln    1100

ACGCAGCTGAGTCGGAAGCTCCCGGGGACGACGCTGACTGCCCTGGAGGCCGCAGCCAAC    3360
ThrGlnLeuSerArgLysLeuProGlyThrThrLeuThrAlaLeuGluAlaAlaAlaAsn    1120

CCGGCACTGCCCTCAGACTTCAAGACCATCCTGGAC                            3420
ProAlaLeuProSerAspPheLysThrIleLeuAsp                            1132
```

*Fig. 11AE*

Truncated protein 3 (ver. 2)

```
                                 ATGCCGCGCGCTCCCCGCTGCCGAGCCGTGCGCTCCCTGCTGCGCAGCCACTACCGCGAGGTGCTGCCGCTGGCCACGTTCGTG
                                  M P R A P R C R A V R S L L R S H Y R E V L P L A T F V

CGGCGCCTGGGGCCCCAGGGCTGGCGGCTGGTGCAGCGCGGGGACCCGGCGGCTTTCCGCGCGCTGGTGGCCCAGTGCCTGGTGTGCGTGCCCTGGGACGCACGGCCGCCCCCGCCGC
 R R L G P Q G W R L V Q R G D P A A F R A L V A Q C L V C V P W D A R P P P A A

GGCCTCCCCGGGGTCGGCGTCCGGCTGGGGTTGAGGGCGGCCGGGGGGAACCAGCGACATGCGGAGAGCAGCGCAGGCGACTCAGGGCGCTTCCCCCGCAGGTG
                         G L P G V G V R L G L R A A G G N Q R H A E S S A G D S G R F P R R
                         A S P G S A S G W G * G R P G G T S D M R R A A Q A T Q G A S P A G
                         P P R G R R P A G V E G G R G E P A T C G E Q R R R L R A L P P Q V
                         |.
CCCCTCCTTCCGCCAGGTGTCCTGCCTGAAGGAGCTGGTGGCCCGAGTGCTGCAGAGGCTGTGCGAGCGCGGCGCGAAGAACGTGCTGGCCTTCGGCTTCGCGCTGCTGGACGGGGCCCG
 P S F R Q V S C L K E L V A R V L Q R L C E R G A K N V L A F G F A L L D G A R

CGGGGGCCCCCCGAGGCCTTCACCACCAGCGTGCGCAGCTACCTGCCCAACACGGTGACCGACGCACTGCGGGGGAGCGGGGCGTGGGGGCTGCTGCTGCGCCGCGTGGGCGACGACGT
 G G P P E A F T T S V R S Y L P N T V T D A L R G S G A W G L L L R R V G D D V

GCTGGTTCACCTGCTGGCACGCTGCGCGCTCTTTGTGCTGGTGGCTCCCAGCTGCGCCTACCAGGTGTGCGGGCCGCCGCTGTACCAGCTCGGCGCTGCCACTCAGGCCCGGCCCCCGCC
 L V H L L A R C A L F V L V A P S C A Y Q V C G P P L Y Q L G A A T Q A R P P P

ACACGCTAGTGGACCCCGAAGGCGTCTGGGATGCGAACGGGCCTGGAACCATAGCGTCAGGGAGGCCGGGGTCCCCCTGGGCCTGCCAGCCCCGGGTGCGAGGAGGCGCGGGGCAGTGC
 H A S G P R R R L G C E R A W N H S V R E A G V P L G L P A P G A R R R G G S A

CAGCCGAAGTCTGCCGTTGCCCAAGAGGCCCAGGCGTGGCGCTGCCCCTGAGCCGGAGCGGACGCCCGTTGGGCAGGGGTCCTGGGCCCACCCGGGCAGGACGCGTGGACCGAGTGACCG
 S R S L P L P K R P R R G A A P E P E R T P V G Q G S W A H P G R T R G P S D R

TGGTTTCTGTGTGGTGTCACCTGCCAGACCCGCCGAAGAAGCCACCTCTTTGGAGGGTGCGCTCTCTGGCACGCGCCACTCCCACCCATCCGTGGGCCGCCAGCACCACGCGGGCCCCCC
 G F C V V S P A R P A E E A T S L E G A L S G T R H S H P S V G R Q H H A G P P

ATCCACATCGCGGCCACCACGTCCCTGGGACACGCCTTGTCCCCCGGTGTACGCCGAGACCAAGCACTTCCTCTACTCCTCAGGCGACAAGGAGCAGCTGCGGCCCTCCTTCCTACTCAG
 S T S R P P R P W D T P C P P V Y A E T K H F L Y S S G D K E Q L R P S F L L S

CTCTCTGAGGCCCAGCCTGACTGGCGCTCGGAGGCTCGTGGAGACCATCTTTCTGGGTTCCAGGCCCTGGATGCCAGGGACTCCCCGCAGGTTGCCCCGCCTGCCCCAGCGCTACTGGCA
 S L R P S L T G A R R L V E T I F L G S R P W M P G T P R R L P R L P Q R Y W Q

AATGCGGCCCCTGTTTCTGGAGCTGCTTGGGAACCACGCGCAGTGCCCCTACGGGGTGCTCCTCAAGACGCACTGCCCGCTGCGAGCTGCGGTCACCCCAGCAGCCGGTGTCTGTGCCCG
 M R P L F L E L L G N H A Q C P Y G V L L K T H C P L R A A V T P A A G V C A R

GGAGAAGCCCCAGGGCTCTGTGGCGGCCCCCGAGGAGGAGGACACAGACCCCCGTCGCCTGGTGCAGCTGCTCCGCCAGCACAGCAGCCCCTGGCAGGTGTACGGCTTCGTGCGGGCCTG
 E K P Q G S V A A P E E E D T D P R R L V Q L L R Q H S S P W Q V Y G F V R A C

CCTGCGCCGGCTGGTGCCCCCAGGCCTCTGGGGCTCCAGGCACAACGAACGCCGCTTCCTCAGGAACACCAAGAAGTTCATCTCCCTGGGGAAGCATGCCAAGCTCTCGCTGCAGGAGCT
 L R R L V P P G L W G S R H N E R R F L R N T K K F I S L G K H A K L S L Q E L
```

*Fig. 11AF*

```
GACGTGGAAGATGAGCGTGCGGGACTGCGCTTGGCTGCGCAGGAGCCCAGGGGTTGGCTGTGTTCCGGCCGCAGAGCACCGTCTGCGTGAGGAGATCCTGGCCAAGTTCCTGCACTGGCT
 T  W  K  M  S  V  R  D  C  A  W  L  R  R  S  P  G  V  G  C  V  P  A  A  E  H  R  L  R  E  E  I  L  A  K  F  L  H  W  L

GATGAGTGTGTACGTCGTCGAGCTGCTCAGGTCTTTCTTTTATGTCACGGAGACCACGTTTCAAAAGAACAGGCTCTTTTTCTACCGGAAGAGTGTCTGGAGCAAGTTGCAAAGCATTGG
 M  S  V  Y  V  V  E  L  L  R  S  F  F  Y  V  T  E  T  T  F  Q  K  N  R  L  F  F  Y  R  K  S  V  W  S  K  L  Q  S  I  G

AATCAGACAGCACTTGAAGAGGGTGCAGCTGCGGGAGCTGTCGGAAGCAGAGGTCAGGCAGCATCGGGAAGCCAGGCCCGCCCTGCTGACGTCCAGACTCCGCTTCATCCCCAAGCCTGA
 I  R  Q  H  L  K  R  V  Q  L  R  E  L  S  E  A  E  V  R  Q  H  R  E  A  R  P  A  L  L  T  S  R  L  R  F  I  P  K  P  D

CGGGCTGCGGCCGATTGTGAACATGGACTACGTCGTGGGAGCCAGAACGTTCCGCAGAGAAAAGAGGGCCGAGCGTCTCACCTCGAGGGTGAAGGCACTGTTCAGCGTGCTCAACTACGA
 G  L  R  P  I  V  N  M  D  Y  V  V  G  A  R  T  F  R  R  E  K  R  A  E  R  L  T  S  R  V  K  A  L  F  S  V  L  N  Y  E

GCGGGCGCGGCGCCCCGGCCTCCTGGGCGCCTCTGTGCTGGGCCTGGACGATATCCACAGGGCCTGGCGCACCTTCGTGCTGCGTGTGCGGGCCCAGGACCCGCCGCCTGAGCTGTACTT
 R  A  R  R  P  G  L  L  G  A  S  V  L  G  L  D  D  I  H  R  A  W  R  T  F  V  L  R  V  R  A  Q  D  P  P  P  E  L  Y  F

TGTCAAGGTGGATGTGACGGGCGCGTACGACACCATCCCCCAGGACAGGCTCACGGAGGTCATCGCCAGCATCATCAAACCCCAGAACACGTACTGCGTGCGTCGGTATGCCGTGGTCCA
 V  K  V  D  V  T  G  A  Y  D  T  I  P  Q  D  R  L  T  E  V  I  A  S  I  I  K  P  Q  N  T  Y  C  V  R  R  Y  A  V  V  Q

GAAGGCCGCCCATGGGCACGTCCGCAAGGCCTTCAAGAGCCACGTCTCTACCTTGACAGACCTCCAGCCGTACATGCGACAGTTCGTGGCTCACCTGCAGGAGACCAGCCCGCTGAGGGA
 K  A  A  H  G  H  V  R  K  A  F  K  S  H  V  S  T  L  T  D  L  Q  P  Y  M  R  Q  F  V  A  H  L  Q  E  T  S  P  L  R  D

TGCCGTCGTCATCGAGCAGAGCTCCTCCCTGAATGAGGCCAGCAGTGGCCTCTTCGACGTCTTCCTACGCTTCATGTGCCACCACGCCGTGCGCATCAGGGGCAAGTCCTACGTCCAGTG
 A  V  V  I  E  Q  S  S  S  L  N  E  A  S  S  G  L  F  D  V  F  L  R  F  M  C  H  H  A  V  R  I  R  G  K  S  Y  V  Q  C

CCAGGGGATCCCGCAGGGCTCCATCCTCTCCACGCTGCTCTGCAGCCTGTGCTACGGCGACATGGAGAACAAGCTGTTTGCGGGGATTCGGCGGGACGGGCTGCTCCTGCGTTTGGTGGA
 Q  G  I  P  Q  G  S  I  L  S  T  L  L  C  S  L  C  Y  G  D  M  E  N  K  L  F  A  G  I  R  R  D  G  L  L  L  R  L  V  D

TGATTTCTTGTTGGTGACACCTCACCTCACCCACGCGAAAACCTTCCTCAGGACCCTGGTCCGAGGTGTCCCTGAGTATGGCTGCGTGGTGAACTTGCGGAAGACAGTGGTGAACTTCCC
 D  F  L  L  V  T  P  H  L  T  H  A  K  T  F  L  R  T  L  V  R  G  V  P  E  Y  G  C  V  V  N  L  R  K  T  V  V  N  F  P

TGTAGAAGACGAGGCCCTGGGTGGCACGGCTTTTGTTCAGATGCCGGCCCACGGCCTATTCCCCTGGTGCGGCCTGCTGCTGGATACCCGGACCCTGGAGGTGCAGAGCGACTACTCCAG
 V  E  D  E  A  L  G  G  T  A  F  V  Q  M  P  A  H  G  L  F  P  W  C  G  L  L  L  D  T  R  T  L  E  V  Q  S  D  Y  S  R

GTGAGCGCACCTGGCCGGAAGTGGAGCCTGTGCCCGGCTGGGGCAGGTGCTGCTGCAGGGCCGTTGCGTCCACCTCTGCTTCCGTGTGGGGCAGGCGACTGCCAATCCCAAAGGGTCAGA
 *

TGCCACAGGGTGCCCCTCGTCCCATCTGGGGCTGAGCACAAATGCATCTTTCTGTGGGAGTGAGGGTGCCTCACAACGGGAGCAGTTTTCTGTGCTATTTTGGTAA—
```

*Fig. 11AG*

Altered C-terminus protein (ver. 2)

```
                            ATGCCGCGCGCTCCCCGCTGCCGAGCCGTGCGCTCCCTGCTGCGCAGCCACTACCGCGAGGTGCTGCCGCTGGCCACGTTCGTG
                            M P R A P R C R A V R S L L R S H Y R E V L P L A T F V

CGGCGCCTGGGGCCCCAGGGCTGGCGGCTGGTGCAGCGCGGGGACCCGGCGGCTTTCCGCGCGCTGGTGGCCCAGTGCCTGGTGTGCGTGCCCTGGGACGCACGGCCGCCCCCCGCCGC
R R L G P Q G W R L V Q R G D P A A F R A L V A Q C L V C V P W D A R P P P A A

GGCCTCCCCGGGGTCGGCGTCCGGCTGGGGTTGAGGGCGGCCGGGGGGAACCAGCGACATGCGGAGAGCAGCGCAGGCGACTCAGGGCGCTTCCCCCGCAGGTG
            G L P G V G V R L G L R A A G G N Q R H A E S S A G D S G R F P R R
            A S P G S A S G W G * G R P G G T S D M R R A A Q A T Q G A S P A G
            P P R G R R P A G V E G G R E P A T C G E Q R R L R A L P P Q V
            |.
CCCCTCCTTCCGCCAGGTGTCCTGCCTGAAGGAGCTGGTGGCCCGAGTGCTGCAGAGGCTGTGCGAGCGCGGCGCGAAGAACGTGCTGGCCTTCGGCTTCGCGCTGCTGGACGGGGCCCG
P S F R Q V S C L K E L V A R V L Q R L C E R G A K N V L A F G F A L L D G A R

CGGGGGCCCCCCCGAGGCCTTCACCACCAGCGTGCGCAGCTACCTGCCCAACACGGTGACCGACGCACTGCGGGGGAGCGGGGCGTGGGGGCTGCTGCTGCGCCGCGTGGGCGACGACGT
G G P P E A F T T S V R S Y L P N T V T D A L R G S G A W G L L L R R V G D D V

GCTGGTTCACCTGCTGGCACGCTGCGCGCTCTTTGTGCTGGTGGCTCCCAGCTGCGCCTACCAGGTGTGCGGGCCGCCGCTGTACCAGCTCGGCGCTGCCACTCAGGCCCGGCCCCCGCC
L V H L L A R C A L F V L V A P S C A Y Q V C G P P L Y Q L G A A T Q A R P P P

ACACGCTAGTGGACCCCGAAGGCGTCTGGGATGCGAACGGGCCTGGAACCATAGCGTCAGGGAGGCCGGGGTCCCCCTGGGCCTGCCAGCCCCGGGTGCGAGGAGGCGCGGGGGCAGTGC
H A S G P R R R L G C E R A W N H S V R E A G V P L G L P A P G A R R R G G S A

CAGCCGAAGTCTGCCGTTGCCCAAGAGGCCCAGGCGTGGCGCTGCCCCTGAGCCGGAGCGGACGCCCGTTGGGCAGGGGTCCTGGGCCCACCCGGGCAGGACGCGTGGACCGAGTGACCG
S R S L P L P K R P R R G A A P E P E R T P V G Q G S W A H P G R T R G P S D R

TGGTTTCTGTGTGGTGTCACCTGCCAGACCCGCCGAAGAAGCCACCTCTTTGGAGGGTGCGCTCTCTGGCACGCGCCACTCCCACCCATCCGTGGGCCGCCAGCACCACGCGGGCCCCCC
G F C V V S P A R P A E E A T S L E G A L S G T R H S H P S V G R Q H H A G P P

ATCCACATCGCGGCCACCACGTCCCTGGGACACGCCTTGTCCCCCGGTGTACGCCGAGACCAAGCACTTCCTCTACTCCTCAGGCGACAAGGAGCAGCTGCGGCCCTCCTTCCTACTCAG
S T S R P P R P W D T P C P P V Y A E T K H F L Y S S G D K E Q L R P S F L L S

CTCTCTGAGGCCCAGCCTGACTGGCGCTCGGAGGCTCGTGGAGACCATCTTTCTGGGTTCCAGGCCCTGGATGCCAGGGACTCCCCGCAGGTTGCCCCGCCTGCCCCAGCGCTACTGGCA
S L R P S L T G A R R L V E T I F L G S R P W M P G T P R R L P R L P Q R Y W Q

AATGCGGCCCCTGTTTCTGGAGCTGCTTGGGAACCACGCGCAGTGCCCCTACGGGGTGCTCCTCAAGACGCACTGCCCGCTGCGAGCTGCGGTCACCCCAGCAGCCGGTGTCTGTGCCCG
N R P L F L E L L G N H A Q C P Y G V L L K T H C P L R A A V T P A A G V C A R

GGAGAAGCCCCAGGGCTCTGTGGCGGCCCCCGAGGAGGAGGACACAGACCCCCGTCGCCTGGTGCAGCTGCTCCGCCAGCACAGCAGCCCCTGGCAGGTGTACGGCTTCGTGCGGGCCTG
E K P Q G S V A A P E E E D T D P R R L V Q L L R Q H S S P W Q V Y G F V R A C

CCTGCGCCGGCTGGTGCCCCCAGGCCTCTGGGGCTCCAGGCACAACGAACGCCGCTTCCTCAGGAACACCAAGAAGTTCATCTCCCTGGGGAAGCATGCCAAGCTCTCGCTGCAGGAGCT
L R R L V P P G L W G S R H N E R R F L R N T K K F I S L G K H A K L S L Q E L
```

*Fig. 11AH*

```
GACGTGGAAGATGAGCGTGCGGGACTGCGCTTGGCTGCGCAGGAGCCCAGGGGTTGGCTGTGTTCCGGCCGCAGAGCACCGTCTGCGTGAGGAGATCCTGGCCAAGTTCCTGCACTGGCT
 T  W  K  M  S  V  R  D  C  A  W  L  R  R  S  P  G  V  G  C  V  P  A  A  E  H  R  L  R  E  E  I  L  A  K  F  L  H  W  L

GATGAGTGTGTACGTCGTCGAGCTGCTCAGGTCTTTCTTTTATGTCACGGAGACCACGTTTCAAAAGAACAGGCTCTTTTTCTACCGGAAGAGTGTCTGGAGCAAGTTGCAAAGCATTGG
 M  S  V  Y  V  V  E  L  L  R  S  F  F  Y  V  T  E  T  T  F  Q  K  N  R  L  F  F  Y  R  K  S  V  W  S  K  L  Q  S  I  G

AATCAGACAGCACTTGAAGAGGGTGCAGCTGCGGGAGCTGTCGGAAGCAGAGGTCAGGCAGCATCGGGAAGCCAGGCCCGCCTGCTGACGTCCAGACTCCGCTTCATCCCCAAGCCTGA
 I  R  Q  H  L  K  R  V  Q  L  R  E  L  S  E  A  E  V  R  Q  H  R  E  A  R  P  A  L  L  T  S  R  L  R  F  I  P  K  P  D

CGGGCTGCGGCCGATTGTGAACATGGACTACGTCGTGGGAGCCAGAACGTTCCGCAGAGAAAAGAGGGCCGAGCGTCTCACCTCGAGGGTGAAGGCACTGTTCAGCGTGCTCAACTACGA
 G  L  R  P  I  V  N  M  D  Y  V  V  G  A  R  T  F  R  R  E  K  R  A  E  R  L  T  S  R  V  K  A  L  F  S  V  L  N  Y  E

GCGGGCGCGGCGCCCCGGCCTCCTGGGCGCCTCTGTGCTGGGCCTGGACGATATCCACAGGGCCTGGCGCACCTTCGTGCTGCGTGTGCGGGCCCAGGACCCGCCGCCTGAGCTGTACTT
 R  A  R  R  P  G  L  L  G  A  S  V  L  G  L  D  D  I  H  R  A  W  R  T  F  V  L  R  V  R  A  Q  D  P  P  P  E  L  Y  F

TGTCAAGGTGGATGTGACGGGCGCGTACGACACCATCCCCCAGGACAGGCTCACGGAGGTCATCGCCAGCATCATCAAACCCCAGAACACGTACTGCGTGCGTCGGTATGCCGTGGTCCA
 V  K  V  D  V  T  G  A  Y  D  T  I  P  Q  D  R  L  T  E  V  I  A  S  I  I  K  P  Q  N  T  Y  C  V  R  R  Y  A  V  V  Q

GAAGGCCGCCCATGGGCACGTCCGCAAGGCCTTCAAGAGCCACGTCTCTACCTTGACAGACCTCCAGCCGTACATGCGACAGTTCGTGGCTCACCTGCAGGAGACCAGCCCGCTGAGGGA
 K  A  A  H  G  H  V  R  K  A  F  K  S  H  V  S  T  L  T  D  L  Q  P  Y  M  R  Q  F  V  A  H  L  Q  E  T  S  P  L  R  D

TGCCGTCGTCATCGAGCAGAGCTCCTCCCTGAATGAGGCCAGCAGTGGCCTCTTCGACGTCTTCCTACGCTTCATGTGCCACCACGCCGTGCGCATCAGGGGCAAGTCCTACGTCCAGTG
 A  V  V  I  E  Q  S  S  S  L  N  E  A  S  S  G  L  F  D  V  F  L  R  F  M  C  H  H  A  V  R  I  R  G  K  S  Y  V  Q  C

CCAGGGGATCCCGCAGGGCTCCATCCTCTCCACGCTGCTCTGCAGCCTGTGCTACGGCGACATGGAGAACAAGCTGTTTGCGGGGATTCGGCGGGACGGGCTGCTCCTGCGTTTGGTGGA
 Q  G  I  P  Q  G  S  I  L  S  T  L  L  C  S  L  C  Y  G  D  M  E  N  K  L  F  A  G  I  R  R  D  G  L  L  L  R  L  V  D

TGATTTCTTGTTGGTGACACCTCACCTCACCCACGCGAAAACCTTCCTCAGGACCCTGGTCCGAGGTGTCCCTGAGTATGGCTGCGTGGTGAACTTGCGGAAGACAGTGGTGAACTTCCC
 D  F  L  L  V  T  P  H  L  T  H  A  K  T  F  L  R  T  L  V  R  G  V  P  E  Y  G  C  V  V  N  L  R  K  T  V  V  N  F  P

TGTAGAAGACGAGGCCCTGGGTGGCACGGCTTTTGTTCAGATGCCGGCCCACGGCCTATTCCCCTGGTGCGGCCTGCTGCTGGATACCCGGACCCTGGAGGTGCAGAGCGACTACTCCAG
 V  E  D  E  A  L  G  G  T  A  F  V  Q  M  P  A  H  G  L  F  P  W  C  G  L  L  L  D  T  R  T  L  E  V  Q  S  D  Y  S  S

CTATGCCCGGACCTCCATCAGAGCCAGTCTCACCTTCAACCGCGGCCTTCAAGGCTGGGAGGAACATGCGTCGCAAACTCTTTGGGGTCTTGCGGCTGAAGTGTCACAGCCTGTTTCTGGA
 Y  A  R  T  S  I  R  A  S  L  T  F  N  R  G  F  K  A  G  R  N  M  R  R  K  L  F  G  V  L  R  L  K  C  H  S  L  F  L  D

TTTGCAGGTGAACAGCCTCCAGACGGTGTGCACCAACATCTACAAGATCCTCCTGCTGCAGGCGTACAGGTTTCACGCATGTGTGCTGCAGCTCCCATTTCATCAGCAAGTTTGGAAGAA
 L  Q  V  N  S  L  Q  T  V  C  T  N  I  Y  K  I  L  L  L  Q  A  Y  R  F  H  A  C  V  L  Q  L  P  F  H  Q  Q  V  W  K  N

CCCCACATTTTTCCTGCGCGTCATCTCTGACACGGCCTCCCTCTGCTACTCCATCCTGAAAGCCAAGAACGCAGGGATGTCGCTGGGGGCCAAGGGCGCCGCCGGCCCTCTGCCCTCCGA
 P  T  F  F  L  R  V  I  S  D  T  A  S  L  C  Y  S  I  L  K  A  K  N  A  E
                                                                          |
                                                   CCGAAGAAACATTTCTGTCGTGACTCCTGCGGTGCTTGGGTC
                                                    E  E  N  I  L  V  V  T  P  A  V  L  G  S

GGGACAGCCAGAGATGGAGCCACCCCGCAGACCGTCGGGTGTGGGCAGCTTTCCGGTGTCTCCTGGGAGGGGAGTTGGGCTGGGCCTGTGACTCCTCAGCCTCTGTTTTCCCCCAG
 G  Q  P  E  M  E  P  P  R  R  P  S  G  V  G  S  F  P  V  S  P  G  R  G  V  G  L  G  L  *
```

*Fig. 11AI*

Protein that lacks motif A (ver. 2)

```
                                 ATGCCGCGCGCTCCCCGCTGCCGAGCCGTGCGCTCCCTGCTGCGCAGCCACTACCGCGAGGTGCTGCCGCTGGCCACGTTCGTG
                                  M  P  R  A  P  R  C  R  A  V  R  S  L  L  R  S  H  Y  R  E  V  L  P  L  A  T  F  V

CGGCGCCTGGGGCCCCAGGGCTGGCGGCTGGTGCAGCGCGGGGACCCGGCGGCTTTCCGCGCGCTGGTGGCCCAGTGCCTGGTGTGCGTGCCCTGGGACGCACGGCCGCCCCCGCCGC
 R  R  L  G  P  Q  G  W  R  L  V  Q  R  G  D  P  A  A  F  R  A  L  V  A  Q  C  L  V  C  V  P  W  D  A  R  P  P  A  A

GGCCTCCCCGGGGTCGGCGTCCGGCTGGGGTTGAGGGCGGCCGGGGGGAACCAGCGACATGCGGAGAGCAGCGCAGGCGACTCAGGGCGCTTCCCCCGCAGGTG
                  G  L  P  G  V  G  V  R  L  G  L  R  A  A  G  G  N  Q  R  H  A  E  S  S  A  G  D  S  G  R  F  P  R  R
                   A  S  P  G  S  A  S  G  W  G  *  G  R  P  G  G  T  S  D  H  R  R  A  A  Q  A  T  Q  G  A  S  P  A  G
                    P  P  R  G  R  R  P  A  G  V  E  G  G  R  E  P  A  T  C  G  E  Q  R  R  L  R  A  L  P  P  Q  V

CCCCTCCTTCCGCCAGGTGTCCTGCCTGAAGGAGCTGGTGGCCCGAGTGCTGCAGAGGCTGTGCGAGCGCGGCGCGAAGAACGTGCTGGCCTTCGGCTTCGCGCTGCTGGACGGGCCCG
 P  S  F  R  Q  V  S  C  L  K  E  L  V  A  R  V  L  Q  R  L  C  E  R  G  A  K  N  V  L  A  F  G  F  A  L  L  D  G  A  R

CGGGGGCCCCCCGAGGCCTTCACCACCAGCGTGCGCAGCTACCTGCCCAACACGGTGACCGACGCACTGCGGGGGAGCGGGGCGTGGGGGCTGCTGCTGCGCCGCGTGGGCGACGACGT
 G  G  P  P  E  A  F  T  T  S  V  R  S  Y  L  P  N  T  V  T  D  A  L  R  G  S  G  A  W  G  L  L  L  R  R  V  G  D  D  V

GCTGGTTCACCTGCTGGCACGCTGCGCGCTCTTTGTGCTGGTGGCTCCCAGCTGCGCCTACCAGGTGTGCGGGCCGCCGCTGTACCAGCTCGGCGCTGCCACTCAGGCCCGGCCCCCGCC
 L  V  H  L  L  A  R  C  A  L  F  V  L  V  A  P  S  C  A  Y  Q  V  C  G  P  P  L  Y  Q  L  G  A  A  T  Q  A  R  P  P  P

ACACGCTAGTGGACCCCGAAGGCGTCTGGGATGCGAACGGGCCTGGAACCATAGCGTCAGGGAGGCCGGGGTCCCCCTGGGCCTGCCAGCCCCGGGTGCGAGGAGGCGCGGGGGCAGTGC
 H  A  S  G  P  R  R  R  L  G  C  E  R  A  W  N  H  S  V  R  E  A  G  V  P  L  G  L  P  A  P  G  A  R  R  R  G  G  S  A

CAGCCGAAGTCTGCCGTTGCCCAAGAGGCCCAGGCGTGGCGCTGCCCCTGAGCCGGAGCGGACGCCCGTTGGGCAGGGGTCCTGGGCCCACCCGGGCAGGACGCGTGGACCGAGTGACCG
 S  R  S  L  P  L  P  K  R  P  R  R  G  A  A  P  E  P  E  R  T  P  V  G  Q  G  S  W  A  H  P  G  R  T  R  G  P  S  D  R

TGGTTTCTGTGTGGTGTCACCTGCCAGACCCGCCGAAGAAGCCACCTCTTTGGAGGGTGCGCTCTCTGGCACGCGCCACTCCCACCCATCCGTGGGCCGCCAGCACCACGCGGGCCCCC
 G  F  C  V  V  S  P  A  R  P  A  E  E  A  T  S  L  E  G  A  L  S  G  T  R  H  S  H  P  S  V  G  R  Q  H  H  A  G  P  P

ATCCACATCGCGGCCACCACGTCCCTGGGACACGCCTTGTCCCCCGGTGTACGCCGAGACCAAGCACTTCCTCTACTCCTCAGGCGACAAGGAGCAGCTGCGGCCCTCCTTCCTACTCAG
 S  T  S  R  P  P  R  P  W  D  T  P  C  P  P  V  Y  A  E  T  K  H  F  L  Y  S  S  G  D  K  E  Q  L  R  P  S  F  L  L  S

CTCTCTGAGGCCCAGCCTGACTGGCGCTCGGAGGCTCGTGGAGACCATCTTTCTGGGTTCCAGGCCCTGGATGCCAGGGACTCCCCGCAGGTTGCCCCGCCTGCCCCAGCGCTACTGGCA
 S  L  R  P  S  L  T  G  A  R  R  L  V  E  T  I  F  L  G  S  R  P  W  M  P  G  T  P  R  R  L  P  R  L  P  Q  R  Y  W  Q

AATGCGGCCCCTGTTTCTGGAGCTGCTTGGGAACCACGCGCAGTGCCCCTACGGGGTGCTCCTCAAGACGCACTGCCCGCTGCGAGCTGCGGTCACCCCAGCAGCCGGTGTCTGTGCCCG
 M  R  P  L  F  L  E  L  L  G  N  H  A  Q  C  P  Y  G  V  L  L  K  T  H  C  P  L  R  A  A  V  T  P  A  A  G  V  C  A  R

GGAGAAGCCCCAGGGCTCTGTGGCGGCCCCCGAGGAGGAGGACACAGACCCCCGTCGCCTGGTGCAGCTGCTCCGCCAGCACAGCAGCCCCTGGCAGGTGTACGGCTTCGTGCGGGCCTG
 E  K  P  Q  G  S  V  A  A  P  E  E  E  D  T  D  P  R  R  L  V  Q  L  L  R  Q  H  S  S  P  W  Q  V  Y  G  F  V  R  A  C

CCTGCGCCGGCTGGTGCCCCCAGGCCTCTGGGGCTCCAGGCACAACGAACGCCGCTTCCTCAGGAACACCAAGAAGTTCATCTCCCTGGGGAAGCATGCCAAGCTCTCGCTGCAGGAGCT
 L  R  R  L  V  P  P  G  L  W  G  S  R  H  N  E  R  R  F  L  R  N  T  K  K  F  I  S  L  G  K  H  A  K  L  S  L  Q  E  L
```

*Fig. 11AJ*

```
GACGTGGAAGATGAGCGTGCGGGACTGCGCTTGGCTGCGCAGGAGCCCAGGGGTTGGCTGTGTTCCGGCCGCAGAGCACCGTCTGCGTGAGGAGATCCTGGCCAAGTTCCTGCACTGGCT
 T  W  K  M  S  V  R  D  C  A  W  L  R  R  S  P  G  V  G  C  V  P  A  A  E  H  R  L  R  E  E  I  L  A  K  F  L  H  W  L

GATGAGTGTGTACGTCGTCGAGCTGCTCAGGTCTTTCTTTTATGTCACGGAGACCACGTTTCAAAAGAACAGGCTCTTTTTCTACCGGAAGAGTGTCTGGAGCAAGTTGCAAAGCATTGG
 M  S  V  Y  V  V  E  L  L  R  S  F  F  Y  V  T  E  T  T  F  Q  K  N  R  L  F  F  Y  R  K  S  V  W  S  K  L  Q  S  I  G

AATCAGACAGCACTTGAAGAGGGTGCAGCTGCGGGAGCTGTCGGAAGCAGAGGTCAGGCAGCATCGGGAAGCCAGGCCCGCCCTGCTGACGTCCAGACTCCGCTTCATCCCCAAGCCTGA
 I  R  Q  H  L  K  R  V  Q  L  R  E  L  S  E  A  E  V  R  Q  H  R  E  A  R  P  A  L  L  T  S  R  L  R  F  I  P  K  P  D

CGGGCTGCGGCCGATTGTGAACATGGACTACGTCGTGGGAGCCAGAACGTTCCGCAGAGAAAAGAGGGCCGAGCGTCTCACCTCGAGGGTGAAGGCACTGTTCAGCGTGCTCAACTACGA
 G  L  R  P  I  V  N  M  D  Y  V  V  G  A  R  T  F  R  R  E  K  R  A  E  R  L  T  S  R  V  K  A  L  F  S  V  L  N  Y  E

GCGGGCGCGGCGCCCCGGCCTCCTGGGCGCCTCTGTGCTGGGCCTGGACGATATCCACAGGGCCTGGCGCACCTTCGTGCTGCGTGTGCGGGCCCAGGACCCGCCGCCTGAGCTGTACTT
 R  A  R  R  P  G  L  L  G  A  S  V  L  G  L  D  D  I  H  R  A  W  R  T  F  V  L  R  V  R  A  Q  D  P  P  P  E  L  Y  F

TGTCAAG                         GACAGGCTCACGGAGGTCATCGCCAGCATCATCAAACCCCAGAACACGTACTGCGTGCGTCGGTATGCCGTGGTCCA
 V  K                            D  R  L  T  E  V  I  A  S  I  I  K  P  Q  N  T  Y  C  V  R  R  Y  A  V  V  Q

GAAGGCCGCCCATGGGCACGTCCGCAAGGCCTTCAAGAGCCACGTCTCTACCTTGACAGACCTCCAGCCGTACATGCGACAGTTCGTGGCTCACCTGCAGGAGACCAGCCCGCTGAGGGA
 K  A  A  H  G  H  V  R  K  A  F  K  S  H  V  S  T  L  T  D  L  Q  P  Y  M  R  Q  F  V  A  H  L  Q  E  T  S  P  L  R  D

TGCCGTCGTCATCGAGCAGAGCTCCTCCCTGAATGAGGCCAGCAGTGGCCTCTTCGACGTCTTCCTACGCTTCATGTGCCACCACGCCGTCGCATCAGGGGCAAGTCCTACGTCCAGTG
 A  V  V  I  E  Q  S  S  S  L  N  E  A  S  S  G  L  F  D  V  F  L  R  F  M  C  H  H  A  V  R  I  R  G  K  S  Y  V  Q  C

CCAGGGGATCCCGCAGGGCTCCATCCTCTCCACGCTGCTCTGCAGCCTGTGCTACGGCGACATGGAGAACAAGCTGTTTGCGGGGATTCGGCGGGACGGGCTGCTCCTGCGTTTGGTGGA
 Q  G  I  P  Q  G  S  I  L  S  T  L  L  C  S  L  C  Y  G  D  M  E  N  K  L  F  A  G  I  R  R  D  G  L  L  L  R  L  V  D

TGATTTCTTGTTGGTGACACCTCACCTCACCCACGCGAAAACCTTCCTCAGGACCCTGGTCCGAGGTGTCCCTGAGTATGGCTGCGTGGTGAACTTGCGGAAGACAGTGGTGAACTTCCC
 D  F  L  L  V  T  P  H  L  T  H  A  K  T  F  L  R  T  L  V  R  G  V  P  E  Y  G  C  V  V  N  L  R  K  T  V  V  N  F  P

TGTAGAAGACGAGGCCCTGGGTGGCACGGCTTTTGTTCAGATGCCGGCCCACGGCCTATTCCCCTGGTGCGGCCTGCTGCTGGATACCCGGACCCTGGAGGTGCAGAGCGACTACTCCAG
 V  E  D  E  A  L  G  G  T  A  F  V  Q  M  P  A  H  G  L  F  P  W  C  G  L  L  L  D  T  R  T  L  E  V  Q  S  D  Y  S  S

CTATGCCCGGACCTCCATCAGAGCCAGTCTCACCTTCAACCGCGGCTTCAAGGCTGGGAGGAACATGCGTCGCAAACTCTTTGGGGTCTTGCGGCTGAAGTGTCACAGCCTGTTTCTGGA
 Y  A  R  T  S  I  R  A  S  L  T  F  N  R  G  F  K  A  G  R  N  M  R  R  K  L  F  G  V  L  R  L  K  C  H  S  L  F  L  D

TTTGCAGGTGAACAGCCTCCAGACGGTGTGCACCAACATCTACAAGATCCTCCTGCTGCAGGCGTACAGGTTTCACGCATGTGTGCTGCAGCTCCCATTTCATCAGCAAGTTTGGAAGAA
 L  Q  V  N  S  L  Q  T  V  C  T  N  I  Y  K  I  L  L  L  Q  A  Y  R  F  H  A  C  V  L  Q  L  P  F  H  Q  Q  V  W  K  N

CCCCACATTTTTCCTGCGCGTCATCTCTGACACGGCCTCCCTCTGCTACTCCATCCTGAAAGCCAAGAACGCAGGGATGTCGCTGGGGGCCAAGGGCGCCGCCGGCCCTCTGCCCTCCGA
 P  T  F  F  L  R  V  I  S  D  T  A  S  L  C  Y  S  I  L  K  A  K  N  A  G  M  S  L  G  A  K  G  A  A  G  P  L  P  S  E

GGCCGTGCAGTGGCTGTGCCACCAAGCATTCCTGCTCAAGCTGACTCGACACCGTGTCACCTACGTGCCACTCCTGGGGTCACTCAGGACAGCCCAGACGCAGCTGAGTCGGAAGCTCCC
 A  V  Q  W  L  C  H  Q  A  F  L  L  K  L  T  R  H  R  V  T  Y  V  P  L  L  G  S  L  R  T  A  Q  T  Q  L  S  R  K  L  P

GGGGACGACGCTGACTGCCCTGGAGGCCGCAGCCAACCCGGCACTGCCCCTCAGACTTCAAGACCATCCTGGACTGATGGCCACCCGCCCACAGCCAGGCCGAGAGCAGACACCAGCAGCC
 G  T  T  L  T  A  L  E  A  A  A  N  P  A  L  P  S  D  F  K  T  I  L  D
```

*Fig. 11AK*

CTGTCACGCCGGGCTCTACGTCCCAGGGAGGGAGGGGCGGCCCACACCCAGGCCCGCACCGCTGGGAGTCTGAGGCCTGAGTGAGTGTTTGGCCGAGGCCTGCATGTCCGGCTGAAGGCT

GAGTGTCCGGCTGAGGCCTGAGCGAGTGTCCAGCCAAGGGCTGAGTGTCCAGCACACCTGCCGTCTTCACTTCCCCACAGGCTGGCGCTCGGCTCCACCCCAGGGCCAGCTTTTCCTCAC

CAGGAGCCCGGCTTCCACTCCCCACATAGGAATAGTCCATCCCCAGATTCGCCATTGTTCACCCCTCGCCCTGCCCTCCTTTGCCTTCCACCCCCACCATCCAGGTGGAGACCCTGAGAA

GGACCCTGGGAGCTCTGGGAATTTGGAGTGACCAAAGGTGTGCCCTGTACACAGGCGAGGACCCTGCACCTGGATGGGGGTCCCTGTGGGTCAAATTGGGGGGAGGTGCTGTGGGAGTAA

AATACTGAATATATGAGTTTTTCAGTTTTGA

*Fig. 11AL*

Truncated protein that lacks motif A (ver. 2)

ATGCCGCGCGCTCCCCGCTGCCGAGCCGTGCGCTCCCTGCTGCGCAGCCACTACCGCGAGGTGCTGCCGCTGGCCACGTTCGTG
M  P  R  A  P  R  C  R  A  V  R  S  L  L  R  S  H  Y  R  E  V  L  P  L  A  T  F  V

CGGCGCCTGGGGCCCCAGGGCTGGCGGCTGGTGCAGCGCGGGGACCCGGCGGCTTTCCGCGCGCTGGTGGCCCAGTGCCTGGTGTGCGTGCCCTGGGACGCACGGCCGCCCCCGCCGC
R  R  L  G  P  Q  G  W  R  L  V  Q  R  G  D  P  A  A  F  R  A  L  V  A  Q  C  L  V  C  V  P  W  D  A  R  P  P  P  A  A

GGCCTCCCCGGGGTCGGCGTCCGGCTGGGGTTGAGGGCGGCCGGGGGGAACCAGCGACATGCGGAGAGCAGCGCAGGCGACTCAGGGCGCTTCCCCCGCAGGTG
G  L  P  G  V  G  V  R  L  G  L  R  A  A  G  G  N  Q  R  H  A  E  S  S  A  G  D  S  G  R  F  P  R  R
 A  S  P  G  S  A  S  G  W  G  *  G  R  P  G  G  T  S  D  M  R  R  A  A  Q  A  T  Q  G  A  S  P  A  G
  P  P  R  G  R  R  P  A  G  V  E  G  G  R  G  E  P  A  T  C  G  E  Q  R  R  L  R  A  L  P  P  Q  V

CCCCTCCTTCCGCCAGGTGTCCTGCCTGAAGGAGCTGGTGGCCCGAGTGCTGCAGAGGCTGTGCGAGCGCGGCGCGAAGAACGTGCTGGCCTTCGGCTTCGCGCTGCTGGACGGGGCCCG
P  S  F  R  Q  V  S  C  L  K  E  L  V  A  R  V  L  Q  R  L  C  E  R  G  A  K  N  V  L  A  F  G  F  A  L  L  D  G  A  R

CGGGGGCCCCCCCGAGGCCTTCACCACCAGCGTGCGCAGCTACCTGCCCAACACGGTGACCGACGCACTGCGGGGGAGCGGGGCGTGGGGGCTGCTGCTGCGCCGCGTGGGCGACGACGT
G  G  P  P  E  A  F  T  T  S  V  R  S  Y  L  P  N  T  V  T  D  A  L  R  G  S  G  A  W  G  L  L  L  R  R  V  G  D  D  V

GCTGGTTCACCTGCTGGCACGCTGCGCGCTCTTTGTGCTGGTGGCTCCCAGCTGCGCCTACCAGGTGTGCGGGCCGCCGCTGTACCAGCTCGGCGCTGCCACTCAGGCCCGGCCCCCGCC
L  V  H  L  L  A  R  C  A  L  F  V  L  V  A  P  S  C  A  Y  Q  V  C  G  P  P  L  Y  Q  L  G  A  A  T  Q  A  R  P  P  P

ACACGCTAGTGGACCCCGAAGGCGTCTGGGATGCGAACGGGCCTGGAACCATAGCGTCAGGGAGGCCGGGGTCCCCCTGGGCCTGCCAGCCCCGGGTGCGAGGAGGCGCGGGGCAGTGC
H  A  S  G  P  R  R  R  L  G  C  E  R  A  W  N  H  S  V  R  E  A  G  V  P  L  G  L  P  A  P  G  A  R  R  R  G  G  S  A

CAGCCGAAGTCTGCCGTTGCCCAAGAGGCCCAGGCGTGGCGCTGCCCCTGAGCCGGAGCGGACGCCCGTTGGGCAGGGGTCCTGGGCCCACCCGGGCAGGACGCGTGGACCGAGTGACCG
S  R  S  L  P  L  P  K  R  P  R  R  G  A  A  P  E  P  E  R  T  P  V  G  Q  G  S  W  A  H  P  G  R  T  R  G  P  S  D  R

TGGTTTCTGTGTGGTGTCACCTGCCAGACCCGCCGAAGAAGCCACCTCTTTGGAGGGTGCGCTCTCTGGCACGCGCCACTCCCACCCATCCGTGGGCCGCCAGCACCACGCGGGCCCCC
G  F  C  V  V  S  P  A  R  P  A  E  E  A  T  S  L  E  G  A  L  S  G  T  R  H  S  H  P  S  V  G  R  Q  H  H  A  G  P  P

ATCCACATCGCGGCCACCACGTCCCTGGGACACGCCTTGTCCCCCGGTGTACGCCGAGACCAAGCACTTCCTCTACTCCTCAGGCGACAAGGAGCAGCTGCGGCCCTCCTTCCTACTCAG
S  T  S  R  P  P  R  P  W  D  T  P  C  P  P  V  Y  A  E  T  K  H  F  L  Y  S  S  G  D  K  E  Q  L  R  P  S  F  L  L  S

CTCTCTGAGGCCCAGCCTGACTGGCGCTCGGAGGCTCGTGGAGACCATCTTTCTGGGTTCCAGGCCCTGGATGCCAGGGACTCCCCGCAGGTTGCCCCGCCTGCCCCAGCGCTACTGGCA
S  L  R  P  S  L  T  G  A  R  R  L  V  E  T  I  F  L  G  S  R  P  W  M  P  G  T  P  R  R  L  P  R  L  P  Q  R  Y  W  Q

AATGCGGCCCCTGTTTCTGGAGCTGCTTGGGAACCACGCGCAGTGCCCCTACGGGGTGCTCCTCAAGACGCACTGCCCGCTGCGAGCTGCGGTCACCCCAGCAGCCGGTGTCTGTGCCCG
M  R  P  L  F  L  E  L  L  G  N  H  A  Q  C  P  Y  G  V  L  L  K  T  H  C  P  L  R  A  A  V  T  P  A  A  G  V  C  A  R

GGAGAAGCCCCAGGGCTCTGTGGCGGCCCCCGAGGAGGAGGACACAGACCCCCGTCGCCTGGTGCAGCTGCTCCGCCAGCACAGCAGCCCCTGGCAGGTGTACGCCTTCGTGCGGGCCTG
E  K  P  Q  G  S  V  A  A  P  E  E  E  D  T  D  P  R  R  L  V  Q  L  L  R  Q  H  S  S  P  W  Q  V  Y  G  F  V  R  A  C

CCTGCGCCGGCTGGTGCCCCCAGGCCTCTGGGGCTCCAGGCACAACGAACGCCGCTTCCTCAGGAACACCAAGAAGTTCATCTCCCTGGGGAAGCATGCCAAGCTCTCGCTGCAGGAGCT
L  R  R  L  V  P  P  G  L  W  G  S  R  H  N  E  R  R  F  L  R  N  T  K  K  F  I  S  L  G  K  H  A  K  L  S  L  Q  E  L

*Fig. 11AM*

```
GACGTGGAAGATGAGCGTGCGGGACTGCGCTTGGCTGCGCAGGAGCCCAGGGGTTGGCTGTGTTCCGGCCGCAGAGCACCGTCTGCGTGAGGAGATCCTGGCCAAGTTCCTGCACTGGCT
 T  W  K  M  S  V  R  D  C  A  W  L  R  R  S  P  G  V  G  C  V  P  A  A  E  H  R  L  R  E  E  I  L  A  K  F  L  H  W  L

GATGAGTGTGTACGTCGTCGAGCTGCTCAGGTCTTTCTTTTATGTCACGGAGACCACGTTTCAAAAGAACAGGCTCTTTTTCTACCGGAAGAGTGTCTGGAGCAAGTTGCAAAGCATTGG
 M  S  V  Y  V  V  E  L  L  R  S  F  F  Y  V  T  E  T  T  F  Q  K  N  R  L  F  F  Y  R  K  S  V  W  S  K  L  Q  S  I  G

AATCAGACAGCACTTGAAGAGGGTGCAGCTGCGGGAGCTGTCGGAAGCAGAGGTCAGGCAGCATCGGGAAGCCAGGCCCGCCCTGCTGACGTCCAGACTCCGCTTCATCCCCAAGCCTGA
 I  R  Q  H  L  K  R  V  Q  L  R  E  L  S  E  A  E  V  R  Q  H  R  E  A  R  P  A  L  L  T  S  R  L  R  F  I  P  K  P  D

CGGGCTGCGGCCGATTGTGAACATGGACTACGTCGTGGGAGCCAGAACGTTCCGCAGAGAAAAGAGGGCCGAGCGTCTCACCTCGAGGGTGAAGGCACTGTTCAGCGTGCTCAACTACGA
 G  L  R  P  I  V  N  M  D  Y  V  V  G  A  R  T  F  R  R  E  K  R  A  E  R  L  T  S  R  V  K  A  L  F  S  V  L  N  Y  E

GCGGGCGCGGCGCCCGGCCTCCTGGGCGCCTCTGTGCTGGGCCTGGACGATATCCACAGGGCCTGGCGCACCTTCGTGCTGCGTGTGCGGGCCCAGGACCCGCCGCCTGAGCTGTACTT
 R  A  R  R  P  G  L  L  G  A  S  V  L  G  L  D  D  I  H  R  A  W  R  T  F  V  L  R  V  R  A  Q  D  P  P  P  E  L  Y  F

TGTCAAG                        GACAGGCTCACGGAGGTCATCGCCAGCATCATCAAACCCCAGAACACGTACTGCGTGCGTCGGTATGCCGTGGTCCA
 V  K                           D  R  L  T  E  V  I  A  S  I  I  K  P  Q  N  T  Y  C  V  R  R  Y  A  V  V  Q

GAAGGCCGCCCATGGGCACGTCCGCAAGGCCTTCAAGAGCCACGTCTCTACCTTGACAGACCTCCAGCCGTACATGCGACAGTTCGTGGCTCACCTGCAGGAGACCAGCCCGCTGAGGGA
 K  A  A  H  G  H  V  R  K  A  F  K  S  H  V  S  T  L  T  D  L  Q  P  Y  M  R  Q  F  V  A  H  L  Q  E  T  S  P  L  R  D

TGCCGTCGTCATCGAGCAGAGCTCCTCCCTGAATGAGGCCAGCAGTGGCCTCTTCGACGTCTTCCTACGCTTCATGTGCCACCACGCCGTGCGCATCAGGGGCAAGTCCTACGTCCAGTG
 A  V  V  I  E  Q  S  S  S  L  N  E  A  S  S  G  L  F  D  V  F  L  R  F  M  C  H  H  A  V  R  I  R  G  K  S  Y  V  Q  C

CCAGGGGATCCCGCAGGGCTCCATCCTCTCCACGCTGCTCTGCAGCCTGTGCTACGGCGACATGGAGAACAAGCTGTTTGCGGGGATTCGGCGGGACGGGCTGCTCCTGCGTTTGGTGGA
 Q  G  I  P  Q  G  S  I  L  S  T  L  L  C  S  L  C  Y  G  D  M  E  N  K  L  F  A  G  I  R  R  D  G  L  L  L  R  L  V  D

TGATTTCTTGTTGGTGACACCTCACCTCACCCACGCGAAAACCTTCCTCAGGACCCTGGTCCGAGGTGTCCCTGAGTATGGCTGCGTGGTGAACTTGCGGAAGACAGTGGTGAACTTCCC
 D  F  L  L  V  T  P  H  L  T  H  A  K  T  F  L  R  T  L  V  R  G  V  P  E  Y  G  C  V  V  N  L  R  K  T  V  V  N  F  P

TGTAGAAGACGAGGCCCTGGGTGGCACGGCTTTTGTTCAGATGCCGGCCCACGGCCTATTCCCCTGGTGCGGCCTGCTGCTGGATACCCGGACCCTGGAGGTGCAGAGCGACTACTCCAG
 V  E  D  E  A  L  G  G  T  A  F  V  Q  M  P  A  H  G  L  F  P  W  C  G  L  L  L  D  T  R  T  L  E  V  Q  S  D  Y  S  R

GTGAGCGCACCTGGCCGGAAGTGGAGCCTGTGCCCGGCTGGGGCAGGTGCTGCTGCAGGGCCGTTGCGTCCACCTCTGCTTCCGTGGGGCAGGCGACTGCCAATCCCAAAGGGTCAGA
 *

TGCCACAGGGTGCCCCTCGTCCCATCTGGGGCTGAGCACAAATGCATCTTTCTGTGGGAGTGAGGGTGCCTCACAACGGGAGCAGTTTTCTGTGCTATTTTGGTAA__
```

*Fig. 11AN*

Lacks motif A and altered C-terminus (ver. 2)

```
ATGCCGCGCGCTCCCCGCTGCCGAGCCGTGCGCTCCCTGCTGCGCAGCCACTACCGCGAGGTGCTGCCGCTGGCCACGTTCGTG
M  P  R  A  P  R  C  R  A  V  R  S  L  L  R  S  H  Y  R  E  V  L  P  L  A  T  F  V

CGGCGCCTGGGGCCCCAGGGCTGGCGGCTGGTGCAGCGCGGGGACCCGGCGGCTTTCCGCGCGCTGGTGGCCCAGTGCCTGGTGTGCGTGCCCTGGGACGCACGGCCGCCCCCCGCCGC
R  R  L  G  P  Q  G  W  R  L  V  Q  R  G  D  P  A  A  F  R  A  L  V  A  Q  C  L  V  C  V  P  W  D  A  R  P  P  P  A  A

GGCCTCCCCGGGGTCGGCGTCCGGCTGGGGTTGAGGGCGGCCGGGGGGAACCAGCGACATGCGGAGAGCAGCGCAGGCGACTCAGGGCGCTTCCCCCGCAGGTG
G  L  P  G  V  G  V  R  L  G  L  R  A  A  G  G  N  Q  R  H  A  E  S  S  A  G  D  S  G  R  F  P  R  R
A  S  P  G  S  A  S  G  W  G  *  G  R  P  G  G  T  S  D  M  R  R  A  A  Q  A  T  Q  G  A  S  P  A  G
P  P  R  G  R  R  P  A  G  V  E  G  G  R  G  E  P  A  T  C  G  E  Q  R  R  R  L  R  A  L  P  P  Q  V

CCCCTCCTTCCGCCAGGTGTCCTGCCTGAAGGAGCTGGTGGCCCGAGTGCTGCAGAGGCTGTGCGAGCGCGGCGCGAAGAACGTGCTGGCCTTCGGCTTCGCGCTGCTGGACGGGGCCCG
P  S  F  R  Q  V  S  C  L  K  E  L  V  A  R  V  L  Q  R  L  C  E  R  G  A  K  N  V  L  A  F  G  F  A  L  L  D  G  A  R

CGGGGGCCCCCCCGAGGCCTTCACCACCAGCGTGCGCAGCTACCTGCCCAACACGGTGACCGACGCACTGCGGGGGAGCGGGGCGTGGGGGCTGCTGCTGCGCCGCGTGGGCGACGACGT
G  G  P  P  E  A  F  T  T  S  V  R  S  Y  L  P  N  T  V  T  D  A  L  R  G  S  G  A  W  G  L  L  L  R  R  V  G  D  D  V

GCTGGTTCACCTGCTGGCACGCTGCGCGCTCTTTGTGCTGGTGGCTCCCAGCTGCGCCTACCAGGTGTGCGGGCCGCCGCTGTACCAGCTCGGCGCTGCCACTCAGGCCCGGCCCCCGCC
L  V  H  L  L  A  R  C  A  L  F  V  L  V  A  P  S  C  A  Y  Q  V  C  G  P  P  L  Y  Q  L  G  A  A  T  Q  A  R  P  P  P

ACACGCTAGTGGACCCCGAAGGCGTCTGGGATGCGAACGGGCCTGGAACCATAGCGTCAGGGAGGCCGGGGTCCCCCTGGGCCTGCCAGCCCCGGGTGCGAGGAGGCGCGGGGGCAGTGC
H  A  S  G  P  R  R  R  L  G  C  E  R  A  W  N  H  S  V  R  E  A  G  V  P  L  G  L  P  A  P  G  A  R  R  R  G  G  S  A

CAGCCGAAGTCTGCCGTTGCCCAAGAGGCCCAGGCGTGGCGCTGCCCCTGAGCCGGAGCGGACGCCCGTTGGGCAGGGGTCCTGGGCCCACCCGGGCAGGACGCGTGGACCGAGTGACCG
S  R  S  L  P  L  P  K  R  P  R  R  G  A  A  P  E  P  E  R  T  P  V  G  Q  G  S  W  A  H  P  G  R  T  R  G  P  S  D  R

TGGTTTCTGTGTGGTGTCACCTGCCAGACCCGCCGAAGAAGCCACCTCTTTGGAGGGTGCGCTCTCTGGCACGCGCCACTCCCACCCATCCGTGGGCCGCCAGCACCACGCGGGCCCCCC
G  F  C  V  V  S  P  A  R  P  A  E  E  A  T  S  L  E  G  A  L  S  G  T  R  H  S  H  P  S  V  G  R  Q  H  H  A  G  P  P

ATCCACATCGCGGCCACCACGTCCCTGGGACACGCCTTGTCCCCCGGTGTACGCCGAGACCAAGCACTTCCTCTACTCCTCAGGCGACAAGGAGCAGCTGCGGCCCTCCTTCCTACTCAG
S  T  S  R  P  P  R  P  W  D  T  P  C  P  P  V  Y  A  E  T  K  H  F  L  Y  S  S  G  D  K  E  Q  L  R  P  S  F  L  L  S

CTCTCTGAGGCCCAGCCTGACTGGCGCTCGGAGGCTCGTGGAGACCATCTTTCTGGGTTCCAGGCCCTGGATGCCAGGGACTCCCCGCAGGTTGCCCCGCCTGCCCCAGCGCTACTGGCA
S  L  R  P  S  L  T  G  A  R  R  L  V  E  T  I  F  L  G  S  R  P  W  M  P  G  T  P  R  R  L  P  R  L  P  Q  R  Y  W  Q

AATGCGGCCCCTGTTTCTGGAGCTGCTTGGGAACCACGCGCAGTGCCCCTACGGGGTGCTCCTCAAGACGCACTGCCCGCTGCGAGCTGCGGTCACCCCAGCAGCCGGTGTCTGTGCCCG
M  R  P  L  F  L  E  L  L  G  N  H  A  Q  C  P  Y  G  V  L  L  K  T  H  C  P  L  R  A  A  V  T  P  A  A  G  V  C  A  R

GGAGAAGCCCCAGGGCTCTGTGGCGGCCCCCGAGGAGGAGGACACAGACCCCCGTCGCCTGGTGCAGCTGCTCCGCCAGCACAGCAGCCCCTGGCAGGTGTACGGCTTCGTGCGGGCCTG
E  K  P  Q  G  S  V  A  A  P  E  E  E  D  T  D  P  R  R  L  V  Q  L  L  R  Q  H  S  S  P  W  Q  V  Y  G  F  V  R  A  C

CCTGCGCCGGCTGGTGCCCCCAGGCCTCTGGGGCTCCAGGCACAACGAACGCCGCTTCCTCAGGAACACCAAGAAGTTCATCTCCCTGGGGAAGCATGCCAAGCTCTCGCTGCAGGAGCT
L  R  R  L  V  P  P  G  L  W  G  S  R  H  N  E  R  R  F  L  R  N  T  K  K  F  I  S  L  G  K  H  A  K  L  S  L  Q  E  L
```

*Fig. 11AO*

```
GACGTGGAAGATGAGCGTGCGGGACTGCGCTTGGCTGCGCAGGAGCCCAGGGGTTGGCTGTGTTCCGGCCGCAGAGCACCGTCTGCGTGAGGAGATCCTGGCCAAGTTCCTGCACTGGCT
 T  W  K  M  S  V  R  D  C  A  W  L  R  R  S  P  G  V  G  C  V  P  A  A  E  H  R  L  R  E  E  I  L  A  K  F  L  H  W  L

GATGAGTGTGTACGTCGTCGAGCTGCTCAGGTCTTTCTTTTATGTCACGGAGACCACGTTTCAAAAGAACAGGCTCTTTTTCTACCGGAAGAGTGTCTGGAGCAAGTTGCAAAGCATTGG
 M  S  V  Y  V  V  E  L  L  R  S  F  F  Y  V  T  E  T  T  F  Q  K  N  R  L  F  F  Y  R  K  S  V  W  S  K  L  Q  S  I  G

AATCAGACAGCACTTGAAGAGGGTGCAGCTGCGGGAGCTGTCGGAAGCAGAGGTCAGGCAGCATCGGGAAGCCAGGCCCGCCTGCTGACGTCCAGACTCCGCTTCATCCCCAAGCCTGA
 I  R  Q  H  L  K  R  V  Q  L  R  E  L  S  E  A  E  V  R  Q  H  R  E  A  R  P  A  L  L  T  S  R  L  R  F  I  P  K  P  D

CGGGCTGCGGCCGATTGTGAACATGGACTACGTCGTGGGAGCCAGAACGTTCCGCAGAGAAAAGAGGGCCGAGCGTCTCACCTCGAGGGTGAAGGCACTGTTCAGCGTGCTCAACTACGA
 G  L  R  P  I  V  N  M  D  Y  V  V  G  A  R  T  F  R  R  E  K  R  A  E  R  L  T  S  R  V  K  A  L  F  S  V  L  N  Y  E

GCGGGCGCGGCGCCCCGGCCTCCTGGGCGCCTCTGTGCTGGGCCTGGACGATATCCACAGGGCCTGGCGCACCTTCGTGCTGCGTGTGCGGGCCCAGGACCCGCCGCCTGAGCTGTACTT
 R  A  R  R  P  G  L  L  G  A  S  V  L  G  L  D  D  I  H  R  A  W  R  T  F  V  L  R  V  R  A  Q  D  P  P  P  E  L  Y  F

TGTCAAG                               GACAGGCTCACGGAGGTCATCGCCAGCATCATCAAACCCCAGAACACGTACTGCGTGCGTCGGTATGCCGTGGTCCA
 V  K                                  D  R  L  T  E  V  I  A  S  I  I  K  P  Q  N  T  Y  C  V  R  R  Y  A  V  V  Q

GAAGGCCGCCCATGGGCACGTCCGCAAGGCCTTCAAGAGCCACGTCTCTACCTTGACAGACCTCCAGCCGTACATGCGACAGTTCGTGGCTCACCTGCAGGAGACCAGCCCGCTGAGGGA
 K  A  A  H  G  H  V  R  K  A  F  K  S  H  V  S  T  L  T  D  L  Q  P  Y  M  R  Q  F  V  A  H  L  Q  E  T  S  P  L  R  D

TGCCGTCGTCATCGAGCAGAGCTCCTCCCTGAATGAGGCCAGCAGTGGCCTCTTCGACGTCTTCCTACGCTTCATGTGCCACCACGCCGTGCGCATCAGGGGCAAGTCCTACGTCCAGTG
 A  V  V  I  E  Q  S  S  S  L  N  E  A  S  S  G  L  F  D  V  F  L  R  F  M  C  H  H  A  V  R  I  R  G  K  S  Y  V  Q  C

CCAGGGGATCCCGCAGGGCTCCATCCTCTCCACGCTGCTCTGCAGCCTGTGCTACGGCGACATGGAGAACAAGCTGTTTGCGGGGATTCGGCGGGACGGGCTGCTCCTGCGTTTGGTGGA
 Q  G  I  P  Q  G  S  I  L  S  T  L  L  C  S  L  C  Y  G  D  M  E  N  K  L  F  A  G  I  R  R  D  G  L  L  L  R  L  V  D

TGATTTCTTGTTGGTGACACCTCACCTCACCCACGCGAAAACCTTCCTCAGGACCCTGGTCGAGGTGTCCCTGAGTATGGCTGCGTGGTGAACTTGCGGAAGACAGTGGTGAACTTCCC
 D  F  L  L  V  T  P  H  L  T  H  A  K  T  F  L  R  T  L  V  R  G  V  P  E  Y  G  C  V  V  N  L  R  K  T  V  V  N  F  P

TGTAGAAGACGAGGCCCTGGGTGGCACGGCTTTTGTTCAGATGCCGGCCCACGGCCTATTCCCCTGGTGCGGCCTGCTGCTGGATACCCGGACCCTGGAGGTGCAGAGCGACTACTCCAG
 V  E  D  E  A  L  G  G  T  A  F  V  Q  M  P  A  H  G  L  F  P  W  C  G  L  L  L  D  T  R  T  L  E  V  Q  S  D  Y  S  S

CTATGCCCGGACCTCCATCAGAGCCAGTCTCACCTTCAACCGCGGCTTCAAGGCTGGGAGGAACATGCGTCGCAAACTCTTTGGGGTCTTGCGGCTGAAGTGTCACAGCCTGTTTCTGGA
 Y  A  R  T  S  I  R  A  S  L  T  F  N  R  G  F  K  A  G  R  N  M  R  R  K  L  F  G  V  L  R  L  K  C  H  S  L  F  L  D

TTTGCAGGTGAACAGCCTCCAGACGGTGTGCACCAACATCTACAAGATCCTCCTGCTGCAGGCGTACAGGTTTCACGCATGTGTGCTGCAGCTCCCATTTCATCAGCAAGTTTGGAAGAA
 L  Q  V  N  S  L  Q  T  V  C  T  N  I  Y  K  I  L  L  L  Q  A  Y  R  F  H  A  C  V  L  Q  L  P  F  H  Q  Q  V  W  K  N

CCCCACATTTTTCCTGCGCGTCATCTCTGACACGGCCTCCCTCTGCTACTCCATCCTGAAAGCCAAGAACGCAGGGATGTCGCTGGGGGCCAAGGGCGCCGCCGGCCCTCTGCCCTCCGA
 P  T  F  F  L  R  V  I  S  D  T  A  S  L  C  Y  S  I  L  K  A  K  N  A  E
                                                                           |
                                                    CCGAAGAAAACATTTCTGTCGTGACTCCTGCGGTGCTTGGGTC
                                                     E  E  N  I  L  V  V  T  P  A  V  L  G  S

GGGACAGCCAGAGATGGAGCCACCCCGCAGACCGTCGGGTGTGGGCAGCTTTCCGGTGTCTCCTGGGAGGGGAGTTGGGCTGGGCCTGTGACTCCTCAGCCTCTGTTTTCCCCCAG
 G  Q  P  E  M  E  P  P  R  R  P  S  G  V  G  S  F  P  V  S  P  G  R  G  V  G  L  G  L  *
```

*Fig. 11AP*

```
LOCUS       pAKI28.4     7615 bp dsDNA    Circular
DEFINITION  Human telomerase clone with exon beta spliced out 1 tcgacctgca ggcatgcaag cttggcactg gccgtcgttt tacaacgtcg tgactgggaa
  61 aaccctggcg ttacccaact taatcgcctt gcagcacatc cccctttcgc cagctggcgt
 121 aatagcgaag aggcccgcac cgatcgccct tcccaacagt tgcgcagcct gaatggcgaa
 181 tggcgcctga tgcggtattt tctccttacg catctgtgcg gtatttcaca ccgcataaat
 241 tccctgtttt ggcggatgag agaagatttt cagcctgata cagattaaat cagaacgcag
 301 aagcggtctg ataaaacaga atttgcctgg cggcagtagc gcggtggtcc cacctgaccc
 361 catgccgaac tcagaagtga aacgccgtag cgccgatggt agtgtggggt ctccccatgc
 421 gagagtaggg aactgccagg catcaaataa aacgaaaggc tcagtcgaaa gactgggcct
 481 ttcgttttat ctgttgtttg tcggtgaacg ctctcctgag taggacaaat ccgccgggag
 541 cggatttgaa cgttgcgaag caacggcccg gagggtggcg ggcaggacgc ccgccataaa
 601 ctgccaggca tcaaattaag cagaaggcca tcctgacgga tggcctttt gcgtttctac
 661 aaactcttcc tgtcgtcata tctacaagcc atcccccac agatacggta aactagcctc
 721 gtttttgcat caggaaagca gggaatttat ggtgcactct cagtacaatc tgctctgatg
 781 ccgcatagtt aagccagccc cgacacccgc caacacccgc tgacgcgccc tgacgggctt
 841 gtctgctccc ggcatccgct tacagacaag ctgtgaccgt ctccgggagc tgcatgtgtc
 901 agaggttttc accgtcatca ccgaaacgcg cgagacgaaa gggcctcgtg atacgcctat
 961 ttttataggt taatgtcatg ataataatgg tttcttagac gtgaggttct gtacccgaca
1021 ccatcgaatg gtgcaaaacc tttcgcggta tggcatgata gcgcccggaa gagagtcaat
1081 tcagggtggt gaatgtgaaa ccagtaacgt tatacgatgt cgcagagtat gccggtgtct
1141 cttatcagac cgtttcccgc gtggtgaacc aggccagcca cgtttctgcg aaaacgcggg
1201 aaaaagtgga agcggcgatg gcggagctga attacattcc caaccgcgtg gcacaacaac
1261 tggcgggcaa acagtcgttg ctgattggcg ttgccacctc cagtctggcc ctgcacgcgc
1321 cgtcgcaaat tgtcgcggcg attaaatctc gcgccgatca actgggtgcc agcgtggtgg
1381 tgtcgatggt agaacgaagc ggcgtcgaag cctgtaaagc ggcggtgcac aatcttctcg
1441 cgcaacgcgt cagtgggctg atcattaact atccgctgga tgaccaggat gccattgctg
1501 tggaagctgc ctgcactaat gttccggcgt tatttcttga tgtctctgac cagacaccca
1561 tcaacagtat tattttctcc catgaagacg gtacgcgact gggcgtggag catctggtcg
1621 cattgggtca ccagcaaatc gcgctgttag cgggcccatt aagttctgtc tcggcgcgtc
1681 tgcgtctggc tggctggcat aaatatctca ctcgcaatca aattcagccg atagcggaac
1741 gggaaggcga ctggagtgcc atgtccggtt ttcaacaaac catgcaaatg ctgaatgagg
1801 gcatcgttcc cactgcgatg ctggttgcca acgatcagat ggcgctgggc gcaatgcgcg
1861 ccattaccga gtccgggctg cgcgttggtg cggatatctc ggtagtggga tacgacgata
1921 ccgaagacag ctcatgttat atcccgccgt taaccaccat caaacaggat tttcgcctgc
1981 tggggcaaac cagcgtggac cgcttgctgc aactctctca gggccaggcg gtgaagggca
2041 atcagctgtt gcccgtctca ctggtgaaaa gaaaaaccac cctggcgccc aatacgcaaa
2101 ccgcctctcc ccgcgcgttg gccgattcat taatgcagct ggcacgacag gtttcccgac
2161 tggaaagcgg gcagtgagcg caacgcaatt aatgtaagtt agctcactca ttaggcaccc
2221 caggctttac actttatgct tccgacctgc aagaacctca cgtcaggtgg cacttttcgg
2281 ggaaatgtgc gcggaacccc tatttgttta ttttctaaa tacattcaaa tatgtatccg
2341 ctcatgagac aataaccctg ataaatgctt caataatatt gaaaaggaa gagtatgagt
2401 attcaacatt tccgtgtcgc ccttattccc ttttttgcgg cattttgcct tcctgttttt
2461 gctcacccag aaacgctggt gaaagtaaaa gatgctgaag atcagttggg tgcacgagtg
2521 ggttacatcg agaactggat ctcaacagcg gtaagatcct tgagagtttt cgccccgaag
2581 aacgttttcc aatgatgagc acttttaaag ttctgctatg tggcgcggta ttatcccgta
2641 ttgacgccgg gcaagagcaa ctcggtcgcc gcatacacta ttctcagaat gacttggttg
```

*Fig. 13B*

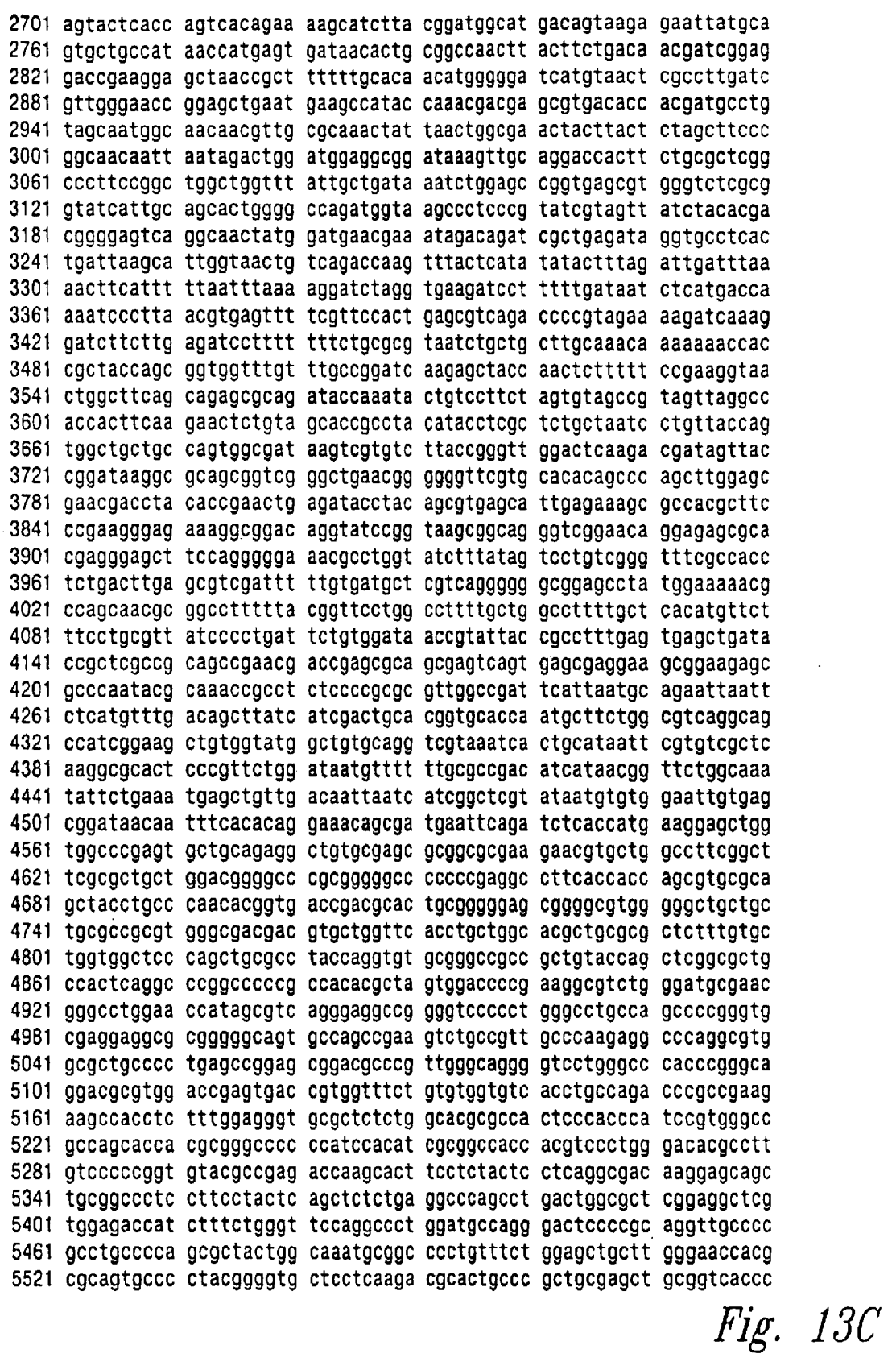

```
2701 agtactcacc agtcacagaa aagcatctta cggatggcat gacagtaaga gaattatgca
2761 gtgctgccat aaccatgagt gataacactg cggccaactt acttctgaca acgatcggag
2821 gaccgaagga gctaaccgct tttttgcaca acatggggga tcatgtaact cgccttgatc
2881 gttgggaacc ggagctgaat gaagccatac caaacgacga gcgtgacacc acgatgcctg
2941 tagcaatggc aacaacgttg cgcaaactat taactggcga actacttact ctagcttccc
3001 ggcaacaatt aatagactgg atggaggcgg ataaagttgc aggaccactt ctgcgctcgg
3061 cccttccggc tggctggttt attgctgata aatctggagc cggtgagcgt gggtctcgcg
3121 gtatcattgc agcactgggg ccagatggta agccctcccg tatcgtagtt atctacacga
3181 cggggagtca ggcaactatg gatgaacgaa atagacagat cgctgagata ggtgcctcac
3241 tgattaagca ttggtaactg tcagaccaag tttactcata tatactttag attgatttaa
3301 aacttcattt ttaatttaaa aggatctagg tgaagatcct ttttgataat ctcatgacca
3361 aaatccctta acgtgagttt cgttccact gagcgtcaga ccccgtagaa aagatcaaag
3421 gatcttcttg atcctttt tttctgcgcg taatctgctg cttgcaaaca aaaaaaccac
3481 cgctaccagc ggtggtttgt ttgccggatc aagagctacc aactctttt ccgaaggtaa
3541 ctggcttcag cagagcgcag ataccaaata ctgtccttct agtgtagccg tagttaggcc
3601 accacttcaa gaactctgta gcaccgccta catacctcgc tctgctaatc ctgttaccag
3661 tggctgctgc cagtggcgat aagtcgtgtc ttaccgggtt ggactcaaga cgatagttac
3721 cggataaggc gcagcggtcg ggctgaacgg ggggttcgtg cacacagccc agcttggagc
3781 gaacgaccta caccgaactg agatacctac agcgtgagca ttgagaaagc gccacgcttc
3841 ccgaagggag aaaggcggac aggtatccgg taagcggcag ggtcggaaca ggagagcgca
3901 cgagggagct tccagggggga aacgcctggt atctttatag tcctgtcggg tttcgccacc
3961 tctgacttga gcgtcgattt ttgtgatgct cgtcaggggg gcggagccta tggaaaaacg
4021 ccagcaacgc ggcctttta cggttcctgg ccttttgctg gccttttgct cacatgttct
4081 ttcctgcgtt atcccctgat tctgtggata accgtattac cgcctttgag tgagctgata
4141 ccgctcgccg cagccgaacg accgagcgca gcgagtcagt gagcgaggaa gcggaagagc
4201 gcccaatacg caaaccgcct ctccccgcgc gttggccgat tcattaatgc agaattaatt
4261 ctcatgtttg acagcttatc atcgactgca cggtgcacca atgcttctgg cgtcaggcag
4321 ccatcggaag ctgtggtatg gctgtgcagg tcgtaaatca ctgcataatt cgtgtcgctc
4381 aaggcgcact cccgttctgg ataatgtttt ttgcgccgac atcataacgg ttctggcaaa
4441 tattctgaaa tgagctgttg acaattaatc atcggctcgt ataatgtgtg gaattgtgag
4501 cggataacaa tttcacacag gaaacagcga tgaattcaga tctcaccatg aaggagctgg
4561 tggcccgagt gctgcagagg ctgtgcgagc gcggcgcgaa gaacgtgctg gccttcggct
4621 tcgcgctgct ggacggggcc cgcgggggcc ccccgaggc cttcaccacc agcgtgcgca
4681 gctacctgcc caacacggtg accgacgcac tgcgggggag cggggcgtgg gggctgctgc
4741 tgcgccgcgt gggcgacgac gtgctggttc acctgctggc acgctgcgcg ctctttgtgc
4801 tggtgctcc cagctgcgcc taccaggtgt gcgggccgcc gctgtaccag ctcggcgctg
4861 ccactcaggc ccggcccccg ccacacgcta gtggaccccg aaggcgtctg ggatgcgaac
4921 gggcctggaa ccatagcgtc agggaggccg ggtcccccct gggcctgcca gccccgggtg
4981 cgaggaggcg cgggggcagt gccagccgaa gtctgccgtt gcccaagagg cccaggcgtg
5041 gcgctgcccc tgagccggag cggacgcccg ttgggcaggg gtcctgggcc cacccgggca
5101 ggacgcgtgg accgagtgac cgtggtttct gtgtggtgtc acctgccaga cccgccgaag
5161 aagccaccct ctttggagggt gcgctctctg cacgcgcca ctcccaccca tccgtgggcc
5221 gccagcacca cgcgggcccc ccatccacat cgcggccacc acgtccctgg gacacgcctt
5281 gtcccccggt gtacgccgag accaagcact tcctctactc ctcaggcgac aaggagcagc
5341 tgcggccctc cttcctactc agctctctga ggcccagcct gactggcgct cggaggctcg
5401 tggagaccat cttcctgggt tccaggccct ggatgccagg gactccccgc aggttgcccc
5461 gcctgcccca gcgctactgg caaatgcggc ccctgtttct ggagctgctt gggaaccacg
5521 cgcagtgccc ctacggggtg ctcctcaaga cgcactgccc gctgcgagct gcggtcaccc
```

*Fig. 13C*

```
5581 cagcagccgg tgtctgtgcc cgggagaagc cccagggctc tgtggcggcc cccgaggagg
5641 aggacacaga cccccgtcgc ctggtgcagc tgctccgcca gcacagcagc ccctggcagg
5701 tgtacggctt cgtgcgggcc tgcctgcgcc ggctggtgcc cccaggcctc tggggctcca
5761 ggcacaacga acgccgcttc ctcaggaaca ccaagaagtt catctccctg gggaagcatg
5821 ccaagctctc gctgcaggag ctgacgtgga agatgagcgt gcgggactgc gcttggctgc
5881 gcaggagccc aggggttggc tgtgttccgg ccgcagagca ccgtctgcgt gaggagatcc
5941 tggccaagtt cctgcactgg ctgatgagtg tgtacgtcgt cgagctgctc aggtctttct
6001 tttatgtcac ggagaccacg tttcaaaaga acaggctctt tttctaccgg aagagtgtct
6061 ggagcaagtt gcaaagcatt ggaatcagac agcacttgaa gagggtgcag ctgcgggagc
6121 tgtcggaagc agaggtcagg cagcatcggg aagccaggcc cgccctgctg acgtccagac
6181 tccgcttcat ccccaagcct gacgggctgc ggccgattgt gaacatggac tacgtcgtgg
6241 gagccagaac gttccgcaga gaaaagaggg ccgagcgtct cacctcgagg gtgaaggcac
6301 tgttcagcgt gctcaactac gagcgggcgc ggcgccccgg cctcctgggc gcctctgtgc
6361 tgggcctgga cgatatccac agggcctggc gcaccttcgt gctgcgtgtg cgggcccagg
6421 acccgccgcc tgagctgtac tttgtcaagg tggatgtgac gggcgcgtac gacaccatcc
6481 cccaggacag gctcacggag gtcatcgcca gcatcatcaa accccagaac acgtactgcg
6541 tgcgtcggta tgccgtggtc cagaaggccg cccatgggca cgtccgcaag gccttcaaga
6601 gccacgtcct acgtccagtg ccaggggatc ccgcagggct ccatcctctc cacgctgctc
6661 tgcagcctgt gctacggcga catggagaac aagctgtttg cggggattcg gcgggacggg
6721 ctgctcctgc gtttggtgga tgatttcttg ttggtgacac ctcacctcac ccacgcgaaa
6781 acttcctcag gacctggtcc gaagtgtcct gagtatggct gcgtggtgaa cttgcggaag
6841 acagtggtga acttccctgt agaagacgaa gccctgggtg cacggctttt gttcagatg
6901 ccggcccacg gcctattccc ctggtgcggc ctgctgctgg atacccggac cctggaggtg
6961 cagagcgact actccagcta tgcccggacc tccatcagag ccagtctcac cttcaaccgc
7021 ggcttcaagg ctgggaggaa catgcgtcgc aaactctttg gggtcttgcg gctgaagtgt
7081 cacagcctgt ttctggattt gcaggtgaac agcctccaga cggtgtgcac caacatctac
7141 aagatcctcc tgctgcaggc gtacaggttt cacgcatgtg tgctgcagct cccatttcat
7201 cagcaagttt ggaagaaccc cacattttc ctgcgcgtca tctctgacac ggcctccctc
7261 tgctactcca tcctgaaagc caagaacgca gccgaagaaa catttctgt cgtgactcct
7321 gcggtgcttg ggtcgggaca gccagagatg gagccacccc gcagaccgtc gggtgtgggc
7381 agctttccgg tgtctcctgg gagggagtt gggctgggcc tgtgactcct cagcctctgt
7441 tttccccccag ggatgtcgct gggggccaag ggcgccgccg gccctctgcc ctccgaggcc
7501 gtgcagtggc tgtgccacca agcattcctg ctcaagctga ctcgacaccg tgtcacctac
7561 gtgccactcc tggggtcact caggacaggc aagtgtgggt ggaggccagt gcggg
```

*Fig. 13D*

```
LOCUS       pAKI28.7    7797 bp dsDNA   Circular
DEFINITION  Human telomerase clone with alternative C-terminus 1 tcgacctgca ggcatgcaag cttggcactg gccgtcgttt tacaacgtcg tgactgggaa
   61 aaccctggcg ttacccaact taatcgcctt gcagcacatc ccctttcgc cagctggcgt
  121 aatagcgaag aggcccgcac cgatcgccct tcccaacagt tgcgcagcct gaatggcgaa
  181 tggcgcctga tgcggtattt tctccttacg catctgtgcg gtatttcaca ccgcataaat
  241 tccctgtttt ggcggatgag agaagatttt cagcctgata cagattaaat cagaacgcag
  301 aagcggtctg ataaaacaga atttgcctgg cggcagtagc gcggtggtcc cacctgaccc
  361 catgccgaac tcagaagtga aacgccgtag cgccgatggt agtgtggggt ctccccatgc
  421 gagagtaggg aactgccagg catcaaataa aacgaaaggc tcagtcgaaa gactgggcct
  481 ttcgttttat ctgttgtttg tcggtgaacg ctctcctgag taggacaaat ccgccgggag
  541 cggatttgaa cgttgcgaag caacggcccg gagggtggcg gcaggacgc ccgccataaa
  601 ctgccaggca tcaaattaag cagaaggcca tcctgacgga tggccttttt gcgtttctac
  661 aaactcttcc tgtcgtcata tctacaagcc atcccccac agatacggta aactagcctc
  721 gtttttgcat caggaaagca gggaatttat ggtgcactct cagtacaatc tgctctgatg
  781 ccgcatagtt aagccagccc cgacacccgc caacacccgc tgacgcgccc tgacgggctt
  841 gtctgctccc ggcatccgct tacagacaag ctgtgaccgt ctccgggagc tgcatgtgtc
  901 agaggttttc accgtcatca ccgaaacgcg cgagacgaaa gggcctcgtg atacgcctat
  961 ttttataggt taatgtcatg ataataatgg tttcttagac gtgaggttct gtacccgaca
 1021 ccatcgaatg gtgcaaaacc tttcgcggta tggcatgata gcgcccggaa gagagtcaat
 1081 tcagggtggt gaatgtgaaa ccagtaacgt tatacgatgt cgcagagtat gccggtgtct
 1141 cttatcagac cgtttcccgc gtggtgaacc aggccagcca cgtttctgcg aaaacgcggg
 1201 aaaaagtgga agcggcgatg gcggagctga attacattcc caaccgcgtg gcacaacaac
 1261 tggcgggcaa acagtcgttg ctgattggcg ttgccacctc cagtctggcc ctgcacgcgc
 1321 cgtcgcaaat tgtcgcggcg attaaatctc gcgccgatca actgggtgcc agcgtggtgg
 1381 tgtcgatggt agaacgaagc ggcgtcgaag cctgtaaagc ggcggtgcac aatcttctcg
 1441 cgcaacgcgt cagtgggctg atcattaact atccgctgga tgaccaggat gccattgctg
 1501 tggaagctgc ctgcactaat gttccggcgt tatttcttga tgtctctgac cagacaccca
 1561 tcaacagtat tattttctcc catgaagacg gtacgcgact gggcgtggag catctggtcg
 1621 cattgggtca ccagcaaatc gcgctgttag cgggcccatt aagttctgtc tcggcgcgtc
 1681 tgcgtctggc tggctggcat aaatatctca ctcgcaatca aattcagccg atagcggaac
 1741 gggaaggcga ctggagtgcc atgtccggtt ttcaacaaac catgcaaatg ctgaatgagg
 1801 gcatcgttcc cactgcgatg ctggttgcca acgatcagat ggcgctgggc gcaatgcgcg
 1861 ccattaccga gtccgggctg cgcgttggtg cggatatctc ggtagtggga tacgacgata
 1921 ccgaagacag ctcatgttat atcccgccgt taaccaccat caaacaggat tttcgcctgc
 1981 tggggcaaac cagcgtggac cgcttgctgc aactctctca gggccaggcg gtgaagggca
 2041 atcagctgtt gcccgtctca ctggtgaaaa gaaaaaccac cctggcgccc aatacgcaaa
 2101 ccgcctctcc ccgcgcgttg gccgattcat taatgcagct ggcacgacag gtttcccgac
 2161 tggaaagcgg gcagtgagcg caacgcaatt aatgtaagtt agctcactca ttaggcaccc
 2221 caggctttac actttatgct tccgacctgc aagaacctca cgtcaggtgg cacttttcgg
 2281 ggaaatgtgc gcggaacccc tatttgttta ttttctaaa tacattcaaa tatgtatccg
 2341 ctcatgagac aataaccctg ataaatgctt caataatatt gaaaaggaa gagtatgagt
 2401 attcaacatt tccgtgtcgc ccttattccc ttttttgcgg cattttgcct tcctgttttt
 2461 gctcacccag aaacgctggt gaaagtaaaa gatgctgaag atcagttggg tgcacgagtg
 2521 ggttacatcg aaactggatc tcaacagcg gtaagatcct tgagagtttt cgccccgaag
 2581 aacgtttttcc aatgatgagc acttttaaag ttctgctatg tggcgcggta ttatcccgta
 2641 ttgacgccgg gcaagagcaa ctcggtcgcc gcatacacta ttctcagaat gacttggttg
```

```
2701 agtactcacc agtcacagaa aagcatctta cggatggcat gacagtaaga gaattatgca
2761 gtgctgccat aaccatgagt gataacactg cggccaactt acttctgaca acgatcggag
2821 gaccgaagga gctaaccgct tttttgcaca acatggggga tcatgtaact cgccttgatc
2881 gttgggaacc ggagctgaat gaagccatac caaacgacga gcgtgacacc acgatgcctg
2941 tagcaatggc aacaacgttg cgcaaactat taactggcga actacttact ctagcttccc
3001 ggcaacaatt aatagactgg atggaggcgg ataaagttgc aggaccactt ctgcgctcgg
3061 cccttccggc tggctggttt attgctgata aatctggagc cggtgagcgt gggtctcgcg
3121 gtatcattgc agcactgggg ccagatggta agccctcccg tatcgtagtt atctacacga
3181 cggggagtca ggcaactatg gatgaacgaa atagacagat cgctgagata ggtgcctcac
3241 tgattaagca ttggtaactg tcagaccaag tttactcata tatactttag attgatttaa
3301 aacttcattt ttaatttaaa aggatctagg tgaagatcct ttttgataat ctcatgacca
3361 aaatccctta acgtgagttt cgttccact gagcgtcaga ccccgtagaa aagatcaaag
3421 gatcttcttg agatcctttt tttctgcgcg taatctgctg cttgcaaaca aaaaaaccac
3481 cgctaccagc ggtggtttgt ttgccggatc aagagctacc aactcttttt ccgaaggtaa
3541 ctggcttcag cagagcgcag ataccaaata ctgtccttct agtgtagccg tagttaggcc
3601 accacttcaa gaactctgta gcaccgccta catacctcgc tctgctaatc ctgttaccag
3661 tggctgctgc cagtggcgat aagtcgtgtc ttaccgggtt ggactcaaga cgatagttac
3721 cggataaggc gcagcggtcg ggctgaacgg ggggttcgtg cacacagccc agcttggagc
3781 gaacgaccta caccgaactg agatacctac agcgtgagca ttgagaaagc gccacgcttc
3841 ccgaagggag aaaggcggac aggtatccgg taagcggcag ggtcggaaca ggagagcgca
3901 cgagggagct tccaggggga aacgcctggt atctttatag tcctgtcggg tttcgccacc
3961 tctgacttga gcgtcgattt ttgtgatgct cgtcaggggg gcggagccta tggaaaaacg
4021 ccagcaacgc ggcctttta cggttcctgg ccttttgctg gccttttgct cacatgttct
4081 ttcctgcgtt atcccctgat tctgtggata accgtattac cgcctttgag tgagctgata
4141 ccgctcgccg cagccgaacg accgagcgca gcgagtcagt gagcgaggaa gcggaagagc
4201 gcccaatacg caaaccgcct ctccccgcgc gttggccgat tcattaatgc agaattaatt
4261 ctcatgtttg acagcttatc atcgactgca cggtgcacca atgcttctgg cgtcaggcag
4321 ccatcggaag ctgtggtatg gctgtgcagg tcgtaaatca ctgcataatt cgtgtcgctc
4381 aaggcgcact cccgttctgg ataatgtttt ttgcgccgac atcataacgg ttctggcaaa
4441 tattctgaaa tgagctgttg acaattaatc atcggctcgt ataatgtgtg gaattgtgag
4501 cggataacaa tttcacacag gaaacagcga tgaattcaga tctcaccatg aaggagctgg
4561 tggcccgagt gctgcagagg ctgtgcgagc gcggcgcgaa gaacgtgctg gccttcggct
4621 tcgcgctgct ggacggggcc cgcggggcc ccccgaggc cttcaccacc agcgtgcgca
4681 gctacctgcc caacacggtg accgacgcac tgcggggag cggggcgtgg gggctgctgc
4741 tgcgccgcgt gggcgacgac gtgctggttc acctgctggc acgctgcgcg ctctttgtgc
4801 tggtggctcc cagctgcgcc taccaggtgt gcgggccgcc gctgtaccag ctcggcgctg
4861 ccactcaggc ccggccccg ccacacgcta gtggaccccg aaggcgtctg ggatgcgaac
4921 gggcctggaa ccatagcgt agggaggccg gggtcccct gggcctgcca gccccgggtg
4981 cgaggaggcg cggggcagt gccagccgaa gtctgccgtt gcccaagagg cccaggcgtg
5041 gcgctgcccc tgagccggag cggacgcccg ttgggcaggg gtcctgggcc cacccgggca
5101 ggacgcgtgg accgagtgac cgtggtttct gtgtggtgtc acctgccaga cccgccgaag
5161 aagccacctc tttggagggt gcgctctctg gcacgcgcca ctcccaccca tccgtgggcc
5221 gccagcacca cgcgggcccc ccatccacat cgcggccacc acgtccctgg gacacgcctt
5281 gtccccggt gtacgccgag accaagcact tcctctactc ctcaggcgac aaggagcagc
5341 tgcggccctc cttcctactc agctctctga ggcccagcct gactggcgct cggaggctcg
5401 tggagaccat cttctggggt tccaggccct ggatgccagg gactccccgc aggttgcccc
5461 gcctgcccca gcgctactgg caaatgcggc ccctgttcct ggagctgctt gggaaccacg
5521 cgcagtgccc ctacggggtg ctcctcaaga cgcactgccc gctgcgagct gcggtcaccc
```

*Fig. 14C*

```
5581 cagcagccgg tgtctgtgcc cgggagaagc cccagggctc tgtggcggcc cccgaggagg
5641 aggacacaga cccccgtcgc ctggtgcagc tgctccgcca gcacagcagc ccctggcagg
5701 tgtacggctt cgtgcgggcc tgcctgcgcc ggctggtgcc cccaggcctc tggggctcca
5761 ggcacaacga acgccgcttc ctcaggaaca ccaagaagtt catctccctg gggaagcatg
5821 ccaagctctc gctgcaggag ctgacgtgga agatgagcgt gcgggactgc gcttggctgc
5881 gcaggagccc aggggttggc tgtgttccgg ccgcagagca ccgtctgcgt gaggagatcc
5941 tggccaagtt cctgcactgg ctgatgagtg tgtacgtcgt cgagctgctc aggtctttct
6001 tttatgtcac ggagaccacg tttcaaaaga acaggctctt tttctaccgg aagagtgtct
6061 ggagcaagtt gcaaagcatt ggaatcagac agcacttgaa gagggtgcag ctgcgggagc
6121 tgtcggaagc agaggtcagg cagcatcggg aagccaggcc cgccctgctg acgtccagac
6181 tccgcttcat ccccaagcct gacgggctgc ggccgattgt gaacatggac tacgtcgtgg
6241 gagccagaac gttccgcaga gaaaagaggg ccgagcgtct cacctcgagg gtgaaggcac
6301 tgttcagcgt gctcaactac gagcgggcgc ggcgccccgg cctcctgggc gcctctgtgc
6361 tgggcctgga cgatatccac agggcctggc gcaccttcgt gctgcgtgtg cgggcccagg
6421 acccgccgcc tgagctgtac tttgtcaagg tggatgtgac gggcgcgtac gacaccatcc
6481 cccaggacag gctcacggag gtcatcgcca gcatcatcaa accccagaac acgtactgcg
6541 tgcgtcggta tgccgtggtc cagaaggccg cccatgggca cgtccgcaag gccttcaaga
6601 gccacgtctc taccttgaca gacctccagc cgtacatgcg acagttcgtg gctcacctgc
6661 aggagaccag cccgctgagg gatgccgtcg tcatcgagca gagctcctcc ctgaatgagg
6721 ccagcagtgg cctcttcgac gtcttcctac gcttcatgtg ccaccacgcc gtgcgcatca
6781 ggggcaagtc ctacgtccag tgccagggga tcccgcaggg ctccatcctc tccacgctgc
6841 tctgcagcct gtgctacggc gacatggaga caagctgtt tgcggggatt cggcgggacg
6901 ggctgctcct gcgtttggtg gatgatttct tgttggtgac acctcacctc acccacgcga
6961 aaacttcctc aggacctggt ccgaagtgtc ctgagtatgg ctgcgtggtg aacttgcgga
7021 agacagtggt gaacttccct gtagaagacg aagccctggg tggcacggct tttgttcaga
7081 tgccggccca cggcctattc ccctggtgcg gcctgctgct ggatacccgg accctggagg
7141 tgcagagcga ctactccagc tatgcccgga cctccatcag agccagtctc accttcaacc
7201 gcggcttcaa ggctgggagg aacatgcgtc gcaaactctt tggggtcttg cggctgaagt
7261 gtcacagcct gtttctggat ttgcaggtga acagcctcca gacggtgtgc accaacatct
7321 acaagatcct cctgctgcag gcgtacaggt ttcacgcatg tgtgctgcag ctcccatttc
7381 atcagcaagt ttggaagaac cccacatttt cctgcgcgt catctctgac acggcctccc
7441 tctgctactc catcctgaaa gccaagaacg cagccgaaga aaacatttct gtcgtgactc
7501 ctgcggtgct tgggtcggga cagccagaga tggagccacc ccgcagaccg tcgggtgtgg
7561 gcagctttcc ggtgtctcct gggaggggag ttgggctggg cctgtgactc ctcagcctct
7621 gttttccccc agggatgtcg ctggggggcca agggcgccgc cggccctctg ccctccgagg
7681 ccgtgcagtg gctgtgccac caagcattcc tgctcaagct gactcgacac cgtgtcacct
7741 acgtgccact cctggggtca ctcaggacag gcaagtgtgg gtggaggcca gtgcggg
```

Fig. 14D

```
LOCUS       pAKI28.14    7688 bp dsDNA    Circular
DEFINITION  Human telomerase clone with exon alpha spliced out 1 tcgacctgca ggcatgcaag cttggcactg gccgtcgttt tacaacgtcg tgactgggaa
  61 aaccctggcg ttacccaact taatcgcctt gcagcacatc cccctttcgc cagctggcgt
 121 aatagcgaag aggcccgcac cgatcgccct tcccaacagt tgcgcagcct gaatggcgaa
 181 tggcgcctga tgcggtattt tctccttacg catctgtgcg gtatttcaca ccgcataaat
 241 tccctgtttt ggcggatgag agaagatttt cagcctgata cagattaaat cagaacgcag
 301 aagcggtctg ataaaacaga atttgcctgg cggcagtagc gcggtggtcc cacctgaccc
 361 catgccgaac tcagaagtga aacgccgtag cgccgatggt agtgtggggt ctccccatgc
 421 gagagtaggg aactgccagg catcaaataa aacgaaaggc tcagtcgaaa gactgggcct
 481 ttcgttttat ctgttgtttg tcggtgaacg ctctcctgag taggacaaat ccgccgggag
 541 cggatttgaa cgttgcgaag caacggcccg gagggtggcg ggcaggacgc ccgccataaa
 601 ctgccaggca tcaaattaag cagaaggcca tcctgacgga tggcctttt gcgtttctac
 661 aaactcttcc tgtcgtcata tctacaagcc atcccccac agatacggta aactagcctc
 721 gtttttgcat caggaaagca gggaatttat ggtgcactct cagtacaatc tgctctgatg
 781 ccgcatagtt aagccagccc cgacacccgc caacacccgc tgacgcgccc tgacgggctt
 841 gtctgctccc ggcatccgct tacagacaag ctgtgaccgt ctccgggagc tgcatgtgtc
 901 agaggttttc accgtcatca ccgaaacgcg cgagacgaaa gggcctcgtg atacgcctat
 961 ttttataggt taatgtcatg ataataatgg tttcttagac gtgaggttct gtacccgaca
1021 ccatcgaatg gtgcaaaacc tttcgcggta tggcatgata gcgcccggaa gagagtcaat
1081 tcagggtggt gaatgtgaaa ccagtaacgt tatacgatgt cgcagagtat gccggtgtct
1141 cttatcagac cgtttcccgc gtggtgaacc aggccagcca cgtttctgcg aaaacgcggg
1201 aaaaagtgga agcggcgatg gcggagctga attacattcc caaccgcgtg gcacaacaac
1261 tggcgggcaa acagtcgttg ctgattggcg ttgccacctc cagtctggcc ctgcacgcgc
1321 cgtcgcaaat tgtcgcggcg attaaatctc gcgccgatca actgggtgcc agcgtggtgg
1381 tgtcgatggt agaacgaagc ggcgtcgaag cctgtaaagc ggcggtgcac aatcttctcg
1441 cgcaacgcgt cagtgggctg atcattaact atccgctgga tgaccaggat gccattgctg
1501 tggaagctgc ctgcactaat gttccggcgt tatttcttga tgtctctgac cagacaccca
1561 tcaacagtat tattttctcc catgaagacg gtacgcgact gggcgtggag catctggtcg
1621 cattgggtca ccagcaaatc gcgctgttag cgggcccatt aagttctgtc tcggcgcgtc
1681 tgcgtctggc tggctggcat aaatatctca ctcgcaatca aattcagccg atagcggaac
1741 gggaaggcga ctggagtgcc atgtccggtt ttcaacaaac catgcaaatg ctgaatgagg
1801 gcatcgttcc cactgcgatg ctggttgcca acgatcagat ggcgctgggc gcaatgcgcg
1861 ccattaccga gtccgggctg cgcgttggtg cggatatctc ggtagtggga tacgacgata
1921 ccgaagacag ctcatgttat atcccgccgt taaccaccat caaacaggat tttcgcctgc
1981 tggggcaaac cagcgtggac cgcttgctgc aactctctca gggccaggcg gtgaagggca
2041 atcagctgtt gcccgtctca ctggtgaaaa gaaaaaccac cctggcgccc aatacgcaaa
2101 ccgcctctcc ccgcgcgttg gccgattcat taatgcagct ggcacgacag gtttcccgac
2161 tggaaagcgg gcagtgagcg caacgcaatt aatgtaagtt agctcactca ttaggcaccc
2221 caggctttac actttatgct tccgacctgc aagaacctca cgtcaggtgg cacttttcgg
2281 ggaaatgtgc gcggaacccc tatttgttta ttttctaaa tacattcaaa tatgtatccg
2341 ctcatgagac aataaccctg ataaatgctt caataatatt gaaaaaggaa gagtatgagt
2401 attcaacatt tccgtgtcgc ccttattccc ttttttgcgg cattttgcct tcctgttttt
2461 gctcacccag aaacgctggt gaaagtaaaa gatgctgaag atcagttggg tgcacgagtg
2521 ggttacatcg aaactggat ctcaacagcg gtaagatcct tgagagtttt cgccccgaag
2581 aacgttttcc aatgatgagc acttttaaag ttctgctatg tggcgcggta ttatcccgta
2641 ttgacgccgg gcaagagcaa ctcggtcgcc gcatacacta ttctcagaat gacttggttg
```

*Fig. 15B*

```
2701 agtactcacc agtcacagaa aagcatctta cggatggcat gacagtaaga gaattatgca
2761 gtgctgccat aaccatgagt gataacactg cggccaactt acttctgaca acgatcggag
2821 gaccgaagga gctaaccgct tttttgcaca acatgggga tcatgtaact cgccttgatc
2881 gttgggaacc ggagctgaat gaagccatac caaacgacga gcgtgacacc acgatgcctg
2941 tagcaatggc aacaacgttg cgcaaactat taactggcga actacttact ctagcttccc
3001 ggcaacaatt aatagactgg atggaggcgg ataaagttgc aggaccactt ctgcgctcgg
3061 cccttccggc tggctggttt attgctgata atctggagc cggtgagcgt gggtctcgcg
3121 gtatcattgc agcactgggg ccagatggta agccctcccg tatcgtagtt atctacacga
3181 cggggagtca ggcaactatg gatgaacgaa atagacagat cgctgagata ggtgcctcac
3241 tgattaagca ttggtaactg tcagaccaag tttactcata tatactttag attgatttaa
3301 aacttcattt ttaatttaaa aggatctagg tgaagatcct ttttgataat ctcatgacca
3361 aaatccctta acgtgagttt tcgttccact gagcgtcaga ccccgtagaa aagatcaaag
3421 gatcttcttg agatcctttt tttctgcgcg taatctgctg cttgcaaaca aaaaaaccac
3481 cgctaccagc ggtggtttgt ttgccggatc aagagctacc aactcttttt ccgaaggtaa
3541 ctggcttcag cagagcgcag ataccaaata ctgtccttct agtgtagccg tagttaggcc
3601 accacttcaa gaactctgta gcaccgccta catacctcgc tctgctaatc ctgttaccag
3661 tggctgctgc cagtggcgat aagtcgtgtc ttaccgggtt ggactcaaga cgatagttac
3721 cggataaggc gcagcggtcg ggctgaacgg ggggttcgtg cacacagccc agcttggagc
3781 gaacgaccta caccgaactg agatacctac agcgtgagca ttgagaaagc gccacgcttc
3841 ccgaagggag aaaggcggac aggtatccgg taagcggcag ggtcggaaca ggagagcgca
3901 cgagggagct ccagggggga aacgcctggt atctttatag tcctgtcggg tttcgccacc
3961 tctgacttga gcgtcgattt ttgtgatgct cgtcagggg cggagccta tggaaaaacg
4021 ccagcaacgc ggcctttta cggttcctgg ccttttgctg gccttttgct cacatgttct
4081 ttcctgcgtt atccctgat tctgtggata accgtattac cgcctttgag tgagctgata
4141 ccgctcgccg cagccgaacg accgagcgca gcgagtcagt gagcgaggaa gcggaagagc
4201 gcccaatacg caaaccgcct ctccccgcgc gttggccgat tcattaatgc agaattaatt
4261 ctcatgtttg acagcttatc atcgactgca cggtgcacca atgcttctgg cgtcaggcag
4321 ccatcggaag ctgtggtatg gctgtgcagg tcgtaaatca ctgcataatt cgtgtcgctc
4381 aaggcgcact cccgttctgg ataatgtttt ttgcgccgac atcataacgg ttctggcaaa
4441 tattctgaaa tgagctgttg acaattaatc atcggctcgt ataatgtgtg gaattgtgag
4501 cggataacaa tttcacacag gaaacagcga tgaattcaga tctcaccatg aaggagctgg
4561 tggcccgagt gctgcagagg ctgtgcgagc gcggcgcgaa gaacgtgctg gccttcggct
4621 tcgcgctgct ggacggggcc cgcggggggcc ccccgaggc cttcaccacc agcgtgcgca
4681 gctacctgcc caacacggtg accgacgcac tgcgggggag cggggcgtgg gggctgctgc
4741 tgcgccgcgt gggcgacgac gtgctggttc acctgctggc acgctgcgcg ctctttgtgc
4801 tggtggctcc cagctgcgcc taccaggtgt gcgggccgcc gctgtaccag ctcggcgctg
4861 ccactcaggc ccggcccccc ccacacgcta gtggaccccg aaggcgtctg ggatgcgaac
4921 gggcctggaa ccatagcgtc agggaggccg gggtcccct gggcctgcca gccccgggtg
4981 cgaggaggcg cggggcagt gccagccgaa gtctgccgtt gccaagagg cccaggcgtg
5041 gcgctgcccc tgagccggag cggacgcccg ttgggcaggg gtcctgggcc cacccgggca
5101 ggacgcgtgg accgagtgac cgtggtttct gtgtggtgtc acctgccaga cccgccgaag
5161 aagccacctc tttggagggt gcgctctctg gcacgcgcca ctcccaccca tccgtgggcc
5221 gccagcacca cgcggggccc ccatccacat cgcggccacc acgtccctgg gacacgcctt
5281 gtccccggt gtacgccgag accaagcact tcctctactc tcaggcgac aaggagcagc
5341 tgcggccctc cttcctactc agctctctga ggcccagcct gactggcgct cggaggctcg
5401 tggagaccat ctttctgggt tccaggccct ggatgccagg gactccccgc aggttgcccc
5461 gcctgcccca gcgctactgg caaatgcggc cctgtttct ggagctgctt gggaaccacg
5521 cgcagtgccc ctacggggtg ctcctcaaga cgcactgccc gctgcgagct gcggtcaccc
```

*Fig. 15C*

```
5581 cagcagccgg tgtctgtgcc cgggagaagc cccagggctc tgtggcggcc cccgaggagg
5641 aggacacaga cccccgtcgc ctggtgcagc tgctccgcca gcacagcagc ccctggcagg
5701 tgtacggctt cgtgcgggcc tgcctgcgcc ggctggtgcc cccaggcctc tggggctcca
5761 ggcacaacga acgccgcttc ctcaggaaca ccaagaagtt catctccctg gggaagcatg
5821 ccaagctctc gctgcaggag ctgacgtgga agatgagcgt gcgggactgc gcttggctgc
5881 gcaggagccc aggggttggc tgtgttccgg ccgcagagca ccgtctgcgt gaggagatcc
5941 tggccaagtt cctgcactgg ctgatgagtg tgtacgtcgt cgagctgctc aggtctttct
6001 tttatgtcac ggagaccacg tttcaaaaga acaggctctt tttctaccgg aagagtgtct
6061 ggagcaagtt gcaaagcatt ggaatcagac agcacttgaa gagggtgcag ctgcgggagc
6121 tgtcggaagc agaggtcagg cagcatcggg aagccaggcc cgccctgctg acgtccagac
6181 tccgcttcat ccccaagcct gacgggctgc ggccgattgt gaacatggac tacgtcgtgg
6241 gagccagaac gttccgcaga gaaagagggg ccgagcgtct cacctcgagg gtgaaggcac
6301 tgttcagcgt gctcaactac gagcgggcgc ggcgccccgg cctcctgggc gcctctgtgc
6361 tgggcctgga cgatatccac agggcctggc gcacttcgt gctgcgtgtg cgggcccagg
6421 acccgccgcc tgagctgtac tttgtcaagg acaggctcac ggaggtcatc gccagcatca
6481 tcaaacccag aacacgtact gcgtgcgtcg gtatgccgtg gtccagaagg ccgcccatgg
6541 gcacgtccgc aaggccttca agagccacgt ctctaccttg acagacctcc agccgtacat
6601 gcgacagttc gtggctcacc tgcaggagac cagcccgctg agggatgccg tcgtcatcga
6661 gcagagctcc tccctgaatg aggccagcag tggcctcttc gacgtcttcc tacgcttcat
6721 gtgccaccac gccgtgcgca tcaggggcaa gtcctacgtc cagtgccagg ggatcccgca
6781 gggctccatc ctctccacgc tgctctgcag cctgtgctac ggcgacatgg agaacaagct
6841 gtttgcgggg attcggcggg acgggctgct cctgcgtttg gtggatgatt tcttgttggt
6901 gacacctcac ctcacccacg cgaaaaacctt cctcaggacc ctggtccgag tgtccctga
6961 gtatggctgc gtggtgaact gcggaagac agtggtgaac ttccctgtag aagacgaggc
7021 cctgggtggc acggcttttg ttcagatgcc ggcccacggc ctattcccct ggtgcggcct
7081 gctgctggat acccggaccc tggaggtgca gagcgactac tccagctatg cccggacctc
7141 catcagagcc agtctcacct tcaaccgcgg cttcaaggct gggaggaaca tgcgtcgcaa
7201 actctttggg gtcttgcggc tgaagtgtca cagcctgttt ctggatttgc aggtgaacag
7261 cctccagacg gtgtgcacca acatctacaa gatcctcctg ctgcaggcgt acaggtttca
7321 cgcatgtgtg ctgcagctcc catttcatca gcaagtttgg aagaacccca cattttcct
7381 gcgcgtcatc tctgacacgg cctccctctg ctactccatc ctgaaagcca agaacgcagg
7441 gatgtcgctg ggggccaagg gcgccgccgg ccctctgccc tccgaggccg tgcagtggct
7501 gtgccaccaa gcattcctgc tcaagctgac tcgacaccgt gtcacctacg tgccactcct
7561 ggggtcactc aggacagccc agacgcagct gagtcggaag ctcccgggga cgacgctgac
7621 tgccctggag ccgcagccaa accggcact gccctcagac ttcaagacca tcctggactg
7681 atctagag
```

*Fig. 15D*

VERTEBRATE TELOMERASE GENES AND PROTEINS AND USES THEREOF

CROSS-RELATED APPLICATIONS

This application is a continuation of U.S. patent application Ser. No. 09/108,401, filed Jun. 30, 1998, now abandoned; which application claims the benefit of U.S. Provisional Application Nos. 60/051,410, filed Jul. 1, 1997; 60/053,018, filed Jul. 19, 1997; 60/053,329, filed Jul. 21, 1997; 60/054,642, filed Aug. 4, 1997; and 60/058,287, filed Sep. 9, 1997, all of which are incorporated by reference in their entirety.

TECHNICAL FIELD

This invention relates generally to telomerases, and particularly to the human telomerase gene and protein and uses for diagnostics and therapy.

BACKGROUND OF THE INVENTION

Non-circular chromosomes require a specialized mechanism for maintaining chromosome ends after each cell division because the polymerases responsible for replication of chromosomal DNA are unable to fully replicate linear DNA molecules, creating an "end replicating problem." To meet this challenge, eukaryotic cells depend upon an enzyme, telomerase, to add short, typically G-rich, relatively conserved repeats onto chromosomal ends. These repeat structures are termed telomeres.

The presence of telomeres is essential for cell viability. The absence of even a single telomere leads to cell cycle arrest in yeast, a eukaryotic cell (Sandell and Zakian, *Cell* 75:729, 1993). Telomeres shorten during replication; telomerase restores the telomeres. Thus, as expected, telomerase activity is primarily detected in actively dividing cells. As such, telomerase activity is constitutive in unicellular organisms and is regulated in more complex organisms, relatively abundant in germline and embryonic tissues and cells as well as tumor cells. In contrast, telomerase activity is difficult to detect in normal somatic human tissues. Moreover, rather than cessation of replication resulting in decreased telomerase, recent data indicate that telomerase inhibition might be one of the critical events in this transition. The seemingly direct correlation of telomerase/replication activities have prompted much speculation that inhibitors of telomerase could be a "universal" cancer therapeutic, effective for essentially all tumor types, whereas stimulators of telomerase could overcome the observed natural senescence of normal cells.

Spurred by these models, characterization of telomerase for culmination in isolation and cloning of telomerase has been a high priority. The mechanism of telomere elongation has been shown to center on the G-rich strand of the telomeric repeats. This G-rich strand, which extends to the 3' end of the chromosome, is extended by telomerase, a ribonucleoprotein, from the RNA component, which acts as a template. Various components of this complex have been isolated and cloned. The RNA component of the complex has been isolated and cloned from many different organisms, including humans (Feng et al. *Science* 269: 1236, 1995), mice and other mammalian species, *Saccharomyces cerevisiae*, *Tetrahymena*, *Euplotes*, and *Oxytricha* (see, Singer and Gottschling, *Science*, 266: 404, 1994; Lingner et al. *Genes & Develop.* 8: 1984, 1994; and Romero and Blackburn, *Cell* 67: 343, 1994). Protein components have been relatively refractory to isolation. Recently, the nucleotide sequences of several protein components have been determined (an 80 kD/95 kD dimeric protein from *Tetrahymena*, WO 96/19580; and a 67 kD protein from humans, WO 97/08314).

The present invention discloses nucleotide and amino acid sequences of telomerase, uses of these sequences for diagnostics and therapeutic uses, and further provides other related advantages.

SUMMARY OF THE INVENTION.

In one aspect, this invention generally provides isolated nucleic acid molecules encoding vertebrate telomerase (including variants thereof). Representative examples of vertebrates include mammals such as humans, old world monkeys (e.g., macaques, chimps, and baboons), dogs, rats, and mice, as well as non-mammalian organisms such as birds. In a preferred embodiment, the nucleic acid molecule encoding a vertebrate telomerase is provided, wherein the nucleic acid molecule comprises the sequence presented in FIG. 1, or hybridizes under stringent conditions to the complement of the sequence presented in FIG. 1 provided that the nucleic acid molecule is not EST AA281296.

In other preferred embodiments, the nucleic acid molecule comprises any of the sequences presented in FIG. 11 or encodes any of the amino acid sequences presented in FIG. 11, or hybridizes under normal stringency conditions to the complement of the sequences thereof, provided that the nucleic acid molecule is not EST AA281296. In other embodiments, the nucleic acid molecule comprises any of the sequences presented in FIG. 10, or hybridizes under normal stringency conditions to the complement of the sequences thereof.

In another aspect, the invention provides an oligonucleotide comprising from 10 to 100 contiguous nucleotides from the sequence presented in FIG. 1 or its complement and from 10 to 100 contiguous nucleotides from the sequences presented in FIG. 10 or the complements thereof. The oligonucleotides may be labeled with a detectable label.

In yet another aspect, an expression vector is provided, comprising a heterologous promoter operably linked to a nucleic acid molecule of human telomerase. The vector may be selected from the group consisting of bacterial vectors, retroviral vectors, adenoviral vectors and yeast vectors. Host cells containing such vectors are also provided.

In another aspect, the invention provides an isolated protein comprising a human telomerase protein. The protein may comprise the amino acid sequence presented in FIG. 1 or variant thereof or any of the amino acid sequences presented in FIG. 11 or variant thereof. In a related aspect, the protein is a portion of a human telomerase protein, which may derive from the sequences presented in FIG. 1 or 11. In preferred embodiments, the portion is from 10 to 100 amino acids long.

In other aspects, antibodies that specifically binds to human telomerase protein or portions are provided.

In a preferred aspect, an oligonucleotide (e.g., a nucleic acid probe or primer) is provided that is capable of specifically hybridizing to a nucleic acid molecule encoding a human telomerase under conditions of normal stringency. Within certain embodiments, the nucleic acid molecule has a detectable label. Within certain embodiments, the nucleic acid molecule is selected such that it does not hybridize to nucleotides 1624–2012 presented in FIG. 1. Within certain embodiments of the invention, the nucleic acid probe or primer may differ from a wild-type telomerase sequence by one or more nucleotides.

In a related aspect, the invention provides a pair of oligonucleotide primers capable of specifically amplifying all or a portion of a nucleic acid molecule encoding human telomerase. In specific embodiments, the nucleic acid molecule comprises the sequence presented in FIG. 1, FIG. 11, or complements thereof. In preferred embodiments, the pair of primers is capable of specifically amplifying sequence comprising all or a part of alternative intron/exon 1, alternative intron/exon α, alternative intron/exon β, alternative intron/exon 2, alternative intron/exon 3, alternative intron/exon X or alternative intron/exon Y. In a related aspect, the invention provides an oligonucleotide that hybridizes specifically to a nucleic acid sequence in alternative intron/exon 1, alternative intron/exon α, alternative intron/exon β, alternative intron/exon 2, alternative intron/exon 3, alternative intron/exon X or alternative intron/exon Y.

Methods for diagnosing cancer in a patent are also provided. These methods comprise preparing tumor cDNA and amplifying the tumor cDNA using primers that specifically amplify human telomerase nucleic acid sequence, wherein the detection of telomerase nucleic acid sequences is indicative of a diagnosis of cancer. The amount of detected sequences may be compared to the amount of amplified telomerase sequence to a control, wherein increase telomerase nucleic acid sequences over the control is indicative of a diagnosis of cancer.

In yet another aspect, a method of determining a pattern of telomerase RNA expression in cells is provided, comprising preparing cDNA from mRNA isolated from the cells, amplifying the cDNA using primers according to claim 35, therefrom determining the pattern of telomerase RNA expression. In preferred embodiments, the method further comprises detecting the amplified product by hybridization with an oligonucleotide having all or part of the sequence of alternative intron/exon 1, alternative intron/exon α, alternative intron/exon β, alternative intron/exon 2, alternative intron/exon 3, alternative intron/exon X or alternative intron/exon Y. These methods may be used to diagnose cancer in a patient, wherein the pattern is indicative of a diagnosis of cancer.

The invention also provides non-human transgenic animals whose cells contain a human telomerase gene that is operably linked to a promoter effective for the expression of the gene. In preferred embodiments, the animal is a mouse and the promoter is tissue-specific. In a related aspect, the invention provides a mouse whose cells have an endogenous telomerase gene disrupted by homologous recombination with a nonfunctional telomerase gene, wherein the mouse is unable to express endogenous telomerase.

The invention also provides inhibitors of human telomerase activity, as well as assays for identifying inhibitors of telomerase activity wherein the inhibitor binds to telomerase and is not a nucleoside analogue. The inhibitor may be an antisense nucleic acid complementary to human telomerase mRNA, a ribozyme and the like. The inhibitors may be used to treat cancer.

Also provided are methods for identifying an effector of telomerase activity, comprising the general steps of (a) adding a candidate effector to a mixture of telomerase protein, RNA component and template, wherein the telomerase protein is encoded by an isolated nucleic acid molecule as described above; (b) detecting telomerase activity, and (c) comparing the amount of activity in step (b) to the amount of activity in a control mixture without candidate effector, therefrom identifying an effector. Within further embodiments the effector is an inhibitor. With yet other embodiments the nucleic acid molecule encodes human telomerase.

These and other aspects of the present invention will become evident upon reference to the following detailed description and attached drawings. In addition, various references are set forth below which describe in more detail certain procedures or compositions (e.g., plasmids, etc.), and are therefore incorporated by reference in their entirety.

BRIEF DESCRIPTION OF THE DRAWINGS

FIGS. 1A–E present a DNA sequence (SEQ ID No:1) and predicted amino acid sequence (SEQ ID No.2) of human telomerase.

FIG. 2 presents an alignment of *Euplotes aediculatus* p123 (SEQ ID No:3), yeast (EST2) (SEQ ID No:4) and human (HT1) telomerase protein (amino acids 29–1132; SEQ ID NO:5) sequences. Reverse transcriptase motifs are indicated. The region of high homology among all three proteins is defined as the Telomerase region. The sequences are aligned with ClustalW.

FIGS. 7A–C show some alternative splicing patterns of the hT1 transcript. A, Schematic representation of six splicing variants. B, Combinations of some identified RNA variants (SEQ ID NOs 6–17). C, Sequences of putative exon/intron junctions of RNA variants. Variants are marked as in part A. A complete DNA sequence (with protein translation) (SEQ ID No:16 and 17) of variant 3 is presented. Amino acids corresponding to a potential c-Abl/SH3 binding site are underlined. Putative exon/intron junctions are marked with | and sequence coordinates are as in FIG. 1. Putative spliced exons are in lower case and putative unspliced introns are in bold.

FIGS. 10A–B present DNA sequence of variant regions of telomerase (SEQ ID NOS: 18–33).

FIGS. 11A–W presents DNA and amino acid sequences of exemplary variant telomerase proteins (SEQ ID NOS: 2, 34–86 and 155).

FIGS. 13A–D present a schematic diagram of plasmid pAK128.4 and the DNA sequence of the plasmid (SEQ ID NO: 87).

FIGS. 14A–E present a schematic diagram of plasmid pAK128.7 and the DNA sequence of the plasmid (SEQ ID NO: 88).

FIGS. 15A–D present a schematic diagram of plasmid pAK128.14 and the DNA sequence of the plasmid (SEQ ID NO: 89).

DETAILED DESCRIPTION OF THE INVENTION

Figure 3:
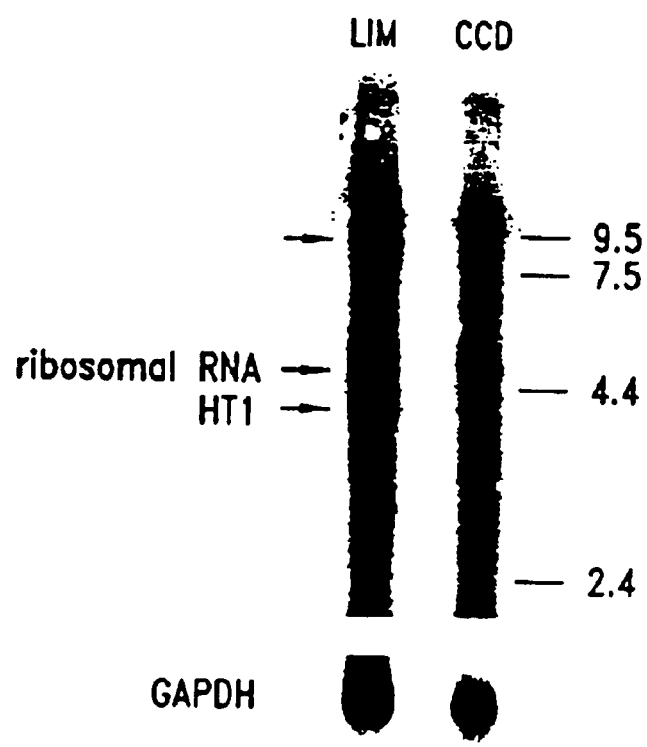
FIG. 3 is a scanned image of a Northern analysis showing that the telomerase catalytic subunit is expressed in LIM 1215 colon carcinoma cells but not in CCD primary fibroblasts. An mRNA of approximately 3.8 kb hybridizes to the hT1 probe. An additional cross-hybridizing mRNA of higher molecular weight is indicated by the top arrowhead. Cross-hybridization to ribosomal RNA present in the polyA$^+$ RNA preparation is indicated. The same blot is also hybridized to a probe from the GAPDH gene as a loading control (lower panel). Marker sizes are indicated in kb.

Prior to setting forth the invention, it may be helpful to an understanding thereof to define certain terms used herein.

As used herein, "wild-type telomerase" generally refers to a polypeptide that enzymatically synthesizes nucleic acid sequences comprising simple repeat sequences (e.g., CCCTAA, see Zakian, Science 270: 1601, 1995) to ends of chromosomes. The amino acid sequence of one representative wild-type telomerase from human has been deduced and is presented in FIG. 1 (SEQ ID No. 2). Within the context of this invention, it should be understood that telomerases of this invention include not only wild-type protein, but also variants (including alleles) of the wild-type protein sequence. Such variants may not necessarily exhibit enzymatic function. Briefly, such variants may result from natural polymorphisms, including RNA splice variants, generated by genetic recombination, or be synthesized by recombinant methodology, and moreover, may differ from wild-type protein by one or more amino acid substitutions, insertions, deletions, rearrangements or the like. Typically, when the result of synthesis, amino acid substitutions are conservative, i.e., substitution of amino acids within groups of polar, non-polar, aromatic, charged, etc. amino acids. In the region of homology to the wild-type sequence in the RTase motif regions variants will preferably have at least 90% amino acid sequence identity, and within certain embodiments, greater than 92%, 95%, or 97% identity. Outside the RTase motif region, variants will preferably have 75% amino acid identity, and within certain embodiments, at least 80%, 85%, 90%, 92%, 95% or 97% identity.

As will be appreciated by those skilled in the art, a nucleotide sequence encoding telomerase may differ from the wild-type sequence presented in the Figures; due to codon degeneracies, nucleotide polymorphisms, or amino acid differences. In other embodiments, variants should preferably hybridize to the wild-type nucleotide sequence at conditions of normal stringency, which is approximately 25–30° C. below Tm of the native duplex (e.g., 1 M Na+ at 65° C.; 5× SSPE, 0.5% SDS, 5× Denhardt's solution, at 65° C. or equivalent conditions; see generally, Sambrook et al. *Molecular Cloning: A Laboratory Manual*, 2nd ed., Cold Spring Harbor Press, 1987; Ausubel et al., *Current Protocols in Molecular Biology*, Greene Publishing, 1987). Tm for other than short oligonucleotides can be calculated by the formula Tm=81.5+0.41%(G+C)–log(Na+). Low stringency hybridizations are performed at conditions approximately 40° C. below Tm, and high stringency hybridizations are performed at conditions approximately 10° C. below Tm. Variants preferably have at least 75% nucleotide identity to wild-type sequence in the RTase motif region, preferably at least 80%, 85%, and most preferably at least 90% nucleotide identity.

As used herein, a "promoter" refers to a nucleotide sequence that contains elements that direct the transcription of a linked gene. At minimum, a promoter contains an RNA polymerase binding site. More typically, in eukaryotes, promoter sequences contain binding sites for other transcriptional factors that control the rate and timing of gene expression. Such sites include TATA box, CAAT box, POU box, AP1 binding site, and the like. Promoter regions may also contain enhancer elements. When a promoter is linked to a gene so as to enable transcription of the gene, it is "operatively linked".

An "isolated nucleic acid molecule" refers to a polynucleotide molecule in the form of a separate fragment or as a component of a larger nucleic acid construct, that has been separated from its source cell (including the chromosome it normally resides in) at least once in a substantially pure form. Nucleic acid molecules may be comprised of a wide variety of nucleotides, including DNA, RNA, nucleotide analogues, or some combination of these.

I. Telomerase, Telomerase Genes and Gene Products

As noted above, the invention provides compositions relating to vertebrate telomerase genes and gene products, and methods for the use of the genes and gene products. Given the disclosure provided herein, a telomerase gene can be isolated from a variety of cell types that express telomerase, including immortalized or transformed cells. As exemplified herein, a cDNA and variants encoding telomerase from human cells are identified, isolated, and characterized. Telomerase protein is then readily produced by host cells transfected with an expression vector encoding telomerase.

A. Isolation of Telomerase Gene

As described herein, the invention provides genes encoding telomerase. Within one embodiment of the invention, a gene encoding human telomerase can be identified by amplification of a cDNA library using a primer pair designed from an EST sequence. The EST sequence GenBank Accession No. AA281296, is identified by sequence identity and similarity to a *Euplotes aediculatus* telomerase gene (GenBank accession no. U95964; Lingner et al., *Science* 276: 561, 1997). Sequence comparisons between the *Euplotes* telomerase gene and the EST show approximately 38% amino acid identity and 59% amino acid similarity.

Telomerase genes may be isolated from genomic DNA or cDNA. Genomic DNA is preferred when the promoter region or other flanking regions are desired. Genomic DNA libraries constructed in chromosomal vectors, such as YACs (yeast artificial chromosomes), bacteriophage vectors, such as λEMBL3, λgt10, cosmids, or plasmids, and cDNA libraries constructed in bacteriophage vectors (e.g., λZAPII), plasmids, or others, are suitable for screening. Such libraries may be constructed using methods and techniques known in the art (see Sambrook et al., *Molecular Cloning: A Laboratory Manual*, Cold Spring Harbor Press, 1989) or purchased from commercial sources (e.g., Clontech, Palo Alto, Calif.). The DNA may be isolated from vertebrate cells, such as human cells, mouse cells, other rodent or primatic cells, avian cells, and the like.

Within one embodiment, the telomerase gene is isolated by amplification using cDNA library DNA as templates. Using the reported EST sequence, human telomerase may be isolated. Briefly, sets of amplification primers are designed based upon the EST nucleotide sequence. Examples of such primers are presented in Table 2 (see also Example 1). Amplification of cDNA libraries made from cells with high telomerase activity is preferred. The primers described herein amplify a fragment that has a length predicted from the EST sequence from a LIM1215 cDNA library. LIM1215 is a human colon cancer cell line. Confirmation of the nature of the fragment is obtained by DNA sequence analysis.

DNA fragments encompassing additional sequence are amplified in reactions using a primer that hybridizes to vector sequence in conjunction with one of the EST primers. By using vector primers from either side of the cloning site in combination with the EST primers, a 1.6 kb fragment derived from the 3' region of h-TEL (human telomerase) and a 0.7 kb fragment derived from the 5' region are isolated. These fragments are verified as containing telomerase coding sequence by amplification with a pair of primers internal to the EST sequence. The two fragments are cloned into pBluescript and subjected to DNA sequence analysis. Additional DNA sequence is obtained by C-RACE and amplification procedures to obtain the 5' end of a cDNA as well as by hybridization and isolation of clones from the cDNA library.

The compiled DNA sequence and predicted amino acid sequence of a reference human telomerase are presented in FIG. 1. As shown, the coding region of the reference telomerase is 3396 bases long and has an approximately 620 base long 3' untranslated region. The predicted amino acid sequence is 1132 amino acids long and may be delineated into four major domains: N-terminal, basic, reverse transcriptase (RT) and C-terminal. Furthermore, human telomerase contains regions of homology to other telomerases (e.g., from *Euplotes* and *S. pombe*) and reverse transcriptases. These motifs are identified herein and in Kilian et al. (*Human Molecular Genetics*, 12: 2011–2019, 1997) as domains 1, 2, A, B, C, and D, in Nakamura et al., (*Science*, 277: 955–959) as domains 1, 2, A, B', C, D, and E, and in Meyerson et al. (*Cell*, 90: 785–795, 1997) as motifs 1–6. Regardless of the name used, these motifs encompass amino acids 621–626 (motif 1) and 631–634 (motif 2), 708–720 (motif A), 827–839 (motif B), 863–871 (motif C), and 895–902 (motif D). Because the boundaries of these motifs are based on similarity and identity with other telomerases, the functional boundary of each motif may be different.

In addition, variants of the reference telomerase sequence are obtained by amplifications, which are described herein. Their: DNA and predicted amino acid sequences are presented in FIG. 11 and discussed in further detail below. Briefly, some of these variants encode truncated proteins and others have different C-terminal sequences. These variants likely result from alternative RNA splicing because telomerase appears to be a single copy gene in humans (see Example 2).

Alternatively, other methods may be used to obtain a nucleic acid molecule that encodes telomerase. For example, a nucleic acid molecule encoding telomerase may be obtained from an expression library by screening with an antibody or antibodies reactive to telomerase (see, Sambrook et al. *Molecular Cloning: A Laboratory Manual,* 2nd Ed., Cold Spring Harbor Laboratory Press, NY, 1987; Ausubel et al. *Current Protocols in Molecular Biology*, Greene Publishing Associates and Wiley-Interscience, NY, 1995). In another embodiment, nucleic acid molecules encoding telomerase may be isolated by hybridization screening of cDNA or genomic libraries. Oligonucleotides for hybridization screening may be designed based on the DNA sequence of human telomerase presented herein. Oligonucleotides for screening are typically at least 11 bases long and more usually at least 20 or 25 bases long. In one embodiment, the oligonucleotide is 20–30 bases long. Such an oligonucleotide may be synthesized in an automated fashion. To facilitate detection, the oligonucleotide may be conveniently labeled, generally at the 5' end, with a reporter molecule, such as a radionuclide, (e.g., $^{32}P$), enzymatic label, protein label, fluorescent label, or biotin. A library is generally plated as colonies or phage, depending upon the vector, and the recombinant DNA is transferred to nylon or nitrocellulose membranes. Hybridization conditions are tailored to the length and GC content of the oligonucleotide. Following denaturation, neutralization, and fixation of the DNA to the membrane, membranes are hybridized with labeled probe. Suitable hybridization conditions may be found in Sambrook et al., supra, Ausubel et al., supra, and furthermore hybridization solutions may contain additives such as tetramethylammonium chloride or other chaotropic reagents or hybotropic reagents to increase specificity of hybridization (see for example, PCT/US97/17413). Following hybridization, suitable detection methods reveal hybridizing colonies or phage that are then isolated and propagated. Candidate clones or amplified fragments may be verified as containing telomerase DNA by any of various means. For example, the candidate clones may be hybridized with a second, non-overlapping probe or subjected to DNA sequence analysis. In these ways, clones containing a telomerase gene or gene fragment, which are suitable for use in the present invention, are isolated.

Telomerase DNA may also be obtained by amplification of cDNA or genomic DNA. Oligonucleotide primers for amplification of a full-length cDNA are preferably derived from sequences at the 5' and 3' ends of the coding region. Amplification of genomic sequences will use primers that span intronic sequences and may use conditions that favor long amplification products (see Promega catalogue). Briefly, oligonucleotides used as amplification primers preferably do not have self-complementary sequences nor have complementary sequences at their 3' end (to prevent primer-dimer formation). Preferably, the primers have a GC content of about 50% and contain restriction sites to facilitate cloning. Generally, primers are between 15 and 50 nucleotides long, and more usually between 20 and 35 nucleotides long. The primers are annealed to cDNA or genomic DNA and sufficient amplification cycles are performed to yield a detectable product, preferably one that is readily visualized by gel electrophoresis and staining. The amplified fragment is purified and inserted into a vector (e.g., a viral, phagemid or plasmid vector, such as λgt10 or pBS(M13+)) and propagated.

Telomerase genes from a multitude of species can be isolated using the compositions provided herein. For closely related species, the human sequence or portion thereof may be utilized as a probe on a genomic or cDNA library. For example, a fragment of the telomerase gene that encompasses the catalytic site (approximately corresponding to amino acids 605–915 of FIG. 1) may be labeled and used as a probe on a library constructed from mouse, primate, rat, dog, or other vertebrate, warm-blooded, or mammalian species. An initial hybridization at normal stringency may yield clones or fragments encoding telomerase. If no hybridization is observed, relaxed (low) stringency hybridizations may be pursued. Guidelines for varying the stringency of the hybridization may be acquired from Sambrook et al., supra, and other well-known sources. Such probes may also be used on libraries from evolutionarily diverse species, such as Drosophila, although hybridization conditions will typically be more relaxed.

Other methods may alternatively be used to isolate telomerase genes from non-human species. These methods include, but are not limited to, amplification using primers derived from conserved areas (e.g., RTase motifs), amplification using degenerate primers from various regions of telomerase including the RTase region, antibody probing of expression libraries, telomerase RNA probing of expression libraries, and the like. A gene sequence is identified as a telomerase by amino acid similarity and/or nucleic acid identity. Generally, amino acid similarity, which allows for conservative differences, is preferred to identify a telomerase, From diverse species, amino acid similarity is generally at least 30% and preferably at least 40% or at least 50%. Nucleic acid identity may be lower and thus difficult to assess. Several readily available computer analysis programs, such as BLASTN and BLASTP, are useful to determine relatedness of genes and gene products. Candidate telomerase genes are examined for enzyme activity by one of the functional assays described herein or other equivalent assays.

B. Variant Telomerase Genes

Variants (including alleles) of the telomerase nucleic acid or amino acid sequence provided herein may be readily isolated from natural variants (e.g., polymorphisms, splice variants, mutants), synthesized, or constructed. Depending upon the intended use, mutants may be constructed to exhibit altered or deficient telomerase function. Particularly useful telomerase genes encode a protein lacking enzyme activity but that has a dominant negative phenotype. The telomerase variants, moreover, may lack one or more of known telomerase activities, including reverse transcriptase activity, nucleolytic activity, telomere binding activity, dNTP binding activity, and telomerase RNA (hTR) binding activity.

One skilled in the art recognizes that many methods have been developed for generating mutants (see, generally, Sambrook et al., supra; Ausubel et al., supra). Briefly, preferred methods for generating a few nucleotide substitutions utilize an oligonucleotide that spans the base or bases to be mutated and contains the mutated base or bases. The oligonucleotide is hybridized to complementary single stranded nucleic acid and second strand synthesis is primed from the oligonucleotide. Similarly, deletions and/or insertions may be constructed by any of a variety of known methods. For example, the gene can be digested with restriction enzymes and religated such that some sequence is deleted or ligated with an isolated fragment having cohesive ends so that an insertion or large substitution is made. In another embodiment, variants are generated by "exon shuffling" (see U.S. Pat. No. 5,605,793). Variant sequences may also be generated by "molecular evolution" techniques (see U.S. Pat. No. 5,723,323). Other means to generate variant sequences may be found, for example, in Sambrook et al. (supra) and Ausubel et al. (supra). Verification of variant sequences is typically accomplished by restriction enzyme mapping, sequence analysis, or probe hybridization, although other methods may be used. The double-stranded nucleic acid is transformed into host cells, typically E. coli, but alternatively, other prokaryotes, yeast, or larger eukaryotes may be used. Standard screening protocols, such as nucleic acid hybridization, amplification, and DNA sequence analysis, will identify mutant sequences.

In preferred embodiments, variant telomerases are inactive with respect to enzyme activity and impart a dominant negative phenotype to a host cell. Regardless of the actual mechanism, when a dominant negative telomerase is expressed in a cell, the native active telomerase is rendered inactive. In the catalytic domain, RTase motifs share conserved aspartic acid residues. Human telomerase also contains these critical residues: Asp 712, Asp 718, Asp 868, and Asp 869. Mutation of one or more of these Asp residues to a non-coservative amino acid (e.g., alanine) will likely destroy enzymatic activity and or affect telomere shortening. For each of these mutants, dominant negativity is assayed. Preferred mutants are dominant negative and induce a senescence phenotype in certain embodiments. Other dominant negative variants may be generated by deletion of one or more of the RTase motifs or alteration of the region involved in DNA priming (such as motif E), binding site for the RNA component, the template binding site, the metal ion binding site (such as motif C), and the like.

In other embodiments, the nucleic acid molecule encoding telomerase may be fused to another nucleic acid molecule. As will be appreciated, the fusion partner gene may contribute, within certain embodiments, a coding region. Thus, it may be desirable to use only the catalytic site of telomerase (e.g., amino acids 609–915), individual RTase motifs (described above), any of the splicing variant telomerases described herein, the telomerase RNA binding site and the like, The choice of the fusion partner depends in part upon the desired application. The fusion partner may be used to alter specificity of the telomerase, provide a reporter function, provide a tag sequence for identification or purification protocols, and the like. The reporter or tag can be any protein that allows convenient and sensitive measurement or facilitates isolation of the gene product and does not interfere with the function of the telomerase. For reporter function, β-glucuronidase (U.S. Pat. No: 5,268,463), green fluorescent protein and β-galactosidase are readily available as DNA sequences. A peptide tag is a short sequence, usually derived from a native protein, which is recognized by an antibody or other molecule. Peptide tags include FLAG®, Glu-Glu tag (Chiron Corp., Emeryville, Calif.) KT3 tag (Chiron Corp.), T7 gene 10 tag (Invitrogen, La Jolla, Calif.), T7 major capsid protein tag (Novagen, Madison, Wis.), $His_6$ (hexa-His), and HSV tag (Novagen). Besides tags, other types of proteins or peptides, such as glutathione-S-transferase may be used.

C. Fragments and Oligonucleotide Derived from Telomerase Genes

In addition, portions or fragments of telomerase gene may be isolated or constructed for use in the present invention. For example, restriction fragments can be isolated by well-known techniques from, template DNA, e.g., plasmid DNA, and DNA fragments, including restriction fragments, can be generated by amplification. Furthermore, oligonucleotides can be synthesized or isolated from recombinant DNA molecules. One skilled in the art will appreciated that other methods are available to obtain DNA or RNA molecules having at least a portion of a telomerase sequence. Moreover, for particular applications, these nucleic acids may be labeled by techniques known in the art with a radiolabel (e.g., $^{32}P$, $^{33}P$, $^{35}S$, $^{125}I$, $^{131}I$, $^{3}H$, $^{14}C$), fluorescent label (e.g., FITC, Cy5, RITC, Texas Red), chemiluminescent label, enzyme, biotin and the like.

Methods for obtaining fragments are well-known in the art. Portions that are particularly useful within the context of this invention contain the catalytic site, individual RTase motifs, the putative alternative intron/exon sequences (see FIG. 10), and the like. Oligonucleotides are generally synthesized by automated fashion; methods and apparatus for synthesis are readily available (e.g., Applied Biosystems Inc, CA). Oligonucleotides may contain non-naturally occurring nucleotides, such as nucleotide analogues, a modified backbone (e.g., peptide backbone), nucleotide derivatives (e.g., biotinylated nucleotide), and the like. As used herein, oligonucleotides refers to a nucleic acid sequence of at least about 7 nucleotides and generally not longer than about 100 nucleotides. Usually, oligonucleotides are between about 10 and about 50 bases, more often between about 18 and about 35 nucleotides long. Oligonucleotides can be single-stranded or in some cases double-stranded. As used herein, portions of a nucleic acid refer to a polynucleotide that contains less than the entire parental nucleic acid sequence. For example, a portion of telomerase coding sequence contains less than a full-length telomerase sequence. A 'portion' is generally at least about seven nucleotides, and may be as many as 10, 20, 25 or more nucleotides in length. A fragment refers to a polynucleotide molecule of any length and can encompass an oligonucleotide, although more usually, but not to be limiting, the term oligonucleotide is used to denote short polynucleotides and the term fragment is used to denote longer polynucleotides.

Oligonucleotides for use as primers for amplification and probes for hybridization screening may be designed based on the DNA sequence of human telomerase presented herein. Oligonucleotide primers for amplification of a full-length cDNA are preferably derived from sequences at the 5' and 3' ends. Primers for amplification of specific regions are chosen to generate products of an easily detectable size. In preferred embodiments, primers are chosen that flank the sequences subject to alternative RNA splicing. In preferred embodiments, one set of primers is chosen such that both the product that spans spliced-in sequence as well as the product that spans spliced-out sequence are suitable sizes to be detected under the same reaction conditions. In other embodiments, two sets of primers are used to detect the alternative spliced RNAs. For example, one set of primers flanks the splice junction in order to detect a spliced-out product. The second set of primers may be derived very close to the junction (such that a spliced-out amplification product is the same size or barely larger than a primer-dimer length) or one or more of the set may be derived from the spliced-in sequence (such that the spliced-out RNA would not yield any product).

Amplification primers preferably do not have self-complementary sequences nor have complementary sequences at their 3' end (to prevent primer-dimer formation). Preferably, the primers have a GC content of about 50% and may contain restriction sites to facilitate cloning. Amplification primers usually are at least 15 bases and usually are not longer than 50 bases, although in some circumstances and conditions shorter or longer lengths can be used. More usually, primers are from 17 to 40 bases long, 17 to 35 bases long, or 20 to 30 bases long. The primers are annealed to cDNA or genomic DNA and sufficient amplification cycles, generally 20–40 cycles, are performed to yield a product readily visualized by gel electrophoresis and staining or by hybridization. The amplified fragment can be purified and inserted into a vector, such as λgt10 or pBS (M13+), and propagated, isolated and subjected to DNA sequence analysis, subjected to hybridization, or the like.

An oligonucleotide hybridization probe suitable for screening genomic, cDNA or other types (e.g., mutant telomerase sequences) of libraries, probing southern, northern, or northwestern blots, amplification products, and the like may be designed based on the sequences provided herein. Oligonucleotides for hybridization are typically at least 11 bases long, generally less than 100 bases long, and preferably at least 15 bases long, at least 20 bases long, at least 25 bases long, and preferably 20–70, 25–50, or 30–40 bases long. To facilitate detection, the oligonucleotide may be conveniently labeled, generally at the 5' end, with a reporter molecule, such as a radionuclide, (e.g., $^{32}P$), enzymatic label, protein label, fluorescent label, or biotin. (see Ausubel et al., and Sambrook et al., supra). A library is generally plated as colonies or phage, depending upon the vector, and the recombinant DNA is transferred to nylon or nitrocellulose membranes. Following denaturation, neutralization, and fixation of the DNA to the membrane, membranes are hybridized with labeled probe, and washed. Suitable detection methods reveal hybridizing colonies or phage that are then isolated and propagated. Methods for transferring nucleic acids to membranes and performing hybridizations are well known. In certain embodiments, additives to hybridization solution, such as a chaotrope (e.g., tetramethylammonium chloride) or a hybotrope (e.g., ammonium trichloroacetate; see PCT/US97/17413) are added to increase sensitivity and specificity of hybridization. A probe specifically hybridizes to a nucleic acid if it remains detectably annealed after washing under conditions equivalent to hybridization conditions (expressed herein as the number of degrees less than Tm).

D. Splicing Variants of Human Telomerase

In addition to the reference telomerase DNA and protein sequences presented in FIG. 1, several RNA splice variants are observed. Although some of the variants may reflect incompletely processed mRNA, it is noteworthy that such variants are abundant in an RNA sample (LIM1215) preselected for polyadenylated mRNA. These findings, together with their clustering in the RT domain, suggest that the insertion variants more likely reflect regulation of hT1 protein expression. For example, variants in which exons are deleted (see α, β, FIG. 7) are likely alternative mature coding for variant proteins. Because these regions are alternatively spliced in or out in the splice variants disclosed herein they are referred to as intron/exon 1, 2, 3, α, β, X, and Y. Additional evidence in support of alternative proteins comes from sequence analysis of cDNA clones identified in a LIM1215 cDNA library that contained both deletions and insertions compared to the reference sequence.

At least seven different putative alternative intron/exons appear to be retained in mRNAs (see FIG. 7, which displays 6 of the 7 alternative intron/exons). The alternative intron/exons may be independently retained, thus, a particular mRNA may have none, any one, two, etc. up to seven alternative intron/exons. The maximum number of different mRNAs resulting from seven independently 7 spliced alternative intron/exons is $2^7$, or 128 different mRNAs. DNA sequences of these alternative intron/exons are presented in FIG. 10. The 5' most alternative intron/exon, called alternative X, is an unknown length, and only a partial sequence is presented.

The reference telomerase sequence (FIG. 1) includes alternative intron/exon α, and alternative intron/exon β. In the following discussion, the effect of presence/absence and location of each alternative intron/exon is presented on the basis that it is the only alteration. It will be appreciated that a particular alternative intron/exon may alter the sequence of the translated product, regardless of whether other alternative intron/exons are spliced in or out. For example, the presence of alternative intron/exon 1 results in a frameshift and truncated protein, regardless of whether alternative intron/exons α, β, 2 or 3 are spliced in or out.

The presence of alternative intron/exon X results in a truncated protein that contains approximately 600 N-terminal amino acids and lacks all of the RTase motifs. The presence of alternative intron/exon Y at base 222 results in a frameshifted protein that terminates within three codons past the alternative intron/exon. As the Y intron/exon is very GC rich, approximately 78%, which is difficult to sequence, it is possible that alternative intron/exon Y causes an insertion of about 35 amino acids and not a frameshift.

Alternative intron/exon 1 at nucleotide 1950 is 38 bp and its presence in mRNA causes a frameshift and ultimate translation of a truncated protein (stop codon at nt 1973). This truncated protein contains only RTase domains 1 and 2.

Intron α, located from bases 2131–2166 is frequently observed spliced out of telomerase mRNA. A protein translated from such an RNA is deleted for 12 amino acids, removing RTase motif A. This motif appears to be critical for RT function; a single amino acid mutation within this domain in the yeast EST2 protein results in a protein that functions as a dominant negative and results in cellular senescence and telomere shortening.

Figure 8:
FIG. 8 shows various splicing patterns of hT1 transcript in different tumor samples. Nested amplification (14 cycles) is performed using HT2026F (SEQ ID No: 115) and HT2482R (SEQ ID No: 119) primers on primary RT-PCR products generated with HT1875F (SEQ ID No: 112) and HT2781R (SEQ ID No: 121) primers. a: Lung carcinoma; b: Lymphoma; c: Lung carcinoma; d: Medulloblastoma; e: Lymphoma; f: Lymphoma; g: T47D; h: Pheochromocytoma; i: Lymphoma; j: Glioma; k: Lymphoma; l: No template control.

Another of the variant sequences, the β-exon deletion at base 2286–2468, encodes a truncated protein, due to a reading frameshift at base 2287, which is joined to base 2469, and subsequently a termination codon at base 2605. This variant protein has RTase domains 1, 2, A, B, and part of C, but lacks another motif; in addition to the RTase domain motifs, another sequence motif (AVRIRGKS) (SEQ ID No.: 99) identified in the β insert of hT1 matches a P-loop motif consensus AXXXXGK(S). (SEQ ID No: 91) (Saraste et al., *Trends Biochem. Sci.* 15, 430–434, 1990). This motif is found in a large number of protein families including a number of kinases, bacterial dnaA, recA, recF, mutS and ATP-binding helicases (Devereaux et al., *Nucleic Acids Res.*, 12, 387–395, 1984). The P-loop is thus present only in a subpopulation of the h-TEL mRNAs in most RNA samples analyzed and completely absent from several tumor samples (FIG. 8).

Alternative intron/exon 2 at base 2843 contains an in-frame termination codon, resulting in a truncated protein that has the entire RTase domain region, but lacks the C-terminus. As the C-terminus may play a regulatory role, protein activity will likely be affected. When alternative intron/exon 3 is retained, a smaller protein is also produced because the alternative intron/exon contains an in-frame stop codon. Thus, the protein has an altered C-terminal sequence. What activity such proteins might have is currently unknown. The crystal structure of the HIV-1 reverse transcriptase demonstrates that a short form of the protein (p51) that lacks the RNAase domain is inhibited by the C-terminal 'connection' folding into the catalytic cleft. If hT1 is assumed to adopt a similar structure to HIV-RT, then C-terminal hT1 protein variants may reflect a similar mechanism of regulation.

In addition to variants that lack the reference C-terminal domain, a variant with exon 3 at base 2157 expresses an alternative C-terminal domain. Furthermore, the coding region donated by exon 3 has a potential SH3 binding site, SGQPEMEPPRRPSGCVG (SEQ ID No: 92), which matches the consensus c-Abl SH3 binding peptide (PXXXXPXXP) (SEQ ID No: 93) found in proteins such as ataxia telangiectasia mutated (ATM). A second example of this motif is found within the N-terminal end of the hT1 protein in the peptide HAGPPSTSRPPRPWDTP (SEQ ID No: 94). Other alternative C-terminal domains are found in telomerase cDNAs; the EST12462 (GenBank Accession No. AA299878) has about 50 bases of identical sequence up to base 2157 and then diverges from the reference telomerase sequence as well as exon 3. This new sequence has an internal stop condon in 50 bases that would result in a truncated C-terminus.

The variant detected in one ALT cell line (FIG. 6, lane i) opens up the possibility that the basic domain of hT1 may contribute to the ALT mechanism in at least some ALT cell lines. Interestingly, this ALT cell line expresses the hTR gene. One possible mechanism of ALT could involve dysregulated telomerase components that are inactive in the TRAP assay.

The following table summarizes the splice variants and resulting proteins. For simplicity, only a single variant is listed for each resulting protein. Furthermore, as noted above, the presence of alternative intron/exon Y appears to cause a frameshift resulting in a truncated protein, but may cause an insertion. Thus, each reading frame of alternative intron/exon Y is presented and the table is constructed as if the insertion does not cause a truncated protein. An independent assortment of these known alternative intron/exons would lead to 128 different mRNA sequences. The DNA and amino acid sequences for the variants in Table 1 are presented in FIG. 11.

TABLE 1

| Protein | Insert sequences | | | | | | SEQ. ID NO. Nucleotide/ Amino Acid |
|---|---|---|---|---|---|---|---|
| | Y | 1 | α | β | 2 | 3 | |
| truncated #1 | 0 | + | 0 | 0 | 0 | 0 | 36/37 |
| truncated #2 | 0 | 0 | + | 0 | 0 | 0 | 38/39 |
| reference protein | 0 | 0 | + | + | 0 | 0 | 1/2 |
| truncated #3 | 0 | 0 | + | + | + | 0 | 41/42 |
| altered C-terminus | 0 | 0 | + | + | 0 | + | 43/44 |
| lacks motif A | 0 | 0 | 0 | + | 0 | 0 | 45/46 |
| truncated #3; lacks motif A | 0 | 0 | 0 | + | + | 0 | 47/48 |
| lacks motif A; altered C-terminus | 0 | 0 | 0 | + | 0 | + | 49/50 |
| truncated #1 (ver 2) | + | + | 0 | 0 | 0 | 0 | 55/56, 57, 58 |
| truncated #2 (ver 2) | + | 0 | + | 0 | 0 | 0 | 59/60, 61, 62 |
| reference protein (ver 2) | + | 0 | + | + | 0 | 0 | 63/64, 65, 66 |
| truncated #3 (ver 2) | + | 0 | + | + | + | 0 | 67/68, 69, 70 |
| altered C-terminus (ver 2) | + | 0 | + | + | 0 | + | 71/72, 73, 74 |

TABLE 1-continued

| | Insert sequences | | | | | | SEQ. ID NO. Nucleotide/ Amino Acid |
|---|---|---|---|---|---|---|---|
| Protein | Y | 1 | α | β | 2 | 3 | |
| lacks motif A (ver 2) | + | 0 | 0 | + | 0 | 0 | 75/76, 77, 78 |
| truncated #3 (ver 2) | + | 0 | 0 | + | + | 0 | 79/80, 81, 82 |
| lacks motif A; altered C-terminus (ver 2) | + | 0 | 0 | + | 0 | + | 83/84, 85, 86 |

E. Vectors, Host Cells and Means of Expressing and Producing Protein

Telomerase protein may be expressed in a variety of host organisms. In one embodiment, telomerase is produced in bacteria, such as *E. coli*, for which many expression vectors have been developed and are readily available. Other suitable host organisms include other bacterial species, and eukaryotes, such as yeast (e.g., *Saccharomyces cerevisiae*), mammalian cells (e.g., CHO and COS-7), and insect cells (e.g., Sf9).

A DNA sequence encoding telomerase, a portion thereof, a variant, fusion protein or the like, is introduced into an expression vector appropriate for the host. In certain embodiments, telomerase is inserted into a vector such that a fusion protein is produced. The telomerase sequence is derived from an existing fragment, cDNA clone, or synthesized. A preferred means of synthesis is amplification of the gene from cDNA using a set of primers that flank the coding region or the desired portion of the protein. As discussed above, the telomerase sequence may contain alternative codons for each amino acid with multiple codons. The alternative codons can be chosen as "optimal" for the host species. Restriction sites are typically incorporated into the primer sequences and are chosen with regard to the cloning site of the vector. If necessary, translational initiation and termination codons can be engineered into the primer sequences.

At minimum, the vector must contain a promoter sequence. Other regulatory sequences may be included. Such sequences include a transcription termination signal sequence, secretion signal sequence, origin of replication, selectable marker, and the like. The regulatory sequences are operationally associated with one another to allow transcription or translation.

The plasmids used herein for expression of telomerase include a promoter designed for expression of the proteins in a host cell (e.g., bacterial). Suitable promoters are widely available and are well known in the art. Inducible or constitutive promoters are preferred. Such promoters for expression in bacteria include promoters from the T7 phage and other phages, such as T3, T5, and SP6, and the trp, lpp, and lac operons. Hybrid promoters (see, U.S. Pat. No. 4,551,433), such as tac and trc, may also be used. Promoters for expression in eukaryotic cells include the P10 or polyhedron gene promoter of baculovirus/insect cell expression systems (see, e.g., U.S. Pat. Nos. 5,243,041, 5,242,687, 5,266,317, 4,745,051, and 5,169,784), MMTV LTR, CMV IE promoter, RSV LTR, SV40, metallothionein promoter (see, e.g., U.S. Pat. No. 4,870,009) and other inducible promoters. For expression of the proteins, a promoter is inserted in operative linkage with the coding region for the telomerase protein.

The promoter controlling transcription of the telomerase may itself be controlled by a repressor. In some systems, the promoter can be derepressed by altering the physiological conditions of the cell, for example, by the addition of a molecule that competitively binds the repressor, or by altering the temperature of the growth media. Preferred repressor proteins include, but are not limited to, the *E. coli* lacI repressor, which is responsive to IPTG induction, the temperature sensitive λcI857 repressor, and the like. The *E. coli* lacI repressor is preferred.

In other preferred embodiments, the vector also includes a transcription terminator sequence, which has either a sequence that provides a signal that terminates transcription by the polymerase that recognizes the selected promoter and/or a signal sequence for polyadenylation.

Preferably, the vector is capable of replication in the host cells. Thus, when the host cell is a bacterium, the vector preferably contains a bacterial origin of replication. Preferred bacterial origins of replication include the f1-ori arid col E1 origins of replication, especially the ori derived from pUC plasmids. In yeast, ARS or CEN sequences can be used to assure replication. A well-used system in mammalian cells is SV40 ori.

The plasmids also preferably include at least one selectable marker that is functional in the host. A selectable marker gene includes any gene that confers a phenotype on the host that allows transformed cells to be identified and selectively grown. Suitable selectable marker genes for bacterial hosts include the ampicillin resistance gene (Amp$^r$), tetracycline resistance gene (Tc$^r$) and the kanamycin resistance gene (Kan$^r$). The kanamycin resistance gene is presently preferred. Suitable markers for eukaryotes usually require a complementary deficiency in the host (e.g., thymidine kinase (tk) in tk- hosts). However, drug markers are also available (e.g., G418 resistance and hygromycin resistance).

The sequence of nucleotides encoding the telomerase may also include a secretion signal, whereby the resulting peptide is a synthesized as precursor protein and is subsequently processed and secreted. The resulting processed protein may be recovered from periplasmic space or fermentation medium. Secretion signals suitable for use are widely available and are well known in the art (von Heijne, *J. Mol. Biol.* 184:99–105, 1985). Prokaryotic and eukaryotic secretion signals that are functional in *E. coli* (or other host) may be employed. The presently preferred secretion signals include, but are not limited to, those encoded by the following *E. coli* genes: pe1B (Lei et al., *J. Bacteriol.* 169:4379, 1987), phoA, ompA, ompT, ompF, ompc, beta-lactamase, and alkaline phosphatasc.

One skilled in the art appreciates that there are a wide variety of suitable vectors for expression in bacterial cells and which are readily obtainable. Vectors such as the pET series (Novagen, Madison, Wis.), the tac and trc series (Pharmacia, Uppsala, Sweden), pTTQ18 (Amersham International plc, England), pACYC 177, pGEX series, and the like arc suitable for expression of a telomerase. Baculovirus vectors, such as pBlueBac (see, e.g., U.S. Pat. Nos. 5,278, 050, 5,244,805, 5,243,041, 5,242,687, 5,266,317, 4,745,051, and 5,169,784; available from Invitrogen, San Diego) may be used for expression of the telomerase in insect cells, such as *Spodoptera frugiperda* sf9 cells (see, U.S. Pat. No. 4,745,051). The choice of a host for the expression of a telomerase is dictated in part by the vector. Commercially available vectors are paired with suitable hosts.

A wide variety of suitable vectors for expression in eukaryotic cells are available. Such vectors include pCMVLacI, pXT1 (Stratagene Cloning Systems, La Jolla, Calif.); pCDNA series, pREP series, pEBVHis (Invitrogen, Carlsbad, Calif.). In certain embodiments, telomerase, gene is cloned into a gene targeting vector, such as pMC1neo, a pOG series vector (Stragene).

Telomerase protein is isolated by standard methods, such as affinity chromatography, size exclusion chromatography, metal ion chromatography, ionic exchange chromatography, HPLC, and other known protein isolation methods. (see generally Ausubel et al., supra; Sambrook et al., supra). An isolated purified protein gives a single band on SDS-PAGE when stained with Coomassie blue.

In one embodiment, the telomerase protein is expressed as a hexa-his fusion protein and isolated by metal-containing chromatography, such as nickel-coupled beads. Briefly, a sequence encoding $His_6$ is linked to a DNA sequence encoding a telomerase. Although the $His_6$ sequence can be positioned anywhere in the molecule, preferably it is linked at the 3' end immediately preceding the termination codon. The His-hTI fusion may be constructed by any of a variety of methods. A convenient method is amplification of the TEL gene using a downstream primer that contains the codons for $His_6$.

F. Peptides and Proteins of Telomerase

In one aspect of the present invention, peptides having telomerase sequence are provided. Peptides may be used as immunogens to raise antibodies, as inhibitors or enhancers of telomerase function, in assays described herein and the like. Peptides are generally five to 100 amino acids long, and more usually 10 to 50 amino acids. Peptides are readily chemically synthesized in an automated fashion (PerkinEtmer ABI Peptide Synthesizer) or may be obtained commercially. Peptides may be further purified by a variety of methods, including high-performance liquid chromatography. Furthermore, peptides and proteins may contain amino acids other than the 20 naturally occurring amino acids or may contain derivatives and modification of the amino acids.

Peptides of particular interest within the context of this invention have the sequence of the alternative intron/exon sequences (FIG. 10), the RTase motifs, and the like. In certain embodiments, telomerase proteins have the amino acid sequences presented in FIGS. 1 or 11, or a portion thereof which is at least 8 amino acids in length (and may be 10, 15, 20 or more amino acids in length). In other embodiments, the protein has one or more amino acid substitutions, additions, deletions. In yet other embodiments, the protein has an amino acid sequence determined by a nucleic acid sequence that hybridizes under normal stringency conditions to the complement of any of the sequences in FIG. 11. As indicated above, variants of telomerase include allelic variants.

II. Telomerase Assays

A variety of assays are available to determine telomerase activity and expression. Such assays include in vitro assays that measure the ability of telomerase to extend a telomeric DNA substrate, nucleolytic activity, primer (telomere) binding activity, dNTP binding activity, telomerase RNA (hTR) binding activity, in vivo gain-of-function assays, in vivo loss-of function assays, in situ hybridization, RNase probe protection, Northern analysis, amplification of cDNA, antibody staining, and the like.

A. Assays for Catalytic Activity

Various assays for catalytic activity are described in U.S. Pat. Nos. 5,629,154; 5,639,613; 5,645,986 among others. In one conventional assay for telomerase activity, a single-stranded DNA primer having the sequence of the host telomere (e.g., $[TTAGGG]_n$) and the telomerase enzyme are used (see Shay et al., Methods in Molecular Genetics 5:263, 1994; Greider and Blackburn, Cell 43:405, 1985; Morin, Cell 59:521, 1989; U.S. Pat. No. 5,629,154). A preferred assay incorporates a detergent-based extraction with an amplification-based assay. This assay, called TRAP (telomeric repeats amplification protocol), has improved sensitivity (Kim et al., Science 266: 2011, 1994). Briefly, in TRAP, telomerase synthesizes extension products, which then serve as templates for amplification. The telomerase products are amplified with a primer derived from a non-telomeric region of the oligonucleotide and a primer derived from the telomeric region. When the amplification products are analyzed, such as by gel electrophoresis, a ladder of products is observed when telomerase activity is present. Permutations of this assay have been described (Krupp et al., Nucl. Acids Res. 25: 919, 1997; Savoysky et al., Nucl. Acids Res. 24: 1175, 1996). As well, other telomerase assays are available (Faraoni et al., J. Chemother 8: 394, 1996, describing an in vitro chemosensitivity assay; Tatematsu et al., Oncogene 13: 2265, 1996, describing a "stretch PCR assay"; Lin and Zakian, Cell 81: 1127, 1995, describing an in vitro assay for Saccharomyces).

In addition, catalytic or other activities may be measured by an in vitro reconstitution system (see Examples). Briefly, the assays, such as those described herein, are performed using purified telomerase protein that is produced by recombinant meant and other necessary components, such as the telomerase RNA component, other proteins such as described in WO 98/14593.

B. Assays for Other Activities

Nucleolytic activity may be assessed by protocols described for example in Collins and Grieder, Genes and Development 7: 1364, 1993). The nucleolytic activity is excision of a nucleotide (G from the telomeric repeat TTAGG) from the 3' end of a nucleotide sequence that is positioned at the 5' boundary of the DNA template. Briefly, the activity can be measured by a reaction that uses a nucleic acid template with a 3' nucleotide that is blocking, i.e., cannot serve as a primer for a polymerase, unless removed by nucleolytic activity.

Telomere binding activity and assays are described in for example Harrington et al., J. Biol. Chem. 270: 8893, 1995. In general, any assay such as a gel-shift assay, that detects protein-nucleic acid interactions may be used. DNTP and RNA binding activity assays are described in Morin, Eur. J. Cancer 33: 750 for example.

C. Gain and Loss of Function

In vivo gain-of-function assays may be performed by transfecting an expression vector encoding telomerase into cells that have no or little detectable endogenous activity. Activity is then measured by an in vitro assay, such as those described herein. Another gain of function assay can be performed in tumor cells or other cells expressing telomerase or reverse transcriptase. A telomerase gene is transfected into the cells, expressed at high levels, and these cells are treated with inhibitors of reverse transcriptase. Telomerase activity is then observed as decreased sensitivity to such inhibitors. Furthermore, rescue of function in the yeast telomerase mutant EST2 may be measured.

Loss of function may be measured in cells expressing high levels of telomerase activity, such as LIM 1215 cells or other tumor cells. In this assay, anti-sense oligonucleotide molecules are introduced into the cells, generally in an expression vector. Telomerase gene is verified by diminished telomerase activity. In another assay, antibodies to telomerase that inhibit function can be used to demonstrate a functional molecule.

D. Expression of Telomerase

Expression of telomerase in various cells may be assayed by standard assays using the sequences provided herein. For example, in situ hybridization with radioactive or fluorescent-labeled probes (fragments or oligonucleotides) may be used on tissue sections or fixed cells. Alternatively, RNA may be isolated from the cells and used in Northern, RNase probe protection assays, and the like. Probes for particular regions and probes that are variant specific will generate expression profiles of the various telomerase transcripts.

In a preferred embodiment, telomerase expression is assayed by amplification. Primer pairs for telomerase, including primer pairs for particular variants, are used to amplify cDNA synthesized from cellular RNA. The cDNA may be synthesized from either total RNA or poly(A)+RNA. Methods and protocols for RNA isolation are well known. The cDNA may be initiated by an oligo(dT) primer, random primers (e.g., $dN_6$), telomerase specific primer, and the like. The choice of a primer will depend at least in part on the quantity of RNA and the purpose of the assay. Amplification primers are designed to amplify any one of, particular combinations, or all of the variants present in vertebrate cells. Conditions for amplification are chosen to be commensurate with the primer length, base content, length of amplified product and the like. Various amplification systems are available (see Lee et al., *Nucleic Acid Amplification Technologies*, BioTechniques Books, Eaton Publishing, Natick, Mass., 1997; Larrick, *The PCR Technique: Quantitative PCR*, BioTechniques Books, Eaton Publishing, Natick, Mass., 1997).

Other assays for measuring expression qualitatively and quantitatively are well known. RNase probe protection and Northern analysis are amenable when the amount of telomerase mRNA is sufficient. When very few cells are available, a single cell analysis is desirable, or when the fraction of telomerase RNA in the sample is very low, an amplification protocol is preferred. RNase probe protection, in particular, is well suited for detecting splice variants, mutations, as well as quantitating these RNAs.

As discussed above, in preferred embodiments, expression of the various RNA species is monitored. The different species may be assayed by any method which distinguishes one of the species over the others. Thus, length determination by Northern, RNase probe protection, cloning and amplification are some of the available methods. In preferred embodiments, RNase probe protection and amplification are used. For RNase probe protection, the probe will generally be a fragment derived from the junction of the reference sequence and the alternative intron/exon sequence or derived from the sequence surrounding the alternative intron/exon insertion site. For example, a fragment of the reference telomerase that spans nucleotide 1950–1951 (e.g., nucleotides 1910–1980) will protect the reference sequence as a 71 base fragment, but will protect a telomerase with intron/exon 1 as two fragments of 41 and 30 bases. In contrast, a fragment that contains nucleotides 1910–1950 and 30 bases of alternative intron/exon 1 will protect an alternative intron/exon 1 variant as a 71 base fragment and the reference telomerase as a 41 base fragment. Fragments for RNase probe protection are chosen usually in the range of 30 to 400 bases and are positioned to yield readily distinguishable protection products.

Another method that can be used to distinguish variants is amplification. Amplification primer design and strategy are described above. Briefly, primers that will individually amplify each spliced-in or spliced-out variant are preferred. Multiple reactions can be performed to identify variants with more than one splice-in or splice-out event.

Methods that measure telomerase protein are also useful within the context of the present invention. By way of example, antibodies to telomerase may be used to stain tissue sections or permeabilized cells. Antibodies may also be used to detect protein by immunoprecipitation, Western blot and the like. Furthermore, subcellular localization of telomerase and telomerase variants may be determined using the antibodies described herein.

E. Antibodies to Telomerase

Antibodies to the telomerase proteins, fragments, or peptides discussed herein may readily be prepared. Such antibodies may specifically recognize wild type telomerase protein and not a mutant (or variant) protein, mutant (or variant) telomerase protein and not wild type protein, or equally recognize both the mutant (or variant) and wild-type forms. Antibodies may be used for isolation of the protein, inhibiting (antagonist) activity of the protein, or enhancing (agonist) activity of the protein. As well, assays for small molecules that interact with telomerase will be facilitated by the development of antibodies.

Within the context of the present invention, antibodies are understood to include monoclonal antibodies, polyclonal antibodies, anti-idiotypic antibodies, antibody fragments (e.g., Fab, and $F(ab')_2$, $F_V$ variable regions, or complementarity determining regions). Antibodies are generally accepted as specific against telomerase protein if they bind with a $K_d$ of greater than or equal to $10^{-7}M$, preferably greater than of equal to $10^{-8}M$. The affinity of a monoclonal antibody or binding partner can be readily determined by one of ordinary skill in the art (see Scatchard, *Ann. N.Y. Acad. Sci.* 51:660–672, 1949).

Briefly, a polyclonal antibody preparation may be readily generated in a variety of warm-blooded animals such as rabbits, mice, or rats. Typically, an animal is immunized with telomerase protein or peptide thereof, which is preferably conjugated to a carrier protein, such as keyhole limpet hemocyanin. Routes of administration include intraperitoneal, intramuscular, intraocular, or subcutaneous injections, usually in an adjuvant (e.g., Freund's complete or incomplete adjuvant). Particularly preferred polyclonal antisera demonstrate binding in an assay that is at least three times greater than background.

Monoclonal antibodies may also be readily generated from hybridoma cell lines using conventional techniques (see U.S. Pat. Nos. RE 32,011, 4,902,614, 4,543,439, and 4,411,993; see also *Antibodies: A Laboratory Manual*, Harlow and Lane (eds.), Cold Spring Harbor Laboratory Press, 1988). Briefly, within one embodiment, a subject animal such as a rat or mouse is injected with telomerase or a portion thereof.

The protein may be administered as an emulsion in an adjuvant such as Freund's complete or incomplete adjuvant in order to increase the immune response. Between one and three weeks after the initial immunization the animal is generally boosted and may tested for reactivity to the protein utilizing well-known assays. The spleen and/or lymph nodes are harvested and immortalized. Various immortalization techniques, such as mediated by Epstein-Barr virus or fusion to produce a hybridoma, may be used. In a preferred embodiment, immortalization occurs by fusion with a suitable myeloma cell line to create a hybridoma that secretes monoclonal antibody. Suitable myeloma lines include, for example, NS-1 (ATCC No. TIB 18), and P3X63—Ag 8.653 (ATCC No. CRL 1580). The preferred fusion partners do not express endogenous antibody genes. Following fusion, the cells are cultured in medium containing a reagent that selectively allows for the growth of fused spleen and myeloma cells such as HAT (hypoxanthine, aminopterin, and thymidine). After about seven days, the hybridomas may be screened for the presence of antibodies that are reactive against a telomerase protein. A wide variety of assays may be utilized, including for example countercurrent immuno-electrophoresis, radioimmunoassays, radioimmuno-precipitations, enzyme-linked immuno-sorbent assays (ELISA), dot blot assays, western blots, immunopre-cipitation, inhibition or competition assays, and sandwich assays (see U.S. Pat. Nos. 4,376,110 and 4,486,530; see also *Antibodies: A Laboratory Manual*, Harlow and Lane (eds.), Cold Spring Harbor Laboratory Press, 1988).

Other techniques may also be utilized to construct monoclonal antibodies (see Huse et al., *Science* 246:1275–1281, 1989; Sastry et al., *Proc. Natl. Acad. Sci. USA* 86:5728–5732, 1989; Alting-Mees et al., *Strategies in Molecular Biology* 3:1–9, 1990; describing recombinant techniques). Briefly, mRNA is isolated from a B cell population and utilized to create heavy and light chain immuno-globulin cDNA expression libraries in suitable vectors, such as λImmunoZap(H) and λImmunoZap(L). These vectors may be screened individually or co-expressed to form Fab fragments or antibodies (see Huse et al., supra; Sastry et al., supra). Positive plaques may subsequently be converted to a non-lytic plasmid that allows high level expression of monoclonal antibody fragments from *E. coli*.

Similarly, portions or fragments, such as Fab and Fv fragments, of antibodies may also be constructed utilizing conventional enzymatic digestion or recombinant DNA techniques to yield isolated variable regions of an antibody. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources (e.g. Stratacyte, La Jolla, Calif.) Amplification products are inserted into vectors such as ImmunoZAP™ H or ImmunoZAP™ (Stratacyte), which are then introduced into *E. coli*, yeast, or mammalian-based systems for expression. Utilizing these techniques, large amounts of a single-chain protein containing a fusion of the $V_H$ and $V_L$ domains may be produced (see Bird et al., *Science* 242:423426, 1988). In addition, techniques may be utilized to change a "murine" antibody to a "human" antibody, without altering the binding specificity of the antibody.

Once suitable antibodies have been obtained, they may be isolated or purified by many techniques well known to those of ordinary skill in the art (see *Antibodies: A Laboratory Manual*, Harlow and Lane (eds.), Cold Spring Harbor Laboratory Press, 1988). Suitable techniques include peptide or protein affinity columns, HPLC or RP-HPLC, purification on protein A or protein G columns, or any combination of these techniques.

F Proteins that Interact with Telomerase

Proteins that directly interact with telomerase can be detected by an assay such as a yeast 2-hybrid binding system. Briefly, in a two-hybrid system, a fusion of a DNA-binding domain-telomerase protein (e.g., GAL4-telomerase fusion) is constructed and transfected into a cell containing a GAL4 binding site linked to a selectable marker gene. The whole telomerase protein or subregions of telomerase may be used. A library of cDNAs fused to the GAL4 activation domain is also constructed and co-transfected. When the cDNA in the cDNA-GA4 activation domain fusion encodes a protein that interacts with telomerase, the selectable marker is expressed. Cells containing the cDNA are then grown, the construct isolated and characterized. Other assays may also be used to identify interacting proteins. Such assays include ELISA, Western blotting, co-immunoprecipitations and the like.

III. Inhibitors and Enhancers of Telomerase Activity

Candidate inhibitors and enhancers (collectively referred to as "effectors") may be isolated or procured from a variety of sources, such as bacteria, fungi, plants, parasites, libraries of chemicals (e.g., combinatorial libraries), random peptides or the like. Effectors may also be peptides or variant peptides of telomerase, variants of telomerase, antisense nucleic acids, antibodies to telomerase, inhibitors of promoter activity of telomerase, and the like. Inhibitors and enhancers may be also be rationally designed, based on the protein structure determined from X-ray crystallography (see, Livnah et al., *Science* 273:464, 1996). In certain preferred embodiments, the inhibitor targets a specific telomerase, such as a variant.

An inhibitor may act by preventing binding of telomerase to other components of the ribonucleoprotein complex or to the telomere, by causing dissociation of the bound proteins, or by other mechanism. An inhibitor may act directly or indirectly. In preferred embodiments, inhibitors interfere in the binding of the telomerase protein to either the telomerase RNA or to the telomeres. In other preferred embodiments, the inhibitors are small molecules. In a most preferred embodiment, the inhibitors cause a cell to cease replication. Inhibitors should have a minimum of side effects and are preferably non-toxic. Inhibitors that can penetrate cells are preferred.

In other preferred embodiments, an effector is a protein or peptide of telomerase that acts in a dominant negative fashion (see, Ball et al., *Current Biology* 7:71, 1997; *Current Biology* 6:84, 1996). For example, a peptide of telomerase that competitively inhibits the binding of telomerase to telomeres will disrupt the lengthening of telomeres. Generally, these peptides have native sequence, but variants may have increased activity (see, Ball et al., supra). Variants may be constructed by the methods described herein. Other peptides may bind telomerase and inhibit one or more of its activities, but do not have telomerase amino acid sequence. Such peptides may be identified by the assays described herein. The proteins or peptides may also increase telomerase activity. For effective inhibition, peptide inhibitors are preferably expressed from vectors transfected or infected into host cells, but may also be introduced by other means, such as liposome-mediated fusion, and the like. Eukaryotic vectors are well known and readily available. Vectors include plasmids, viral-based vectors, and the like.

In another preferred embodiment, the inhibitor is a ribozyme. "Ribozyme" refers to a nucleic acid molecule which is capable of cleaving a telomerase nucleic acid sequence. Ribozymes may be composed of DNA, RNA, nucleic acid analogues, or any combination of these (e.g., DNA/RNA hybrids). A "ribozyme gene" refers to a nucleic acid molecule which, when transcribed into RNA, yields the ribozyme, and a "ribozyme vector" refers to an assembly that is capable of transcribing a ribozyme gene of interest, and may be composed of either DNA or RNA. Within certain embodiments of the invention, the vector may include one or more restriction site(s) and selectable marker (s). Furthermore, depending on the choice of vector and host cell, additional elements such as an origin of replication, polyadenylation site, and enhancers may be included in the vectors described herein.

As noted above, the present invention also provides ribozymes having the ability to inhibit expression of the telomerase gene. Briefly, a wide variety of ribozymes may be generated for use within the present invention, including for example, hairpin ribozymes (see e.g., Hampel et al., Nucl. Acid Res. 18:299–304, 1990, EPO 360,257, and U.S. Pat. No. 5,254,678), hammerhead ribozymes (see e.g., Rossi, J. J. et al., *Pharmac. Ther.* 50:245–254, 1991; Forster and Symons, *Cell* 48:211–220, 1987; Haseloff and Gerlach, *Nature* 328:596–600, 1988; Walbot and Bruening, *Nature* 334:196, 1988; Haseloff and Gerlach, *Nature* 334:585, 1988; Haseloff et al., U.S. Pat. No. 5,254,678), hepatitis delta virus ribozymes (see, e.g, Perrotta and Been, *Biochem.* 31:16, 1992), Group I intron ribozymes such as those based upon the *Tetrahymena* ribosomal RNA (see, e.g, Cech et al., U.S. Pat. No. 4,987,071) RNase P ribozymes (see, e.g, Takada et al., *Cell* 35:849, 1983); as well as a variety of other nucleic acid structures with the capability to cleave a desired or selected target sequence (see e.g., WO 95/29241, and WO 95/31551). Within certain embodiments of the invention, the ribozymes may be altered from their traditional structure in order to include tetraloops or other structures that increase stability (see, e.g., Anderson et al., *Nucl. Acids Res.* 22:1096–1100, 1994; Cheong et al., *Nature* 346:680–682, 1990), or which make the ribozyme resistant to RNase or endonuclease activity (see e.g., Rossi et al., *Pharmac. Ther.* 50:245–254, 1991).

Within one embodiment of the invention, hairpin and hammerhead ribozymes are provided with the capability of cleaving telomerase nucleic acid sequences. Briefly, hairpin ribozymes are generated so that they recognize the target sequence $N_3XN^*GUC(N_{>6})$ (SEQ ID No: 95), wherein N is G, U, C, or A, X is G, C, or U, and * is the cleavage site. Similarly, hammerhead ribozymes are generated so that they recognize the sequence NUX, wherein N is G, U, C, or A. The additional nucleotides of the hammerhead ribozyme or hairpin ribozyme is determined by the target flanking nucleotides and the hammerhead consensus sequence (see Ruffner et al., *Biochemistry* 29:10695–10702, 1990). The preparation and use of certain ribozymes is described in Cech et al. (U.S. Pat. No. 4,987,071). The ribozymes are preferably expressed from a vector introduced into the host cells.

Ribozymes of the present invention, as well as DNA encoding such ribozymes can be readily generated utilizing published protocols (e.g., Promega, Madison Wis., Heidenreich et al., *J. FASEB* 70:90–6, 1993; Sproat, *Curr. Opin. Biotechnol.* 4:20–28, 1993). Alternatively, ribozymes may be generated from a DNA or cDNA molecule which encodes a ribozyme and which is operably linked to a RNA polymerase promoter (e.g., SP6 or T7). An RNA ribozyme is generated upon transcription of the DNA or cDNA molecule.

In other preferred embodiments, inhibitors diminish promoter activity of telomerase. A eukaryotic promoter comprises sequences bound by RNA polymerase and other proteins participating in control of the transcription unit. Telomerase transcription appears to be highly regulated; the protein is expressed mainly in stem, embryonic, and cancer cells, and expressed at much lower levels, if at all, in most somatic cells. Thus, the promoter is a potential target for inhibitors. The inhibitors may disrupt or prevent binding of one or more of the factors that control transcription of telomerase, causing transcription to diminish or cease. The levels of transcription need only fall to a low enough level that at least one telomere becomes absent.

Another inhibitor of the present invention is antisense RNA or DNA to telomerase coding or non-coding sequence. Antisense nucleic acids directed to a particular mRNA molecule have been shown to inhibit protein expression of the encoded protein Based upon the telomerase sequences presented herein, an antisense sequence is designed and preferably inserted into a vector suitable for transfection into host cells and expression of the antisense. The antisense may bind to any part of the hTI RNA. In certain embodiments, the antisense is designed to bind specifically to one or more variants. Specific binding means that under physiological conditions, the antisense binds to RNAs that have the complementary sequence, but not other RNAs. Because telomerase RNAs that contain any particular alternative intron/exon sequence may be a heterogeneous group of variants due to independent assortment of splice variants, more than one species of RNA may be bound and inactivated. The antisense polynucleotides herein are at least 7 nucleotides long and generally not longer than 100 to 200 bases, and are more typically at least 10 to 50 bases long. Considerations for design of antisense molecules and means for introduction into cells are found in U.S. Pat. Nos. 5,681,747; 5,734,033; 5,767,102; 5,756,476; 5,749,847; 5,747,470; 5,744,362; 5,716,846).

In addition, enhancers of telomerase activity or expression are desirable in certain circumstances. At times, increasing the proliferation potential of cells will have a therapeutic effect. For example, organ regeneration or differentiation after injury or diseases, nerve cell or brain cell growth following injury, proliferation of hematopoietic stem cells used in bone marrow transplantation or other organ stem cells, and the like may be limiting and thus benefit from an enhancer of telomerase. Enhancers may stabilize endogenous protein, increase transcription or translation, or act through other mechanisms. As is apparent to one skilled in the art, many of the guidelines presented above apply to the design of enhancers as well.

Screening assays for inhibitors and enhancers will vary according to the type of inhibitor and nature of the activity that is being inhibited. Assays include the TRAP assay or variation, a non-amplification based polymerase assay, yeast two-hybrid, release of repression in yeast transfected with a vertebrate telomerase, and the like. For screening compounds that interact With the promoter for telomerase, a reporter gene driven assay is convenient.

IV. Uses for Telomerase

Nucleotide sequence for telomerase and telomerase protein are used in a variety of contexts in this invention. In preferred embodiments, the compositions of the present invention are used either as diagnostic reagents or as therapeutics.

A. Diagnostics

Expression of mRNA encoding telomerase and/or protein may be used for detection of dividing cells, especially tumor cells and stem cells. Detection methods include antibody staining or tagged telomerase binding compounds for detection of protein, nucleic acid hybridization in situ for mRNA, hybridization on DNA "chips", Northern analysis, RNase probe protection, amplification by PCR or other method, ligase-mediated amplification and the like. Furthermore, expression of RNA splice variants may be assayed conveniently by amplification, RNase probe protection, other disclosed methods and the like. In particular, oligonucleotide primers surrounding the site of frequent splice variants, such as the primers described herein (e.g., Htel Intron T and HT 2482R) may be used to detect splice variants in various cell types. As shown in the examples, various tumor cell types exhibit different RNA splice variations. Correlation of the splice variant pattern with tumor stage, metastasis potential and the like may be determined. As such, assays for the particular variants may be used as a diagnostic. Cells with increased telomerase activity, such as cancer cells or hyperproliferative cells, may be identified by assaying qualitatively or quantitatively by any of the assays described herein. Typically, telomerase activity or expression will be compared between suspect cells and normal counterpart cells from the same or different individual. Increased activity indicative of a tumor or excessive proliferation is established by direct comparison or by detecting activity in cells otherwise known to be absent in telomerase activity or expression. In addition, monitoring cancer progression or response to therapy can be performed using the assays described herein and comparing activity or expression over a time course.

The variant detected in one ALT cell line, which expresses telomerase, suggests that the basic domain of hT1 may contribute to the ALT mechanism in at least some ALT cell lines. One possible mechanism of ALT could involve dysregulated telomerase components that are inactive in the TRAP assay. Thus, identification of the variants may be useful for following tumorigenesis.

Alternative mRNA splicing is a common mechanism for regulating gene expression in higher eukaryotes and there are many examples of tissue-specific, development-specific and sex-specific alterations in splicing events. Importantly, 15% of mutations linked to disease states in mammals affect splicing patterns (Horowitz and Krainer Trends Genet., 10, 100–106, 1994). Changes in cell physiology can also induce altered splicing patterns. Indeed, tumorigenesis itself has been suggested to enhance the expression of mRNA spliced variants by compromising the alternative splicing mechanisms. Although other, novel minor alternatively spliced hT1 variants may play a role in tumor development, the altered relative expression levels of the major transcripts found in various tumors compared to normal cells, and in post-crisis cell lines compared to limited life-span pre-crisis cells, are likely to play a major role in the establishment and progression of cancers. In addition, the existence of the alternative spliced variants of hT1 that are seen in both testis and colonic crypt, as well as tumor cell lines, suggests complex regulation of this gene in normal development.

Expression of the major hT1 products is found in most tumors and in all telomerase-positive immortalized cell lines. Transcriptional control of hT1 may therefore be a major aspect of the regulation of telomerase activity, in addition to other functions. For example, telomerase may be involved in the healing of chromosome breaks in addition to its role in maintaining telomere length in the germline. The composition of telomerase may vary according to these functional roles.

Therefore, the alternative intron/exon sequences may be especially useful for diagnostic applications. For example, detection and identification of diseases, such as cancer, aging, wound healing, neuronal regeneration, regenerative cells (e.g., stem cells), may be important preludes to determining effective therapy. In this regard, detection of wound healing can facilitate development and identification of an ameliorative compound. Currently, wound healing assays are expensive and time consuming, whereas an amplification or hybridization-based assay would be quick and cost effective. In any of these applications, detection may be quantitative or qualitative. In a qualitative assay, a particular amplification primer pair or hybridization probe for one of the variant sequences (e.g., alternative intron/exons that are variably spliced) can be used to detect the presence or absence of the variant sequence.

Probes useful in the context of the present invention include nucleic acid molecules that hybridize to the sequences presented in FIG. 10 or to their complements. Probes for hybridization are generally at least 24 bases, but may range from 12 to full-length sequence. The probes may comprise additional sequence that does not hybridize to hT1 DNA or RNA. Probes are generally DNA, but may be RNA, PNA, or derivatives thereof. Hybridization conditions will be chosen appropriate for the length of the probe and method of hybridization (e.g., on nylon support, on silicon-based chip). Conditions are well known in the art. One of the sequences in FIG. 10 is a genomic sequence, not found in telomerase mRNA. A probe derived from this sequence may be used to detect genomic DNA in RNA preparations and amplification reactions. Hybridization probes may be labeled with a radiolabel, chemiluminescent label, or any of the myriad other known labels.

Hybridization can be performed on mRNA preparations, cDNA preparations, affixed to a solid support, in solution, or in situ tissues, and the like. One type of hybridization analysis is annealing to oligonucleotides immobilized on a solid substrate, such as a functionalized glass slide or silicon chip. Such chips may be commercially procured or made according to methods and procedures set out in e.g., PCT/US94/12282; U.S. Pat. No. 5,405,783; U.S. Pat. No. 5,412,087; U.S. Pat. No. 5,424,186; U.S. Pat. No. 5,436,327; U.S. Pat. No. 5,429,807; U.S. Pat. No. 5,510,270; WO 95/35505; U.S. Pat. No. 5,474,796Oligonucleotides are generally arranged in an array form, such that the position of each oligonucleotide sequence can be determined.

For amplification assays, primer pairs that either flank the alternative intron/exons or require the presence of the alternative intron/exon for amplification are desirable. Many such primer pairs are disclosed herein. Others may be designed from the sequences presented herein. Generally, the primer pairs are designed to only allow amplification of a single alternative intron/exon, however, in some circumstances detection of multiple alternative intron/exons in the same RNA preparation may be preferred.

Other diagnostic assays, such as in situ hybridization, RNase protection, and the like may be used alternatively or in addition to the assays discussed above. The principles that guide these assays are provided by the present invention, while the techniques are well known.

Transgenic mice and mice that are null mutants (e.g., "knockout mice") may be constructed to facilitate testing of candidate inhibitors. The telomerase gene is preferably under control of a tissue-specific promoter for transgenic mice vector constructs. Mice that overexpress telomerase can be used as a model system for testing inhibitors. In these mice, cells overexpressing telomerase are expected to be continuously proliferating. Administration of candidate inhibitors is followed by observation and measurement of cell growth. Inhibitors that slow or diminish growth are candidate therapeutic agents.

Telomerase may also be transfected into cells to immortalize various cell types. Transient immortalization may be achieved by non-stable transfection of an expression vector containing telomerase. Alternatively, proliferation of stable transformants of telomerase gene under control of an inducible promoter can be turned on and off by the addition and absence of the inducer. Similarly, the presence and absence of an inhibitor of telomerase activity may be used to selectively immortalize cells. Expression of part of all of the protein in yeast may act as a dominant negative, as many human proteins interact with components of a complex in yeast, but do so imperfectly and therefore unproductively. As such, these genes act as dominant negatives. Thus, the yeast will eventually senesce. Such cells may be used in screens for inhibitory drugs, which will allow growth of yeast past the time of senescence.

Purified telomerase protein, reference variant protein, or fragments, may be used in assays to screen for inhibitory drugs. These assays will typically be performed in vitro and utilize any of the methods described above or that are known in the art. The protein may also be crystallized and subjected to X-ray analysis to determine its 3-dimensional structure.

B. Therapeutics

The compositions and methods disclosed herein may also be used as therapeutics in the treatment of diseases and disorders to effect any of the telomerase activities in a cell. Treatment means any amelioration of the disease or disorder, such as alleviating symptoms of the disease or disorder, reduction of tumor cell mass and the like. For example, inhibitors of enzyme activity may be used to restrict proliferation of cells.

Many diseases and disorders are tightly associated with proliferation and proliferative potential. One of the most apparent diseases involving unwanted proliferation is cancer. The methods and compositions described herein may be used to treat cancers, such as melanomas, other skin cancers, neuroblastomas, breast carcinomas, colon carcinomas, leukemias, lymphomas, osteosarcomas, and the like. Other diseases and disorders amenable for treatment within the context of the present invention include those of excessive cell proliferation (increased proliferation rate over normal counterpart cells from the same or different individual) such as smooth muscle cell hyperplasias, skin growths, and the like. Yet other diseases and disorders would benefit from increased telomerase activity. Enhancers of telomerase may be used to stimulate stem cell proliferation and possibly differentiation. As such, expansion of hematopoietic stem cells could be administered in the bone marrow transplant context. As well, many tissues have stem cells. Proliferation of these cells may be beneficial for wound healing, hair growth, treatment of diseases, such as Wilm's tumor, and the like.

Certain of the inhibitors or enhancers may be administered by way of an expression vector. Many techniques for introduction of nucleic acids into cells are known. Such methods include retroviral vectors and subsequent retrovirus infection, adenovirals or adeno-associated viral vectors and subsequent infection, complexes of nucleic acid with a condensing agent (e.g., poly-lysine), these complexes or viral vectors may be targeted to particular cell types by way of an incorporated ligand. Many ligands specific for tumor cells and other cells are well known in the art.

As noted above, within certain aspects of the present invention, nucleic acids encoding ribozymes, antisense, dominant-negative telomerases, portions of telomerase and the like may be utilized to inhibit telomerase activity by introducing a functional gene to a cell of interest. This may be accomplished by either delivering a synthesized gene to the cell or by delivery of DNA or cDNA capable of in vivo transcription of the gene product. More specifically, in order to produce products in vivo, a nucleic acid sequence coding for the product is placed under the control of a eukaryotic promoter (e.g., a pol III promoter, CMV or SV40 promoter). Where it is desired to more specifically control transcription, the gene may be placed under the control of a tissue or cell specific promoter (e.g., to target cells in the liver), or an inducible promoter.

A wide variety of vectors may be utilized within the context of the present invention, including for example, plasmids, viruses, retrotransposons and cosmids. Representative examples include adenoviral vectors (e.g., WO 94/26914, WO 93/9191; Yei et al., *Gene Therapy* 1:192–200, 1994; Kolls et al., *PNAS* 91(1):215–219, 1994; Kass-Eisler et al., *PNAS* 90(24):11498–502, 1993; Guzman et al., *Circulation* 88(6):2838–48, 1993; Guzman et al., *Cir. Res.* 73(6):1202–1207, 1993; Zabner et al., *Cell* 75(2):207–216, 1993; Li et al., *Hum Gene Ther.* 4(4):403–409, 1993; Caillaud et al., *Eur. J. Neurosci.* 5(10):1287–1291, 1993), adeno-associated type 1 ("AAV-1") or adeno-associated type 2 ("AAV-2") vectors (see WO 95/13365; Flotte et al., *PNAS* 90(22):10613–10617, 1993), hepatitis delta vectors, live, attenuated delta viruses and herpes viral vectors (e.g., U.S. Pat. No. 5,288,641), as well as vectors which are disclosed within U.S. Pat. No. 5,166,320. Other representative vectors include retroviral vectors (e.g., EP 0 415 731; WO 90/07936; WO 91/02805; WO 94/03622; WO 93/25698; WO 93/25234; U.S. Pat. No. 5,219,740; WO 93/11230; WO 93/10218. For methods and other compositions, see U.S. Pat. Nos. 5,756,264; 5,741,486; 5,733,761; 5,707,618; 5,702,384; 5,656,465; 5,547,932; 5,529,774; 5,672,510; 5,399,346, and 5,712,378.)

Within certain aspects of the invention, nucleic acid molecules may be introduced into a host cell utilizing a vehicle, or by various physical methods. Representative examples of such methods include transformation using calcium phosphate precipitation (Dubensky et al., *PNAS* 81:7529–7533, 1984), direct microinjection of such nucleic acid molecules into intact target cells (Acsadi et al., *Nature* 352:815–818, 1991), and electroporation whereby cells suspended in a conducting solution are subjected to an intense electric field in order to transiently polarize the membrane, allowing entry of the nucleic acid molecules. Other procedures include the use of nucleic acid molecules linked to an inactive adenovirus (Cotton et al., *PNAS* 89:6094, 1990), lipofection (Felgner et al., *Proc. Natl. Acad. Sci. USA* 84:7413–7417, 1989), microprojectile bombardment (Williams et al., *PNAS* 88:2726–2730, 1991), polycation compounds such as polylysine, receptor specific ligands, liposomes entrapping the nucleic acid molecules, spheroplast fusion whereby *E. coli* containing the nucleic acid molecules are stripped of their outer cell walls and fused to animal cells using polyethylene glycol, viral transduction, (Cline et al., *Pharmac. Ther.* 29:69, 1985; and Friedmarn et al., *Science* 244:1275, 1989), and DNA ligand (Wu et al, *J. of Biol. Chem.* 264:16985–16987, 1989), as well as psoralen inactivated viruses such as Sendai or Adenovirus. In one embodiment, the nucleic acid molecule is introduced into the host cell using a liposome.

Administration of effectors will generally follow established protocols. The compounds of the present invention may be administered either alone, or as a pharmaceutical composition. Briefly, pharmaceutical compositions of the present invention may comprise one or more of the inhibitors or enhancers as described herein, in combination with one or more pharmaceutically or physiologically acceptable carriers, diluents or excipients. Such compositions may comprise buffers such as neutral buffered saline, phosphate buffered saline and the like, carbohydrates such as glucose, mannose, sucrose or dextrans, mannitol, proteins, polypeptides or amino acids such as glycine, antioxidants, chelating agents such as EDTA or glutathione, adjuvants (e.g., aluminum hydroxide) and preservatives. In addition, pharmaceutical compositions of the present invention may also contain one or more additional active ingredients. Effectors may be further coupled with a targeting moiety that binds a cell surface receptor specific to the proliferating cells.

Compositions of the present invention may be formulated for the manner of administration indicated, including for example, for oral, nasal, venous, intracranial, intraperitoneal, subcutaneous, or intramuscular administration. Within other embodiments of the invention, the compositions described herein may be administered as part of a sustained release implant. Within yet other embodiments, compositions of the present invention may be formulized as a lyophilizate, utilizing appropriate excipients which provide stability as a lyophilizate, and subsequent to rehydration.

As noted above, pharmaceutical compositions also are provided by this invention. These compositions contain any of the above described ribozymes, DNA molecules, proteins, chemicals, vectors, or host cells, along with a pharmaceutically or physiologically acceptable carrier, excipients or diluents. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents.

In addition, the pharmaceutical compositions of the present invention may be prepared as medicaments for administration by a variety of different routes, including for example intraarticularly, intracranially, intradermally, intrahepatically, intramuscularly, intraocularly, intraperitoneally, intrathecally, intravenously, subcutaneously or even directly into a tumor. In addition, pharmaceutical compositions of the present invention may be placed within containers, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition. Pharmaceutical compositions are useful for both diagnostic or therapeutic purposes.

Pharmaceutical compositions of the present invention may be administered in a manner appropriate to the disease to be treated (or prevented). The quantity and frequency of administration will be determined by such factors as the condition of the patient, and the type and severity of the patient's disease. Dosages may be determined most accurately during clinical trials. Patients may be monitored for therapeutic effectiveness by appropriate technology, including signs of clinical exacerbation, imaging and the like.

The following examples are offered by way of illustration, and not by way of limitation.

EXAMPLES

Example 1

Identification and Isolation of the Human Telomerase Gene

A human telomerase gene is identified in a cDNA library constructed from a cancer cell line. The cDNA is subjected to DNA sequence analysis (Kilian et al., supra).

An EST sequence, GenBank Accession No. AA281296, is identified as partial telomerase gene sequence by a BLAST search against the *Euplotes* telomerase sequence, GenBank Accession No. U95964 ($p=3.2 \times 10^{-6}$). Amino acid sequence identity between the two sequences is approximately 38% and amino acid sequence similarity is approximately 60%.

To obtain longer clones of hT1, a number of cDNA libraries prepared from tumor cells are screened by amplification using primers from within the EST sequence. Primers HT1553F (SEQ ID No: 108) and HT1920R (SEQ ID No: 114), based on the EST sequence, are used to amplify an approximately 350 bp fragment in a variety of cDNA libraries. The amplification reaction is performed under "hot start" conditions. Amplification cycles are 4 min at 95° C.; 1 min at 80° C.; 30 cycles of 30 sec at 94° C., 30 sec at 55°C., 1 min at 72° C.; and 5 min at 72° C. An amplified product of the expected size (~350 bp) is detected in only 3 of the 12 libraries screened. No fragment is detectable in a testis cDNA library, somatic cell libraries, and a variety of cancer cell cDNA libraries. However, an abundant 350 bp fragment is detected in a cDNA library from LIM 1215 cells, a colon cancer cell line. In this library, and in several others, an additional fragment of around 170 bp was amplified.

Two approaches are followed to obtain longer clones from the LIM 1215 library: screening plaques with a $^{32}$P-labeled EST probe and amplification on library DNA. A single positive plaque, designated 53.2, with a 1.9 kb insert is obtained by hybridization of the library with the EST probe. DNA sequence analysis of this clone demonstrates that it extends both 5' and 3' of the EST sequence, but did not contain a single open reading frame (ORF). A fragment obtained from amplification analysis of the library is similar in sequence to the 53.2 fragment but also contains two additional sequences of 36 bp and >300 bp. Both insertions demonstrate characteristics of splice acceptor and donor sequences at their boundaries relative to the 53.2 sequence and may represent unspliced introns. Amplification using primers T7 and HT1553F (SEQ ID No: 108), yields an approximately 1.6 kb fragment; and using primers T3 and HT1893R (SEQ ID No: 113), yields an approximately 0.7 kb fragment. Each of these fragments support amplification of a 320 bp fragment using primers HTEL1553F (SEQ ID No: 108) and HT1893R (SEQ ID No: 113).

Longer clones may also be obtained by amplification of mRNA samples. Reverse transcriptase PCR (RT-PCR) on LIM1215 mRNA identifies a number of additional PCR products, including one with a 182 bp insertion relative to 53.2 that results in a single open reading frame (ORF). cDNA is synthesized from RNAs isolated from normal and tumor tissues. RT-PCR followed by nested amplification is performed using the Titan RT-PCR system (Boehringer-Mannheim). Amplification conditions are as follows: 95° C. for 2 min, two cycles of 94° C. for 30 sec, 65° C. for 30 sec and 68° C. for 3 min, 2 cycles of 94° C. for 30 sec, 63° C. for 30 sec, 68° C. for 3 min, 34 cycles of 94° C. for 30 sec, 60° C. for 30 sec and 68° C. for 3 min RT-PCR products are diluted 100 fold, and 1 µl is used for nested amplification using Taq polymerase with buffer Q (Qiagen). Amplification conditions are as above, except that the final step is 14 cycles. For normal tissues and tumors, amplification products are resolved by electrophoresis in 1.5% agarose gel, transferred to Zetaprobe membrane and probed with radiolabeled oligonucleotide HT1691F (SEQ ID No: 111).

The DNA sequence is also extended 5' and 3' using a combination of cRACE and 3' RACE, respectively, on LIM1215 mRNA to give a fragment of 3871 bp designated hT1 (FIG. 1). Two rounds of cRACE are carried out to extend the sequence of hT1 and map the transcription initiation site. 500 ng LIM1215 polyA+ RNA is used as the template. First strand cDNA synthesis is primed using the HT1576R (SEQ ID No: 109) primer. The first round of amplification on the ligation product (using the XL-PCR system) employs the HT1157R (SEQ ID No: 107) and HT1262F (SEQ ID No: 105) primers. Amplification products are purified using Qiagen columns, and further amplified using primers HT1114R (SEQ ID No: 106) and HT1553F (SEQ ID No: 108). A resulting 1.4 kb band is subjected to DNA sequence analysis, and a new set of primers are designed based on this sequence. For the second round of cRACE, the first strand cDNA is primed with the HT220(SEQ ID No: 104) R primer. The first round of amplification utilizes the HT0142R (SEQ ID No: 102) and HT0141F (SEQ ID No: 101) primers. Products are purified as above and amplified using HT0093 (SEQ ID No: 100) and HT0163F (SEQ ID No: 103) primers. A product of 100 bp is observed and subjected to sequence analysis in two independent experiments to define the 5' end of the hT1 transcript. The 5' end of the transcript is also obtained by amplification using primer HtelFulcodT 5'-AGGAGATCTCGCGATGCCGCGCGCTC-3'(SEQ ID No: 96) and HtelFulcodB 5'-TCCACGCGTCCT-GCCGGGTG-3' (SEQ ID No: 97) LIM1215 RNA. The resulting amplified product was digested with Mlu I and Bgl II and ligated to the remaining telomerase cDNA sequence.

The 3'-most sequences of the transcript are obtained by two rounds of amplification (XL-PCR system) using EBHT18 in both rounds as the reverse primer, and HT2761F (SEQ ID No: 120) and HT3114F (SEQ ID No: 122) as the forward primers in the first and second rounds, respectively.

The size of hT1 accords well with the size estimated from the Northern blot (see below) for the most abundant RNA species in LIM1215 RNA. Approximately 3.9 kb of DNA sequence is presented in FIG. 1. The sequence found in the EST is located from nucleotides 1624–2012. The predicted amino acid sequence of the largest open reading frame is also presented in FIG. 1. As presented, the protein is 1132 amino acids.

| Name | Oligo Sequence | Seq Id No: |
| --- | --- | --- |
| HT0028F | 5'-GCTGGTGCAGCGCGGGGACC | 98 |
| HT 5'Met | 5'-CACAAGCTTGAATTCACATCTCACCATGAAGGAGCTGGTGGCCC | 99 |
| HT0093R | 5'-GGCACGCACACCAGGCACTG | 100 |
| HT0141F | 5'-CCTGCCTGAAGGAGCTGGTG | 101 |
| HT0142R | 5'-GGACACCTGGCGGAAGGAG | 102 |
| HT0163F | 5'-CCGAGTGCTGCAGAGGCTGT | 103 |
| HT0220R | 5'-GAAGCCGAAGGCCAGCACGTTCTT | 104 |
| HT1262F | 5'-GTGCAGCTGCTCCGCCAGCACA | 105 |
| HT1114R | 5'-GTTCCCAAGCAGCTCCAGAAACAG | 106 |
| HT1157R | 5'-GGCAGTGCGTCTTGAGGAGCA | 107 |
| HT1553F | 5'-CACTGGCTGATGAGTGTGTAC | 108 |
| HT1576R | 5'-GACGTACACACTCATCAGCCAG | 109 |
| HT1590F | 5'-GGTCTTTCTTTTATGTCACGGAG | 110 |
| HT1691F | 5'-CACTTGAAGAGGGTGCAGCT | 111 |
| HT1875F | 5'-GTCTCACCTCGAGGGTGAAG | 112 |
| HT1893R | 5'-TTCACCCTCGAGGTGAGACGCT | 113 |
| HT1920R | 5'-TCGTAGTTGAGCACGCTGAAC | 114 |
| HT2026F | 5'-GCCTGAGCTGTACTTTGTCAA | 115 |
| HTM2028F | 5'-CTGAGCTGTACTTTGTCAAGGACA | 116 |
| HT2230F | 5'-GTACATGCGACAGTTCGTGGCTCA | 117 |
| HT2356R | 5'-CATGAAGCGTAGGAAGACGTCGAAGA | 118 |
| HT2482R | 5'-CGCAAACAGCTTGTTCTCCATGTC | 119 |
| HT2761F | 5'-CTATGCCCGGACCTCCATCAGA | 120 |
| HT2781R | 5'-CTGATGGAGGTCCGGGCATAG | 121 |
| HT3114F | 5'-CCTCCGAGGCCGTGCAGT | 122 |
| HT3292B | 5'-CACCTCAAGCTTTCTAGATCAGTCCAGGATGGTCTTGAAGTCA | 123 |
| HT3689R | 5'-GGAAGGCAAAGGAGGGCAGGGCGA | 124 |
| EBHT18 | 5'-CACGAATTCGGATCCAAGCTTTTTTTTTTTTTTTTTT | 125 |
| HT-RNA-F | 5'-GGGTTGCGGAGGGTGGGC | 126 |
| HT-RNA451R | 5'-GCAGTGGTGAGCCGAGTCCTG | 127 |
| HT-RNA598F | 5'-CGACTTTGGAGGTGCCTTCA | 128 |
| HTel 5'T | 5'-GCTGGTGCAGCGCGGGACC | 129 |
| HTel979T | 5'-GAGGTGCAGAGCGACTACTCCA | 130 |
| HTel1335T | 5'-GTCTCACCTCGAGGGTGAAG | 131 |
| HTel71T | 5'-GGCTGCTCCTGCGTTTGGTGGA | 132 |
| HTel21B(Top) | 5'-GCCAGAGATGGAGCCACCC | 133 |
| HTel21TBot) | 5'-GGGTGGCTCCATCTCTGGC | 134 |
| HTel-7B | 5'-CCGCACGCTCATCTTCCACGT | 135 |
| HTel+256B | 5'-GCTTGGGGATGAAGCGGTC | 136 |
| HtelIntronT | 5'-CGCCTGAGCTGTACTTTGTCA | 137 |
| Htel 3'CODB | 5'-CACCTCAAGCTTTCTAGATCAGCTAGCGGCCCAGCCCAACTCCC | 138 |
| Htel 1210B | 5'-GCAGCACACATGCGTGAAACCTGT | 139 |
| Htel 1274B | 5'-GTGTCAGAGATGACGCGCAGGAA | 140 |
| Htel 1624b | 5'-ACCCACACTTGCCTGTCCTGAGT | 141 |
| hTR TAC | 5'-ACTGGATCCTTGACAATTAATGCATCGGCTCGTATAATGTGTGGAGGGTGGTGGGC | 142 |
| hTR 5'T7 | 5'-CTGTAATACGACTCACTATAGGGTTGCGGAGGGTGGGC | 143 |
| hTR 3'PstI | 5'-CACCTGCAGACATGCGTTTCGTCCTCACGGACTCATCAGGCCAGCTGGCGTGTGAGCCGAGTCCTG | 144 |
| BT-177 | 5'-GGATCCGCCGCAGAGCACCGTCTG | 145 |
| BT-178 | 5'-CGAAGCTTTCAGTGGGCCGGCATCTGAAC | 146 |
| BT-179 | 5'-CGAAGCTTTCACAGGCCCAGCCCAACTCC | 147 |
| BT-182 | 5'-GCGGATCCAGAGCCACGTCCTACGTC | 148 |
| BT-183 | 5'-GCGGATCCGTTCAGATGCCGGCCCAC | 149 |

Example 2 hT1 Sequence and Alignment with other Telomerases

Multiple sequence alignment demonstrates that the predicted hT1 protein is co-linear with the *Euplotes* and *S. cerevisae* telomerase catalytic subunits over their entire lengths (FIG. 2). Although the overall homology between the three proteins is relatively low (approximately 40% similarity in all pairwise combinations) the overall structure of the protein seems to be well conserved. Four major domains: N-terminal, basic, reverse transcriptase (RT) and C-terminal are present in all three proteins. The highest area of sequence similarity is within the RT domain. Notably, all the motifs characteristic of the *Euplotes* RT domain are present and all amino acid residues implicated in RT catalysis are conserved in the hT1 sequence (Lingner et al., *Science* 276: 561–567, 1997).

Recently, protein phosphatase 2A treatment of human breast cancer cell extracts has been shown to inhibit telomerase activity (Li et al., *J. Biol. Chem.* 272: 16729–16732, 1997). It is not known whether this effect is direct, but it raises the possibility of regulation of telomerase activity by protein phosphorylation. The predicted hT1 protein does contain numerous potential phosphorylation sites, including 11 SP or TP dipeptides, which are potential sites for cell cycle dependent kinases.

Example 3

Characterization of Telomerase Gene

Northern analysis and Southern analysis are performed to determine the size of the telomerase transcript and whether telomerase gene is amplified in tumors cells.

For Northern analysis, polyA mRNA is isolated from LIM 1215 cells and from CCD fibroblasts. CCD is a primary human fibroblast cell line. Briefly cells are lysed by homogenization in a buffered solution (0.1 M NaCl, 10 mM Tris, pH 7.4, 1 mM EDTA) containing detergent (0.1 % SDS) and 200 µg/ml of proteinase K. SDS is added to the lysate to a final concentration of 0.5%, and the lysate is incubated at 60° C. for 1 hr and 37° C. for 20 min. The lysate is then incubated for 1 hr with a slurry oligo dT-cellulose that has been pre-cycled in 0.1 M NaOH and equilibrated in 0.5 M NaCl, 10 mM Tris pH 7.4, 1 mM EDTA, and 0.1% SDS. The resin is collected by centrifugation, batch washed in the equilibration buffer, and loaded into a column. The mRNA is eluted with warmed (37° C.) buffer (10 mM Tris pH 7.4, 0.1 mM EDTA) and ethanol precipitated.

Approximately 3 µg of polyadenylated RNA is electrophoresed in a 0.85% formaldehyde-agarose gel (see Sampbrook et al., supra) and transferred overnight to Genescreen plus (Bio-Rad, CA). The membrane is hybridized with a $^{32}$P-labeled telomerase-specific probe (390 bp insert corresponding to the EST sequence). After washing the blot at high stringency, a prominent ~3.8 kb band is observed in mRNA from LIM 1215, but not in mRNA from CCD fibroblasts (FIG. 3). Subsequent hybridization of the same membrane with a probe for glyceraldehyde 6-phosphate dehydrogenate demonstrated an equivalently strong band in both mRNAs, indicating that each lane contained a similar amount of high quality RNA. The presence of larger transcripts (especially a ~8 kb heterodispersed band) is also visible only in LIM1215 RNA (FIG. 10, upper panel.). These findings provide an indication of additional hT1-specific mRNA and also that hT1 may be preferentially expressed in tumor versus normal cells.

Figure 4:
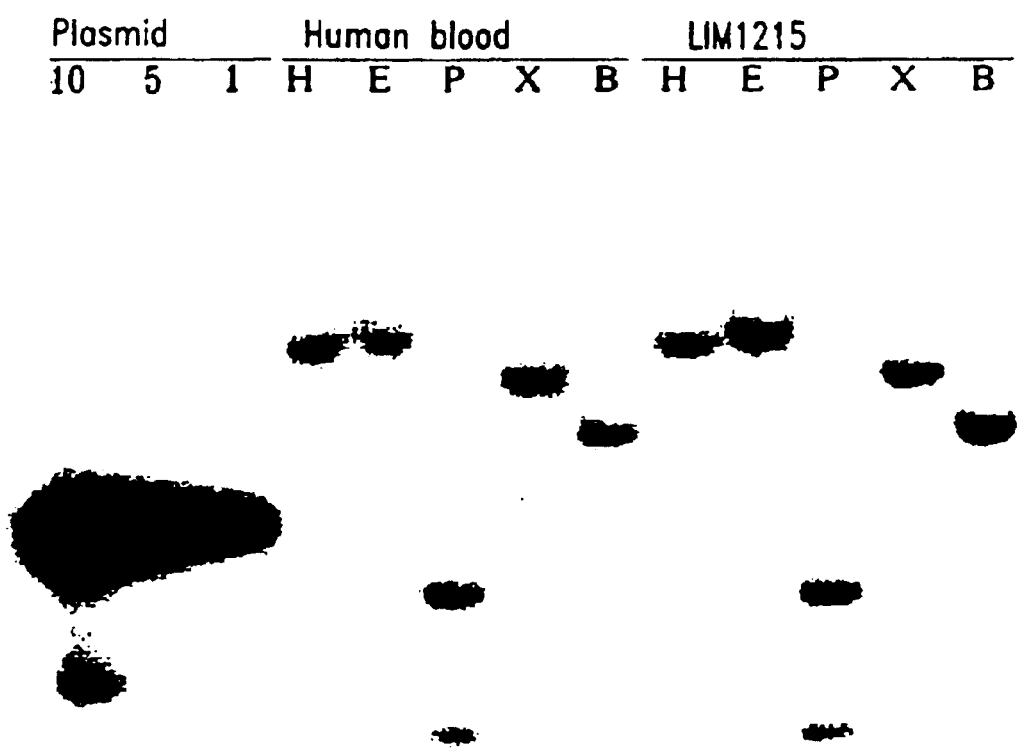
FIG. 4 is a scanned image of a Southern analysis showing that the telomerase catalytic subunit is encoded by a single gene and is not amplified in LIM 1215 cells. Genomic DNA isolated from peripheral human blood and LIM 1215 cell line is probed with a hT1 probe. The blot also contains dilutions of probe plasmid to control for the sensitivity of detection. The plasmid is diluted to approximately 10, 5 and 1 genome equivalents. H, Hind III; E, Eco RI; P, Pst I; X, Xba I; B, Bam HI.

For Southern analysis, DNA is isolated from human peripheral blood mononuclear cells and LIM 1215. Approximately 10 µg of DNAs are digested with Hind III, Xba I, Eco RI, BamHI, and PstI, electrophoresed in a 1% agarose gel, and transferred to a nylon membrane. For controls, plasmid DNA containing human telomerase is titrated to approximately the equivalent of 10 copies, 5 copies, and 1 copy per 10 µg genomic DNA and electrophoresed on the same gel. A 390 bp fragment of telomerase gene (containing the EST sequence) is $^{32}$P-labeled and hybridized under normal stringency conditions. The filter is washed in 2× SSC, 0.1% SDS at 55° C. A scanned phosphor image is presented in FIG. 4. As shown, the telomerase gene does not appear to be amplified or rearranged in LIM1215 as there is not significant difference in the pattern or intensity of hybridization when comparing LIM 1215 to PBMC DNA. Moreover, telomerase appears to be a single copy gene, as all digestions except Pst I yielded a single band.

Example 4 hT1 Expression Patterns

Although telomerase activity has been widely associated with tumor cells and the germline, it has only recently been recognized that certain normal mammalian tissues express low levels of telomerase activity. hT1 expression is not detected in primary fibroblast RNA, and amplification of several commercially available cDNA libraries from lung, heart, liver, pancreas, hippocampus, fetal brain, and testis using primers for the EST region, did not reveal any products.

Figure 5:
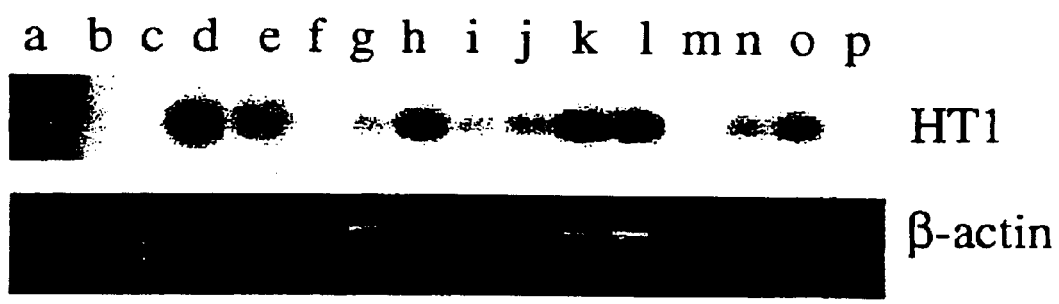
FIG. 5 shows the results of amplification of cDNAs synthesized from various tissues. Amplification is performed using primers from the hT1 cDNA sequence and the products are blotted and probed with a radiolabeled oligonucleotide from the hT1 sequence. Amplification is also performed on the same samples with a pair of primers from the β-actin gene as a loading control. a: hT1 cDNA control; b: human genomic DNA control; c: no template control; d: normal colon RNA; e: normal testis RNA; f: normal lymphocyte RNA; g: melanoma RNA (cerebral metastasis); h: melanoma RNA (subcutaneous ankle metastasis); i: melanoma RNA (liver metastasis); j: melanoma RNA (lung metastasis); k: melanoma RNA (axillary lymph node metastasis); l: melanoma RNA (skin metastasis); m: breast carcinoma RNA; n: breast carcinoma RNA; o: breast carcinoma RNA; p: breast carcinoma RNA.

However, the expression of hT1 in normal tissues that have previously been shown to have telomerase activity (colon, testis and peripheral blood lymphocytes) are examined, as well as a number of melanoma and breast cancer samples. RNA is isolated from normal human colon, testis and circulating lymphocytes, and from tissue sections of tumor samples, and subjected to RT-PCR analysis. Amplification products from cDNA are easily distinguished from products resulting from contaminating genomic DNA, as a product of ~300 bp is observed using cDNA as a template and a product of 2.7 kb is observed using genomic DNA as a template. hT1 transcripts are detected in both colon and testis, in the majority of tumor samples, and very weakly in the lymphocyte RNA (FIG. 5, upper panel). Interestingly, two of the breast cancer samples are negative for hT1 expression, despite containing comparable amounts of RNA to the other samples, as judged by amplification of β-actin as a positive control (FIG. 5, lower panel).

Figure 6:
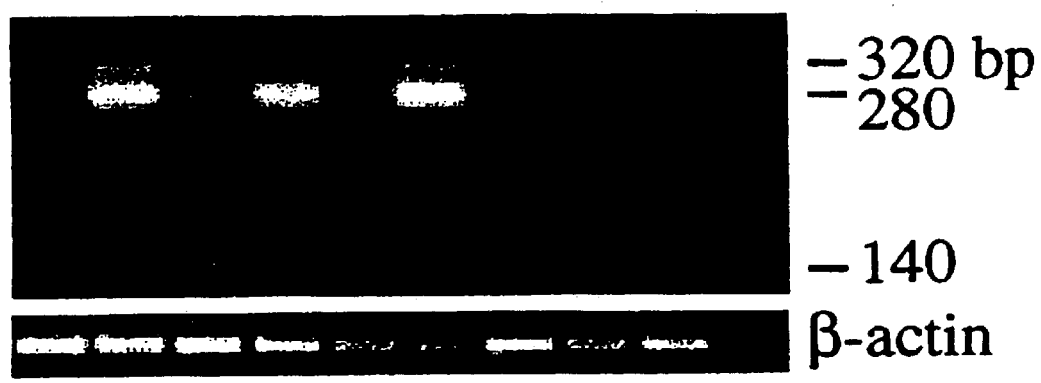
FIG. 6 presents results showing hT1 expression in pre-crisis cells and post-crisis cell lines. Upper panel: Nested amplification using primers within the original EST. Lower panel: Control RT-PCR using β-actin primers. a: BET-3K passage (p) 7 (pre-crisis); b: BET-3K p32 (post-crisis); c: BFT-3K p14 (pre-crisis); d: BFT-3K p 22 (post-crisis); e: BFT-3B p15 (pre-crisis); f: BFT-3B p29 (post-crisis); g: GM897 (ALT); h: IIICF/c (ALT); i: IIICF-T/B1 (ALT); j: No template control.

Acquisition of telomerase activity appears to be an important aspect of the immortalization process. The expression of hT1 in a number of matched pairs of pre-crisis cell cultures and post-crisis cell lines is determined using RT-PCR followed by amplification from nested primers (FIG. 6, upper panel). These cell lines are telomerase negative (pre-crisis cell line) and positive (post-crisis cell lines), respectively, using the TRAP assay (Bryan et al., *EMBO J.* 14: 4240–4248, 1995). In two matched pairs, BFT-3B and BET-3K, hT1 is detected only in the post-crisis cell lines (compare lanes a and b, lanes e and f). While the post-crisis line (lanes d, f) in the BFT-3K set shows an abundant hT1 band, a fragment of the same size is also weakly present in the pre-crisis (lanes c, e) culture sample. In addition, two of the three post-crisis cell lines demonstrate the presence of an additional unexpected fragment of 320 bp, and this product is also observed when colon and testis mRNA are analyzed on high resolution gels.

Three immortalized telomerase-negative (ALT) cell lines are also analyzed for hT1 expression (FIG. 6, lanes g, h, i). Two of the lines appear negative for hT1 expression, but in one line (IIIECF-T/B 1), a product of approximately 320 bp is again amplified (FIG. 6, lane i), similar to the post-crisis, colon and testis samples. DNA sequence analysis of the 320 bp product from the line IIICF-T/B1 (ALT) reveals the presence of a 38 bp insertion, relative to the expected product. The possibility that this is an amplification from genomic DNA rather than mRNA is ruled out by performing amplification with the same primers but using genomic DNA as the template. Under these conditions, a 2.7 kb fragment is amplified and its authenticity confirmed by partial sequence analysis.

Example 5

Identification of Alternative Splicing Patterns of Telomerase mRNA

Figures 7A, 7B:
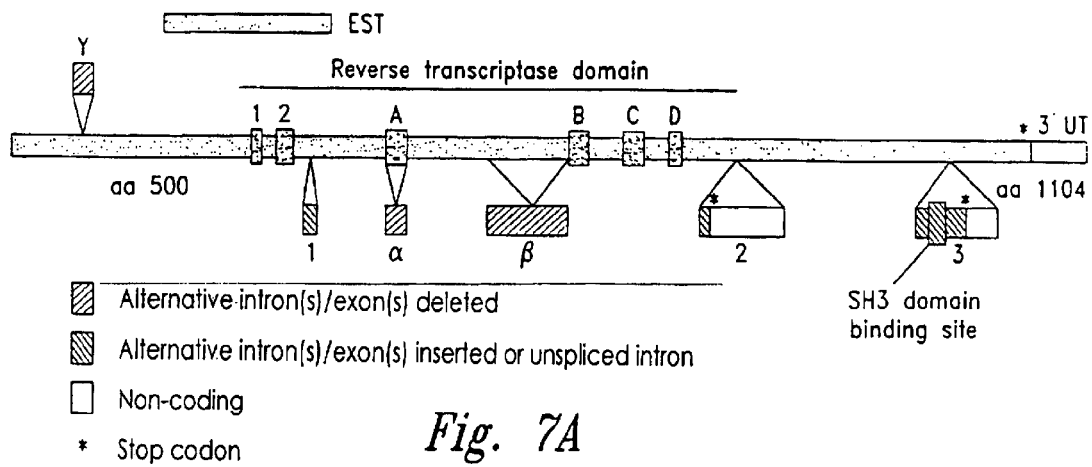

DNA sequence analysis of clones from the LIM1215 cDNA library and the RT-PCR data presented above for the pre-crisis and post-crisis cultures indicated that there is a number of different sequence variants within the hT1 transcript. To systematically survey for variants, RT-PCR is performed using primer pairs covering the whole sequence. No variants are observed in the N-terminal and the basic domains, but several variants are observed in the RT domain and, to a lesser extent, the C-terminal domain. Most notably, there are several RNA variants between RT Motif A and RT Motif B (FIG. 7A).

Samples of mRNA prepared from several different tumors using conventional protocols. The tumors are: (1) SLL lung carcinoma, (2) Lymphoma C, (3) Lung carcioma, (4) Medullablastoma A, (5) Lymphoma B, (6) Lymphoma E, (7) Tumor sample 47D, (8) Pheochromocystoma, (9) Lymphoma F, (10) Glioma, and (11) Lymphoma G. The mRNAs from these samples are first reverse transcribed to cDNAs and then amplified using primers HT1875F (SEQ ID No: 112) and HT2781R (SEQ ID No.: 121), followed by amplification with nested primers HT2026F (SEQ ID No: 115) and HT2482R (SEQ ID No: 119). Four different amplified products are observed in FIG. 8: 220 bp (band 1), 250 bp (band 2), 400 bp (band 3) and 430 bp (band 4). Strikingly, there is considerable variation among the tumor samples tested both in the total number of amplified products and in the quantitative distribution among the products.

Three of these products are isolated from a number of tumor tissues and subjected to DNA sequence analysis. One of them, a 220 bp fragment, is equivalent to the 53.2 cDNA from the LIM1215 library. The fragment of the ~250 bp (band 2) contains a 36 bp in-frame insertion, the same insertion that was identified in an amplified product from a LIM1215 cDNA library. As the RT-PCR product had the same sequence as the product from the cDNA library, it is apparent that the 36 bp insertion is not an artifact generated during library construction. The largest product (band 4) contains a 182 bp insertion (the same as the larger product amplified earlier from LIM1215 RNA) compared to the 250 bp amplicon. Unambiguous sequence for the 400 bp band (band 3) is not obtained. Based on its size, it may contain the 182 bp insert but missing the 36 bp insertion present in bands 2 and 4 and absent from band 1.

Figure 9:
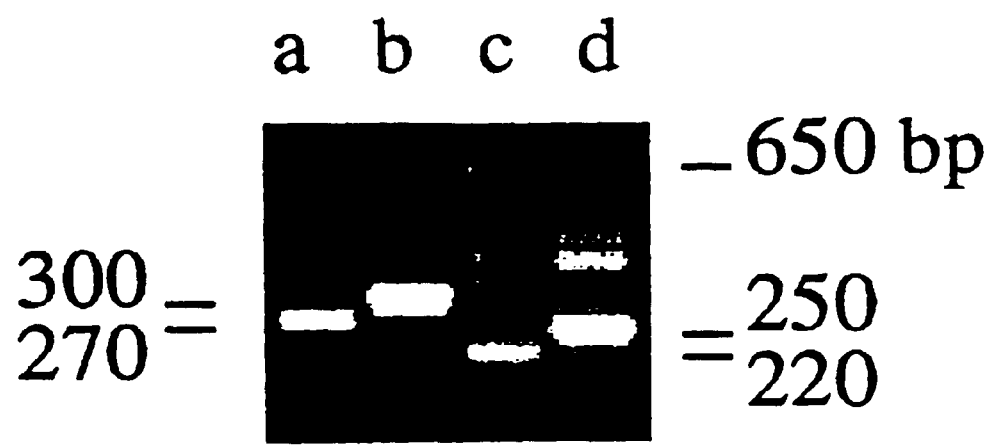
FIG. 9 shows the results of amplification on cDNA synthesized from LIM 1215 cDNA. As shown, reverse transcriptase motif A is deleted from splicing variants containing sequence α. Primer combinations are: a, HTM2028F (SEQ ID No: 116 )+HT2356R; (SEQ ID No: 118); b, HT2026F (SEQ ID No: 115)+HT2482R (SEQ ID No: 119); c, HTM2028F (SEQ ID No: 116)+HT2482R (SEQ ID No: 119); d. HT2026F (SEQ ID No: 115)+HT2482R (SEQ ID No: 119).

To test the hypothesis that such a transcript exists, a primer, HTM2028F, is designed such that amplification ensues only when the 36 bp fragment was missing. Amplification using HTM2028F (SEQ ID No: 116) and HT2026F (SEQ ID No: 115) primers in combination with HT2356R (SEQ ID No: 118) demonstrate that transcripts containing the 182 bp fragment but missing the 36 bp fragment are present in LIM1215 RNA (FIG. 9, lanes a and b). The same top strand primers (HTM2028F (SEQ ID No: 116) and HT2026F (SEQ ID No: 115)) in combination with HT2482R (SEQ ID No: 119) primer amplify a number of products from LIM1215 RNA FIG. 9, lanes c and d), most of which represent bands 1–4 as determined by direct sequence analysis of PCR products. An amplified fragment of 650 bp using HTM2028F (SEQ ID No: 116) and HT2482R (SEQ ID No: 119) primers represents another, not yet fully characterized, alternatively spliced telomerase variant in the RT-MotifA/RT Motif B region. For clarity of presentation, the protein sequence giving the best match with *Euplotes* and *S. cerevisiae* proteins is presented in FIG. 1 as the reference sequence.

Specifically, there are at least seven inserts or exons that can be present (or absent) from telomerase RNA. (1) The 5'-most sequence (Y) is located between bases 222 and 223. (2) the insert (X) is located between bases 1766 and 1767. A partial sequence is determine and is presented in FIG. 10. Termination codons are present in all three reading frames. Thus, a truncated protein without any of the Rtase motifs would be produced. (2) A sequence, indicated as "1" in FIG. 7, is located between bases 1950 and 1951. This exonic sequence is 38 bp (FIG. 10) and appears to be present in ALT and most tumor lines. The presence of this sequence adds 13 amino acids and shifts the reading frame such that a termination codon (TGA) is in frame at nucleotide 1973. (3) A sequence, indicated as "α" in FIG. 7, is located between bases 2130 and 2167. This sequence is 36 bp (FIG. 10) and its absence removes RTase motif "A" but does not alter the reading frame (4) A sequence, indicated as "β" in FIG. 7 is present between bases 2286 and 2469. The insert is 182 bases (FIG. 10) and its absence causes a reading frame-shift and a termination codon in RTase motif 5 at nucleotide 2604. (5) The sequence "2" in FIG. 7 is present between bases 2823 and 2824. Its length is undetermined; its partial sequence is presented in FIG. 10. The presence of this insert causes a truncated telomerase protein, as the first codon of the insert is a termination codon. (6) The sequence 3is a 159 bp insert (FIG. 10) between bases 3157 and 3158. Its presence leads to a telomerase protein with an altered COOH-terminus. The insert contains a stop codon. Moreover, sequence "3" has a putative binding site for the SH3 domain of c-abl (PXXXXPXXP (SEQ ID No: 93); PEMEPPRRP (SEQ ID No: 150)).

The transcript that most closely aligns with *Euplotes* and yeast telomerases by amino acid similarity contains sequences A and B, and does not contain sequence C. The nucleotide and amino acid sequences of eight variants resulting from mRNAs comprising combinations of sequences A, B, and C are presented in FIG. 8.

Example 6

Recombinant Expression of Human Telomerase

Human telomerase is cloned into bacterial expression vectors. The sequence shown in FIG. 1 is amplified from LIM 1215 mRNA in two pieces and then ligated together.

For the amplification, first strand cDNA is synthesized and used in an amplification reaction (Titan system, Boehringer, IN) with a mixture of DNA polymerases, such that a proofreading thermostable enzyme (e.g. rTth)is used with Taq DNA polymerase. As much of the mRNA in LIM 1215 lacks sequence B (FIG. 9), the amplification primers are designed such that one primer of each pair is within sequence B, on either side of the Sac I site at nucleotide 2271 (FIG. 1). The 5' portion is first amplified from cDNA using HT2356R (SEQ ID No: 118) and HT0028F (SEQ ID No: 98) primers (cycle conditions: 70° C., 2 min; then added primer sequences equilibrated to 50° C.; 50° C., 30 min; 95° C., 2 min; 2 cycles of 94° C., 30 sec; 65° C., 30 sec; 3 cycles of 94° C., 30 sec; 63° C., 30 sec; 68° C. 3 min; 32 cycles of 94° C., 30 sec; 60° C., 30 sec; 68° C., 3 min). The extreme 5' portion of the telomerase gene is then ligated in Eco RI/Sac I digested pTTQ18 (Amersham International plc, Buckinghamshire, England) and pBluescriptII KS+, and the sequence verified.

To obtain the 3' end, LIM 1215 cDNA is amplified using HT2230F (SEQ ID No: 117) and a HT3292B (SEQ ID No: 123) primer that is complementary to the sequence encoding the very C-terminus of telomerase. The amplification products are digested with Hind III and Sac I and inserted into pTTQ18 and pBluescript II KS+. The 5' and 3' ends are also cloned joined at the native Sac I site in pTTQ18 both as a Hexa-His fusion and a non-fusion protein.

primers are telRNA T (SEQ ID No: 126) and telRNA 598B (SEQ ID No: 128) (FIG. 5). Amplification conditions are 95° C., 3 min; addition of polymerase; 80° C. 2 min; 35 cycles of 94° C., 30 sec; 68° C., 2 min.

The amplified product is inserted into pBluescript after another amplification using hTR TAC (SEQ ID No: 142) (has a tac promoter sequence) and hTR 3'Pst (SEQ ID No: 144) (has a cis-acting ribozyme sequence) primers. The pBluescript insert is then isolated and ligated to pACYC177.

Example 8

Expression of Human Telomerase Subregions

The RTase domain of human telomerase is determined by sequence comparison with Moloney MULV reverse transcriptase. The fingers/palm region of Moloney MuLV reverse transcriptase forms a stable unit for crystallization (Georgiadis et al., *Structure* 3: 879, 1995). A number of residues and motifs are conserved in the active site of both proteins. Primers are designed to amplify the RTase domain and the fingers/palm domain for insertion into an expression vector and subsequent protein isolation.

| Fragment ID | Primers | Amino acids |
| --- | --- | --- |
| I | BT-177/BT-178 | AAEH . . . → . . . VQMPAH |
|  | (SEQ ID No: 145)/(SEQ ID No: 146) | (SEQ ID No: 151) . . . → . . . (SEQ ID No: 152) |
| II | BT-177/BT-179 | AAEH . . . → . . . VGLGL |
|  | (SEQ ID No: 145)/(SEQ ID No: 147) | (SEQ ID No: 151) . . . → . . . (SEQ ID No: 153) |
| III | BT-182/BT-179 | RATS . . . → . . . VGLGL |
|  | (SEQ ID No: 148)/(SEQ ID No: 147) | (SEQ ID No: 154) . . . → . . . (SEQ ID No: 153) |
| IV | BT-183/BT-179 | VQMPAH . . . → . . . VGLGL |
|  | (SEQ ID No: 149)/(SEQ ID No: 147) | (SEQ ID No: 152) . . . → . . . (SEQ ID No: 153) |

The plasmid pTTQ18-Htel is transfected into bacterial cells (e.g., BL21(DE3)). Over expression of the protein is accomplished upon induction with IPTG. The bacteria are collected by centrifugation and lysed in lysis buffer (20 mM $NaPO_4$, pH 7.0, 5 mM EDTA, 5 mM EGTA, 1 mM DTT, 0.5 µg/ml leupeptin, 1 µg/ml aprotinin, 0.7 µg/ml pepstatin). This mixture is evenly suspended via a Polytron homogenizer and the cells are broken open by agitation with glass beads or passage through a microfluidizer. The resulting lysate is centrifuged at 50,000 rpm for 45 min. The supernatant is diluted with 20 mM $NaPO_4$, 1 mM EDTA, pH 7.0 (buffer A). The diluted lysate supernatant is then loaded onto a SP-Sepharose or equivalent column, and a linear gradient of 0 to 30% SP Buffer B (1 M NaCl, 20 mM $NaPO_4$, 1 mM EDTA, pH 7.0) in Buffer A with a total of 6 column volumes is applied. Fractions containing telomerase are combined. Further purifications can be performed.

For hexa-His fusion proteins, the lysate is clarified by centrifugation and batch absorbed on a Ni-IDA-Sepharose column. The matrix is poured into a column and washed with buffer, typically either 50 mM Tris pH 7.6, 1 mM DTT; 50 mM MES pH 7.0, or IMAC buffer (for hexa-his fusions). The telomerase protein bound to the matrix is eluted in NaCl containing buffer.

Example 7

Recombinant Expression of Human Telomerase RNA Component

The human telomerase RNA component is first isolated by amplification from genomic DNA. The amplification Fragment I encodes the "fingers and palm" domain that corresponds to MoMuLV. The C-terminal "thumb" and "connection" (see, Kohlstaedt et al., *Science* 256: 1783, 1992) are deleted. Fragment II encodes the telomerase reverse transcriptase domain, as well as the C-terminal "connection" domain. The N-terminus is chosen by size comparison with the MoMuLV RTase structure. Fragment III encodes the C-terminus of the protein. The RATS sequence is located within the RTase domain (palm region) of the protein. Fragment IV encodes the C-terminal region containing the "thumb" and "connection" domains and may function as a regulatory element. The connection domain in HIV-1 is able to block the catalytic cleft of HIV RTase in the absence of the RNase domain (Kohlstaedt et al, supra). In an analogous fashion, the C-terminal region may be useful as a regulatory (inhibitory) fragment. Moreover, sequence C has a putative binding site for the SH3 domain of c-abl (PXXXXPXXP (SEQ ID No: 93); PEMEPPRRP (SEQ ID No: 150), see variant 2 sequence of FIG. 8). c-abl protein interacts directly with the ATM (ataxia telangiectasia) protein (Shafinan et al., *Nature* 389: 520, 1997), a protein apparently involved in cell-cycle control, meiotic recombination, telomere length monitoring and DNA damage response. Binding of c-abl protein may be assessed in standard protein-protein interaction methods. As such, an interaction of telomerase and c-abl or other SH3-domain containing proteins (e.g., erb2) and regulation by movement of the telomerase C-terminus in and out of the catalytic cleft may be controllable using the constructs and products described herein. In one instance, regulation may be mediated by phosphorylation/dephosphorylation reactions.

All primers have either a Hind III or a Bam HI site. The amplification reaction is performed in 1× Pfu buffer, 250 µM dNTPs, 100 ng each primer, clone 53.2 template DNA using the following cycling conditions: 94° C. for 2 min; 25 cycles of either 55° C., 60° C., or 65° C. for 2 min, 72° C. for 2 min, 94° C. for 1 min; followed by 72° C. for 10 min. Products of the predicted length are obtained (966 bp for BT-177/BT-178; 1479 bp for BT-177/BT-179; 824 bp for BT-182/BT-179; 529 bp for BT-183/BT-179). The amplified products are extracted with phenol:CHCL3 and precipitated with ethanol. The products are resuspended and digested with the appropriate enzyme that cleaves in the primer sequence.

The digested products are ligated to pBluescript that is digested with enzymes that leave compatible ends. The inserts arc digested with Hind III and partially digested with Bam HI for ligation to pGEX. The plasmid is transfected in BL21(DE3) cells and selected on ampicillin plates. Colonies are picked and grown overnight in liquid broth. An aliquot is diluted in Terrific Broth with 100 μg/ml ampicillin. The cells are grown at 37° C. and induced with 0.5 mM IPTG at approximately O.D. 0.8. Growth is continued for 5 hours. Cells are collected by centrifugation and may be processed immediately or frozen at −70° C. until needed.

Protein is purified from lysed cells. Cell pellets are lysed by vortexing in 50 mM Tris pH 8.0, 10 mM 2-ME, 1 mg/ml lysozyme, 0.5% Triton X-100, 1 μg/ml pepstatin, 10 μg/ml leupeptin, 10 μg/ml aprotinin, 0.5 mM PMSF, and 2 mM EDTA and a freeze/thaw cycle. Lysates are clarified by centrifugation. Supernatant is added to a 50% slurry of GSH-Sepharose, rotated at 4° C. for 2 hr. The matrix is washed twice with lysis buffer, followed by 50 mM Tris, pH 8.0, 10 mM 2-ME. For analysis by SDS-PAGE gel electrophoresis, sample buffer with 150 mM 2-ME is added and the samples boiled.

Example 9

Isolation of Murine Telomerase Gene

The murine telomerase gene is isolated from genomic or cDNA library. A mouse genomic library is constructed in λFIX II vector from strain 129 DNA. The library is plated, and plaques are lifted onto nylon membranes. The membranes are hybridized with the insert from clone 53.1 (1.9 kb) under normal stringency conditions. Six hybridizing plaques are chosen for further analysis.

Example 10

Demonstration of Telomerase Activity Using HT-1 Telomerase Variants

Full-length hT-1 sequence is cloned into an expression vector and the resulting protein is assayed for telomerase activity. Vector pRc/CMV2 (Invitrogen, Carlsbad, Calif.) is a eukaryotic expression vector that has a multi-cloning site positioned between a promoter, the RSV LTR, and a polyadenylation signal and transcription termination sequences from the bovine growth hormone gene. Telomerase sequence in which Leu49 codon was converted to a Met codon was inserted into pRc/CMV2. One clone, phTC51, is chosen for further study. The DNA sequence of the 5' junction was determined and confirmed the orientation of the insert. Subsequently, the sequence of the 3' junction was determined and showed a deletion of the polyA signal, but no deletion of telomerase coding sequence.

Figure 12:
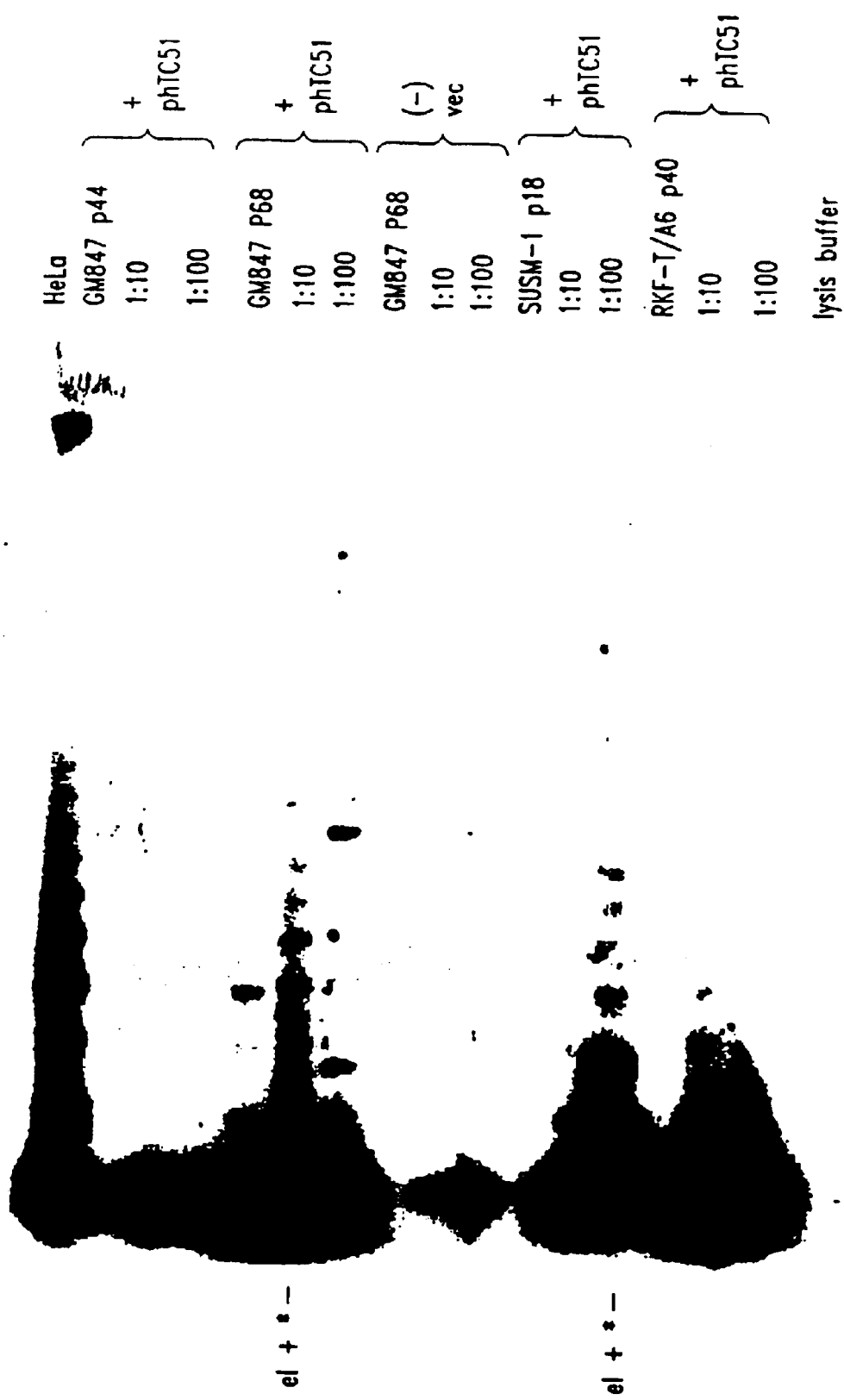
FIG. 12 is a scanned image of a telomerase activity assay.

The clone is transfected into HeLa GM847 cells at passages 44 and 68, SUSM-1 cells at passage 18, and RKF-T/A6 cells at passage 40. Cell extracts are assayed for telomerase activity by the TRAP assay as described herein. As shown in FIG. 12, a ladder of products indicative of telomerase activity is seen at the 1:100 dilution of extract from SUSM-1 cells and is not seen in control cells. A ladder is not readily detectable at the higher concentration of extract, which may be due to nuclease s activity in the extract.

Figure 13A:
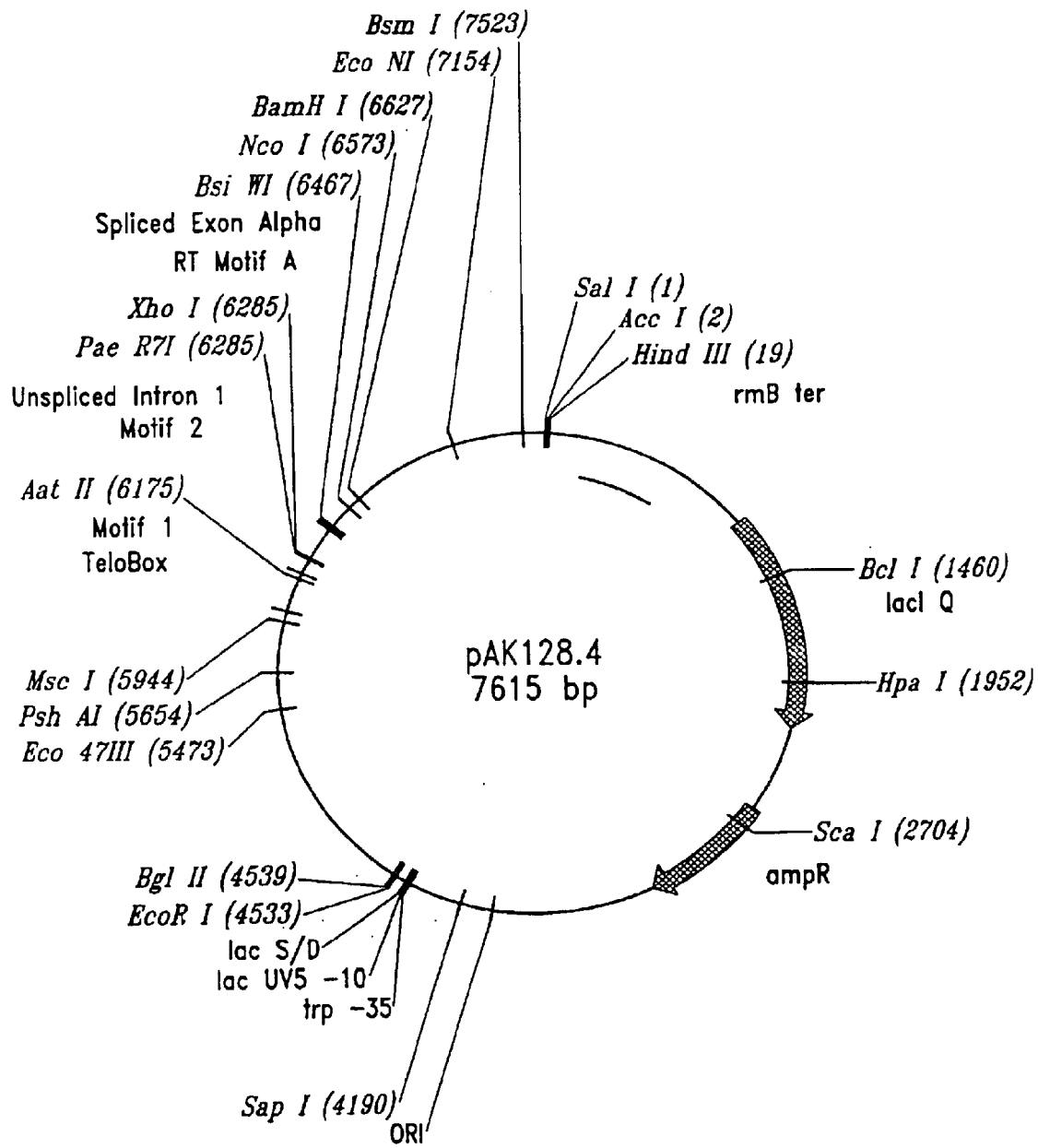
Figure 14A:
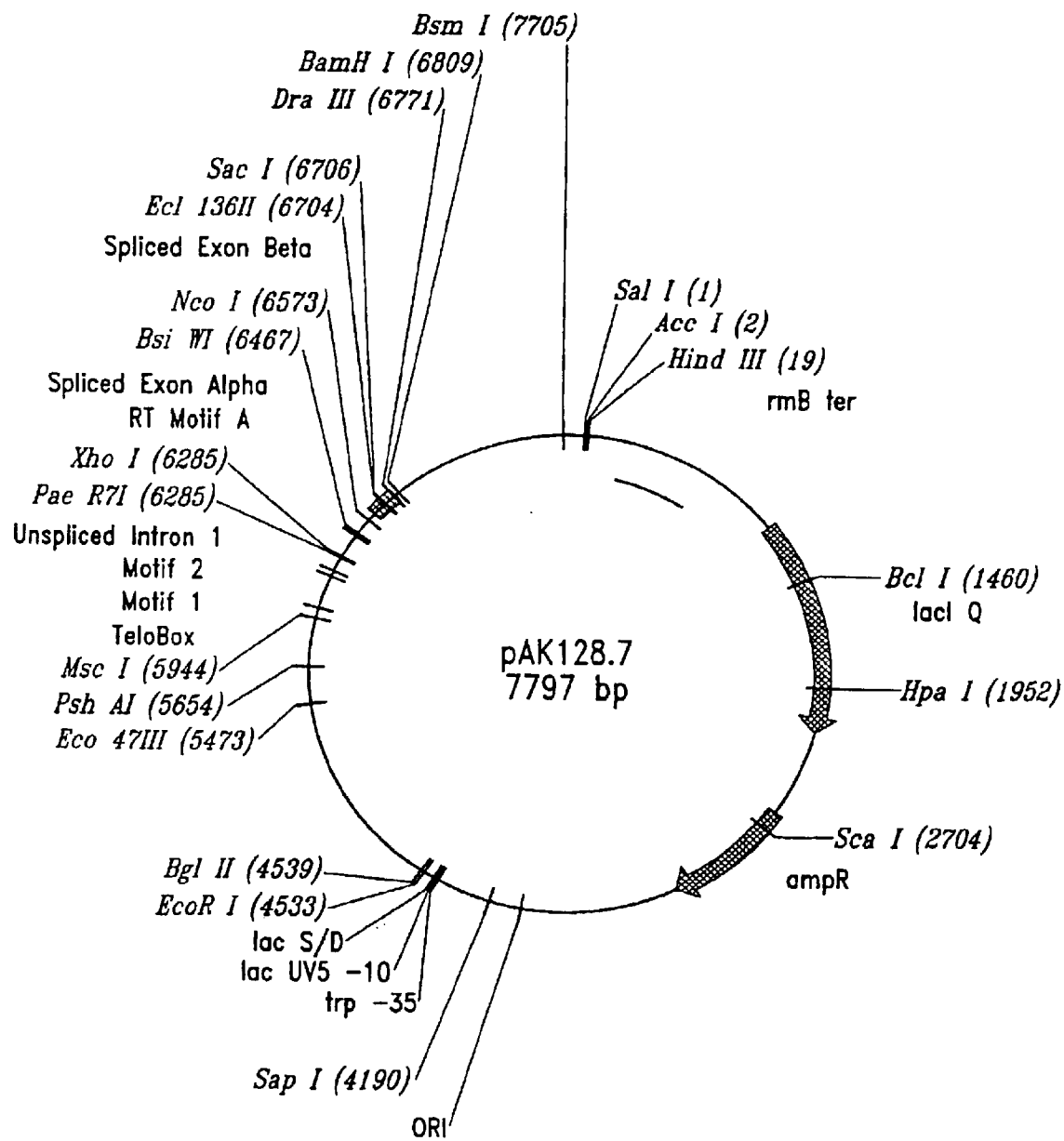
Figure 15A:
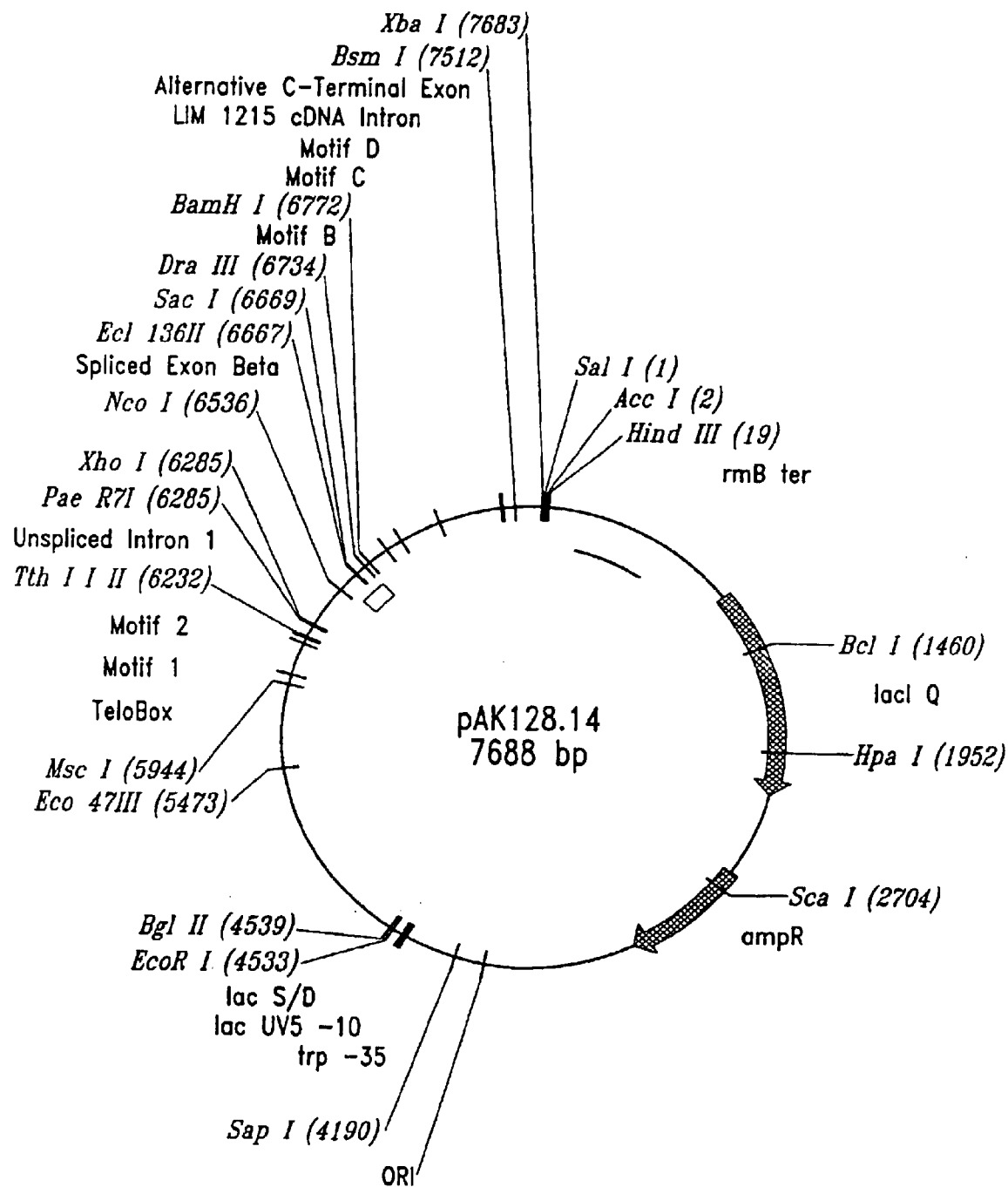

Three telomerase variants are constructed: pAKI.4 is telomerase with the alternative intron/exon beta region spliced out (FIG. 13); pAKI.7 is telomerase with the alternative C-terminus alternative intron/exon 3 (FIG. 14); and pAKI.14 is telomerase with the alternative intron/exon alpha spliced out (FIG. 15). The 5' end of the telomerase gene was inserted into each of these three vectors and the inserts moved to pCIneo expression vector. The variants, along with reference telomerase in pCIneo are transiently transfected into GM847 cells, which are ALT cells having no detectable telomerase activity but which express the RNA subunit. Cell extracts are tested in a TRAP assay. The reference telomerase exhibits activity, as well as the telomerase with insert 3 (pAKI.7 insert), but the other variants do not express activity.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated nucleic acid molecule encoding a splice variant of a gene sequence capable of being spliced to result in a reference human telomerase encoding SEQ ID No: 2, wherein the splice variant has at least one of the following insertions or deletions:
   (a) an insertion of sequences X (comprising SEQ ID No: 32) at nucleotide 1766 of SEQ ID No: 1;
   (b) an insertion of nucleic acid sequence encoding sequence 1 (SEQ ID No: 24) at nucleotide 1950 of SEQ ID No: 1;
   (c) a deletion of nucleotides 2131 through 2166 of SEQ ID No: 1;
   (d) a deletion of nucleotides 2287 through 2468 of SEQ ID No: 1;
   (e) an insertion of sequence 2 comprising SEQ ID No: 29 at nucleotide 2843 of SEQ ID No: 1; and
   (f) an insertion of nucleic acid sequence encoding sequence 3 (SEQ ID No: 31) at nucleotide 3157 of SEQ ID No: 1,
   and wherein the splice variant does not encode SEQ ID No: 2.

2. The nucleic acid molecule of claim 1, wherein the nucleic acid molecule encodes one of SEQ ID Nos: 35, 37, 39, 42, 44, 46, 48, 50, 52–54, 56–58, 60–62, 64–66, 68–70, 72–74, 76–78, 80–82, 84–86.

3. An isolated nucleic acid molecule encoding any of SEQ ID Nos: 35, 37, 39, 42, 44, 46, 48, 50, 56–58, 60–62, 64–66, 68–70, 72–74, 76–78, 80–82, 84–86 or a variant thereof,
   wherein said variant has at least 95% amino acid identity with said amino acid sequences and binds telomerase RNA (hTR) or has telomerase activity; and
   wherein the nucleic acid does not encode SEQ ID No: 2.

4. An isolated nucleic acid molecule consisting of any of SEQ ID Nos: 23, 25, 27, 29, 30, 32, 33, or the complement thereof.

5. An isolated nucleic acid molecule encoding any of SEQ ID Nos: 24, 26, 28, or 31.

6. An expression vector, comprising a heterologous promoter operably linked to a nucleic acid molecule according to any of claims 1, 2–4, and 5.

7. The expression vector of claim 6, wherein the vector is selected from the group consisting of bacterial vectors, retroviral vectors, adenoviral vectors and yeast vectors.

8. A host cell containing a vector according to claim 6.

9. The host cell of claim 8, wherein the cell is selected from the group consisting of human cell, monkey cell, mouse cell, rat cell, yeast cell and bacterial cell.

10. The host cell of claim 8, wherein the cell is a human cell.

11. A nucleic acid probe that is capable of specifically hybridizing to a nucleic acid molecule encoding a splice variant of human telomerase according to claim 1
    wherein the probe consists of one of SEQ ID Nos: 23, 25, 27, 29, 30, 32 or 33 or the complement thereof;
    or a fragment of SEQ ID Nos: 23, 29, 30, 31 or 32 or the complement thereof.

12. The probe of claim 11, wherein the fragment is from 12 to 200 nucleotides long.

13. The probe of claim 11, wherein the fragment is from 20 to 50 nucleotides long.

14. The probe of claim 11, wherein the nucleic acid molecule is labeled.

15. An isolated nucleic acid molecule consisting of a sequence selected from the group consisting of region 1 (SEQ ID No:23), region α (SEQ ID No:25), region β (SEQ ID No:27), region 2 (SEQ ID No:29), and region 3 (SEQ ID No:30).

16. The nucleic acid molecule of claim 1, wherein the splice variant of human telomerase has at least a deletion of nucleotides 2131–2166 of SEQ ID No: 1.

17. The complement of the nucleic acid molecules of any of claims 1, 2, 3, 4 and 5.

18. The nucleic acid molecule of any of claims 2, 3, 4 and 5, wherein said molecule is a DNA molecule.

19. The nucleic acid molecule of any of claims 1, 2, 3, 4 and 5, wherein said molecule is an RNA or cDNA molecule.

20. A pair of oligonucleotide primers that amplify nucleic acid sequence of human telomerase containing a splice junction, wherein only one primer of each primer pair flanks nucleotide 1950, 2131–2166, 2287–2468, 2843, or 3157 as presented in FIG. 1 (SEQ ID No: 1) and the other primer of the pair has sequence corresponding to all or a portion of one of the sequences presented in FIG. 10 (SEQ ID Nos: 23, 25, 27, 29, 30, 32, 33) or complements thereof.

21. The probe of claim 14, wherein the label is a chemiluminescent label, a radioactive label, or biotin.

22. The nucleic acid molecule of claim 1, wherein the splice variant of human telomerase has at least an insertion of nucleic acid sequence encoding sequence 3 (SEQ ID No:31) at nucleotide 3157 of SEQ ID No: 1.

23. An oligonucleotide consisting of 15–100 contiguous nucleotides of one of the sequences selected from the group consisting of SEQ ID Nos. 23, 29, 30, 32, 33 or complements thereof.

24. The oligonucleotide of claim 23, wherein the oligonucleotide is labeled.

25. The oligonucleotide of claim 24, wherein the label is a radiolabel, a chemiluminescent label, or biotin.

26. A pair of nucleotide primers that amplify sequence selected from the group consisting of region 1 (SEQ ID No: 23), region α (SEQ ID No: 25), region β (SEQ ID No: 27), region 2 (SEQ ID No: 29), region 3 (SEQ ID No: 30), region X (SEQ ID No: 32), wherein the primers comprise at least 15 contiguous nucleotides of one of SEQ ID Nos: 23, 25, 27, 29, 30, 32, or 18 or complements thereof and wherein the primers are from 15 to 50 nucleotides in length.

27. A method of determining a pattern of telomerase RNA expression in cells, comprising:

(a) preparing cDNA from mRNA isolated from the cells, (b) amplifying the cDNA using primers that amplify a splice variant of nucleic acid encoding human telomerase to form an amplified product and (c) hybridizing the amplified product with one or more of the following:

all or at least 15 contiguous nucleotides of the sequence of region 1 (SEQ ID No: 23), all or at least 15 contiguous nucleotides of the sequence of region β (SEQ ID No: 27), all or at least 15 contiguous nucleotides of the sequence of region 2 (SEQ ID No.: 29), all or at least 15 contiguous nucleotides of the sequence of region 3 (SEQ ID No: 30), or all or at least 15 contiguous nucleotides of the sequence of region X (SEQ ID No: 32); or a complement thereof; and (d) detecting hybridization;

therefrom determining the pattern of telomerase RNA expression.

28. A method of determining a pattern of telomerase RNA expression in cells, comprising, (a) preparing cDNA from mRNA isolated from the cells, (b) amplifying the cDNA using primers that amplify a splice variant of nucleic acid encoding human telomerase to form an amplified product and (c) hybridizing the amplified product with two or more of the following:

all or at least 15 contiguous nucleotides of the sequence of region 1 (SEQ ID No: 23), all or at least 15 contiguous nucleotides of the sequence of region α (SEQ ID No: 25), all or at least 15 contiguous nucleotides of the sequence of region β (SEQ ID No: 27), all or at least 15 contiguous nucleotides of the sequence of region 2 (SEQ ID No: 29), all or at least 15 contiguous nucleotides of the sequence of region 3 (SEQ ID No: 30), all or at least 15 contiguous nucleotides of the sequence of region X (SEQ ID No: 32) or all or at least 15 contiguous nucleotides of the sequence of region Y (SEQ ID No: 18); or a complement thereof; and (d) detecting hybridization;

therefrom determining the pattern of telomerase RNA expression.

29. The method of either of claims 27 or 28, wherein the contiguous nucleotides contain a label.

30. The method of claim 29, wherein the label is radioactive, chemiluminescent, or biotin.

* * * * *

UNITED STATES PATENT AND TRADEMARK OFFICE
CERTIFICATE OF CORRECTION

PATENT NO. : 6,916,642 B1
DATED : July 12, 2005
INVENTOR(S) : Andrzej Kilian and David Bowtell It is certified that error appears in the above-identified patent and that said Letters Patent is hereby corrected as shown below:

Column 337,
Lines 25-26, replace "result in" with -- encode --.
Line 26, replace "encoding" with -- of --.
Lines 29-30, replace "sequences X (comprising SEQ ID NO:32) at" with
-- alternative intron/exon X comprising SEQ ID No:32 at its 5' -end following --.
Line 32, replace "sequence 1 (SEQ ID No:24) at" with -- alternative intron/exon 1 (SEQ ID No:24) following --.
Lines 38-39, replace "sequence 2 comprising SEQ ID No:29 at" with -- alternative intron/exon 2 comprising SEQ ID No:29 at its 5' -end following --.
Line 41, replace "sequence 3 (SEQ ID No:31) at" with -- alternative intron/exon 3 (SEQ ID No:31) following --.
Lines 41-42, replace "SEQ ID NO: 1." with -- SEQ ID No: 1; --.
Lines 46-47, replace "The nucleic acid molecule of Claim 1, wherein the nucleic acid molecule" with -- An isolated nucleic acid molecule which --.
Lines 49 and 52, insert -- or -- following "80-82,".
Line 60, insert -- a peptide consisting of -- following "encoding".

Column 338,
Line 29, delete "specifically".
Line 31, insert -- under the following stringency conditions: 1 M Na+, 5X SSPE, 0.5% SDS, 5X Denhardt's solution at 65 C -- following "according to claim 1".
Line 34, delete "31".
Line 43, replace "region 1" with -- alternative intron/exon 1 --.
Line 44, replace "region alpha" with -- alternative intron/exon alpha --.
Line 44, replace "region beta" with -- alternative intron/exon beta --.
Line 45, replace "region 2" with -- alternative intron/exon 2 --.
Line 45, replace "region 3" with -- alternative intron/exon 3 --.
Line 52, insert -- 1, -- following "claims".

Column 339,
Lines 1-2, replace "sequence 3 (SEQ ID No:31) at" with -- alternative intron/exon 3 (SEQ ID No:31) following --.
Line 11, replace "nucleotide" with -- oligonucleotide --.
Lines 12 and 29, replace "region 1" with -- alternative intron/exon 1 --.
Line 13, replace "region alpha" with -- alternative intron/exon alpha --.
Lines 13 and 30, replace "region beta" with -- alternative intron/exon beta --.
Lines 14 and 32, replace "region 2" with -- alternative intron/exon 2 --.
Lines 14 and 34, replace "region 3" with -- alternative intron/exon 3 --.
Lines 14-15, replace "region X" with -- and alternative intron/exon X --.
Line 35, replace "region X" with -- alternative intron/exon X --.

UNITED STATES PATENT AND TRADEMARK OFFICE
CERTIFICATE OF CORRECTION

PATENT NO. : 6,916,642 B1
DATED : July 12, 2005
INVENTOR(S) : Andrzej Kilian and David Bowtell It is certified that error appears in the above-identified patent and that said Letters Patent is hereby corrected as shown below:

Column 340,
Line 15, replace "region 1" with -- alternative intron/exon 1 --.
Line 16, replace "region alpha" with -- alternative intron/exon alpha --.
Line 18, replace "region beta" with -- alternative intron/exon beta --.
Line 20, replace "region 2" with -- alternative intron/exon 2 --.
Line 21, replace "region 3" with -- alternative intron/exon 3 --.
Line 23, replace "region X" with -- alternative intron/exon X --.
Line 24, replace "region Y" with -- alternative intron/exon Y --.

Signed and Sealed this

Twenty-fifth Day of October, 2005

JON W. DUDAS
*Director of the United States Patent and Trademark Office*

SEQUENCE LISTING

<160> NUMBER OF SEQ ID NOS: 155

<210> SEQ ID NO 1
<211> LENGTH: 3964
<212> TYPE: DNA
<213> ORGANISM: Homo sapiens

<400> SEQUENCE: 1
atgccgcgcg ctccccgctg ccgagccgtg cgctccctgc tgcgcagcca ctaccgcgag    60

-continued

| | |
|---|---|
| gtgctgccgc tggccacgtt cgtgcggcgc ctggggcccc agggctggcg gctggtgcag | 120 |
| cgcggggacc cggcggcttt ccgcgcgctg gtggcccagt gcctggtgtg cgtgccctgg | 180 |
| gacgcacggc cgcccccgc cgcccctcc ttccgccagg tgtcctgcct gaaggagctg | 240 |
| gtggcccgag tgctgcagag gctgtgcgag cgcggcgcga agaacgtgct ggccttcggc | 300 |
| ttcgcgctgc tggacggggc cgcgggggc ccccgagg ccttcaccac cagcgtgcgc | 360 |
| agctacctgc ccaacacggt gaccgacgca ctgcggggga gcgggcgtg ggggctgctg | 420 |
| ttgcgccgcg tgggcgacga cgtgctggtt cacctgctgg cacgctgcgc gctctttgtg | 480 |
| ctggtggctc ccagctgcgc ctaccaggtg tgcgggccgc cgctgtacca gctcggcgct | 540 |
| gccactcagg cccggccccc gccacacgct agtggacccc gaaggcgtct gggatgcgaa | 600 |
| cgggcctgga accatagcgt cagggaggcc ggggtccccc tgggcctgcc agccccgggt | 660 |
| gcgaggaggc gcggggcag tgccagccga agtctgccgt tgcccaagag gcccaggcgt | 720 |
| ggcgctgccc ctgagccgga gcggacgccc gttgggcagg gtcctgggc ccacccgggc | 780 |
| aggacgcgtg gaccgagtga ccgtggtttc tgtgtggtgt cacctgccag acccgccgaa | 840 |
| gaagccacct ctttggaggg tgcgctctct ggcacgcgcc actcccaccc atccgtgggc | 900 |
| cgccagcacc acgcgggccc cccatccaca tcgcggccac cacgtccctg ggacacgcct | 960 |
| tgtcccccgg tgtacgccga gaccaagcac ttcctctact cctcaggcga caaggagcag | 1020 |
| ctgcggccct ccttcctact cagctctctg aggcccagcc tgactggcgc tcggaggctc | 1080 |
| gtggagacca tctttctggg ttccaggccc tggatgccag ggactccccg caggttgccc | 1140 |
| cgcctgcccc agcgctactg gcaaatgcgg cccctgtttc tggagctgct tgggaaccac | 1200 |
| gcgcagtgcc cctacggggt gctcctcaag acgcactgcc cgctgcgagc tgcggtcacc | 1260 |
| ccagcagccg gtgtctgtgc ccgggagaag ccccagggct ctgtggcggc ccccgaggag | 1320 |
| gaggacacag acccccgtcg cctggtgcag ctgctccgcc agcacagcag cccctggcag | 1380 |
| gtgtacggct tcgtgcgggc ctgcctgcgc cggctggtgc cccaggcct ctggggctcc | 1440 |
| aggcacaacg aacgccgctt cctcaggaac accaagaagt tcatctcccct ggggaagcat | 1500 |
| gccaagctct cgctgcagga gctgacgtgg aagatgagcg tgcggggctg cgcttggctg | 1560 |
| cgcaggagcc caggggttgg ctgtgttccg gccgcagagc accgtctgcg tgaggagatc | 1620 |
| ctggccaagt tcctgcactg gctgatgagt gtgtacgtcg tcgagctgct caggtctttc | 1680 |
| ttttatgtca cggagaccac gtttcaaaag aacaggctct ttttctaccg gaagagtgtc | 1740 |
| tggagcaagt tgcaaagcat tggaatcaga cagcacttga gagggtgca gctgcgggag | 1800 |
| ctgtcggaag cagaggtcag gcagcatcgg gaagccaggc ccgccctgct gacgtccaga | 1860 |
| ctccgcttca tccccaagcc tgacgggctg cggccgattg tgaacatgga ctacgtcgtg | 1920 |
| ggagccagaa cgttccgcag agaaaagagg gccgagcgtc tcacctcgag ggtgaaggca | 1980 |
| ctgttcagcg tgctcaacta cgagcgggcg cggcgccccg gctcctggg cgcctctgtg | 2040 |
| ctgggcctgg acgatatcca cagggcctgg cgcaccttcg tgctgcgtgt gcgggcccag | 2100 |
| gacccgccgc ctgagctgta ctttgtcaag gtggatgtga cgggcgcgta cgacaccatc | 2160 |
| ccccaggaca ggctcacgga ggtcatcgcc agcatcatca accccagaa cacgtactgc | 2220 |
| gtgcgtcggt atgccgtggt ccagaaggcc gcccatgggc acgtccgcaa ggccttcaag | 2280 |
| agccacgtct ctaccttgac agacctccag ccgtacatgc acagttcgt ggctcacctg | 2340 |
| caggagacca gcccgctgag ggatgccgtc gtcatcgagc agagctcctc cctgaatgag | 2400 |
| gccagcagtg gcctcttcga cgtcttccta cgcttcatgt gccaccacgc cgtgcgcatc | 2460 |

```
agggcaagt cctacgtcca gtgccagggg atcccgcagg gctccatcct ctccacgctg   2520
ctctgcagcc tgtgctacgg cgacatggag aacaagctgt ttgcggggat tcggcgggac   2580
gggctgctcc tgcgtttggt ggatgatttc ttgttggtga cacctcacct cacccacgcg   2640
aaaaccttcc tcaggaccct ggtccgaggt gtccctgagt atggctgcgt ggtgaacttg   2700
cggaagacag tggtgaactt ccctgtagaa gacgaggccc tgggtggcac ggcttttgtt   2760
cagatgccgg cccacggcct attcccctgg tgcggcctgc tgctggatac ccggacccctg  2820 gaggtgcaga gcgactactc cagctatgcc cggacctcca tcagagccag tctcaccttc   2880
aaccgcggct tcaaggctgg gaggaacatg cgtcgcaaac tctttggggt cttgcggctg   2940
aagtgtcaca gcctgtttct ggatttgcag gtgaacagcc tccagacggt gtgcaccaac   3000
atctacaaga tcctcctgct gcaggcgtac aggtttcacg catgtgtgct gcagctccca   3060
tttcatcagc aagtttggaa gaaccccaca ttttcctgc gcgtcatctc tgacacggcc    3120
tccctctgct actccatcct gaaagccaag aacgcaggga tgtcgctggg ggccaagggc   3180
gccgccggcc ctctgccctc cgaggccgtg cagtggctgt gccaccaagc attcctgctc   3240
aagctgactc gacaccgtgt cacctacgtg ccactcctgg ggtcactcag gacagcccag   3300
acgcagctga gtcggaagct cccgggggacg acgctgactg ccctggaggc cgcagccaac   3360
ccggcactgc cctcagactt caagaccatc ctggactgat ggccacccgc cacagccag    3420 gccgagagca gacaccagca gccctgtcac gccgggctct acgtcccagg gagggagggg   3480
cggcccacac ccaggcccgc accgctggga gtctgaggcc tgagtgagtg tttggccgag   3540
gcctgcatgt ccggctgaag gctgagtgtc cggctgaggc ctgagcgagt gtccagccaa   3600
gggctgagtg tccagcacac ctgccgtctt cacttcccca caggctggcg ctcggctcca   3660
ccccagggcc agcttttcct caccaggagc ccggcttcca ctccccacat aggaatagtc   3720
catccccaga ttcgccattg ttcaccctc gccctgccct cctttgcctt ccaccccac     3780 catccaggtg gagaccctga gaaggaccct gggagctctg ggaatttgga gtgaccaaag   3840
gtgtgccctg tacacaggcg aggacctgc acctggatgg gggtccctgt gggtcaaatt    3900
ggggggaggt gctgtgggag taaatactg aatatgag ttttcagtt ttgaaaaaa       3960 aaaa                                                                3964

<210> SEQ ID NO 2
<211> LENGTH: 1132
<212> TYPE: PRT
<213> ORGANISM: Homo sapiens

<400> SEQUENCE: 2

Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95
```

-continued

```
Leu Ala Phe Gly Phe Ala Leu Leu Asp Gly Ala Arg Gly Gly Pro Pro
                100                 105                 110
Glu Ala Phe Thr Thr Ser Val Arg Ser Tyr Leu Pro Asn Thr Val Thr
            115                 120                 125
Asp Ala Leu Arg Gly Ser Gly Ala Trp Gly Leu Leu Arg Arg Val
        130                 135                 140
Gly Asp Val Leu Val His Leu Leu Ala Arg Cys Ala Leu Phe Val
145                 150                 155                 160
Leu Val Ala Pro Ser Cys Ala Tyr Gln Val Cys Gly Pro Pro Leu Tyr
                165                 170                 175
Gln Leu Gly Ala Ala Thr Gln Ala Arg Pro Pro His Ala Ser Gly
                180                 185                 190
Pro Arg Arg Leu Gly Cys Glu Arg Ala Trp Asn His Ser Val Arg
        195                 200                 205
Glu Ala Gly Val Pro Leu Gly Leu Pro Ala Pro Gly Ala Arg Arg
        210                 215                 220
Gly Gly Ser Ala Ser Arg Ser Leu Pro Leu Pro Lys Arg Pro Arg Arg
225                 230                 235                 240
Gly Ala Ala Pro Glu Pro Glu Arg Thr Pro Val Gly Gln Gly Ser Trp
                245                 250                 255
Ala His Pro Gly Arg Thr Arg Gly Pro Ser Asp Arg Gly Phe Cys Val
                260                 265                 270
Val Ser Pro Ala Arg Pro Ala Glu Glu Ala Thr Ser Leu Glu Gly Ala
                275                 280                 285
Leu Ser Gly Thr Arg His Ser His Pro Ser Val Gly Arg Gln His His
                290                 295                 300
Ala Gly Pro Pro Ser Thr Ser Arg Pro Pro Arg Pro Trp Asp Thr Pro
305                 310                 315                 320
Cys Pro Pro Val Tyr Ala Glu Thr Lys His Phe Leu Tyr Ser Ser Gly
                325                 330                 335
Asp Lys Glu Gln Leu Arg Pro Ser Phe Leu Leu Ser Ser Leu Arg Pro
                340                 345                 350
Ser Leu Thr Gly Ala Arg Arg Leu Val Glu Thr Ile Phe Leu Gly Ser
                355                 360                 365
Arg Pro Trp Met Pro Gly Thr Pro Arg Arg Leu Pro Arg Leu Pro Gln
                370                 375                 380
Arg Tyr Trp Gln Met Arg Pro Leu Phe Leu Glu Leu Leu Gly Asn His
385                 390                 395                 400
Ala Gln Cys Pro Tyr Gly Val Leu Leu Lys Thr His Cys Pro Leu Arg
                405                 410                 415
Ala Ala Val Thr Pro Ala Ala Gly Val Cys Ala Arg Glu Lys Pro Gln
                420                 425                 430
Gly Ser Val Ala Ala Pro Glu Glu Asp Thr Asp Pro Arg Arg Leu
                435                 440                 445
Val Gln Leu Leu Arg Gln His Ser Ser Pro Trp Gln Val Tyr Gly Phe
                450                 455                 460
Val Arg Ala Cys Leu Arg Arg Leu Val Pro Pro Gly Leu Trp Gly Ser
465                 470                 475                 480
Arg His Asn Glu Arg Arg Phe Leu Arg Asn Thr Lys Lys Phe Ile Ser
                485                 490                 495
Leu Gly Lys His Ala Lys Leu Ser Leu Gln Glu Leu Thr Trp Lys Met
                500                 505                 510
Ser Val Arg Asp Cys Ala Trp Leu Arg Arg Ser Pro Gly Val Gly Cys
```

-continued

```
            515                 520                 525
Val Pro Ala Ala Glu His Arg Leu Arg Glu Ile Leu Ala Lys Phe
            530                 535                 540
Leu His Trp Leu Met Ser Val Tyr Val Glu Leu Leu Arg Ser Phe
545                 550                 555                 560
Phe Tyr Val Thr Glu Thr Thr Phe Gln Lys Asn Arg Leu Phe Phe Tyr
                565                 570                 575
Arg Lys Ser Val Trp Ser Lys Leu Gln Ser Ile Gly Ile Arg Gln His
                580                 585                 590
Leu Lys Arg Val Gln Leu Arg Glu Leu Ser Glu Ala Glu Val Arg Gln
                595                 600                 605
His Arg Glu Ala Arg Pro Ala Leu Leu Thr Ser Arg Leu Arg Phe Ile
            610                 615                 620
Pro Lys Pro Asp Gly Leu Arg Pro Ile Val Asn Met Asp Tyr Val Val
625                 630                 635                 640
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
                660                 665                 670
Pro Gly Leu Leu Gly Ala Ser Val Leu Gly Leu Asp Asp Ile His Arg
                675                 680                 685
Ala Trp Arg Thr Phe Val Leu Arg Val Arg Ala Gln Asp Pro Pro
            690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
                725                 730                 735
Asn Thr Tyr Cys Val Arg Arg Tyr Ala Val Val Gln Lys Ala Ala His
                740                 745                 750
Gly His Val Arg Lys Ala Phe Lys Ser His Val Ser Thr Leu Thr Asp
                755                 760                 765
Leu Gln Pro Tyr Met Arg Gln Phe Val Ala His Leu Gln Glu Thr Ser
            770                 775                 780
Pro Leu Arg Asp Ala Val Val Ile Glu Gln Ser Ser Ser Leu Asn Glu
785                 790                 795                 800
Ala Ser Ser Gly Leu Phe Asp Val Phe Leu Arg Phe Met Cys His His
                805                 810                 815
Ala Val Arg Ile Arg Gly Lys Ser Tyr Val Gln Cys Gln Gly Ile Pro
                820                 825                 830
Gln Gly Ser Ile Leu Ser Thr Leu Leu Cys Ser Leu Cys Tyr Gly Asp
                835                 840                 845
Met Glu Asn Lys Leu Phe Ala Gly Ile Arg Arg Asp Gly Leu Leu Leu
            850                 855                 860
Arg Leu Val Asp Asp Phe Leu Leu Val Thr Pro His Leu Thr His Ala
865                 870                 875                 880
Lys Thr Phe Leu Arg Thr Leu Val Arg Gly Val Pro Glu Tyr Gly Cys
                885                 890                 895
Val Val Asn Leu Arg Lys Thr Val Val Asn Phe Pro Val Glu Asp Glu
                900                 905                 910
Ala Leu Gly Gly Thr Ala Phe Val Gln Met Pro Ala His Gly Leu Phe
                915                 920                 925
Pro Trp Cys Gly Leu Leu Leu Asp Thr Arg Thr Leu Glu Val Gln Ser
            930                 935                 940
```

-continued

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
            965                 970                 975

Val Leu Arg Leu Lys Cys His Ser Leu Phe Leu Asp Leu Gln Val Asn
        980                 985                 990

Ser Leu Gln Thr Val Cys Thr Asn Ile Tyr Lys Ile Leu Leu Leu Gln
    995                 1000                1005

Ala Tyr Arg Phe His Ala Cys Val Leu Gln Leu Pro Phe His Gln Gln
1010                1015                1020

Val Trp Lys Asn Pro Thr Phe Phe Leu Arg Val Ile Ser Asp Thr Ala
1025                1030                1035                1040

Ser Leu Cys Tyr Ser Ile Leu Lys Ala Lys Asn Ala Gly Met Ser Leu
            1045                1050                1055

Gly Ala Lys Gly Ala Ala Gly Pro Leu Pro Ser Glu Ala Val Gln Trp
        1060                1065                1070

Leu Cys His Gln Ala Phe Leu Leu Lys Leu Thr Arg His Arg Val Thr
    1075                1080                1085

Tyr Val Pro Leu Leu Gly Ser Leu Arg Thr Ala Gln Thr Gln Leu Ser
1090                1095                1100

Arg Lys Leu Pro Gly Thr Thr Leu Thr Ala Leu Glu Ala Ala Ala Asn
1105                1110                1115                1120

Pro Ala Leu Pro Ser Asp Phe Lys Thr Ile Leu Asp
            1125                1130

<210> SEQ ID NO 3
<211> LENGTH: 1031
<212> TYPE: PRT
<213> ORGANISM: Euplotes aediculatus

<400> SEQUENCE: 3

Met Glu Val Asp Val Asp Asn Gln Ala Asp Asn His Gly Ile His Ser
1               5                   10                  15

Ala Leu Lys Thr Cys Glu Glu Ile Lys Glu Ala Lys Thr Leu Tyr Ser
            20                  25                  30

Trp Ile Gln Lys Val Ile Arg Cys Arg Asn Gln Ser Gln Ser His Tyr
        35                  40                  45

Lys Asp Leu Glu Asp Ile Lys Ile Phe Ala Gln Thr Asn Ile Val Ala
    50                  55                  60

Thr Pro Arg Asp Tyr Asn Glu Glu Asp Phe Lys Val Ile Ala Arg Lys
65                  70                  75                  80

Glu Val Phe Ser Thr Gly Leu Met Ile Glu Leu Ile Asp Lys Cys Leu
            85                  90                  95

Val Glu Leu Leu Ser Ser Ser Asp Val Ser Asp Arg Gln Lys Leu Gln
            100                 105                 110

Cys Phe Gly Phe Gln Leu Lys Gly Asn Gln Leu Ala Lys Thr His Leu
        115                 120                 125

Leu Thr Ala Leu Ser Thr Gln Lys Gln Tyr Phe Gln Asp Glu Trp
    130                 135                 140

Asn Gln Val Arg Ala Met Ile Gly Asn Glu Leu Phe Arg His Leu Tyr
145                 150                 155                 160

Thr Lys Tyr Leu Ile Phe Gln Arg Thr Ser Glu Gly Thr Leu Val Gln
            165                 170                 175

Phe Cys Gly Asn Asn Val Phe Asp His Leu Lys Val Asn Asp Lys Phe

-continued

```
                180                 185                 190
Asp Lys Lys Gln Lys Gly Gly Ala Ala Asp Met Asn Glu Pro Arg Cys
            195                 200                 205
Cys Ser Thr Cys Lys Tyr Asn Val Lys Asn Glu Lys Asp His Phe Leu
        210                 215                 220
Asn Asn Ile Asn Val Pro Asn Trp Asn Asn Met Lys Ser Arg Thr Arg
225                 230                 235                 240
Ile Phe Tyr Cys Thr His Phe Asn Arg Asn Asn Gln Phe Phe Lys Lys
                245                 250                 255
His Glu Phe Val Ser Asn Lys Asn Asn Ile Ser Ala Met Asp Arg Ala
            260                 265                 270
Gln Thr Ile Phe Thr Asn Ile Phe Arg Phe Asn Arg Ile Arg Lys Lys
        275                 280                 285
Leu Lys Asp Lys Val Ile Glu Lys Ile Ala Tyr Met Leu Glu Lys Val
    290                 295                 300
Lys Asp Phe Asn Phe Asn Tyr Tyr Leu Thr Lys Ser Cys Pro Leu Pro
305                 310                 315                 320
Glu Asn Trp Arg Glu Arg Lys Gln Lys Ile Glu Asn Leu Ile Asn Lys
                325                 330                 335
Thr Arg Glu Glu Lys Ser Lys Tyr Tyr Glu Glu Leu Phe Ser Tyr Thr
            340                 345                 350
Thr Asp Asn Lys Cys Val Thr Gln Phe Ile Asn Glu Phe Phe Tyr Asn
        355                 360                 365
Ile Leu Pro Lys Asp Phe Leu Thr Gly Arg Asn Arg Lys Asn Phe Gln
    370                 375                 380
Lys Lys Val Lys Lys Tyr Val Glu Leu Asn Lys His Glu Leu Ile His
385                 390                 395                 400
Lys Asn Leu Leu Leu Glu Lys Ile Asn Thr Arg Glu Ile Ser Trp Met
                405                 410                 415
Gln Val Glu Thr Ser Ala Lys His Phe Tyr Phe Asp His Glu Asn
            420                 425                 430
Ile Tyr Val Leu Trp Lys Leu Leu Arg Trp Ile Phe Glu Asp Leu Val
        435                 440                 445
Val Ser Leu Ile Arg Cys Phe Phe Tyr Val Thr Glu Gln Gln Lys Ser
    450                 455                 460
Tyr Ser Lys Thr Tyr Tyr Tyr Arg Lys Asn Ile Trp Asp Val Ile Met
465                 470                 475                 480
Lys Met Ser Ile Ala Asp Leu Lys Lys Glu Thr Leu Ala Glu Val Gln
                485                 490                 495
Glu Lys Glu Val Glu Glu Trp Lys Lys Ser Leu Gly Phe Ala Pro Gly
            500                 505                 510
Lys Leu Arg Leu Ile Pro Lys Lys Thr Thr Phe Arg Pro Ile Met Thr
        515                 520                 525
Phe Asn Lys Lys Ile Val Asn Ser Asp Arg Lys Thr Thr Lys Leu Thr
    530                 535                 540
Thr Asn Thr Lys Leu Leu Asn Ser His Leu Met Leu Lys Thr Leu Lys
545                 550                 555                 560
Asn Arg Met Phe Lys Asp Pro Phe Gly Phe Ala Val Phe Asn Tyr Asp
                565                 570                 575
Asp Val Met Lys Lys Tyr Glu Glu Phe Val Cys Lys Trp Lys Gln Val
            580                 585                 590
Gly Gln Pro Lys Leu Phe Phe Ala Thr Met Asp Ile Glu Lys Cys Tyr
        595                 600                 605
```

-continued

```
Asp Ser Val Asn Arg Glu Lys Leu Ser Thr Phe Leu Lys Thr Thr Lys
    610                 615                 620
Leu Leu Ser Ser Asp Phe Trp Ile Met Thr Ala Gln Ile Leu Lys Arg
625                 630                 635                 640
Lys Asn Asn Ile Val Ile Asp Ser Lys Asn Phe Arg Lys Lys Glu Met
                    645                 650                 655
Lys Asp Tyr Phe Arg Gln Lys Phe Gln Lys Ile Ala Leu Glu Gly Gly
                660                 665                 670
Gln Tyr Pro Thr Leu Phe Ser Val Leu Glu Asn Glu Gln Asn Asp Leu
                675                 680                 685
Asn Ala Lys Lys Thr Leu Ile Val Glu Ala Lys Gln Arg Asn Tyr Phe
690                 695                 700
Lys Lys Asp Asn Leu Leu Gln Pro Val Ile Asn Ile Cys Gln Tyr Asn
705                 710                 715                 720
Tyr Ile Asn Phe Asn Gly Lys Phe Tyr Lys Gln Thr Lys Gly Ile Pro
                    725                 730                 735
Gln Gly Leu Cys Val Ser Ser Ile Leu Ser Ser Phe Tyr Tyr Ala Thr
                740                 745                 750
Leu Glu Glu Ser Ser Leu Gly Phe Leu Arg Asp Glu Ser Met Asn Pro
            755                 760                 765
Glu Asn Pro Asn Val Asn Leu Leu Met Arg Leu Thr Asp Asp Tyr Leu
770                 775                 780
Leu Ile Thr Thr Gln Glu Asn Asn Ala Val Leu Phe Ile Glu Lys Leu
785                 790                 795                 800
Ile Asn Val Ser Arg Glu Asn Gly Phe Lys Phe Asn Met Lys Lys Leu
                    805                 810                 815
Gln Thr Ser Phe Pro Leu Ser Pro Ser Lys Phe Ala Lys Tyr Gly Met
                820                 825                 830
Asp Ser Val Glu Glu Gln Asn Ile Val Gln Asp Tyr Cys Asp Trp Ile
            835                 840                 845
Gly Ile Ser Ile Asp Met Lys Thr Leu Ala Leu Met Pro Asn Ile Asn
850                 855                 860
Leu Arg Ile Glu Gly Ile Leu Cys Thr Leu Asn Leu Asn Met Gln Thr
865                 870                 875                 880
Lys Lys Ala Ser Met Trp Leu Lys Lys Leu Lys Ser Phe Leu Met
                    885                 890                 895
Asn Asn Ile Thr His Tyr Phe Arg Lys Thr Ile Thr Thr Glu Asp Phe
                900                 905                 910
Ala Asn Lys Thr Leu Asn Lys Leu Phe Ile Ser Gly Gly Tyr Lys Tyr
            915                 920                 925
Met Gln Cys Ala Lys Glu Tyr Lys Asp His Phe Lys Lys Asn Leu Ala
930                 935                 940
Met Ser Ser Met Ile Asp Leu Glu Val Ser Lys Ile Ile Tyr Ser Val
945                 950                 955                 960
Thr Arg Ala Phe Phe Lys Tyr Leu Val Cys Asn Ile Lys Asp Thr Ile
                    965                 970                 975
Phe Gly Glu Glu His Tyr Pro Asp Phe Phe Leu Ser Thr Leu Lys His
                980                 985                 990
Phe Ile Glu Ile Phe Ser Thr Lys Lys Tyr Ile Phe Asn Arg Val Cys
            995                 1000                1005
Met Ile Leu Lys Ala Lys Glu Ala Lys Leu Lys Ser Asp Gln Cys Gln
1010                1015                1020
```

```
Ser Leu Ile Gln Tyr Asp Ala
1025             1030

<210> SEQ ID NO 4
<211> LENGTH: 1104
<212> TYPE: PRT
<213> ORGANISM: Saccharomyces cerevisiae

<400> SEQUENCE: 4

Arg Arg Leu Gly Pro Gln Gly Trp Arg Leu Val Gln Arg Gly Asp Pro
  1               5                  10                  15

Ala Ala Phe Arg Ala Leu Val Ala Gln Cys Leu Val Cys Val Pro Trp
             20                  25                  30

Asp Ala Arg Pro Pro Ala Ala Pro Ser Phe Arg Gln Val Ser Cys
         35                  40                  45

Leu Lys Glu Leu Val Ala Arg Val Leu Gln Arg Leu Cys Glu Arg Gly
     50                  55                  60

Ala Lys Asn Val Leu Ala Phe Gly Phe Ala Leu Leu Asp Gly Ala Arg
 65                  70                  75                  80

Gly Gly Pro Pro Glu Ala Phe Thr Thr Ser Val Arg Ser Tyr Leu Pro
                 85                  90                  95

Asn Thr Val Thr Asp Ala Leu Arg Gly Ser Gly Ala Trp Gly Leu Leu
            100                 105                 110

Leu Arg Arg Val Gly Asp Asp Val Leu Val His Leu Leu Ala Arg Cys
        115                 120                 125

Ala Leu Phe Val Leu Val Ala Pro Ser Cys Ala Tyr Gln Val Cys Gly
130                 135                 140

Pro Pro Leu Tyr Gln Leu Gly Ala Ala Thr Gln Ala Arg Pro Pro Pro
145                 150                 155                 160

His Ala Ser Gly Pro Arg Arg Leu Gly Cys Glu Arg Ala Trp Asn
                165                 170                 175

His Ser Val Arg Glu Ala Gly Val Pro Leu Gly Leu Pro Ala Pro Gly
            180                 185                 190

Ala Arg Arg Arg Gly Gly Ser Ala Ser Arg Ser Leu Pro Leu Pro Lys
        195                 200                 205

Arg Pro Arg Arg Gly Ala Ala Pro Glu Pro Glu Arg Thr Pro Val Gly
    210                 215                 220

Gln Gly Ser Trp Ala His Pro Gly Arg Thr Arg Gly Pro Ser Asp Arg
225                 230                 235                 240

Gly Phe Cys Val Val Ser Pro Ala Arg Pro Ala Glu Glu Ala Thr Ser
                245                 250                 255

Leu Glu Gly Ala Leu Ser Gly Thr Arg His Ser His Pro Ser Val Gly
            260                 265                 270

Arg Gln His His Ala Gly Pro Pro Ser Thr Ser Arg Pro Pro Arg Pro
        275                 280                 285

Trp Asp Thr Pro Cys Pro Pro Val Tyr Ala Glu Thr Lys His Phe Leu
    290                 295                 300

Tyr Ser Ser Gly Asp Lys Glu Gln Leu Arg Pro Ser Phe Leu Leu Ser
305                 310                 315                 320

Ser Leu Arg Pro Ser Leu Thr Gly Ala Arg Arg Leu Val Glu Thr Ile
                325                 330                 335

Phe Leu Gly Ser Arg Pro Trp Met Pro Gly Thr Pro Arg Arg Leu Pro
            340                 345                 350

Arg Leu Pro Gln Arg Tyr Trp Gln Met Arg Pro Leu Phe Leu Glu Leu
        355                 360                 365
```

-continued

Leu Gly Asn His Ala Gln Cys Pro Tyr Gly Val Leu Lys Thr His
    370                 375                 380

Cys Pro Leu Arg Ala Ala Val Thr Pro Ala Ala Gly Val Cys Ala Arg
385                 390                 395                 400

Glu Lys Pro Gln Gly Ser Val Ala Ala Pro Glu Glu Asp Thr Asp
                405                 410                 415

Pro Arg Arg Leu Val Gln Leu Leu Arg Gln His Ser Ser Pro Trp Gln
            420                 425                 430

Val Tyr Gly Phe Val Arg Ala Cys Leu Arg Arg Leu Val Pro Pro Gly
        435                 440                 445

Leu Trp Gly Ser Arg His Asn Glu Arg Arg Phe Leu Arg Asn Thr Lys
    450                 455                 460

Lys Phe Ile Ser Leu Gly Lys His Ala Lys Leu Ser Leu Gln Glu Leu
465                 470                 475                 480

Thr Trp Lys Met Ser Val Arg Asp Cys Ala Trp Leu Arg Arg Ser Pro
                485                 490                 495

Gly Val Gly Cys Val Pro Ala Ala Glu His Arg Leu Arg Glu Glu Ile
            500                 505                 510

Leu Ala Lys Phe Leu His Trp Leu Met Ser Val Tyr Val Glu Leu
    515                 520                 525

Leu Arg Ser Phe Phe Tyr Val Thr Glu Thr Thr Phe Gln Lys Asn Arg
530                 535                 540

Leu Phe Phe Tyr Arg Lys Ser Val Trp Ser Lys Leu Gln Ser Ile Gly
545                 550                 555                 560

Ile Arg Gln His Leu Lys Arg Val Gln Leu Arg Glu Leu Ser Glu Ala
                565                 570                 575

Glu Val Arg Gln His Arg Glu Ala Arg Pro Ala Leu Leu Thr Ser Arg
            580                 585                 590

Leu Arg Phe Ile Pro Lys Pro Asp Gly Leu Arg Pro Ile Val Asn Met
        595                 600                 605

Asp Tyr Val Val Gly Ala Arg Thr Phe Arg Arg Glu Lys Arg Ala Glu
    610                 615                 620

Arg Leu Thr Ser Arg Val Lys Ala Leu Phe Ser Val Leu Asn Tyr Glu
625                 630                 635                 640

Arg Ala Arg Arg Pro Gly Leu Leu Gly Ala Ser Val Leu Gly Leu Asp
                645                 650                 655

Asp Ile His Arg Ala Trp Arg Thr Phe Val Leu Arg Val Arg Ala Gln
            660                 665                 670

Asp Pro Pro Pro Glu Leu Tyr Phe Val Lys Val Asp Val Thr Gly Ala
        675                 680                 685

Tyr Asp Thr Ile Pro Gln Asp Arg Leu Thr Glu Val Ile Ala Ser Ile
    690                 695                 700

Ile Lys Pro Gln Asn Thr Tyr Cys Val Arg Arg Tyr Ala Val Val Gln
705                 710                 715                 720

Lys Ala Ala His Gly His Val Arg Lys Ala Phe Lys Ser His Val Ser
                725                 730                 735

Thr Leu Thr Asp Leu Gln Pro Tyr Met Arg Gln Phe Val Ala His Leu
            740                 745                 750

Gln Glu Thr Ser Pro Leu Arg Asp Ala Val Val Ile Glu Gln Ser Ser
        755                 760                 765

Ser Leu Asn Glu Ala Ser Ser Gly Leu Phe Asp Val Phe Leu Arg Phe
    770                 775                 780

-continued

Met Cys His His Ala Val Arg Ile Arg Gly Lys Ser Tyr Val Gln Cys
785                 790                 795                 800

Gln Gly Ile Pro Gln Gly Ser Ile Leu Ser Thr Leu Cys Ser Leu
            805                 810                 815

Cys Tyr Gly Asp Met Glu Asn Lys Leu Phe Ala Gly Ile Arg Arg Asp
            820                 825                 830

Gly Leu Leu Leu Arg Leu Val Asp Asp Phe Leu Leu Val Thr Pro His
            835                 840                 845

Leu Thr His Ala Lys Thr Phe Leu Arg Thr Leu Val Arg Gly Val Pro
    850                 855                 860

Glu Tyr Gly Cys Val Val Asn Leu Arg Lys Thr Val Val Asn Phe Pro
865                 870                 875                 880

Val Glu Asp Glu Ala Leu Gly Gly Thr Ala Phe Val Gln Met Pro Ala
            885                 890                 895

His Gly Leu Phe Pro Trp Cys Gly Leu Leu Leu Asp Thr Arg Thr Leu
            900                 905                 910

Glu Val Gln Ser Asp Tyr Ser Ser Tyr Ala Arg Thr Ser Ile Arg Ala
            915                 920                 925

Ser Leu Thr Phe Asn Arg Gly Phe Lys Ala Gly Arg Asn Met Arg Arg
    930                 935                 940

Lys Leu Phe Gly Val Leu Arg Leu Lys Cys His Ser Leu Phe Leu Asp
945                 950                 955                 960

Leu Gln Val Asn Ser Leu Gln Thr Val Cys Thr Asn Ile Tyr Lys Ile
            965                 970                 975

Leu Leu Leu Gln Ala Tyr Arg Phe His Ala Cys Val Leu Gln Leu Pro
            980                 985                 990

Phe His Gln Gln Val Trp Lys Asn Pro Thr Phe Phe Leu Arg Val Ile
            995                 1000                1005

Ser Asp Thr Ala Ser Leu Cys Tyr Ser Ile Leu Lys Ala Lys Asn Ala
    1010                1015                1020

Gly Met Ser Leu Gly Ala Lys Gly Ala Ala Gly Pro Leu Pro Ser Glu
1025                1030                1035                1040

Ala Val Gln Trp Leu Cys His Gln Ala Phe Leu Leu Lys Leu Thr Arg
            1045                1050                1055

His Arg Val Thr Tyr Val Pro Leu Leu Gly Ser Leu Arg Thr Ala Gln
            1060                1065                1070

Thr Gln Leu Ser Arg Lys Leu Pro Gly Thr Thr Leu Thr Ala Leu Glu
    1075                1080                1085

Ala Ala Ala Asn Pro Ala Leu Pro Ser Asp Phe Lys Thr Ile Leu Asp
    1090                1095                1100

<210> SEQ ID NO 5
<211> LENGTH: 884
<212> TYPE: PRT
<213> ORGANISM: Homo sapiens

<400> SEQUENCE: 5

Met Lys Ile Leu Phe Glu Phe Ile Gln Asp Lys Leu Asp Ile Asp Leu
1               5                   10                  15

Gln Thr Asn Ser Thr Tyr Lys Glu Asn Leu Lys Cys Gly His Phe Asn
            20                  25                  30

Gly Leu Asp Glu Ile Leu Thr Thr Cys Phe Ala Leu Pro Asn Ser Arg
        35                  40                  45

Lys Ile Ala Leu Pro Cys Leu Pro Gly Asp Leu Ser His Lys Ala Val
    50                  55                  60

```
Ile Asp His Cys Ile Ile Tyr Leu Leu Thr Gly Glu Leu Tyr Asn Asn
 65                  70                  75                  80

Val Leu Thr Phe Gly Tyr Lys Ile Ala Arg Asn Glu Asp Val Asn Asn
             85                  90                  95

Ser Leu Phe Cys His Ser Ala Asn Val Asn Val Thr Leu Leu Lys Gly
            100                 105                 110

Ala Ala Trp Lys Met Phe His Ser Leu Val Gly Thr Tyr Ala Phe Val
            115                 120                 125

Asp Leu Leu Ile Asn Tyr Thr Val Ile Gln Phe Asn Gly Gln Phe Phe
130                 135                 140

Thr Gln Ile Val Gly Asn Arg Cys Asn Glu Pro His Leu Pro Pro Lys
145                 150                 155                 160

Trp Val Gln Arg Ser Ser Ser Ser Ala Thr Ala Ala Gln Ile Lys
                165                 170                 175

Gln Leu Thr Glu Pro Val Thr Asn Lys Gln Phe Leu His Lys Leu Asn
            180                 185                 190

Ile Asn Ser Ser Ser Phe Phe Pro Tyr Ser Lys Ile Leu Pro Ser Ser
            195                 200                 205

Ser Ser Ile Lys Lys Leu Thr Asp Leu Arg Glu Ala Ile Phe Pro Thr
210                 215                 220

Asn Leu Val Lys Ile Pro Gln Arg Leu Lys Val Arg Ile Asn Leu Thr
225                 230                 235                 240

Leu Gln Lys Leu Leu Lys Arg His Lys Arg Leu Asn Tyr Val Ser Ile
                245                 250                 255

Leu Asn Ser Ile Cys Pro Pro Leu Glu Gly Thr Val Leu Asp Leu Ser
            260                 265                 270

His Leu Ser Arg Gln Ser Pro Lys Glu Arg Val Leu Lys Phe Ile Ile
            275                 280                 285

Val Ile Leu Gln Lys Leu Leu Pro Gln Glu Met Phe Gly Ser Lys Lys
290                 295                 300

Asn Lys Gly Lys Ile Ile Lys Asn Leu Asn Leu Leu Leu Ser Leu Pro
305                 310                 315                 320

Leu Asn Gly Tyr Leu Pro Phe Asp Ser Leu Leu Lys Lys Leu Arg Leu
                325                 330                 335

Lys Asp Phe Arg Trp Leu Phe Ile Ser Asp Ile Trp Phe Thr Lys His
            340                 345                 350

Asn Phe Glu Asn Leu Asn Gln Leu Ala Ile Cys Phe Ile Ser Trp Leu
            355                 360                 365

Phe Arg Gln Leu Ile Pro Lys Ile Ile Gln Thr Phe Phe Tyr Cys Thr
370                 375                 380

Glu Ile Ser Ser Thr Val Thr Ile Val Tyr Phe Arg His Asp Thr Trp
385                 390                 395                 400

Asn Lys Leu Ile Thr Pro Phe Ile Val Glu Tyr Phe Lys Thr Tyr Leu
                405                 410                 415

Val Glu Asn Asn Val Cys Arg Asn His Asn Ser Tyr Thr Leu Ser Asn
            420                 425                 430

Phe Asn His Ser Lys Met Arg Ile Ile Pro Lys Lys Ser Asn Asn Glu
            435                 440                 445

Phe Arg Ile Ile Ala Ile Pro Cys Arg Gly Ala Asp Glu Glu Glu Phe
450                 455                 460

Thr Ile Tyr Lys Glu Asn His Lys Asn Ala Ile Gln Pro Thr Gln Lys
465                 470                 475                 480
```

```
Ile Leu Glu Tyr Leu Arg Asn Lys Arg Pro Thr Ser Phe Thr Lys Ile
                485                 490                 495

Tyr Ser Pro Thr Gln Ile Ala Asp Arg Ile Lys Glu Phe Lys Gln Arg
            500                 505                 510

Leu Leu Lys Lys Phe Asn Asn Val Leu Pro Glu Leu Tyr Phe Met Lys
        515                 520                 525

Phe Asp Val Lys Ser Cys Tyr Asp Ser Ile Pro Arg Met Glu Cys Met
    530                 535                 540

Arg Ile Leu Lys Asp Ala Leu Lys Asn Glu Asn Gly Phe Phe Val Arg
545                 550                 555                 560

Ser Gln Tyr Phe Phe Asn Thr Asn Thr Gly Val Leu Lys Leu Phe Asn
                565                 570                 575

Val Val Asn Ala Ser Arg Val Pro Lys Pro Tyr Glu Leu Tyr Ile Asp
            580                 585                 590

Asn Val Arg Thr Val His Leu Ser Asn Gln Asp Val Ile Asn Val Val
        595                 600                 605

Glu Met Glu Ile Phe Lys Thr Ala Leu Trp Val Glu Asp Lys Cys Tyr
    610                 615                 620

Ile Arg Glu Asp Gly Leu Phe Gln Gly Ser Ser Leu Ser Ala Pro Ile
625                 630                 635                 640

Val Asp Leu Val Tyr Asp Asp Leu Leu Glu Phe Tyr Ser Glu Phe Lys
                645                 650                 655

Ala Ser Pro Ser Gln Asp Thr Leu Ile Leu Lys Leu Ala Asp Asp Phe
            660                 665                 670

Leu Ile Ile Ser Thr Asp Gln Gln Val Ile Asn Ile Lys Lys Leu
        675                 680                 685

Ala Met Gly Gly Phe Gln Lys Tyr Asn Ala Lys Ala Asn Arg Asp Lys
    690                 695                 700

Ile Leu Ala Val Ser Ser Gln Ser Asp Asp Thr Val Ile Gln Phe
705                 710                 715                 720

Cys Ala Met His Ile Phe Val Lys Glu Leu Glu Val Trp Lys His Ser
                725                 730                 735

Ser Thr Met Asn Asn Phe His Ile Arg Ser Lys Ser Ser Lys Gly Ile
            740                 745                 750

Phe Arg Ser Leu Ile Ala Leu Phe Asn Thr Arg Ile Ser Tyr Lys Thr
        755                 760                 765

Ile Asp Thr Asn Leu Asn Ser Thr Asn Thr Val Leu Met Gln Ile Asp
    770                 775                 780

His Val Val Lys Asn Ile Ser Glu Cys Tyr Lys Ser Ala Phe Lys Asp
785                 790                 795                 800

Leu Ser Ile Asn Val Thr Gln Asn Met Gln Phe His Ser Phe Leu Gln
                805                 810                 815

Arg Ile Ile Glu Met Thr Val Ser Gly Cys Pro Ile Thr Lys Cys Asp
            820                 825                 830

Pro Leu Ile Glu Tyr Glu Val Arg Phe Thr Ile Leu Asn Gly Phe Leu
        835                 840                 845

Glu Ser Leu Ser Ser Asn Thr Ser Lys Phe Lys Asp Asn Ile Ile Leu
    850                 855                 860

Leu Arg Lys Glu Ile Gln His Leu Gln Ala Tyr Ile Tyr Ile Tyr Ile
865                 870                 875                 880

His Ile Val Asn

<210> SEQ ID NO 6
```

```
<211> LENGTH: 13
<212> TYPE: DNA
<213> ORGANISM: Homo sapiens
<220> FEATURE:
<221> NAME/KEY: intron
<222> LOCATION: (8)..(13)
<223> OTHER INFORMATION: First six bases of Y intron

<400> SEQUENCE: 6
ccaggtgggc ctc                                                          13

<210> SEQ ID NO 7
<211> LENGTH: 14
<212> TYPE: DNA
<213> ORGANISM: Homo sapiens
<220> FEATURE:
<221> NAME/KEY: intron
<222> LOCATION: (1)..(7)
<223> OTHER INFORMATION: Last seven bases of intron Y

<400> SEQUENCE: 7
gcaggtgtcc tgcc                                                         14

<210> SEQ ID NO 8
<211> LENGTH: 14
<212> TYPE: DNA
<213> ORGANISM: Homo sapiens
<220> FEATURE:
<221> NAME/KEY: intron
<222> LOCATION: (8)..(14)
<223> OTHER INFORMATION: First 7 bases of Intron 1

<400> SEQUENCE: 8
aaagagggtg gctg                                                         14

<210> SEQ ID NO 9
<211> LENGTH: 14
<212> TYPE: DNA
<213> ORGANISM: Homo sapiens
<220> FEATURE:
<221> NAME/KEY: intron
<222> LOCATION: (1)..(7)
<223> OTHER INFORMATION: Last 7 bases of Intron 1

<400> SEQUENCE: 9
aacagaagcc gagc                                                         14

<210> SEQ ID NO 10
<211> LENGTH: 14
<212> TYPE: DNA
<213> ORGANISM: Homo sapiens
<220> FEATURE:
<221> NAME/KEY: intron
<222> LOCATION: (8)..(14)
<223> OTHER INFORMATION: First 7 bases of Intron Alpha

<400> SEQUENCE: 10
tgtcaaggtg gatg                                                         14

<210> SEQ ID NO 11
<211> LENGTH: 14
<212> TYPE: DNA
<213> ORGANISM: Homo sapiens
<220> FEATURE:
<221> NAME/KEY: intron
<222> LOCATION: (1)..(7)
<223> OTHER INFORMATION: Last 7 bases of Intron Alpha

<400> SEQUENCE: 11
```

-continued cccccaggac aggc                                                      14

<210> SEQ ID NO 12
<211> LENGTH: 14
<212> TYPE: DNA
<213> ORGANISM: Homo sapiens
<220> FEATURE:
<221> NAME/KEY: intron
<222> LOCATION: (8)..(14)
<223> OTHER INFORMATION: First 7 bases of Intron Beta

<400> SEQUENCE: 12
gagccacgtc tcta                                                      14

<210> SEQ ID NO 13
<211> LENGTH: 14
<212> TYPE: DNA
<213> ORGANISM: Homo sapiens
<220> FEATURE:
<221> NAME/KEY: intron
<222> LOCATION: (1)..(7)
<223> OTHER INFORMATION: Last 7 bases of Intron Beta

<400> SEQUENCE: 13
ggggcaagtc ctac                                                      14

<210> SEQ ID NO 14
<211> LENGTH: 14
<212> TYPE: DNA
<213> ORGANISM: Homo sapiens
<220> FEATURE:
<221> NAME/KEY: intron
<222> LOCATION: (8)..(14)
<223> OTHER INFORMATION: First 7 base of Intron 2

<400> SEQUENCE: 14
actccaggtg agcg                                                      14

<210> SEQ ID NO 15
<211> LENGTH: 14
<212> TYPE: DNA
<213> ORGANISM: Homo sapiens
<220> FEATURE:
<221> NAME/KEY: modified_base
<222> LOCATION: (1)..(7)
<223> OTHER INFORMATION: Wherein N is any nucleotide
<220> FEATURE:
<221> NAME/KEY: intron
<222> LOCATION: (1)..(7)
<223> OTHER INFORMATION: Last 7 bases of Intron 2

<400> SEQUENCE: 15
nnnnnnncta tgcc                                                      14

<210> SEQ ID NO 16
<211> LENGTH: 173
<212> TYPE: DNA
<213> ORGANISM: Homo sapiens
<220> FEATURE:
<221> NAME/KEY: intron
<222> LOCATION: (8)..(166)
<223> OTHER INFORMATION: Full Sequence of Intron 3

<400> SEQUENCE: 16
aacgcagccg aagaaaacat ttctgtcgtg actcctgcgg tgcttgggtc gggacagcca      60
gagatggagc caccccgcag accgtcgggt gtgggcagct ttccggtgtc tcctgggagg     120

-continued

```
ggagttgggc tgggcctgtg actcctcagc ctctgttttc ccccagggat gtc        173
```

```
<210> SEQ ID NO 17
<211> LENGTH: 46
<212> TYPE: PRT
<213> ORGANISM: Homo sapiens

<400> SEQUENCE: 17
```

```
Thr Ala Ala Glu Glu Asn Ile Leu Val Val Thr Pro Ala Val Leu Gly
  1               5                  10                  15

Ser Gly Gln Pro Glu Met Glu Pro Pro Arg Arg Pro Ser Gly Val Gly
             20                  25                  30

Ser Phe Pro Val Ser Pro Gly Arg Gly Val Gly Leu Gly Leu
         35                  40                  45
```

```
<210> SEQ ID NO 18
<211> LENGTH: 104
<212> TYPE: DNA
<213> ORGANISM: Homo sapiens
<220> FEATURE:
<223> OTHER INFORMATION: Intron Y

<400> SEQUENCE: 18
```

```
ggcctccccg gggtcggcgt ccggctgggg ttgagggcgg ccggggggaa ccagcgacat    60
gcggagagca gcgcaggcga ctcagggcgc ttcccccgca ggtg                   104
```

```
<210> SEQ ID NO 19
<211> LENGTH: 34
<212> TYPE: PRT
<213> ORGANISM: Homo sapiens
<220> FEATURE:
<223> OTHER INFORMATION: Reding Frame One of Intron Y

<400> SEQUENCE: 19
```

```
Gly Leu Pro Gly Val Gly Val Arg Leu Gly Leu Arg Ala Ala Gly Gly
  1               5                  10                  15

Asn Gln Arg His Ala Glu Ser Ser Ala Gly Asp Ser Gly Arg Phe Pro
             20                  25                  30

Arg Arg
```

```
<210> SEQ ID NO 20
<211> LENGTH: 10
<212> TYPE: PRT
<213> ORGANISM: Homo sapiens
<220> FEATURE:
<223> OTHER INFORMATION: Reading Frame Two of Intron Y before
      termination Codon

<400> SEQUENCE: 20
```

```
Ala Ser Pro Gly Ser Ala Ser Gly Trp Gly
  1               5                  10
```

```
<210> SEQ ID NO 21
<211> LENGTH: 23
<212> TYPE: PRT
<213> ORGANISM: Homo sapiens
<220> FEATURE:
<223> OTHER INFORMATION: Reading Frame Two of Intron Y after
      termination Codon

<400> SEQUENCE: 21
```

```
Gly Arg Pro Gly Gly Thr Ser Asp Met Arg Arg Ala Ala Gln Ala Thr
  1               5                  10                  15
```

-continued

```
Gln Gly Ala Ser Pro Ala Gly
            20

<210> SEQ ID NO 22
<211> LENGTH: 34
<212> TYPE: PRT
<213> ORGANISM: Homo sapiens
<220> FEATURE:
<223> OTHER INFORMATION: Reading Frame Three of Intron Y

<400> SEQUENCE: 22

Pro Pro Arg Gly Arg Arg Pro Ala Gly Val Glu Gly Gly Arg Gly Glu
  1               5                  10                  15

Pro Ala Thr Cys Gly Glu Gln Arg Arg Arg Leu Arg Ala Leu Pro Pro
            20                  25                  30

Gln Val

<210> SEQ ID NO 23
<211> LENGTH: 38
<212> TYPE: DNA
<213> ORGANISM: Homo sapiens
<220> FEATURE:
<223> OTHER INFORMATION: Intron 1

<400> SEQUENCE: 23
gtggctgtgc tttggtttaa cttccttttt aaccagaa                          38

<210> SEQ ID NO 24
<211> LENGTH: 13
<212> TYPE: PRT
<213> ORGANISM: Homo sapiens
<220> FEATURE:
<223> OTHER INFORMATION: Intron 1 Translation

<400> SEQUENCE: 24

Val Ala Val Leu Trp Phe Asn Phe Leu Phe Asn Gln Lys
  1               5                  10

<210> SEQ ID NO 25
<211> LENGTH: 36
<212> TYPE: DNA
<213> ORGANISM: Homo sapiens
<220> FEATURE:
<223> OTHER INFORMATION: Intron Alpha

<400> SEQUENCE: 25
gtggatgtga cgggcgcgta cgacaccatc ccccag                            36

<210> SEQ ID NO 26
<211> LENGTH: 12
<212> TYPE: PRT
<213> ORGANISM: Homo sapiens
<220> FEATURE:
<223> OTHER INFORMATION: Intron Alpha Translation

<400> SEQUENCE: 26

Val Asp Val Thr Gly Ala Tyr Asp Thr Ile Pro Gln
  1               5                  10

<210> SEQ ID NO 27
<211> LENGTH: 182
<212> TYPE: DNA
<213> ORGANISM: Homo sapiens
<220> FEATURE:
<223> OTHER INFORMATION: Intron Beta
```

```
<400> SEQUENCE: 27
gtctctacct tgacagacct ccagccgtac atgcgacagt tcgtggctca cctgcaggag      60
accagcccgc tgagggatgc cgtcgtcatc gagcagagct cctccctgaa tgaggccagc     120
agtggcctct cgacgtcttc ctacgcttc atgtgccacc acgccgtgcg catcagggc      180 aa                                                                    182

<210> SEQ ID NO 28
<211> LENGTH: 61
<212> TYPE: PRT
<213> ORGANISM: Homo sapiens
<220> FEATURE:
<223> OTHER INFORMATION: Intron Beta Translation

<400> SEQUENCE: 28

Val Ser Thr Leu Thr Asp Leu Gln Pro Tyr Met Arg Gln Phe Val Ala
 1               5                  10                  15

His Leu Gln Glu Thr Ser Pro Leu Arg Asp Ala Val Val Ile Glu Gln
            20                  25                  30

Ser Ser Ser Leu Asn Glu Ala Ser Ser Gly Leu Phe Asp Val Phe Leu
        35                  40                  45

Arg Phe Met Cys His His Ala Val Arg Ile Arg Gly Lys
    50                  55                  60

<210> SEQ ID NO 29
<211> LENGTH: 226
<212> TYPE: DNA
<213> ORGANISM: Homo sapiens
<220> FEATURE:
<223> OTHER INFORMATION: Intron 2

<400> SEQUENCE: 29
gtgagcgcac ctggccggaa gtggagcctg tgcccggctg gggcaggtgc tgctgcaggg      60
ccgttgcgtc cacctctgct tccgtgtggg gcaggcgact gccaatccca aagggtcaga    120
tgccacaggg tgcccctcgt cccatctggg gctgagcaca aatgcatctt tctgtgggag    180
tgagggtgcc tcacaacggg agcagttttc tgtgctattt tggtaa                   226

<210> SEQ ID NO 30
<211> LENGTH: 159
<212> TYPE: DNA
<213> ORGANISM: Homo sapiens
<220> FEATURE:
<223> OTHER INFORMATION: Intron 3

<400> SEQUENCE: 30
ccgaagaaaa catttctgtc gtgactcctg cggtgcttgg gtcgggacag ccagagatgg      60
agccaccccg cagaccgtcg ggtgtgggca gctttccggt gtctcctggg aggggagttg     120
ggctgggcct gtgactcctc agcctctgtt ttcccccag                            159

<210> SEQ ID NO 31
<211> LENGTH: 44
<212> TYPE: PRT
<213> ORGANISM: Homo sapiens
<220> FEATURE:
<223> OTHER INFORMATION: Intron 3 Translation

<400> SEQUENCE: 31

Ala Glu Glu Asn Ile Ser Val Val Thr Pro Ala Val Leu Gly Ser Gly
 1               5                  10                  15
```

```
Gln Pro Glu Met Glu Pro Pro Arg Arg Pro Ser Gly Val Gly Ser Phe
        20                  25                  30

Pro Val Ser Pro Gly Arg Gly Val Gly Leu Gly Leu
        35                  40
```

<210> SEQ ID NO 32
<211> LENGTH: 262
<212> TYPE: DNA
<213> ORGANISM: Homo sapiens
<220> FEATURE:
<223> OTHER INFORMATION: Intron X.  Complete length unknown

<400> SEQUENCE: 32

| | | |
|---|---|---|
| gacagtcacc aggggggttg accgccggac tgggcgtccc cagggttgac tataggacca | 60 |
| ggtgtccagg tgccctgcaa gtagaggggc tctcagaggc gtctggctgg catgggtgga | 120 |
| cgtggccccg ggcatggcct tctgcgtgtg ctgccgtggg tgccctgagc cctcactgag | 180 |
| tcggtggggg cttgtggctt cccgtgagct tcccccctagt ctgttgtctg gctgagcaag | 240 |
| cctcctgagg ggctctctat tg | 262 |

<210> SEQ ID NO 33
<211> LENGTH: 218
<212> TYPE: DNA
<213> ORGANISM: Homo sapiens
<220> FEATURE:
<223> OTHER INFORMATION: Partial Sequence of Genomic Intron
      (approximately 2.7 kb)

<400> SEQUENCE: 33

| | |
|---|---|
| gtggctgtgc tttggtttaa cttccttttt aaccagaagt gcgtttgagc cccacatttg | 60 |
| gtatcagctt agatgaaggg cccggaggag gggccacggg acacagccag ggccatggca | 120 |
| cggcgcccac ccatttgtgc gcacagtgag gtggccgagg tgccggtgcc tccagaaaag | 180 |
| cagcgtgggg gtgtaggggg agctcctggg gcagggac | 218 |

<210> SEQ ID NO 34
<211> LENGTH: 2031
<212> TYPE: DNA
<213> ORGANISM: Homo sapiens
<220> FEATURE:
<221> NAME/KEY: modified_base
<222> LOCATION: (1767)..(1769)
<223> OTHER INFORMATION: Wherein N is A, C, G or T
<220> FEATURE:
<223> OTHER INFORMATION: Truncated Telomerase

<400> SEQUENCE: 34

| | |
|---|---|
| atgccgcgcg ctccccgctg ccgagccgtg cgctccctgc tgcgcagcca ctaccgcgag | 60 |
| gtgctgccgc tggccacgtt cgtgcggcgc ctggggcccc agggctggcg gctggtgcag | 120 |
| cgcggggacc cggcggcttt ccgcgcgctg gtggcccagt gcctggtgtg cgtgccctgg | 180 |
| gacgcacggc cgcccccgc cgcccctcc ttccgccagg tgtcctgcct gaaggagctg | 240 |
| gtggcccgag tgctgcagag gctgtgcgag cgcggcgcga gaacgtgct ggccttcggc | 300 |
| ttcgcgctgc tggacggggc ccgcggggc ccccccgagg ccttcaccac cagcgtgcgc | 360 |
| agctacctgc caacacggt gaccgacgca ctgcggggga gcggggcgtg ggggctgctg | 420 |
| ctgcgccgcg tgggcgacga cgtgctggtt cacctgctgg cacgctgcgc gctctttgtg | 480 |
| ctggtggctc ccagctgcgc ctaccaggtg tgcgggccgc cgctgtacca gctcggcgct | 540 |
| gccactcagg cccggccccc gccacacgct agtggacccg aaggcgtct gggatgcgaa | 600 |

-continued

```
cgggcctgga accatagcgt cagggaggcc ggggtccccc tgggcctgcc agccccgggt    660
gcgaggaggc gcgggggcag tgccagccga agtctgccgt tgcccaagag gcccaggcgt    720
ggcgctgccc ctgagccgga gcggacgccc gttgggcagg ggtcctgggc ccacccgggc    780
aggacgcgtg gaccgagtga ccgtggtttc tgtgtggtgt cacctgccag acccgccgaa    840
gaagccacct ctttggaggg tgcgctctct ggcacgcgcc actcccaccc atccgtgggc    900
cgccagcacc acgcgggccc cccatccaca tcgcggccac cacgtccctg ggacacgcct    960
tgtcccccgg tgtacgccga gaccaagcac ttcctctact cctcaggcga caaggagcag   1020
ctgcggcccct ccttcctact cagctctctg aggcccagcc tgactggcgc tcggaggctc   1080
gtggagacca tctttctggg ttccaggccc tggatgccag ggactccccg caggttgccc   1140
cgcctgcccc agcgctactg gcaaatgcgg cccctgtttc tggagctgct tgggaaccac   1200
gcgcagtgcc cctacggggt gctcctcaag acgcactgcc cgctgcgagc tgcggtcacc   1260
ccagcagccg gtgtctgtgc ccgggagaag ccccagggct ctgtggcggc ccccgaggag   1320
gaggacacag accccgtcg cctggtgcag ctgctccgcc agcacagcag cccctggcag   1380
gtgtacggct tcgtgcgggc ctgcctgcgc ggctggtgc ccccaggcct ctggggctcc   1440
aggcacaacg aacgccgctt cctcaggaac accaagaagt tcatctccct ggggaagcat   1500
gccaagctct cgctgcagga gctgacgtgg aagatgagcg tgcgggactg cgcttggctg   1560
cgcaggagcc caggggttgg ctgtgttccg gccgcagagc accgtctgcg tgaggagatc   1620
ctggccaagt tcctgcactg gctgatgagt gtgtacgtcg tcgagctgct caggtctttc   1680
ttttatgtca cggagaccac gtttcaaaag aacaggctct ttttctaccg gaagagtgtc   1740
tggagcaagt tgcaaagcat tggaatnnng acagtcacca gggggggttga ccgccggact   1800
gggcgtcccc agggttgact ataggaccag gtgtccaggt gccctgcaag tagaggggct   1860
ctcagaggcg tctggctggc atgggtggac gtggccccgg gcatggcctt ctgcgtgtgc   1920
tgccgtgggt gccctgagcc ctcactgagt cggtgggggc ttgtggcttc ccgtgagctt   1980
cccctagtc tgttgtctgg ctgagcaagc ctcctgaggg gctctctatt g             2031
```

<210> SEQ ID NO 35
<211> LENGTH: 588
<212> TYPE: PRT
<213> ORGANISM: Homo sapiens
<220> FEATURE:
<223> OTHER INFORMATION: Protein Predicted by SEQ ID NO:34

<400> SEQUENCE: 35

```
Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110
```

```
Glu Ala Phe Thr Thr Ser Val Arg Ser Tyr Leu Pro Asn Thr Val Thr
            115                 120                 125
Asp Ala Leu Arg Gly Ser Gly Ala Trp Gly Leu Leu Leu Arg Arg Val
130                 135                 140
Gly Asp Asp Val Leu Val His Leu Leu Ala Arg Cys Ala Leu Phe Val
145                 150                 155                 160
Leu Val Ala Pro Ser Cys Ala Tyr Gln Val Cys Gly Pro Pro Leu Tyr
                165                 170                 175
Gln Leu Gly Ala Ala Thr Gln Ala Arg Pro Pro His Ala Ser Gly
            180                 185                 190
Pro Arg Arg Leu Gly Cys Glu Arg Ala Trp Asn His Ser Val Arg
        195                 200                 205
Glu Ala Gly Val Pro Leu Gly Leu Pro Ala Pro Gly Ala Arg Arg
    210                 215                 220
Gly Gly Ser Ala Ser Arg Ser Leu Pro Leu Pro Lys Arg Pro Arg Arg
225                 230                 235                 240
Gly Ala Ala Pro Glu Pro Glu Arg Thr Pro Val Gly Gln Gly Ser Trp
                245                 250                 255
Ala His Pro Gly Arg Thr Arg Gly Pro Ser Asp Arg Gly Phe Cys Val
                260                 265                 270
Val Ser Pro Ala Arg Pro Ala Glu Glu Ala Thr Ser Leu Glu Gly Ala
            275                 280                 285
Leu Ser Gly Thr Arg His Ser His Pro Ser Val Gly Arg Gln His His
        290                 295                 300
Ala Gly Pro Pro Ser Thr Ser Arg Pro Arg Pro Trp Asp Thr Pro
305                 310                 315                 320
Cys Pro Pro Val Tyr Ala Glu Thr Lys His Phe Leu Tyr Ser Ser Gly
                325                 330                 335
Asp Lys Glu Gln Leu Arg Pro Ser Phe Leu Ser Ser Leu Arg Pro
            340                 345                 350
Ser Leu Thr Gly Ala Arg Arg Leu Val Glu Thr Ile Phe Leu Gly Ser
            355                 360                 365
Arg Pro Trp Met Pro Gly Thr Pro Arg Arg Leu Pro Arg Leu Pro Gln
370                 375                 380
Arg Tyr Trp Gln Met Arg Pro Leu Phe Leu Glu Leu Leu Gly Asn His
385                 390                 395                 400
Ala Gln Cys Pro Tyr Gly Val Leu Leu Lys Thr His Cys Pro Leu Arg
                405                 410                 415
Ala Ala Val Thr Pro Ala Ala Gly Val Cys Ala Arg Glu Lys Pro Gln
            420                 425                 430
Gly Ser Val Ala Ala Pro Glu Glu Asp Thr Asp Pro Arg Arg Leu
        435                 440                 445
Val Gln Leu Leu Arg Gln His Ser Ser Pro Trp Gln Val Tyr Gly Phe
        450                 455                 460
Val Arg Ala Cys Leu Arg Arg Leu Val Pro Pro Gly Leu Trp Gly Ser
465                 470                 475                 480
Arg His Asn Glu Arg Arg Phe Leu Arg Asn Thr Lys Lys Phe Ile Ser
                485                 490                 495
Leu Gly Lys His Ala Lys Leu Ser Leu Gln Glu Leu Thr Trp Lys Met
            500                 505                 510
Ser Val Arg Asp Cys Ala Trp Leu Arg Arg Ser Pro Gly Val Gly Cys
            515                 520                 525
```

| Val | Pro | Ala | Ala | Glu | His | Arg | Leu | Arg | Glu | Glu | Ile | Leu | Ala | Lys | Phe |
|---|---|---|---|---|---|---|---|---|---|---|---|---|---|---|---|
| | 530 | | | | 535 | | | | | 540 | | | | | |

| Leu | His | Trp | Leu | Met | Ser | Val | Tyr | Val | Val | Glu | Leu | Leu | Arg | Ser | Phe |
|---|---|---|---|---|---|---|---|---|---|---|---|---|---|---|---|
| 545 | | | | | 550 | | | | | 555 | | | | | 560 |

| Phe | Tyr | Val | Thr | Glu | Thr | Thr | Phe | Gln | Lys | Asn | Arg | Leu | Phe | Phe | Tyr |
|---|---|---|---|---|---|---|---|---|---|---|---|---|---|---|---|
| | | | | 565 | | | | | 570 | | | | | 575 | |

| Arg | Lys | Ser | Val | Trp | Ser | Lys | Leu | Gln | Ser | Ile | Gly |
|---|---|---|---|---|---|---|---|---|---|---|---|
| | | | 580 | | | | | 585 | | | |

<210> SEQ ID NO 36
<211> LENGTH: 2041
<212> TYPE: DNA
<213> ORGANISM: Homo sapiens
<220> FEATURE:
<223> OTHER INFORMATION: Truncated Protein 1; Intron 1 Addition

<400> SEQUENCE: 36

```
atgccgcgcg ctccccgctg ccgagccgtg cgctccctgc tgcgcagcca ctaccgcgag     60
gtgctgccgc tggccacgtt cgtgcggcgc ctggggcccc agggctggcg gctggtgcag    120
cgcggggacc cggcggcttt ccgcgcgctg gtggcccagt gcctggtgtg cgtgccctgg    180
gacgcacggc cgcccccgc cgcccctcc ttccgccagg tgtcctgcct gaaggagctg    240
gtggcccgag tgctgcagag gctgtgcgag cgcggcgcga agaacgtgct ggccttcggc    300
ttcgcgctgc tggacggggc ccgcggggc cccccgagg ccttcaccac cagcgtgcgc    360
agctacctgc ccaacacggt gaccgacgca ctgcggggga gcgggcgtg ggggctgctg    420
ctgcgccgcg tgggcgacga cgtgctggtt cacctgctgg cacgctgcgc gctcttttgtg    480
ctggtggctc ccagctgcgc ctaccaggtg tgcgggccgc cgctgtacca gctcggcgct    540
gccactcagg cccggccccc gccacacgct agtggacccc gaaggcgtct gggatgcgaa    600
cgggcctgga accatagcgt cagggaggcc ggggtccccc tgggcctgcc agccccgggt    660
gcgaggaggc gcgggggcag tgccagccga agtctgccgt tgcccaagag gcccaggcgt    720
ggcgctgccc ctgagccgga gcggacgccc gttgggcagg gtcctgggcc caccccgggc    780
aggacgcgtg gaccgagtga ccgtggtttc tgtgtggtgt cacctgccag acccgccgaa    840
gaagccacct ctttggaggg tgcgctctct ggcacgcgcc actccacccc atccgtgggc    900
cgccagcacc acgcgggccc cccatccaca tcgcggccac cacgtccctg gacacgcct    960
tgtcccccgg tgtacgccga gaccaagcac ttcctctact cctcaggcga caaggagcag   1020
ctgcggcccc ccttcctact cagctctctg aggcccagcc tgactggcgc tcggaggctc   1080
gtggagacca tctttctggg ttccaggcc tggatgccag ggactccccg caggttgccc   1140
cgcctgcccc agcgctactg gcaaatgcgg ccccctgttc tggagctgct gggaaccac   1200
gcgcagtgcc cctacggggt gctcctcaag acgcactgcc cgctgcgagc tgcggtcacc   1260
ccagcagccg gtgtctgtgc ccgggagaag ccccagggct ctgtggcggc ccccgaggag   1320
gaggacacag acccccgtcg cctggtgcag ctgctccgcc agcacagcag cccctggcag   1380
gtgtacggct tcgtgcgggc ctgcctgcgc ggctggtgc ccccaggcct ctggggctcc   1440
aggcacaacg aacgccgctt cctcaggaac accaagaagt tcatctccct ggggaagcat   1500
gccaagctct cgctgcagga gctgacgtgg aagatgagcg tgcgggactg cgcttggctg   1560
cgcaggagcc cagggggtgg ctgtgttccg gccgcagagc accgtctgcg tgaggagatc   1620
ctggccaagt tcctgcactg gctgatgagt gtgtacgtcg tcgagctgct caggtctttc   1680
ttttatgtca cggagaccac gtttcaaaag aacaggctct ttttctaccg gaagagtgtc   1740
```

-continued

```
tggagcaagt tgcaaagcat tggaatcaga cagcacttga agagggtgca gctgcgggag    1800
ctgtcggaag cagaggtcag gcagcatcgg gaagccaggc ccgccctgct gacgtccaga    1860
ctccgcttca tccccaagcc tgacgggctg cggccgattg tgaacatgga ctacgtcgtg    1920
ggagccagaa cgttccgcag agaaaagagg gtggctgtgc tttggtttaa cttccttttt    1980
aaccagaagc cgagcgtctc acctcgaggg tgaaggcact gttcagcgtg ctcaactacg    2040
a                                                                    2041
```

<210> SEQ ID NO 37
<211> LENGTH: 670
<212> TYPE: PRT
<213> ORGANISM: Homo sapiens
<220> FEATURE:
<223> OTHER INFORMATION: Truncated Protein 1; Encoded by SEQ ID NO:36

<400> SEQUENCE: 37

```
Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
             20                  25                  30

Pro Gln Gly Trp Arg Leu Val Gln Arg Gly Asp Pro Ala Ala Phe Arg
         35                  40                  45

Ala Leu Val Ala Gln Cys Leu Val Cys Val Pro Trp Asp Ala Arg Pro
     50                  55                  60

Pro Pro Ala Ala Pro Ser Phe Arg Gln Val Ser Cys Leu Lys Glu Leu
 65                  70                  75                  80

Val Ala Arg Val Leu Gln Arg Leu Cys Glu Arg Gly Ala Lys Asn Val
                 85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300
```

```
Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
            325                 330                 335

Asp Lys Glu Gln Leu Arg Pro Ser Phe Leu Ser Ser Leu Arg Pro
        340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Ile Leu Ala Lys Phe
    530                 535                 540

Leu His Trp Leu Met Ser Val Tyr Val Glu Leu Leu Arg Ser Phe
545                 550                 555                 560

Phe Tyr Val Thr Glu Thr Thr Phe Gln Lys Asn Arg Leu Phe Phe Tyr
            565                 570                 575

Arg Lys Ser Val Trp Ser Lys Leu Gln Ser Ile Gly Ile Arg Gln His
        580                 585                 590

Leu Lys Arg Val Gln Leu Arg Glu Leu Ser Glu Ala Glu Val Arg Gln
    595                 600                 605

His Arg Glu Ala Arg Pro Ala Leu Leu Thr Ser Arg Leu Arg Phe Ile
610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Val Ala Val Leu Trp Phe
            645                 650                 655

Thr Phe Leu Phe Asn Gln Lys Pro Ser Val Ser Phe Arg Gly
            660                 665                 670

<210> SEQ ID NO 38
<211> LENGTH: 2541
<212> TYPE: DNA
<213> ORGANISM: Homo sapiens
<220> FEATURE:
<223> OTHER INFORMATION: Truncated Protein 2; Alpha Intron Addition

<400> SEQUENCE: 38
```

-continued

```
atgccgcgcg ctccccgctg ccgagccgtg cgctccctgc tgcgcagcca ctaccgcgag      60
gtgctgccgc tggccacgtt cgtgcggcgc ctggggcccc agggctggcg gctggtgcag     120
cgcggggacc cggcggcttt ccgcgcgctg gtgcccagt gcctggtgtg cgtgccctgg      180
gacgcacggc cgccccccgc cgccccctcc ttccgccagg tgtcctgcct gaaggagctg     240
gtggcccgag tgctgcagag gctgtgcgag cgcggcgcga agaacgtgct ggccttcggc     300
ttcgcgctgc tggacggggc ccgcggggggc cccccgagg ccttcaccac cagcgtgcgc     360
agctacctgc ccaacacggt gaccgacgca ctgcggggga gcgggcgtg ggggctgctg      420
ctgcgccgcg tgggcgacga cgtgctggtt cacctgctgg cacgctgcgc gctctttgtg     480
ctggtggctc ccagctgcgc ctaccaggtg tgcgggccgc cgctgtacca gctcggcgct     540
gccactcagg cccggccccc gccacacgct agtggacccc gaaggcgtct gggatgcgaa     600
cgggcctgga accatagcgt cagggaggcc ggggtccccc tgggcctgcc agccccgggt     660
gcgaggaggc gcggggcag tgccagccga agtctgccgt tgcccaagag gcccaggcgt      720
ggcgctgccc ctgagccgga gcggacgccc gttgggcagg gtcctgggc ccacccgggc      780
aggacgcgtg gaccgagtga ccgtggtttc tgtgtggtgt cacctgccag acccgccgaa     840
gaagccacct cttttggaggg tgcgctctct ggcacgcgcc actcccaccc atccgtgggc    900
cgccagcacc acgcgggccc cccatccaca tcgcggccac cacgtccctg ggacacgcct    960
tgtccccggg tgtacgccga gaccaagcac ttcctctact cctcaggcga caaggagcag    1020
ctgcggccct ccttcctact cagctctctg aggcccagcc tgactggcgc tcggaggctc    1080
gtggagacca tcttttctggg ttccaggccc tggatgccag ggactcccccg caggttgccc    1140
cgcctgcccc agcgctactg gcaaatgcgg cccctgtttc tggagctgct tgggaaccac    1200
gcgcagtgcc cctacggggt gctcctcaag acgcactgcc cgctgcgagc tgcggtcacc    1260
ccagcagccg gtgtctgtgc ccgggagaag ccccagggct ctgtggcggc ccccgaggag    1320
gaggacacag accccccgtcg cctggtgcag ctgctccgcc agcacagcag ccctggcag    1380
gtgtacggct tcgtgcgggc ctgcctgcgc ggctggtgc ccccaggcct ctgggctcc     1440
aggcacaacg aacgccgctt cctcaggaac accaagaagt tcatctccct ggggaagcat    1500
gccaagctct cgctgcagga gctgacgtgg aagatgagcg tgcgggactg cgcttggctg    1560
cgcaggagcc cagggggttgg ctgtgttccg gccgcagagc accgtctgcg tgaggagatc    1620
ctggccaagt cctgcactg gctgatgagt gtgtacgtcg tcgagctgct caggtctttc    1680
ttttatgtca cggagaccac gtttcaaaag aacaggctct ttttctaccg gaagagtgtc    1740
tggagcaagt tgcaaagcat tggaatcaga cagcacttga gagggtgca gctgcgggag    1800
ctgtcggaag cagaggtcag gcagcatcgg gaagccaggc ccgccctgct gacgtccaga    1860
ctccgcttca tccccaagcc tgacgggctg cggccgattg tgaacatgga ctacgtcgtg    1920
ggagccagaa cgttccgcag agaaaagagg gccgagcgtc tcacctcgag ggtgaaggca    1980
ctgttcagcg tgctcaacta cgagcgggcg cggcgcccg gcctcctggg cgcctctgtg    2040
ctgggcctgg acgatatcca cagggcctgg cgcaccttcg tgctgcgtgt gcgggcccag    2100
gacccgccgc ctgagctgta ctttgtcaag gtggatgtga cgggcgcgta cgacaccatc    2160
ccccaggaca ggctcacgga ggtcatcgcc agcatcatca aaccccagaa cacgtactgc    2220
gtgcgtcggt atgccgtggt ccagaaggcc gcccatgggc acgtccgcaa ggccttcaag    2280
agccacgtcc tacgtccagt gccagggga tcccgcaggg c tccatcctct ccacgctgct   2340
```

```
ctgcagcctg tgctacggcg acatggagaa caagctgttt gcggggattc ggcgggacgg    2400
gctgctcctg cgtttggtgg atgatttctt gttggtgaca cctcacctca cccacgcgaa    2460
aaccttcctc aggaccctgg tccgaggtgt ccctgagtat ggctgcgtgg tgaacttgcg    2520
gaagacagtg gtgaacttcc c                                              2541
```

<210> SEQ ID NO 39
<211> LENGTH: 807
<212> TYPE: PRT
<213> ORGANISM: Homo sapiens
<220> FEATURE:
<223> OTHER INFORMATION: Truncated Protein 2; Encoded by SEQ ID NO:38

<400> SEQUENCE: 39

```
Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
             20                  25                  30

Pro Gln Gly Trp Arg Leu Val Gln Arg Gly Asp Pro Ala Ala Phe Arg
         35                  40                  45

Ala Leu Val Ala Gln Cys Leu Val Cys Val Pro Trp Asp Ala Arg Pro
     50                  55                  60

Pro Pro Ala Ala Pro Ser Phe Arg Gln Val Ser Cys Leu Lys Glu Leu
 65                  70                  75                  80

Val Ala Arg Val Leu Gln Arg Leu Cys Glu Arg Gly Ala Lys Asn Val
                 85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
```

-continued

```
                325                 330                 335
Asp Lys Glu Gln Leu Arg Pro Ser Phe Leu Leu Ser Ser Leu Arg Pro
                340                 345                 350

Ser Leu Thr Gly Ala Arg Arg Leu Val Glu Thr Ile Phe Leu Gly Ser
                355                 360                 365

Arg Pro Trp Met Pro Gly Thr Pro Arg Arg Leu Pro Arg Leu Pro Gln
        370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
                420                 425                 430

Gly Ser Val Ala Ala Pro Glu Glu Asp Thr Asp Pro Arg Arg Leu
                435                 440                 445

Val Gln Leu Leu Arg Gln His Ser Ser Pro Trp Gln Val Tyr Gly Phe
        450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
        515                 520                 525

Val Pro Ala Ala Glu His Arg Leu Arg Glu Glu Ile Leu Ala Lys Phe
530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
                660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro
690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
                740                 745                 750
```

Gly His Val Arg Lys Ala Phe Lys Ser His Val Leu Arg Pro Val Pro
        755                 760                 765

Gly Asp Pro Ala Gly Leu His Pro Leu His Ala Ala Leu Gln Pro Val
        770                 775                 780

Leu Arg Arg His Gly Glu Gln Ala Val Cys Gly Asp Ser Ala Gly Arg
785                 790                 795                 800

Ala Ala Pro Ala Phe Gly Gly
            805

<210> SEQ ID NO 40
<211> LENGTH: 3396
<212> TYPE: DNA
<213> ORGANISM: Homo sapiens
<220> FEATURE:
<223> OTHER INFORMATION: Reference Telomerase; with Intron Alpha and
      Beta

<400> SEQUENCE: 40

```
atgccgcgcg ctccccgctg ccgagccgtg cgctccctgc tgcgcagcca ctaccgcgag      60
gtgctgccgc tggccacgtt cgtgcggcgc ctggggcccc agggctggcg gctggtgcag     120
cgcggggacc cggcggcttt ccgcgcgctg gtgcccagt gcctggtgtg cgtgccctgg      180
gacgcacggc cgccccccgc cgccccctcc ttccgccagg tgtcctgcct gaaggagctg     240
gtggcccgag tgctgcagag gctgtgcgag cgcggcgcga gaacgtgct ggccttcggc      300 ttcgcgctgc tggacggggc ccgcgggggc ccccccgagg ccttcaccac cagcgtgcgc     360
agctacctgc ccaacacggt gaccgacgca ctgcggggga gcggggcgtg ggggctgctg     420
ttgcgccgcg tgggcgacga cgtgctggtt cacctgctgg cacgctgcgc gctctttgtg     480
ctggtggctc ccagctgcgc ctaccaggtg tgcgggccgc cgctgtacca gctcggcgct     540
gccactcagg cccggccccc gccacacgct agtggacccc gaaggcgtct gggatgcgaa     600
cgggcctgga accatagcgt cagggaggcc gggtccccc tgggcctgcc agccccgggt      660
gcgaggaggc gcgggggcag tgccagccga agtctgccgt tgcccaagag gcccaggcgt     720
ggcgctgccc ctgagccgga gcggacgccc gttgggcagg ggtcctgggc ccacccgggc     780
aggacgcgtg gaccgagtga ccgtggtttc tgtgtggtgt cacctgccag acccgccgaa     840
gaagccacct cttggaggg tgcgctctct ggcacgcgcc actcccaccc atccgtgggc      900
cgccagcacc acgcgggccc cccatccaca tcgcggccac cacgtccctg ggacacgcct     960
tgtcccccgg tgtacgccga gaccaagcac ttcctctact cctcaggcga caaggagcag    1020
ctgcggccct ccttcctact cagctctctg aggcccagcc tgactggcgc tcggaggctc    1080
gtggagacca tctttctggg ttccaggccc tggatgccag ggactcccg caggttgccc     1140 cgcctgcccc agcgctactg gcaaatgcgg cccctgtttc tggagctgct tgggaaccac    1200
gcgcagtgcc cctacggggt gctcctcaag acgcactgcc cgctgcgagc tgcggtcacc    1260
ccagcagccg tgtctgtgc ccgggagaag ccccagggct ctgtggcggc ccccgaggag     1320
gaggacacag accccgtcg cctggtgcag ctgctccgcc agcacagcag ccctggcag     1380 gtgtacggct tcgtgcgggc ctgcctgcgc cggctggtgc ccccaggcct ctggggctcc    1440
aggcacaacg aacgccgctt cctcaggaac accaagaagt tcatctccct ggggaagcat    1500
gccaagctct cgctgcagga gctgacgtgg aagatgagcg tgcggggctg cgcttggctg    1560
cgcaggagcc aggggttgg ctgtgttccg gccgcagagc accgtctgcg tgaggagatc     1620
ctggccaagt tcctgcactg gctgatgagt gtgtacgtcg tcgagctgct caggtctttc    1680
```

```
ttttatgtca cggagaccac gtttcaaaag aacaggctct ttttctaccg gaagagtgtc      1740
tggagcaagt tgcaaagcat tggaatcaga cagcacttga agagggtgca gctgcgggag      1800
ctgtcggaag cagaggtcag gcagcatcgg gaagccaggc ccgccctgct gacgtccaga      1860
ctccgcttca tccccaagcc tgacgggctg cggccgattg tgaacatgga ctacgtcgtg      1920
ggagccagaa cgttccgcag agaaaagagg gccgagcgtc tcacctcgag ggtgaaggca      1980
ctgttcagcg tgctcaacta cgagcgggcg cggcgccccg gcctcctggg cgcctctgtg      2040
ctgggcctgg acgatatcca cagggcctgg cgcaccttcg tgctgcgtgt gcgggcccag      2100
gacccgccgc ctgagctgta ctttgtcaag gtggatgtga cgggcgcgta cgacaccatc      2160
ccccaggaca ggctcacgga ggtcatcgcc agcatcatca accccagaa cacgtactgc       2220 gtgcgtcggt atgccgtggt ccagaaggcc gcccatgggc acgtccgcaa ggccttcaag      2280
agccacgtct ctaccttgac agacctccag ccgtacatgc gacagttcgt ggctcacctg      2340
caggagacca gcccgctgag ggatgccgtc gtcatcgagc agagctcctc cctgaatgag      2400
gccagcagtg gcctcttcga cgtcttccta cgcttcatgt gccaccacgc cgtgcgcatc      2460
aggggcaagt cctacgtcca gtgccagggg atcccgcagg gctccatcct ctccacgctg      2520
ctctgcagcc tgtgctacgg cgacatggag aacaagctgt ttgcggggat tcggcgggac      2580
gggctgctcc tgcgtttggt ggatgatttc ttgttggtga cacctcacct cacccacgcg      2640
aaaaccttcc tcaggaccct ggtccgaggt gtccctgagt atggctgcgt ggtgaacttg      2700
cggaagacag tggtgaactt ccctgtagaa gacgaggccc tgggtggcac ggcttttgtt      2760
cagatgccgg cccacggcct attccctgg tgcggcctgc tgctggatac ccggaccctg       2820
gaggtgcaga gcgactactc cagctatgcc cggacctcca tcagagccag tctcaccttc      2880
aaccgcggct tcaaggctgg gaggaacatg cgtcgcaaac tctttggggt cttgcggctg      2940
aagtgtcaca gcctgtttct ggatttgcag gtgaacagcc tccagacggt gtgcaccaac      3000
atctacaaga tcctcctgct gcaggcgtac aggtttcacg catgtgtgct gcagctccca      3060
tttcatcagc aagtttggaa gaaccccaca ttttcctgc gcgtcatctc tgacacggcc       3120
tccctctgct actccatcct gaaagccaag aacgcaggga tgtcgctggg ggccaagggc      3180
gccgccggcc ctctgccctc cgaggccgtg cagtggctgt gccaccaagc attcctgctc      3240
aagctgactc gacaccgtgt cacctacgtg ccactcctgg ggtcactcag gacagcccag      3300
acgcagctga gtcggaagct cccggggacg acgctgactg ccctggaggc cgcagccaac      3360
ccggcactgc cctcagactt caagaccatc ctggac                                3396
```

<210> SEQ ID NO 41
<211> LENGTH: 3069
<212> TYPE: DNA
<213> ORGANISM: Homo sapiens
<220> FEATURE:
<223> OTHER INFORMATION: Truncated Protein 3; with Introns Alpha, Beta
      and 2

<400> SEQUENCE: 41

```
atgccgcgcg ctcccgctg ccgagccgtg cgctccctgc tgcgcagcca ctaccgcgag       60
gtgctgccgc tggccacgtt cgtgcggcgc ctggggcccc agggctggcg gctggtgcag     120
cgcggggacc cggcggcttt ccgcgcgctg gtgcccagt gcctggtgtg cgtgccctgg       180
gacgcacggc cgcccccgc cgcccctcc ttcgccagg tgtcctgcct gaaggagctg        240
gtggcccgag tgctgcagag gctgtgcgag cgcggcgcga agaacgtgct ggccttcggc      300
```

-continued

```
ttcgcgctgc tggacggggc cgcggggc cccccgagg ccttcaccac cagcgtgcgc      360
agctacctgc ccaacacggt gaccgacgca ctgcggggga gcgggcgtg ggggctgctg      420
ctgcgccgcg tggcgacga cgtgctggtt cacctgctgg cacgctgcgc gctctttgtg      480
ctggtggctc ccagctgcgc ctaccaggtg tgcgggccgc cgctgtacca gctcggcgct      540
gccactcagg cccggccccc gccacacgct agtggacccc gaaggcgtct gggatgcgaa      600
cgggcctgga accatagcgt cagggaggcc ggggtccccc tgggcctgcc agccccgggt      660
gcgaggaggc gcggggcag tgccagccga agtctgccgt tgcccaagag gcccaggcgt      720
ggcgctgccc ctgagccgga gcggacgccc gttgggcagg ggtcctgggc ccacccgggc      780
aggacgcgtg gaccgagtga ccgtggtttc tgtgtggtgt cacctgccag acccgccgaa      840
gaagccacct ctttggaggg tgcgctctct ggcacgcgcc actcccaccc atccgtgggc      900
cgccagcacc acgcgggccc cccatccaca tcgcggccac cacgtccctg gacacgcct      960
tgtcccccgg tgtacgccga gaccaagcac ttcctctact cctcaggcga caaggagcag      1020
ctgcggccct ccttcctact cagctctctg aggcccagcc tgactggcgc tcggaggctc      1080
gtggagacca tctttctggg ttccaggccc tggatgccag ggactcccg caggttgccc      1140
cgcctgcccc agcgctactg gcaaatgcgg cccctgtttc tggagctgct tgggaaccac      1200
gcgcagtgcc cctacgggt gctcctcaag acgcactgcc cgctgcgagc tgcggtcacc      1260
ccagcagccg tgtctgtgc ccgggagaag ccccaggct ctgtggcggc ccccgaggag      1320
gaggacacag accccgtcg cctggtgcag ctgctccgcc agcacagcag ccctggcag       1380
gtgtacggct tcgtgcgggc ctgcctgcgc cggctggtgc ccccaggcct ctggggctcc      1440
aggcacaacg aacgccgctt cctcaggaac accaagaagt tcatctccct ggggaagcat      1500
gccaagctct cgctgcagga gctgacgtgg aagatgagcg tgcgggactg cgcttggctg      1560
cgcaggagcc caggggttgg ctgtgttccg gccgcagagc accgtctgcg tgaggagatc      1620
ctggccaagt tcctgcactg gctgatgagt gtgtacgtcg tcgagctgct caggtctttc      1680
ttttatgtca cggagaccac gtttcaaaag aacaggctct ttttctaccg gaagagtgtc      1740
tggagcaagt tgcaaagcat tggaatcaga cagcacttga agagggtgca gctgcgggag      1800
ctgtcggaag cagaggtcag gcagcatcgg gaagccaggc ccgccctgct gacgtccaga      1860
ctccgcttca tccccaagcc tgacgggctg cggccgattg tgaacatgga ctacgtcgtg      1920
ggagccagaa cgttccgcag agaaaagagg gccgagcgtc tcacctcgag ggtgaaggca      1980
ctgttcagcg tgctcaacta cgagcgggcg cggcgccccg gcctcctggg cgcctctgtg      2040
ctgggcctgg acgatatcca cagggcctgg cgcaccttcg tgctgcgtgt gcgggcccag      2100
gacccgccgc ctgagctgta ctttgtcaag gtggatgtga cgggcgcgta cgacaccatc      2160
ccccaggaca ggctcacgga ggtcatcgcc agcatcatca aacccagaa cacgtactgc      2220
gtgcgtcggt atgccgtggt ccagaaggcc gcccatgggc acgtccgcaa ggccttcaag      2280
agccacgtct ctaccttgac agacctccag ccgtacatgc gacagttcgt ggctcacctg      2340
caggagacca gcccgctgag ggatgccgtc gtcatcgagc agagctcctc cctgaatgag      2400
gccagcagtg gcctcttcga cgtcttccta cgcttcatgt gccaccacgc cgtgcgcatc      2460
agggcaagt cctacgtcca gtgccagggg atcccgcagg gctccatcct ctccacgctg      2520
ctctgcagcc tgtgctacgg cgacatggag aacaagctgt ttgcggggat tcggcgggac      2580
gggctgctcc tgcgtttggt ggatgatttc ttgttggtga caccctcacct cacccacgcg      2640
```

-continued

```
aaaaccttcc tcaggaccct ggtccgaggt gtccctgagt atggctgcgt ggtgaacttg    2700
cggaagacag tggtgaactt ccctgtagaa gacgaggccc tgggtggcac ggcttttgtt    2760
cagatgccgg cccacggcct attcccctgg tgcggcctgc tgctggatac ccggaccctg    2820
gaggtgcaga gcgactactc caggtgagcg cacctggccg gaagtggagc ctgtgcccgg    2880
ctggggcagg tgctgctgca gggccgttgc gtccacctct gcttccgtgt ggggcaggcg    2940
actgccaatc ccaaagggtc agatgccaca gggtgcccct cgtcccatct ggggctgagc    3000
acaaatgcat ctttctgtgg gagtgagggt gcctcacaac gggagcagtt ttctgtgcta    3060
ttttggtaa                                                            3069
```

<210> SEQ ID NO 42
<211> LENGTH: 948
<212> TYPE: PRT
<213> ORGANISM: Homo sapiens
<220> FEATURE:
<223> OTHER INFORMATION: Truncated Protein 3; Encoded by SEQ ID NO:41

<400> SEQUENCE: 42

```
Met Pro Arg Ala Pro Arg Cys Arg Ala Val Arg Ser Leu Leu Arg Ser
  1               5                  10                  15

His Tyr Arg Glu Val Leu Pro Leu Ala Thr Phe Val Arg Arg Leu Gly
             20                  25                  30

Pro Gln Gly Trp Arg Leu Val Gln Arg Gly Asp Pro Ala Ala Phe Arg
         35                  40                  45

Ala Leu Val Ala Gln Cys Leu Val Cys Val Pro Trp Asp Ala Arg Pro
     50                  55                  60

Pro Pro Ala Ala Pro Ser Phe Arg Gln Val Ser Cys Leu Lys Glu Leu
 65                  70                  75                  80

Val Ala Arg Val Leu Gln Arg Leu Cys Glu Arg Gly Ala Lys Asn Val
                 85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285
```

```
Leu Ser Gly Thr Arg His Ser His Pro Ser Val Gly Arg Gln His His
    290                 295                 300

Ala Gly Pro Pro Ser Thr Ser Arg Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
                340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
    435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
                500                 505                 510

Ser Val Arg Asp Cys Ala Trp Leu Arg Arg Ser Pro Gly Val Gly Cys
            515                 520                 525

Val Pro Ala Ala Glu His Arg Leu Arg Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
                580                 585                 590

Leu Lys Arg Val Gln Leu Arg Glu Leu Ser Glu Ala Glu Val Arg Gln
            595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
                660                 665                 670

Pro Gly Leu Leu Gly Ala Ser Val Leu Gly Leu Asp Asp Ile His Arg
            675                 680                 685

Ala Trp Arg Thr Phe Val Leu Arg Val Arg Ala Gln Asp Pro Pro
    690                 695                 700
```

-continued

```
Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
            725                 730                 735

Asn Thr Tyr Cys Val Arg Arg Tyr Ala Val Val Gln Lys Ala Ala His
        740                 745                 750

Gly His Val Arg Lys Ala Phe Lys Ser His Val Ser Thr Leu Thr Asp
    755                 760                 765

Leu Gln Pro Tyr Met Arg Gln Phe Val Ala His Leu Gln Glu Thr Ser
770                 775                 780

Pro Leu Arg Asp Ala Val Ile Glu Gln Ser Ser Leu Asn Glu
785                 790                 795                 800

Ala Ser Ser Gly Leu Phe Asp Val Phe Leu Arg Phe Met Cys His His
            805                 810                 815

Ala Val Arg Ile Arg Gly Lys Ser Tyr Val Gln Cys Gln Gly Ile Pro
        820                 825                 830

Gln Gly Ser Ile Leu Ser Thr Leu Leu Cys Ser Leu Cys Tyr Gly Asp
    835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
            885                 890                 895

Val Val Asn Leu Arg Lys Thr Val Val Asn Phe Pro Val Glu Asp Glu
        900                 905                 910

Ala Leu Gly Gly Thr Ala Phe Val Gln Met Pro Ala His Gly Leu Phe
    915                 920                 925

Pro Trp Cys Gly Leu Leu Leu Asp Thr Arg Thr Leu Glu Val Gln Ser
930                 935                 940

Asp Tyr Ser Arg
945
```

```
<210> SEQ ID NO 43
<211> LENGTH: 3362
<212> TYPE: DNA
<213> ORGANISM: Homo sapiens
<220> FEATURE:
<223> OTHER INFORMATION: Altered C-terminus Protein; with Intron Alpha,
      Beta and 3

<400> SEQUENCE: 43
atgccgcgcg ctccccgctg ccgagccgtg cgctccctgc tgcgcagcca ctaccgcgag      60
gtgctgccgc tggccacgtt cgtgcggcgc ctggggcccc agggctggcg gctggtgcag     120
cgcggggacc cggcggcttt ccgcgcgctg gtggcccagt gcctggtgtg cgtgccctgg     180
gacgcacggc cgcccccgc cgcccctcc ttccgccagg tgtcctgcct gaaggagctg      240
gtggcccgag tgctgcagag gctgtgcgag cgcggcgcga gaacgtgct ggccttcggc      300 ttcgcgctgc tggacggggc ccgcggggc cccccgagg ccttcaccac cagcgtgcgc      360
agctacctgc ccaacacggt gaccgacgca ctgcggggga gcgggcgtg ggggctgctg     420 ctgcgccgcg tgggcgacga cgtgctggtt cacctgctgg cacgctgcgc gctctttgtg    480
ctggtggctc ccagctgcgc ctaccaggtg tgcgggccgc cgctgtacca gctcggcgct    540
gccactcagg cccggccccc gccacacgct agtggacccc gaaggcgtct gggatgcgaa    600
```

-continued

```
cgggcctgga accatagcgt cagggaggcc ggggtccccc tgggcctgcc agccccgggt    660
gcgaggaggc gcgggggcag tgccagccga agtctgccgt tgcccaagag gcccaggcgt    720
ggcgctgccc ctgagccgga gcggacgccc gttgggcagg ggtcctgggc ccacccgggc    780
aggacgcgtg gaccgagtga ccgtggtttc tgtgtggtgt cacctgccag acccgccgaa    840
gaagccacct cttttggaggg tgcgctctct ggcacgcgcc actcccaccc atccgtgggc    900
cgccagcacc acgcgggccc cccatccaca tcgcggccac cacgtccctg ggacacgcct    960
tgtcccccgg tgtacgccga gaccaagcac ttcctctact cctcaggcga caaggagcag   1020
ctgcggccct ccttcctact cagctctctg aggcccagcc tgactggcgc tcggaggctc   1080
gtggagacca tctttctggg ttccaggccc tggatgccag ggactccccg caggttgccc   1140
cgcctgcccc agcgctactg gcaaatgcgg cccctgtttc tggagctgct gggaaccac    1200
gcgcagtgcc cctacggggt gctcctcaag acgcactgcc cgctgcgagc tgcggtcacc   1260
ccagcagccg tgtctgtgc ccgggagaag ccccagggct ctgtggcggc ccccgaggag    1320
gaggacacag accccgtcg cctggtgcag ctgctccgcc agcacagcag cccctggcag    1380
gtgtacggct tcgtgcgggc ctgcctgcgc cggctggtgc ccccaggcct ctggggctcc   1440
aggcacaacg aacgccgctt cctcaggaac accaagaagt tcatctccct ggggaagcat   1500
gccaagctct cgctgcagga gctgacgtgg aagatgagcg tgcgggactg cgcttggctg   1560
cgcaggagcc caggggttgg ctgtgttccg gccgcagagc accgtctgcg tgaggagatc   1620
ctggccaagt cctgcactg gctgatgagt gtgtacgtcg tcgagctgct caggtctttc   1680
ttttatgtca cggagaccac gtttcaaaag acaggctct ttttctaccg gaagagtgtc    1740
tggagcaagt tgcaaagcat tggaatcaga cagcacttga gagggtgca gctgcgggag    1800
ctgtcggaag cagaggtcag gcagcatcgg gaagccaggc ccgccctgct gacgtccaga   1860
ctccgcttca tccccaagcc tgacgggctg cggccgattg tgaacatgga ctacgtcgtg   1920
ggagccagaa cgttccgcag agaaaagagg gccgagcgtc tcacctcgag ggtgaaggca   1980
ctgttcagcg tgctcaacta cgagcgggcg cggcgcccg gcctcctggg cgcctctgtg   2040
ctgggcctgg acgatatcca cagggcctgg cgcaccttcg tgctgcgtgt gcgggcccag   2100
gacccgccgc ctgagctgta cttttgtcaag gtggatgtga cgggcgcgta cgacaccatc   2160
ccccaggaca ggctcacgga ggtcatcgcc agcatcatca aacccagaa cacgtactgc    2220
gtgcgtcggt atgccgtggt ccagaaggcc gcccatgggc acgtccgcaa ggccttcaag   2280
agccacgtct ctaccttgac agacctccag ccgtacatgc gacagttcgt ggctcacctg   2340
caggagacca gcccgctgag ggatgccgtc gtcatcgagc agagctcctc cctgaatgag   2400
gccagcagtg gcctcttcga cgtcttccta cgcttcatgt gccaccacgc cgtgcgcatc   2460
agggcaagt cctacgtcca gtgccagggg atcccgcagg gctccatcct ctccacgctg   2520
ctctgcagcc tgtgctacgg cgacatggag aacaagctgt tgcggggat tcggcgggac   2580
gggctgctcc tgcgtttggt ggatgatttc ttgttggtga cacctcacct cacccacgcg   2640
aaaaccttcc tcaggaccct ggtccgaggt gtccctgagt atggctgcgt ggtgaacttg   2700
cggaagacag tggtgaactt ccctgtagaa gacgaggccc tgggtggcac ggcttttgtt   2760
cagatgccgg cccacggcct attccctgg tgcggcctgc tgctggatac ccggaccctg   2820
gaggtgcaga gcgactactc cagctatgcc cggacctcca tcagagccag tctcaccttc   2880
aaccgcggct tcaaggctgg gaggaacatg cgtcgcaaac tctttggggt cttgcggctg   2940
aagtgtcaca gcctgttct ggatttgcag gtgaacagcc tccagacggt gtgcaccaac   3000
```

```
atctacaaga tcctcctgct gcaggcgtac aggtttcacg catgtgtgct gcagctccca    3060
tttcatcagc aagtttggaa gaccccaca ttttcctgc gcgtcatctc tgacacggcc      3120
tccctctgct actccatcct gaaagccaag aacgcagccg aagaaaacat ttctgtcgtg    3180
actcctgcgg tgcttgggtc gggacagcca gagatggagc caccccgcag accgtcgggt    3240
gtgggcagct ttccggtgtc tcctgggagg ggagttgggc tgggcctgtg actcctcagc    3300
ctctgttttc ccccagggat gtcgctgggg gccaagggcg ccgccggccc tctgccctcc    3360
ga                                                                   3362
```

<210> SEQ ID NO 44
<211> LENGTH: 1096
<212> TYPE: PRT
<213> ORGANISM: Homo sapiens
<220> FEATURE:
<223> OTHER INFORMATION: Altered C-terminus Protein; Encoded by SEQ ID
      NO:43

<400> SEQUENCE: 44

```
Met Pro Arg Ala Pro Arg Cys Arg Ala Val Arg Ser Leu Leu Arg Ser
  1               5                  10                  15

His Tyr Arg Glu Val Leu Pro Leu Ala Thr Phe Val Arg Arg Leu Gly
             20                  25                  30

Pro Gln Gly Trp Arg Leu Val Gln Arg Gly Asp Pro Ala Ala Phe Arg
         35                  40                  45

Ala Leu Val Ala Gln Cys Leu Val Cys Val Pro Trp Asp Ala Arg Pro
     50                  55                  60

Pro Pro Ala Ala Pro Ser Phe Arg Gln Val Ser Cys Leu Lys Glu Leu
 65                  70                  75                  80

Val Ala Arg Val Leu Gln Arg Leu Cys Glu Arg Gly Ala Lys Asn Val
                 85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285
```

-continued

Leu Ser Gly Thr Arg His Ser His Pro Ser Val Gly Arg Gln His His
    290                 295                 300

Ala Gly Pro Pro Ser Thr Ser Arg Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
                340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
            435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
            515                 520                 525

Val Pro Ala Ala Glu His Arg Leu Arg Glu Glu Ile Leu Ala Lys Phe
    530                 535                 540

Leu His Trp Leu Met Ser Val Tyr Val Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro Pro
    690                 695                 700

-continued

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
            725                 730                 735

Asn Thr Tyr Cys Val Arg Arg Tyr Ala Val Val Gln Lys Ala Ala His
        740                 745                 750

Gly His Val Arg Lys Ala Phe Lys Ser His Val Ser Thr Leu Thr Asp
    755                 760                 765

Leu Gln Pro Tyr Met Arg Gln Phe Val Ala His Leu Gln Glu Thr Ser
770                 775                 780

Pro Leu Arg Asp Ala Val Ile Glu Gln Ser Ser Leu Asn Glu
785                 790                 795                 800

Ala Ser Ser Gly Leu Phe Asp Val Phe Leu Arg Phe Met Cys His His
            805                 810                 815

Ala Val Arg Ile Arg Gly Lys Ser Tyr Val Gln Cys Gln Gly Ile Pro
        820                 825                 830

Gln Gly Ser Ile Leu Ser Thr Leu Leu Cys Ser Leu Cys Tyr Gly Asp
    835                 840                 845

Met Glu Asn Lys Leu Phe Ala Gly Ile Arg Arg Asp Gly Leu Leu Leu
850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
            885                 890                 895

Val Val Asn Leu Arg Lys Thr Val Val Asn Phe Pro Val Glu Asp Glu
        900                 905                 910

Ala Leu Gly Gly Thr Ala Phe Val Gln Met Pro Ala His Gly Leu Phe
    915                 920                 925

Pro Trp Cys Gly Leu Leu Leu Asp Thr Arg Thr Leu Glu Val Gln Ser
930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
            965                 970                 975

Val Leu Arg Leu Lys Cys His Ser Leu Phe Leu Asp Leu Gln Val Asn
        980                 985                 990

Ser Leu Gln Thr Val Cys Thr Asn Ile Tyr Lys Ile Leu Leu Leu Gln
    995                 1000                1005

Ala Tyr Arg Phe His Ala Cys Val Leu Gln Leu Pro Phe His Gln Gln
1010                1015                1020

Val Trp Lys Asn Pro Thr Phe Leu Arg Val Ile Ser Asp Thr Ala
1025                1030                1035                1040

Ser Leu Cys Tyr Ser Ile Leu Lys Ala Lys Asn Ala Glu Glu Asn
            1045                1050                1055

Ile Leu Val Val Thr Pro Ala Val Leu Gly Ser Gly Gln Pro Glu Met
        1060                1065                1070

Glu Pro Pro Arg Arg Pro Ser Gly Val Gly Ser Phe Pro Val Ser Pro
    1075                1080                1085

Gly Arg Gly Val Gly Leu Gly Leu
    1090                1095

<210> SEQ ID NO 45
<211> LENGTH: 3918
<212> TYPE: DNA

<213> ORGANISM: Homo sapiens
<220> FEATURE:
<223> OTHER INFORMATION: Protein that lacks Motif A; with Intron Beta

<400> SEQUENCE: 45

| | | | | | |
|---|---|---|---|---|---|
| atgccgcgcg | ctccccgctg | ccgagccgtg | cgctccctgc | tgcgcagcca | ctaccgcgag | 60 |
| gtgctgccgc | tggccacgtt | cgtgcggcgc | ctggggcccc | agggctggcg | gctggtgcag | 120 |
| cgcggggacc | cggcggcttt | ccgcgcgctg | gtgcccagt | gcctggtgtg | cgtgccctgg | 180 |
| gacgcacggc | cgcccccgc | cgccccctcc | ttccgccagg | tgtcctgcct | gaaggagctg | 240 |
| gtgcccgag | tgctgcagag | gctgtgcgag | cgcggcgcga | gaacgtgct | ggccttcggc | 300 |
| ttcgcgctgc | tggacggggc | cgcgggggc | ccccccgagg | ccttcaccac | cagcgtgcgc | 360 |
| agctacctgc | ccaacacggt | gaccgacgca | ctgcggggga | gcgggcgtg | ggggctgctg | 420 |
| ctgcgccgcg | tgggcgacga | cgtgctggtt | cacctgctgg | cacgctgcgc | gctctttgtg | 480 |
| ctggtggctc | ccagctgcgc | ctaccaggtg | tgcgggccgc | cgctgtacca | gctcggcgct | 540 |
| gccactcagg | cccggccccc | gccacacgct | agtggacccc | gaaggcgtct | gggatgcgaa | 600 |
| cgggcctgga | accatagcgt | cagggaggcc | ggggtccccc | tgggcctgcc | agccccgggt | 660 |
| gcgaggaggc | gcggggcag | tgccagccga | agtctgccgt | tgcccaagag | gcccaggcgt | 720 |
| ggcgctgccc | ctgagccgga | gcggacgccc | gttgggcagg | ggtcctgggc | ccacccgggc | 780 |
| aggacgcgtg | gaccgagtga | ccgtggtttc | tgtgtggtgt | cacctgccag | acccgccgaa | 840 |
| gaagccacct | ctttggaggg | tgcgctctct | ggcacgcgcc | actcccaccc | atccgtgggc | 900 |
| cgccagcacc | acgcgggccc | cccatccaca | tcgcggccac | cacgtccctg | ggacacgcct | 960 |
| tgtcccccgg | tgtacgccga | gaccaagcac | ttcctctact | cctcaggcga | caaggagcag | 1020 |
| ctgcggccct | ccttcctact | cagctctctg | aggcccagcc | tgactggcgc | tcggaggctc | 1080 |
| gtggagacca | tctttctggg | ttccaggccc | tggatgccag | ggactccccg | caggttgccc | 1140 |
| cgcctgcccc | agcgctactg | gcaaatgcgg | cccctgtttc | tggagctgct | tgggaaccac | 1200 |
| gcgcagtgcc | cctacggggt | gctcctcaag | acgcactgcc | cgctgcgagc | tgcggtcacc | 1260 |
| ccagcagccg | gtgtctgtgc | ccgggagaag | ccccagggct | ctgtggcggc | ccccgaggag | 1320 |
| gaggacacag | accccgtcg | cctggtgcag | ctgctccgcc | agcacagcag | ccctggcag | 1380 |
| gtgtacggct | tcgtgcgggc | ctgcctgcgc | cggctggtgc | ccccaggcct | ctggggctcc | 1440 |
| aggcacaacg | aacgccgctt | cctcaggaac | accaagaagt | tcatctccct | ggggaagcat | 1500 |
| gccaagctct | cgctgcagga | gctgacgtgg | aagatgagcg | tgcgggactg | cgcttggctg | 1560 |
| cgcaggagcc | caggggttgg | ctgtgttccg | gccgcagagc | accgtctgcg | tgaggagatc | 1620 |
| ctggccaagt | tcctgcactg | gctgatgagt | gtgtacgtcg | tcgagctgct | caggtctttc | 1680 |
| ttttatgtca | cggagaccac | gtttcaaaag | aacaggctct | ttttctaccg | gaagagtgtc | 1740 |
| tggagcaagt | tgcaaagcat | tggaatcaga | cagcacttga | gagggtgca | gctgcgggag | 1800 |
| ctgtcggaag | cagaggtcag | gcagcatcgg | gaagccaggc | ccgccctgct | gacgtccaga | 1860 |
| ctccgcttca | tccccaagcc | tgacgggctg | cggccgattg | tgaacatgga | ctacgtcgtg | 1920 |
| ggagccagaa | cgttccgcag | agaaaagagg | gccgagcgtc | tcacctcgag | ggtgaaggca | 1980 |
| ctgttcagcg | tgctcaacta | cgagcgggcg | cggcgccccg | gctcctgggg | cgcctctgtg | 2040 |
| ctgggcctgg | acgatatcca | caggcctgg | cgcaccttcg | tgctgcgtgt | gcgggcccag | 2100 |
| gacccgccgc | ctgagctgta | ctttgtcaag | gacaggctca | cggaggtcat | cgccagcatc | 2160 |
| atcaaacccc | agaacacgta | ctgcgtgcgt | cggtatgccg | tggtccagaa | ggccgcccat | 2220 |

-continued

```
gggcacgtcc gcaaggcctt caagagccac gtctctacct tgacagacct ccagccgtac    2280
atgcgacagt tcgtggctca cctgcaggag accagcccgc tgagggatgc cgtcgtcatc    2340
gagcagagct cctccctgaa tgaggccagc agtggcctct tcgacgtctt cctacgcttc    2400
atgtgccacc acgccgtgcg catcaggggc aagtcctacg tccagtgcca ggggatcccg    2460
cagggctcca tcctctccac gctgctctgc agcctgtgct acggcgacat ggagaacaag    2520
ctgtttgcgg ggattcggcg ggacgggctg ctcctgcgtt tggtggatga tttcttgttg    2580
gtgacacctc acctcaccca cgcgaaaacc ttcctcagga ccctggtccg aggtgtccct    2640
gagtatggct gcgtggtgaa cttgcggaag acagtggtga acttccctgt agaagacgag    2700
gccctgggtg gcacggcttt tgttcagatg ccggcccacg gcctattccc ctggtgcggc    2760
ctgctgctgg ataccccggac cctggaggtg cagagcgact actccagcta tgcccggacc    2820
tccatcagag ccagtctcac cttcaaccgc ggcttcaagg ctgggaggaa catgcgtcgc    2880
aaactctttg gggtcttgcg gctgaagtgt cacagcctgt ttctggattt gcaggtgaac    2940
agcctccaga cggtgtgcac caacatctac aagatcctcc tgctgcaggc gtacaggttt    3000
cacgcatgtg tgctgcagct cccatttcat cagcaagttt ggaagaaccc cacattttc    3060 ctgcgcgtca tctctgacac ggcctccctc tgctactcca tcctgaaagc caagaacgca    3120
gggatgtcgc tgggggccaa gggcgccgcc ggccctctgc cctccgaggc cgtgcagtgg    3180
ctgtgccacc aagcattcct gctcaagctg actcgacacc gtgtcaccta cgtgccactc    3240
ctggggtcac tcaggacagc ccagacgcag ctgagtcgga agctcccggg gacgacgctg    3300
actgccctgg aggccgcagc caacccggca ctgccctcag acttcaagac catcctggac    3360
tgatggccac ccgcccacag ccaggccgag agcagacacc agcagccctg tcacgccggg    3420
ctctacgtcc cagggaggga ggggcggccc acacccaggc ccgcaccgct gggagtctga    3480
ggcctgagtg agtgttttggc cgaggcctgc atgtccggct gaaggctgag tgtccggctg    3540
aggcctgagc gagtgtccag ccaagggctg agtgtccagc acacctgccg tcttcacttc    3600
cccacaggct ggcgctcggc tccaccccag ggccagcttt tcctcaccag gagcccggct    3660
tccactcccc acataggaat agtccatccc cagattcgcc attgttcacc cctcgccctg    3720
ccctcctttg ccttccaccc ccaccatcca ggtggagacc ctgagaagga ccctgggagc    3780
tctgggaatt tggagtgacc aaaggtgtgc cctgtacaca ggcgaggacc ctgcacctgg    3840 atggggggtcc ctgtgggtca aattgggggg aggtgctgtg ggagtaaaat actgaatata    3900 tgagttttttc agttttga                                                  3918
```

<210> SEQ ID NO 46
<211> LENGTH: 1120
<212> TYPE: PRT
<213> ORGANISM: Homo sapiens
<220> FEATURE:
<223> OTHER INFORMATION: Protein that lacks Motif A; Encoded by SEQ ID NO:45

<400> SEQUENCE: 46

```
Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
                20                  25                  30

Pro Gln Gly Trp Arg Leu Val Gln Arg Gly Asp Pro Ala Ala Phe Arg
            35                  40                  45
```

```
Ala Leu Val Ala Gln Cys Leu Val Cys Val Pro Trp Asp Ala Arg Pro
     50                  55                  60

Pro Pro Ala Ala Pro Ser Phe Arg Gln Val Ser Cys Leu Lys Glu Leu
 65              70                  75                      80

Val Ala Arg Val Leu Gln Arg Leu Cys Glu Arg Gly Ala Lys Asn Val
                 85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
            115                 120             125

Asp Ala Leu Arg Gly Ser Gly Ala Trp Gly Leu Leu Leu Arg Arg Val
        130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
            180                 185                 190

Pro Arg Arg Arg Leu Gly Cys Glu Arg Ala Trp Asn His Ser Val Arg
                195                 200                 205

Glu Ala Gly Val Pro Leu Gly Leu Pro Ala Pro Gly Ala Arg Arg Arg
210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
            275                 280                 285

Leu Ser Gly Thr Arg His Ser His Pro Ser Val Gly Arg Gln His His
            290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Leu Pro Arg Leu Pro Gln
            370                 375                 380

Arg Tyr Trp Gln Met Arg Pro Leu Phe Leu Glu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
            435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
```

-continued

```
            465                 470                 475                 480
Arg His Asn Glu Arg Arg Phe Leu Arg Asn Thr Lys Lys Phe Ile Ser
                    485                 490                 495
Leu Gly Lys His Ala Lys Leu Ser Leu Gln Glu Leu Thr Trp Lys Met
                    500                 505                 510
Ser Val Arg Asp Cys Ala Trp Leu Arg Arg Ser Pro Gly Val Gly Cys
                    515                 520                 525
Val Pro Ala Ala Glu His Arg Leu Arg Glu Glu Ile Leu Ala Lys Phe
                    530                 535                 540
Leu His Trp Leu Met Ser Val Tyr Val Val Glu Leu Leu Arg Ser Phe
545                 550                 555                 560
Phe Tyr Val Thr Glu Thr Thr Phe Gln Lys Asn Arg Leu Phe Phe Tyr
                    565                 570                 575
Arg Lys Ser Val Trp Ser Lys Leu Gln Ser Ile Gly Ile Arg Gln His
                    580                 585                 590
Leu Lys Arg Val Gln Leu Arg Glu Leu Ser Glu Ala Glu Val Arg Gln
                    595                 600                 605
His Arg Glu Ala Arg Pro Ala Leu Leu Thr Ser Arg Leu Arg Phe Ile
                    610                 615                 620
Pro Lys Pro Asp Gly Leu Arg Pro Ile Val Asn Met Asp Tyr Val Val
625                 630                 635                 640
Gly Ala Arg Thr Phe Arg Arg Glu Lys Arg Ala Glu Arg Leu Thr Ser
                    645                 650                 655
Arg Val Lys Ala Leu Phe Ser Val Leu Asn Tyr Glu Arg Ala Arg Arg
                    660                 665                 670
Pro Gly Leu Leu Gly Ala Ser Val Leu Gly Leu Asp Asp Ile His Arg
                    675                 680                 685
Ala Trp Arg Thr Phe Val Leu Arg Val Arg Ala Gln Asp Pro Pro Pro
                    690                 695                 700
Glu Leu Tyr Phe Val Lys Asp Arg Leu Thr Glu Val Ile Ala Ser Ile
705                 710                 715                 720
Ile Lys Pro Gln Asn Thr Tyr Cys Val Arg Arg Tyr Ala Val Val Gln
                    725                 730                 735
Lys Ala Ala His Gly His Val Arg Lys Ala Phe Lys Ser His Val Ser
                    740                 745                 750
Thr Leu Thr Asp Leu Gln Pro Tyr Met Arg Gln Phe Val Ala His Leu
                    755                 760                 765
Gln Glu Thr Ser Pro Leu Arg Asp Ala Val Ile Glu Gln Ser Ser
                    770                 775                 780
Ser Leu Asn Glu Ala Ser Ser Gly Leu Phe Asp Val Phe Leu Arg Phe
785                 790                 795                 800
Met Cys His His Ala Val Arg Ile Arg Gly Lys Ser Tyr Val Gln Cys
                    805                 810                 815
Gln Gly Ile Pro Gln Gly Ser Ile Leu Ser Thr Leu Leu Cys Ser Leu
                    820                 825                 830
Cys Tyr Gly Asp Met Glu Asn Lys Leu Phe Ala Gly Ile Arg Arg Asp
                    835                 840                 845
Gly Leu Leu Leu Arg Leu Val Asp Asp Phe Leu Leu Val Thr Pro His
                    850                 855                 860
Leu Thr His Ala Lys Thr Phe Leu Arg Thr Leu Val Arg Gly Val Pro
865                 870                 875                 880
Glu Tyr Gly Cys Val Val Asn Leu Arg Lys Thr Val Val Asn Phe Pro
                    885                 890                 895
```

Val Glu Asp Glu Ala Leu Gly Gly Thr Ala Phe Val Gln Met Pro Ala
                900                 905                 910

His Gly Leu Phe Pro Trp Cys Gly Leu Leu Leu Asp Thr Arg Thr Leu
            915                 920                 925

Glu Val Gln Ser Asp Tyr Ser Ser Tyr Ala Arg Thr Ser Ile Arg Ala
        930                 935                 940

Ser Leu Thr Phe Asn Arg Gly Phe Lys Ala Gly Arg Asn Met Arg Arg
945                 950                 955                 960

Lys Leu Phe Gly Val Leu Arg Leu Lys Cys His Ser Leu Phe Leu Asp
                965                 970                 975

Leu Gln Val Asn Ser Leu Gln Thr Val Cys Thr Asn Ile Tyr Lys Ile
            980                 985                 990

Leu Leu Leu Gln Ala Tyr Arg Phe His Ala Cys Val Leu Gln Leu Pro
        995                 1000                1005

Phe His Gln Gln Val Trp Lys Asn Pro Thr Phe Phe Leu Arg Val Ile
    1010                1015                1020

Ser Asp Thr Ala Ser Leu Cys Tyr Ser Ile Leu Lys Ala Lys Asn Ala
1025                1030                1035                1040

Gly Met Ser Leu Gly Ala Lys Gly Ala Ala Gly Pro Leu Pro Ser Glu
                1045                1050                1055

Ala Val Gln Trp Leu Cys His Gln Ala Phe Leu Leu Lys Leu Thr Arg
            1060                1065                1070

His Arg Val Thr Tyr Val Pro Leu Leu Gly Ser Leu Arg Thr Ala Gln
        1075                1080                1085

Thr Gln Leu Ser Arg Lys Leu Pro Gly Thr Thr Leu Thr Ala Leu Glu
    1090                1095                1100

Ala Ala Ala Asn Pro Ala Leu Pro Ser Asp Phe Lys Thr Ile Leu Asp
1105                1110                1115                1120

```
<210> SEQ ID NO 47
<211> LENGTH: 3033
<212> TYPE: DNA
<213> ORGANISM: Homo sapiens
<220> FEATURE:
<223> OTHER INFORMATION: Truncated Protein that lacks Motif A; with
      Introns Beta and 2

<400> SEQUENCE: 47
atgccgcgcg ctccccgctg ccgagccgtg cgctccctgc tgcgcagcca ctaccgcgag      60
gtgctgccgc tggccacgtt cgtgcggcgc ctggggcccc agggctggcg gctggtgcag     120
cgcggggacc cggcggcttt ccgcgcgctg gtggcccagt gcctggtgtg cgtgccctgg     180
gacgcacggc cgcccccgc cgcccctcc ttccgccagg tgtcctgcct gaaggagctg       240
gtggcccgag tgctgcagag gctgtgcgag cgcggcgcga agaacgtgct ggccttcggc     300
ttcgcgctgc tggacggggc ccgcgggggc ccccccgagg ccttcaccac cagcgtgcgc     360
agctacctgc ccaacacggt gaccgacgca ctgcggggga gcgggcgtg ggggctgctg      420 ctgcgccgcg tggcgacga cgtgctggtt cacctgctgg cacgctgcgc gctctttgtg      480
ctggtggctc ccagctgcgc ctaccaggtg tgcgggccgc cgctgtacca gctcggcgct    540
gccactcagg cccggccccc gccacacgct agtggacccc gaaggcgtct gggatgcgaa     600
cgggcctgga accatagcgt cagggaggcc ggggtccccc tgggcctgcc agccccgggt    660
gcgaggaggc gcgggggcag tgccagccga agtctgccgt tgcccaagag gcccaggcgt    720
ggcgctgccc ctgagccgga gcggacgccc gttgggcagg ggtcctgggc ccacccgggc    780
```

-continued

```
aggacgcgtg gaccgagtga ccgtggtttc tgtgtggtgt cacctgccag acccgccgaa    840
gaagccacct ctttggaggg tgcgctctct ggcacgcgcc actcccaccc atccgtgggc    900
cgccagcacc acgcgggccc cccatccaca tcgcggccac cacgtccctg ggacacgcct    960
tgtcccccgg tgtacgccga gaccaagcac ttcctctact cctcaggcga caaggagcag   1020
ctgcggcccct ccttcctact cagctctctg aggcccagcc tgactggcgc tcggaggctc   1080
gtggagacca tctttctggg ttccaggccc tggatgccag ggactccccg caggttgccc   1140
cgcctgcccc agcgctactg gcaaatgcgg cccctgtttc tggagctgct tgggaaccac   1200
gcgcagtgcc cctacggggt gctcctcaag acgcactgcc cgctgcgagc tgcggtcacc   1260
ccagcagccg gtgtctgtgc ccgggagaag ccccagggct ctgtggcggc ccccgaggag   1320
gaggacacag accccgtcg cctggtgcag ctgctccgcc agcacagcag cccctggcag   1380
gtgtacggct tcgtgcgggc ctgcctgcgc cggctggtgc ccccaggcct ctggggctcc   1440
aggcacaacg aacgccgctt cctcaggaac accaagaagt tcatctccct ggggaagcat   1500
gccaagctct cgctgcagga gctgacgtgg aagatgagcg tgcggactg cgcttggctg   1560
cgcaggagcc caggggttgg ctgtgttccg gccgcagagc accgtctgcg tgaggagatc   1620
ctggccaagt tcctgcactg gctgatgagt gtgtacgtcg tcgagctgct caggtctttc   1680
ttttatgtca cggagaccac gtttcaaaag aacaggctct ttttctaccg gaagagtgtc   1740
tggagcaagt tgcaaagcat tggaatcaga cagcacttga agagggtgca gctgcgggag   1800
ctgtcggaag cagaggtcag gcagcatcgg gaagccaggc ccgccctgct gacgtccaga   1860
ctccgcttca tccccaagcc tgacgggctg cggccgattg tgaacatgga ctacgtcgtg   1920
ggagccagaa cgttccgcag agaaaagagg gccgagcgtc tcacctcgag ggtgaaggca   1980
ctgttcagcg tgctcaacta cgagcgggcg cggcgccccg gcctcctggg cgcctctgtg   2040
ctgggcctgg acgatatcca cagggcctgg cgcaccttcg tgctgcgtgt gcgggcccag   2100
gacccgccgc ctgagctgta ctttgtcaag gacaggctca cggaggtcat cgccagcatc   2160
atcaaacccc agaacacgta ctgcgtgcgt cggtatgccg tggtccagaa ggccgcccat   2220
gggcacgtcc gcaaggcctt caagagccac gtctctacct tgacagacct ccagccgtac   2280
atgcgacagt tcgtggctca cctgcaggag accagcccgc tgagggatgc cgtcgtcatc   2340
gagcagagct cctccctgaa tgaggccagc agtggcctct tcgacgtctt cctacgcttc   2400
atgtgccacc acgccgtgcg catcaggggc aagtcctacg tccagtgcca ggggatcccg   2460
cagggctcca tcctctccac gctgctctgc agcctgtgct acggcgacat ggagaacaag   2520
ctgtttgcgg ggattcggcg ggacgggctg ctcctgcgtt tggtggatga tttcttgttg   2580
gtgacacctc acctcaccca cgcgaaaacc ttcctcagga ccctggtccg aggtgtccct   2640
gagtatggct gcgtggtgaa cttgcggaag acagtggtga acttccctgt gaagacgag   2700
gccctgggtg gcacggcttt tgttcagatg ccggcccacg gctattccc ctggtgcggc   2760
ctgctgctgg atacccggac cctggaggtg cagagcgact actccaggtg agcgcacctg   2820
gccggaagtg gagcctgtgc ccggctgggg caggtgctgc tgcagggccg ttgcgtccac   2880
ctctgcttcc gtgtgggggca ggcgactgcc aatcccaaag gtcagatgc cacagggtgc   2940
ccctcgtccc atctggggct gagcacaaat gcatctttct gtgggagtga gggtgcctca   3000
caacgggagc agttttctgt gctattttgg taa                                 3033
```

<210> SEQ ID NO 48

-continued

```
<211> LENGTH: 936
<212> TYPE: PRT
<213> ORGANISM: Homo sapiens
<220> FEATURE:
<223> OTHER INFORMATION: Truncated Protein that lacks Motif A; Encoded
      by SEQ ID NO:47

<400> SEQUENCE: 48

Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
    130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
```

```
                370             375             380
Arg Tyr Trp Gln Met Arg Pro Leu Phe Leu Glu Leu Leu Gly Asn His
385             390             395             400

Ala Gln Cys Pro Tyr Gly Val Leu Leu Lys Thr His Cys Pro Leu Arg
                405             410             415

Ala Ala Val Thr Pro Ala Ala Gly Val Cys Ala Arg Glu Lys Pro Gln
                420             425             430

Gly Ser Val Ala Ala Pro Glu Glu Asp Thr Asp Pro Arg Arg Leu
            435             440             445

Val Gln Leu Leu Arg Gln His Ser Ser Pro Trp Gln Val Tyr Gly Phe
450             455             460

Val Arg Ala Cys Leu Arg Arg Leu Val Pro Pro Gly Leu Trp Gly Ser
465             470             475             480

Arg His Asn Glu Arg Arg Phe Leu Arg Asn Thr Lys Lys Phe Ile Ser
                485             490             495

Leu Gly Lys His Ala Lys Leu Ser Leu Gln Glu Leu Thr Trp Lys Met
            500             505             510

Ser Val Arg Asp Cys Ala Trp Leu Arg Arg Ser Pro Gly Val Gly Cys
            515             520             525

Val Pro Ala Ala Glu His Arg Leu Arg Glu Ile Leu Ala Lys Phe
530             535             540

Leu His Trp Leu Met Ser Val Tyr Val Val Glu Leu Leu Arg Ser Phe
545             550             555             560

Phe Tyr Val Thr Glu Thr Thr Phe Gln Lys Asn Arg Leu Phe Phe Tyr
                565             570             575

Arg Lys Ser Val Trp Ser Lys Leu Gln Ser Ile Gly Ile Arg Gln His
            580             585             590

Leu Lys Arg Val Gln Leu Arg Glu Leu Ser Glu Ala Glu Val Arg Gln
            595             600             605

His Arg Glu Ala Arg Pro Ala Leu Leu Thr Ser Arg Leu Arg Phe Ile
610             615             620

Pro Lys Pro Asp Gly Leu Arg Pro Ile Val Asn Met Asp Tyr Val Val
625             630             635             640

Gly Ala Arg Thr Phe Arg Arg Glu Lys Arg Ala Glu Arg Leu Thr Ser
                645             650             655

Arg Val Lys Ala Leu Phe Ser Val Leu Asn Tyr Glu Arg Ala Arg Arg
                660             665             670

Pro Gly Leu Leu Gly Ala Ser Val Leu Gly Leu Asp Asp Ile His Arg
            675             680             685

Ala Trp Arg Thr Phe Val Leu Arg Val Arg Ala Gln Asp Pro Pro
690             695             700

Glu Leu Tyr Phe Val Lys Asp Arg Leu Thr Glu Val Ile Ala Ser Ile
705             710             715             720

Ile Lys Pro Gln Asn Thr Tyr Cys Val Arg Arg Tyr Ala Val Val Gln
                725             730             735

Lys Ala Ala His Gly His Val Arg Lys Ala Phe Lys Ser His Val Ser
            740             745             750

Thr Leu Thr Asp Leu Gln Pro Tyr Met Arg Gln Phe Val Ala His Leu
            755             760             765

Gln Glu Thr Ser Pro Leu Arg Asp Ala Val Val Ile Glu Gln Ser Ser
            770             775             780

Ser Leu Asn Glu Ala Ser Ser Gly Leu Phe Asp Val Phe Leu Arg Phe
785             790             795             800
```

```
Met Cys His His Ala Val Arg Ile Arg Gly Lys Ser Tyr Val Gln Cys
            805                 810                 815
Gln Gly Ile Pro Gln Gly Ser Ile Leu Ser Thr Leu Cys Ser Leu
            820                 825                 830
Cys Tyr Gly Asp Met Glu Asn Lys Leu Phe Ala Gly Ile Arg Arg Asp
            835                 840                 845
Gly Leu Leu Arg Leu Val Asp Asp Phe Leu Leu Val Thr Pro His
    850                 855                 860
Leu Thr His Ala Lys Thr Phe Leu Arg Thr Leu Val Arg Gly Val Pro
865                 870                 875                 880
Glu Tyr Gly Cys Val Val Asn Leu Arg Lys Thr Val Val Asn Phe Pro
            885                 890                 895
Val Glu Asp Glu Ala Leu Gly Gly Thr Ala Phe Val Gln Met Pro Ala
            900                 905                 910
His Gly Leu Phe Pro Trp Cys Gly Leu Leu Leu Asp Thr Arg Thr Leu
            915                 920                 925
Glu Val Gln Ser Asp Tyr Ser Arg
    930                 935

<210> SEQ ID NO 49
<211> LENGTH: 3326
<212> TYPE: DNA
<213> ORGANISM: Homo sapiens
<220> FEATURE:
<223> OTHER INFORMATION: Protein Lacking Motif A and Altered C-Terminus;
      with Introns Beta and 3

<400> SEQUENCE: 49
atgccgcgcg ctccccgctg ccgagccgtg cgctccctgc tgcgcagcca ctaccgcgag      60
gtgctgccgc tggccacgtt cgtgcggcgc ctggggcccc agggctggcg gctggtgcag     120
cgcggggacc cggcggcttt ccgcgcgctg gtggcccagt gcctggtgtg cgtgccctgg     180
gacgcacggc cgccccccgc cgccccctcc ttccgccagg tgtcctgcct gaaggagctg     240
gtggcccgag tgctgcagag gctgtgcgag cgcggcgcga agaacgtgct ggccttcggc     300
ttcgcgctgc tggacggggc ccgcggggc cccccgagg ccttcaccac cagcgtgcgc      360
agctacctgc ccaacacggt gaccgacgca ctgggggga gcgggcgtg ggggctgctg      420 ctgcgccgcg tgggcgacga cgtgctggtt cacctgctgg cacgctgcgc gctctttgtg     480
ctggtggctc ccagctgcgc ctaccaggtg tgcgggccgc cgctgtacca gctcggcgct     540
gccactcagg cccggccccc gccacacgct agtggacccc gaaggcgtct gggatgcgaa     600
cgggcctgga accatagcgt cagggaggcc ggggtccccc tgggcctgcc agccccgggt     660
gcgaggaggc gcgggggcag tgccagccga agtctgccgt tgcccaagag gcccaggcgt     720
ggcgctgccc ctgagccgga gcggacgccc gttgggcagg gtcctgggc ccacccgggc      780 aggacgcgtg gaccgagtga ccgtggtttc tgtgtggtgt cacctgccag accgccgaa      840 gaagccacct ctttggaggg tgcgctctct ggcacgcgcc actcccaccc atccgtgggc     900
cgccagcacc acgcgggccc cccatccaca tcgcggccac acgtccctg ggacacgcct      960 tgtcccccgg tgtacgccga gaccaagcac ttcctctact cctcaggcga caaggagcag    1020
ctgcggccct ccttcctact cagctctctg aggcccagcc tgactggcgc tcggaggctc    1080
gtggagacca tctttctggg ttccaggcc tggatgccag ggactcccg caggttgccc      1140 cgcctgcccc agcgctactg gcaaatgcgg cccctgtttc tggagctgct tgggaaccac    1200
```

```
gcgcagtgcc cctacggggt gctcctcaag acgcactgcc cgctgcgagc tgcggtcacc    1260
ccagcagccg gtgtctgtgc ccgggagaag ccccagggct ctgtggcggc ccccgaggag    1320
gaggacacag accccgtcg cctggtgcag ctgctccgcc agcacagcag ccctggcag     1380 gtgtacggct tcgtgcgggc ctgcctgcgc cggctggtgc ccccaggcct ctggggctcc    1440
aggcacaacg aacgccgctt cctcaggaac accaagaagt tcatctccct ggggaagcat    1500
gccaagctct cgctgcagga gctgacgtgg aagatgagcg tgcgggactg cgcttggctg    1560
cgcaggagcc caggggttgg ctgtgttccg gccgcagagc accgtctgcg tgaggagatc    1620
ctggccaagt cctgcactg gctgatgagt gtgtacgtcg tcgagctgct caggtctttc    1680
ttttatgtca cggagaccac gtttcaaaag aacaggctct ttttctaccg gaagagtgtc    1740
tggagcaagt tgcaaagcat tggaatcaga cagcacttga gagggtgca gctgcgggag    1800 ctgtcggaag cagaggtcag gcagcatcgg gaagccaggc ccgccctgct gacgtccaga    1860
ctccgcttca tccccaagcc tgacgggctg cggccgattg tgaacatgga ctacgtcgtg    1920
ggagccagaa cgttccgcag agaaaagagg gccgagcgtc tcacctcgag ggtgaaggca    1980
ctgttcagcg tgctcaacta cgagcgggcg cggcgcccg gcctcctggg cgcctctgtg    2040
ctgggcctgg acgatatcca cagggcctgg cgcaccttcg tgctgcgtgt gcgggcccag    2100
gacccgccgc tgagctgta cttttgtcaag gacaggctca cggaggtcat cgccagcatc    2160
atcaaacccc agaacacgta ctgcgtgcgt cggtatgccg tggtccagaa ggccgcccat    2220
gggcacgtcc gcaaggcctt caagagccac gtctctacct tgacagacct ccagccgtac    2280
atgcgacagt tcgtggctca cctgcaggag accagcccgc tgagggatgc cgtcgtcatc    2340
gagcagagct cctccctgaa tgaggccagc agtggcctct tcgacgtctt cctacgcttc    2400
atgtgccacc acgccgtgcg catcagggc aagtcctacg tccagtgcca ggggatcccg    2460
cagggctcca tcctctccac gctgctctgc agcctgtgct acggcgacat ggagaacaag    2520
ctgtttgcgg ggattcggcg ggacgggctg ctcctgcgtt tggtggatga tttcttgttg    2580
gtgacacctc acctcaccca cgcgaaaacc ttcctcagga ccctggtccg aggtgtccct    2640
gagtatggct gcgtggtgaa cttgcggaag acagtggtga acttccctgt agaagacgag    2700
gccctgggtg gcacggcttt tgttcagatg ccggcccacg gcctattccc ctggtgcggc    2760
ctgctgctgg ataccccggac cctggaggtg cagagcgact actccagcta tgcccggacc    2820
tccatcagag ccagtctcac cttcaaccgc ggcttcaagg ctgggaggaa catgcgtcgc    2880
aaactctttg gggtcttgcg gctgaagtgt cacagcctgt ttctggattt gcaggtgaac    2940
agcctccaga cggtgtgcac caacatctac aagatcctcc tgctgcaggc gtacaggttt    3000
cacgcatgtg tgctgcagct cccatttcat cagcaagttt ggaagaaccc cacatttttc    3060
ctgcgcgtca tctctgacac ggcctccctc tgctactcca tcctgaaagc caagaacgca    3120
gccgaagaaa acatttctgt cgtgactcct gcggtgcttg gtcgggaca gccagagatg    3180 gagccacccc gcagaccgtc gggtgtgggc agctttccgg tgtctcctgg gagggagtt    3240 gggctgggcc tgtgactcct cagcctctgt tttccccag ggatgtcgct gggggccaag    3300
ggcgccgccg gccctctgcc ctccga                                        3326
```

<210> SEQ ID NO 50
<211> LENGTH: 1084
<212> TYPE: PRT
<213> ORGANISM: Homo sapiens
<220> FEATURE:
<223> OTHER INFORMATION: Protein Lacking Motif A and Altered C-Terminus;

-continued

Encoded by SEQ ID NO:49

<400> SEQUENCE: 50

```
Met Pro Arg Ala Pro Arg Cys Arg Ala Val Arg Ser Leu Leu Arg Ser
  1               5                  10                  15

His Tyr Arg Glu Val Leu Pro Leu Ala Thr Phe Val Arg Arg Leu Gly
             20                  25                  30

Pro Gln Gly Trp Arg Leu Val Gln Arg Gly Asp Pro Ala Ala Phe Arg
         35                  40                  45

Ala Leu Val Ala Gln Cys Leu Val Cys Val Pro Trp Asp Ala Arg Pro
     50                  55                  60

Pro Pro Ala Ala Pro Ser Phe Arg Gln Val Ser Cys Leu Lys Glu Leu
 65                  70                  75                  80

Val Ala Arg Val Leu Gln Arg Leu Cys Glu Arg Gly Ala Lys Asn Val
                 85                  90                  95

Leu Ala Phe Gly Phe Ala Leu Leu Asp Gly Ala Arg Gly Gly Pro Pro
                100                 105                 110

Glu Ala Phe Thr Thr Ser Val Arg Ser Tyr Leu Pro Asn Thr Val Thr
            115                 120                 125

Asp Ala Leu Arg Gly Ser Gly Ala Trp Gly Leu Leu Leu Arg Arg Val
130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
    210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400
```

```
Ala Gln Cys Pro Tyr Gly Val Leu Leu Lys Thr His Cys Pro Leu Arg
            405                 410                 415
Ala Ala Val Thr Pro Ala Ala Gly Val Cys Ala Arg Glu Lys Pro Gln
        420                 425                 430
Gly Ser Val Ala Ala Pro Glu Glu Asp Thr Asp Pro Arg Arg Leu
            435                 440                 445
Val Gln Leu Leu Arg Gln His Ser Ser Pro Trp Gln Val Tyr Gly Phe
450                 455                 460
Val Arg Ala Cys Leu Arg Arg Leu Val Pro Pro Gly Leu Trp Gly Ser
465                 470                 475                 480
Arg His Asn Glu Arg Arg Phe Leu Arg Asn Thr Lys Lys Phe Ile Ser
            485                 490                 495
Leu Gly Lys His Ala Lys Leu Ser Leu Gln Glu Leu Thr Trp Lys Met
            500                 505                 510
Ser Val Arg Asp Cys Ala Trp Leu Arg Arg Ser Pro Gly Val Gly Cys
            515                 520                 525
Val Pro Ala Ala Glu His Arg Leu Arg Glu Glu Ile Leu Ala Lys Phe
        530                 535                 540
Leu His Trp Leu Met Ser Val Tyr Val Val Glu Leu Leu Arg Ser Phe
545                 550                 555                 560
Phe Tyr Val Thr Glu Thr Thr Phe Gln Lys Asn Arg Leu Phe Phe Tyr
                565                 570                 575
Arg Lys Ser Val Trp Ser Lys Leu Gln Ser Ile Gly Ile Arg Gln His
            580                 585                 590
Leu Lys Arg Val Gln Leu Arg Glu Leu Ser Glu Ala Glu Val Arg Gln
        595                 600                 605
His Arg Glu Ala Arg Pro Ala Leu Leu Thr Ser Arg Leu Arg Phe Ile
    610                 615                 620
Pro Lys Pro Asp Gly Leu Arg Pro Ile Val Asn Met Asp Tyr Val Val
625                 630                 635                 640
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
            660                 665                 670
Pro Gly Leu Leu Gly Ala Ser Val Leu Gly Leu Asp Asp Ile His Arg
        675                 680                 685
Ala Trp Arg Thr Phe Val Leu Arg Val Arg Ala Gln Asp Pro Pro
    690                 695                 700
Glu Leu Tyr Phe Val Lys Asp Arg Leu Thr Glu Val Ile Ala Ser Ile
705                 710                 715                 720
Ile Lys Pro Gln Asn Thr Tyr Cys Val Arg Arg Tyr Ala Val Val Gln
                725                 730                 735
Lys Ala Ala His Gly His Val Arg Lys Ala Phe Lys Ser His Val Ser
            740                 745                 750
Thr Leu Thr Asp Leu Gln Pro Tyr Met Arg Gln Phe Val Ala His Leu
        755                 760                 765
Gln Glu Thr Ser Pro Leu Arg Asp Ala Val Val Ile Glu Gln Ser Ser
    770                 775                 780
Ser Leu Asn Glu Ala Ser Ser Gly Leu Phe Asp Val Phe Leu Arg Phe
785                 790                 795                 800
Met Cys His His Ala Val Arg Ile Arg Gly Lys Ser Tyr Val Gln Cys
                805                 810                 815
Gln Gly Ile Pro Gln Gly Ser Ile Leu Ser Thr Leu Leu Cys Ser Leu
```

-continued

```
                        820             825             830
Cys Tyr Gly Asp Met Glu Asn Lys Leu Phe Ala Gly Ile Arg Arg Asp
            835                 840                 845
Gly Leu Leu Arg Leu Val Asp Asp Phe Leu Leu Val Thr Pro His
        850                 855                 860
Leu Thr His Ala Lys Thr Phe Leu Arg Thr Leu Val Arg Gly Val Pro
865                 870                 875                 880
Glu Tyr Gly Cys Val Val Asn Leu Arg Lys Thr Val Val Asn Phe Pro
                    885                 890                 895
Val Glu Asp Glu Ala Leu Gly Gly Thr Ala Phe Val Gln Met Pro Ala
            900                 905                 910
His Gly Leu Phe Pro Trp Cys Gly Leu Leu Asp Thr Arg Thr Leu
        915                 920                 925
Glu Val Gln Ser Asp Tyr Ser Ser Tyr Ala Arg Thr Ser Ile Arg Ala
        930                 935                 940
Ser Leu Thr Phe Asn Arg Gly Phe Lys Ala Gly Arg Asn Met Arg Arg
945                 950                 955                 960
Lys Leu Phe Gly Val Leu Arg Leu Lys Cys His Ser Leu Phe Leu Asp
                965                 970                 975
Leu Gln Val Asn Ser Leu Gln Thr Val Cys Thr Asn Ile Tyr Lys Ile
            980                 985                 990
Leu Leu Leu Gln Ala Tyr Arg Phe His Ala Cys Val Leu Gln Leu Pro
        995                 1000                1005
Phe His Gln Gln Val Trp Lys Asn Pro Thr Phe Phe Leu Arg Val Ile
    1010                1015                1020
Ser Asp Thr Ala Ser Leu Cys Tyr Ser Ile Leu Lys Ala Lys Asn Ala
1025                1030                1035                1040
Glu Glu Glu Asn Ile Leu Val Val Thr Pro Ala Val Leu Gly Ser Gly
                1045                1050                1055
Gln Pro Glu Met Glu Pro Pro Arg Arg Pro Ser Gly Val Gly Ser Phe
            1060                1065                1070
Pro Val Ser Pro Gly Arg Gly Val Gly Leu Gly Leu
        1075                1080
```

<210> SEQ ID NO 51
<211> LENGTH: 2135
<212> TYPE: DNA
<213> ORGANISM: Homo sapiens
<220> FEATURE:
<221> NAME/KEY: modified_base
<222> LOCATION: (1871)..(1873)
<223> OTHER INFORMATION: Wherein N is A, C, G or T
<220> FEATURE:
<223> OTHER INFORMATION: Truncated Telomerase (ver. 2); with
      Intron Y

<400> SEQUENCE: 51
atgccgcgcg ctccccgctg ccgagccgtg cgctccctgc tgcgcagcca ctaccgcgag     60
gtgctgccgc tggccacgtt cgtgcggcgc ctggggcccc agggctggcg gctggtgcag    120
cgcggggacc cggcggcttt ccgcgcgctg gtggcccagt gcctggtgtg cgtgccctgg    180
gacgcacggc cgccccccgc cgccccctcc ttccgccagg tgggcctccc cggggtcggc    240
gtccggctgg ggttgagggc ggccgggggg aaccagcgac atgcggagag cagcgcaggc    300
gactcagggc gcttcccccg caggtgtcct gcctgaagga gctggtggcc cgagtgctgc    360
agaggctgtg cgagcgcggc gcgaagaacg tgctggcctt cggcttcgcg ctgctggacg    420

```
gggcccgcgg gggcccccc gaggccttca ccaccagcgt gcgcagctac ctgcccaaca        480
cggtgaccga cgcactgcgg gggagcgggg cgtgggggct gctgctgcgc cgcgtgggcg        540
acgacgtgct ggttcacctg ctggcacgct gcgcgctctt tgtgctggtg gctcccagct        600
gcgcctacca ggtgtgcggg ccgccgctgt accagctcgg cgctgccact caggcccggc        660
ccccgccaca cgctagtgga ccccgaaggc gtctgggatg cgaacgggcc tggaaccata        720
gcgtcaggga ggccggggtc ccctgggcc tgccagcccc gggtgcgagg aggcgcgggg         780
gcagtgccag ccgaagtctg ccgttgccca agaggcccag gcgtggcgct gcccctgagc        840
cggagcggac gcccgttggg cagggtcct gggcccaccc gggcaggacg cgtggaccga         900
gtgaccgtgg tttctgtgtg gtgtcacctg ccagacccgc cgaagaagcc acctctttgg        960
agggtgcgct ctctggcacg cgccactccc acccatccgt gggccgccag caccacgcgg       1020
gccccccatc cacatcgcgg ccaccacgtc cctgggacac gccttgtccc ccggtgtacg       1080
ccgagaccaa gcacttcctc tactcctcag gcgacaagga gcagctgcgg ccctccttcc       1140
tactcagctc tctgaggccc agcctgactg gcgctcggag gctcgtggag accatctttc       1200
tgggttccag gccctggatg ccagggactc cccgcaggtt gccccgcctg ccccagcgct       1260
actggcaaat gcggcccctg tttctggagc tgcttgggaa ccacgcgcag tgcccctacg       1320
gggtgctcct caagacgcac tgcccgctgc gagctgcggt cacccagca gccggtgtct        1380
gtgcccggga gaagcccag ggtctgtgg cggcccccga ggaggaggac acagaccccc         1440
gtcgcctggt gcagctgctc cgccagcaca gcagcccctg gcaggtgtac ggcttcgtgc       1500
gggcctgcct gcgccggctg gtgcccccag gcctctgggg ctccaggcac aacgaacgcc       1560
gcttcctcag gaacaccaag aagttcatct ccctggggaa gcatgccaag ctctcgctgc       1620
aggagctgac gtggaagatg agcgtgcggg actgcgcttg gctgcgcagg agcccagggg       1680
ttggctgtgt tccggccgca gagcaccgtc tgcgtgagga gatcctggcc aagttcctgc       1740
actggctgat gagtgtgtac gtcgtcgagc tgctcaggtc tttctttat gtcacggaga        1800
ccacgtttca aaagaacagg ctcttttct accggaagag tgtctggagc aagttgcaaa        1860
gcattggaat nnngacagtc accaggggg ttgaccgccg gactgggcgt ccccagggtt        1920
gactatagga ccaggtgtcc aggtgccctg caagtagagg ggctctcaga ggcgtctggc       1980
tggcatgggt ggacgtggcc ccgggcatgg ccttctgcgt gtgctgccgt gggtgccctg       2040
agccctcact gagtcggtgg gggcttgtgg cttcccgtga gcttccccct agtctgttgt       2100
ctggctgagc aagcctcctg agggctctc tattg                                   2135
```

<210> SEQ ID NO 52
<211> LENGTH: 622
<212> TYPE: PRT
<213> ORGANISM: Homo sapiens
<220> FEATURE:
<223> OTHER INFORMATION: Truncated Telomerase (ver.2); encoded
      by SEQ ID NO:51 and ORF1 of Intron Y

<400> SEQUENCE: 52

Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro

-continued

```
                50                      55                      60
Pro Pro Ala Ala Pro Ser Phe Arg Gln Val Gly Leu Pro Gly Val Gly
65                      70                      75                      80

Val Arg Leu Gly Leu Arg Ala Ala Gly Gly Asn Gln Arg His Ala Glu
                    85                      90                      95

Ser Ser Ala Gly Asp Ser Gly Arg Phe Pro Arg Arg Ser Cys Leu Lys
                    100                     105                     110

Glu Leu Val Ala Arg Val Leu Gln Arg Leu Cys Glu Arg Gly Ala Lys
                    115                     120                     125

Asn Val Leu Ala Phe Gly Phe Ala Leu Leu Asp Gly Ala Arg Gly Gly
130                     135                     140

Pro Pro Glu Ala Phe Thr Thr Ser Val Arg Ser Tyr Leu Pro Asn Thr
145                     150                     155                     160

Val Thr Asp Ala Leu Arg Gly Ser Gly Ala Trp Gly Leu Leu Leu Arg
                    165                     170                     175

Arg Val Gly Asp Asp Val Leu Val His Leu Leu Ala Arg Cys Ala Leu
                    180                     185                     190

Phe Val Leu Val Ala Pro Ser Cys Ala Tyr Gln Val Cys Gly Pro Pro
                    195                     200                     205

Leu Tyr Gln Leu Gly Ala Ala Thr Gln Ala Arg Pro Pro His Ala
210                     215                     220

Ser Gly Pro Arg Arg Arg Leu Gly Cys Glu Arg Ala Trp Asn His Ser
225                     230                     235                     240

Val Arg Glu Ala Gly Val Pro Leu Gly Leu Pro Ala Pro Gly Ala Arg
                    245                     250                     255

Arg Arg Gly Gly Ser Ala Ser Arg Ser Leu Pro Leu Pro Lys Arg Pro
                    260                     265                     270

Arg Arg Gly Ala Ala Pro Glu Pro Glu Arg Thr Pro Val Gly Gln Gly
                    275                     280                     285

Ser Trp Ala His Pro Gly Arg Thr Arg Gly Pro Ser Asp Arg Gly Phe
                    290                     295                     300

Cys Val Val Ser Pro Ala Arg Pro Ala Glu Glu Ala Thr Ser Leu Glu
305                     310                     315                     320

Gly Ala Leu Ser Gly Thr Arg His Ser His Pro Ser Val Gly Arg Gln
                    325                     330                     335

His His Ala Gly Pro Pro Ser Thr Ser Arg Pro Pro Arg Pro Trp Asp
                    340                     345                     350

Thr Pro Cys Pro Pro Val Tyr Ala Glu Thr Lys His Phe Leu Tyr Ser
                    355                     360                     365

Ser Gly Asp Lys Glu Gln Leu Arg Pro Ser Phe Leu Leu Ser Ser Leu
                    370                     375                     380

Arg Pro Ser Leu Thr Gly Ala Arg Arg Leu Val Glu Thr Ile Phe Leu
385                     390                     395                     400

Gly Ser Arg Pro Trp Met Pro Gly Thr Pro Arg Arg Leu Pro Arg Leu
                    405                     410                     415

Pro Gln Arg Tyr Trp Gln Met Arg Pro Leu Phe Leu Glu Leu Leu Gly
                    420                     425                     430

Asn His Ala Gln Cys Pro Tyr Gly Val Leu Leu Lys Thr His Cys Pro
                    435                     440                     445

Leu Arg Ala Ala Val Thr Pro Ala Ala Gly Val Cys Ala Arg Glu Lys
                    450                     455                     460

Pro Gln Gly Ser Val Ala Ala Pro Glu Glu Glu Asp Thr Asp Pro Arg
465                     470                     475                     480
```

```
Arg Leu Val Gln Leu Leu Arg Gln His Ser Ser Pro Trp Gln Val Tyr
            485                 490                 495
Gly Phe Val Arg Ala Cys Leu Arg Arg Leu Val Pro Pro Gly Leu Trp
            500                 505                 510
Gly Ser Arg His Asn Glu Arg Arg Phe Leu Arg Asn Thr Lys Lys Phe
            515                 520                 525
Ile Ser Leu Gly Lys His Ala Lys Leu Ser Leu Gln Glu Leu Thr Trp
            530                 535                 540
Lys Met Ser Val Arg Asp Cys Ala Trp Leu Arg Arg Ser Pro Gly Val
545                 550                 555                 560
Gly Cys Val Pro Ala Ala Glu His Arg Leu Arg Glu Glu Ile Leu Ala
            565                 570                 575
Lys Phe Leu His Trp Leu Met Ser Val Tyr Val Val Glu Leu Leu Arg
            580                 585                 590
Ser Phe Phe Tyr Val Thr Glu Thr Thr Phe Gln Lys Asn Arg Leu Phe
            595                 600                 605
Phe Tyr Arg Lys Ser Val Trp Ser Lys Leu Gln Ser Ile Gly
            610                 615                 620

<210> SEQ ID NO 53
<211> LENGTH: 84
<212> TYPE: PRT
<213> ORGANISM: Homo sapiens
<220> FEATURE:
<223> OTHER INFORMATION: Splicing Variant of Human Telomerase encoded by
      Intron Y, ORF2, berfore the termination codon.
      SEQ ID NOs: 51,55,59,63,67,71,75,79,83 encode this
      fragment

<400> SEQUENCE: 53

Met Pro Arg Ala Pro Arg Cys Arg Ala Val Arg Ser Leu Leu Arg Ser
 1               5                  10                  15
His Tyr Arg Glu Val Leu Pro Leu Ala Thr Phe Val Arg Arg Leu Gly
            20                  25                  30
Pro Gln Gly Trp Arg Leu Val Gln Arg Gly Asp Pro Ala Ala Phe Arg
            35                  40                  45
Ala Leu Val Ala Gln Cys Leu Val Cys Val Pro Trp Asp Ala Arg Pro
        50                  55                  60
Pro Pro Ala Ala Pro Ser Phe Arg Gln Val Ala Ser Pro Gly Ser Ala
65                  70                  75                  80
Ser Gly Trp Gly

<210> SEQ ID NO 54
<211> LENGTH: 537
<212> TYPE: PRT
<213> ORGANISM: Homo sapiens
<220> FEATURE:
<223> OTHER INFORMATION: Truncated Telomerase (ver. 2); encoded
      by SEQ ID NO:51, with Y intron, ORF2, after the
      termination codon

<400> SEQUENCE: 54

Gly Arg Pro Gly Gly Thr Ser Asp Met Arg Arg Ala Ala Gln Ala Thr
 1               5                  10                  15
Gln Gly Ala Ser Pro Ala Gly Ser Cys Leu Lys Glu Leu Val Ala Arg
            20                  25                  30
Val Leu Gln Arg Leu Cys Glu Arg Gly Ala Lys Asn Val Leu Ala Phe
            35                  40                  45
```

```
Gly Phe Ala Leu Leu Asp Gly Ala Arg Gly Pro Pro Glu Ala Phe
     50                  55                  60
Thr Thr Ser Val Arg Ser Tyr Leu Pro Asn Thr Val Thr Asp Ala Leu
 65                  70                  75                  80
Arg Gly Ser Gly Ala Trp Gly Leu Leu Leu Arg Arg Val Gly Asp Asp
                 85                  90                  95
Val Leu Val His Leu Leu Ala Arg Cys Ala Leu Phe Val Leu Val Ala
            100                 105                 110
Pro Ser Cys Ala Tyr Gln Val Cys Gly Pro Pro Leu Tyr Gln Leu Gly
        115                 120                 125
Ala Ala Thr Gln Ala Arg Pro Pro His Ala Ser Gly Pro Arg Arg
130                 135                 140
Arg Leu Gly Cys Glu Arg Ala Trp Asn His Ser Val Arg Glu Ala Gly
145                 150                 155                 160
Val Pro Leu Gly Leu Pro Ala Pro Gly Ala Arg Arg Gly Gly Ser
                165                 170                 175
Ala Ser Arg Ser Leu Pro Leu Pro Lys Arg Pro Arg Gly Ala Ala
            180                 185                 190
Pro Glu Pro Glu Arg Thr Pro Val Gly Gln Gly Ser Trp Ala His Pro
        195                 200                 205
Gly Arg Thr Arg Gly Pro Ser Asp Arg Gly Phe Cys Val Val Ser Pro
210                 215                 220
Ala Arg Pro Ala Glu Glu Ala Thr Ser Leu Glu Gly Ala Leu Ser Gly
225                 230                 235                 240
Thr Arg His Ser His Pro Ser Val Gly Arg Gln His His Ala Gly Pro
                245                 250                 255
Pro Ser Thr Ser Arg Pro Arg Pro Trp Asp Thr Pro Cys Pro Pro
            260                 265                 270
Val Tyr Ala Glu Thr Lys His Phe Leu Tyr Ser Ser Gly Asp Lys Glu
        275                 280                 285
Gln Leu Arg Pro Ser Phe Leu Leu Ser Ser Leu Arg Pro Ser Leu Thr
    290                 295                 300
Gly Ala Arg Arg Leu Val Glu Thr Ile Phe Leu Gly Ser Arg Pro Trp
305                 310                 315                 320
Met Pro Gly Thr Pro Arg Arg Leu Pro Arg Leu Pro Gln Arg Tyr Trp
                325                 330                 335
Gln Met Arg Pro Leu Phe Leu Glu Leu Leu Gly Asn His Ala Gln Cys
            340                 345                 350
Pro Tyr Gly Val Leu Leu Lys Thr His Cys Pro Leu Arg Ala Ala Val
        355                 360                 365
Thr Pro Ala Ala Gly Val Cys Ala Arg Glu Lys Pro Gln Gly Ser Val
    370                 375                 380
Ala Ala Pro Glu Glu Glu Asp Thr Asp Pro Arg Arg Leu Val Gln Leu
385                 390                 395                 400
Leu Arg Gln His Ser Ser Pro Trp Gln Val Tyr Gly Phe Val Arg Ala
                405                 410                 415
Cys Leu Arg Arg Leu Val Pro Pro Gly Leu Trp Gly Ser Arg His Asn
            420                 425                 430
Glu Arg Arg Phe Leu Arg Asn Thr Lys Lys Phe Ile Ser Leu Gly Lys
        435                 440                 445
His Ala Lys Leu Ser Leu Gln Glu Leu Thr Trp Lys Met Ser Val Arg
    450                 455                 460
Asp Cys Ala Trp Leu Arg Arg Ser Pro Gly Val Gly Cys Val Pro Ala
```

```
                465                 470                 475                 480
Ala Glu His Arg Leu Arg Glu Ile Leu Ala Lys Phe Leu His Trp
                    485                 490                 495
Leu Met Ser Val Tyr Val Val Glu Leu Leu Arg Ser Phe Phe Tyr Val
            500                 505                 510
Thr Glu Thr Thr Phe Gln Lys Asn Arg Leu Phe Phe Tyr Arg Lys Ser
        515                 520                 525
Val Trp Ser Lys Leu Gln Ser Ile Gly
    530                 535

<210> SEQ ID NO 55
<211> LENGTH: 2145
<212> TYPE: DNA
<213> ORGANISM: Homo sapiens
<220> FEATURE:
<223> OTHER INFORMATION: Truncated Protein 1 (ver.2); with Introns Y
      and 1

<400> SEQUENCE: 55
atgccgcgcg ctccccgctg ccgagccgtg cgctccctgc tgcgcagcca ctaccgcgag      60
gtgctgccgc tggccacgtt cgtgcggcgc ctggggcccc agggctggcg gctggtgcag     120
cgcggggacc cggcggcttt ccgcgcgctg gtggcccagt gcctggtgtg cgtgccctgg     180
gacgcacggc cgccccccgc cgccccctcc ttccgccagg tgggcctccc cggggtcggc     240
gtccggctgg ggttgagggc ggccgggggg aaccagcgac atgcggagag cagcgcaggc     300
gactcagggc gcttcccccg caggtgtcct gcctgaagga gctggtggcc cgagtgctgc     360
agaggctgtg cgagcgcggc gcgaagaacg tgctggcctt cggcttcgcg ctgctggacg     420
gggcccgcgg gggcccccc gaggccttca ccaccagcgt cgcgcagcta cctgcccaaca     480
cggtgaccga cgcactgcgg gggagcgggg cgtgggggct gctgctgcgc gcgtgggcg     540
acgacgtgct ggttcacctg ctggcacgct gcgcgctctt tgtgctggtg ctcccagct     600
gcgcctacca ggtgtgcggg ccgccgctgt accagctcgg cgctgccact caggcccggc     660
ccccgccaca cgctagtgga ccccgaaggc gtctgggatg cgaacgggcc tggaaccata     720
gcgtcaggga ggccggggtc cccctgggcc tgccagcccc gggtgcgagg aggcgcgggg     780
gcagtgccag ccgaagtctg ccgttgccca agaggcccag cgtggcgct gcccctgagc     840
cggagcggac gcccgttggg cagggtcct gggcccaccc gggcaggacg cgtggaccga     900
gtgaccgtgg tttctgtgtg gtgtcacctg ccagacccgc cgaagaagcc acctcttggg     960
agggtgcgct ctctggcacg cgccactccc acccatccgt gggccgccag caccacgcgg    1020
gcccccatc cacatcgcgg ccaccacgtc cctgggacac gccttgtccc ccggtgtacg    1080
ccgagaccaa gcacttcctc tactcctcag gcgacaagga gcagctgcgg ccctccttcc    1140
tactcagctc tctgaggccc agcctgactg gcgctcggag gctcgtggag accatctttc    1200
tgggttccag gccctggatg ccagggactc cccgcaggtt gccccgcctg cccagcgct    1260
actggcaaat gcggccctg tttctggagc tgcttgggaa ccacgcgcag tgcccctacg    1320
gggtgctcct caagacgcac tgcccgctgc gagctgcggt caccccagca gccggtgtct    1380
gtgcccggga aagcccag ggctctgtgg cggcccccga ggaggaggac acagaccccc    1440
gtcgcctggt gcagctgctc cgccagcaca gcagcccctg gcaggtgtac ggcttcgtgc    1500
gggcctgcct cgccggctg gtgccccag gcctctgggg ctccaggcac aacgaacgcc    1560
gcttcctcag gaacaccaag aagttcatct ccctgggaa gcatgccaag ctctcgctgc    1620
```

-continued

```
aggagctgac gtggaagatg agcgtgcggg actgcgcttg gctgcgcagg agcccagggg   1680
ttggctgtgt tccggccgca gagcaccgtc tgcgtgagga gatcctggcc aagttcctgc   1740
actggctgat gagtgtgtac gtcgtcgagc tgctcaggtc tttctttat gtcacggaga    1800 ccacgtttca aaagaacagg ctcttttct accggaagag tgtctggagc aagttgcaaa    1860
gcattggaat cagacagcac ttgaagaggg tgcagctgcg ggagctgtcg aagcagagg    1920 tcaggcagca tcgggaagcc aggcccgccc tgctgacgtc cagactccgc ttcatcccca   1980
agcctgacgg gctgcggccg attgtgaaca tggactacgt cgtgggagcc agaacgttcc   2040
gcagagaaaa gagggtggct gtgctttggt ttaacttcct ttttaaccag aagccgagcg   2100
tctcacctcg agggtgaagg cactgttcag cgtgctcaac tacga                  2145
```

<210> SEQ ID NO 56
<211> LENGTH: 704
<212> TYPE: PRT
<213> ORGANISM: Homo sapiens
<220> FEATURE:
<223> OTHER INFORMATION: Truncated Protein 1 (ver.2); encoded by SEQ ID
NO:55, with Y Intron ORF1

<400> SEQUENCE: 56

```
Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Gly Leu Pro Gly Val Gly
65                  70                  75                  80

Val Arg Leu Gly Leu Arg Ala Ala Gly Gly Asn Gln His Ala Glu
                85                  90                  95

Ser Ser Ala Gly Asp Ser Gly Arg Phe Pro Arg Arg Ser Cys Leu Lys
            100                 105                 110

Glu Leu Val Ala Arg Val Leu Gln Arg Leu Cys Glu Arg Gly Ala Lys
        115                 120                 125

Asn Val Leu Ala Phe Gly Phe Ala Leu Leu Asp Gly Ala Arg Gly Gly
    130                 135                 140

Pro Pro Glu Ala Phe Thr Thr Ser Val Arg Ser Tyr Leu Pro Asn Thr
145                 150                 155                 160

Val Thr Asp Ala Leu Arg Gly Ser Gly Ala Trp Gly Leu Leu Leu Arg
                165                 170                 175

Arg Val Gly Asp Asp Val Leu Val His Leu Leu Ala Arg Cys Ala Leu
            180                 185                 190

Phe Val Leu Val Ala Pro Ser Cys Ala Tyr Gln Val Cys Gly Pro Pro
        195                 200                 205

Leu Tyr Gln Leu Gly Ala Ala Thr Gln Ala Arg Pro Pro Pro His Ala
    210                 215                 220

Ser Gly Pro Arg Arg Arg Leu Gly Cys Glu Arg Ala Trp Asn His Ser
225                 230                 235                 240

Val Arg Glu Ala Gly Val Pro Leu Gly Leu Pro Ala Pro Gly Ala Arg
                245                 250                 255

Arg Arg Gly Gly Ser Ala Ser Arg Ser Leu Pro Leu Pro Lys Arg Pro
            260                 265                 270
```

-continued

Arg Arg Gly Ala Ala Pro Glu Pro Glu Arg Thr Pro Val Gly Gln Gly
        275                 280                 285

Ser Trp Ala His Pro Gly Arg Thr Arg Gly Pro Ser Asp Arg Gly Phe
    290                 295                 300

Cys Val Val Ser Pro Ala Arg Pro Ala Glu Glu Ala Thr Ser Leu Glu
305                 310                 315                 320

Gly Ala Leu Ser Gly Thr Arg His Ser His Pro Ser Val Gly Arg Gln
                325                 330                 335

His His Ala Gly Pro Pro Ser Thr Ser Arg Pro Pro Arg Pro Trp Asp
            340                 345                 350

Thr Pro Cys Pro Pro Val Tyr Ala Glu Thr Lys His Phe Leu Tyr Ser
        355                 360                 365

Ser Gly Asp Lys Glu Gln Leu Arg Pro Ser Phe Leu Leu Ser Ser Leu
    370                 375                 380

Arg Pro Ser Leu Thr Gly Ala Arg Arg Leu Val Glu Thr Ile Phe Leu
385                 390                 395                 400

Gly Ser Arg Pro Trp Met Pro Gly Thr Pro Arg Arg Leu Pro Arg Leu
                405                 410                 415

Pro Gln Arg Tyr Trp Gln Met Arg Pro Leu Phe Leu Glu Leu Leu Gly
            420                 425                 430

Asn His Ala Gln Cys Pro Tyr Gly Val Leu Leu Lys Thr His Cys Pro
        435                 440                 445

Leu Arg Ala Ala Val Thr Pro Ala Ala Gly Val Cys Ala Arg Glu Lys
    450                 455                 460

Pro Gln Gly Ser Val Ala Ala Pro Glu Glu Asp Thr Asp Pro Arg
465                 470                 475                 480

Arg Leu Val Gln Leu Leu Arg Gln His Ser Ser Pro Trp Gln Val Tyr
                485                 490                 495

Gly Phe Val Arg Ala Cys Leu Arg Arg Leu Val Pro Pro Gly Leu Trp
            500                 505                 510

Gly Ser Arg His Asn Glu Arg Arg Phe Leu Arg Asn Thr Lys Lys Phe
        515                 520                 525

Ile Ser Leu Gly Lys His Ala Lys Leu Ser Leu Gln Glu Leu Thr Trp
    530                 535                 540

Lys Met Ser Val Arg Asp Cys Ala Trp Leu Arg Arg Ser Pro Gly Val
545                 550                 555                 560

Gly Cys Val Pro Ala Ala Glu His Arg Leu Arg Glu Glu Ile Leu Ala
                565                 570                 575

Lys Phe Leu His Trp Leu Met Ser Val Tyr Val Val Glu Leu Leu Arg
            580                 585                 590

Ser Phe Phe Tyr Val Thr Glu Thr Thr Phe Gln Lys Asn Arg Leu Phe
        595                 600                 605

Phe Tyr Arg Lys Ser Val Trp Ser Lys Leu Gln Ser Ile Gly Ile Arg
    610                 615                 620

Gln His Leu Lys Arg Val Gln Leu Arg Glu Leu Ser Glu Ala Glu Val
625                 630                 635                 640

Arg Gln His Arg Glu Ala Arg Pro Ala Leu Leu Thr Ser Arg Leu Arg
                645                 650                 655

Phe Ile Pro Lys Pro Asp Gly Leu Arg Pro Ile Val Asn Met Asp Tyr
            660                 665                 670

Val Val Gly Ala Arg Thr Phe Arg Arg Glu Lys Arg Val Ala Val Leu
        675                 680                 685

```
Trp Phe Thr Phe Leu Phe Asn Gln Lys Pro Ser Val Ser Phe Arg Gly
    690                 695                 700
```

<210> SEQ ID NO 57
<211> LENGTH: 619
<212> TYPE: PRT
<213> ORGANISM: Homo sapiens
<220> FEATURE:
<223> OTHER INFORMATION: Truncated Protein 1 (ver.2): encoded by SEQ ID
      NO:55, with Intron Y ORF2 after the termination
      codon

<400> SEQUENCE: 57

```
Gly Arg Pro Gly Gly Thr Ser Asp Met Arg Arg Ala Ala Gln Ala Thr
  1               5                  10                  15

Gln Gly Ala Ser Pro Ala Gly Ser Cys Leu Lys Glu Leu Val Ala Arg
             20                  25                  30

Val Leu Gln Arg Leu Cys Glu Arg Gly Ala Lys Asn Val Leu Ala Phe
         35                  40                  45

Gly Phe Ala Leu Leu Asp Gly Arg Gly Gly Pro Pro Glu Ala Phe
     50                  55                  60

Thr Thr Ser Val Arg Ser Tyr Leu Pro Asn Thr Val Thr Asp Ala Leu
 65                  70                  75                  80

Arg Gly Ser Gly Ala Trp Gly Leu Leu Leu Arg Arg Val Gly Asp Asp
                 85                  90                  95

Val Leu Val His Leu Leu Ala Arg Cys Ala Leu Phe Val Leu Val Ala
                100                 105                 110

Pro Ser Cys Ala Tyr Gln Val Cys Gly Pro Pro Leu Tyr Gln Leu Gly
            115                 120                 125

Ala Ala Thr Gln Ala Arg Pro Pro His Ala Ser Gly Pro Arg Arg
        130                 135                 140

Arg Leu Gly Cys Glu Arg Ala Trp Asn His Ser Val Arg Glu Ala Gly
145                 150                 155                 160

Val Pro Leu Gly Leu Pro Ala Pro Gly Ala Arg Arg Gly Gly Ser
                165                 170                 175

Ala Ser Arg Ser Leu Pro Leu Pro Lys Arg Pro Arg Gly Ala Ala
            180                 185                 190

Pro Glu Pro Glu Arg Thr Pro Val Gly Gln Gly Ser Trp Ala His Pro
        195                 200                 205

Gly Arg Thr Arg Gly Pro Ser Asp Arg Gly Phe Cys Val Val Ser Pro
    210                 215                 220

Ala Arg Pro Ala Glu Glu Ala Thr Ser Leu Glu Gly Ala Leu Ser Gly
225                 230                 235                 240

Thr Arg His Ser His Pro Ser Val Gly Arg Gln His Ala Gly Pro
                245                 250                 255

Pro Ser Thr Ser Arg Pro Pro Arg Pro Trp Asp Thr Pro Cys Pro Pro
            260                 265                 270

Val Tyr Ala Glu Thr Lys His Phe Leu Tyr Ser Ser Gly Asp Lys Glu
        275                 280                 285

Gln Leu Arg Pro Ser Phe Leu Leu Ser Ser Leu Arg Pro Ser Leu Thr
    290                 295                 300

Gly Ala Arg Arg Leu Val Glu Thr Ile Phe Leu Gly Ser Arg Pro Trp
305                 310                 315                 320

Met Pro Gly Thr Pro Arg Arg Leu Pro Arg Leu Pro Gln Arg Tyr Trp
                325                 330                 335

Gln Met Arg Pro Leu Phe Leu Glu Leu Leu Gly Asn His Ala Gln Cys
```

-continued

```
                340                 345                 350
Pro Tyr Gly Val Leu Leu Lys Thr His Cys Pro Leu Arg Ala Ala Val
            355                 360                 365
Thr Pro Ala Ala Gly Val Cys Ala Arg Glu Lys Pro Gln Gly Ser Val
        370                 375                 380
Ala Ala Pro Glu Glu Glu Asp Thr Asp Pro Arg Arg Leu Val Gln Leu
385                 390                 395                 400
Leu Arg Gln His Ser Ser Pro Trp Gln Val Tyr Gly Phe Val Arg Ala
                405                 410                 415
Cys Leu Arg Arg Leu Val Pro Pro Gly Leu Trp Gly Ser Arg His Asn
            420                 425                 430
Glu Arg Arg Phe Leu Arg Asn Thr Lys Lys Phe Ile Ser Leu Gly Lys
        435                 440                 445
His Ala Lys Leu Ser Leu Gln Glu Leu Thr Trp Lys Met Ser Val Arg
    450                 455                 460
Asp Cys Ala Trp Leu Arg Arg Ser Pro Gly Val Gly Cys Val Pro Ala
465                 470                 475                 480
Ala Glu His Arg Leu Arg Glu Glu Ile Leu Ala Lys Phe Leu His Trp
                485                 490                 495
Leu Met Ser Val Tyr Val Val Glu Leu Leu Arg Ser Phe Phe Tyr Val
            500                 505                 510
Thr Glu Thr Thr Phe Gln Lys Asn Arg Leu Phe Phe Tyr Arg Lys Ser
        515                 520                 525
Val Trp Ser Lys Leu Gln Ser Ile Gly Ile Arg Gln His Leu Lys Arg
    530                 535                 540
Val Gln Leu Arg Glu Leu Ser Glu Ala Glu Val Arg Gln His Arg Glu
545                 550                 555                 560
Ala Arg Pro Ala Leu Leu Thr Ser Arg Leu Arg Phe Ile Pro Lys Pro
                565                 570                 575
Asp Gly Leu Arg Pro Ile Val Asn Met Asp Tyr Val Val Gly Ala Arg
            580                 585                 590
Thr Phe Arg Arg Glu Lys Arg Val Ala Val Leu Trp Phe Thr Phe Leu
        595                 600                 605
Phe Asn Gln Lys Pro Ser Val Ser Phe Arg Gly
    610                 615
```

<210> SEQ ID NO 58
<211> LENGTH: 704
<212> TYPE: PRT
<213> ORGANISM: Homo sapiens
<220> FEATURE:
<223> OTHER INFORMATION: Truncated Protein 1 (ver.2); encoded by SEQ ID
      NO:55, with Intron Y ORF3

<400> SEQUENCE: 58

```
Met Pro Arg Ala Pro Arg Cys Arg Ala Val Arg Ser Leu Leu Arg Ser
  1               5                  10                  15
His Tyr Arg Glu Val Leu Pro Leu Ala Thr Phe Val Arg Arg Leu Gly
            20                  25                  30
Pro Gln Gly Trp Arg Leu Val Gln Arg Gly Asp Pro Ala Ala Phe Arg
        35                  40                  45
Ala Leu Val Ala Gln Cys Leu Val Cys Val Pro Trp Asp Ala Arg Pro
    50                  55                  60
Pro Pro Ala Ala Pro Ser Phe Arg Gln Val Pro Pro Arg Gly Arg Arg
65                  70                  75                  80
```

```
Pro Ala Gly Val Glu Gly Gly Arg Gly Glu Pro Ala Thr Cys Gly Glu
             85                  90                  95
Gln Arg Arg Arg Leu Arg Ala Leu Pro Pro Gln Val Ser Cys Leu Lys
            100                 105                 110
Glu Leu Val Ala Arg Val Leu Gln Arg Leu Cys Glu Arg Gly Ala Lys
            115                 120                 125
Asn Val Leu Ala Phe Gly Phe Ala Leu Leu Asp Gly Ala Arg Gly Gly
        130                 135                 140
Pro Pro Glu Ala Phe Thr Thr Ser Val Arg Ser Tyr Leu Pro Asn Thr
145                 150                 155                 160
Val Thr Asp Ala Leu Arg Gly Ser Gly Ala Trp Gly Leu Leu Leu Arg
                165                 170                 175
Arg Val Gly Asp Asp Val Leu Val His Leu Leu Ala Arg Cys Ala Leu
            180                 185                 190
Phe Val Leu Val Ala Pro Ser Cys Ala Tyr Gln Val Cys Gly Pro Pro
        195                 200                 205
Leu Tyr Gln Leu Gly Ala Ala Thr Gln Ala Arg Pro Pro His Ala
    210                 215                 220
Ser Gly Pro Arg Arg Leu Gly Cys Glu Arg Ala Trp Asn His Ser
225                 230                 235                 240
Val Arg Glu Ala Gly Val Pro Leu Gly Leu Pro Ala Pro Gly Ala Arg
                245                 250                 255
Arg Arg Gly Gly Ser Ala Ser Arg Ser Leu Pro Leu Pro Lys Arg Pro
            260                 265                 270
Arg Arg Gly Ala Ala Pro Glu Pro Glu Arg Thr Pro Val Gly Gln Gly
        275                 280                 285
Ser Trp Ala His Pro Gly Arg Thr Arg Gly Pro Ser Asp Arg Gly Phe
    290                 295                 300
Cys Val Val Ser Pro Ala Arg Pro Ala Glu Glu Ala Thr Ser Leu Glu
305                 310                 315                 320
Gly Ala Leu Ser Gly Thr Arg His Ser His Pro Ser Val Gly Arg Gln
                325                 330                 335
His His Ala Gly Pro Pro Ser Thr Ser Arg Pro Pro Arg Pro Trp Asp
            340                 345                 350
Thr Pro Cys Pro Pro Val Tyr Ala Glu Thr Lys His Phe Leu Tyr Ser
        355                 360                 365
Ser Gly Asp Lys Glu Gln Leu Arg Pro Ser Phe Leu Leu Ser Ser Leu
370                 375                 380
Arg Pro Ser Leu Thr Gly Ala Arg Arg Leu Val Glu Thr Ile Phe Leu
385                 390                 395                 400
Gly Ser Arg Pro Trp Met Pro Gly Thr Pro Arg Arg Leu Pro Arg Leu
                405                 410                 415
Pro Gln Arg Tyr Trp Gln Met Arg Pro Leu Phe Leu Glu Leu Leu Gly
            420                 425                 430
Asn His Ala Gln Cys Pro Tyr Gly Val Leu Leu Lys Thr His Cys Pro
        435                 440                 445
Leu Arg Ala Ala Val Thr Pro Ala Ala Gly Val Cys Ala Arg Glu Lys
    450                 455                 460
Pro Gln Gly Ser Val Ala Ala Pro Glu Glu Asp Thr Asp Pro Arg
465                 470                 475                 480
Arg Leu Val Gln Leu Leu Arg Gln His Ser Ser Pro Trp Gln Val Tyr
                485                 490                 495
Gly Phe Val Arg Ala Cys Leu Arg Arg Leu Val Pro Pro Gly Leu Trp
```

```
                500              505              510
Gly Ser Arg His Asn Glu Arg Arg Phe Leu Arg Asn Thr Lys Lys Phe
            515                  520                  525
Ile Ser Leu Gly Lys His Ala Lys Leu Ser Leu Gln Glu Leu Thr Trp
        530                  535                  540
Lys Met Ser Val Arg Asp Cys Ala Trp Leu Arg Arg Ser Pro Gly Val
545                  550                  555                  560
Gly Cys Val Pro Ala Ala Glu His Arg Leu Arg Glu Glu Ile Leu Ala
                565                  570                  575
Lys Phe Leu His Trp Leu Met Ser Val Tyr Val Glu Leu Leu Arg
            580                  585                  590
Ser Phe Phe Tyr Val Thr Glu Thr Thr Phe Gln Lys Asn Arg Leu Phe
        595                  600                  605
Phe Tyr Arg Lys Ser Val Trp Ser Lys Leu Gln Ser Ile Gly Ile Arg
        610                  615                  620
Gln His Leu Lys Arg Val Gln Leu Arg Glu Leu Ser Glu Ala Glu Val
625                  630                  635                  640
Arg Gln His Arg Glu Ala Arg Pro Ala Leu Leu Thr Ser Arg Leu Arg
                645                  650                  655
Phe Ile Pro Lys Pro Asp Gly Leu Arg Pro Ile Val Asn Met Asp Tyr
            660                  665                  670
Val Val Gly Ala Arg Thr Phe Arg Arg Glu Lys Arg Val Ala Val Leu
        675                  680                  685
Trp Phe Thr Phe Leu Phe Asn Gln Lys Pro Ser Val Ser Phe Arg Gly
    690                  695                  700

<210> SEQ ID NO 59
<211> LENGTH: 2645
<212> TYPE: DNA
<213> ORGANISM: Homo sapiens
<220> FEATURE:
<223> OTHER INFORMATION: Truncated Protein 2 (ver.2); with Intron Y and
      Alpha

<400> SEQUENCE: 59
atgccgcgcg ctccccgctg ccgagccgtg cgctccctgc tgcgcagcca ctaccgcgag      60
gtgctgccgc tggccacgtt cgtgcggcgc ctggggcccc agggctggcg gctggtgcag     120
cgcggggacc cggcggcttt ccgcgcgctg gtggcccagt gcctggtgtg cgtgccctgg     180
gacgcacggc cgccccccgc cgccccctcc ttccgccagg tgggcctccc cggggtcggc     240
gtccggctgg ggttgagggc ggccgggggg aaccagcgac atgcggagag cagcgcaggc     300
gactcagggc gcttcccccg caggtgtcct gcctgaagga gctggtggcc cgagtgctgc     360
agaggctgtg cgagcgcggc gcgaagaacg tgctggcctt cggcttcgcg ctgctggacg     420
gggcccgcgg gggcccccccc gaggccttca ccaccagcgt gcgcagctac ctgcccaaca     480
cggtgaccga cgcactgcgg gggagcgggg cgtgggggct gctgctgcgc gcgtgggcg     540 acgacgtgct ggttcacctg ctggcacgct gcgcgctctt tgtgctggtg gctcccagct     600
gcgcctacca ggtgtgcggg ccgccgctgt accagctcgg cgctgccact caggcccggc     660
ccccgccaca cgctagtgga ccccgaaggc gtctgggatg cgaacgggcc tggaaccata     720
gcgtcaggga ggccggggtc ccctgggcc tgccagcccc gggtgcgagg aggcgcgggg     780
gcagtgccag ccgaagtctg ccgttgccca gaggcccag gcgtggcgct gcccctgagc     840
cggagcggac gcccgttggg cagggtcct gggcccaccc gggcaggacg cgtggaccga     900
```

-continued

```
gtgaccgtgg tttctgtgtg gtgtcacctg ccagacccgc cgaagaagcc acctctttgg      960
agggtgcgct ctctggcacg cgccactccc acccatccgt gggccgccag caccacgcgg     1020
gcccccatc cacatcgcgg ccaccacgtc cctgggacac gccttgtccc ccggtgtacg      1080
ccgagaccaa gcacttcctc tactcctcag gcgacaagga gcagctgcgg ccctccttcc    1140
tactcagctc tctgaggccc agcctgactg gcgctcggag gctcgtggag accatctttc    1200
tgggttccag gccctggatg ccagggactc cccgcaggtt gccccgcctg ccccagcgct    1260
actggcaaat gcggcccctg tttctggagc tgcttgggaa ccacgcgcag tgcccctacg    1320
gggtgctcct caagacgcac tgcccgctgc gagctgcgt caccccagca gccggtgtct    1380
gtgcccggga gaagcccag ggctctgtgg cggccccga ggaggaggac acagaccccc    1440
gtcgcctggt gcagctgctc cgccagcaca gcagcccctg gcaggtgtac ggcttcgtgc    1500
gggcctgcct gcgccggctg gtgcccccag gcctctgggg ctccaggcac aacgaacgcc    1560
gcttcctcag gaacaccaag aagttcatct ccctggggaa gcatgccaag ctctcgctgc    1620
aggagctgac gtggaagatg agcgtgcggg actgcgcttg gctgcgcagg agcccagggg    1680
ttggctgtgt tccggccgca gagcaccgtc tgcgtgagga gatcctggcc aagttcctgc    1740
actggctgat gagtgtgtac gtcgtcgagc tgctcaggtc tttctttat gtcacggaga    1800
ccacgtttca aaagaacagg ctcttttct accggaagag tgtctggagc aagttgcaaa    1860
gcattggaat cagacagcac ttgaagaggg tgcagctgcg ggagctgtcg aagcagagg    1920
tcaggcagca tcgggaagcc aggcccgccc tgctgacgtc cagactccgc ttcatcccca    1980
agcctgacgg gctgcggccg attgtgaaca tggactacgt cgtgggagcc agaacgttcc    2040
gcagagaaaa gagggccgag cgtctcacct cgagggtgaa ggcactgttc agcgtgctca    2100
actacgagcg ggcgcggcgc cccggcctcc tgggcgcctc tgtgctgggc ctggacgata    2160
tccacagggc ctggcgcacc ttcgtgctgc gtgtgcgggc caggacccg ccgcctgagc    2220
tgtactttgt caaggtggat gtgacgggcg cgtacgacac catcccccag gacaggctca    2280
cggaggtcat cgccagcatc atcaaacccc agaacgta ctgcgtgcgt cggtatgccg    2340
tggtccagaa ggccgcccat gggcacgtcc gcaaggcctt caagagccac gtcctacgtc    2400
cagtgccagg ggatcccgca gggctccatc ctctccacgc tgctctgcag cctgtgctac    2460
ggcgacatgg agaacaagct gttttgcggg attcggcggg acgggctgct cctgcgtttg    2520
gtggatgatt tcttgttggt gacacctcac ctcacccacg cgaaaaccttt cctcaggacc    2580
ctggtccgag gtgtccctga gtatggctgc gtggtgaact tgcggaagac agtggtgaac    2640
ttccc                                                                 2645
```

<210> SEQ ID NO 60
<211> LENGTH: 841
<212> TYPE: PRT
<213> ORGANISM: Homo sapiens
<220> FEATURE:
<223> OTHER INFORMATION: Truncated Protein 2 (ver.2); encoded by SEQ ID
      NO:59, with Intron Y ORF1

<400> SEQUENCE: 60

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

-continued

```
Ala Leu Val Ala Gln Cys Leu Val Cys Val Pro Trp Asp Ala Arg Pro
     50                  55                  60

Pro Pro Ala Ala Pro Ser Phe Arg Gln Val Gly Leu Pro Gly Val Gly
 65                  70                  75                  80

Val Arg Leu Gly Leu Arg Ala Ala Gly Gly Asn Gln Arg His Ala Glu
                 85                  90                  95

Ser Ser Ala Gly Asp Ser Gly Arg Phe Pro Arg Arg Ser Cys Leu Lys
                100                 105                 110

Glu Leu Val Ala Arg Val Leu Gln Arg Leu Cys Glu Arg Gly Ala Lys
                115                 120                 125

Asn Val Leu Ala Phe Gly Phe Ala Leu Leu Asp Gly Ala Arg Gly Gly
130                 135                 140

Pro Pro Glu Ala Phe Thr Thr Ser Val Arg Ser Tyr Leu Pro Asn Thr
145                 150                 155                 160

Val Thr Asp Ala Leu Arg Gly Ser Gly Ala Trp Gly Leu Leu Leu Arg
                165                 170                 175

Arg Val Gly Asp Asp Val Leu Val His Leu Leu Ala Arg Cys Ala Leu
                180                 185                 190

Phe Val Leu Val Ala Pro Ser Cys Ala Tyr Gln Val Cys Gly Pro Pro
                195                 200                 205

Leu Tyr Gln Leu Gly Ala Ala Thr Gln Ala Arg Pro Pro His Ala
210                 215                 220

Ser Gly Pro Arg Arg Leu Gly Cys Glu Arg Ala Trp Asn His Ser
225                 230                 235                 240

Val Arg Glu Ala Gly Val Pro Leu Gly Leu Pro Ala Pro Gly Ala Arg
                245                 250                 255

Arg Arg Gly Gly Ser Ala Ser Arg Ser Leu Pro Leu Pro Lys Arg Pro
                260                 265                 270

Arg Arg Gly Ala Ala Pro Glu Pro Glu Arg Thr Pro Val Gly Gln Gly
                275                 280                 285

Ser Trp Ala His Pro Gly Arg Thr Arg Gly Pro Ser Asp Arg Gly Phe
290                 295                 300

Cys Val Val Ser Pro Ala Arg Pro Ala Glu Glu Ala Thr Ser Leu Glu
305                 310                 315                 320

Gly Ala Leu Ser Gly Thr Arg His Ser His Pro Ser Val Gly Arg Gln
                325                 330                 335

His His Ala Gly Pro Pro Ser Thr Ser Arg Pro Pro Arg Pro Trp Asp
                340                 345                 350

Thr Pro Cys Pro Pro Val Tyr Ala Glu Thr Lys His Phe Leu Tyr Ser
                355                 360                 365

Ser Gly Asp Lys Glu Gln Leu Arg Pro Ser Phe Leu Leu Ser Ser Leu
                370                 375                 380

Arg Pro Ser Leu Thr Gly Ala Arg Arg Leu Val Glu Thr Ile Phe Leu
385                 390                 395                 400

Gly Ser Arg Pro Trp Met Pro Gly Thr Pro Arg Arg Leu Pro Arg Leu
                405                 410                 415

Pro Gln Arg Tyr Trp Gln Met Arg Pro Leu Phe Leu Glu Leu Leu Gly
                420                 425                 430

Asn His Ala Gln Cys Pro Tyr Gly Val Leu Leu Lys Thr His Cys Pro
                435                 440                 445

Leu Arg Ala Ala Val Thr Pro Ala Ala Gly Val Cys Ala Arg Glu Lys
450                 455                 460
```

```
Pro Gln Gly Ser Val Ala Ala Pro Glu Glu Asp Thr Asp Pro Arg
465                 470                 475                 480

Arg Leu Val Gln Leu Leu Arg Gln His Ser Ser Pro Trp Gln Val Tyr
                485                 490                 495

Gly Phe Val Arg Ala Cys Leu Arg Arg Leu Val Pro Pro Gly Leu Trp
                500                 505                 510

Gly Ser Arg His Asn Glu Arg Arg Phe Leu Arg Asn Thr Lys Lys Phe
                515                 520                 525

Ile Ser Leu Gly Lys His Ala Lys Leu Ser Leu Gln Glu Leu Thr Trp
            530                 535                 540

Lys Met Ser Val Arg Asp Cys Ala Trp Leu Arg Arg Ser Pro Gly Val
545                 550                 555                 560

Gly Cys Val Pro Ala Ala Glu His Arg Leu Arg Glu Glu Ile Leu Ala
                565                 570                 575

Lys Phe Leu His Trp Leu Met Ser Val Tyr Val Val Glu Leu Leu Arg
                580                 585                 590

Ser Phe Phe Tyr Val Thr Glu Thr Thr Phe Gln Lys Asn Arg Leu Phe
            595                 600                 605

Phe Tyr Arg Lys Ser Val Trp Ser Lys Leu Gln Ser Ile Gly Ile Arg
            610                 615                 620

Gln His Leu Lys Arg Val Gln Leu Arg Glu Leu Ser Glu Ala Glu Val
625                 630                 635                 640

Arg Gln His Arg Glu Ala Arg Pro Ala Leu Leu Thr Ser Arg Leu Arg
                645                 650                 655

Phe Ile Pro Lys Pro Asp Gly Leu Arg Pro Ile Val Asn Met Asp Tyr
                660                 665                 670

Val Val Gly Ala Arg Thr Phe Arg Arg Glu Lys Arg Ala Glu Arg Leu
            675                 680                 685

Thr Ser Arg Val Lys Ala Leu Phe Ser Val Leu Asn Tyr Glu Arg Ala
690                 695                 700

Arg Arg Pro Gly Leu Leu Gly Ala Ser Val Leu Gly Leu Asp Asp Ile
705                 710                 715                 720

His Arg Ala Trp Arg Thr Phe Val Leu Arg Val Arg Ala Gln Asp Pro
                725                 730                 735

Pro Pro Glu Leu Tyr Phe Val Lys Val Asp Val Thr Gly Ala Tyr Asp
                740                 745                 750

Thr Ile Pro Gln Asp Arg Leu Thr Glu Val Ile Ala Ser Ile Ile Lys
            755                 760                 765

Pro Gln Asn Thr Tyr Cys Val Arg Arg Tyr Ala Val Val Gln Lys Ala
            770                 775                 780

Ala His Gly His Val Arg Lys Ala Phe Lys Ser His Val Leu Arg Pro
785                 790                 795                 800

Val Pro Gly Asp Pro Ala Gly Leu His Pro Leu His Ala Ala Leu Gln
                805                 810                 815

Pro Val Leu Arg Arg His Gly Glu Gln Ala Val Cys Gly Asp Ser Ala
            820                 825                 830

Gly Arg Ala Ala Pro Ala Phe Gly Gly
                835                 840

<210> SEQ ID NO 61
<211> LENGTH: 756
<212> TYPE: PRT
<213> ORGANISM: Homo sapiens
<220> FEATURE:
<223> OTHER INFORMATION: Truncated Protein 2 (ver.2); encoded by SEQ ID
```

NO:59 with Intron Y ORF2 after the termination
codon

<400> SEQUENCE: 61

Gly Arg Pro Gly Gly Thr Ser Asp Met Arg Ala Ala Gln Ala Thr
1               5                  10                  15

Gln Gly Ala Ser Pro Ala Gly Ser Cys Leu Lys Glu Leu Val Ala Arg
            20                  25                  30

Val Leu Gln Arg Leu Cys Glu Arg Gly Ala Lys Asn Val Leu Ala Phe
        35                  40                  45

Gly Phe Ala Leu Leu Asp Gly Ala Arg Gly Gly Pro Pro Glu Ala Phe
    50                  55                  60

Thr Thr Ser Val Arg Ser Tyr Leu Pro Asn Thr Val Thr Asp Ala Leu
65                  70                  75                  80

Arg Gly Ser Gly Ala Trp Gly Leu Leu Arg Arg Val Gly Asp Asp
            85                  90                  95

Val Leu Val His Leu Leu Ala Arg Cys Ala Leu Phe Val Leu Val Ala
            100                 105                 110

Pro Ser Cys Ala Tyr Gln Val Cys Gly Pro Pro Leu Tyr Gln Leu Gly
        115                 120                 125

Ala Ala Thr Gln Ala Arg Pro Pro His Ala Ser Gly Pro Arg Arg
130                 135                 140

Arg Leu Gly Cys Glu Arg Ala Trp Asn His Ser Val Arg Glu Ala Gly
145                 150                 155                 160

Val Pro Leu Gly Leu Pro Ala Pro Gly Ala Arg Arg Gly Gly Ser
            165                 170                 175

Ala Ser Arg Ser Leu Pro Leu Pro Lys Arg Pro Arg Arg Gly Ala Ala
            180                 185                 190

Pro Glu Pro Glu Arg Thr Pro Val Gly Gln Gly Ser Trp Ala His Pro
        195                 200                 205

Gly Arg Thr Arg Gly Pro Ser Asp Arg Gly Phe Cys Val Val Ser Pro
    210                 215                 220

Ala Arg Pro Ala Glu Glu Ala Thr Ser Leu Glu Gly Ala Leu Ser Gly
225                 230                 235                 240

Thr Arg His Ser His Pro Ser Val Gly Arg Gln His His Ala Gly Pro
                245                 250                 255

Pro Ser Thr Ser Arg Pro Pro Arg Pro Trp Asp Thr Pro Cys Pro Pro
            260                 265                 270

Val Tyr Ala Glu Thr Lys His Phe Leu Tyr Ser Ser Gly Asp Lys Glu
        275                 280                 285

Gln Leu Arg Pro Ser Phe Leu Leu Ser Ser Leu Arg Pro Ser Leu Thr
    290                 295                 300

Gly Ala Arg Arg Leu Val Glu Thr Ile Phe Leu Gly Ser Arg Pro Trp
305                 310                 315                 320

Met Pro Gly Thr Pro Arg Arg Leu Pro Arg Leu Pro Gln Arg Tyr Trp
                325                 330                 335

Gln Met Arg Pro Leu Phe Leu Glu Leu Leu Gly Asn His Ala Gln Cys
            340                 345                 350

Pro Tyr Gly Val Leu Leu Lys Thr His Cys Pro Leu Arg Ala Ala Val
        355                 360                 365

Thr Pro Ala Ala Gly Val Cys Ala Arg Glu Lys Pro Gln Gly Ser Val
    370                 375                 380

Ala Ala Pro Glu Glu Glu Asp Thr Asp Pro Arg Arg Leu Val Gln Leu
385                 390                 395                 400

```
Leu Arg Gln His Ser Ser Pro Trp Gln Val Tyr Gly Phe Val Arg Ala
            405                 410                 415
Cys Leu Arg Arg Leu Val Pro Pro Gly Leu Trp Gly Ser Arg His Asn
            420                 425                 430
Glu Arg Arg Phe Leu Arg Asn Thr Lys Lys Phe Ile Ser Leu Gly Lys
            435                 440                 445
His Ala Lys Leu Ser Leu Gln Glu Leu Thr Trp Lys Met Ser Val Arg
        450                 455                 460
Asp Cys Ala Trp Leu Arg Arg Ser Pro Gly Val Gly Cys Val Pro Ala
465                 470                 475                 480
Ala Glu His Arg Leu Arg Glu Ile Leu Ala Lys Phe Leu His Trp
                485                 490                 495
Leu Met Ser Val Tyr Val Val Glu Leu Leu Arg Ser Phe Phe Tyr Val
            500                 505                 510
Thr Glu Thr Thr Phe Gln Lys Asn Arg Leu Phe Phe Tyr Arg Lys Ser
            515                 520                 525
Val Trp Ser Lys Leu Gln Ser Ile Gly Ile Arg Gln His Leu Lys Arg
            530                 535                 540
Val Gln Leu Arg Glu Leu Ser Glu Ala Glu Val Arg Gln His Arg Glu
545                 550                 555                 560
Ala Arg Pro Ala Leu Leu Thr Ser Arg Leu Arg Phe Ile Pro Lys Pro
                565                 570                 575
Asp Gly Leu Arg Pro Ile Val Asn Met Asp Tyr Val Val Gly Ala Arg
                580                 585                 590
Thr Phe Arg Arg Glu Lys Arg Ala Glu Arg Leu Thr Ser Arg Val Lys
            595                 600                 605
Ala Leu Phe Ser Val Leu Asn Tyr Glu Arg Ala Arg Arg Pro Gly Leu
            610                 615                 620
Leu Gly Ala Ser Val Leu Gly Leu Asp Asp Ile His Arg Ala Trp Arg
625                 630                 635                 640
Thr Phe Val Leu Arg Val Arg Ala Gln Asp Pro Pro Glu Leu Tyr
                645                 650                 655
Phe Val Lys Val Asp Val Thr Gly Ala Tyr Asp Thr Ile Pro Gln Asp
                660                 665                 670
Arg Leu Thr Glu Val Ile Ala Ser Ile Ile Lys Pro Gln Asn Thr Tyr
            675                 680                 685
Cys Val Arg Arg Tyr Ala Val Val Gln Lys Ala Ala His Gly His Val
            690                 695                 700
Arg Lys Ala Phe Lys Ser His Val Leu Arg Pro Val Pro Gly Asp Pro
705                 710                 715                 720
Ala Gly Leu His Pro Leu His Ala Ala Leu Gln Pro Val Leu Arg Arg
                725                 730                 735
His Gly Glu Gln Ala Val Cys Gly Asp Ser Ala Gly Arg Ala Ala Pro
            740                 745                 750
Ala Phe Gly Gly
        755

<210> SEQ ID NO 62
<211> LENGTH: 841
<212> TYPE: PRT
<213> ORGANISM: Homo sapiens
<220> FEATURE:
<223> OTHER INFORMATION: Truncated Protein 2 (ver.2); encoded by SEQ ID
      NO:59 with Intron Y ORF3
```

-continued

```
<400> SEQUENCE: 62

Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Cys Val Pro Trp Asp Ala Arg Pro
    50                  55                  60

Pro Pro Ala Ala Pro Ser Phe Arg Gln Val Pro Pro Arg Gly Arg Arg
65                  70                  75                  80

Pro Ala Gly Val Glu Gly Gly Arg Gly Glu Pro Ala Thr Cys Gly Glu
                85                  90                  95

Gln Arg Arg Arg Leu Arg Ala Leu Pro Pro Gln Val Ser Cys Leu Lys
            100                 105                 110

Glu Leu Val Ala Arg Val Leu Gln Arg Leu Cys Glu Arg Gly Ala Lys
        115                 120                 125

Asn Val Leu Ala Phe Gly Phe Ala Leu Leu Asp Gly Ala Arg Gly Gly
130                 135                 140

Pro Pro Glu Ala Phe Thr Thr Ser Val Arg Ser Tyr Leu Pro Asn Thr
145                 150                 155                 160

Val Thr Asp Ala Leu Arg Gly Ser Gly Ala Trp Gly Leu Leu Leu Arg
                165                 170                 175

Arg Val Gly Asp Asp Val Leu Val His Leu Leu Ala Arg Cys Ala Leu
            180                 185                 190

Phe Val Leu Val Ala Pro Ser Cys Ala Tyr Gln Val Cys Gly Pro Pro
        195                 200                 205

Leu Tyr Gln Leu Gly Ala Ala Thr Gln Ala Arg Pro Pro His Ala
    210                 215                 220

Ser Gly Pro Arg Arg Leu Gly Cys Glu Arg Ala Trp Asn His Ser
225                 230                 235                 240

Val Arg Glu Ala Gly Val Pro Leu Gly Leu Pro Ala Pro Gly Ala Arg
                245                 250                 255

Arg Arg Gly Gly Ser Ala Ser Arg Ser Leu Pro Leu Pro Lys Arg Pro
            260                 265                 270

Arg Arg Gly Ala Ala Pro Glu Pro Glu Arg Thr Pro Val Gly Gln Gly
        275                 280                 285

Ser Trp Ala His Pro Gly Arg Thr Arg Gly Pro Ser Asp Arg Gly Phe
    290                 295                 300

Cys Val Val Ser Pro Ala Arg Pro Ala Glu Ala Thr Ser Leu Glu
305                 310                 315                 320

Gly Ala Leu Ser Gly Thr Arg His Ser His Pro Ser Val Gly Arg Gln
                325                 330                 335

His His Ala Gly Pro Pro Ser Thr Ser Arg Pro Pro Arg Pro Trp Asp
            340                 345                 350

Thr Pro Cys Pro Pro Val Tyr Ala Glu Thr Lys His Phe Leu Tyr Ser
        355                 360                 365

Ser Gly Asp Lys Glu Gln Leu Arg Pro Ser Phe Leu Leu Ser Ser Leu
    370                 375                 380

Arg Pro Ser Leu Thr Gly Ala Arg Arg Leu Val Glu Thr Ile Phe Leu
385                 390                 395                 400

Gly Ser Arg Pro Trp Met Pro Gly Thr Pro Arg Arg Leu Pro Arg Leu
                405                 410                 415
```

-continued

```
Pro Gln Arg Tyr Trp Gln Met Arg Pro Leu Phe Leu Glu Leu Leu Gly
            420                 425                 430

Asn His Ala Gln Cys Pro Tyr Gly Val Leu Leu Lys Thr His Cys Pro
            435                 440                 445

Leu Arg Ala Ala Val Thr Pro Ala Ala Gly Val Cys Ala Arg Glu Lys
            450                 455                 460

Pro Gln Gly Ser Val Ala Ala Pro Glu Glu Asp Thr Asp Pro Arg
465                 470                 475                 480

Arg Leu Val Gln Leu Leu Arg Gln His Ser Ser Pro Trp Gln Val Tyr
                485                 490                 495

Gly Phe Val Arg Ala Cys Leu Arg Arg Leu Val Pro Pro Gly Leu Trp
                500                 505                 510

Gly Ser Arg His Asn Glu Arg Arg Phe Leu Arg Asn Thr Lys Lys Phe
                515                 520                 525

Ile Ser Leu Gly Lys His Ala Lys Leu Ser Leu Gln Glu Leu Thr Trp
                530                 535                 540

Lys Met Ser Val Arg Asp Cys Ala Trp Leu Arg Arg Ser Pro Gly Val
545                 550                 555                 560

Gly Cys Val Pro Ala Ala Glu His Arg Leu Arg Glu Ile Leu Ala
                565                 570                 575

Lys Phe Leu His Trp Leu Met Ser Val Tyr Val Val Glu Leu Leu Arg
                580                 585                 590

Ser Phe Phe Tyr Val Thr Glu Thr Thr Phe Gln Lys Asn Arg Leu Phe
                595                 600                 605

Phe Tyr Arg Lys Ser Val Trp Ser Lys Leu Gln Ser Ile Gly Ile Arg
                610                 615                 620

Gln His Leu Lys Arg Val Gln Leu Arg Glu Leu Ser Glu Ala Glu Val
625                 630                 635                 640

Arg Gln His Arg Glu Ala Arg Pro Ala Leu Leu Thr Ser Arg Leu Arg
                645                 650                 655

Phe Ile Pro Lys Pro Asp Gly Leu Arg Pro Ile Val Asn Met Asp Tyr
                660                 665                 670

Val Val Gly Ala Arg Thr Phe Arg Arg Glu Lys Arg Ala Glu Arg Leu
                675                 680                 685

Thr Ser Arg Val Lys Ala Leu Phe Ser Val Leu Asn Tyr Glu Arg Ala
                690                 695                 700

Arg Arg Pro Gly Leu Leu Gly Ala Ser Val Leu Gly Leu Asp Asp Ile
705                 710                 715                 720

His Arg Ala Trp Arg Thr Phe Val Leu Arg Val Arg Ala Gln Asp Pro
                725                 730                 735

Pro Pro Glu Leu Tyr Phe Val Lys Val Asp Val Thr Gly Ala Tyr Asp
                740                 745                 750

Thr Ile Pro Gln Asp Arg Leu Thr Glu Val Ile Ala Ser Ile Ile Lys
                755                 760                 765

Pro Gln Asn Thr Tyr Cys Val Arg Arg Tyr Ala Val Val Gln Lys Ala
                770                 775                 780

Ala His Gly His Val Arg Lys Ala Phe Lys Ser His Val Leu Arg Pro
785                 790                 795                 800

Val Pro Gly Asp Pro Ala Gly Leu His Pro Leu His Ala Ala Leu Gln
                805                 810                 815

Pro Val Leu Arg Arg His Gly Glu Gln Ala Val Cys Gly Asp Ser Ala
                820                 825                 830
```

Gly Arg Ala Ala Pro Ala Phe Gly Gly
        835                 840

<210> SEQ ID NO 63
<211> LENGTH: 3500
<212> TYPE: DNA
<213> ORGANISM: Homo sapiens
<220> FEATURE:
<223> OTHER INFORMATION: Reference Protein (ver.2); with Introns Y,
      Alpha and Beta

<400> SEQUENCE: 63

| | | | | | |
|---|---|---|---|---|---|
| atgccgcgcg | ctccccgctg | ccgagccgtg | cgctccctgc | tgcgcagcca | ctaccgcgag | 60 |
| gtgctgccgc | tggccacgtt | cgtgcggcgc | ctggggcccc | agggctggcg | gctggtgcag | 120 |
| cgcggggacc | cggcggcttt | ccgcgcgctg | gtggcccagt | gcctggtgtg | cgtgccctgg | 180 |
| gacgcacggc | cgcccccgc | cgccccctcc | ttccgccagg | tgggcctccc | cggggtcggc | 240 |
| gtccggctgg | ggttgagggc | ggccgggggg | aaccagcgac | atgcggagag | cagcgcaggc | 300 |
| gactcagggc | gcttccccg | caggtgtcct | gcctgaagga | gctggtggcc | cgagtgctgc | 360 |
| agaggctgtg | cgagcgcggc | gcgaagaacg | tgctggcctt | cggcttcgcg | ctgctggacg | 420 |
| ggcccgcgg | gggcccccc | gaggccttca | ccaccagcgt | gcgcagctac | ctgcccaaca | 480 |
| cggtgaccga | cgcactgcgg | gggagcgggg | cgtggggggct | gctgttgcgc | gcgtggggcg | 540 |
| acgacgtgct | ggttcacctg | ctggcacgct | gcgcgctctt | tgtgctggtg | gctcccagct | 600 |
| gcgcctacca | ggtgtgcggg | ccgccgctgt | accagctcgg | cgctgccact | caggcccggc | 660 |
| ccccgccaca | cgctagtgga | ccccgaaggc | gtctgggatg | cgaacgggcc | tggaaccata | 720 |
| gcgtcaggga | ggccggggtc | ccctgggcc | tgccagcccc | gggtgcgagg | aggcgcgggg | 780 |
| gcagtgccag | ccgaagtctg | ccgttgccca | agaggcccag | gcgtggcgct | gccctgagc | 840 |
| cggagcggac | gcccgttggg | cagggtcct | gggcccaccc | gggcaggacg | cgtggaccga | 900 |
| gtgaccgtgg | tttctgtgtg | gtgtcacctg | ccagacccgc | cgaagaagcc | acctctttgg | 960 |
| agggtgcgct | ctctggcacg | cgccactccc | acccatccgt | gggccgccag | caccacgcgg | 1020 |
| gccccccatc | cacatcgcgg | ccaccacgtc | cctgggacac | gccttgtccc | ccggtgtacg | 1080 |
| ccgagaccaa | gcacttcctc | tactcctcag | gcgacaagga | gcagctgcgg | ccctccttcc | 1140 |
| tactcagctc | tctgaggccc | agcctgactg | gcgctcggag | gctcgtggag | accatctttc | 1200 |
| tgggttccag | gccctggatg | ccagggactc | cccgcaggtt | gccccgcctg | cccagcgct | 1260 |
| actggcaaat | gcggcccctg | tttctggagc | tgcttgggaa | ccacgcgcag | tgcccctacg | 1320 |
| gggtgctcct | caagacgcac | tgcccgctgc | gagctgcggt | cacccagca | gccggtgtct | 1380 |
| gtgcccggga | gaagccccag | ggctctgtgg | cggcccccga | ggaggaggac | acagacccc | 1440 |
| gtcgcctggt | gcagctgctc | cgccagcaca | gcagcccctg | gcaggtgtac | ggcttcgtgc | 1500 |
| gggcctgcct | cgcgccggctg | gtgccccag | gcctctgggg | ctccaggcac | aacgaacgcc | 1560 |
| gcttcctcag | gaacaccaag | aagttcatct | ccctgggaa | gcatgccaag | ctctcgctgc | 1620 |
| aggagctgac | gtggaagatg | agcgtgcggg | gctgcgcttg | gctgcgcagg | agcccagggg | 1680 |
| ttggctgtgt | tccggccgca | gagcaccgtc | tgcgtgagga | gatcctggcc | aagttcctgc | 1740 |
| actggctgat | gagtgtgtac | gtcgtcgagc | tgctcaggtc | tttctttat | gtcacggaga | 1800 |
| ccacgtttca | aaagaacagg | ctctttttct | accggaagag | tgtctggagc | aagttgcaaa | 1860 |
| gcattggaat | cagacagcac | ttgaagaggg | tgcagctgcg | ggagctgtcg | gaagcagagg | 1920 |
| tcaggcagca | tcgggaagcc | aggccccgcc | tgctgacgtc | cagactccgc | ttcatcccca | 1980 |

-continued

```
agcctgacgg gctgcggccg attgtgaaca tggactacgt cgtgggagcc agaacgttcc    2040
gcagagaaaa gagggccgag cgtctcacct cgagggtgaa ggcactgttc agcgtgctca    2100
actacgagcg ggcgcggcgc cccggcctcc tgggcgcctc tgtgctgggc ctggacgata    2160
tccacagggc ctggcgcacc ttcgtgctgc gtgtgcgggc ccaggacccg ccgcctgagc    2220
tgtactttgt caaggtggat gtgacgggcg cgtacgacac catcccccag gacaggctca    2280
cggaggtcat cgccagcatc atcaaacccc agaacacgta ctgcgtgcgt cggtatgccg    2340
tggtccagaa ggccgcccat gggcacgtcc gcaaggcctt caagagccac gtctctacct    2400
tgacagacct ccagccgtac atgcgacagt tcgtggctca cctgcaggag accagcccgc    2460
tgagggatgc cgtcgtcatc gagcagagct cctccctgaa tgaggccagc agtggcctct    2520
tcgacgtctt cctacgcttc atgtgccacc acgccgtgcg catcaggggc aagtcctacg    2580
tccagtgcca ggggatcccg cagggctcca tcctctccac gctgctctgc agcctgtgct    2640
acggcgacat ggagaacaag ctgtttgcgg ggattcggcg ggacgggctg ctcctgcgtt    2700
tggtggatga tttcttgttg gtgacacctc acctcaccca cgcgaaaacc ttcctcagga    2760
ccctggtccg aggtgtccct gagtatggct gcgtggtgaa cttgcggaag acagtggtga    2820
acttccctgt agaagacgag gccctgggtg gcacggcttt tgttcagatg ccggcccacg    2880
gcctattccc ctggtgcggc ctgctgctgg atacccggac cctggaggtg cagagcgact    2940
actccagcta tgcccggacc tccatcagag ccagtctcac cttcaaccgc ggcttcaagg    3000
ctgggaggaa catgcgtcgc aaactctttg gggtcttgcg gctgaagtgt cacagcctgt    3060
ttctggattt gcaggtgaac agcctccaga cggtgtgcac caacatctac aagatcctcc    3120
tgctgcaggc gtacaggttt cacgcatgtg tgctgcagct cccatttcat cagcaagttt    3180
ggaagaaccc cacattttc ctgcgcgtca tctctgacac ggcctccctc tgctactcca    3240
tcctgaaagc caagaacgca gggatgtcgc tgggggccaa gggcgccgcc ggccctctgc    3300
cctccgaggc cgtgcagtgg ctgtgccacc aagcattcct gctcaagctg actcgacacc    3360
gtgtcaccta cgtgccactc ctggggtcac tcaggacagc ccagacgcag ctgagtcgga    3420
agctcccggg gacgacgctg actgccctgg aggccgcagc caacccggca ctgccctcag    3480
acttcaagac catcctggac                                                 3500
```

<210> SEQ ID NO 64
<211> LENGTH: 1165
<212> TYPE: PRT
<213> ORGANISM: Homo sapiens
<220> FEATURE:
<223> OTHER INFORMATION: Reference Protein (ver.2); encoded by SEQ ID
      NO:63 with Intron Y ORF1

<400> SEQUENCE: 64

```
Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
                20                  25                  30

Pro Gln Gly Trp Arg Leu Val Gln Arg Gly Asp Pro Ala Ala Phe Arg
            35                  40                  45

Ala Leu Val Ala Gln Cys Leu Val Cys Val Pro Trp Asp Ala Arg Pro
        50                  55                  60

Pro Pro Ala Ala Pro Ser Phe Arg Gln Val Gly Leu Pro Gly Val Gly
    65                  70                  75                  80
```

-continued

```
Val Arg Leu Gly Leu Arg Ala Ala Gly Gly Asn Gln Arg His Ala Glu
                85                  90                  95

Ser Ser Ala Gly Asp Ser Gly Arg Phe Pro Arg Arg Ser Cys Leu Lys
            100                 105                 110

Glu Leu Val Ala Arg Val Leu Gln Arg Leu Cys Glu Arg Gly Ala Lys
        115                 120                 125

Asn Val Leu Ala Phe Gly Phe Ala Leu Leu Asp Gly Ala Arg Gly Gly
    130                 135                 140

Pro Pro Glu Ala Phe Thr Thr Ser Val Arg Ser Tyr Leu Pro Asn Thr
145                 150                 155                 160

Val Thr Asp Ala Leu Arg Gly Ser Gly Ala Trp Gly Leu Leu Leu Arg
                165                 170                 175

Arg Val Gly Asp Asp Val Leu Val His Leu Leu Ala Arg Cys Ala Leu
            180                 185                 190

Phe Val Leu Val Ala Pro Ser Cys Ala Tyr Gln Val Cys Gly Pro Pro
        195                 200                 205

Leu Tyr Gln Leu Gly Ala Ala Thr Gln Ala Arg Pro Pro His Ala
    210                 215                 220

Ser Gly Pro Arg Arg Leu Gly Cys Glu Arg Ala Trp Asn His Ser
225                 230                 235                 240

Val Arg Glu Ala Gly Val Pro Leu Gly Leu Pro Ala Pro Gly Ala Arg
                245                 250                 255

Arg Arg Gly Gly Ser Ala Ser Arg Ser Leu Pro Leu Pro Lys Arg Pro
            260                 265                 270

Arg Arg Gly Ala Ala Pro Glu Pro Glu Arg Thr Pro Val Gly Gln Gly
        275                 280                 285

Ser Trp Ala His Pro Gly Arg Thr Arg Gly Pro Ser Asp Arg Gly Phe
    290                 295                 300

Cys Val Val Ser Pro Ala Arg Pro Ala Glu Glu Ala Thr Ser Leu Glu
305                 310                 315                 320

Gly Ala Leu Ser Gly Thr Arg His Ser His Pro Ser Val Gly Arg Gln
                325                 330                 335

His His Ala Gly Pro Pro Ser Thr Ser Arg Pro Pro Arg Pro Trp Asp
            340                 345                 350

Thr Pro Cys Pro Pro Val Tyr Ala Glu Thr Lys His Phe Leu Tyr Ser
        355                 360                 365

Ser Gly Asp Lys Glu Gln Leu Arg Pro Ser Phe Leu Leu Ser Ser Leu
    370                 375                 380

Arg Pro Ser Leu Thr Gly Ala Arg Arg Leu Val Glu Thr Ile Phe Leu
385                 390                 395                 400

Gly Ser Arg Pro Trp Met Pro Gly Thr Pro Arg Arg Leu Pro Arg Leu
                405                 410                 415

Pro Gln Arg Tyr Trp Gln Met Arg Pro Leu Phe Leu Glu Leu Leu Gly
            420                 425                 430

Asn His Ala Gln Cys Pro Tyr Gly Val Leu Leu Lys Thr His Cys Pro
        435                 440                 445

Leu Arg Ala Ala Val Thr Pro Ala Ala Gly Val Cys Ala Arg Glu Lys
    450                 455                 460

Pro Gln Gly Ser Val Ala Ala Pro Glu Glu Asp Thr Asp Pro Arg
465                 470                 475                 480

Arg Leu Val Gln Leu Leu Arg Gln His Ser Ser Pro Trp Gln Val Tyr
                485                 490                 495

Gly Phe Val Arg Ala Cys Leu Arg Arg Leu Val Pro Pro Gly Leu Trp
```

-continued

```
            500                 505                 510
Gly Ser Arg His Asn Glu Arg Arg Phe Leu Arg Asn Thr Lys Lys Phe
            515                 520                 525
Ile Ser Leu Gly Lys His Ala Lys Leu Ser Leu Gln Glu Leu Thr Trp
    530                 535                 540
Lys Met Ser Val Arg Asp Cys Ala Trp Leu Arg Arg Ser Pro Gly Val
545                 550                 555                 560
Gly Cys Val Pro Ala Ala Glu His Arg Leu Arg Glu Ile Leu Ala
                565                 570                 575
Lys Phe Leu His Trp Leu Met Ser Val Tyr Val Glu Leu Leu Arg
            580                 585                 590
Ser Phe Phe Tyr Val Thr Glu Thr Phe Gln Lys Asn Arg Leu Phe
        595                 600                 605
Phe Tyr Arg Lys Ser Val Trp Ser Lys Leu Gln Ser Ile Gly Ile Arg
        610                 615                 620
Gln His Leu Lys Arg Val Gln Leu Arg Glu Leu Ser Glu Ala Glu Val
625                 630                 635                 640
Arg Gln His Arg Glu Ala Arg Pro Ala Leu Leu Thr Ser Arg Leu Arg
                645                 650                 655
Phe Ile Pro Lys Pro Asp Gly Leu Arg Pro Ile Val Asn Met Asp Tyr
            660                 665                 670
Val Val Gly Ala Arg Thr Phe Arg Arg Glu Lys Arg Ala Glu Arg Leu
        675                 680                 685
Thr Ser Arg Val Lys Ala Leu Phe Ser Val Leu Asn Tyr Glu Arg Ala
    690                 695                 700
Arg Arg Pro Gly Leu Leu Gly Ala Ser Val Leu Gly Leu Asp Asp Ile
705                 710                 715                 720
His Arg Ala Trp Arg Thr Phe Val Leu Arg Val Arg Ala Gln Asp Pro
                725                 730                 735
Pro Pro Glu Leu Tyr Phe Val Lys Val Asp Val Thr Gly Ala Tyr Asp
            740                 745                 750
Thr Ile Pro Gln Asp Arg Leu Thr Glu Val Ile Ala Ser Ile Ile Lys
        755                 760                 765
Pro Gln Asn Thr Tyr Cys Val Arg Arg Tyr Ala Val Val Gln Lys Ala
    770                 775                 780
Ala His Gly His Val Arg Lys Ala Phe Lys Ser His Val Ser Thr Leu
785                 790                 795                 800
Thr Asp Leu Gln Pro Tyr Met Arg Gln Phe Val Ala His Leu Gln Glu
                805                 810                 815
Thr Ser Pro Leu Arg Asp Ala Val Val Ile Glu Gln Ser Ser Ser Leu
            820                 825                 830
Asn Glu Ala Ser Ser Gly Leu Phe Asp Val Phe Leu Arg Phe Met Cys
        835                 840                 845
His His Ala Val Arg Ile Arg Gly Lys Ser Tyr Val Gln Cys Gln Gly
    850                 855                 860
Ile Pro Gln Gly Ser Ile Leu Ser Thr Leu Leu Cys Ser Leu Cys Tyr
865                 870                 875                 880
Gly Asp Met Glu Asn Lys Leu Phe Ala Gly Ile Arg Arg Asp Gly Leu
                885                 890                 895
Leu Leu Arg Leu Val Asp Asp Phe Leu Leu Val Thr Pro His Leu Thr
            900                 905                 910
His Ala Lys Thr Phe Leu Arg Thr Leu Val Arg Gly Val Pro Glu Tyr
        915                 920                 925
```

```
Gly Cys Val Val Asn Leu Arg Lys Thr Val Val Asn Phe Pro Val Glu
        930                 935                 940

Asp Glu Ala Leu Gly Gly Thr Ala Phe Val Gln Met Pro Ala His Gly
945                 950                 955                 960

Leu Phe Pro Trp Cys Gly Leu Leu Asp Thr Arg Thr Leu Glu Val
                965                 970                 975

Gln Ser Asp Tyr Ser Ser Tyr Ala Arg Thr Ser Ile Arg Ala Ser Leu
            980                 985                 990

Thr Phe Asn Arg Gly Phe Lys Ala Gly Arg Asn Met Arg Arg Lys Leu
        995                1000                1005

Phe Gly Val Leu Arg Leu Lys Cys His Ser Leu Phe Leu Asp Leu Gln
   1010                1015                1020

Val Asn Ser Leu Gln Thr Val Cys Thr Asn Ile Tyr Lys Ile Leu Leu
1025                1030                1035                1040

Leu Gln Ala Tyr Arg Phe His Ala Cys Val Leu Gln Leu Pro Phe His
            1045                1050                1055

Gln Gln Val Trp Lys Asn Pro Thr Phe Phe Leu Arg Val Ile Ser Asp
        1060                1065                1070

Thr Ser Leu Cys Tyr Ser Ile Leu Lys Ala Lys Asn Ala Gly Met Ser
   1075                1080                1085

Leu Gly Ala Lys Gly Ala Ala Gly Pro Leu Pro Ser Glu Ala Val Gln
1090                1095                1100

Trp Leu Cys His Gln Ala Phe Leu Leu Lys Leu Thr Arg His Arg Val
1105                1110                1115                1120

Thr Tyr Val Pro Leu Leu Gly Ser Leu Arg Thr Ala Gln Thr Gln Leu
            1125                1130                1135

Ser Arg Lys Leu Pro Gly Thr Thr Leu Thr Ala Leu Glu Ala Ala Ala
            1140                1145                1150

Asn Pro Ala Leu Pro Ser Asp Phe Lys Thr Ile Leu Asp
        1155                1160                1165

<210> SEQ ID NO 65
<211> LENGTH: 1081
<212> TYPE: PRT
<213> ORGANISM: Homo sapiens
<220> FEATURE:
<223> OTHER INFORMATION: Reference Protein (ver.2); encoded by SEQ ID
      NO:63 with Intron Y ORF2 after the termination codon

<400> SEQUENCE: 65

Gly Arg Pro Gly Gly Thr Ser Asp Met Arg Arg Ala Ala Gln Ala Thr
 1               5                  10                  15

Gln Gly Ala Ser Pro Ala Gly Ser Cys Leu Lys Glu Leu Val Ala Arg
            20                  25                  30

Val Leu Gln Arg Leu Cys Glu Arg Gly Ala Lys Asn Val Leu Ala Phe
        35                  40                  45

Gly Phe Ala Leu Leu Asp Gly Ala Arg Gly Gly Pro Pro Glu Ala Phe
    50                  55                  60

Thr Thr Ser Val Arg Ser Tyr Leu Pro Asn Thr Val Thr Asp Ala Leu
65                  70                  75                  80

Arg Gly Ser Gly Ala Trp Gly Leu Leu Arg Arg Val Gly Asp Asp
                85                  90                  95

Val Leu Val His Leu Leu Ala Arg Cys Ala Leu Phe Val Leu Val Ala
                100                 105                 110
```

-continued

Pro Ser Cys Ala Tyr Gln Val Cys Gly Pro Pro Leu Tyr Gln Leu Gly
    115                 120                 125

Ala Ala Thr Gln Ala Arg Pro Pro His Ala Ser Gly Pro Arg Arg
130                 135                 140

Arg Leu Gly Cys Glu Arg Ala Trp Asn His Ser Val Arg Glu Ala Gly
145                 150                 155                 160

Val Pro Leu Gly Leu Pro Ala Pro Gly Ala Arg Arg Gly Gly Ser
                165                 170                 175

Ala Ser Arg Ser Leu Pro Leu Pro Lys Arg Pro Arg Gly Ala Ala
                180                 185                 190

Pro Glu Pro Glu Arg Thr Pro Val Gly Gln Gly Ser Trp Ala His Pro
    195                 200                 205

Gly Arg Thr Arg Gly Pro Ser Asp Arg Gly Phe Cys Val Val Ser Pro
    210                 215                 220

Ala Arg Pro Ala Glu Glu Ala Thr Ser Leu Glu Gly Ala Leu Ser Gly
225                 230                 235                 240

Thr Arg His Ser His Pro Ser Val Gly Arg Gln His His Ala Gly Pro
                245                 250                 255

Pro Ser Thr Ser Arg Pro Pro Arg Pro Trp Asp Thr Pro Cys Pro Pro
                260                 265                 270

Val Tyr Ala Glu Thr Lys His Phe Leu Tyr Ser Ser Gly Asp Lys Glu
    275                 280                 285

Gln Leu Arg Pro Ser Phe Leu Leu Ser Ser Leu Arg Pro Ser Leu Thr
    290                 295                 300

Gly Ala Arg Arg Leu Val Glu Thr Ile Phe Leu Gly Ser Arg Pro Trp
305                 310                 315                 320

Met Pro Gly Thr Pro Arg Arg Leu Pro Arg Leu Pro Gln Arg Tyr Trp
                325                 330                 335

Gln Met Arg Pro Leu Phe Leu Glu Leu Leu Gly Asn His Ala Gln Cys
                340                 345                 350

Pro Tyr Gly Val Leu Leu Lys Thr His Cys Pro Leu Arg Ala Ala Val
                355                 360                 365

Thr Pro Ala Ala Gly Val Cys Ala Arg Glu Lys Pro Gln Gly Ser Val
    370                 375                 380

Ala Ala Pro Glu Glu Glu Asp Thr Asp Pro Arg Arg Leu Val Gln Leu
385                 390                 395                 400
Leu Arg Gln His Ser Ser Pro Trp Gln Val Tyr Gly Phe Val Arg Ala
                405                 410                 415
Cys Leu Arg Arg Leu Val Pro Pro Gly Leu Trp Gly Ser Arg His Asn
                420                 425                 430

Glu Arg Arg Phe Leu Arg Asn Thr Lys Lys Phe Ile Ser Leu Gly Lys
                435                 440                 445

His Ala Lys Leu Ser Leu Gln Glu Leu Thr Trp Lys Met Ser Val Arg
    450                 455                 460

Asp Cys Ala Trp Leu Arg Arg Ser Pro Gly Val Gly Cys Val Pro Ala
465                 470                 475                 480

Ala Glu His Arg Leu Arg Glu Glu Ile Leu Ala Lys Phe Leu His Trp
                485                 490                 495

Leu Met Ser Val Tyr Val Val Glu Leu Leu Arg Ser Phe Phe Tyr Val
                500                 505                 510

Thr Glu Thr Thr Phe Gln Lys Asn Arg Leu Phe Phe Tyr Arg Lys Ser
    515                 520                 525

Val Trp Ser Lys Leu Gln Ser Ile Gly Ile Arg Gln His Leu Lys Arg

```
                530                 535                 540
Val Gln Leu Arg Glu Leu Ser Glu Ala Glu Val Arg Gln His Arg Glu
545                 550                 555                 560

Ala Arg Pro Ala Leu Leu Thr Ser Arg Leu Arg Phe Ile Pro Lys Pro
                565                 570                 575

Asp Gly Leu Arg Pro Ile Val Asn Met Asp Tyr Val Gly Ala Arg
                580                 585                 590

Thr Phe Arg Arg Glu Lys Arg Ala Glu Arg Leu Thr Ser Arg Val Lys
                595                 600                 605

Ala Leu Phe Ser Val Leu Asn Tyr Glu Arg Ala Arg Pro Gly Leu
610                 615                 620

Leu Gly Ala Ser Val Leu Gly Leu Asp Asp Ile His Arg Ala Trp Arg
625                 630                 635                 640

Thr Phe Val Leu Arg Val Arg Ala Gln Asp Pro Pro Glu Leu Tyr
                645                 650                 655

Phe Val Lys Val Asp Val Thr Gly Ala Tyr Asp Thr Ile Pro Gln Asp
                660                 665                 670

Arg Leu Thr Glu Val Ile Ala Ser Ile Ile Lys Pro Gln Asn Thr Tyr
                675                 680                 685

Cys Val Arg Arg Tyr Ala Val Val Gln Lys Ala Ala His Gly His Val
                690                 695                 700

Arg Lys Ala Phe Lys Ser His Val Ser Thr Leu Thr Asp Leu Gln Pro
705                 710                 715                 720

Tyr Met Arg Gln Phe Val Ala His Leu Gln Glu Thr Ser Pro Leu Arg
                725                 730                 735

Asp Ala Val Val Ile Glu Gln Ser Ser Ser Leu Asn Glu Ala Ser Ser
                740                 745                 750

Gly Leu Phe Asp Val Phe Leu Arg Phe Met Cys His His Ala Val Arg
                755                 760                 765

Ile Arg Gly Lys Ser Tyr Val Gln Cys Gln Gly Ile Pro Gln Gly Ser
                770                 775                 780

Ile Leu Ser Thr Leu Leu Cys Ser Leu Cys Tyr Gly Asp Met Glu Asn
785                 790                 795                 800

Lys Leu Phe Ala Gly Ile Arg Arg Asp Gly Leu Leu Leu Arg Leu Val
                805                 810                 815

Asp Asp Phe Leu Leu Val Thr Pro His Leu Thr His Ala Lys Thr Phe
                820                 825                 830

Leu Arg Thr Leu Val Arg Gly Val Pro Glu Tyr Gly Cys Val Val Asn
                835                 840                 845

Leu Arg Lys Thr Val Val Asn Phe Pro Val Glu Asp Glu Ala Leu Gly
850                 855                 860

Gly Thr Ala Phe Val Gln Met Pro Ala His Gly Leu Phe Pro Trp Cys
865                 870                 875                 880

Gly Leu Leu Leu Asp Thr Arg Thr Leu Glu Val Gln Ser Asp Tyr Ser
                885                 890                 895

Ser Tyr Ala Arg Thr Ser Ile Arg Ala Ser Leu Thr Phe Asn Arg Gly
                900                 905                 910

Phe Lys Ala Gly Arg Asn Met Arg Arg Lys Leu Phe Gly Val Leu Arg
                915                 920                 925

Leu Lys Cys His Ser Leu Phe Leu Asp Leu Gln Val Asn Ser Leu Gln
                930                 935                 940

Thr Val Cys Thr Asn Ile Tyr Lys Ile Leu Leu Leu Gln Ala Tyr Arg
945                 950                 955                 960
```

-continued

```
Phe His Ala Cys Val Leu Gln Leu Pro Phe His Gln Val Trp Lys
            965                 970                 975

Asn Pro Thr Phe Phe Leu Arg Val Ile Ser Asp Thr Ala Ser Leu Cys
            980                 985                 990

Tyr Ser Ile Leu Lys Ala Lys Asn Ala Gly Met Ser Leu Gly Ala Lys
            995                1000                1005

Gly Ala Ala Gly Pro Leu Pro Ser Glu Ala Val Gln Trp Leu Cys His
    1010                1015                1020

Gln Ala Phe Leu Leu Lys Leu Thr Arg His Arg Val Thr Tyr Val Pro
1025                1030                1035                1040

Leu Leu Gly Ser Leu Arg Thr Ala Gln Thr Gln Leu Ser Arg Lys Leu
                1045                1050                1055

Pro Gly Thr Thr Leu Thr Ala Leu Glu Ala Ala Ala Asn Pro Ala Leu
                1060                1065                1070

Pro Ser Asp Phe Lys Thr Ile Leu Asp
            1075                1080
```

<210> SEQ ID NO 66
<211> LENGTH: 1165
<212> TYPE: PRT
<213> ORGANISM: Homo sapiens
<220> FEATURE:
<223> OTHER INFORMATION: Reference Protein (ver.2); encoded by SEQ ID
      NO:63 with Intron Y ORF3

<400> SEQUENCE: 66

```
Met Pro Arg Ala Pro Arg Cys Arg Ala Val Arg Ser Leu Leu Arg Ser
  1               5                  10                  15

His Tyr Arg Glu Val Leu Pro Leu Ala Thr Phe Val Arg Arg Leu Gly
             20                  25                  30

Pro Gln Gly Trp Arg Leu Val Gln Arg Gly Asp Pro Ala Ala Phe Arg
         35                  40                  45

Ala Leu Val Ala Gln Cys Leu Val Cys Val Pro Trp Asp Ala Arg Pro
     50                  55                  60

Pro Pro Ala Ala Pro Ser Phe Arg Gln Val Pro Arg Gly Arg Arg
 65                  70                  75                  80

Pro Ala Gly Val Glu Gly Gly Arg Gly Glu Pro Ala Thr Cys Gly Glu
                 85                  90                  95

Gln Arg Arg Arg Leu Arg Ala Leu Pro Pro Gln Val Ser Cys Leu Lys
            100                 105                 110

Glu Leu Val Ala Arg Val Leu Gln Arg Leu Cys Glu Arg Gly Ala Lys
        115                 120                 125

Asn Val Leu Ala Phe Gly Phe Ala Leu Leu Asp Gly Ala Arg Gly Gly
    130                 135                 140

Pro Pro Glu Ala Phe Thr Thr Ser Val Arg Ser Tyr Leu Pro Asn Thr
145                 150                 155                 160

Val Thr Asp Ala Leu Arg Gly Ser Gly Ala Trp Gly Leu Leu Leu Arg
                165                 170                 175

Arg Val Gly Asp Asp Val Leu Val His Leu Leu Ala Arg Cys Ala Leu
            180                 185                 190

Phe Val Leu Val Ala Pro Ser Cys Ala Tyr Gln Val Cys Gly Pro Pro
        195                 200                 205

Leu Tyr Gln Leu Gly Ala Ala Thr Gln Ala Arg Pro Pro Pro His Ala
    210                 215                 220

Ser Gly Pro Arg Arg Arg Leu Gly Cys Glu Arg Ala Trp Asn His Ser
```

-continued

```
               225                 230                 235                 240
       Val Arg Glu Ala Gly Val Pro Leu Gly Leu Pro Ala Pro Gly Ala Arg
                       245                 250                 255

Arg Arg Gly Gly Ser Ala Ser Arg Ser Leu Pro Leu Pro Lys Arg Pro
                       260                 265                 270

Arg Arg Gly Ala Ala Pro Glu Pro Glu Arg Thr Pro Val Gly Gln Gly
                       275                 280                 285

Ser Trp Ala His Pro Gly Arg Thr Arg Gly Pro Ser Asp Arg Gly Phe
               290                 295                 300

Cys Val Val Ser Pro Ala Arg Pro Ala Glu Ala Thr Ser Leu Glu
       305                 310                 315                 320

Gly Ala Leu Ser Gly Thr Arg His Ser His Pro Ser Val Gly Arg Gln
                       325                 330                 335

His His Ala Gly Pro Pro Ser Thr Ser Arg Pro Pro Arg Pro Trp Asp
                       340                 345                 350

Thr Pro Cys Pro Pro Val Tyr Ala Glu Thr Lys His Phe Leu Tyr Ser
                       355                 360                 365

Ser Gly Asp Lys Glu Gln Leu Arg Pro Ser Phe Leu Leu Ser Ser Leu
               370                 375                 380

Arg Pro Ser Leu Thr Gly Ala Arg Arg Leu Val Glu Thr Ile Phe Leu
       385                 390                 395                 400

Gly Ser Arg Pro Trp Met Pro Gly Thr Pro Arg Arg Leu Pro Arg Leu
                       405                 410                 415

Pro Gln Arg Tyr Trp Gln Met Arg Pro Leu Phe Leu Glu Leu Leu Gly
                       420                 425                 430

Asn His Ala Gln Cys Pro Tyr Gly Val Leu Leu Lys Thr His Cys Pro
                       435                 440                 445

Leu Arg Ala Ala Val Thr Pro Ala Ala Gly Val Cys Ala Arg Glu Lys
               450                 455                 460

Pro Gln Gly Ser Val Ala Ala Pro Glu Glu Glu Asp Thr Asp Pro Arg
       465                 470                 475                 480

Arg Leu Val Gln Leu Leu Arg Gln His Ser Ser Pro Trp Gln Val Tyr
                       485                 490                 495

Gly Phe Val Arg Ala Cys Leu Arg Arg Leu Val Pro Pro Gly Leu Trp
                       500                 505                 510

Gly Ser Arg His Asn Glu Arg Arg Phe Leu Arg Asn Thr Lys Lys Phe
                       515                 520                 525

Ile Ser Leu Gly Lys His Ala Lys Leu Ser Leu Gln Glu Leu Thr Trp
               530                 535                 540

Lys Met Ser Val Arg Asp Cys Ala Trp Leu Arg Arg Ser Pro Gly Val
       545                 550                 555                 560

Gly Cys Val Pro Ala Ala Glu His Arg Leu Arg Glu Glu Ile Leu Ala
                       565                 570                 575

Lys Phe Leu His Trp Leu Met Ser Val Tyr Val Val Glu Leu Leu Arg
                       580                 585                 590

Ser Phe Phe Tyr Val Thr Glu Thr Thr Phe Gln Lys Asn Arg Leu Phe
                       595                 600                 605

Phe Tyr Arg Lys Ser Val Trp Ser Lys Leu Gln Ser Ile Gly Ile Arg
                       610                 615                 620

Gln His Leu Lys Arg Val Gln Leu Arg Glu Leu Ser Glu Ala Glu Val
       625                 630                 635                 640

Arg Gln His Arg Glu Ala Arg Pro Ala Leu Leu Thr Ser Arg Leu Arg
                       645                 650                 655
```

-continued

```
Phe Ile Pro Lys Pro Asp Gly Leu Arg Pro Ile Val Asn Met Asp Tyr
            660                 665                 670
Val Val Gly Ala Arg Thr Phe Arg Arg Glu Lys Arg Ala Glu Arg Leu
        675                 680                 685
Thr Ser Arg Val Lys Ala Leu Phe Ser Val Leu Asn Tyr Glu Arg Ala
    690                 695                 700
Arg Arg Pro Gly Leu Leu Gly Ala Ser Val Leu Gly Leu Asp Asp Ile
705                 710                 715                 720
His Arg Ala Trp Arg Thr Phe Val Leu Arg Val Arg Ala Gln Asp Pro
                725                 730                 735
Pro Pro Glu Leu Tyr Phe Val Lys Val Asp Val Thr Gly Ala Tyr Asp
            740                 745                 750
Thr Ile Pro Gln Asp Arg Leu Thr Glu Val Ile Ala Ser Ile Ile Lys
        755                 760                 765
Pro Gln Asn Thr Tyr Cys Val Arg Arg Tyr Ala Val Val Gln Lys Ala
    770                 775                 780
Ala His Gly His Val Arg Lys Ala Phe Lys Ser His Val Ser Thr Leu
785                 790                 795                 800
Thr Asp Leu Gln Pro Tyr Met Arg Gln Phe Val Ala His Leu Gln Glu
                805                 810                 815
Thr Ser Pro Leu Arg Asp Ala Val Val Ile Glu Gln Ser Ser Ser Leu
            820                 825                 830
Asn Glu Ala Ser Ser Gly Leu Phe Asp Val Phe Leu Arg Phe Met Cys
        835                 840                 845
His His Ala Val Arg Ile Arg Gly Lys Ser Tyr Val Gln Cys Gln Gly
    850                 855                 860
Ile Pro Gln Gly Ser Ile Leu Ser Thr Leu Leu Cys Ser Leu Cys Tyr
865                 870                 875                 880
Gly Asp Met Glu Asn Lys Leu Phe Ala Gly Ile Arg Arg Asp Gly Leu
                885                 890                 895
Leu Leu Arg Leu Val Asp Asp Phe Leu Leu Val Thr Pro His Leu Thr
            900                 905                 910
His Ala Lys Thr Phe Leu Arg Thr Leu Val Arg Gly Val Pro Glu Tyr
        915                 920                 925
Gly Cys Val Val Asn Leu Arg Lys Thr Val Val Asn Phe Pro Val Glu
    930                 935                 940
Asp Glu Ala Leu Gly Gly Thr Ala Phe Val Gln Met Pro Ala His Gly
945                 950                 955                 960
Leu Phe Pro Trp Cys Gly Leu Leu Leu Asp Thr Arg Thr Leu Glu Val
                965                 970                 975
Gln Ser Asp Tyr Ser Ser Tyr Ala Arg Thr Ser Ile Arg Ala Ser Leu
            980                 985                 990
Thr Phe Asn Arg Gly Phe Lys Ala Gly Arg Asn Met Arg Arg Lys Leu
        995                 1000                1005
Phe Gly Val Leu Arg Leu Lys Cys His Ser Leu Phe Leu Asp Leu Gln
    1010                1015                1020
Val Asn Ser Leu Gln Thr Val Cys Thr Asn Ile Tyr Lys Ile Leu Leu
1025                1030                1035                1040
Leu Gln Ala Tyr Arg Phe His Ala Cys Val Leu Gln Leu Pro Phe His
                1045                1050                1055
Gln Gln Val Trp Lys Asn Pro Thr Phe Phe Leu Arg Val Ile Ser Asp
            1060                1065                1070
```

-continued

```
Thr Ser Leu Cys Tyr Ser Ile Leu Lys Ala Lys Asn Ala Gly Met Ser
        1075                1080                1085
Leu Gly Ala Lys Gly Ala Ala Gly Pro Leu Pro Ser Glu Ala Val Gln
    1090                1095                1100
Trp Leu Cys His Gln Ala Phe Leu Leu Lys Leu Thr Arg His Arg Val
1105                1110                1115                1120
Thr Tyr Val Pro Leu Leu Gly Ser Leu Arg Thr Ala Gln Thr Gln Leu
            1125                1130                1135
Ser Arg Lys Leu Pro Gly Thr Thr Leu Thr Ala Leu Glu Ala Ala Ala
        1140                1145                1150
Asn Pro Ala Leu Pro Ser Asp Phe Lys Thr Ile Leu Asp
        1155                1160                1165

<210> SEQ ID NO 67
<211> LENGTH: 3173
<212> TYPE: DNA
<213> ORGANISM: Homo sapiens
<220> FEATURE:
<223> OTHER INFORMATION: Truncated Protein (ver.2); with Introns Y,
      Alpha, Beta and 2

<400> SEQUENCE: 67
atgccgcgcg ctccccgctg ccgagccgtg cgctccctgc tgcgcagcca ctaccgcgag      60
gtgctgccgc tggccacgtt cgtgcggcgc ctggggcccc aggctggcg gctggtgcag     120
cgcggggacc cggcggcttt ccgcgcgctg gtggcccagt gcctggtgtg cgtgccctgg     180
gacgcacggc cgcccccgc cgcccccctcc ttccgcaggt tgggcctccc cggggtcggc     240
gtccggctgg ggttgagggc ggccgggggg aaccagcgac atgcggagag cagcgcaggc     300
gactcagggc gcttccccg caggtgtcct gcctgaagga gctggtggcc cgagtgctgc     360
agaggctgtg cgagcgcggc gcgaagaacg tgctggcctt cggcttcgcg ctgctggacg     420
gggcccgcgg gggccccccc gaggccttca ccaccagcgt gcgcagctac ctgcccaaca     480
cggtgaccga cgcactgcgg gggagcgggg cgtgggggct gctgctgcgc gcgtgggcg     540
acgacgtgct ggttcacctg ctggcacgct gcgcgctctt tgtgctggtg gctcccagct     600
gcgcctacca ggtgtgcggg ccgccgctgt accagctcgg cgctgccact caggcccggc     660
ccccgccaca cgctagtgga ccccgaaggc gtctgggatg cgaacgggcc tggaaccata     720
gcgtcaggga ggccggggtc ccctggggcc tgccagcccc gggtgcgagg aggcgcgggg     780
gcagtgccag ccgaagtctg ccgttgccca agaggcccag gcgtggcgct gcccctgagc     840
cggagcggac gcccgttggg caggggtcct gggcccaccc gggcaggacg cgtggaccga     900
gtgaccgtgg tttctgtgtg gtgtcacctg ccagacccgc cgaagaagcc acctctttgg     960
agggtgcgct ctctggcacg cgccactccc acccatccgt gggccgccag caccacgcgg    1020
gcccccatc cacatcgcgg ccaccacgtc cctgggacac gccttgtccc ccggtgtacg    1080
ccgagaccaa gcacttcctc tactcctcag gcgacaagga gcagctgcgg ccctccttcc    1140
tactcagctc tctgaggccc agcctgactg gcgctcggag gctcgtggag accatctttc    1200
tgggttccag gccctggatg ccagggactc cccgcaggtt gccccgcctg ccccagcgct    1260
actggcaaat gcggcccctg tttctggagc tgcttgggaa ccacgcgcag tgcccctacg    1320
gggtgctcct caagacgcac tgcccgctgc gagctgcggt caccccagca gccggtgtct    1380
gtgcccggga gaagcccag ggctctgtgg cggcccccga ggaggaggac acagaccccc    1440
gtcgcctggt gcagctgctc cgccagcaca gcagcccctg gcaggtgtac ggcttcgtgc    1500
```

```
gggcctgcct gcgccggctg gtgcccccag gcctctgggg ctccaggcac aacgaacgcc    1560
gcttcctcag gaacaccaag aagttcatct ccctggggaa gcatgccaag ctctcgctgc    1620
aggagctgac gtggaagatg agcgtgcggg actgcgcttg gctgcgcagg agcccagggg    1680
ttggctgtgt tccggccgca gagcaccgtc tgcgtgagga tcctggcc aagttcctgc     1740
actggctgat gagtgtgtac gtcgtcgagc tgctcaggtc tttcttttat gtcacggaga    1800
ccacgtttca aagaacagg ctcttttct accggaagag tgtctggagc aagttgcaaa     1860
gcattggaat cagacagcac ttgaagaggg tgcagctgcg ggagctgtcg aagcagagg     1920
tcaggcagca tcgggaagcc aggcccgccc tgctgacgtc cagactccgc ttcatcccca    1980
agcctgacgg gctgcggccg attgtgaaca tggactacgt cgtgggagcc agaacgttcc    2040
gcagagaaaa gagggccgag cgtctcacct cgagggtgaa ggcactgttc agcgtgctca    2100
actacgagcg ggcgcggcgc cccggcctcc tgggcgcctc tgtgctgggc ctggacgata    2160
tccacagggc ctggcgcacc ttcgtgctgc gtgtgcgggc ccaggacccg ccgcctgagc    2220
tgtactttgt caaggtggat gtgacgggcg cgtacgacac catcccccag gacaggctca    2280
cggaggtcat cgccagcatc atcaaacccc agaacacgta ctgcgtgcgt cggtatgccg    2340
tggtccagaa ggccgcccat gggcacgtcc gcaaggcctt caagagccac gtctctacct    2400
tgacagacct ccagccgtac atgcgacagt tcgtggctca cctgcaggag accagcccgc    2460
tgagggatgc cgtcgtcatc gagcagagct cctccctgaa tgaggccagc agtggcctct    2520
tcgacgtctt cctacgcttc atgtgccacc acgccgtgcg catcagggc aagtcctacg     2580
tccagtgcca ggggatcccg cagggctcca tcctctccac gctgctctgc agcctgtgct    2640
acggcgacat ggagaacaag ctgttttgcgg ggattcggcg ggacgggctg ctcctgcgtt    2700
tggtggatga tttcttgttg gtgacacctc acctcaccca cgcgaaaacc ttcctcagga    2760
ccctggtccg aggtgtccct gagtatggct gcgtggtgaa cttgcggaag acagtggtga    2820
acttccctgt agaagacgag gccctggtg gcacggcttt tgttcagatg ccggcccacg    2880
gcctattccc ctggtgcggc ctgctgctgg atacccggac cctggagtg cagagcgact    2940
actccaggtg agcgcacctg gccggaagtg gagcctgtgc ccggctgggg caggtgctgc    3000
tgcagggccg ttgcgtccac ctctgcttcc gtgtggggca ggcgactgcc aatcccaaag    3060
ggtcagatgc cacagggtgc ccctcgtccc atctgggct gagcacaaat gcatctttct    3120
gtgggagtga gggtgcctca caacgggagc agttttctgt gctatttttgg taa          3173
```

<210> SEQ ID NO 68
<211> LENGTH: 982
<212> TYPE: PRT
<213> ORGANISM: Homo sapiens
<220> FEATURE:
<223> OTHER INFORMATION: Truncated Protein 3 (ver.2); encoded by SEQ ID
      NO:67 with Intron Y ORF1

<400> SEQUENCE: 68

Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

```
Pro Pro Ala Ala Pro Ser Phe Arg Gln Val Gly Leu Pro Gly Val Gly
 65                  70                  75                  80

Val Arg Leu Gly Leu Arg Ala Ala Gly Gly Asn Gln Arg His Ala Glu
                 85                  90                  95

Ser Ser Ala Gly Asp Ser Gly Arg Phe Pro Arg Arg Ser Cys Leu Lys
            100                 105                 110

Glu Leu Val Ala Arg Val Leu Gln Arg Leu Cys Glu Arg Gly Ala Lys
            115                 120                 125

Asn Val Leu Ala Phe Gly Phe Ala Leu Leu Asp Gly Ala Arg Gly Gly
            130                 135                 140

Pro Pro Glu Ala Phe Thr Thr Ser Val Arg Ser Tyr Leu Pro Asn Thr
145                 150                 155                 160

Val Thr Asp Ala Leu Arg Gly Ser Gly Ala Trp Gly Leu Leu Leu Arg
                165                 170                 175

Arg Val Gly Asp Asp Val Leu Val His Leu Leu Ala Arg Cys Ala Leu
            180                 185                 190

Phe Val Leu Val Ala Pro Ser Cys Ala Tyr Gln Val Cys Gly Pro Pro
            195                 200                 205

Leu Tyr Gln Leu Gly Ala Ala Thr Gln Ala Arg Pro Pro His Ala
    210                 215                 220

Ser Gly Pro Arg Arg Leu Gly Cys Glu Arg Ala Trp Asn His Ser
225                 230                 235                 240

Val Arg Glu Ala Gly Val Pro Leu Gly Leu Pro Ala Pro Gly Ala Arg
                245                 250                 255

Arg Arg Gly Gly Ser Ala Ser Arg Ser Leu Pro Leu Pro Lys Arg Pro
            260                 265                 270

Arg Arg Gly Ala Ala Pro Glu Pro Glu Arg Thr Pro Val Gly Gln Gly
            275                 280                 285

Ser Trp Ala His Pro Gly Arg Thr Arg Gly Pro Ser Asp Arg Gly Phe
    290                 295                 300

Cys Val Val Ser Pro Ala Arg Pro Ala Glu Glu Ala Thr Ser Leu Glu
305                 310                 315                 320

Gly Ala Leu Ser Gly Thr Arg His Ser His Pro Ser Val Gly Arg Gln
                325                 330                 335

His His Ala Gly Pro Pro Ser Thr Ser Arg Pro Pro Arg Pro Trp Asp
            340                 345                 350

Thr Pro Cys Pro Pro Val Tyr Ala Glu Thr Lys His Phe Leu Tyr Ser
            355                 360                 365

Ser Gly Asp Lys Glu Gln Leu Arg Pro Ser Phe Leu Leu Ser Ser Leu
    370                 375                 380

Arg Pro Ser Leu Thr Gly Ala Arg Arg Leu Val Glu Thr Ile Phe Leu
385                 390                 395                 400

Gly Ser Arg Pro Trp Met Pro Gly Thr Pro Arg Arg Leu Pro Arg Leu
                405                 410                 415

Pro Gln Arg Tyr Trp Gln Met Arg Pro Leu Phe Leu Glu Leu Leu Gly
            420                 425                 430

Asn His Ala Gln Cys Pro Tyr Gly Val Leu Leu Lys Thr His Cys Pro
            435                 440                 445

Leu Arg Ala Ala Val Thr Pro Ala Ala Gly Val Cys Ala Arg Glu Lys
    450                 455                 460

Pro Gln Gly Ser Val Ala Ala Pro Glu Glu Glu Asp Thr Asp Pro Arg
465                 470                 475                 480

Arg Leu Val Gln Leu Leu Arg Gln His Ser Ser Pro Trp Gln Val Tyr
```

-continued

```
                485                 490                 495
Gly Phe Val Arg Ala Cys Leu Arg Arg Leu Val Pro Pro Gly Leu Trp
            500                 505                 510
Gly Ser Arg His Asn Glu Arg Arg Phe Leu Arg Asn Thr Lys Lys Phe
            515                 520                 525
Ile Ser Leu Gly Lys His Ala Lys Leu Ser Leu Gln Glu Leu Thr Trp
            530                 535                 540
Lys Met Ser Val Arg Asp Cys Ala Trp Leu Arg Arg Ser Pro Gly Val
545                 550                 555                 560
Gly Cys Val Pro Ala Ala Glu His Arg Leu Arg Glu Glu Ile Leu Ala
            565                 570                 575
Lys Phe Leu His Trp Leu Met Ser Val Tyr Val Glu Leu Leu Arg
            580                 585                 590
Ser Phe Phe Tyr Val Thr Glu Thr Thr Phe Gln Lys Asn Arg Leu Phe
            595                 600                 605
Phe Tyr Arg Lys Ser Val Trp Ser Lys Leu Gln Ser Ile Gly Ile Arg
            610                 615                 620
Gln His Leu Lys Arg Val Gln Leu Arg Glu Leu Ser Glu Ala Glu Val
625                 630                 635                 640
Arg Gln His Arg Glu Ala Arg Pro Ala Leu Leu Thr Ser Arg Leu Arg
            645                 650                 655
Phe Ile Pro Lys Pro Asp Gly Leu Arg Pro Ile Val Asn Met Asp Tyr
            660                 665                 670
Val Val Gly Ala Arg Thr Phe Arg Arg Glu Lys Arg Ala Glu Arg Leu
            675                 680                 685
Thr Ser Arg Val Lys Ala Leu Phe Ser Val Leu Asn Tyr Glu Arg Ala
            690                 695                 700
Arg Arg Pro Gly Leu Leu Gly Ala Ser Val Leu Gly Leu Asp Asp Ile
705                 710                 715                 720
His Arg Ala Trp Arg Thr Phe Val Leu Arg Val Arg Ala Gln Asp Pro
            725                 730                 735
Pro Pro Glu Leu Tyr Phe Val Lys Val Asp Val Thr Gly Ala Tyr Asp
            740                 745                 750
Thr Ile Pro Gln Asp Arg Leu Thr Glu Val Ile Ala Ser Ile Ile Lys
            755                 760                 765
Pro Gln Asn Thr Tyr Cys Val Arg Arg Tyr Ala Val Val Gln Lys Ala
            770                 775                 780
Ala His Gly His Val Arg Lys Ala Phe Lys Ser His Val Ser Thr Leu
785                 790                 795                 800
Thr Asp Leu Gln Pro Tyr Met Arg Gln Phe Val Ala His Leu Gln Glu
            805                 810                 815
Thr Ser Pro Leu Arg Asp Ala Val Val Ile Glu Gln Ser Ser Ser Leu
            820                 825                 830
Asn Glu Ala Ser Ser Gly Leu Phe Asp Val Phe Leu Arg Phe Met Cys
            835                 840                 845
His His Ala Val Arg Ile Arg Gly Lys Ser Tyr Val Gln Cys Gln Gly
            850                 855                 860
Ile Pro Gln Gly Ser Ile Leu Ser Thr Leu Leu Cys Ser Leu Cys Tyr
865                 870                 875                 880
Gly Asp Met Glu Asn Lys Leu Phe Ala Gly Ile Arg Arg Asp Gly Leu
            885                 890                 895
Leu Leu Arg Leu Val Asp Asp Phe Leu Leu Val Thr Pro His Leu Thr
            900                 905                 910
```

-continued

His Ala Lys Thr Phe Leu Arg Thr Leu Val Arg Gly Val Pro Glu Tyr
            915                 920                 925

Gly Cys Val Val Asn Leu Arg Lys Thr Val Val Asn Phe Pro Val Glu
            930                 935                 940

Asp Glu Ala Leu Gly Gly Thr Ala Phe Val Gln Met Pro Ala His Gly
945                 950                 955                 960

Leu Phe Pro Trp Cys Gly Leu Leu Leu Asp Thr Arg Thr Leu Glu Val
                965                 970                 975

Gln Ser Asp Tyr Ser Arg
            980

<210> SEQ ID NO 69
<211> LENGTH: 897
<212> TYPE: PRT
<213> ORGANISM: Homo sapiens
<220> FEATURE:
<223> OTHER INFORMATION: Truncated Protein 3 (ver.2); encoded by SEQ ID
      NO:67 with Intron Y ORF2 after the termination
      codon

<400> SEQUENCE: 69

Gly Arg Pro Gly Gly Thr Ser Asp Met Arg Arg Ala Ala Gln Ala Thr
1               5                   10                  15

Gln Gly Ala Ser Pro Ala Gly Ser Cys Leu Lys Glu Leu Val Ala Arg
            20                  25                  30

Val Leu Gln Arg Leu Cys Glu Arg Gly Ala Lys Asn Val Leu Ala Phe
        35                  40                  45

Gly Phe Ala Leu Leu Asp Gly Ala Arg Gly Gly Pro Pro Glu Ala Phe
    50                  55                  60

Thr Thr Ser Val Arg Ser Tyr Leu Pro Asn Thr Val Thr Asp Ala Leu
65                  70                  75                  80

Arg Gly Ser Gly Ala Trp Gly Leu Leu Leu Arg Arg Val Gly Asp Asp
                85                  90                  95

Val Leu Val His Leu Leu Ala Arg Cys Ala Leu Phe Val Leu Val Ala
            100                 105                 110

Pro Ser Cys Ala Tyr Gln Val Cys Gly Pro Pro Leu Tyr Gln Leu Gly
        115                 120                 125

Ala Ala Thr Gln Ala Arg Pro Pro His Ala Ser Gly Pro Arg Arg
    130                 135                 140

Arg Leu Gly Cys Glu Arg Ala Trp Asn His Ser Val Arg Glu Ala Gly
145                 150                 155                 160

Val Pro Leu Gly Leu Pro Ala Pro Gly Ala Arg Arg Gly Gly Ser
                165                 170                 175

Ala Ser Arg Ser Leu Pro Leu Pro Lys Arg Pro Arg Arg Gly Ala Ala
            180                 185                 190

Pro Glu Pro Glu Arg Thr Pro Val Gly Gln Gly Ser Trp Ala His Pro
        195                 200                 205

Gly Arg Thr Arg Gly Pro Ser Asp Arg Gly Phe Cys Val Val Ser Pro
    210                 215                 220

Ala Arg Pro Ala Glu Glu Ala Thr Ser Leu Glu Gly Ala Leu Ser Gly
225                 230                 235                 240

Thr Arg His Ser His Pro Ser Val Gly Arg Gln His His Ala Gly Pro
                245                 250                 255

Pro Ser Thr Ser Arg Pro Pro Arg Pro Trp Asp Thr Pro Cys Pro Pro
            260                 265                 270

-continued

```
Val Tyr Ala Glu Thr Lys His Phe Leu Tyr Ser Ser Gly Asp Lys Glu
            275                 280                 285

Gln Leu Arg Pro Ser Phe Leu Leu Ser Ser Leu Arg Pro Ser Leu Thr
            290                 295                 300

Gly Ala Arg Arg Leu Val Glu Thr Ile Phe Leu Gly Ser Arg Pro Trp
305                 310                 315                 320

Met Pro Gly Thr Pro Arg Arg Leu Pro Arg Leu Pro Gln Arg Tyr Trp
                325                 330                 335

Gln Met Arg Pro Leu Phe Leu Glu Leu Leu Gly Asn His Ala Gln Cys
            340                 345                 350

Pro Tyr Gly Val Leu Leu Lys Thr His Cys Pro Leu Arg Ala Ala Val
            355                 360                 365

Thr Pro Ala Ala Gly Val Cys Ala Arg Glu Lys Pro Gln Gly Ser Val
            370                 375                 380

Ala Ala Pro Glu Glu Asp Thr Asp Pro Arg Arg Leu Val Gln Leu
385                 390                 395                 400

Leu Arg Gln His Ser Ser Pro Trp Gln Val Tyr Gly Phe Val Arg Ala
                405                 410                 415

Cys Leu Arg Arg Leu Val Pro Pro Gly Leu Trp Gly Ser Arg His Asn
            420                 425                 430

Glu Arg Arg Phe Leu Arg Asn Thr Lys Lys Phe Ile Ser Leu Gly Lys
            435                 440                 445

His Ala Lys Leu Ser Leu Gln Glu Leu Thr Trp Lys Met Ser Val Arg
            450                 455                 460

Asp Cys Ala Trp Leu Arg Arg Ser Pro Gly Val Gly Cys Val Pro Ala
465                 470                 475                 480

Ala Glu His Arg Leu Arg Glu Glu Ile Leu Ala Lys Phe Leu His Trp
                485                 490                 495

Leu Met Ser Val Tyr Val Val Glu Leu Leu Arg Ser Phe Phe Tyr Val
            500                 505                 510

Thr Glu Thr Thr Phe Gln Lys Asn Arg Leu Phe Phe Tyr Arg Lys Ser
            515                 520                 525

Val Trp Ser Lys Leu Gln Ser Ile Gly Ile Arg Gln His Leu Lys Arg
            530                 535                 540

Val Gln Leu Arg Glu Leu Ser Glu Ala Glu Val Arg Gln His Arg Glu
545                 550                 555                 560

Ala Arg Pro Ala Leu Leu Thr Ser Arg Leu Arg Phe Ile Pro Lys Pro
                565                 570                 575

Asp Gly Leu Arg Pro Ile Val Asn Met Asp Tyr Val Val Gly Ala Arg
            580                 585                 590

Thr Phe Arg Arg Glu Lys Arg Ala Glu Arg Leu Thr Ser Arg Val Lys
            595                 600                 605

Ala Leu Phe Ser Val Leu Asn Tyr Glu Arg Ala Arg Arg Pro Gly Leu
610                 615                 620

Leu Gly Ala Ser Val Leu Gly Leu Asp Asp Ile His Arg Ala Trp Arg
625                 630                 635                 640

Thr Phe Val Leu Arg Val Arg Ala Gln Asp Pro Pro Glu Leu Tyr
                645                 650                 655

Phe Val Lys Val Asp Val Thr Gly Ala Tyr Asp Thr Ile Pro Gln Asp
                660                 665                 670

Arg Leu Thr Glu Val Ile Ala Ser Ile Ile Lys Pro Gln Asn Thr Tyr
            675                 680                 685

Cys Val Arg Arg Tyr Ala Val Val Gln Lys Ala Ala His Gly His Val
```

-continued

```
            690                 695                 700
Arg Lys Ala Phe Lys Ser His Val Ser Thr Leu Thr Asp Leu Gln Pro
705                 710                 715                 720

Tyr Met Arg Gln Phe Val Ala His Leu Gln Glu Thr Ser Pro Leu Arg
                725                 730                 735

Asp Ala Val Val Ile Glu Gln Ser Ser Ser Leu Asn Glu Ala Ser Ser
                740                 745                 750

Gly Leu Phe Asp Val Phe Leu Arg Phe Met Cys His His Ala Val Arg
                755                 760                 765

Ile Arg Gly Lys Ser Tyr Val Gln Cys Gln Gly Ile Pro Gln Gly Ser
770                 775                 780

Ile Leu Ser Thr Leu Leu Cys Ser Leu Cys Tyr Gly Asp Met Glu Asn
785                 790                 795                 800

Lys Leu Phe Ala Gly Ile Arg Arg Asp Gly Leu Leu Leu Arg Leu Val
                805                 810                 815

Asp Asp Phe Leu Leu Val Thr Pro His Leu Thr His Ala Lys Thr Phe
                820                 825                 830

Leu Arg Thr Leu Val Arg Gly Val Pro Glu Tyr Gly Cys Val Val Asn
                835                 840                 845

Leu Arg Lys Thr Val Val Asn Phe Pro Val Glu Asp Glu Ala Leu Gly
                850                 855                 860

Gly Thr Ala Phe Val Gln Met Pro Ala His Gly Leu Phe Pro Trp Cys
865                 870                 875                 880

Gly Leu Leu Leu Asp Thr Arg Thr Leu Glu Val Gln Ser Asp Tyr Ser
                885                 890                 895

Arg

<210> SEQ ID NO 70
<211> LENGTH: 982
<212> TYPE: PRT
<213> ORGANISM: Homo sapiens
<220> FEATURE:
<223> OTHER INFORMATION: Truncated Protein 3 (Ver.2); encoded by SEQ ID
      NO:67 with Intron Y ORF3

<400> SEQUENCE: 70

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
                20                  25                  30

Pro Gln Gly Trp Arg Leu Val Gln Arg Gly Asp Pro Ala Ala Phe Arg
            35                  40                  45

Ala Leu Val Ala Gln Cys Leu Val Cys Val Pro Trp Asp Ala Arg Pro
        50                  55                  60

Pro Pro Ala Ala Pro Ser Phe Arg Gln Val Pro Pro Arg Gly Arg Arg
65                  70                  75                  80

Pro Ala Gly Val Glu Gly Gly Arg Gly Glu Pro Ala Thr Cys Gly Glu
                85                  90                  95

Gln Arg Arg Arg Leu Arg Ala Leu Pro Pro Gln Val Ser Cys Leu Lys
            100                 105                 110

Glu Leu Val Ala Arg Val Leu Gln Arg Leu Cys Glu Arg Gly Ala Lys
        115                 120                 125

Asn Val Leu Ala Phe Gly Phe Ala Leu Leu Asp Gly Ala Arg Gly Gly
    130                 135                 140

Pro Pro Glu Ala Phe Thr Thr Ser Val Arg Ser Tyr Leu Pro Asn Thr
```

-continued

```
            145                 150                 155                 160
        Val Thr Asp Ala Leu Arg Gly Ser Gly Ala Trp Gly Leu Leu Leu Arg
                        165                 170                 175
        Arg Val Gly Asp Asp Val Leu Val His Leu Leu Ala Arg Cys Ala Leu
                        180                 185                 190
        Phe Val Leu Val Ala Pro Ser Cys Ala Tyr Gln Val Cys Gly Pro Pro
                        195                 200                 205
        Leu Tyr Gln Leu Gly Ala Ala Thr Gln Ala Arg Pro Pro His Ala
                210                 215                 220
        Ser Gly Pro Arg Arg Leu Gly Cys Glu Arg Ala Trp Asn His Ser
        225                 230                 235                 240
        Val Arg Glu Ala Gly Val Pro Leu Gly Leu Pro Ala Pro Gly Ala Arg
                        245                 250                 255
        Arg Arg Gly Gly Ser Ala Ser Arg Ser Leu Pro Leu Pro Lys Arg Pro
                        260                 265                 270
        Arg Arg Gly Ala Ala Pro Glu Pro Glu Arg Thr Pro Val Gly Gln Gly
                        275                 280                 285
        Ser Trp Ala His Pro Gly Arg Thr Arg Gly Pro Ser Asp Arg Gly Phe
                290                 295                 300
        Cys Val Val Ser Pro Ala Arg Pro Ala Glu Glu Ala Thr Ser Leu Glu
        305                 310                 315                 320
        Gly Ala Leu Ser Gly Thr Arg His Ser His Pro Ser Val Gly Arg Gln
                        325                 330                 335
        His His Ala Gly Pro Pro Ser Thr Ser Arg Pro Arg Pro Trp Asp
                340                 345                 350
        Thr Pro Cys Pro Pro Val Tyr Ala Glu Thr Lys His Phe Leu Tyr Ser
                        355                 360                 365
        Ser Gly Asp Lys Glu Gln Leu Arg Pro Ser Phe Leu Leu Ser Ser Leu
                370                 375                 380
        Arg Pro Ser Leu Thr Gly Ala Arg Arg Leu Val Glu Thr Ile Phe Leu
        385                 390                 395                 400
        Gly Ser Arg Pro Trp Met Pro Gly Thr Pro Arg Arg Leu Pro Arg Leu
                        405                 410                 415
        Pro Gln Arg Tyr Trp Gln Met Arg Pro Leu Phe Leu Glu Leu Leu Gly
                        420                 425                 430
        Asn His Ala Gln Cys Pro Tyr Gly Val Leu Leu Lys Thr His Cys Pro
                        435                 440                 445
        Leu Arg Ala Ala Val Thr Pro Ala Ala Gly Val Cys Ala Arg Glu Lys
                450                 455                 460
        Pro Gln Gly Ser Val Ala Ala Pro Glu Glu Asp Thr Asp Pro Arg
        465                 470                 475                 480
        Arg Leu Val Gln Leu Leu Arg Gln His Ser Ser Pro Trp Gln Val Tyr
                        485                 490                 495
        Gly Phe Val Arg Ala Cys Leu Arg Leu Val Pro Pro Gly Leu Trp
                        500                 505                 510
        Gly Ser Arg His Asn Glu Arg Arg Phe Leu Arg Asn Thr Lys Lys Phe
                        515                 520                 525
        Ile Ser Leu Gly Lys His Ala Lys Leu Ser Leu Gln Glu Leu Thr Trp
                530                 535                 540
        Lys Met Ser Val Arg Asp Cys Ala Trp Leu Arg Arg Ser Pro Gly Val
        545                 550                 555                 560
        Gly Cys Val Pro Ala Ala Glu His Arg Leu Arg Glu Glu Ile Leu Ala
                        565                 570                 575
```

```
Lys Phe Leu His Trp Leu Met Ser Val Tyr Val Glu Leu Leu Arg
            580                 585                 590

Ser Phe Phe Tyr Val Thr Glu Thr Thr Phe Gln Lys Asn Arg Leu Phe
        595                 600                 605

Phe Tyr Arg Lys Ser Val Trp Ser Lys Leu Gln Ser Ile Gly Ile Arg
            610                 615                 620

Gln His Leu Lys Arg Val Gln Leu Arg Glu Leu Ser Glu Ala Glu Val
625                 630                 635                 640

Arg Gln His Arg Glu Ala Arg Pro Ala Leu Leu Thr Ser Arg Leu Arg
                645                 650                 655

Phe Ile Pro Lys Pro Asp Gly Leu Arg Pro Ile Val Asn Met Asp Tyr
            660                 665                 670

Val Val Gly Ala Arg Thr Phe Arg Glu Lys Arg Ala Glu Arg Leu
            675                 680                 685

Thr Ser Arg Val Lys Ala Leu Phe Ser Val Leu Asn Tyr Glu Arg Ala
        690                 695                 700

Arg Arg Pro Gly Leu Leu Gly Ala Ser Val Leu Gly Leu Asp Asp Ile
705                 710                 715                 720

His Arg Ala Trp Arg Thr Phe Val Leu Arg Val Arg Ala Gln Asp Pro
                725                 730                 735

Pro Pro Glu Leu Tyr Phe Val Lys Val Asp Val Thr Gly Ala Tyr Asp
            740                 745                 750

Thr Ile Pro Gln Asp Arg Leu Thr Glu Val Ile Ala Ser Ile Ile Lys
            755                 760                 765

Pro Gln Asn Thr Tyr Cys Val Arg Arg Tyr Ala Val Val Gln Lys Ala
        770                 775                 780

Ala His Gly His Val Arg Lys Ala Phe Lys Ser His Val Ser Thr Leu
785                 790                 795                 800

Thr Asp Leu Gln Pro Tyr Met Arg Gln Phe Val Ala His Leu Gln Glu
                805                 810                 815

Thr Ser Pro Leu Arg Asp Ala Val Val Ile Glu Gln Ser Ser Ser Leu
            820                 825                 830

Asn Glu Ala Ser Ser Gly Leu Phe Asp Val Phe Leu Arg Phe Met Cys
        835                 840                 845

His His Ala Val Arg Ile Arg Gly Lys Ser Tyr Val Gln Cys Gln Gly
        850                 855                 860

Ile Pro Gln Gly Ser Ile Leu Ser Thr Leu Leu Cys Ser Leu Cys Tyr
865                 870                 875                 880

Gly Asp Met Glu Asn Lys Leu Phe Ala Gly Ile Arg Arg Asp Gly Leu
                885                 890                 895

Leu Leu Arg Leu Val Asp Asp Phe Leu Leu Val Thr Pro His Leu Thr
            900                 905                 910

His Ala Lys Thr Phe Leu Arg Thr Leu Val Arg Gly Val Pro Glu Tyr
            915                 920                 925

Gly Cys Val Val Asn Leu Arg Lys Thr Val Val Asn Phe Pro Val Glu
        930                 935                 940

Asp Glu Ala Leu Gly Gly Thr Ala Phe Val Gln Met Pro Ala His Gly
945                 950                 955                 960

Leu Phe Pro Trp Cys Gly Leu Leu Leu Asp Thr Arg Thr Leu Glu Val
                965                 970                 975

Gln Ser Asp Tyr Ser Arg
            980
```

-continued

<210> SEQ ID NO 71
<211> LENGTH: 3466
<212> TYPE: DNA
<213> ORGANISM: Homo sapiens
<220> FEATURE:
<223> OTHER INFORMATION: Altered C-Terminus Protein (ver.2); with
      Introns Y, Alpha, Beta and 3

<400> SEQUENCE: 71

```
atgccgcgcg ctccccgctg ccgagccgtg cgctccctgc tgcgcagcca ctaccgcgag      60
gtgctgccgc tggccacgtt cgtgcggcgc ctggggcccc agggctggcg gctggtgcag     120
cgcggggacc cggcggcttt ccgcgcgctg gtggcccagt gcctggtgtg cgtgccctgg     180
gacgcacggc cgcccccgc cgcccccctcc ttccgccagg tgggcctccc cggggtcggc     240
gtccggctgg ggttgagggc ggccgggggg aaccagcgac atgcggagag cagcgcaggc     300
gactcagggc gcttccccg caggtgtcct gcctgaagga gctggtggcc cgagtgctgc     360
agaggctgtg cgagcgcggc gcgaagaacg tgctggcctt cggcttcgcg ctgctggacg     420
gggcccgcgg gggcccccc gaggccttca ccaccagcgt gcgcagctac ctgcccaaca     480
cggtgaccga cgcactgcgg gggagcgggg cgtggggggct gctgctgcgc cgcgtgggcg     540
acgacgtgct ggttcacctg ctggcacgct gcgcgctctt tgtgctggtg gctcccagct     600
gcgcctacca ggtgtgcggg ccgccgctgt accagctcgg cgctgccact caggcccggc     660
ccccgccaca cgctagtgga ccccgaaggc gtctgggatg cgaacgggcc tggaaccata     720
gcgtcaggga ggccgggggtc cccctgggcc tgccagcccc gggtgcgagg aggcgcgggg     780
gcagtgccag ccgaagtctg ccgttgccca agaggcccag gcgtggcgct gcccctgagc     840
cggagcggac gcccgttggg cagggtcct ggggccaccc gggcaggacg cgtggaccga     900
gtgaccgtgg tttctgtgtg gtgtcacctg ccagacccgc cgaagaagcc acctctttgg     960
agggtgcgct ctctggcacg cgccactccc acccatccgt gggccgccag caccacgcgg    1020 gcccccatc cacatcgcgg ccaccacgtc cctgggacac gccttgtccc ccggtgtacg    1080
ccgagaccaa gcacttcctc tactcctcag gcgacaagga gcagctgcgg ccctccttcc    1140
tactcagctc tctgaggccc agcctgactg gcgctcggag gctcgtggag accatctttc    1200
tgggttccag gccctggatg ccagggactc cccgcaggtt gccccgcctg cccagcgct    1260 actggcaaat gcggcccctg tttctggagc tgcttgggaa ccacgcgcag tgcccctacg    1320
gggtgctcct caagacgcac tgcccgctgc gagctgcggt cacccagca gccggtgtct    1380 gtgcccggga gaagccccag ggctctgtgg cggccccga ggaggaggac acagacccc    1440 gtcgcctggt gcagctgctc cgccagcaca gcagcccctg gcaggtgtac ggcttcgtgc    1500
gggcctgcct gcgccggctg gtgccccag gcctctgggg ctccaggcac aacgaacgcc    1560
gcttcctcag gaacaccaag aagttcatct ccctggggaa gcatgccaag ctctcgctgc    1620
aggagctgac gtggaagatg agcgtgcggg actgcgcttg gctgcgcagg agcccagggg    1680
ttggctgtgt ccggccgca gagcaccgtc tgcgtgagga gatcctggcc aagttcctgc    1740
actggctgat gagtgtgtac gtcgtcgagc tgctcaggtc tttcttttat gtcacggaga    1800 ccacgttttca aaagaacagg ctcttttttct accggaagag tgtctggagc aagttgcaaa    1860
gcattggaat cagacagcac ttgaagaggg tgcagctgcg ggagctgtcg gaagcagagg    1920
tcaggcagca tcgggaagcc aggcccgccc tgctgacgtc cagactccgc ttcatcccca    1980
agcctgacgg gctgcggccg attgtgaaca tggactacgt cgtgggagcc agaacgttcc    2040
```

```
gcagagaaaa gagggccgag cgtctcacct cgagggtgaa ggcactgttc agcgtgctca    2100
actacgagcg ggcgcggcgc cccggcctcc tgggcgcctc tgtgctgggc ctggacgata    2160
tccacagggc ctggcgcacc ttcgtgctgc gtgtgcgggc ccaggacccg ccgcctgagc    2220
tgtactttgt caaggtggat gtgacgggcg cgtacgacac catcccccag gacaggctca    2280
cggaggtcat cgccagcatc atcaaacccc agaacacgta ctgcgtgcgt cggtatgccg    2340
tggtccagaa ggccgcccat gggcacgtcc gcaaggcctt caagagccac gtctctacct    2400
tgacagacct ccagccgtac atgcgacagt tcgtggctca cctgcaggag accagcccgc    2460
tgagggatgc cgtcgtcatc gagcagagct cctccctgaa tgaggccagc agtggcctct    2520
tcgacgtctt cctacgcttc atgtgccacc acgccgtgcg catcaggggc aagtcctacg    2580
tccagtgcca ggggatcccg cagggctcca tcctctccac gctgctctgc agcctgtgct    2640
acggcgacat ggagaacaag ctgtttgcgg ggattcggcg ggacgggctg ctcctgcgtt    2700
tggtggatga tttcttgttg gtgacacctc acctcaccca cgcgaaaacc ttcctcagga    2760
ccctggtccg aggtgtccct gagtatggct gcgtggtgaa cttgcggaag acagtggtga    2820
acttccctgt agaagacgag gccctgggtg cacggctttt gttcagatg ccggcccacg    2880
gcctattccc ctggtgcggc ctgctgctgg atacccggac cctggaggtg cagagcgact    2940
actccagcta tgcccggacc tccatcagag ccagtctcac cttcaaccgc ggcttcaagg    3000
ctgggaggaa catgcgtcgc aaactctttg gggtcttgcg gctgaagtgt cacagcctgt    3060
ttctggattt gcaggtgaac agcctccaga cggtgtgcac caacatctac aagatcctcc    3120
tgctgcaggc gtacaggttt cacgcatgtg tgctgcagct cccatttcat cagcaagttt    3180
ggaagaaccc cacatttttc ctgcgcgtca tctctgacac ggcctccctc tgctactcca    3240
tcctgaaagc caagaacgca gccgaagaaa acatttctgt cgtgactcct gcggtgcttg    3300
ggtcgggaca gccagagatg gagccacccc gcagaccgtc gggtgtgggc agctttccgg    3360
tgtctcctgg gaggggagtt gggctgggcc tgtgactcct cagcctctgt tttcccccag    3420
ggatgtcgct gggggccaag ggcgccgccg ccctctgcc ctccga                    3466
```

<210> SEQ ID NO 72  
<211> LENGTH: 1130  
<212> TYPE: PRT  
<213> ORGANISM: Homo sapiens  
<220> FEATURE:  
<223> OTHER INFORMATION: Altered C-Terminus Protein (ver.2); encoded by
    SEQ ID NO:71 with Intron Y ORF1

<400> SEQUENCE: 72

```
Met Pro Arg Ala Pro Arg Cys Arg Ala Val Arg Ser Leu Leu Arg Ser
  1               5                  10                  15

His Tyr Arg Glu Val Leu Pro Leu Ala Thr Phe Val Arg Arg Leu Gly
             20                  25                  30

Pro Gln Gly Trp Arg Leu Val Gln Arg Gly Asp Pro Ala Ala Phe Arg
         35                  40                  45

Ala Leu Val Ala Gln Cys Leu Val Cys Val Pro Trp Asp Ala Arg Pro
     50                  55                  60

Pro Pro Ala Ala Pro Ser Phe Arg Gln Val Ser Leu Pro Gly Val Gly
 65                  70                  75                  80

Val Arg Leu Gly Leu Arg Ala Ala Gly Gly Asn Gln Arg His Ala Glu
                 85                  90                  95

Ser Ser Ala Gly Asp Ser Gly Arg Phe Pro Arg Arg Ser Cys Leu Lys
            100                 105                 110
```

```
Glu Leu Val Ala Arg Val Leu Gln Arg Leu Cys Glu Arg Gly Ala Lys
        115                 120                 125

Asn Val Leu Ala Phe Gly Phe Ala Leu Leu Asp Gly Ala Arg Gly Gly
130                 135                 140

Pro Pro Glu Ala Phe Thr Thr Ser Val Arg Ser Tyr Leu Pro Asn Thr
145                 150                 155                 160

Val Thr Asp Ala Leu Arg Gly Ser Gly Ala Trp Gly Leu Leu Leu Arg
                165                 170                 175

Arg Val Gly Asp Asp Val Leu Val His Leu Leu Ala Arg Cys Ala Leu
            180                 185                 190

Phe Val Leu Val Ala Pro Ser Cys Ala Tyr Gln Val Cys Gly Pro Pro
        195                 200                 205

Leu Tyr Gln Leu Gly Ala Ala Thr Gln Ala Arg Pro Pro His Ala
        210                 215                 220

Ser Gly Pro Arg Arg Leu Gly Cys Glu Arg Ala Trp Asn His Ser
225                 230                 235                 240

Val Arg Glu Ala Gly Val Pro Leu Gly Leu Pro Ala Pro Gly Ala Arg
                245                 250                 255

Arg Arg Gly Gly Ser Ala Ser Arg Ser Leu Pro Leu Pro Lys Arg Pro
                260                 265                 270

Arg Arg Gly Ala Ala Pro Glu Pro Glu Arg Thr Pro Val Gly Gln Gly
            275                 280                 285

Ser Trp Ala His Pro Gly Arg Thr Arg Gly Pro Ser Asp Arg Gly Phe
        290                 295                 300

Cys Val Val Ser Pro Ala Arg Pro Ala Glu Glu Ala Thr Ser Leu Glu
305                 310                 315                 320

Gly Ala Leu Ser Gly Thr Arg His Ser His Pro Ser Val Gly Arg Gln
                325                 330                 335

His His Ala Gly Pro Pro Ser Thr Ser Arg Pro Arg Pro Trp Asp
            340                 345                 350

Thr Pro Cys Pro Pro Val Tyr Ala Glu Thr Lys His Phe Leu Tyr Ser
        355                 360                 365

Ser Gly Asp Lys Glu Gln Leu Arg Pro Ser Phe Leu Leu Ser Ser Leu
370                 375                 380

Arg Pro Ser Leu Thr Gly Ala Arg Arg Leu Val Glu Thr Ile Phe Leu
385                 390                 395                 400

Gly Ser Arg Pro Trp Met Pro Gly Thr Pro Arg Arg Leu Pro Arg Leu
                405                 410                 415

Pro Gln Arg Tyr Trp Gln Met Arg Pro Leu Phe Leu Glu Leu Leu Gly
            420                 425                 430

Asn His Ala Gln Cys Pro Tyr Gly Val Leu Leu Lys Thr His Cys Pro
        435                 440                 445

Leu Arg Ala Ala Val Thr Pro Ala Ala Gly Val Cys Ala Arg Glu Lys
    450                 455                 460

Pro Gln Gly Ser Val Ala Ala Pro Glu Glu Asp Thr Asp Pro Arg
465                 470                 475                 480

Arg Leu Val Gln Leu Leu Arg Gln His Ser Ser Pro Trp Gln Val Tyr
                485                 490                 495

Gly Phe Val Arg Ala Cys Leu Arg Leu Val Pro Pro Gly Leu Trp
                500                 505                 510

Gly Ser Arg His Asn Glu Arg Arg Phe Leu Arg Asn Thr Lys Lys Phe
        515                 520                 525
```

-continued

```
Ile Ser Leu Gly Lys His Ala Lys Leu Ser Leu Gln Glu Leu Thr Trp
530                 535                 540

Lys Met Ser Val Arg Asp Cys Ala Trp Leu Arg Arg Ser Pro Gly Val
545                 550                 555                 560

Gly Cys Val Pro Ala Ala Glu His Arg Leu Arg Glu Glu Ile Leu Ala
                565                 570                 575

Lys Phe Leu His Trp Leu Met Ser Val Tyr Val Glu Leu Leu Arg
                580                 585                 590

Ser Phe Phe Tyr Val Thr Glu Thr Thr Phe Gln Lys Asn Arg Leu Phe
                595                 600                 605

Phe Tyr Arg Lys Ser Val Trp Ser Lys Leu Gln Ser Ile Gly Ile Arg
610                 615                 620

Gln His Leu Lys Arg Val Gln Leu Arg Glu Leu Ser Glu Ala Glu Val
625                 630                 635                 640

Arg Gln His Arg Glu Ala Arg Pro Ala Leu Leu Thr Ser Arg Leu Arg
                645                 650                 655

Phe Ile Pro Lys Pro Asp Gly Leu Arg Pro Ile Val Asn Met Asp Tyr
                660                 665                 670

Val Val Gly Ala Arg Thr Phe Arg Arg Glu Lys Arg Ala Glu Arg Leu
                675                 680                 685

Thr Ser Arg Val Lys Ala Leu Phe Ser Val Leu Asn Tyr Glu Arg Ala
690                 695                 700

Arg Arg Pro Gly Leu Leu Gly Ala Ser Val Leu Gly Leu Asp Asp Ile
705                 710                 715                 720

His Arg Ala Trp Arg Thr Phe Val Leu Arg Val Arg Ala Gln Asp Pro
                725                 730                 735

Pro Pro Glu Leu Tyr Phe Val Lys Val Asp Val Thr Gly Ala Tyr Asp
                740                 745                 750

Thr Ile Pro Gln Asp Arg Leu Thr Glu Val Ile Ala Ser Ile Ile Lys
                755                 760                 765

Pro Gln Asn Thr Tyr Cys Val Arg Arg Tyr Ala Val Val Gln Lys Ala
770                 775                 780

Ala His Gly His Val Arg Lys Ala Phe Lys Ser His Val Ser Thr Leu
785                 790                 795                 800

Thr Asp Leu Gln Pro Tyr Met Arg Gln Phe Val Ala His Leu Gln Glu
                805                 810                 815

Thr Ser Pro Leu Arg Asp Ala Val Val Ile Glu Gln Ser Ser Ser Leu
                820                 825                 830

Asn Glu Ala Ser Ser Gly Leu Phe Asp Val Phe Leu Arg Phe Met Cys
835                 840                 845

His His Ala Val Arg Ile Arg Gly Lys Ser Tyr Val Gln Cys Gln Gly
850                 855                 860

Ile Pro Gln Gly Ser Ile Leu Ser Thr Leu Leu Cys Ser Leu Cys Tyr
865                 870                 875                 880

Gly Asp Met Glu Asn Lys Leu Phe Ala Gly Ile Arg Arg Asp Gly Leu
                885                 890                 895

Leu Leu Arg Leu Val Asp Asp Phe Leu Leu Val Thr Pro His Leu Thr
                900                 905                 910

His Ala Lys Thr Phe Leu Arg Thr Leu Val Arg Gly Val Pro Glu Tyr
                915                 920                 925

Gly Cys Val Val Asn Leu Arg Lys Thr Val Val Asn Phe Pro Val Glu
930                 935                 940

Asp Glu Ala Leu Gly Gly Thr Ala Phe Val Gln Met Pro Ala His Gly
```

```
945                 950                 955                 960

Leu Phe Pro Trp Cys Gly Leu Leu Leu Asp Thr Arg Thr Leu Glu Val
            965                 970                 975

Gln Ser Asp Tyr Ser Ser Tyr Ala Arg Thr Ser Ile Arg Ala Ser Leu
            980                 985                 990

Thr Phe Asn Arg Gly Phe Lys Ala Gly Arg Asn Met Arg Arg Lys Leu
            995                1000                1005

Phe Gly Val Leu Arg Leu Lys Cys His Ser Leu Phe Leu Asp Leu Gln
   1010                1015                1020

Val Asn Ser Leu Gln Thr Val Cys Thr Asn Ile Tyr Lys Ile Leu Leu
1025                1030                1035                1040

Leu Gln Ala Tyr Arg Phe His Ala Cys Val Leu Gln Leu Pro Phe His
           1045                1050                1055

Gln Gln Val Trp Lys Asn Pro Thr Phe Phe Leu Arg Val Ile Ser Asp
           1060                1065                1070

Thr Ala Ser Leu Cys Tyr Ser Ile Leu Lys Ala Lys Asn Ala Glu Glu
           1075                1080                1085

Glu Asn Ile Leu Val Val Thr Pro Ala Val Leu Gly Ser Gly Gln Pro
   1090                1095                1100

Glu Met Glu Pro Pro Arg Arg Pro Ser Gly Val Gly Ser Phe Pro Val
1105                1110                1115                1120

Ser Pro Gly Arg Gly Val Gly Leu Gly Leu
           1125                1130

<210> SEQ ID NO 73
<211> LENGTH: 1045
<212> TYPE: PRT
<213> ORGANISM: Homo sapiens
<220> FEATURE:
<223> OTHER INFORMATION: Altered C-Terminus Protein (ver.2); encoded by
      SEQ ID NO:71 with Intron Y ORF2 after the termination
      codon

<400> SEQUENCE: 73

Gly Arg Pro Gly Gly Thr Ser Asp Met Arg Arg Ala Ala Gln Ala Thr
  1               5                  10                  15

Gln Gly Ala Ser Pro Ala Gly Ser Cys Leu Lys Glu Leu Val Ala Arg
             20                  25                  30

Val Leu Gln Arg Leu Cys Glu Arg Gly Ala Lys Asn Val Leu Ala Phe
         35                  40                  45

Gly Phe Ala Leu Leu Asp Gly Ala Arg Gly Pro Pro Glu Ala Phe
     50                  55                  60

Thr Thr Ser Val Arg Ser Tyr Leu Pro Asn Thr Val Thr Asp Ala Leu
 65                  70                  75                  80

Arg Gly Ser Gly Ala Trp Gly Leu Leu Leu Arg Arg Val Gly Asp Asp
                 85                  90                  95

Val Leu Val His Leu Leu Ala Arg Cys Ala Leu Phe Val Leu Val Ala
            100                 105                 110

Pro Ser Cys Ala Tyr Gln Val Cys Gly Pro Pro Leu Tyr Gln Leu Gly
        115                 120                 125

Ala Ala Thr Gln Ala Arg Pro Pro His Ala Ser Gly Pro Arg Arg
    130                 135                 140

Arg Leu Gly Cys Glu Arg Ala Trp Asn His Ser Val Arg Glu Ala Gly
145                 150                 155                 160

Val Pro Leu Gly Leu Pro Ala Pro Gly Ala Arg Arg Arg Gly Gly Ser
                165                 170                 175
```

```
Ala Ser Arg Ser Leu Pro Leu Pro Lys Arg Pro Arg Gly Ala Ala
            180                 185                 190

Pro Glu Pro Glu Arg Thr Pro Val Gly Gln Gly Ser Trp Ala His Pro
        195                 200                 205

Gly Arg Thr Arg Gly Pro Ser Asp Arg Gly Phe Cys Val Val Ser Pro
        210                 215                 220

Ala Arg Pro Ala Glu Glu Ala Thr Ser Leu Glu Gly Ala Leu Ser Gly
225                 230                 235                 240

Thr Arg His Ser His Pro Ser Val Gly Arg Gln His His Ala Gly Pro
                245                 250                 255

Pro Ser Thr Ser Arg Pro Pro Arg Pro Trp Asp Thr Pro Cys Pro Pro
                260                 265                 270

Val Tyr Ala Glu Thr Lys His Phe Leu Tyr Ser Ser Gly Asp Lys Glu
            275                 280                 285

Gln Leu Arg Pro Ser Phe Leu Leu Ser Ser Leu Arg Pro Ser Leu Thr
        290                 295                 300

Gly Ala Arg Arg Leu Val Glu Thr Ile Phe Leu Gly Ser Arg Pro Trp
305                 310                 315                 320

Met Pro Gly Thr Pro Arg Arg Leu Pro Arg Leu Pro Gln Arg Tyr Trp
                325                 330                 335

Gln Met Arg Pro Leu Phe Leu Glu Leu Leu Gly Asn His Ala Gln Cys
            340                 345                 350

Pro Tyr Gly Val Leu Leu Lys Thr His Cys Pro Leu Arg Ala Ala Val
        355                 360                 365

Thr Pro Ala Ala Gly Val Cys Ala Arg Glu Lys Pro Gln Gly Ser Val
    370                 375                 380

Ala Ala Pro Glu Glu Glu Asp Thr Asp Pro Arg Arg Leu Val Gln Leu
385                 390                 395                 400

Leu Arg Gln His Ser Ser Pro Trp Gln Val Tyr Gly Phe Val Arg Ala
                405                 410                 415

Cys Leu Arg Arg Leu Val Pro Pro Gly Leu Trp Gly Ser Arg His Asn
            420                 425                 430

Glu Arg Arg Phe Leu Arg Asn Thr Lys Lys Phe Ile Ser Leu Gly Lys
        435                 440                 445

His Ala Lys Leu Ser Leu Gln Glu Leu Thr Trp Lys Met Ser Val Arg
    450                 455                 460

Asp Cys Ala Trp Leu Arg Arg Ser Pro Gly Val Gly Cys Val Pro Ala
465                 470                 475                 480

Ala Glu His Arg Leu Arg Glu Glu Ile Leu Ala Lys Phe Leu His Trp
                485                 490                 495

Leu Met Ser Val Tyr Val Val Glu Leu Leu Arg Ser Phe Phe Tyr Val
            500                 505                 510

Thr Glu Thr Thr Phe Gln Lys Asn Arg Leu Phe Phe Tyr Arg Lys Ser
        515                 520                 525

Val Trp Ser Lys Leu Gln Ser Ile Gly Ile Arg Gln His Leu Lys Arg
530                 535                 540

Val Gln Leu Arg Glu Leu Ser Glu Ala Glu Val Arg Gln His Arg Glu
545                 550                 555                 560

Ala Arg Pro Ala Leu Leu Thr Ser Arg Leu Arg Phe Ile Pro Lys Pro
                565                 570                 575

Asp Gly Leu Arg Pro Ile Val Asn Met Asp Tyr Val Val Gly Ala Arg
            580                 585                 590
```

-continued

```
Thr Phe Arg Arg Glu Lys Arg Ala Glu Arg Leu Thr Ser Arg Val Lys
            595                 600                 605
Ala Leu Phe Ser Val Leu Asn Tyr Glu Arg Ala Arg Arg Pro Gly Leu
        610                 615                 620
Leu Gly Ala Ser Val Leu Gly Leu Asp Asp Ile His Arg Ala Trp Arg
625                 630                 635                 640
Thr Phe Val Leu Arg Val Arg Ala Gln Asp Pro Pro Glu Leu Tyr
            645                 650                 655
Phe Val Lys Val Asp Val Thr Gly Ala Tyr Asp Thr Ile Pro Gln Asp
        660                 665                 670
Arg Leu Thr Glu Val Ile Ala Ser Ile Ile Lys Pro Gln Asn Thr Tyr
            675                 680                 685
Cys Val Arg Arg Tyr Ala Val Val Gln Lys Ala Ala His Gly His Val
        690                 695                 700
Arg Lys Ala Phe Lys Ser His Val Ser Thr Leu Thr Asp Leu Gln Pro
705                 710                 715                 720
Tyr Met Arg Gln Phe Val Ala His Leu Gln Glu Thr Ser Pro Leu Arg
            725                 730                 735
Asp Ala Val Val Ile Glu Gln Ser Ser Ser Leu Asn Glu Ala Ser Ser
        740                 745                 750
Gly Leu Phe Asp Val Phe Leu Arg Phe Met Cys His His Ala Val Arg
            755                 760                 765
Ile Arg Gly Lys Ser Tyr Val Gln Cys Gln Gly Ile Pro Gln Gly Ser
        770                 775                 780
Ile Leu Ser Thr Leu Leu Cys Ser Leu Cys Tyr Gly Asp Met Glu Asn
785                 790                 795                 800
Lys Leu Phe Ala Gly Ile Arg Arg Asp Gly Leu Leu Leu Arg Leu Val
            805                 810                 815
Asp Asp Phe Leu Leu Val Thr Pro His Leu Thr His Ala Lys Thr Phe
        820                 825                 830
Leu Arg Thr Leu Val Arg Gly Val Pro Glu Tyr Gly Cys Val Val Asn
            835                 840                 845
Leu Arg Lys Thr Val Val Asn Phe Pro Val Glu Asp Glu Ala Leu Gly
850                 855                 860
Gly Thr Ala Phe Val Gln Met Pro Ala His Gly Leu Phe Pro Trp Cys
865                 870                 875                 880
Gly Leu Leu Leu Asp Thr Arg Thr Leu Glu Val Gln Ser Asp Tyr Ser
            885                 890                 895
Ser Tyr Ala Arg Thr Ser Ile Arg Ala Ser Leu Thr Phe Asn Arg Gly
        900                 905                 910
Phe Lys Ala Gly Arg Asn Met Arg Arg Lys Leu Phe Gly Val Leu Arg
            915                 920                 925
Leu Lys Cys His Ser Leu Phe Leu Asp Leu Gln Val Asn Ser Leu Gln
        930                 935                 940
Thr Val Cys Thr Asn Ile Tyr Lys Ile Leu Leu Leu Gln Ala Tyr Arg
945                 950                 955                 960
Phe His Ala Cys Val Leu Gln Leu Pro Phe His Gln Gln Val Trp Lys
            965                 970                 975
Asn Pro Thr Phe Phe Leu Arg Val Ile Ser Asp Thr Ala Ser Leu Cys
            980                 985                 990
Tyr Ser Ile Leu Lys Ala Lys Asn Ala Glu Glu Asn Ile Leu Val
            995                 1000                1005
Val Thr Pro Ala Val Leu Gly Ser Gly Gln Pro Glu Met Glu Pro Pro
```

```
                1010                1015                1020
Arg Arg Pro Ser Gly Val Gly Ser Phe Pro Val Ser Pro Gly Arg Gly
1025                1030                1035                1040

Val Gly Leu Gly Leu
            1045

<210> SEQ ID NO 74
<211> LENGTH: 1130
<212> TYPE: PRT
<213> ORGANISM: Homo sapiens
<220> FEATURE:
<223> OTHER INFORMATION: Altered C-Terminus Protein (ver.2); encoded by
      SEQ ID NO:71 with Intron Y ORF3

<400> SEQUENCE: 74

Met Pro Arg Ala Pro Arg Cys Arg Ala Val Arg Ser Leu Leu Arg Ser
  1               5                  10                  15

His Tyr Arg Glu Val Leu Pro Leu Ala Thr Phe Val Arg Arg Leu Gly
             20                  25                  30

Pro Gln Gly Trp Arg Leu Val Gln Arg Gly Asp Pro Ala Ala Phe Arg
         35                  40                  45

Ala Leu Val Ala Gln Cys Leu Val Cys Val Pro Trp Asp Ala Arg Pro
     50                  55                  60

Pro Pro Ala Ala Pro Ser Phe Arg Gln Val Pro Pro Arg Gly Arg Arg
 65                  70                  75                  80

Pro Ala Gly Val Glu Gly Gly Arg Gly Glu Pro Ala Thr Cys Gly Glu
                 85                  90                  95

Gln Arg Arg Arg Leu Arg Ala Leu Pro Pro Gln Val Ser Cys Leu Lys
            100                 105                 110

Glu Leu Val Ala Arg Val Leu Gln Arg Leu Cys Glu Arg Gly Ala Lys
        115                 120                 125

Asn Val Leu Ala Phe Gly Phe Ala Leu Leu Asp Gly Ala Arg Gly Gly
    130                 135                 140

Pro Pro Glu Ala Phe Thr Thr Ser Val Arg Ser Tyr Leu Pro Asn Thr
145                 150                 155                 160

Val Thr Asp Ala Leu Arg Gly Ser Gly Ala Trp Gly Leu Leu Leu Arg
                165                 170                 175

Arg Val Gly Asp Asp Val Leu Val His Leu Leu Ala Arg Cys Ala Leu
            180                 185                 190

Phe Val Leu Val Ala Pro Ser Cys Ala Tyr Gln Val Cys Gly Pro Pro
        195                 200                 205

Leu Tyr Gln Leu Gly Ala Ala Thr Gln Ala Arg Pro Pro His Ala
    210                 215                 220

Ser Gly Pro Arg Arg Arg Leu Gly Cys Glu Arg Ala Trp Asn His Ser
225                 230                 235                 240

Val Arg Glu Ala Gly Val Pro Leu Gly Leu Pro Ala Pro Gly Ala Arg
                245                 250                 255

Arg Arg Gly Gly Ser Ala Ser Arg Ser Leu Pro Leu Pro Lys Arg Pro
            260                 265                 270

Arg Arg Gly Ala Ala Pro Glu Pro Glu Arg Thr Pro Val Gly Gln Gly
        275                 280                 285

Ser Trp Ala His Pro Gly Arg Thr Arg Gly Pro Ser Asp Arg Gly Phe
    290                 295                 300

Cys Val Val Ser Pro Ala Arg Pro Ala Glu Glu Ala Thr Ser Leu Glu
305                 310                 315                 320
```

```
Gly Ala Leu Ser Gly Thr Arg His Ser His Pro Ser Val Gly Arg Gln
            325                 330                 335

His His Ala Gly Pro Pro Ser Thr Ser Arg Pro Pro Arg Pro Trp Asp
            340                 345                 350

Thr Pro Cys Pro Pro Val Tyr Ala Glu Thr Lys His Phe Leu Tyr Ser
            355                 360                 365

Ser Gly Asp Lys Glu Gln Leu Arg Pro Ser Phe Leu Leu Ser Ser Leu
        370                 375                 380

Arg Pro Ser Leu Thr Gly Ala Arg Arg Leu Val Glu Thr Ile Phe Leu
385                 390                 395                 400

Gly Ser Arg Pro Trp Met Pro Gly Thr Pro Arg Arg Leu Pro Arg Leu
                405                 410                 415

Pro Gln Arg Tyr Trp Gln Met Arg Pro Leu Phe Leu Glu Leu Leu Gly
            420                 425                 430

Asn His Ala Gln Cys Pro Tyr Gly Val Leu Leu Lys Thr His Cys Pro
            435                 440                 445

Leu Arg Ala Ala Val Thr Pro Ala Ala Gly Val Cys Ala Arg Glu Lys
    450                 455                 460

Pro Gln Gly Ser Val Ala Ala Pro Glu Glu Asp Thr Asp Pro Arg
465                 470                 475                 480

Arg Leu Val Gln Leu Leu Arg Gln His Ser Ser Pro Trp Gln Val Tyr
                485                 490                 495

Gly Phe Val Arg Ala Cys Leu Arg Arg Leu Val Pro Pro Gly Leu Trp
            500                 505                 510

Gly Ser Arg His Asn Glu Arg Arg Phe Leu Arg Asn Thr Lys Lys Phe
            515                 520                 525

Ile Ser Leu Gly Lys His Ala Lys Leu Ser Leu Gln Glu Leu Thr Trp
    530                 535                 540

Lys Met Ser Val Arg Asp Cys Ala Trp Leu Arg Arg Ser Pro Gly Val
545                 550                 555                 560

Gly Cys Val Pro Ala Ala Glu His Arg Leu Arg Glu Ile Leu Ala
                565                 570                 575

Lys Phe Leu His Trp Leu Met Ser Val Tyr Val Glu Leu Leu Arg
            580                 585                 590

Ser Phe Phe Tyr Val Thr Glu Thr Phe Gln Lys Asn Arg Leu Phe
        595                 600                 605

Phe Tyr Arg Lys Ser Val Trp Ser Lys Leu Gln Ser Ile Gly Ile Arg
    610                 615                 620

Gln His Leu Lys Arg Val Gln Leu Arg Glu Leu Ser Glu Ala Glu Val
625                 630                 635                 640

Arg Gln His Arg Glu Ala Arg Pro Ala Leu Leu Thr Ser Arg Leu Arg
                645                 650                 655

Phe Ile Pro Lys Pro Asp Gly Leu Arg Pro Ile Val Asn Met Asp Tyr
            660                 665                 670

Val Val Gly Ala Arg Thr Phe Arg Arg Glu Lys Arg Ala Glu Arg Leu
            675                 680                 685

Thr Ser Arg Val Lys Ala Leu Phe Ser Val Leu Asn Tyr Glu Arg Ala
        690                 695                 700

Arg Arg Pro Gly Leu Leu Gly Ala Ser Val Leu Gly Leu Asp Asp Ile
705                 710                 715                 720

His Arg Ala Trp Arg Thr Phe Val Leu Arg Val Arg Ala Gln Asp Pro
                725                 730                 735

Pro Pro Glu Leu Tyr Phe Val Lys Val Asp Val Thr Gly Ala Tyr Asp
```

-continued

```
                740                 745                 750
Thr Ile Pro Gln Asp Arg Leu Thr Glu Val Ile Ala Ser Ile Ile Lys
            755                 760                 765
Pro Gln Asn Thr Tyr Cys Val Arg Arg Tyr Ala Val Val Gln Lys Ala
        770                 775                 780
Ala His Gly His Val Arg Lys Ala Phe Lys Ser His Val Ser Thr Leu
785                 790                 795                 800
Thr Asp Leu Gln Pro Tyr Met Arg Gln Phe Val Ala His Leu Gln Glu
                805                 810                 815
Thr Ser Pro Leu Arg Asp Ala Val Val Ile Glu Gln Ser Ser Ser Leu
            820                 825                 830
Asn Glu Ala Ser Ser Gly Leu Phe Asp Val Phe Leu Arg Phe Met Cys
        835                 840                 845
His His Ala Val Arg Ile Arg Gly Lys Ser Tyr Val Gln Cys Gln Gly
850                 855                 860
Ile Pro Gln Gly Ser Ile Leu Ser Thr Leu Leu Cys Ser Leu Cys Tyr
865                 870                 875                 880
Gly Asp Met Glu Asn Lys Leu Phe Ala Gly Ile Arg Arg Asp Gly Leu
                885                 890                 895
Leu Leu Arg Leu Val Asp Asp Phe Leu Leu Val Thr Pro His Leu Thr
            900                 905                 910
His Ala Lys Thr Phe Leu Arg Thr Leu Val Arg Gly Val Pro Glu Tyr
        915                 920                 925
Gly Cys Val Val Asn Leu Arg Lys Thr Val Val Asn Phe Pro Val Glu
    930                 935                 940
Asp Glu Ala Leu Gly Gly Thr Ala Phe Val Gln Met Pro Ala His Gly
945                 950                 955                 960
Leu Phe Pro Trp Cys Gly Leu Leu Asp Thr Arg Thr Leu Glu Val
                965                 970                 975
Gln Ser Asp Tyr Ser Ser Tyr Ala Arg Thr Ser Ile Arg Ala Ser Leu
            980                 985                 990
Thr Phe Asn Arg Gly Phe Lys Ala Gly Arg Asn Met Arg Arg Lys Leu
        995                 1000                1005
Phe Gly Val Leu Arg Leu Lys Cys His Ser Leu Phe Leu Asp Leu Gln
    1010                1015                1020
Val Asn Ser Leu Gln Thr Val Cys Thr Asn Ile Tyr Lys Ile Leu Leu
1025                1030                1035                1040
Leu Gln Ala Tyr Arg Phe His Ala Cys Val Leu Gln Leu Pro Phe His
                1045                1050                1055
Gln Gln Val Trp Lys Asn Pro Thr Phe Phe Leu Arg Val Ile Ser Asp
            1060                1065                1070
Thr Ala Ser Leu Cys Tyr Ser Ile Leu Lys Ala Lys Asn Ala Glu Glu
        1075                1080                1085
Glu Asn Ile Leu Val Val Thr Pro Ala Val Leu Gly Ser Gly Gln Pro
    1090                1095                1100
Glu Met Glu Pro Pro Arg Arg Pro Ser Gly Val Gly Ser Phe Pro Val
1105                1110                1115                1120
Ser Pro Gly Arg Gly Val Gly Leu Gly Leu
                1125                1130
```

<210> SEQ ID NO 75
<211> LENGTH: 4022
<212> TYPE: DNA
<213> ORGANISM: Homo sapiens -continued
<220> FEATURE:
<223> OTHER INFORMATION: Protein Lacking Motif A (ver.2); with Introns Y and Beta

<400> SEQUENCE: 75

```
atgccgcgcg ctccccgctg ccgagccgtg cgctccctgc tgcgcagcca ctaccgcgag        60
gtgctgccgc tggccacgtt cgtgcggcgc ctggggcccc agggctggcg gctggtgcag       120
cgcggggacc cggcggcttt ccgcgcgctg gtggcccagt gcctggtgtg cgtgccctgg       180
gacgcacggc cgcccccgc cgcccccctcc ttccgccagg tgggcctccc cggggtcggc       240
gtccggctgg ggttgagggc ggccgggggg aaccagcgac atgcggagag cagcgcaggc       300
gactcagggc gcttcccccg caggtgtcct gcctgaagga gctggtggcc cgagtgctgc       360
agaggctgtg cgagcgcggc gcgaagaacg tgctggcctt cggcttcgcg ctgctggacg       420
ggcccgcgg gggccccccc gaggccttca ccaccagcgt gcgcagctac ctgcccaaca       480
cggtgaccga cgcactgcgg gggagcgggg cgtgggggct gctgctgcgc gcgtgggcg       540
acgacgtgct ggttcacctg ctggcacgct gcgcgctctt tgtgctggtg ctcccagct       600
gcgcctacca ggtgtgcggg ccgccgctgt accagctcgg cgctgccact caggcccggc       660
ccccgccaca cgctagtgga ccccgaaggc gtctgggatg cgaacgggcc tggaaccata       720
gcgtcaggga ggccggggtc cccctgggcc tgccagcccc gggtgcgagg aggcgcgggg       780
gcagtgccag ccgaagtctg ccgttgccca agaggcccag gcgtggcgct gcccctgagc       840
cggagcggac gcccgttggg cagggtcct gggcccaccc gggcaggacg cgtggaccga       900
gtgaccgtgg tttctgtgtg gtgtcacctg ccagacccgc cgaagaagcc acctctttgg       960
agggtgcgct ctctggcacg cgccactccc acccatccgt gggccgccag caccacgcgg      1020
gccccccatc cacatcgcgg ccaccacgtc cctgggacac gccttgtccc ccggtgtacg      1080
ccgagaccaa gcacttcctc tactcctcag gcgacaagga gcagctgcgg ccctccttcc      1140
tactcagctc tctgaggccc agcctgactg gcgctcggag gctcgtggag accatctttc      1200
tgggttccag gccctggatg ccagggactc ccgcaggtt gccccgcctg cccagcgct       1260
actggcaaat gcggcccctg tttctggagc tgcttgggaa ccacgcgcag tgcccctacg      1320
gggtgctcct caagacgcac tgcccgctgc gagctgcggt cacccccagca gccggtgtct      1380
gtgcccggga gaagccccag ggctctgtgg cggcccccga ggaggaggac acagaccccc      1440
gtcgcctggt gcagctgctc cgccagcaca gcagcccctg gcaggtgtac ggcttcgtgc      1500
gggcctgcct gcgccggctg gtgccccag gcctctgggg ctccaggcac aacgaacgcc      1560
gcttcctcag gaacaccaag aagttcatct ccctggggaa gcatgccaag ctctcgctgc      1620
aggagctgac gtggaagatg agcgtgcggg actgcgcttg gctgcgcagg agcccagggg      1680
ttggctgtgt ccggccgcga gagcaccgtc tgcgtgagga gatcctggcc aagttcctgc      1740
actggctgat gagtgtgtac gtcgtcgagc tgctcaggtc ttctttttat gtcacggaga      1800
ccacgtttca aaagaacagg ctcttttct accggaagag tgtctggagc aagttgcaaa      1860
gcattggaat cagacagcac ttgaagaggg tgcagctgcg ggagctgtcg gaagcagagg      1920
tcaggcagca tcgggaagcc aggcccgccc tgctgacgtc cagactccgc ttcatcccca      1980
agcctgacgg gctgcggccg attgtgaaca tggactacgt cgtgggagcc agaacgttcc      2040
gcagagaaaa gagggccgag cgtctcacct cgagggtgaa ggcactgttc agcgtgctca      2100
actacgagcg ggcgcggcgc cccggcctcc tgggcgcctc tgtgctgggc ctggacgata      2160
tccacagggc ctggcgcacc ttcgtgctgc gtgtgcgggc ccaggacccg ccgcctgagc      2220
```

-continued

```
tgtactttgt caaggacagg ctcacggagg tcatcgccag catcatcaaa ccccagaaca      2280
cgtactgcgt gcgtcggtat gccgtggtcc agaaggccgc ccatgggcac gtccgcaagg      2340
ccttcaagag ccacgtctct accttgacag acctccagcc gtacatgcga cagttcgtgg      2400
ctcacctgca ggagaccagc ccgctgaggg atgccgtcgt catcgagcag agctcctccc      2460
tgaatgaggc cagcagtggc ctcttcgacg tcttcctacg cttcatgtgc caccacgccg      2520
tgcgcatcag gggcaagtcc tacgtccagt gccagggat cccgcagggc tccatcctct       2580
ccacgctgct ctgcagcctg tgctacgcg acatggagaa caagctgttt gcggggattc       2640
ggcgggacgg gctgctcctg cgtttggtgg atgatttctt gttggtgaca cctcacctca     2700
cccacgcgaa aaccttcctc aggacccctgg tccgaggtgt ccctgagtat ggctgcgtgg    2760
tgaacttgcg gaagacagtg gtgaacttcc ctgtagaaga cgaggccctg ggtggcacgg     2820
cttttgttca gatgccggcc cacggcctat tcccctggtg cggcctgctg ctggataccc     2880
ggaccctgga ggtgcagagc gactactcca gctatgcccg gacctccatc agagccagtc    2940
tcaccttcaa ccgcggcttc aaggctggga ggaacatgcg tcgcaaactc tttgggtct    3000 tgcggctgaa gtgtcacagc ctgtttctgg atttgcaggt gaacagcctc cagacggtgt    3060
gcaccaacat ctacaagatc ctcctgctgc aggcgtacag gtttcacgca tgtgtgctgc   3120
agctcccatt tcatcagcaa gtttggaaga accccacatt tttcctgcgc gtcatctctg   3180
acacggcctc cctctgctac tccatcctga agccaagaa cgcagggatg tcgctggggg   3240
ccaagggcgc cgccggccct ctgccctccg aggccgtgca gtggcgtgtg caccaagcat   3300
tcctgctcaa gctgactcga caccgtgtca cctacgtgcc actcctgggg tcactcagga   3360
cagcccagac gcagctgagt cggaagctcc cggggacgac gctgactgcc ctggaggccg   3420
cagccaaccc ggcactgccc tcagacttca agaccatcct ggactgatgg ccacccgccc   3480
acagccaggc cgagagcaga caccagcagc cctgtcacgc cgggctctac gtcccaggga   3540
gggaggggcg gcccacaccc aggcccgcac cgctgggagt ctgaggcctg agtgagtgtt   3600
tggccgaggc ctgcatgtcc ggctgaaggc tgagtgtccg gctgaggcct gagcgagtgt   3660
ccagccaagg gctgagtgtc cagcacacct gccgtcttca cttccccaca ggctggcgct   3720
cggctccacc ccagggccag cttttcctca ccaggagccc ggcttccact ccccacatag   3780
gaatagtcca tccccagatt cgccattgtt cacccctcgc cctgccctcc tttgccttcc   3840 accccccacca tccaggtgga gaccctgaga aggaccctgg gagctctggg aatttggagt  3900
gaccaaaggt gtgccctgta cacaggcgag gaccctgcac ctggatgggg gtccctgtgg  3960
gtcaaattgg ggggaggtgc tgtgggagta aatactgaa tatatgagtt tttcagtttt    4020
ga                                                                    4022
```

<210> SEQ ID NO 76
<211> LENGTH: 1154
<212> TYPE: PRT
<213> ORGANISM: Homo sapiens
<220> FEATURE:
<223> OTHER INFORMATION: Protein Lacking Motif A (ver.2); encoded by SEQ
      ID NO:75 with Intron Y ORF1

<400> SEQUENCE: 76

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

-continued

```
Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Gly Leu Pro Gly Val Gly
65                  70                  75                  80

Val Arg Leu Gly Leu Arg Ala Ala Gly Asn Gln Arg His Ala Glu
                85                  90                  95

Ser Ser Ala Gly Asp Ser Gly Arg Phe Pro Arg Arg Ser Cys Leu Lys
                100                 105                 110

Glu Leu Val Ala Arg Val Leu Gln Arg Leu Cys Glu Arg Gly Ala Lys
            115                 120                 125

Asn Val Leu Ala Phe Gly Phe Ala Leu Leu Asp Gly Ala Arg Gly Gly
            130                 135                 140

Pro Pro Glu Ala Phe Thr Thr Ser Val Arg Ser Tyr Leu Pro Asn Thr
145                 150                 155                 160

Val Thr Asp Ala Leu Arg Gly Ser Gly Ala Trp Gly Leu Leu Leu Arg
                165                 170                 175

Arg Val Gly Asp Asp Val Leu Val His Leu Leu Ala Arg Cys Ala Leu
                180                 185                 190

Phe Val Leu Val Ala Pro Ser Cys Ala Tyr Gln Val Cys Gly Pro Pro
            195                 200                 205

Leu Tyr Gln Leu Gly Ala Ala Thr Gln Ala Arg Pro Pro His Ala
    210                 215                 220

Ser Gly Pro Arg Arg Leu Gly Cys Glu Arg Ala Trp Asn His Ser
225                 230                 235                 240

Val Arg Glu Ala Gly Val Pro Leu Gly Leu Pro Ala Pro Gly Ala Arg
                245                 250                 255

Arg Arg Gly Gly Ser Ala Ser Arg Ser Leu Pro Leu Pro Lys Arg Pro
            260                 265                 270

Arg Arg Gly Ala Ala Pro Glu Pro Glu Arg Thr Pro Val Gly Gln Gly
            275                 280                 285

Ser Trp Ala His Pro Gly Arg Thr Arg Gly Pro Ser Asp Arg Gly Phe
    290                 295                 300

Cys Val Val Ser Pro Ala Arg Pro Ala Glu Ala Thr Ser Leu Glu
305                 310                 315                 320

Gly Ala Leu Ser Gly Thr Arg His Ser His Pro Ser Val Gly Arg Gln
                325                 330                 335

His His Ala Gly Pro Pro Ser Thr Ser Arg Pro Pro Arg Pro Trp Asp
            340                 345                 350

Thr Pro Cys Pro Pro Val Tyr Ala Glu Thr Lys His Phe Leu Tyr Ser
        355                 360                 365

Ser Gly Asp Lys Glu Gln Leu Arg Pro Ser Phe Leu Leu Ser Ser Leu
    370                 375                 380

Arg Pro Ser Leu Thr Gly Ala Arg Arg Leu Val Glu Thr Ile Phe Leu
385                 390                 395                 400

Gly Ser Arg Pro Trp Met Pro Gly Thr Pro Arg Arg Leu Pro Arg Leu
                405                 410                 415

Pro Gln Arg Tyr Trp Gln Met Arg Pro Leu Phe Leu Glu Leu Leu Gly
                420                 425                 430

Asn His Ala Gln Cys Pro Tyr Gly Val Leu Leu Lys Thr His Cys Pro
            435                 440                 445
```

```
Leu Arg Ala Ala Val Thr Pro Ala Gly Val Cys Ala Arg Glu Lys
    450                 455                 460

Pro Gln Gly Ser Val Ala Ala Pro Glu Glu Glu Asp Thr Asp Pro Arg
465                 470                 475                 480

Arg Leu Val Gln Leu Leu Arg Gln His Ser Ser Pro Trp Gln Val Tyr
                485                 490                 495

Gly Phe Val Arg Ala Cys Leu Arg Arg Leu Val Pro Pro Gly Leu Trp
            500                 505                 510

Gly Ser Arg His Asn Glu Arg Arg Phe Leu Arg Asn Thr Lys Lys Phe
            515                 520                 525

Ile Ser Leu Gly Lys His Ala Lys Leu Ser Leu Gln Glu Leu Thr Trp
    530                 535                 540

Lys Met Ser Val Arg Asp Cys Ala Trp Leu Arg Arg Ser Pro Gly Val
545                 550                 555                 560

Gly Cys Val Pro Ala Ala Glu His Arg Leu Arg Glu Glu Ile Leu Ala
                565                 570                 575

Lys Phe Leu His Trp Leu Met Ser Val Tyr Val Glu Leu Leu Arg
            580                 585                 590

Ser Phe Phe Tyr Val Thr Glu Thr Thr Phe Gln Lys Asn Arg Leu Phe
    595                 600                 605

Phe Tyr Arg Lys Ser Val Trp Ser Lys Leu Gln Ser Ile Gly Ile Arg
            610                 615                 620

Gln His Leu Lys Arg Val Gln Leu Arg Glu Leu Ser Glu Ala Glu Val
625                 630                 635                 640

Arg Gln His Arg Glu Ala Arg Pro Ala Leu Leu Thr Ser Arg Leu Arg
                645                 650                 655

Phe Ile Pro Lys Pro Asp Gly Leu Arg Pro Ile Val Asn Met Asp Tyr
            660                 665                 670

Val Val Gly Ala Arg Thr Phe Arg Arg Glu Lys Arg Ala Glu Arg Leu
    675                 680                 685

Thr Ser Arg Val Lys Ala Leu Phe Ser Val Leu Asn Tyr Glu Arg Ala
690                 695                 700

Arg Arg Pro Gly Leu Leu Gly Ala Ser Val Leu Gly Leu Asp Asp Ile
705                 710                 715                 720

His Arg Ala Trp Arg Thr Phe Val Leu Arg Val Arg Ala Gln Asp Pro
                725                 730                 735

Pro Pro Glu Leu Tyr Phe Val Lys Asp Arg Leu Thr Glu Val Ile Ala
            740                 745                 750

Ser Ile Ile Lys Pro Gln Asn Thr Tyr Cys Val Arg Arg Tyr Ala Val
    755                 760                 765

Val Gln Lys Ala Ala His Gly His Val Arg Lys Ala Phe Lys Ser His
    770                 775                 780

Val Ser Thr Leu Thr Asp Leu Gln Pro Tyr Met Arg Gln Phe Val Ala
785                 790                 795                 800

His Leu Gln Glu Thr Ser Pro Leu Arg Asp Ala Val Val Ile Glu Gln
                805                 810                 815

Ser Ser Ser Leu Asn Glu Ala Ser Ser Gly Leu Phe Asp Val Phe Leu
            820                 825                 830

Arg Phe Met Cys His His Ala Val Arg Ile Arg Gly Lys Ser Tyr Val
            835                 840                 845

Gln Cys Gln Gly Ile Pro Gln Gly Ser Ile Leu Ser Thr Leu Leu Cys
    850                 855                 860

Ser Leu Cys Tyr Gly Asp Met Glu Asn Lys Leu Phe Ala Gly Ile Arg
```

-continued

```
                865                 870                 875                 880
Arg Asp Gly Leu Leu Arg Leu Val Asp Asp Phe Leu Leu Val Thr
                    885                 890                 895
Pro His Leu Thr His Ala Lys Thr Phe Leu Arg Thr Leu Val Arg Gly
                    900                 905                 910
Val Pro Glu Tyr Gly Cys Val Val Asn Leu Arg Lys Thr Val Val Asn
                915                 920                 925
Phe Pro Val Glu Asp Glu Ala Leu Gly Gly Thr Ala Phe Val Gln Met
            930                 935                 940
Pro Ala His Gly Leu Phe Pro Trp Cys Gly Leu Leu Asp Thr Arg
945                 950                 955                 960
Thr Leu Glu Val Gln Ser Asp Tyr Ser Ser Tyr Ala Arg Thr Ser Ile
                    965                 970                 975
Arg Ala Ser Leu Thr Phe Asn Arg Gly Phe Lys Ala Gly Arg Asn Met
                980                 985                 990
Arg Arg Lys Leu Phe Gly Val Leu Arg Leu Lys Cys His Ser Leu Phe
            995                 1000                1005
Leu Asp Leu Gln Val Asn Ser Leu Gln Thr Val Cys Thr Asn Ile Tyr
        1010                1015                1020
Lys Ile Leu Leu Gln Ala Tyr Arg Phe His Ala Cys Val Leu Gln
1025                1030                1035                1040
Leu Pro Phe His Gln Gln Val Trp Lys Asn Pro Thr Phe Phe Leu Arg
                1045                1050                1055
Val Ile Ser Asp Thr Ala Ser Leu Cys Tyr Ser Ile Leu Lys Ala Lys
                1060                1065                1070
Asn Ala Gly Met Ser Leu Gly Ala Lys Gly Ala Ala Gly Pro Leu Pro
            1075                1080                1085
Ser Glu Ala Val Gln Trp Leu Cys His Gln Ala Phe Leu Leu Lys Leu
        1090                1095                1100
Thr Arg His Arg Val Thr Tyr Val Pro Leu Leu Gly Ser Leu Arg Thr
1105                1110                1115                1120
Ala Gln Thr Gln Leu Ser Arg Lys Leu Pro Gly Thr Thr Leu Thr Ala
                1125                1130                1135
Leu Glu Ala Ala Ala Asn Pro Ala Leu Pro Ser Asp Phe Lys Thr Ile
            1140                1145                1150
Leu Asp
```

```
<210> SEQ ID NO 77
<211> LENGTH: 1069
<212> TYPE: PRT
<213> ORGANISM: Homo sapiens
<220> FEATURE:
<223> OTHER INFORMATION: Protein Lacking Motif A (ver.2); encoded by SEQ
      ID NO:75 with Intron Y ORF2 after the termination
      codon

<400> SEQUENCE: 77
```

```
Gly Arg Pro Gly Gly Thr Ser Asp Met Arg Arg Ala Ala Gln Ala Thr
1               5                   10                  15
Gln Gly Ala Ser Pro Ala Gly Ser Cys Leu Lys Glu Leu Val Ala Arg
            20                  25                  30
Val Leu Gln Arg Leu Cys Glu Arg Gly Ala Lys Asn Val Leu Ala Phe
        35                  40                  45
Gly Phe Ala Leu Leu Asp Gly Ala Arg Gly Gly Pro Pro Glu Ala Phe
    50                  55                  60
```

```
Thr Thr Ser Val Arg Ser Tyr Leu Pro Asn Thr Val Thr Asp Ala Leu
 65                  70                  75                  80

Arg Gly Ser Gly Ala Trp Gly Leu Leu Arg Arg Val Gly Asp Asp
                 85                  90                  95

Val Leu Val His Leu Leu Ala Arg Cys Ala Leu Phe Val Leu Val Ala
            100                 105                 110

Pro Ser Cys Ala Tyr Gln Val Cys Gly Pro Pro Leu Tyr Gln Leu Gly
        115                 120                 125

Ala Ala Thr Gln Ala Arg Pro Pro His Ala Ser Gly Pro Arg Arg
    130                 135                 140

Arg Leu Gly Cys Glu Arg Ala Trp Asn His Ser Val Arg Glu Ala Gly
145                 150                 155                 160

Val Pro Leu Gly Leu Pro Ala Pro Gly Ala Arg Arg Gly Gly Ser
                165                 170                 175

Ala Ser Arg Ser Leu Pro Leu Pro Lys Arg Pro Arg Arg Gly Ala Ala
            180                 185                 190

Pro Glu Pro Glu Arg Thr Pro Val Gly Gln Gly Ser Trp Ala His Pro
        195                 200                 205

Gly Arg Thr Arg Gly Pro Ser Asp Arg Gly Phe Cys Val Val Ser Pro
210                 215                 220

Ala Arg Pro Ala Glu Glu Ala Thr Ser Leu Glu Gly Ala Leu Ser Gly
225                 230                 235                 240

Thr Arg His Ser His Pro Ser Val Gly Arg Gln His His Ala Gly Pro
                245                 250                 255

Pro Ser Thr Ser Arg Pro Pro Arg Pro Trp Asp Thr Pro Cys Pro Pro
            260                 265                 270

Val Tyr Ala Glu Thr Lys His Phe Leu Tyr Ser Ser Gly Asp Lys Glu
        275                 280                 285

Gln Leu Arg Pro Ser Phe Leu Leu Ser Ser Leu Arg Pro Ser Leu Thr
    290                 295                 300

Gly Ala Arg Arg Leu Val Glu Thr Ile Phe Leu Gly Ser Arg Pro Trp
305                 310                 315                 320

Met Pro Gly Thr Pro Arg Arg Leu Pro Arg Leu Pro Gln Arg Tyr Trp
                325                 330                 335

Gln Met Arg Pro Leu Phe Leu Glu Leu Leu Gly Asn His Ala Gln Cys
            340                 345                 350

Pro Tyr Gly Val Leu Leu Lys Thr His Cys Pro Leu Arg Ala Ala Val
        355                 360                 365

Thr Pro Ala Ala Gly Val Cys Ala Arg Glu Lys Pro Gln Gly Ser Val
    370                 375                 380

Ala Ala Pro Glu Glu Asp Thr Asp Pro Arg Arg Leu Val Gln Leu
385                 390                 395                 400

Leu Arg Gln His Ser Ser Pro Trp Gln Val Tyr Gly Phe Val Arg Ala
                405                 410                 415

Cys Leu Arg Arg Leu Val Pro Pro Gly Leu Trp Gly Ser Arg His Asn
            420                 425                 430

Glu Arg Arg Phe Leu Arg Asn Thr Lys Lys Phe Ile Ser Leu Gly Lys
        435                 440                 445

His Ala Lys Leu Ser Leu Gln Glu Leu Thr Trp Lys Met Ser Val Arg
    450                 455                 460

Asp Cys Ala Trp Leu Arg Arg Ser Pro Gly Val Gly Cys Val Pro Ala
465                 470                 475                 480

Ala Glu His Arg Leu Arg Glu Glu Ile Leu Ala Lys Phe Leu His Trp
```

-continued

```
                485                 490                 495
Leu Met Ser Val Tyr Val Val Glu Leu Leu Arg Ser Phe Phe Tyr Val
                500                 505                 510
Thr Glu Thr Thr Phe Gln Lys Asn Arg Leu Phe Phe Tyr Arg Lys Ser
                515                 520                 525
Val Trp Ser Lys Leu Gln Ser Ile Gly Ile Arg Gln His Leu Lys Arg
                530                 535                 540
Val Gln Leu Arg Glu Leu Ser Glu Ala Glu Val Arg Gln His Arg Glu
545                 550                 555                 560
Ala Arg Pro Ala Leu Leu Thr Ser Arg Leu Arg Phe Ile Pro Lys Pro
                565                 570                 575
Asp Gly Leu Arg Pro Ile Val Asn Met Asp Tyr Val Val Gly Ala Arg
                580                 585                 590
Thr Phe Arg Arg Glu Lys Arg Ala Glu Arg Leu Thr Ser Arg Val Lys
                595                 600                 605
Ala Leu Phe Ser Val Leu Asn Tyr Glu Arg Ala Arg Arg Pro Gly Leu
                610                 615                 620
Leu Gly Ala Ser Val Leu Gly Leu Asp Asp Ile His Arg Ala Trp Arg
625                 630                 635                 640
Thr Phe Val Leu Arg Val Arg Ala Gln Asp Pro Pro Glu Leu Tyr
                645                 650                 655
Phe Val Lys Asp Arg Leu Thr Glu Val Ile Ala Ser Ile Ile Lys Pro
                660                 665                 670
Gln Asn Thr Tyr Cys Val Arg Arg Tyr Ala Val Val Gln Lys Ala Ala
                675                 680                 685
His Gly His Val Arg Lys Ala Phe Lys Ser His Val Ser Thr Leu Thr
                690                 695                 700
Asp Leu Gln Pro Tyr Met Arg Gln Phe Val Ala His Leu Gln Glu Thr
705                 710                 715                 720
Ser Pro Leu Arg Asp Ala Val Val Ile Glu Gln Ser Ser Ser Leu Asn
                725                 730                 735
Glu Ala Ser Ser Gly Leu Phe Asp Val Phe Leu Arg Phe Met Cys His
                740                 745                 750
His Ala Val Arg Ile Arg Gly Lys Ser Tyr Val Gln Cys Gln Gly Ile
                755                 760                 765
Pro Gln Gly Ser Ile Leu Ser Thr Leu Leu Cys Ser Leu Cys Tyr Gly
                770                 775                 780
Asp Met Glu Asn Lys Leu Phe Ala Gly Ile Arg Arg Asp Gly Leu Leu
785                 790                 795                 800
Leu Arg Leu Val Asp Asp Phe Leu Leu Val Thr Pro His Leu Thr His
                805                 810                 815
Ala Lys Thr Phe Leu Arg Thr Leu Val Arg Gly Val Pro Glu Tyr Gly
                820                 825                 830
Cys Val Val Asn Leu Arg Lys Thr Val Val Asn Phe Pro Val Glu Asp
                835                 840                 845
Glu Ala Leu Gly Gly Thr Ala Phe Val Gln Met Pro Ala His Gly Leu
                850                 855                 860
Phe Pro Trp Cys Gly Leu Leu Leu Asp Thr Arg Thr Leu Glu Val Gln
865                 870                 875                 880
Ser Asp Tyr Ser Ser Tyr Ala Arg Thr Ser Ile Arg Ala Ser Leu Thr
                885                 890                 895
Phe Asn Arg Gly Phe Lys Ala Gly Arg Asn Met Arg Arg Lys Leu Phe
                900                 905                 910
```

-continued

```
Gly Val Leu Arg Leu Lys Cys His Ser Leu Phe Leu Asp Leu Gln Val
            915                 920                 925

Asn Ser Leu Gln Thr Val Cys Thr Asn Ile Tyr Lys Ile Leu Leu Leu
        930                 935                 940

Gln Ala Tyr Arg Phe His Ala Cys Val Leu Gln Leu Pro Phe His Gln
945                 950                 955                 960

Gln Val Trp Lys Asn Pro Thr Phe Phe Leu Arg Val Ile Ser Asp Thr
                965                 970                 975

Ala Ser Leu Cys Tyr Ser Ile Leu Lys Ala Lys Asn Ala Gly Met Ser
            980                 985                 990

Leu Gly Ala Lys Gly Ala Ala Gly Pro Leu Pro Ser Glu Ala Val Gln
        995                 1000                1005

Trp Leu Cys His Gln Ala Phe Leu Leu Lys Leu Thr Arg His Arg Val
    1010                1015                1020

Thr Tyr Val Pro Leu Leu Gly Ser Leu Arg Thr Ala Gln Thr Gln Leu
1025                1030                1035                1040

Ser Arg Lys Leu Pro Gly Thr Thr Leu Thr Ala Leu Glu Ala Ala Ala
                1045                1050                1055

Asn Pro Ala Leu Pro Ser Asp Phe Lys Thr Ile Leu Asp
            1060                1065
```

<210> SEQ ID NO 78
<211> LENGTH: 1154
<212> TYPE: PRT
<213> ORGANISM: Homo sapiens
<220> FEATURE:
<223> OTHER INFORMATION: Protein Lacking Motif A (ver.2); encoded by SEQ
      ID NO:75 with Intron Y ORF3

<400> SEQUENCE: 78

```
Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Pro Pro Arg Gly Arg Arg
65                  70                  75                  80

Pro Ala Gly Val Glu Gly Gly Arg Gly Glu Pro Ala Thr Cys Gly Glu
                85                  90                  95

Gln Arg Arg Arg Leu Arg Ala Leu Pro Pro Gln Val Ser Cys Leu Lys
            100                 105                 110

Glu Leu Val Ala Arg Val Leu Gln Arg Leu Cys Glu Arg Gly Ala Lys
        115                 120                 125

Asn Val Leu Ala Phe Gly Phe Ala Leu Leu Asp Gly Ala Arg Gly Gly
    130                 135                 140

Pro Pro Glu Ala Phe Thr Thr Ser Val Arg Ser Tyr Leu Pro Asn Thr
145                 150                 155                 160

Val Thr Asp Ala Leu Arg Gly Ser Gly Ala Trp Gly Leu Leu Leu Arg
                165                 170                 175

Arg Val Gly Asp Asp Val Leu Val His Leu Leu Ala Arg Cys Ala Leu
            180                 185                 190

Phe Val Leu Val Ala Pro Ser Cys Ala Tyr Gln Val Cys Gly Pro Pro
```

-continued

```
            195                 200                 205
Leu Tyr Gln Leu Gly Ala Ala Thr Gln Ala Arg Pro Pro His Ala
    210                 215                 220

Ser Gly Pro Arg Arg Leu Gly Cys Glu Arg Ala Trp Asn His Ser
225                 230                 235                 240

Val Arg Glu Ala Gly Val Pro Leu Gly Leu Pro Ala Pro Gly Ala Arg
                245                 250                 255

Arg Arg Gly Gly Ser Ala Ser Arg Ser Leu Pro Leu Pro Lys Arg Pro
                260                 265                 270

Arg Arg Gly Ala Ala Pro Glu Pro Glu Arg Thr Pro Val Gly Gln Gly
                275                 280                 285

Ser Trp Ala His Pro Gly Arg Thr Arg Gly Pro Ser Asp Arg Gly Phe
    290                 295                 300

Cys Val Val Ser Pro Ala Arg Pro Ala Glu Glu Ala Thr Ser Leu Glu
305                 310                 315                 320

Gly Ala Leu Ser Gly Thr Arg His Ser His Pro Ser Val Gly Arg Gln
                325                 330                 335

His His Ala Gly Pro Pro Ser Thr Ser Arg Pro Pro Arg Pro Trp Asp
                340                 345                 350

Thr Pro Cys Pro Pro Val Tyr Ala Glu Thr Lys His Phe Leu Tyr Ser
        355                 360                 365

Ser Gly Asp Lys Glu Gln Leu Arg Pro Ser Phe Leu Leu Ser Ser Leu
    370                 375                 380

Arg Pro Ser Leu Thr Gly Ala Arg Arg Leu Val Glu Thr Ile Phe Leu
385                 390                 395                 400

Gly Ser Arg Pro Trp Met Pro Gly Thr Pro Arg Arg Leu Pro Arg Leu
                405                 410                 415

Pro Gln Arg Tyr Trp Gln Met Arg Pro Leu Phe Leu Glu Leu Leu Gly
                420                 425                 430

Asn His Ala Gln Cys Pro Tyr Gly Val Leu Leu Lys Thr His Cys Pro
                435                 440                 445

Leu Arg Ala Ala Val Thr Pro Ala Ala Gly Val Cys Ala Arg Glu Lys
    450                 455                 460

Pro Gln Gly Ser Val Ala Ala Pro Glu Glu Asp Thr Asp Pro Arg
465                 470                 475                 480

Arg Leu Val Gln Leu Leu Arg Gln His Ser Ser Pro Trp Gln Val Tyr
                485                 490                 495

Gly Phe Val Arg Ala Cys Leu Arg Arg Leu Val Pro Pro Gly Leu Trp
                500                 505                 510

Gly Ser Arg His Asn Glu Arg Arg Phe Leu Arg Asn Thr Lys Lys Phe
                515                 520                 525

Ile Ser Leu Gly Lys His Ala Lys Leu Ser Leu Gln Glu Leu Thr Trp
    530                 535                 540

Lys Met Ser Val Arg Asp Cys Ala Trp Leu Arg Arg Ser Pro Gly Val
545                 550                 555                 560

Gly Cys Val Pro Ala Ala Glu His Arg Leu Arg Glu Glu Ile Leu Ala
                565                 570                 575

Lys Phe Leu His Trp Leu Met Ser Val Tyr Val Val Glu Leu Leu Arg
                580                 585                 590

Ser Phe Phe Tyr Val Thr Glu Thr Thr Phe Gln Lys Asn Arg Leu Phe
        595                 600                 605

Phe Tyr Arg Lys Ser Val Trp Ser Lys Leu Gln Ser Ile Gly Ile Arg
    610                 615                 620
```

```
Gln His Leu Lys Arg Val Gln Leu Arg Glu Leu Ser Glu Ala Glu Val
625                 630                 635                 640

Arg Gln His Arg Glu Ala Arg Pro Ala Leu Leu Thr Ser Arg Leu Arg
            645                 650                 655

Phe Ile Pro Lys Pro Asp Gly Leu Arg Pro Ile Val Asn Met Asp Tyr
            660                 665                 670

Val Val Gly Ala Arg Thr Phe Arg Glu Lys Arg Ala Glu Arg Leu
        675                 680                 685

Thr Ser Arg Val Lys Ala Leu Phe Ser Val Leu Asn Tyr Glu Arg Ala
690                 695                 700

Arg Arg Pro Gly Leu Leu Gly Ala Ser Val Leu Gly Leu Asp Asp Ile
705                 710                 715                 720

His Arg Ala Trp Arg Thr Phe Val Leu Arg Val Arg Ala Gln Asp Pro
                725                 730                 735

Pro Pro Glu Leu Tyr Phe Val Lys Asp Arg Leu Thr Glu Val Ile Ala
                740                 745                 750

Ser Ile Ile Lys Pro Gln Asn Thr Tyr Cys Val Arg Arg Tyr Ala Val
            755                 760                 765

Val Gln Lys Ala Ala His Gly His Val Arg Lys Ala Phe Lys Ser His
770                 775                 780

Val Ser Thr Leu Thr Asp Leu Gln Pro Tyr Met Arg Gln Phe Val Ala
785                 790                 795                 800

His Leu Gln Glu Thr Ser Pro Leu Arg Asp Ala Val Ile Glu Gln
                805                 810                 815

Ser Ser Ser Leu Asn Glu Ala Ser Ser Gly Leu Phe Asp Val Phe Leu
            820                 825                 830

Arg Phe Met Cys His His Ala Val Arg Ile Arg Gly Lys Ser Tyr Val
            835                 840                 845

Gln Cys Gln Gly Ile Pro Gln Gly Ser Ile Leu Ser Thr Leu Leu Cys
850                 855                 860

Ser Leu Cys Tyr Gly Asp Met Glu Asn Lys Leu Phe Ala Gly Ile Arg
865                 870                 875                 880

Arg Asp Gly Leu Leu Leu Arg Leu Val Asp Asp Phe Leu Leu Val Thr
            885                 890                 895

Pro His Leu Thr His Ala Lys Thr Phe Leu Arg Thr Leu Val Arg Gly
            900                 905                 910

Val Pro Glu Tyr Gly Cys Val Val Asn Leu Arg Lys Thr Val Val Asn
            915                 920                 925

Phe Pro Val Glu Asp Glu Ala Leu Gly Gly Thr Ala Phe Val Gln Met
930                 935                 940

Pro Ala His Gly Leu Phe Pro Trp Cys Gly Leu Leu Leu Asp Thr Arg
945                 950                 955                 960

Thr Leu Glu Val Gln Ser Asp Tyr Ser Ser Tyr Ala Arg Thr Ser Ile
                965                 970                 975

Arg Ala Ser Leu Thr Phe Asn Arg Gly Phe Lys Ala Gly Arg Asn Met
            980                 985                 990

Arg Arg Lys Leu Phe Gly Val Leu Arg Leu Lys Cys His Ser Leu Phe
        995                 1000                1005

Leu Asp Leu Gln Val Asn Ser Leu Gln Thr Val Cys Thr Asn Ile Tyr
    1010                1015                1020

Lys Ile Leu Leu Leu Gln Ala Tyr Arg Phe His Ala Cys Val Leu Gln
1025                1030                1035                1040
```

-continued

```
Leu Pro Phe His Gln Gln Val Trp Lys Asn Pro Thr Phe Phe Leu Arg
            1045                1050                1055
Val Ile Ser Asp Thr Ala Ser Leu Cys Tyr Ser Ile Leu Lys Ala Lys
        1060                1065                1070
Asn Ala Gly Met Ser Leu Gly Ala Lys Gly Ala Ala Gly Pro Leu Pro
    1075                1080                1085
Ser Glu Ala Val Gln Trp Leu Cys His Gln Ala Phe Leu Leu Lys Leu
1090                1095                1100
Thr Arg His Arg Val Thr Tyr Val Pro Leu Leu Gly Ser Leu Arg Thr
1105                1110                1115                1120
Ala Gln Thr Gln Leu Ser Arg Lys Leu Pro Gly Thr Thr Leu Thr Ala
            1125                1130                1135
Leu Glu Ala Ala Ala Asn Pro Ala Leu Pro Ser Asp Phe Lys Thr Ile
        1140                1145                1150
Leu Asp
```

<210> SEQ ID NO 79
<211> LENGTH: 3137
<212> TYPE: DNA
<213> ORGANISM: Homo sapiens
<220> FEATURE:
<223> OTHER INFORMATION: Truncated Protein Lacking Motif A (ver.2); with Introns Y, Beta and 2

<400> SEQUENCE: 79

```
atgccgcgcg ctccccgctg ccgagccgtg cgctccctgc tgcgcagcca ctaccgcgag     60
gtgctgccgc tggccacgtt cgtgcggcgc ctggggcccc agggctggcg gctggtgcag    120
cgcggggacc cggcggcttt ccgcgcgctg gtggcccagt gcctggtgtg cgtgccctgg    180
gacgcacggc cgcccccgc cgcccctcc ttccgccagg tgggcctccc cggggtcggc     240
gtccggctgg ggttgagggc ggccgggggg aaccagcgac atgcggagag cagcgcaggc    300
gactcagggc gcttcccccg caggtgtcct gcctgaagga gctggtggcc cgagtgctgc    360
agaggctgtg cgagcgcggc gcgaagaacg tgctggcctt cggcttcgcg ctgctggacg    420
gggcccgcgg gggccccccc gaggccttca ccaccagcgt gcgcagctac ctgcccaaca    480
cggtgaccga cgcactgcgg gggagcgggg cgtgggggct gctgctgcgc gcgtggggcg    540
acgacgtgct ggttcacctg ctggcacgct gcgcgctctt tgtgctggtg gctcccagct    600
gcgcctacca ggtgtgcggg ccgccgctgt accagctcgg cgctgccact caggcccggc    660
ccccgccaca cgctagtgga ccccgaaggc gtctgggatg cgaacgggcc tggaaccata    720
gcgtcaggga ggccgggggc cccctggggcc tgccagcccc gggtgcgagg aggcgcgggg    780
gcagtgccag ccgaagtctg ccgttgccca agaggcccag cgtggcgct gcccctgagc    840
cggagcggac gcccgttggg caggggtcct gggcccaccc gggcaggacg cgtggaccga    900
gtgaccgtgg tttctgtgtg gtgtcacctg ccagacccgc cgaagaagcc acctctttgg    960
agggtgcgct ctctggcacg cgccactccc acccatccgt gggccgccag caccacgcgg   1020
gccccccatc cacatcgcgg ccaccacgtc cctgggacac gccttgtccc ccggtgtacg   1080
ccgagaccaa gcacttcctc tactcctcag gcgacaagga gcagctgcgg ccctccttcc   1140
tactcagctc tctgaggccc agcctgactg gcgctcggag gctcgtggag accatctttc   1200
tgggttccag gcctggatg ccagggactc ccgcaggtt gccccgcctg cccagcgct   1260
actggcaaat gcgccccctg tttctggagc tgcttgggaa ccacgcgcag tgccctacg   1320
gggtgctcct caagacgcac tgcccgctgc gagctgcggt caccccagca gccggtgtct   1380
```

-continued

```
gtgcccggga gaagccccag ggctctgtgg cggcccccga ggaggaggac acagaccccc      1440
gtcgcctggt gcagctgctc cgccagcaca gcagccctg gcaggtgtac ggcttcgtgc       1500
gggcctgcct cgcgccggctg gtgccccag gcctctgggg ctccaggcac aacgaacgcc      1560
gcttcctcag gaacaccaag aagttcatct ccctggggaa gcatgccaag ctctcgctgc     1620
aggagctgac gtggaagatg agcgtgcggg actgcgcttg gctgcgcagg agcccagggg     1680
ttggctgtgt tccggccgca gagcaccgtc tgcgtgagga gatcctggcc aagttcctgc     1740
actggctgat gagtgtgtac gtcgtcgagc tgctcaggtc tttctttat gtcacggaga      1800 ccacgtttca aaagaacagg ctcttttct accggaagag tgtctggagc aagttgcaaa      1860
gcattggaat cagacagcac ttgaagaggg tgcagctgcg ggagctgtcg aagcagagg      1920 tcaggcagca tcgggaagcc aggcccgccc tgctgacgtc cagactccgc ttcatcccca     1980
agcctgacgg gctgcggccg attgtgaaca tggactacgt cgtgggagcc agaacgttcc     2040
gcagagaaaa gagggccgag cgtctcacct cgagggtgaa ggcactgttc agcgtgctca     2100
actacgagcg ggcgcggcgc cccggcctcc tgggcgcctc tgtgctgggc ctggacgata     2160
tccacagggc ctggcgcacc ttcgtgctgc gtgtgcgggc ccaggacccg ccgcctgagc     2220
tgtactttgt caaggacagg ctcacggagg tcatcgccag catcatcaaa ccccagaaca     2280
cgtactgcgt gcgtcggtat gccgtggtcc agaaggccgc ccatgggcac gtccgcaagg    2340
ccttcaagag ccacgtctct accttgacag acctccagcc gtacatgcga cagttcgtgg    2400
ctcacctgca ggagaccagc ccgctgaggg atgccgtcgt catcgagcag agctcctccc    2460
tgaatgaggc cagcagtggc ctcttcgacg tcttcctacg cttcatgtgc caccacgccg     2520
tgcgcatcag gggcaagtcc tacgtccagt gccaggggat cccgcagggc tccatcctct     2580
ccacgctgct ctgcagcctg tgctacggcg acatggagaa caagctgttt gcggggattc     2640
ggcgggacgg gctgctcctg cgtttggtgg atgatttctt gttggtgaca cctcacctca     2700
cccacgcgaa aaccttcctc aggaccctgg tccgaggtgt ccctgagtat ggctgcgtgg    2760
tgaacttgcg gaagacagtg gtgaacttcc ctgtagaaga cgaggccctg ggtggcacgg    2820
cttttgttca gatgccggcc cacggcctat tcccctggtg cggcctgctg ctggataccc     2880
ggaccctgga ggtgcagagc gactactcca ggtgagcgca cctggccgga agtggagcct    2940
gtgcccggct ggggcaggtg ctgctgcagg gccgttgcgt ccacctctgc ttccgtgtgg    3000
ggcaggcgac tgccaatccc aaagggtcag atgccacagg gtgcccctcg tcccatctgg    3060
ggctgagcac aaatgcatct ttctgtggga gtgagggtgc ctcacaacgg gagcagtttt    3120
ctgtgctatt ttggtaa                                                    3137
```

<210> SEQ ID NO 80
<211> LENGTH: 970
<212> TYPE: PRT
<213> ORGANISM: Homo sapiens
<220> FEATURE:
<223> OTHER INFORMATION: Truncated Protein lacking Motif A (ver.2);
      encoded by SEQ ID NO:79 with Intron Y ORF1

<400> SEQUENCE: 80

Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
             20                  25                  30

Pro Gln Gly Trp Arg Leu Val Gln Arg Gly Asp Pro Ala Ala Phe Arg

-continued

```
                35                  40                  45
Ala Leu Val Ala Gln Cys Leu Val Cys Val Pro Trp Asp Ala Arg Pro
 50                  55                  60
Pro Pro Ala Ala Pro Ser Phe Arg Gln Val Gly Leu Pro Gly Val Gly
 65                  70                  75                  80
Val Arg Leu Gly Leu Arg Ala Ala Gly Asn Gln Arg His Ala Glu
                 85                  90                  95
Ser Ser Ala Gly Asp Ser Gly Arg Phe Pro Arg Arg Ser Cys Leu Lys
                100                 105                 110
Glu Leu Val Ala Arg Val Leu Gln Arg Leu Cys Glu Arg Gly Ala Lys
                115                 120                 125
Asn Val Leu Ala Phe Gly Phe Ala Leu Leu Asp Gly Ala Arg Gly Gly
130                 135                 140
Pro Pro Glu Ala Phe Thr Thr Ser Val Arg Ser Tyr Leu Pro Asn Thr
145                 150                 155                 160
Val Thr Asp Ala Leu Arg Gly Ser Gly Ala Trp Gly Leu Leu Leu Arg
                165                 170                 175
Arg Val Gly Asp Asp Val Leu Val His Leu Leu Ala Arg Cys Ala Leu
                180                 185                 190
Phe Val Leu Val Ala Pro Ser Cys Ala Tyr Gln Val Cys Gly Pro Pro
                195                 200                 205
Leu Tyr Gln Leu Gly Ala Ala Thr Gln Ala Arg Pro Pro His Ala
210                 215                 220
Ser Gly Pro Arg Arg Leu Gly Cys Glu Arg Ala Trp Asn His Ser
225                 230                 235                 240
Val Arg Glu Ala Gly Val Pro Leu Gly Leu Pro Ala Pro Gly Ala Arg
                245                 250                 255
Arg Arg Gly Gly Ser Ala Ser Arg Ser Leu Pro Leu Pro Lys Arg Pro
                260                 265                 270
Arg Arg Gly Ala Ala Pro Glu Pro Glu Arg Thr Pro Val Gly Gln Gly
                275                 280                 285
Ser Trp Ala His Pro Gly Arg Thr Arg Gly Pro Ser Asp Arg Gly Phe
                290                 295                 300
Cys Val Val Ser Pro Ala Arg Pro Ala Glu Glu Ala Thr Ser Leu Glu
305                 310                 315                 320
Gly Ala Leu Ser Gly Thr Arg His Ser His Pro Ser Val Gly Arg Gln
                325                 330                 335
His His Ala Gly Pro Pro Ser Thr Ser Arg Pro Arg Pro Trp Asp
                340                 345                 350
Thr Pro Cys Pro Pro Val Tyr Ala Glu Thr Lys His Phe Leu Tyr Ser
                355                 360                 365
Ser Gly Asp Lys Glu Gln Leu Arg Pro Ser Phe Leu Leu Ser Ser Leu
                370                 375                 380
Arg Pro Ser Leu Thr Gly Ala Arg Arg Leu Val Glu Thr Ile Phe Leu
385                 390                 395                 400
Gly Ser Arg Pro Trp Met Pro Gly Thr Pro Arg Arg Leu Pro Arg Leu
                405                 410                 415
Pro Gln Arg Tyr Trp Gln Met Arg Pro Leu Phe Leu Glu Leu Leu Gly
                420                 425                 430
Asn His Ala Gln Cys Pro Tyr Gly Val Leu Leu Lys Thr His Cys Pro
                435                 440                 445
Leu Arg Ala Ala Val Thr Pro Ala Ala Gly Val Cys Ala Arg Glu Lys
                450                 455                 460
```

-continued

```
Pro Gln Gly Ser Val Ala Ala Pro Glu Glu Asp Thr Asp Pro Arg
465                 470                 475                 480

Arg Leu Val Gln Leu Leu Arg Gln His Ser Ser Pro Trp Gln Val Tyr
            485                 490                 495

Gly Phe Val Arg Ala Cys Leu Arg Arg Leu Val Pro Pro Gly Leu Trp
                500                 505                 510

Gly Ser Arg His Asn Glu Arg Arg Phe Leu Arg Asn Thr Lys Lys Phe
            515                 520                 525

Ile Ser Leu Gly Lys His Ala Lys Leu Ser Leu Gln Glu Leu Thr Trp
    530                 535                 540

Lys Met Ser Val Arg Asp Cys Ala Trp Leu Arg Arg Ser Pro Gly Val
545                 550                 555                 560

Gly Cys Val Pro Ala Ala Glu His Arg Leu Arg Glu Glu Ile Leu Ala
                565                 570                 575

Lys Phe Leu His Trp Leu Met Ser Val Tyr Val Val Glu Leu Leu Arg
            580                 585                 590

Ser Phe Phe Tyr Val Thr Glu Thr Thr Phe Gln Lys Asn Arg Leu Phe
            595                 600                 605

Phe Tyr Arg Lys Ser Val Trp Ser Lys Leu Gln Ser Ile Gly Ile Arg
    610                 615                 620

Gln His Leu Lys Arg Val Gln Leu Arg Glu Leu Ser Glu Ala Glu Val
625                 630                 635                 640

Arg Gln His Arg Glu Ala Arg Pro Ala Leu Leu Thr Ser Arg Leu Arg
                645                 650                 655

Phe Ile Pro Lys Pro Asp Gly Leu Arg Pro Ile Val Asn Met Asp Tyr
            660                 665                 670

Val Val Gly Ala Arg Thr Phe Arg Arg Glu Lys Arg Ala Glu Arg Leu
        675                 680                 685

Thr Ser Arg Val Lys Ala Leu Phe Ser Val Leu Asn Tyr Glu Arg Ala
    690                 695                 700

Arg Arg Pro Gly Leu Leu Gly Ala Ser Val Leu Gly Leu Asp Asp Ile
705                 710                 715                 720

His Arg Ala Trp Arg Thr Phe Val Leu Arg Val Arg Ala Gln Asp Pro
                725                 730                 735

Pro Pro Glu Leu Tyr Phe Val Lys Asp Arg Leu Thr Glu Val Ile Ala
            740                 745                 750

Ser Ile Ile Lys Pro Gln Asn Thr Tyr Cys Val Arg Arg Tyr Ala Val
            755                 760                 765

Val Gln Lys Ala Ala His Gly His Val Arg Lys Ala Phe Lys Ser His
770                 775                 780

Val Ser Thr Leu Thr Asp Leu Gln Pro Tyr Met Arg Gln Phe Val Ala
785                 790                 795                 800

His Leu Gln Glu Thr Ser Pro Leu Arg Asp Ala Val Val Ile Glu Gln
                805                 810                 815

Ser Ser Ser Leu Asn Glu Ala Ser Ser Gly Leu Phe Asp Val Phe Leu
            820                 825                 830

Arg Phe Met Cys His His Ala Val Arg Ile Arg Gly Lys Ser Tyr Val
            835                 840                 845

Gln Cys Gln Gly Ile Pro Gln Gly Ser Ile Leu Ser Thr Leu Leu Cys
    850                 855                 860

Ser Leu Cys Tyr Gly Asp Met Glu Asn Lys Leu Phe Ala Gly Ile Arg
865                 870                 875                 880
```

-continued

Arg Asp Gly Leu Leu Leu Arg Leu Val Asp Asp Phe Leu Leu Val Thr
                885                     890                 895

Pro His Leu Thr His Ala Lys Thr Phe Leu Arg Thr Leu Val Arg Gly
            900                 905                 910

Val Pro Glu Tyr Gly Cys Val Val Asn Leu Arg Lys Thr Val Val Asn
            915                 920                 925

Phe Pro Val Asp Glu Ala Leu Gly Gly Thr Ala Phe Val Gln Met
930                 935                 940

Pro Ala His Gly Leu Phe Pro Trp Cys Gly Leu Leu Asp Thr Arg
945                 950             955                 960

Thr Leu Glu Val Gln Ser Asp Tyr Ser Arg
            965                 970

<210> SEQ ID NO 81
<211> LENGTH: 885
<212> TYPE: PRT
<213> ORGANISM: Homo sapiens
<220> FEATURE:
<223> OTHER INFORMATION: Truncated Protein lacking Motif A (ver.2);
      encoded by SEQ ID NO:79 with Intron Y ORF2 after the
      termination codon

<400> SEQUENCE: 81

Gly Arg Pro Gly Gly Thr Ser Asp Met Arg Arg Ala Ala Gln Ala Thr
1               5                   10                  15

Gln Gly Ala Ser Pro Ala Gly Ser Cys Leu Lys Glu Leu Val Ala Arg
            20                  25                  30

Val Leu Gln Arg Leu Cys Glu Arg Gly Ala Lys Asn Val Leu Ala Phe
        35                  40                  45

Gly Phe Ala Leu Leu Asp Gly Ala Arg Gly Gly Pro Pro Glu Ala Phe
    50                  55                  60

Thr Thr Ser Val Arg Ser Tyr Leu Pro Asn Thr Val Thr Asp Ala Leu
65                  70                  75                  80

Arg Gly Ser Gly Ala Trp Gly Leu Leu Leu Arg Arg Val Gly Asp Asp
                85                  90                  95

Val Leu Val His Leu Leu Ala Arg Cys Ala Leu Phe Val Leu Val Ala
            100                 105                 110

Pro Ser Cys Ala Tyr Gln Val Cys Gly Pro Pro Leu Tyr Gln Leu Gly
        115                 120                 125

Ala Ala Thr Gln Ala Arg Pro Pro His Ala Ser Gly Pro Arg Arg
    130                 135                 140

Arg Leu Gly Cys Glu Arg Ala Trp Asn His Ser Val Arg Glu Ala Gly
145                 150                 155                 160

Val Pro Leu Gly Leu Pro Ala Pro Gly Ala Arg Arg Gly Gly Ser
                165                 170                 175

Ala Ser Arg Ser Leu Pro Leu Pro Lys Arg Pro Arg Arg Gly Ala Ala
            180                 185                 190

Pro Glu Pro Glu Arg Thr Pro Val Gly Gln Gly Ser Trp Ala His Pro
        195                 200                 205

Gly Arg Thr Arg Gly Pro Ser Asp Arg Gly Phe Cys Val Val Ser Pro
    210                 215                 220

Ala Arg Pro Ala Glu Glu Ala Thr Ser Leu Glu Gly Ala Leu Ser Gly
225                 230                 235                 240

Thr Arg His Ser His Pro Ser Val Gly Arg Gln His His Ala Gly Pro
                245                 250                 255

Pro Ser Thr Ser Arg Pro Pro Arg Pro Trp Asp Thr Pro Cys Pro Pro

-continued

```
                260                 265                 270
Val Tyr Ala Glu Thr Lys His Phe Leu Tyr Ser Ser Gly Asp Lys Glu
            275                 280                 285
Gln Leu Arg Pro Ser Phe Leu Leu Ser Ser Leu Arg Pro Ser Leu Thr
        290                 295                 300
Gly Ala Arg Arg Leu Val Glu Thr Ile Phe Leu Gly Ser Arg Pro Trp
305                 310                 315                 320
Met Pro Gly Thr Pro Arg Arg Leu Pro Arg Leu Pro Gln Arg Tyr Trp
                325                 330                 335
Gln Met Arg Pro Leu Phe Leu Glu Leu Leu Gly Asn His Ala Gln Cys
            340                 345                 350
Pro Tyr Gly Val Leu Leu Lys Thr His Cys Pro Leu Arg Ala Ala Val
        355                 360                 365
Thr Pro Ala Ala Gly Val Cys Ala Arg Glu Lys Pro Gln Gly Ser Val
    370                 375                 380
Ala Ala Pro Glu Glu Glu Asp Thr Asp Pro Arg Arg Leu Val Gln Leu
385                 390                 395                 400
Leu Arg Gln His Ser Ser Pro Trp Gln Val Tyr Gly Phe Val Arg Ala
                405                 410                 415
Cys Leu Arg Arg Leu Val Pro Pro Gly Leu Trp Gly Ser Arg His Asn
            420                 425                 430
Glu Arg Arg Phe Leu Arg Asn Thr Lys Lys Phe Ile Ser Leu Gly Lys
        435                 440                 445
His Ala Lys Leu Ser Leu Gln Glu Leu Thr Trp Lys Met Ser Val Arg
    450                 455                 460
Asp Cys Ala Trp Leu Arg Arg Ser Pro Gly Val Gly Cys Val Pro Ala
465                 470                 475                 480
Ala Glu His Arg Leu Arg Glu Glu Ile Leu Ala Lys Phe Leu His Trp
                485                 490                 495
Leu Met Ser Val Tyr Val Val Glu Leu Leu Arg Ser Phe Phe Tyr Val
            500                 505                 510
Thr Glu Thr Thr Phe Gln Lys Asn Arg Leu Phe Phe Tyr Arg Lys Ser
        515                 520                 525
Val Trp Ser Lys Leu Gln Ser Ile Gly Ile Arg Gln His Leu Lys Arg
    530                 535                 540
Val Gln Leu Arg Glu Leu Ser Glu Ala Glu Val Arg Gln His Arg Glu
545                 550                 555                 560
Ala Arg Pro Ala Leu Leu Thr Ser Arg Leu Arg Phe Ile Pro Lys Pro
                565                 570                 575
Asp Gly Leu Arg Pro Ile Val Asn Met Asp Tyr Val Val Gly Ala Arg
            580                 585                 590
Thr Phe Arg Arg Glu Lys Arg Ala Glu Arg Leu Thr Ser Arg Val Lys
        595                 600                 605
Ala Leu Phe Ser Val Leu Asn Tyr Glu Arg Ala Arg Arg Pro Gly Leu
    610                 615                 620
Leu Gly Ala Ser Val Leu Gly Leu Asp Asp Ile His Arg Ala Trp Arg
625                 630                 635                 640
Thr Phe Val Leu Arg Val Arg Ala Gln Asp Pro Pro Glu Leu Tyr
                645                 650                 655
Phe Val Lys Asp Arg Leu Thr Glu Val Ile Ala Ser Ile Ile Lys Pro
            660                 665                 670
Gln Asn Thr Tyr Cys Val Arg Arg Tyr Ala Val Val Gln Lys Ala Ala
        675                 680                 685
```

```
His Gly His Val Arg Lys Ala Phe Lys Ser His Val Ser Thr Leu Thr
        690                 695                 700

Asp Leu Gln Pro Tyr Met Arg Gln Phe Val Ala His Leu Gln Glu Thr
705                 710                 715                 720

Ser Pro Leu Arg Asp Ala Val Val Ile Glu Gln Ser Ser Leu Asn
                725                 730                 735

Glu Ala Ser Ser Gly Leu Phe Asp Val Phe Leu Arg Phe Met Cys His
            740                 745                 750

His Ala Val Arg Ile Arg Gly Lys Ser Tyr Val Gln Cys Gln Gly Ile
        755                 760                 765

Pro Gln Gly Ser Ile Leu Ser Thr Leu Leu Cys Ser Leu Cys Tyr Gly
    770                 775                 780

Asp Met Glu Asn Lys Leu Phe Ala Gly Ile Arg Arg Asp Gly Leu Leu
785                 790                 795                 800

Leu Arg Leu Val Asp Asp Phe Leu Leu Val Thr Pro His Leu Thr His
                805                 810                 815

Ala Lys Thr Phe Leu Arg Thr Leu Val Arg Gly Val Pro Glu Tyr Gly
        820                 825                 830

Cys Val Val Asn Leu Arg Lys Thr Val Val Asn Phe Pro Val Glu Asp
            835                 840                 845

Glu Ala Leu Gly Gly Thr Ala Phe Val Gln Met Pro Ala His Gly Leu
    850                 855                 860

Phe Pro Trp Cys Gly Leu Leu Asp Thr Arg Thr Leu Glu Val Gln
865                 870                 875                 880

Ser Asp Tyr Ser Arg
                885

<210> SEQ ID NO 82
<211> LENGTH: 970
<212> TYPE: PRT
<213> ORGANISM: Homo sapiens
<220> FEATURE:
<223> OTHER INFORMATION: Truncated Protein lacking Motif A (ver.2);
      encoded by SEQ ID NO:79 with Intron Y ORF3

<400> SEQUENCE: 82

Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Pro Pro Arg Gly Arg Arg
65                  70                  75                  80

Pro Ala Gly Val Glu Gly Gly Arg Gly Glu Pro Ala Thr Cys Gly Glu
                85                  90                  95

Gln Arg Arg Arg Leu Arg Ala Leu Pro Pro Gln Val Ser Cys Leu Lys
            100                 105                 110

Glu Leu Val Ala Arg Val Leu Gln Arg Leu Cys Glu Arg Gly Ala Lys
        115                 120                 125

Asn Val Leu Ala Phe Gly Phe Ala Leu Leu Asp Gly Ala Arg Gly Gly
    130                 135                 140

Pro Pro Glu Ala Phe Thr Thr Ser Val Arg Ser Tyr Leu Pro Asn Thr
```

```
                 145                 150                 155                 160
Val Thr Asp Ala Leu Arg Gly Ser Gly Ala Trp Gly Leu Leu Leu Arg
                165                 170                 175
Arg Val Gly Asp Asp Val Leu Val His Leu Leu Ala Arg Cys Ala Leu
                180                 185                 190
Phe Val Leu Val Ala Pro Ser Cys Ala Tyr Gln Val Cys Gly Pro Pro
                195                 200                 205
Leu Tyr Gln Leu Gly Ala Ala Thr Gln Ala Arg Pro Pro His Ala
        210                 215                 220
Ser Gly Pro Arg Arg Leu Gly Cys Glu Arg Ala Trp Asn His Ser
225                 230                 235                 240
Val Arg Glu Ala Gly Val Pro Leu Gly Leu Pro Ala Pro Gly Ala Arg
                245                 250                 255
Arg Arg Gly Gly Ser Ala Ser Arg Ser Leu Pro Leu Pro Lys Arg Pro
                260                 265                 270
Arg Arg Gly Ala Ala Pro Glu Pro Glu Arg Thr Pro Val Gly Gln Gly
                275                 280                 285
Ser Trp Ala His Pro Gly Arg Thr Arg Gly Pro Ser Asp Arg Gly Phe
        290                 295                 300
Cys Val Val Ser Pro Ala Arg Pro Ala Glu Glu Ala Thr Ser Leu Glu
305                 310                 315                 320
Gly Ala Leu Ser Gly Thr Arg His Ser His Pro Ser Val Gly Arg Gln
                325                 330                 335
His His Ala Gly Pro Pro Ser Thr Ser Arg Pro Arg Pro Trp Asp
        340                 345                 350
Thr Pro Cys Pro Pro Val Tyr Ala Glu Thr Lys His Phe Leu Tyr Ser
        355                 360                 365
Ser Gly Asp Lys Glu Gln Leu Arg Pro Ser Phe Leu Leu Ser Ser Leu
        370                 375                 380
Arg Pro Ser Leu Thr Gly Ala Arg Arg Leu Val Glu Thr Ile Phe Leu
385                 390                 395                 400
Gly Ser Arg Pro Trp Met Pro Gly Thr Pro Arg Arg Leu Pro Arg Leu
                405                 410                 415
Pro Gln Arg Tyr Trp Gln Met Arg Pro Leu Phe Leu Glu Leu Leu Gly
                420                 425                 430
Asn His Ala Gln Cys Pro Tyr Gly Val Leu Leu Lys Thr His Cys Pro
        435                 440                 445
Leu Arg Ala Ala Val Thr Pro Ala Ala Gly Val Cys Ala Arg Glu Lys
        450                 455                 460
Pro Gln Gly Ser Val Ala Ala Pro Glu Glu Asp Thr Asp Pro Arg
465                 470                 475                 480
Arg Leu Val Gln Leu Leu Arg Gln His Ser Ser Pro Trp Gln Val Tyr
                485                 490                 495
Gly Phe Val Arg Ala Cys Leu Arg Leu Val Pro Pro Gly Leu Trp
                500                 505                 510
Gly Ser Arg His Asn Glu Arg Arg Phe Leu Arg Asn Thr Lys Lys Phe
        515                 520                 525
Ile Ser Leu Gly Lys His Ala Lys Leu Ser Leu Gln Glu Leu Thr Trp
        530                 535                 540
Lys Met Ser Val Arg Asp Cys Ala Trp Leu Arg Arg Ser Pro Gly Val
545                 550                 555                 560
Gly Cys Val Pro Ala Ala Glu His Arg Leu Arg Glu Glu Ile Leu Ala
                565                 570                 575
```

-continued

```
Lys Phe Leu His Trp Leu Met Ser Val Tyr Val Glu Leu Leu Arg
            580                 585                 590

Ser Phe Phe Tyr Val Thr Glu Thr Thr Phe Gln Lys Asn Arg Leu Phe
        595                 600                 605

Phe Tyr Arg Lys Ser Val Trp Ser Lys Leu Gln Ser Ile Gly Ile Arg
        610                 615                 620

Gln His Leu Lys Arg Val Gln Leu Arg Glu Leu Ser Glu Ala Glu Val
625                 630                 635                 640

Arg Gln His Arg Glu Ala Arg Pro Ala Leu Leu Thr Ser Arg Leu Arg
                645                 650                 655

Phe Ile Pro Lys Pro Asp Gly Leu Arg Pro Ile Val Asn Met Asp Tyr
            660                 665                 670

Val Val Gly Ala Arg Thr Phe Arg Glu Lys Arg Ala Glu Arg Leu
        675                 680                 685

Thr Ser Arg Val Lys Ala Leu Phe Ser Val Leu Asn Tyr Glu Arg Ala
        690                 695                 700

Arg Arg Pro Gly Leu Leu Gly Ala Ser Val Leu Gly Leu Asp Asp Ile
705                 710                 715                 720

His Arg Ala Trp Arg Thr Phe Val Leu Arg Val Arg Ala Gln Asp Pro
                725                 730                 735

Pro Pro Glu Leu Tyr Phe Val Lys Asp Arg Leu Thr Glu Val Ile Ala
            740                 745                 750

Ser Ile Ile Lys Pro Gln Asn Thr Tyr Cys Val Arg Arg Tyr Ala Val
            755                 760                 765

Val Gln Lys Ala Ala His Gly His Val Arg Lys Ala Phe Lys Ser His
    770                 775                 780

Val Ser Thr Leu Thr Asp Leu Gln Pro Tyr Met Arg Gln Phe Val Ala
785                 790                 795                 800

His Leu Gln Glu Thr Ser Pro Leu Arg Asp Ala Val Val Ile Glu Gln
                805                 810                 815

Ser Ser Ser Leu Asn Glu Ala Ser Ser Gly Leu Phe Asp Val Phe Leu
            820                 825                 830

Arg Phe Met Cys His His Ala Val Arg Ile Arg Gly Lys Ser Tyr Val
        835                 840                 845

Gln Cys Gln Gly Ile Pro Gln Gly Ser Ile Leu Ser Thr Leu Leu Cys
        850                 855                 860

Ser Leu Cys Tyr Gly Asp Met Glu Asn Lys Leu Phe Ala Gly Ile Arg
865                 870                 875                 880

Arg Asp Gly Leu Leu Leu Arg Leu Val Asp Asp Phe Leu Leu Val Thr
                885                 890                 895

Pro His Leu Thr His Ala Lys Thr Phe Leu Arg Thr Leu Val Arg Gly
            900                 905                 910

Val Pro Glu Tyr Gly Cys Val Val Asn Leu Arg Lys Thr Val Val Asn
        915                 920                 925

Phe Pro Val Glu Asp Glu Ala Leu Gly Gly Thr Ala Phe Val Gln Met
    930                 935                 940

Pro Ala His Gly Leu Phe Pro Trp Cys Gly Leu Leu Leu Asp Thr Arg
945                 950                 955                 960

Thr Leu Glu Val Gln Ser Asp Tyr Ser Arg
                965                 970
```

<210> SEQ ID NO 83
<211> LENGTH: 3432

-continued

```
<212> TYPE: DNA
<213> ORGANISM: Homo sapiens
<220> FEATURE:
<223> OTHER INFORMATION: Protein Lacking Motif A and Altered C-Terminus
      (ver.2); with Intron Y, Beta and 3

<400> SEQUENCE: 83
atgccgcgcg ctccccgctg ccgagccgtg cgctccctgc tgcgcagcca ctaccgcgag      60
gtgctgccgc tggccacgtt cgtgcggcgc ctggggcccc agggctggcg gctggtgcag     120
cgcggggacc cggcggcttt ccgcgcgctg gtggcccagt gcctggtgtg cgtgccctgg     180
gacgcacggc cgcccccgc cgcccctcc ttccgcagg tgggcctccc cggggtcggc        240
gtccggctgg ggttgagggc ggccgggggg aaccagcgac atgcggagag cagcgcaggc     300
gactcagggc gcttcccccg caggtgtcct gcctgaagga gctggtggcc cgagtgctgc     360
agaggctgtg cgagcgcggc gcgaagaacg tgctggcctt cggcttcgcg ctgctggacg     420
gggcccgcgg gggcccccc gaggccttca ccaccagcgt cgcagctac ctgcccaaca       480 cggtgaccga cgcactgcgg gggagcgggg cgtggggct gctgctgcgc gcgtgggcg       540 acgacgtgct ggttcacctg ctggcacgct gcgcgctctt tgtgctggtg ctcccagct     600 gcgcctacca ggtgtgcggg ccgccgctgt accagctcgg cgctgccact caggcccggc    660
ccccgccaca cgctagtgga ccccgaaggc gtctgggatg cgaacgggcc tggaaccata    720
gcgtcaggga ggccggggtc cccctgggcc tgccagcccc gggtgcgagg aggcgcgggg    780
gcagtgccag ccgaagtctg ccgttgccca gagggcccag gcgtggcgct gcccctgagc    840
cggagcggac gcccgttggg caggggtcct gggcccaccc gggcaggacg cgtggaccga    900
gtgaccgtgg tttctgtgtg gtgtcacctg ccagacccgc cgaagaagcc acctctttgg    960
agggtgcgct ctctggcacg cgccactccc acccatccgt gggccgccag caccacgcgg   1020 gcccccatc cacatcgcgg ccaccacgtc cctgggacac gccttgtccc ccggtgtacg    1080
ccgagaccaa gcacttcctc tactcctcag gcgacaagga gcagctgcgg ccctccttcc   1140
tactcagctc tctgaggccc agcctgactg gcgctcggag gctcgtggag accatctttc   1200
tgggttccag gccctggatg ccagggactc cccgcaggtt gcccgcctg ccccagcgct    1260 actggcaaat gcggcccctg tttctggagc tgcttgggaa ccacgcgcag tgcccctacg   1320
gggtgctcct caagacgcac tgcccgctgc gagctgcggt caccccagca gccggtgtct   1380
gtgcccggga aagcccag ggctctgtgg cggcccccga ggaggaggac acagaccccc     1440
gtcgcctggt gcagctgctc cgccagcaca gcagcccctg gcaggtgtac ggcttcgtgc   1500
gggcctgcct cgccggctg gtgccccag gcctctgggg ctccaggcac aacgaacgcc    1560
gcttcctcag gaacaccaag aagttcatct ccctggggaa gcatgccaag ctctcgctgc   1620
aggagctgac gtggaagatg agcgtgcggg actgcgcttg gctgcgcagg agcccagggg   1680
ttggctgtgt tccggccgca gagcaccgtc tgcgtgagga gatcctggcc aagttcctgc   1740
actggctgat gagtgtgtac gtcgtcgagc tgctcaggtc tttctttat gtcacggaga    1800 ccacgtttca aaagaacagg ctcttttct accggaagag tgtctggagc aagttgcaaa    1860
gcattggaat cagacagcac ttgaagaggg tgcagctgcg ggagctgtcg gaagcagagg   1920
tcaggcagca tcgggaagcc aggcccgccc tgctgacgtc cagactccgc ttcatcccca   1980
agcctgacgg gctgcggccg attgtgaaca tggactacgt cgtgggagcc agaacgttcc   2040
gcagagaaaa gagggccgag cgtctcacct cgagggtgaa ggcactgttc agcgtgctca   2100
actacgagcg ggcgcggcgc cccggcctcc tgggcgcctc tgtgctgggc ctggacgata   2160
```

```
tccacagggc ctggcgcacc ttcgtgctgc gtgtgcgggc ccaggacccg ccgcctgagc    2220
tgtactttgt caaggacagg ctcacggagg tcatcgccag catcatcaaa ccccagaaca    2280
cgtactgcgt gcgtcggtat gccgtggtcc agaaggccgc ccatgggcac gtccgcaagg    2340
ccttcaagag ccacgtctct accttgacag acctccagcc gtacatgcga cagttcgtgg    2400
ctcacctgca ggagaccagc ccgctgaggg atgccgtcgt catcgagcag agctcctccc    2460
tgaatgaggc cagcagtggc ctcttcgacg tcttcctacg cttcatgtgc caccacgccg    2520
tgcgcatcag gggcaagtcc tacgtccagt gccaggggat cccgcagggc tccatcctct    2580
ccacgctgct ctgcagcctg tgctacggcg acatggagaa caagctgttt gcggggattc    2640
ggcgggacgg gctgctcctg cgtttggtgg atgatttctt gttggtgaca cctcacctca    2700
cccacgcgaa aaccttcctc aggaccctgg tccgaggtgt ccctgagtat ggctgcgtgg    2760
tgaacttgcg gaagacagtg gtgaacttcc ctgtagaaga cgaggccctg ggtggcacgg    2820
cttttgttca gatgccggcc cacggcctat tcccctggtg cggcctgctg ctggataccc    2880
ggaccctgga ggtgcagagc gactactcca gctatgcccg gacctccatc agagccagtc    2940
tcaccttcaa ccgcggcttc aaggctggga ggaacatgcg tcgcaaactc tttggggtct    3000
tgcggctgaa gtgtcacagc ctgtttctgg atttgcaggt gaacagcctc cagacggtgt    3060
gcaccaacat ctacaagatc ctcctgctgc aggcgtacag gtttcacgca tgtgtgctgc    3120
agctcccatt tcatcagcaa gtttggaaga accccacatt tttcctgcgc gtcatctctg    3180
acacggcctc cctctgctac tccatcctga agccaagaa cgcagccgaa gaaaacattt    3240
ctgtcgtgac tcctgcggtg cttgggtcgg acagccaga gatggagcca ccccgcagac    3300
cgtcgggtgt gggcagcttt ccggtgtctc ctgggagggg agttgggctg ggcctgtgac    3360
tcctcagcct ctgttttccc ccagggatgt cgctgggggc caagggcgcc gccggccctc    3420
tgccctccga ga                                                        3432
```

<210> SEQ ID NO 84
<211> LENGTH: 1122
<212> TYPE: PRT
<213> ORGANISM: Homo sapiens
<220> FEATURE:
<223> OTHER INFORMATION: Protein Lacking Motif A and Altered C-Terminus
      (ver.2); encoded by SEQ ID NO:83 with Intron Y
      ORF1

<400> SEQUENCE: 84

```
Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Gly Leu Pro Gly Val Gly
65                  70                  75                  80

Val Arg Leu Gly Leu Arg Ala Ala Gly Asn Gln Arg His Ala Glu
                85                  90                  95

Ser Ser Ala Gly Asp Ser Gly Arg Phe Pro Arg Arg Ser Cys Leu Lys
            100                 105                 110

Glu Leu Val Ala Arg Val Leu Gln Arg Leu Cys Glu Arg Gly Ala Lys
```

```
                115                 120                 125
Asn Val Leu Ala Phe Gly Phe Ala Leu Leu Asp Gly Ala Arg Gly Gly
            130                 135                 140

Pro Pro Glu Ala Phe Thr Thr Ser Val Arg Ser Tyr Leu Pro Asn Thr
145                 150                 155                 160

Val Thr Asp Ala Leu Arg Gly Ser Gly Ala Trp Gly Leu Leu Leu Arg
                165                 170                 175

Arg Val Gly Asp Asp Val Leu Val His Leu Leu Ala Arg Cys Ala Leu
            180                 185                 190

Phe Val Leu Val Ala Pro Ser Cys Ala Tyr Gln Val Cys Gly Pro Pro
        195                 200                 205

Leu Tyr Gln Leu Gly Ala Ala Thr Gln Ala Arg Pro Pro His Ala
    210                 215                 220

Ser Gly Pro Arg Arg Leu Gly Cys Glu Arg Ala Trp Asn His Ser
225                 230                 235                 240

Val Arg Glu Ala Gly Val Pro Leu Gly Leu Pro Ala Pro Gly Ala Arg
                245                 250                 255

Arg Arg Gly Gly Ser Ala Ser Arg Ser Leu Pro Leu Pro Lys Arg Pro
            260                 265                 270

Arg Arg Gly Ala Ala Pro Glu Pro Glu Arg Thr Pro Val Gly Gln Gly
        275                 280                 285

Ser Trp Ala His Pro Gly Arg Thr Arg Gly Pro Ser Asp Arg Gly Phe
    290                 295                 300

Cys Val Val Ser Pro Ala Arg Pro Ala Glu Glu Ala Thr Ser Leu Glu
305                 310                 315                 320

Gly Ala Leu Ser Gly Thr Arg His Ser His Pro Ser Val Gly Arg Gln
                325                 330                 335

His His Ala Gly Pro Pro Ser Thr Ser Arg Pro Pro Arg Pro Trp Asp
            340                 345                 350

Thr Pro Cys Pro Pro Val Tyr Ala Glu Thr Lys His Phe Leu Tyr Ser
        355                 360                 365

Ser Gly Asp Lys Glu Gln Leu Arg Pro Ser Phe Leu Leu Ser Ser Leu
    370                 375                 380

Arg Pro Ser Leu Thr Gly Ala Arg Arg Leu Val Glu Thr Ile Phe Leu
385                 390                 395                 400

Gly Ser Arg Pro Trp Met Pro Gly Thr Pro Arg Arg Leu Pro Arg Leu
                405                 410                 415

Pro Gln Arg Tyr Trp Gln Met Arg Pro Leu Phe Leu Glu Leu Leu Gly
            420                 425                 430

Asn His Ala Gln Cys Pro Tyr Gly Val Leu Leu Lys Thr His Cys Pro
        435                 440                 445

Leu Arg Ala Ala Val Thr Pro Ala Ala Gly Val Cys Ala Arg Glu Lys
    450                 455                 460

Pro Gln Gly Ser Val Ala Ala Pro Glu Glu Asp Thr Asp Pro Arg
465                 470                 475                 480

Arg Leu Val Gln Leu Leu Arg Gln His Ser Ser Pro Trp Gln Val Tyr
                485                 490                 495

Gly Phe Val Arg Ala Cys Leu Arg Arg Leu Val Pro Pro Gly Leu Trp
            500                 505                 510

Gly Ser Arg His Asn Glu Arg Arg Phe Leu Arg Asn Thr Lys Lys Phe
        515                 520                 525

Ile Ser Leu Gly Lys His Ala Lys Leu Ser Leu Gln Glu Leu Thr Trp
    530                 535                 540
```

-continued

```
Lys Met Ser Val Arg Asp Cys Ala Trp Leu Arg Arg Ser Pro Gly Val
545                 550                 555                 560

Gly Cys Val Pro Ala Ala Glu His Arg Leu Arg Glu Ile Leu Ala
            565                 570                 575

Lys Phe Leu His Trp Leu Met Ser Val Tyr Val Glu Leu Leu Arg
            580                 585                 590

Ser Phe Phe Tyr Val Thr Glu Thr Phe Gln Lys Asn Arg Leu Phe
            595                 600                 605

Phe Tyr Arg Lys Ser Val Trp Ser Lys Leu Gln Ser Ile Gly Ile Arg
            610                 615                 620

Gln His Leu Lys Arg Val Gln Leu Arg Glu Leu Ser Glu Ala Glu Val
625                 630                 635                 640

Arg Gln His Arg Glu Ala Arg Pro Ala Leu Leu Thr Ser Arg Leu Arg
                    645                 650                 655

Phe Ile Pro Lys Pro Asp Gly Leu Arg Pro Ile Val Asn Met Asp Tyr
                    660                 665                 670

Val Val Gly Ala Arg Thr Phe Arg Arg Glu Lys Arg Ala Glu Arg Leu
            675                 680                 685

Thr Ser Arg Val Lys Ala Leu Phe Ser Val Leu Asn Tyr Glu Arg Ala
690                 695                 700

Arg Arg Pro Gly Leu Leu Gly Ala Ser Val Leu Gly Leu Asp Ile
705                 710                 715                 720

His Arg Ala Trp Arg Thr Phe Val Leu Arg Val Arg Ala Gln Asp Pro
                725                 730                 735

Pro Pro Glu Leu Tyr Phe Val Lys Asp Arg Leu Thr Glu Val Ile Ala
            740                 745                 750

Ser Ile Ile Lys Pro Gln Asn Thr Tyr Cys Val Arg Arg Tyr Ala Val
            755                 760                 765

Val Gln Lys Ala Ala His Gly His Val Arg Lys Ala Phe Lys Ser His
770                 775                 780

Val Ser Thr Leu Thr Asp Leu Gln Pro Tyr Met Arg Gln Phe Val Ala
785                 790                 795                 800

His Leu Gln Glu Thr Ser Pro Leu Arg Asp Ala Val Val Ile Glu Gln
                805                 810                 815

Ser Ser Ser Leu Asn Glu Ala Ser Ser Gly Leu Phe Asp Val Phe Leu
            820                 825                 830

Arg Phe Met Cys His His Ala Val Arg Ile Arg Gly Lys Ser Tyr Val
            835                 840                 845

Gln Cys Gln Gly Ile Pro Gln Gly Ser Ile Leu Ser Thr Leu Leu Cys
850                 855                 860

Ser Leu Cys Tyr Gly Asp Met Glu Asn Lys Leu Phe Ala Gly Ile Arg
865                 870                 875                 880

Arg Asp Gly Leu Leu Leu Arg Leu Val Asp Asp Phe Leu Leu Val Thr
                    885                 890                 895

Pro His Leu Thr His Ala Lys Thr Phe Leu Arg Thr Leu Val Arg Gly
            900                 905                 910

Val Pro Glu Tyr Gly Cys Val Val Asn Leu Arg Lys Thr Val Val Asn
            915                 920                 925

Phe Pro Val Glu Asp Glu Ala Leu Gly Gly Thr Ala Phe Val Gln Met
            930                 935                 940

Pro Ala His Gly Leu Phe Pro Trp Cys Gly Leu Leu Leu Asp Thr Arg
945                 950                 955                 960
```

```
Thr Leu Glu Val Gln Ser Asp Tyr Ser Ser Tyr Ala Arg Thr Ser Ile
            965                 970                 975

Arg Ala Ser Leu Thr Phe Asn Arg Gly Phe Lys Ala Gly Arg Asn Met
            980                 985                 990

Arg Arg Lys Leu Phe Gly Val Leu Arg Leu Lys Cys His Ser Leu Phe
            995                 1000                1005

Leu Asp Leu Gln Val Asn Ser Leu Gln Thr Val Cys Thr Asn Ile Tyr
        1010                1015                1020

Lys Ile Leu Leu Leu Gln Ala Tyr Arg Phe His Ala Cys Val Leu Gln
1025                1030                1035                1040

Leu Pro Phe His Gln Gln Val Trp Lys Asn Pro Thr Phe Phe Leu Arg
            1045                1050                1055

Val Ile Ser Asp Thr Ala Ser Leu Cys Tyr Ser Ile Leu Lys Ala Lys
            1060                1065                1070

Asn Ala Glu Glu Glu Asn Ile Leu Val Val Thr Pro Ala Val Leu Gly
            1075                1080                1085

Ser Gly Gln Pro Glu Met Glu Pro Pro Arg Arg Pro Ser Gly Val Gly
            1090                1095                1100

Ser Phe Pro Val Ser Pro Gly Arg Gly Val Gly Leu Gly Leu Phe Ile
1105                1110                1115                1120

Gly Ala

<210> SEQ ID NO 85
<211> LENGTH: 1037
<212> TYPE: PRT
<213> ORGANISM: Homo sapiens
<220> FEATURE:
<223> OTHER INFORMATION: Protein Lacking Motif A and Altered C-Terminus
      (ver.2); encoded by SEQ ID NO:83 with Intron Y
      ORF2 after the termination codon

<400> SEQUENCE: 85

Gly Arg Pro Gly Gly Thr Ser Asp Met Arg Arg Ala Ala Gln Ala Thr
1               5                   10                  15

Gln Gly Ala Ser Pro Ala Gly Ser Cys Leu Lys Glu Leu Val Ala Arg
            20                  25                  30

Val Leu Gln Arg Leu Cys Glu Arg Gly Ala Lys Asn Val Leu Ala Phe
        35                  40                  45

Gly Phe Ala Leu Leu Asp Gly Ala Arg Gly Gly Pro Pro Glu Ala Phe
    50                  55                  60

Thr Thr Ser Val Arg Ser Tyr Leu Pro Asn Thr Val Thr Asp Ala Leu
65                  70                  75                  80

Arg Gly Ser Gly Ala Trp Gly Leu Leu Leu Arg Arg Val Gly Asp Asp
            85                  90                  95

Val Leu Val His Leu Ala Arg Cys Ala Leu Phe Val Leu Val Ala
            100                 105                 110

Pro Ser Cys Ala Tyr Gln Val Cys Gly Pro Pro Leu Tyr Gln Leu Gly
        115                 120                 125

Ala Ala Thr Gln Ala Arg Pro Pro His Ala Ser Gly Pro Arg Arg
    130                 135                 140

Arg Leu Gly Cys Glu Arg Ala Trp Asn His Ser Val Arg Glu Ala Gly
145                 150                 155                 160

Val Pro Leu Gly Leu Pro Ala Pro Ala Arg Arg Gly Ser
            165                 170                 175

Ala Ser Arg Ser Leu Pro Leu Pro Lys Arg Pro Arg Arg Gly Ala Ala
        180                 185                 190
```

-continued

```
Pro Glu Pro Glu Arg Thr Pro Val Gly Gln Gly Ser Trp Ala His Pro
        195                 200                 205

Gly Arg Thr Arg Gly Pro Ser Asp Arg Gly Phe Cys Val Val Ser Pro
        210                 215                 220

Ala Arg Pro Ala Glu Glu Ala Thr Ser Leu Glu Gly Ala Leu Ser Gly
225                 230                 235                 240

Thr Arg His Ser His Pro Ser Val Gly Arg Gln His His Ala Gly Pro
        245                 250                 255

Pro Ser Thr Ser Arg Pro Pro Arg Pro Trp Asp Thr Pro Cys Pro Pro
        260                 265                 270

Val Tyr Ala Glu Thr Lys His Phe Leu Tyr Ser Ser Gly Asp Lys Glu
        275                 280                 285

Gln Leu Arg Pro Ser Phe Leu Ser Ser Leu Arg Pro Ser Leu Thr
        290                 295                 300

Gly Ala Arg Arg Leu Val Glu Thr Ile Phe Leu Gly Ser Arg Pro Trp
305                 310                 315                 320

Met Pro Gly Thr Pro Arg Arg Leu Pro Arg Leu Pro Gln Arg Tyr Trp
                325                 330                 335

Gln Met Arg Pro Leu Phe Leu Glu Leu Leu Gly Asn His Ala Gln Cys
                340                 345                 350

Pro Tyr Gly Val Leu Leu Lys Thr His Cys Pro Leu Arg Ala Ala Val
                355                 360                 365

Thr Pro Ala Ala Gly Val Cys Ala Arg Glu Lys Pro Gln Gly Ser Val
        370                 375                 380

Ala Ala Pro Glu Glu Glu Asp Thr Asp Pro Arg Arg Leu Val Gln Leu
385                 390                 395                 400

Leu Arg Gln His Ser Ser Pro Trp Gln Val Tyr Gly Phe Val Arg Ala
                405                 410                 415

Cys Leu Arg Arg Leu Val Pro Pro Gly Leu Trp Gly Ser Arg His Asn
                420                 425                 430

Glu Arg Arg Phe Leu Arg Asn Thr Lys Lys Phe Ile Ser Leu Gly Lys
                435                 440                 445

His Ala Lys Leu Ser Leu Gln Glu Leu Thr Trp Lys Met Ser Val Arg
        450                 455                 460

Asp Cys Ala Trp Leu Arg Arg Ser Pro Gly Val Gly Cys Val Pro Ala
465                 470                 475                 480

Ala Glu His Arg Leu Arg Glu Glu Ile Leu Ala Lys Phe Leu His Trp
                485                 490                 495

Leu Met Ser Val Tyr Val Val Glu Leu Leu Arg Ser Phe Phe Tyr Val
                500                 505                 510

Thr Glu Thr Thr Phe Gln Lys Asn Arg Leu Phe Phe Tyr Arg Lys Ser
        515                 520                 525

Val Trp Ser Lys Leu Gln Ser Ile Gly Ile Arg Gln His Leu Lys Arg
        530                 535                 540

Val Gln Leu Arg Glu Leu Ser Glu Ala Glu Val Arg Gln His Arg Glu
545                 550                 555                 560

Ala Arg Pro Ala Leu Leu Thr Ser Arg Leu Arg Phe Ile Pro Lys Pro
                565                 570                 575

Asp Gly Leu Arg Pro Ile Val Asn Met Asp Tyr Val Val Gly Ala Arg
                580                 585                 590

Thr Phe Arg Arg Glu Lys Arg Ala Glu Arg Leu Thr Ser Arg Val Lys
                595                 600                 605
```

-continued

```
Ala Leu Phe Ser Val Leu Asn Tyr Glu Arg Ala Arg Arg Pro Gly Leu
    610                 615                 620

Leu Gly Ala Ser Val Leu Gly Leu Asp Asp Ile His Arg Ala Trp Arg
625                 630                 635                 640

Thr Phe Val Leu Arg Val Arg Ala Gln Asp Pro Pro Glu Leu Tyr
                645                 650                 655

Phe Val Lys Asp Arg Leu Thr Glu Val Ile Ala Ser Ile Ile Lys Pro
            660                 665                 670

Gln Asn Thr Tyr Cys Val Arg Arg Tyr Ala Val Gln Lys Ala Ala
                675                 680                 685

His Gly His Val Arg Lys Ala Phe Lys Ser His Val Ser Thr Leu Thr
    690                 695                 700

Asp Leu Gln Pro Tyr Met Arg Gln Phe Val Ala His Leu Gln Glu Thr
705                 710                 715                 720

Ser Pro Leu Arg Asp Ala Val Val Ile Glu Gln Ser Ser Leu Asn
                725                 730                 735

Glu Ala Ser Ser Gly Leu Phe Asp Val Phe Leu Arg Phe Met Cys His
                740                 745                 750

His Ala Val Arg Ile Arg Gly Lys Ser Tyr Val Gln Cys Gln Gly Ile
    755                 760                 765

Pro Gln Gly Ser Ile Leu Ser Thr Leu Leu Cys Ser Leu Cys Tyr Gly
770                 775                 780

Asp Met Glu Asn Lys Leu Phe Ala Gly Ile Arg Arg Asp Gly Leu Leu
785                 790                 795                 800

Leu Arg Leu Val Asp Asp Phe Leu Leu Val Thr Pro His Leu Thr His
                805                 810                 815

Ala Lys Thr Phe Leu Arg Thr Leu Val Arg Gly Val Pro Glu Tyr Gly
            820                 825                 830

Cys Val Val Asn Leu Arg Lys Thr Val Asn Phe Pro Val Glu Asp
                835                 840                 845

Glu Ala Leu Gly Gly Thr Ala Phe Val Gln Met Pro Ala His Gly Leu
    850                 855                 860

Phe Pro Trp Cys Gly Leu Leu Leu Asp Thr Arg Thr Leu Glu Val Gln
865                 870                 875                 880

Ser Asp Tyr Ser Ser Tyr Ala Arg Thr Ser Ile Arg Ala Ser Leu Thr
                885                 890                 895

Phe Asn Arg Gly Phe Lys Ala Gly Arg Asn Met Arg Arg Lys Leu Phe
                900                 905                 910

Gly Val Leu Arg Leu Lys Cys His Ser Leu Phe Leu Asp Leu Gln Val
            915                 920                 925

Asn Ser Leu Gln Thr Val Cys Thr Asn Ile Tyr Lys Ile Leu Leu Leu
    930                 935                 940

Gln Ala Tyr Arg Phe His Ala Cys Val Leu Gln Leu Pro Phe His Gln
945                 950                 955                 960

Gln Val Trp Lys Asn Pro Thr Phe Phe Leu Arg Val Ile Ser Asp Thr
                965                 970                 975

Ala Ser Leu Cys Tyr Ser Ile Leu Lys Ala Lys Asn Ala Glu Glu
                980                 985                 990

Asn Ile Leu Val Val Thr Pro Ala Val Leu Gly Ser Gly Gln Pro Glu
            995                 1000                1005

Met Glu Pro Pro Arg Arg Pro Ser Gly Val Gly Ser Phe Pro Val Ser
    1010                1015                1020

Pro Gly Arg Gly Val Gly Leu Gly Leu Phe Ile Gly Ala
```

-continued 1025          1030          1035

<210> SEQ ID NO 86
<211> LENGTH: 1122
<212> TYPE: PRT
<213> ORGANISM: Homo sapiens
<220> FEATURE:
<223> OTHER INFORMATION: Protein Lacking Motif A and Altered C-Terminus
      (ver.2); encoded by SEQ ID NO:83 with Intron Y
      ORF3

<400> SEQUENCE: 86

Met Pro Arg Ala Pro Arg Cys Arg Ala Val Arg Ser Leu Leu Arg Ser
 1               5                  10                  15

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
    50                  55                  60

Pro Pro Ala Ala Pro Ser Phe Arg Gln Val Pro Pro Arg Gly Arg Arg
65                  70                  75                  80

Pro Ala Gly Val Glu Gly Gly Arg Gly Glu Pro Ala Thr Cys Gly Glu
                85                  90                  95

Gln Arg Arg Arg Leu Arg Ala Leu Pro Pro Gln Val Ser Cys Leu Lys
            100                 105                 110

Glu Leu Val Ala Arg Val Leu Gln Arg Leu Cys Glu Arg Gly Ala Lys
        115                 120                 125

Asn Val Leu Ala Phe Gly Phe Ala Leu Leu Asp Gly Ala Arg Gly Gly
    130                 135                 140

Pro Pro Glu Ala Phe Thr Thr Ser Val Arg Ser Tyr Leu Pro Asn Thr
145                 150                 155                 160

Val Thr Asp Ala Leu Arg Gly Ser Gly Ala Trp Gly Leu Leu Leu Arg
                165                 170                 175

Arg Val Gly Asp Asp Val Leu Val His Leu Leu Ala Arg Cys Ala Leu
            180                 185                 190

Phe Val Leu Val Ala Pro Ser Cys Ala Tyr Gln Val Cys Gly Pro Pro
        195                 200                 205

Leu Tyr Gln Leu Gly Ala Ala Thr Gln Ala Arg Pro Pro His Ala
    210                 215                 220

Ser Gly Pro Arg Arg Arg Leu Gly Cys Glu Arg Ala Trp Asn His Ser
225                 230                 235                 240

Val Arg Glu Ala Gly Val Pro Leu Gly Leu Pro Ala Pro Gly Ala Arg
                245                 250                 255

Arg Arg Gly Gly Ser Ala Ser Arg Ser Leu Pro Leu Pro Lys Arg Pro
            260                 265                 270

Arg Arg Gly Ala Ala Pro Glu Pro Glu Arg Thr Pro Val Gly Gln Gly
        275                 280                 285

Ser Trp Ala His Pro Gly Arg Thr Arg Gly Pro Ser Asp Arg Gly Phe
    290                 295                 300

Cys Val Val Ser Pro Ala Arg Pro Ala Glu Glu Ala Thr Ser Leu Glu
305                 310                 315                 320

Gly Ala Leu Ser Gly Thr Arg His Ser His Pro Ser Val Gly Arg Gln
                325                 330                 335

His His Ala Gly Pro Pro Ser Thr Ser Arg Pro Pro Arg Pro Trp Asp
            340                 345                 350

```
Thr Pro Cys Pro Pro Val Tyr Ala Glu Thr Lys His Phe Leu Tyr Ser
        355                 360                 365

Ser Gly Asp Lys Glu Gln Leu Arg Pro Ser Phe Leu Leu Ser Ser Leu
    370                 375                 380

Arg Pro Ser Leu Thr Gly Ala Arg Arg Leu Val Glu Thr Ile Phe Leu
385                 390                 395                 400

Gly Ser Arg Pro Trp Met Pro Gly Thr Pro Arg Arg Leu Pro Arg Leu
                405                 410                 415

Pro Gln Arg Tyr Trp Gln Met Arg Pro Leu Phe Leu Glu Leu Leu Gly
            420                 425                 430

Asn His Ala Gln Cys Pro Tyr Gly Val Leu Leu Lys Thr His Cys Pro
        435                 440                 445

Leu Arg Ala Ala Val Thr Pro Ala Ala Gly Val Cys Ala Arg Glu Lys
    450                 455                 460

Pro Gln Gly Ser Val Ala Ala Pro Glu Glu Asp Thr Asp Pro Arg
465                 470                 475                 480

Arg Leu Val Gln Leu Leu Arg Gln His Ser Ser Pro Trp Gln Val Tyr
                485                 490                 495

Gly Phe Val Arg Ala Cys Leu Arg Arg Leu Val Pro Pro Gly Leu Trp
                500                 505                 510

Gly Ser Arg His Asn Glu Arg Arg Phe Leu Arg Asn Thr Lys Lys Phe
            515                 520                 525

Ile Ser Leu Gly Lys His Ala Lys Leu Ser Leu Gln Glu Leu Thr Trp
        530                 535                 540

Lys Met Ser Val Arg Asp Cys Ala Trp Leu Arg Arg Ser Pro Gly Val
545                 550                 555                 560

Gly Cys Val Pro Ala Ala Glu His Arg Leu Arg Glu Glu Ile Leu Ala
                565                 570                 575

Lys Phe Leu His Trp Leu Met Ser Val Tyr Val Glu Leu Leu Arg
            580                 585                 590

Ser Phe Phe Tyr Val Thr Glu Thr Thr Phe Gln Lys Asn Arg Leu Phe
        595                 600                 605

Phe Tyr Arg Lys Ser Val Trp Ser Lys Leu Gln Ser Ile Gly Ile Arg
    610                 615                 620

Gln His Leu Lys Arg Val Gln Leu Arg Glu Leu Ser Glu Ala Glu Val
625                 630                 635                 640

Arg Gln His Arg Glu Ala Arg Pro Ala Leu Leu Thr Ser Arg Leu Arg
                645                 650                 655

Phe Ile Pro Lys Pro Asp Gly Leu Arg Pro Ile Val Asn Met Asp Tyr
                660                 665                 670

Val Val Gly Ala Arg Thr Phe Arg Arg Glu Lys Arg Ala Glu Arg Leu
        675                 680                 685

Thr Ser Arg Val Lys Ala Leu Phe Ser Val Leu Asn Tyr Glu Arg Ala
    690                 695                 700

Arg Arg Pro Gly Leu Leu Gly Ala Ser Val Leu Gly Leu Asp Asp Ile
705                 710                 715                 720

His Arg Ala Trp Arg Thr Phe Val Leu Arg Val Arg Ala Gln Asp Pro
                725                 730                 735

Pro Pro Glu Leu Tyr Phe Val Lys Asp Arg Leu Thr Glu Val Ile Ala
            740                 745                 750

Ser Ile Ile Lys Pro Gln Asn Thr Tyr Cys Val Arg Arg Tyr Ala Val
        755                 760                 765
```

```
Val Gln Lys Ala Ala His Gly His Val Arg Lys Ala Phe Lys Ser His
    770                 775                 780
Val Ser Thr Leu Thr Asp Leu Gln Pro Tyr Met Arg Gln Phe Val Ala
785                 790                 795                 800
His Leu Gln Glu Thr Ser Pro Leu Arg Asp Ala Val Val Ile Glu Gln
                805                 810                 815
Ser Ser Ser Leu Asn Glu Ala Ser Ser Gly Leu Phe Asp Val Phe Leu
            820                 825                 830
Arg Phe Met Cys His His Ala Val Arg Ile Arg Gly Lys Ser Tyr Val
        835                 840                 845
Gln Cys Gln Gly Ile Pro Gln Gly Ser Ile Leu Ser Thr Leu Leu Cys
    850                 855                 860
Ser Leu Cys Tyr Gly Asp Met Glu Asn Lys Leu Phe Ala Gly Ile Arg
865                 870                 875                 880
Arg Asp Gly Leu Leu Leu Arg Leu Val Asp Asp Phe Leu Leu Val Thr
                885                 890                 895
Pro His Leu Thr His Ala Lys Thr Phe Leu Arg Thr Leu Val Arg Gly
            900                 905                 910
Val Pro Glu Tyr Gly Cys Val Val Asn Leu Arg Lys Thr Val Val Asn
        915                 920                 925
Phe Pro Val Glu Asp Glu Ala Leu Gly Gly Thr Ala Phe Val Gln Met
    930                 935                 940
Pro Ala His Gly Leu Phe Pro Trp Cys Gly Leu Leu Leu Asp Thr Arg
945                 950                 955                 960
Thr Leu Glu Val Gln Ser Asp Tyr Ser Ser Tyr Ala Arg Thr Ser Ile
                965                 970                 975
Arg Ala Ser Leu Thr Phe Asn Arg Gly Phe Lys Ala Gly Arg Asn Met
            980                 985                 990
Arg Arg Lys Leu Phe Gly Val Leu Arg Leu Lys Cys His Ser Leu Phe
        995                 1000                1005
Leu Asp Leu Gln Val Asn Ser Leu Gln Thr Val Cys Thr Asn Ile Tyr
    1010                1015                1020
Lys Ile Leu Leu Leu Gln Ala Tyr Arg Phe His Ala Cys Val Leu Gln
1025                1030                1035                1040
Leu Pro Phe His Gln Gln Val Trp Lys Asn Pro Thr Phe Phe Leu Arg
                1045                1050                1055
Val Ile Ser Asp Thr Ala Ser Leu Cys Tyr Ser Ile Leu Lys Ala Lys
            1060                1065                1070
Asn Ala Glu Glu Glu Asn Ile Leu Val Val Thr Pro Ala Val Leu Gly
        1075                1080                1085
Ser Gly Gln Pro Glu Met Glu Pro Pro Arg Arg Pro Ser Gly Val Gly
    1090                1095                1100
Ser Phe Pro Val Ser Pro Gly Arg Gly Val Gly Leu Gly Leu Phe Ile
1105                1110                1115                1120
Gly Ala

<210> SEQ ID NO 87
<211> LENGTH: 7615
<212> TYPE: DNA
<213> ORGANISM: Homo sapiens
<220> FEATURE:
<223> OTHER INFORMATION: Human Telomerase Clone with Exon Beta Spliced
      Out

<400> SEQUENCE: 87
```

-continued

```
tcgacctgca ggcatgcaag cttggcactg gccgtcgttt tacaacgtcg tgactgggaa      60
aaccctggcg ttacccaact taatcgcctt gcagcacatc cccctttcgc cagctggcgt     120
aatagcgaag aggcccgcac cgatcgccct tcccaacagt tgcgcagcct gaatggcgaa     180
tggcgcctga tgcggtattt tctccttacg catctgtgcg gtatttcaca ccgcataaat     240
tccctgtttt ggcggatgag agaagatttt cagcctgata cagattaaat cagaacgcag     300
aagcggtctg ataaaacaga atttgcctgg cggcagtagc gcggtggtcc cacctgaccc     360
catgccgaac tcagaagtga aacgccgtag cgccgatggt agtgtggggt ctccccatgc     420
gagagtaggg aactgccagg catcaaataa acgaaaggc tcagtcgaaa gactgggcct     480
ttcgttttat ctgttgtttg tcggtgaacg ctctcctgag taggacaaat ccgccgggag     540
cggatttgaa cgttgcgaag caacggcccg gagggtggcg gcaggacgc ccgccataaa     600 ctgccaggca tcaaattaag cagaaggcca tcctgacgga tggcctttt gcgtttctac     660 aaactcttcc tgtcgtcata tctacaagcc atcccccac agatacggta aactagcctc     720 gttttttgcat caggaaagca gggaatttat ggtgcactct cagtacaatc tgctctgatg     780
ccgcatagtt aagccagccc cgacacccgc caacacccgc tgacgcgccc tgacgggctt     840
gtctgctccc ggcatccgct tacagacaag ctgtgaccgt ctccgggagc tgcatgtgtc     900
agaggttttc accgtcatca ccgaaacgcg cgagacgaaa gggcctcgtg atacgcctat     960
ttttataggt taatgtcatg ataataatgg tttcttagac gtgaggttct gtacccgaca    1020
ccatcgaatg gtgcaaaacc tttcgcggta tggcatgata cgcccggaa gagagtcaat    1080 tcagggtggt gaatgtgaaa ccagtaacgt tatacgatgt cgcagagtat gccggtgtct    1140
cttatcagac cgtttcccgc gtggtgaacc aggccagcca cgtttctgcg aaaacgcggg    1200
aaaaagtgga agcggcgatg gcggagctga attacattcc caaccgcgtg gcacaacaac    1260
tggcgggcaa acagtcgttg ctgattggcg ttgccacctc cagtctgcc ctgcacgcgc    1320 cgtcgcaaat tgtcgcggcg attaaatctc gcgccgatca actgggtgcc agcgtggtgg    1380
tgtcgatggt agaacgaagc ggcgtcgaag cctgtaaagc ggcggtgcac aatcttctcg    1440
cgcaacgcgt cagtgggctg atcattaact atccgctgga tgaccaggat gccattgctg    1500
tggaagctgc ctgcactaat gttccggcgt tatttcttga tgtctctgac cagacaccca    1560
tcaacagtat tattttctcc catgaagacg gtacgcgact gggcgtggag catctggtcg    1620
cattgggtca ccagcaaatc gcgctgttag cgggcccatt aagttctgtc tcggcgcgtc    1680
tgcgtctggc tggctggcat aaatatctca ctcgcaatca aattcagccg atagcggaac    1740
gggaaggcga ctggagtgcc atgtccggtt ttcaacaaac catgcaaatg ctgaatgagg    1800
gcatcgttcc cactgcgatg ctggttgcca acgatcagat ggcgctgggc gcaatgcgcg    1860
ccattaccga gtccgggctg cgcgttggtg cggatatctc ggtagtggga tacgacgata    1920
ccgaagacag ctcatgttat atcccgccgt taaccaccat caaacaggat tttcgcctgc    1980
tggggcaaac cagcgtggac cgcttgctgc aactctctca gggccaggcg gtgaagggca    2040
atcagctgtt gccgtctca ctggtgaaaa gaaaaaccac cctggcgccc aatacgcaaa    2100
ccgcctctcc ccgcgcgttg gccgattcat taatgcagct ggcacgacag gtttcccgac    2160
tggaaagcgg gcagtgagcg caacgcaatt aatgtaagtt agctcactca ttaggcaccc    2220
caggctttac actttatgct tccgacctgc aagaacctca cgtcaggtgg cacttttcgg    2280
ggaaatgtgc gcggaacccc tatttgttta ttttttctaaa tacattcaaa tatgtatccg    2340
ctcatgagac aataaccctg ataaatgctt caataatatt gaaaaggaa gagtatgagt    2400
```

-continued

```
attcaacatt tccgtgtcgc ccttattccc ttttttgcgg catttttgcct tcctgttttt    2460 gctcacccag aaacgctggt gaaagtaaaa gatgctgaag atcagttggg tgcacgagtg    2520
ggttacatcg agaactggat ctcaacagcg gtaagatcct tgagagtttt cgccccgaag    2580
aacgttttcc aatgatgagc acttttaaag ttctgctatg tggcgcggta ttatcccgta    2640
ttgacgccgg gcaagagcaa ctcggtcgcc gcatacacta ttctcagaat gacttggttg    2700
agtactcacc agtcacagaa aagcatctta cggatggcat gacagtaaga gaattatgca    2760
gtgctgccat aaccatgagt gataacactg cggccaactt acttctgaca acgatcggag    2820
gaccgaagga gctaaccgct tttttgcaca acatgggggga tcatgtaact cgccttgatc    2880
gttgggaacc ggagctgaat gaagccatac caaacgacga gcgtgacacc acgatgcctg    2940
tagcaatggc aacaacgttg cgcaaactat taactggcga actacttact ctagcttccc    3000
ggcaacaatt aatagactgg atggaggcgg ataaagttgc aggaccactt ctgcgctcgg    3060
cccttccggc tggctggttt attgctgata atctggagc cggtgagcgt gggtctcgcg    3120
gtatcattgc agcactgggg ccagatggta agccctcccg tatcgtagtt atctacacga    3180
cggggagtca ggcaactatg gatgaacgaa atagacagat cgctgagata ggtgcctcac    3240
tgattaagca ttggtaactg tcagaccaag tttactcata tactttag attgatttaa    3300 aacttcattt ttaatttaaa aggatctagg tgaagatcct ttttgataat ctcatgacca    3360
aaatccctta acgtgagttt tcgttccact gagcgtcaga ccccgtagaa aagatcaaag    3420
gatcttcttg agatccttttt tttctgcgcg taatctgctg cttgcaaaca aaaaaaccac    3480
cgctaccagc ggtggtttgt ttgccggatc aagagctacc aactctttttt ccgaaggtaa    3540 ctggcttcag cagagcgcag ataccaaata ctgtccttct agtgtagccg tagttaggcc    3600
accacttcaa gaactctgta gcaccgccta catacctcgc tctgctaatc ctgttaccag    3660
tggctgctgc cagtggcgat aagtcgtgtc ttaccgggtt ggactcaaga cgatagttac    3720
cggataaggc gcagcggtcg ggctgaacgg ggggttcgtg cacacagccc agcttggagc    3780
gaacgaccta caccgaactg agatacctac agcgtgagca ttgagaaagc gccacgcttc    3840
ccgaagggag aaaggcggac aggtatccgg taagcggcag ggtcggaaca ggagagcgca    3900
cgagggagct ccaggggga aacgcctggt atctttatag tcctgtcggg tttcgccacc    3960
tctgacttga gcgtcgattt tgtgatgct cgtcagggg gcggagccta tggaaaaacg    4020
ccagcaacgc ggccttttta cggttcctgg cctttttgctg gccttttgct cacatgttct    4080
ttcctgcgtt atcccctgat tctgtggata accgtattac cgcctttgag tgagctgata    4140
ccgctcgccg cagccgaacg accgagcgca gcgagtcagt gagcgaggaa gcggaagagc    4200
gcccaatacg caaaccgcct ctccccgcgc gttggccgat tcattaatgc agaattaatt    4260
ctcatgtttg acagcttatc atcgactgca cggtgcacca atgcttctgg cgtcaggcag    4320
ccatcggaag ctgtggtatg gctgtgcagg tcgtaaatca ctgcataatt cgtgtcgctc    4380
aaggcgcact cccgttctgg ataatgtttt ttgcgccgac atcataacgg ttctggcaaa    4440
tattctgaaa tgagctgttg acaattaatc atcggctcgt ataatgtgtg gaattgtgag    4500
cggataacaa tttcacacag gaaacagcga tgaattcaga tctcaccatg aaggagctgg    4560
tggcccgagt gctgcagagg ctgtgcgagc gcggcgcgaa gaacgtgctg gccttcggct    4620
tcgcgctgct ggacgggccc cgcgggggcc ccccgagggc cttcaccacc agcgtgcgca    4680
gctacctgcc caacacggtg accgacgcac tgcgggggag cggggcgtgg gggctgctgc    4740
```

-continued

```
tgcgccgcgt gggcgacgac gtgctggttc acctgctggc acgctgcgcg ctctttgtgc   4800
tggtggctcc cagctgcgcc taccaggtgt gcgggccgcc gctgtaccag ctcggcgctg   4860
ccactcaggc ccggccccg ccacacgcta gtggaccccg aaggcgtctg ggatgcgaac    4920
gggcctggaa ccatagcgtc agggaggccg gggtccccct gggcctgcca gccccgggtg   4980
cgaggaggcg cggggcagt gccagccgaa gtctgccgtt gcccaagagg cccaggcgtg    5040
gcgctgcccc tgagccggag cggacgcccg ttgggcaggg gtcctgggcc cacccgggca   5100
ggacgcgtgg accgagtgac cgtggtttct gtgtggtgtc acctgccaga cccgccgaag   5160
aagccacctc tttggagggt gcgctctctg cacgcgcca ctcccaccca tccgtgggcc    5220
gccagcacca cgcgggcccc ccatccacat cgcggccacc acgtccctgg gacacgcctt   5280
gtcccccggt gtacgccgag accaagcact tcctctactc ctcaggcgac aaggagcagc   5340
tgcggccctc cttcctactc agctctctga ggcccagcct gactggcgct cggaggctcg   5400
tggagaccat ctttctgggt tccaggcct ggatgccagg gactcccgc aggttgcccc     5460
gcctgcccca gcgctactgg caaatgcggc ccctgtttct ggagctgctt gggaaccacg   5520
cgcagtgccc ctacggggtg ctcctcaaga cgcactgccc gctgcgagct gcggtcaccc   5580
cagcagccgg tgtctgtgcc cgggagaagc ccagggctc tgtggcggcc cccgaggagg   5640
aggacacaga cccccgtcgc ctggtgcagc tgctccgcca gcacagcagc ccctggcagg   5700
tgtacggctt cgtgcgggcc tgcctgcgcc ggctggtgcc cccaggcctc tggggctcca   5760
ggcacaacga acgccgcttc ctcaggaaca ccaagaagtt catctccctg gggaagcatg   5820
ccaagctctc gctgcaggag ctgacgtgga agatgagcgt gcgggactgc gcttggctgc   5880
gcaggagccc aggggttggc tgtgttccgg ccgcagagca ccgtctgcgt gaggagatcc   5940
tggccaagtt cctgcactgg ctgatgagtg tgtacgtcgt cgagctgctc aggtcttct    6000
tttatgtcac ggagaccacg tttcaaaaga acaggctctt tttctaccgg aagagtgtct   6060
ggagcaagtt gcaaagcatt ggaatcagac agcacttgaa gagggtgcag ctgcgggagc   6120
tgtcggaagc agaggtcagg cagcatcggg aagccaggcc cgccctgctg acgtccagac   6180
tccgcttcat ccccaagcct gacgggctgc ggccgattgt gaacatggac tacgtcgtgg   6240
gagccagaac gttccgcaga gaaaagaggg ccgagcgtct cacctcgagg gtgaaggcac   6300
tgttcagcgt gctcaactac gagcgggcgc ggcgccccgg cctcctgggc gcctctgtgc   6360
tgggcctgga cgatatccac agggcctggc gcaccttcgt gctgcgtgtg cgggcccagg   6420
acccgccgcc tgagctgtac tttgtcaagg tggatgtgac gggcgcgtac gacaccatcc   6480
cccaggacag gctcacggag gtcatcgcca gcatcatcaa accccagaac acgtactgcg   6540
tgcgtcggta tgccgtggtc cagaaggccg cccatgggca cgtccgcaag gccttcaaga   6600
gccacgtcct acgtccagtg ccaggggatc ccgcagggct ccatcctctc cacgctgctc   6660
tgcagcctgt gctacggcga catggagaac aagctgtttg cggggattcg gcgggacggg   6720
ctgctcctgc gtttggtgga tgatttcttg ttggtgacac ctcacctcac ccacgcgaaa   6780
acttcctcag gacctggtcc gaagtgtcct gagtatggct gcgtggtgaa cttgcggaag   6840
acagtggtga acttccctgt agaagacgaa gccctgggtg gcacggcttt tgttcagatg   6900
ccggcccacg gctattccc ctggtgcggc ctgctgctgg ataccggac cctggaggtg    6960
cagagcgact actccagcta tgcccggacc tccatcagag ccagtctcac cttcaaccgc   7020
ggcttcaagg ctgggaggaa catgcgtcgc aaactctttg gggtcttgcg gctgaagtgt   7080
cacagcctgt ttctggattt gcaggtgaac agcctccaga cggtgtgcac caacatctac   7140
```

```
aagatcctcc tgctgcaggc gtacaggttt cacgcatgtg tgctgcagct cccatttcat    7200
cagcaagttt ggaagaaccc cacatttttc ctgcgcgtca tctctgacac ggcctccctc    7260
tgctactcca tcctgaaagc caagaacgca gccgaagaaa acatttctgt cgtgactcct    7320
gcggtgcttg ggtcgggaca gccagagatg agccacccc gcagaccgtc gggtgtgggc     7380
agctttccgg tgtctcctgg gaggggagtt gggctgggcc tgtgactcct cagcctctgt    7440
tttcccccag ggatgtcgct gggggccaag ggcgccgccg gccctctgcc ctccgaggcc    7500
gtgcagtggc tgtgccacca agcattcctg ctcaagctga ctcgacaccg tgtcacctac    7560
gtgccactcc tggggtcact caggacaggc aagtgtgggt ggaggccagt gcggg         7615
```

<210> SEQ ID NO 88
<211> LENGTH: 7797
<212> TYPE: DNA
<213> ORGANISM: Homo sapiens
<220> FEATURE:
<223> OTHER INFORMATION: Human Telomerase Clone with Alternative
      C-terminus

<400> SEQUENCE: 88

```
tcgacctgca ggcatgcaag cttggcactg gccgtcgttt tacaacgtcg tgactgggaa      60
aaccctggcg ttacccaact taatcgcctt gcagcacatc cccctttcgc cagctggcgt     120
aatagcgaag aggcccgcac cgatcgccct tcccaacagt tgcgcagcct gaatggcgaa     180
tggcgcctga tgcggtattt tctccttacg catctgtgcg gtatttcaca ccgcataaat     240
tccctgtttt ggcggatgag agaagatttt cagcctgata cagattaaat cagaacgcag     300
aagcggtctg ataaaacaga atttgcctgg cggcagtagc gcggtggtcc cacctgaccc     360
catgccgaac tcagaagtga aacgccgtag cgccgatggt agtgtggggt ctccccatgc     420
gagagtaggg aactgccagg catcaaataa aacgaaaggc tcagtcgaaa gactgggcct     480
ttcgttttat ctgttgtttg tcggtgaacg ctctcctgag taggacaaat ccgccgggag     540
cggatttgaa cgttgcgaag caacggcccg gagggtggcg gcaggacgc ccgccataaa      600 ctgccaggca tcaaattaag cagaaggcca tcctgacgga tggcctttt gcgtttctac      660 aaactcttcc tgtcgtcata tctacaagcc atcccccac agatacggta aactagcctc      720 gttttttgcat caggaaagca gggaatttat ggtgcactct cagtacaatc tgctctgatg     780
ccgcatagtt aagccagccc cgacacccgc caacacccgc tgacgcgccc tgacgggctt     840
gtctgctccc ggcatccgct tacagacaag ctgtgaccgt ctccgggagc tgcatgtgtc     900
agaggttttc accgtcatca ccgaaacgcg cgagacgaaa gggcctcgtg atacgcctat     960
ttttataggt taatgtcatg ataataatgg tttcttagac gtgaggttct gtacccgaca    1020
ccatcgaatg gtgcaaaacc tttcgcggta tggcatgata gcgcccggaa gagagtcaat    1080
tcagggtggt gaatgtgaaa ccagtaacgt tatacgatgt cgcagagtat gccggtgtct    1140
cttatcagac cgtttcccgc gtggtgaacc aggccagcca cgtttctgcg aaaacgcggg    1200
aaaaagtgga agcggcgatg gcggagctga attacattcc caaccgcgtg gcacaacaac    1260
tggcgggcaa acagtcgttg ctgattggcg ttgccacctc cagtctggcc ctgcacgcgc    1320
cgtcgcaaat tgtcgcggcg attaaatctc gcgccgatca actgggtgcc agcgtggtgg    1380
tgtcgatggt agaacgaagc ggcgtcgaag cctgtaaagc ggcggtgcac aatcttctcg    1440
cgcaacgcgt cagtgggctg atcattaact atccgctgga tgaccaggat gccattgctg    1500
tggaagctgc ctgcactaat gttccggcgt tatttcttga tgtctctgac cagacaccca    1560
```

-continued

```
tcaacagtat tattttctcc catgaagacg gtacgcgact gggcgtggag catctggtcg    1620
cattgggtca ccagcaaatc gcgctgttag cgggcccatt aagttctgtc tcggcgcgtc    1680
tgcgtctggc tggctggcat aaatatctca ctcgcaatca aattcagccg atagcggaac    1740
gggaaggcga ctggagtgcc atgtccggtt ttcaacaaac catgcaaatg ctgaatgagg    1800
gcatcgttcc cactgcgatg ctggttgcca acgatcagat ggcgctgggc gcaatgcgcg    1860
ccattaccga gtccgggctg cgcgttggtg cggatatctc ggtagtggga tacgacgata    1920
ccgaagacag ctcatgttat atcccgccgt taaccaccat caaacaggat tttcgcctgc    1980
tggggcaaac cagcgtggac cgcttgctgc aactctctca gggccaggcg gtgaagggca    2040
atcagctgtt gcccgtctca ctggtgaaaa gaaaaaccac cctggcgccc aatacgcaaa    2100
ccgcctctcc ccgcgcgttg gccgattcat taatgcagct ggcacgacag gtttcccgac    2160
tggaaagcgg gcagtgagcg caacgcaatt aatgtaagtt agctcactca ttaggcaccc    2220
caggctttac actttatgct tccgacctgc aagaacctca cgtcaggtgg cacttttcgg    2280
ggaaatgtgc gcggaacccc tatttgttta ttttttctaaa tacattcaaa tatgtatccg    2340
ctcatgagac aataaccctg ataaatgctt caataatatt gaaaaggaa gagtatgagt     2400
attcaacatt tccgtgtcgc ccttattccc ttttttgcgg cattttgcct tcctgttttt    2460
gctcacccag aaacgctggt gaaagtaaaa gatgctgaag atcagttggg tgcacgagtg    2520
ggttacatcg agaactggat ctcaacagcg gtaagatcct tgagagtttt cgccccgaag    2580
aacgttttcc aatgatgagc acttttaaag ttctgctatg tggcgcggta ttatcccgta    2640
ttgacgccgg gcaagagcaa ctcggtcgcc gcatacacta ttctcagaat gacttggttg    2700
agtactcacc agtcacagaa aagcatctta cggatggcat gacagtaaga gaattatgca    2760
gtgctgccat aaccatgagt gataacactg cggccaactt acttctgaca acgatcggag    2820
gaccgaagga gctaaccgct tttttgcaca acatggggga tcatgtaact cgccttgatc    2880
gttgggaacc ggagctgaat gaagccatac caaacgacga gcgtgacacc acgatgcctg    2940
tagcaatggc aacaacgttg cgcaaactat taactggcga actacttact ctagcttccc    3000
ggcaacaatt aatagactgg atggaggcgg ataaagttgc aggaccactt ctgcgctcgg    3060
cccttccggc tggctggttt attgctgata atctggagc cggtgagcgt gggtctcgcg     3120
gtatcattgc agcactgggg ccagatggta agccctcccg tatcgtagtt atctacacga    3180
cggggagtca ggcaactatg gatgaacgaa atagacagat cgctgagata ggtgcctcac    3240
tgattaagca ttggtaactg tcagaccaag tttactcata tactttag attgatttaa      3300
aacttcattt ttaatttaaa aggatctagg tgaagatcct ttttgataat ctcatgacca    3360
aaatccctta acgtgagttt cgttccact gagcgtcaga ccccgtagaa aagatcaaag     3420
gatcttcttg agatcctttt tttctgcgcg taatctgctg cttgcaaaca aaaaaaccac    3480
cgctaccagc ggtggtttgt ttgccggatc aagagctacc aactcttttt ccgaaggtaa    3540
ctggcttcag cagagcgcag ataccaaata ctgtccttct agtgtagccg tagttaggcc    3600
accacttcaa gaactctgta gcaccgccta catacctcgc tctgctaatc ctgttaccag    3660
tggctgctgc cagtggcgat aagtcgtgtc ttaccgggtt ggactcaaga cgatagttac    3720
cggataaggc gcagcggtcg ggctgaacgg ggggttcgtg cacacagccc agcttggagc    3780
gaacgaccta caccgaactg agatacctac agcgtgagca ttgagaaagc gccacgcttc    3840
ccgaagggag aaaggcggac aggtatccgg taagcggcag ggtcggaaca ggagagcgca    3900
```

-continued

```
cgagggagct tccaggggga aacgcctggt atctttatag tcctgtcggg tttcgccacc    3960
tctgacttga gcgtcgattt tgtgatgct cgtcaggggg gcggagccta tggaaaaacg    4020
ccagcaacgc ggccttttta cggttcctgg cctttttgctg cccttttgct cacatgttct  4080
ttcctgcgtt atcccctgat tctgtggata accgtattac cgcctttgag tgagctgata   4140
ccgctcgccg cagccgaacg accgagcgca gcgagtcagt gagcgaggaa gcggaagagc   4200
gcccaatacg caaaccgcct ctccccgcgc gttggccgat tcattaatgc agaattaatt   4260
ctcatgtttg acagcttatc atcgactgca cggtgcacca atgcttctgg cgtcaggcag   4320
ccatcggaag ctgtggtatg gctgtgcagg tcgtaaatca ctgcataatt cgtgtcgctc   4380
aaggcgcact cccgttctgg ataatgtttt tgcgccgac atcataacgg ttctggcaaa    4440
tattctgaaa tgagctgttg acaattaatc atcggctcgt ataatgtgtg gaattgtgag   4500
cggataacaa tttcacacag gaaacagcga tgaattcaga tctcaccatg aaggagctgg   4560
tggcccgagt gctgcagagg ctgtgcgagc gcggcgcgaa gaacgtgctg gccttcggct   4620
tcgcgctgct ggacggggcc cgcgggggcc ccccgaggc cttcaccacc agcgtgcgca    4680
gctacctgcc caacacggtg accgacgcac tgcggggag cggggcgtgg gggctgctgc    4740
tgcgccgcgt gggcgacgac gtgctggttc acctgctggc acgctgcgcg ctctttgtgc   4800
tggtggctcc cagctgcgcc taccaggtgt gcgggccgcc gctgtaccag ctcggcgctg   4860
ccactcaggc ccggcccccg ccacacgcta gtggaccccg aaggcgtctg ggatgcgaac   4920
gggcctggaa ccatagcgtc agggaggccg gggtcccct gggcctgcca gccccgggtg    4980
cgaggaggcg cgggggcagt gccagccgaa gtctgccgtt gcccaagagg cccaggcgtg   5040
gcgctgcccc tgagccggag cggacgcccg ttgggcaggg gtcctgggcc cacccgggca   5100
ggacgcgtgg accgagtgac cgtggtttct gtgtggtgtc acctgccaga cccgccgaag   5160
aagccacctc tttggagggt gcgctctctg gcacgcgcca ctcccaccca tccgtgggcc   5220
gccagcacca cgcgggcccc ccatccacat cgcggccacc acgtccctgg gacacgcctt   5280
gtcccccggt gtacgccgag accaagcact tcctctactc ctcaggcgac aaggagcagc   5340
tgcggccctc cttcctactc agctctctga ggcccagcct gactggcgct cggaggctcg   5400
tggagaccat ctttctgggt tccaggccct ggatgccagg gactccccgc aggttgcccc   5460
gcctgcccca gcgctactgg caaatgcggc ccctgtttct ggagctgctt gggaaccacg   5520
cgcagtgccc ctacggggtg tcctcaaga cgcactgccc gctgcgagct gcggtcaccc    5580
cagcagccgg tgtctgtgcc cgggagaagc cccagggctc tgtggcggcc cccgaggagg   5640
aggacacaga cccccgtcgc ctggtgcagc tgctccgcca gcacagcagc ccctggcagg   5700
tgtacggctt cgtgcgggcc tgcctgcgcc ggctggtgcc cccaggcctc tggggctcca   5760
ggcacaacga acgccgcttc ctcaggaaca ccaagaagtt catctccctg gggaagcatg   5820
ccaagctctc gctgcaggag ctgacgtgga agatgagcgt gcgggactgc gcttggctgc   5880
gcaggagccc aggggttggc tgtgttccgg ccgcagagca ccgtctgcgt gaggagatcc   5940
tggccaagtt cctgcactgg ctgatgagtg tgtacgtcgt cgagctgctc aggtctttct   6000
tttatgtcac ggagaccacg tttcaaaaga acaggctctt tttctaccgg aagagtgtct   6060
ggagcaagtt gcaaagcatt ggaatcagac agcacttgaa gagggtgcag ctgcgggagc   6120
tgtcggaagc agaggtcagg cagcatcggg aagccaggcc cgccctgctg acgtccagac   6180
tccgcttcat ccccaagcct gacgggctgc ggccgattgt gaacatggac tacgtcgtgg   6240
gagccagaac gttccgcaga gaaaagaggg ccgagcgtct cacctcgagg gtgaaggcac   6300
```

```
tgttcagcgt gctcaactac gagcgggcgc ggcgccccgg cctcctgggc gcctctgtgc    6360
tgggcctgga cgatatccac agggcctggc gcaccttcgt gctgcgtgtg cgggcccagg    6420
acccgccgcc tgagctgtac tttgtcaagg tggatgtgac gggcgcgtac gacaccatcc    6480
cccaggacag gctcacggag gtcatcgcca gcatcatcaa accccagaac acgtactgcg    6540
tgcgtcggta tgccgtggtc cagaaggccc ccatgggca cgtccgcaag gccttcaaga    6600
gccacgtctc taccttgaca gacctccagc cgtacatgcg acagttcgtg gctcacctgc    6660
aggagaccag cccgctgagg gatgccgtcg tcatcgagca gagctcctcc ctgaatgagg    6720
ccagcagtgg cctcttcgac gtcttcctac gcttcatgtg ccaccacgcc gtgcgcatca    6780
ggggcaagtc ctacgtccag tgccaggtga tcccgcaggg ctccatcctc tccacgctgc    6840
tctgcagcct gtgctacggc gacatggaga acaagctgtt tgcggggatt cggcgggacg    6900
ggctgctcct gcgtttggtg gatgatttct tgttggtgac acctcacctc acccacgcga    6960
aaacttcctc aggacctggt ccgaagtgtc ctgagtatgg ctgcgtggtg aacttgcgga    7020
agacagtggt gaacttccct gtagaagacg aagcccgggg tggcacggct tttgttcaga    7080
tgccggccca cggcctattc ccctggtgcg gcctgctgct ggatacccgg accctggagg    7140
tgcagagcga ctactccagc tatgcccgga cctccatcag agccagtctc accttcaacc    7200
gcggcttcaa ggctgggagg aacatgcgtc gcaaactctt tggggtcttg cggctgaagt    7260
gtcacagcct gtttctggat ttgcaggtga acagcctcca gacggtgtgc accaacatct    7320
acaagatcct cctgctgcag gcgtacaggt ttcacgcatg tgtgctgcag ctcccattcc    7380
atcagcaagt ttggaagaac cccacatttt tcctgcgcgt catctctgac acggcctccc    7440
tctgctactc catcctgaaa gccaagaacg cagccgaaga aaacatttct gtcgtgactc    7500
ctgcggtgct tgggtcggga cagccagaga tggagccacc ccgcagaccg tcgggtgtgg    7560 gcagcttttcc ggtgtctcct gggaggggag ttgggctggg cctgtgactc ctcagcctct    7620
gttttccccc agggatgtcg ctgggggcca agggcgccgc cggccctctg ccctccgagg    7680
ccgtgcagtg gctgtgccac caagcattcc tgctcaagct gactcgacac cgtgtcacct    7740
acgtgccact cctgggtca ctcaggacag gcaagtgtgg gtggaggcca gtgcggg       7797
```

<210> SEQ ID NO 89
<211> LENGTH: 7688
<212> TYPE: DNA
<213> ORGANISM: Homo sapiens
<220> FEATURE:
<223> OTHER INFORMATION: Human Telomerase Clone with exon Alpha Spliced
      Out

<400> SEQUENCE: 89

```
tcgacctgca ggcatgcaag cttggcactg gccgtcgttt tacaacgtcg tgactgggaa      60
aaccctggcg ttacccaact taatcgcctt gcagcacatc cccctttcgc cagctggcgt     120
aatagcgaag aggcccgcac cgatcgccct tcccaacagt tgcgcagcct gaatggcgaa     180
tggcgcctga tgcggtattt tctccttacg catctgtgcg gtatttcaca ccgcataaat     240
tccctgtttt ggcggatgag agaagatttt cagcctgata cagattaaat cagaacgcag     300
aagcggtctg ataaaacaga atttgcctgg cggcagtagc gcggtggtcc cacctgaccc     360
catgccgaac tcagaagtga aacgccgtag cgccgatggt agtgtggggt ctccccatgc     420
gagagtaggg aactgccagg catcaaataa aacgaaaggc tcagtcgaaa gactgggcct     480
ttcgttttat ctgttgtttg tcggtgaacg ctctcctgag taggacaaat ccgccgggag     540
```

-continued

```
cggatttgaa cgttgcgaag caacggcccg gagggtggcg ggcaggacgc ccgccataaa    600
ctgccaggca tcaaattaag cagaaggcca tcctgacgga tggcctttttt gcgtttctac   660
aaactcttcc tgtcgtcata tctacaagcc atcccccccac agatacggta aactagcctc   720
gttttttgcat caggaaagca gggaatttat ggtgcactct cagtacaatc tgctctgatg   780
ccgcatagtt aagccagccc cgacacccgc caacacccgc tgacgcgccc tgacgggctt    840
gtctgctccc ggcatccgct tacagacaag ctgtgaccgt ctccgggagc tgcatgtgtc    900
agaggttttc accgtcatca ccgaaacgcg cgagacgaaa gggcctcgtg atacgcctat    960
ttttataggt taatgtcatg ataataatgg tttcttagac gtgaggttct gtacccgaca   1020
ccatcgaatg gtgcaaaacc tttcgcggta tggcatgata cgcccggaa gagagtcaat    1080
tcagggtggt gaatgtgaaa ccagtaacgt tatacgatgt cgcagagtat gccggtgtct   1140
cttatcagac cgtttcccgc gtggtgaacc aggccagcca cgtttctgcg aaaacgcggg   1200
aaaaagtgga agcggcgatg gcggagctga attacattcc caaccgcgtg gcacaacaac   1260
tggcgggcaa acagtcgttg ctgattggcg ttgccacctc cagtctggcc ctgcacgcgc   1320
cgtcgcaaat tgtcgcggcg attaaatctc gcgccgatca actgggtgcc agcgtggtgg   1380
tgtcgatggt agaacgaagc ggcgtcgaag cctgtaaagc ggcggtgcac aatcttctcg   1440
cgcaacgcgt cagtgggctg atcattaact atccgctgga tgaccaggat gccattgctg   1500
tggaagctgc ctgcactaat gttccggcgt tatttcttga tgtctctgac cagacaccca   1560
tcaacagtat tattttctcc catgaagacg gtacgcgact gggcgtggag catctggtcg   1620
cattgggtca ccagcaaatc gcgctgttag cgggcccatt aagttctgtc tcggcgcgtc   1680
tgcgtctggc tggctggcat aaatatctca ctcgcaatca aattcagccg atagcggaac   1740
gggaaggcga ctggagtgcc atgtccggtt ttcaacaaac catgcaaatg ctgaatgagg   1800
gcatcgttcc cactgcgatg ctggttgcca acgatcagat ggcgctgggc gcaatgcgcg   1860
ccattaccga gtccgggctg cgcgttggtg cggatatctc ggtagtggga tacgacgata   1920
ccgaagacag ctcatgttat atcccgccgt taaccaccat caaacaggat ttcgcctgc   1980
tggggcaaac cagcgtggac cgcttgctgc aactctctca gggccaggcg gtgaagggca   2040
atcagctgtt gcccgtctca ctggtgaaaa gaaaaaccac cctggcgccc aatacgcaaa   2100
ccgcctctcc ccgcgcgttg gccgattcat taatgcagct ggcacgacag gtttcccgac   2160
tggaaagcgg gcagtgagcg caacgcaatt aatgtaagtt agctcactca ttaggcaccc   2220
caggctttac actttatgct tccgacctgc aagaacctca cgtcaggtgg cacttttcgg   2280
ggaaatgtgc gcggaacccc tatttgttta ttttttctaaa tacattcaaa tatgtatccg   2340
ctcatgagac aataaccctg ataaatgctt caataatatt gaaaaggaa gagtatgagt   2400
attcaacatt tccgtgtcgc ccttattccc ttttttgcgg catttttgcct tcctgttttt   2460
gctcacccag aaacgctggt gaaagtaaaa gatgctgaag atcagttggg tgcacgagtg   2520
ggttacatcg aaactggat ctcaacagcg gtaagatcct tgagagtttt cgccccgaag   2580
aacgttttcc aatgatgagc acttttaaag ttctgctatg tggcgcggta ttatcccgta   2640
ttgacgccgg gcaagagcaa ctcggtcgcc gcatacacta ttctcagaat gacttggttg   2700
agtactcacc agtcacagaa aagcatctta cggatggcat gacagtaaga gaattatgca   2760
gtgctgccat aaccatgagt gataacactg cggccaactt acttctgaca acgatcggag   2820
gaccgaagga gctaaccgct ttttttgcaca acatggggga tcatgtaact cgccttgatc   2880
```

-continued

```
gttgggaacc ggagctgaat gaagccatac caaacgacga gcgtgacacc acgatgcctg    2940
tagcaatggc aacaacgttg cgcaaactat taactggcga actacttact ctagcttccc    3000
ggcaacaatt aatagactgg atggaggcgg ataaagttgc aggaccactt ctgcgctcgg    3060
cccttccggc tggctggttt attgctgata atctggagc cggtgagcgt gggtctcgcg    3120
gtatcattgc agcactgggg ccagatggta agccctcccg tatcgtagtt atctacacga    3180
cggggagtca ggcaactatg gatgaacgaa atagacagat cgctgagata ggtgcctcac    3240
tgattaagca ttggtaactg tcagaccaag tttactcata tatactttag attgatttaa    3300
aacttcattt ttaatttaaa aggatctagg tgaagatcct ttttgataat ctcatgacca    3360
aaatccctta acgtgagttt tcgttccact gagcgtcaga ccccgtagaa aagatcaaag    3420
gatcttcttg agatcctttt tttctgcgcg taatctgctg cttgcaaaca aaaaaaccac    3480
cgctaccagc ggtggtttgt ttgccggatc aagagctacc aactctttt ccgaaggtaa    3540 ctggcttcag cagagcgcag ataccaaata ctgtccttct agtgtagccg tagttaggcc    3600
accacttcaa gaactctgta gcaccgccta catacctcgc tctgctaatc ctgttaccag    3660
tggctgctgc cagtggcgat aagtcgtgtc ttaccgggtt ggactcaaga cgatagttac    3720
cggataaggc gcagcggtcg ggctgaacgg ggggttcgtg cacacagccc agcttggagc    3780
gaacgaccta caccgaactg agatacctac agcgtgagca ttgagaaagc gccacgcttc    3840
ccgaagggag aaaggcggac aggtatccgg taagcggcag ggtcggaaca ggagagcgca    3900
cgagggagct ccagggggga aacgcctggt atctttatag tcctgtcggg tttcgccacc    3960
tctgacttga gcgtcgattt tgtgatgct cgtcagggg gcggagccta tggaaaaacg    4020
ccagcaacgc ggcctttta cggttcctgg ccttttgctg gccttttgct cacatgttct    4080
ttcctgcgtt atcccctgat tctgtggata accgtattac cgcctttgag tgagctgata    4140
ccgctcgccg cagccgaacg accgagcgca gcgagtcagt gagcgaggaa gcggaagagc    4200
gcccaatacg caaaccgcct ctccccgcgc gttggccgat tcattaatgc agaattaatt    4260
ctcatgtttg acagcttatc atcgactgca cggtgcacca atgcttctgg cgtcaggcag    4320
ccatcggaag ctgtggtatg gctgtgcagg tcgtaaatca ctgcataatt cgtgtcgctc    4380
aaggcgcact cccgttctgg ataatgtttt ttgcgccgac atcataacgg ttctggcaaa    4440
tattctgaaa tgagctgttg acaattaatc atcggctcgt ataatgtgtg gaattgtgag    4500
cggataacaa tttcacacag gaaacagcga tgaattcaga tctcaccatg aaggagctgg    4560
tggcccgagt gctgcagagg ctgtgcgagc gcggcgcgaa gaacgtgctg gccttcggct    4620
tcgcgctgct ggacgggccc cgcgggggcc ccccgaggc cttcaccacc agcgtgcgca    4680
gctacctgcc caacacggtg accgacgcac tgcgggggag cggggcgtgg gggctgctgc    4740
tgcgccgcgt gggcgacgac gtgctggttc acctgctggc acgctgcgcg ctctttgtgc    4800
tggtggctcc cagctgcgcc taccaggtgt gcgggccgcc gctgtaccag ctcggcgctg    4860
ccactcaggc ccggccccg ccacacgcta gtggaccccg aaggcgtctg ggatgcgaac    4920
gggcctggaa ccatagcgtc agggaggccg gggtcccct gggcctgcca gccccgggtg    4980
cgaggaggcg cgggggcagt gccagccgaa gtctgccgtt gcccaagagg cccaggcgtg    5040
gcgctgcccc tgagcggag cggacgcccg ttgggcaggg gtcctgggcc cacccgggca    5100
ggacgcgtgg accgagtgac cgtggttcct gtgtggtgtc acctgccaga cccgccgaag    5160
aagccacctc tttggagggt gcgctctctg gcacgcgcca ctcccaccca tccgtgggcc    5220
gccagcacca cgcgggcccc ccatccacat cgcggccacc acgtccctgg gacacgcctt    5280
```

-continued

```
gtcccccggt gtacgccgag accaagcact tcctctactc ctcaggcgac aaggagcagc    5340
tgcggccctc cttcctactc agctctctga ggcccagcct gactggcgct cggaggctcg    5400
tggagaccat ctttctgggt tccaggccct ggatgccagg gactccccgc aggttgcccc    5460
gcctgcccca gcgctactgg caaatgcggc ccctgtttct ggagctgctt gggaaccacg    5520
cgcagtgccc ctacggggtg ctcctcaaga cgcactgccc gctgcgagct gcggtcaccc    5580
cagcagccgg tgtctgtgcc cgggagaagc ccagggctc tgtggcggcc cccgaggagg    5640
aggacacaga cccccgtcgc ctggtgcagc tgctccgcca gcacagcagc ccctggcagg    5700
tgtacggctt cgtgcgggcc tgcctgcgcc ggctggtgcc cccaggcctc tgggctcca    5760 ggcacaacga acgccgcttc ctcaggaaca ccaagaagtt catctccctg gggaagcatg    5820
ccaagctctc gctgcaggag ctgacgtgga agatgagcgt gcgggactgc gcttggctgc    5880
gcaggagccc aggggttggc tgtgttccgg ccgcagagca ccgtctgcgt gaggagatcc    5940
tggccaagtt cctgcactgg ctgatgagtg tgtacgtcgt cgagctgctc aggtctttct    6000
tttatgtcac ggagaccacg tttcaaaaga acaggctctt tttctaccgg aagagtgtct    6060
ggagcaagtt gcaaagcatt ggaatcagac agcacttgaa gagggtgcag ctgcgggagc    6120
tgtcggaagc agaggtcagg cagcatcggg aagccaggcc cgccctgctg acgtccagac    6180
tccgcttcat ccccaagcct gacgggctgc ggccgattgt gaacatggac tacgtcgtgg    6240
gagccagaac gttccgcaga gaaaagaggg ccgagcgtct cacctcgagg gtgaaggcac    6300
tgttcagcgt gctcaactac gagcgggcgc ggcgccccgg cctcctgggc gcctctgtgc    6360
tgggcctgga cgatatccac agggcctggc gcaccttcgt gctgcgtgtg cgggcccagg    6420
acccgccgcc tgagctgtac tttgtcaagg acaggctcac ggaggtcatc gccagcatca    6480
tcaaacccag aacacgtact gcgtgcgtcg gtatgccgtg gtccagaagg ccgcccatgg    6540
gcacgtccgc aaggccttca agagccacgt ctctaccttg acagacctcc agccgtacat    6600
gcgacagttc gtggctcacc tgcaggagac cagcccgctg agggatgccg tcgtcatcga    6660
gcagagctcc tccctgaatg aggccagcag tggcctcttc gacgtcttcc tacgcttcat    6720
gtgccaccac gccgtgcgca tcaggggcaa gtcctacgtc cagtgccagg ggatcccgca    6780
gggctccatc ctctccacgc tgctctgcag cctgtgctac ggcgacatgg agaacaagct    6840 gttttgcgggg attcggcggg acgggctgct cctgcgtttg gtggatgatt tcttgttggt    6900
gacacctcac ctcaccccacg cgaaaaccctt cctcaggacc ctggtccgag gtgtccctga    6960
gtatggctgc gtggtgaact tgcggaagac agtggtgaac ttccctgtag aagacgaggc    7020
cctgggtggc acggcttttg ttcagatgcc ggccacggc ctattcccct ggtgcggcct    7080
gctgctggat acccggaccc tggaggtgca gagcgactac tccagctatg cccggacctc    7140
catcagagcc agtctcacct tcaaccgcgc cttcaaggct gggaggaaca tgcgtcgcaa    7200
actctttggg gtcttgcggc tgaagtgtca cagcctgttt ctggatttgc aggtgaacag    7260
cctccagacg gtgtgcacca acatctacaa gatcctcctg ctgcaggcgt acaggtttca    7320
cgcatgtgtg ctgcagctcc catttcatca gcaagtttgg aagaacccca cattttcct     7380 gcgcgtcatc tctgacacgg cctccctctg ctactccatc ctgaaagcca agaacgcagg    7440
gatgtcgctg ggggccaagg gcgccgccgg ccctctgccc tccgaggccg tgcagtggct    7500
gtgccaccaa gcattcctgc tcaagctgac tcgacaccgt gtcacctacg tgccactcct    7560
ggggtcactc aggacagccc agacgcagct gagtcggaag ctcccgggga cgacgctgac    7620
```

```
tgccctggag gccgcagcca acccggcact gccctcagac ttcaagacca tcctggactg    7680
atctagag                                                              7688
```

<210> SEQ ID NO 90
<211> LENGTH: 8
<212> TYPE: PRT
<213> ORGANISM: Homo sapiens

<400> SEQUENCE: 90

```
Ala Val Arg Ile Arg Gly Lys Ser
  1               5
```

<210> SEQ ID NO 91
<211> LENGTH: 8
<212> TYPE: PRT
<213> ORGANISM: Unknown
<220> FEATURE:
<223> OTHER INFORMATION: Description of Unknown Organism: Consensus
      P-loop Motif Sequence found in large number of protein
      families
<220> FEATURE:
<221> NAME/KEY: MOD_RES
<222> LOCATION: (2)..(5)
<223> OTHER INFORMATION: Wherein Xaa is any residue

<400> SEQUENCE: 91

```
Ala Xaa Xaa Xaa Xaa Gly Lys Ser
  1               5
```

<210> SEQ ID NO 92
<211> LENGTH: 17
<212> TYPE: PRT
<213> ORGANISM: Homo sapiens

<400> SEQUENCE: 92

```
Ser Gly Gln Pro Glu Met Glu Pro Pro Arg Arg Pro Ser Gly Cys Val
  1               5                  10                  15

Gly
```

<210> SEQ ID NO 93
<211> LENGTH: 9
<212> TYPE: PRT
<213> ORGANISM: Unknown
<220> FEATURE:
<223> OTHER INFORMATION: Description of Unknown Organism: Consensus
      c-Alb SH3 binding peptide
<220> FEATURE:
<221> NAME/KEY: MOD_RES
<222> LOCATION: (2)..(5)
<223> OTHER INFORMATION: Wherein Xaa is any residue
<220> FEATURE:
<221> NAME/KEY: MOD_RES
<222> LOCATION: (7)..(8)
<223> OTHER INFORMATION: Wherein Xaa is any residue

<400> SEQUENCE: 93

```
Pro Xaa Xaa Xaa Xaa Pro Xaa Xaa Pro
  1               5
```

<210> SEQ ID NO 94
<211> LENGTH: 17
<212> TYPE: PRT
<213> ORGANISM: Homo sapiens

<400> SEQUENCE: 94

```
His Ala Gly Pro Pro Ser Thr Ser Arg Pro Pro Arg Pro Trp Asp Thr
  1               5                  10                  15
```

Pro

<210> SEQ ID NO 95
<211> LENGTH: 14
<212> TYPE: DNA
<213> ORGANISM: Unknown
<220> FEATURE:
<223> OTHER INFORMATION: Description of Unknown Organism: General
      Target Sequence Recognized by Hairpin Ribozyme
<220> FEATURE:
<221> NAME/KEY: modified_base
<222> LOCATION: (1)..(3)
<223> OTHER INFORMATION: Wherein N is G, U, C or A
<220> FEATURE:
<221> NAME/KEY: modified_base
<222> LOCATION: (5)
<223> OTHER INFORMATION: Wherein N is G, U, C or A
<220> FEATURE:
<221> NAME/KEY: modified_base
<222> LOCATION: (9)..(14)
<223> OTHER INFORMATION: Wherein N is G, U, C or A

<400> SEQUENCE: 95
nnnbngucnn nnnn                                                          14

<210> SEQ ID NO 96
<211> LENGTH: 26
<212> TYPE: DNA
<213> ORGANISM: Artificial Sequence
<220> FEATURE:
<223> OTHER INFORMATION: Description of Artificial Sequence:
      Amplification Primer Design Based on EST Sequence GenBank
      Accession Number AA281296

<400> SEQUENCE: 96
aggagatctc gcgatgccgc gcgctc                                             26

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence:
      Amplification Primer Design Based on EST Sequence GenBank
      Accession Number AA281296

<400> SEQUENCE: 97
tccacgcgtc ctgcccgggt g                                                  21

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence:
      Amplification Primer Design Based on EST Sequence GenBank
      Accession Number AA281296

<400> SEQUENCE: 98
gctggtgcag cgcggggacc                                                    20

<210> SEQ ID NO 99
<211> LENGTH: 48
<212> TYPE: DNA
<213> ORGANISM: Artificial Sequence
<220> FEATURE:
<223> OTHER INFORMATION: Description of Artificial Sequence:
      Amplification Primer Design Based on EST Sequence GenBank
      Accession Number AA281296

-continued

<400> SEQUENCE: 99
cacaagcttg aattcacatc tcaccatgaa ggagctggtg gcccgagt            48

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 100
ggcacgcaca ccaggcactg                                          20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 101
cctgcctgaa ggagctggtg                                          20

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 102
ggacacctgg cggaaggag                                           19

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 103
ccgagtgctg cagaggctgt                                          20

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 104
gaagccgaag gccagcacgt tctt                                     24

<210> SEQ ID NO 105
<211> LENGTH: 22
<212> TYPE: DNA

```
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 105
gtgcagctgc tccgccagca ca                                              22

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 106
gttcccaagc agctccagaa acag                                            24

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 107
ggcagtgcgt cttgaggagc a                                               21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 108
cactggctga tgagtgtgta c                                               21

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 109
gacgtacaca ctcatcagcc ag                                              22

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 110
ggtctttctt ttatgtcacg gag                                             23
```

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthesized
    Amplification Primer Design based on EST Sequence
    GenBank Accession Number AA281296

<400> SEQUENCE: 111
cacttgaaga gggtgcagct                                              20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthesized
    Amplification Primer Design based on EST Sequence
    GenBank Accession Number AA281296

<400> SEQUENCE: 112
gtctcacctc gagggtgaag                                              20

<210> SEQ ID NO 113
<211> LENGTH: 22
<212> TYPE: DNA
<213> ORGANISM: Artificial Sequence
<220> FEATURE:
<223> OTHER INFORMATION: Description of Artificial Sequence: Synthesized
    Amplification Primer Design based on EST Sequence
    GenBank Accession Number AA281296

<400> SEQUENCE: 113
ttcaccctcg aggtgagacg ct                                           22

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthesized
    Amplification Primer Design based on EST Sequence
    GenBank Accession Number AA281296

<400> SEQUENCE: 114
tcgtagttga gcacgctgaa c                                            21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthesized
    Amplification Primer Design based on EST Sequence
    GenBank Accession Number AA281296

<400> SEQUENCE: 115
gcctgagctg tactttgtca a                                            21

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence: Synthesized
    Amplification Primer Design based on EST Sequence GenBank Accession Number AA281296

<400> SEQUENCE: 116
ctgagctgta ctttgtcaag gaca                                              24

<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 117
gtacatgcga cagttcgtgg ctca                                              24

<210> SEQ ID NO 118
<211> LENGTH: 26
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 118
catgaagcgt aggaagacgt cgaaga                                            26

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 119
cgcaaacagc ttgttctcca tgtc                                              24

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 120
ctatgcccgg acctccatca ga                                                22

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 121
ctgatggagg tccgggcata g                                                 21

<210> SEQ ID NO 122
<211> LENGTH: 18

```
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 122
cctccgaggc cgtgcagt                                                   18

<210> SEQ ID NO 123
<211> LENGTH: 43
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 123
cacctcaagc tttctagatc agtccaggat ggtcttgaag tca                       43

<210> SEQ ID NO 124
<211> LENGTH: 24
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 124
ggaaggcaaa ggagggcagg gcga                                            24

<210> SEQ ID NO 125
<211> LENGTH: 37
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 125
cacgaattcg gatccaagct tttttttttt tttttttt                             37

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 126
gggttgcgga gggtgggc                                                   18

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 127
```

-continued gcagtggtga gccgagtcct g                                      21

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 128
cgactttgga ggtgccttca                                        20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 129
gctggtgcag cgcggggacc                                        20

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 130
gaggtgcaga gcgactactc ca                                     22

<210> SEQ ID NO 131
<211> LENGTH: 20
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 131
gtctcacctc gagggtgaag                                        20

<210> SEQ ID NO 132
<211> LENGTH: 22
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 132
ggctgctcct gcgtttggtg ga                                     22

<210> SEQ ID NO 133
<211> LENGTH: 19
<212> TYPE: DNA
<213> ORGANISM: Artificial Sequence
<220> FEATURE:
<223> OTHER INFORMATION: Description of Artificial Sequence: Synthesized Amplification Primer Design based on EST Sequence
GenBank Accession Number AA281296

<400> SEQUENCE: 133
gccagagatg gagccaccc                                                19

<210> SEQ ID NO 134
<211> LENGTH: 19
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 134
gggtggctcc atctctggc                                                19

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 135
ccgcacgctc atcttccacg t                                             21

<210> SEQ ID NO 136
<211> LENGTH: 19
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 136
gcttggggat gaagcggtc                                                19

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 137
cgcctgagct gtactttgtc a                                             21

<210> SEQ ID NO 138
<211> LENGTH: 46
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 138
cacctcaagc tttctagatc agctagcggc ccagcccaac tcccct                  46

<210> SEQ ID NO 139

```
<211> LENGTH: 24
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 139
gcagcacaca tgcgtgaaac ctgt                                          24

<210> SEQ ID NO 140
<211> LENGTH: 23
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 140
gtgtcagaga tgacgcgcag gaa                                           23

<210> SEQ ID NO 141
<211> LENGTH: 23
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 141
acccacactt gcctgtcctg agt                                           23

<210> SEQ ID NO 142
<211> LENGTH: 63
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 142
actggatcct tgacaattaa tgcatcggct cgtataatgt gtggagggtt gcggagggtg   60
ggc                                                                 63

<210> SEQ ID NO 143
<211> LENGTH: 38
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 143
ctgtaatacg actcactata ggttgcgga gggtgggc                            38

<210> SEQ ID NO 144
<211> LENGTH: 73
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296
```

-continued

<400> SEQUENCE: 144
cacctgcaga catgcgtttc gtcctcacgg actcatcagg ccagctggcg acgcatgtgt    60
gagccgagtc ctg    73

<210> SEQ ID NO 145
<211> LENGTH: 24
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 145
ggatccgccg cagagcaccg tctg    24

<210> SEQ ID NO 146
<211> LENGTH: 29
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 146
cgaagctttc agtgggccgg catctgaac    29

<210> SEQ ID NO 147
<211> LENGTH: 29
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 147
cgaagctttc acaggcccag cccaactcc    29

<210> SEQ ID NO 148
<211> LENGTH: 26
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 148
gcggatccag agccacgtcc tacgtc    26

<210> SEQ ID NO 149
<211> LENGTH: 26
<212> TYPE: DNA
<213> ORGANISM: Artificial Sequence
<220> FEATURE:
<223> OTHER INFORMATION: Description of Artificial Sequence: Synthesized
      Amplification Primer Design based on EST Sequence
      GenBank Accession Number AA281296

<400> SEQUENCE: 149
gcggatccgt tcagatgccg gcccac    26

<210> SEQ ID NO 150

-continued

```
<211> LENGTH: 9
<212> TYPE: PRT
<213> ORGANISM: Homo sapiens

<400> SEQUENCE: 150

Pro Glu Met Glu Pro Pro Arg Arg Pro
  1               5

<210> SEQ ID NO 151
<211> LENGTH: 4
<212> TYPE: PRT
<213> ORGANISM: Homo sapiens

<400> SEQUENCE: 151

Ala Ala Glu His
  1

<210> SEQ ID NO 152
<211> LENGTH: 6
<212> TYPE: PRT
<213> ORGANISM: Homo sapiens

<400> SEQUENCE: 152

Val Gln Met Pro Ala His
  1               5

<210> SEQ ID NO 153
<211> LENGTH: 5
<212> TYPE: PRT
<213> ORGANISM: Homo sapiens

<400> SEQUENCE: 153

Val Gly Leu Gly Leu
  1               5

<210> SEQ ID NO 154
<211> LENGTH: 4
<212> TYPE: PRT
<213> ORGANISM: Homo sapiens

<400> SEQUENCE: 154

Arg Ala Thr Ser
  1

<210> SEQ ID NO 155
<211> LENGTH: 622
<212> TYPE: PRT
<213> ORGANISM: Homo sapiens
<220> FEATURE:
<223> OTHER INFORMATION: Truncated Telomerase (ver.2); encoded
      by SEQ ID NO:51, with Y Intron ORF3

<400> SEQUENCE: 155

Met Pro Arg Ala Pro Arg Cys Arg Ala Val Arg Ser Leu Leu Arg Ser
  1               5                  10                  15

His Thr Arg Glu Val Leu Pro Leu Ala Thr Phe Val Arg Arg Leu Gly
             20                  25                  30

Pro Gln Gly Trp Arg Leu Val Gln Arg Gly Asp Pro Ala Ala Phe Arg
         35                  40                  45

Ala Leu Val Ala Gln Cys Leu Val Cys Val Pro Trp Asp Ala Arg Pro
     50                  55                  60

Pro Pro Ala Ala Pro Ser Phe Arg Gln Val Pro Pro Arg Gly Arg Arg
 65                  70                  75                  80
```

-continued

```
Pro Ala Gly Val Glu Gly Arg Gly Glu Pro Ala Thr Cys Gly Glu
                85                  90                  95
Gln Arg Arg Arg Leu Arg Ala Leu Pro Pro Gln Val Ser Cys Leu Lys
                100                 105                 110
Glu Leu Val Ala Arg Val Leu Gln Arg Leu Cys Glu Arg Gly Ala Lys
                115                 120                 125
Asn Val Leu Ala Phe Gly Phe Ala Leu Leu Asp Gly Ala Arg Gly Gly
            130                 135                 140
Pro Pro Glu Ala Phe Thr Thr Ser Val Arg Ser Tyr Leu Pro Asn Thr
145                 150                 155                 160
Val Thr Asp Ala Leu Arg Gly Ser Gly Ala Trp Gly Leu Leu Leu Arg
                165                 170                 175
Arg Val Gly Asp Asp Val Leu Val His Leu Leu Ala Arg Cys Ala Leu
                180                 185                 190
Phe Val Leu Val Ala Pro Ser Cys Ala Tyr Gln Val Cys Gly Pro Pro
            195                 200                 205
Leu Tyr Gln Leu Gly Ala Ala Thr Gln Ala Arg Pro Pro His Ala
    210                 215                 220
Ser Gly Pro Arg Arg Leu Gly Cys Glu Arg Ala Trp Asn His Ser
225                 230                 235                 240
Val Arg Glu Ala Gly Val Pro Leu Gly Leu Pro Ala Pro Gly Ala Arg
                245                 250                 255
Arg Arg Gly Gly Ser Ala Ser Arg Ser Leu Pro Leu Pro Lys Arg Pro
            260                 265                 270
Arg Arg Gly Ala Ala Pro Glu Pro Glu Arg Thr Pro Val Gly Gln Gly
        275                 280                 285
Ser Trp Ala His Pro Gly Arg Thr Arg Gly Pro Ser Asp Arg Gly Phe
    290                 295                 300
Cys Val Val Ser Pro Ala Arg Pro Ala Glu Ala Thr Ser Leu Glu
305                 310                 315                 320
Gly Ala Leu Ser Gly Thr Arg His Ser His Pro Ser Val Gly Arg Gln
                325                 330                 335
His His Ala Gly Pro Pro Ser Thr Ser Arg Pro Pro Arg Pro Trp Asp
            340                 345                 350
Thr Pro Cys Pro Pro Val Tyr Ala Glu Thr Lys His Phe Leu Tyr Ser
        355                 360                 365
Ser Gly Asp Lys Glu Gln Leu Arg Pro Ser Phe Leu Leu Ser Ser Leu
    370                 375                 380
Arg Pro Ser Leu Thr Gly Ala Arg Arg Leu Val Glu Thr Ile Phe Leu
385                 390                 395                 400
Gly Ser Arg Pro Trp Met Pro Gly Thr Pro Arg Arg Leu Pro Arg Leu
                405                 410                 415
Pro Gln Arg Tyr Trp Gln Met Arg Pro Leu Phe Leu Glu Leu Leu Gly
            420                 425                 430
Asn His Ala Gln Cys Pro Tyr Gly Val Leu Leu Lys Thr His Cys Pro
        435                 440                 445
Leu Arg Ala Ala Val Thr Pro Ala Ala Gly Val Cys Ala Arg Glu Lys
    450                 455                 460
Pro Gln Gly Ser Val Ala Ala Pro Glu Glu Asp Thr Asp Pro Arg
465                 470                 475                 480
Arg Leu Val Gln Leu Leu Arg Gln His Ser Ser Pro Trp Gln Val Tyr
                485                 490                 495
Gly Phe Val Arg Ala Cys Leu Arg Arg Leu Val Pro Pro Gly Leu Trp
```

-continued

```
                500                     505                     510
Gly Ser Arg His Asn Glu Arg Arg Phe Leu Arg Asn Thr Lys Lys Phe
            515                     520                     525

Ile Ser Leu Gly Lys His Ala Lys Leu Ser Leu Gln Glu Leu Thr Trp
        530                     535                     540

Lys Met Ser Val Arg Asp Cys Ala Trp Leu Arg Arg Ser Pro Gly Val
545                     550                     555                 560

Gly Cys Val Pro Ala Ala Glu His Arg Leu Arg Glu Glu Ile Leu Ala
                565                     570                     575

Lys Phe Leu His Trp Leu Met Ser Val Tyr Val Val Glu Leu Leu Arg
            580                     585                     590

Ser Phe Phe Tyr Val Thr Glu Thr Thr Phe Gln Lys Asn Arg Leu Phe
        595                     600                     605

Phe Tyr Arg Lys Ser Val Trp Ser Lys Leu Gln Ser Ile Gly
            610                     615                 620
```